United States Patent
Heal et al.

(10) Patent No.: US 11,396,669 B2
(45) Date of Patent: Jul. 26, 2022

(54) PRODUCTION OF STEVIOL GLYCOSIDES IN RECOMBINANT HOSTS

(71) Applicant: EVOLVA SA, Reinach (CH)

(72) Inventors: Jon Heal, Nottinghamshire (GB); Philipp Berninger, Reinach (CH); Kim Olsson, Soborg (DK); Joe Sheridan, Reinach (CH); Laura Occhipinti, Zurich (CH); Laura Brembati, Reinach (CH); Christian Nyffenegger, Reinach (CH); Christophe Folly, Basel (CH)

(73) Assignee: Evolva SA, Reinach (CH)

( * ) Notice: Subject to any disclaimer, the term of this patent is extended or adjusted under 35 U.S.C. 154(b) by 253 days.

(21) Appl. No.: 16/344,477

(22) PCT Filed: Nov. 7, 2017

(86) PCT No.: PCT/EP2017/078473
§ 371 (c)(1),
(2) Date: Apr. 24, 2019

(87) PCT Pub. No.: WO2018/083338
PCT Pub. Date: May 11, 2018

(65) Prior Publication Data
US 2020/0080123 A1    Mar. 12, 2020

Related U.S. Application Data

(60) Provisional application No. 62/418,584, filed on Nov. 7, 2016.

(51) Int. Cl.
| | | |
|---|---|---|
| *C12P 19/56* | (2006.01) | |
| *A23L 27/30* | (2016.01) | |
| *C12N 9/10* | (2006.01) | |
| *C12N 15/52* | (2006.01) | |
| *C12N 15/82* | (2006.01) | |
| *C12P 15/00* | (2006.01) | |

(52) U.S. Cl.
CPC ............. *C12P 19/56* (2013.01); *A23L 27/36* (2016.08); *C12N 9/1051* (2013.01); *C12N 15/52* (2013.01); *C12N 15/8243* (2013.01); *C12P 15/00* (2013.01)

(58) Field of Classification Search
CPC .. C12Y 204/01126; C12P 15/00; C12P 19/56; A23L 27/36; A23L 27/30; C12N 15/52; C12N 15/8243; C12N 9/1051; C12N 15/82; C12N 9/10
See application file for complete search history.

(56) References Cited

U.S. PATENT DOCUMENTS

| | | | |
|---|---|---|---|
| 4,590,160 A | 5/1986 | Nishihashi et al. | |
| 5,198,360 A | 3/1993 | Ballou | |
| 5,204,253 A | 4/1993 | Sanford et al. | |
| 5,306,862 A | 4/1994 | Chappell et al. | |
| 5,460,949 A | 10/1995 | Saunders et al. | |
| 5,538,880 A | 7/1996 | Lundquist et al. | |
| 6,013,863 A | 1/2000 | Lundquist et al. | |
| 6,215,051 B1 | 4/2001 | Yu et al. | |
| 6,255,557 B1 | 7/2001 | Brandie | |
| 6,284,493 B1 | 9/2001 | Roth | |
| 6,284,506 B1 | 9/2001 | Hoshino et al. | |
| 6,329,571 B1 | 12/2001 | Hiei | |
| 6,586,202 B2 | 7/2003 | Hoshino et al. | |
| 6,660,507 B2 | 12/2003 | Cheng et al. | |
| 6,806,076 B1 | 10/2004 | Miyake et al. | |
| 6,969,595 B2 | 11/2005 | Brzostowicz et al. | |
| 7,034,140 B2 | 4/2006 | Bramucci et al. | |
| 7,056,717 B2 | 6/2006 | Cheng et al. | |
| 7,098,000 B2 | 8/2006 | Cheng et al. | |
| 7,129,392 B2 | 10/2006 | Hahn et al. | |
| 7,132,268 B2 | 11/2006 | Miyake et al. | |
| 7,172,886 B2 | 2/2007 | Keasling et al. | |
| 7,183,089 B2 | 2/2007 | Keasling et al. | |
| 7,186,891 B1 | 3/2007 | Chappell et al. | |
| 7,208,298 B2 | 4/2007 | Miyake et al. | |
| 7,335,815 B2 | 2/2008 | Boronat et al. | |
| 7,364,885 B2 | 4/2008 | Miyake et al. | |
| 7,422,884 B2 | 9/2008 | Bai et al. | |
| 7,514,597 B2 | 4/2009 | Nakamura et al. | |
| 7,569,389 B2 | 9/2009 | Feldmann et al. | |
| 7,692,065 B2 | 4/2010 | Harper et al. | |
| 7,838,287 B2 | 11/2010 | Goldsmith et al. | |
| 7,923,541 B2 | 4/2011 | Yang et al. | |
| 7,927,851 B2 | 4/2011 | Brandie et al. | |
| 7,981,647 B2 | 7/2011 | Berry et al. | |
| 9,441,233 B2 | 9/2016 | Apuya et al. | |
| 9,562,251 B2 | 2/2017 | Kishore et al. | |

(Continued)

FOREIGN PATENT DOCUMENTS

| | | |
|---|---|---|
| CN | 101314776 | 12/2008 |
| CN | 101720910 | 6/2010 |

(Continued)

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*

(Continued)

*Primary Examiner* — Ganapathirama Raghu
(74) *Attorney, Agent, or Firm* — McDonnell Boehnen Hulbert & Bergthoff LLP

(57) ABSTRACT

The invention relates to recombinant microorganisms and methods for producing steviol glycosides and steviol glycoside precursors.

15 Claims, 2 Drawing Sheets
Specification includes a Sequence Listing.

(56) References Cited

U.S. PATENT DOCUMENTS

| | | | |
|---|---|---|---|
| 9,957,539 B2 | 5/2018 | Ono et al. | |
| 9,957,540 B2 | 5/2018 | Mikkelsen et al. | |
| 10,364,450 B2 | 7/2019 | Olsson et al. | |
| 10,815,514 B2 * | 10/2020 | Olsson | C12N 9/1051 |
| 10,947,515 B2 | 3/2021 | Boer et al. | |
| 2002/0142408 A1 | 10/2002 | DiCosimo et al. | |
| 2003/0033626 A1 | 2/2003 | Hahn et al. | |
| 2003/0148416 A1 | 8/2003 | Berry et al. | |
| 2003/0148479 A1 | 8/2003 | Keasling et al. | |
| 2003/0190734 A1 | 10/2003 | Hoshino et al. | |
| 2003/0219798 A1 | 11/2003 | Gokarn et al. | |
| 2004/0010815 A1 | 1/2004 | Lange et al. | |
| 2004/0072311 A1 | 4/2004 | DiCosimo et al. | |
| 2004/0078846 A1 | 4/2004 | Desouza et al. | |
| 2004/0176570 A1 | 9/2004 | Bacher et al. | |
| 2004/0194162 A1 | 9/2004 | Hahn et al. | |
| 2005/0003474 A1 | 1/2005 | Desouza | |
| 2005/0032169 A1 | 2/2005 | Miyake et al. | |
| 2006/0014264 A1 | 1/2006 | Sauer | |
| 2006/0079476 A1 | 4/2006 | Keasling et al. | |
| 2006/0083838 A1 | 4/2006 | Jackson et al. | |
| 2007/0004000 A1 | 1/2007 | Miyake et al. | |
| 2007/0077616 A1 | 4/2007 | Keasling et al. | |
| 2007/0099261 A1 | 5/2007 | Keasling et al. | |
| 2007/0118916 A1 | 5/2007 | Puzio et al. | |
| 2007/0128311 A1 | 6/2007 | Prakash et al. | |
| 2007/0166782 A1 | 7/2007 | Keasling et al. | |
| 2007/0202579 A1 | 8/2007 | Berry et al. | |
| 2007/0238157 A1 | 10/2007 | Millis et al. | |
| 2007/0238159 A1 | 10/2007 | Millis et al. | |
| 2007/0238160 A1 | 10/2007 | Millis et al. | |
| 2007/0254354 A1 | 11/2007 | Millis et al. | |
| 2007/0269857 A1 | 11/2007 | Miyake et al. | |
| 2007/0286850 A1 | 12/2007 | Bai et al. | |
| 2008/0064063 A1 | 3/2008 | Brandle | |
| 2008/0081358 A1 | 4/2008 | Vittanen et al. | |
| 2008/0131926 A1 | 6/2008 | Miyake et al. | |
| 2008/0216397 A1 | 9/2008 | Busby et al. | |
| 2008/0261280 A1 | 10/2008 | Hahn et al. | |
| 2008/0271205 A1 | 10/2008 | Yamaguchi et al. | |
| 2008/0286870 A1 | 11/2008 | Vittanen et al. | |
| 2008/0292775 A1 | 11/2008 | Prakash et al. | |
| 2008/0318227 A1 | 12/2008 | Bacher et al. | |
| 2009/0004724 A1 | 1/2009 | Keasling et al. | |
| 2009/0047718 A1 | 2/2009 | Blaschek et al. | |
| 2009/0055974 A1 | 2/2009 | Tanksley et al. | |
| 2009/0074935 A1 | 3/2009 | Lee | |
| 2009/0143308 A1 | 6/2009 | Monk et al. | |
| 2009/0286262 A1 | 11/2009 | Slack | |
| 2010/0112156 A1 | 5/2010 | Abelyan et al. | |
| 2010/0120096 A1 | 5/2010 | Kitaoka et al. | |
| 2010/0221801 A1 | 9/2010 | Van Dyk | |
| 2010/0297722 A1 | 11/2010 | Anterola et al. | |
| 2010/0316782 A1 | 12/2010 | Shi et al. | |
| 2011/0087011 A1 | 4/2011 | Chiang et al. | |
| 2011/0092684 A1 | 4/2011 | Abelyan et al. | |
| 2011/0126318 A1 | 5/2011 | Mien et al. | |
| 2011/0160311 A1 | 6/2011 | Prakash et al. | |
| 2012/0021111 A1 | 1/2012 | Pfister et al. | |
| 2012/0083593 A1 | 4/2012 | Liu et al. | |
| 2012/0164678 A1 | 6/2012 | Stephanopoulos et al. | |
| 2012/0178169 A1 | 7/2012 | Voytas et al. | |
| 2013/0137138 A1 | 5/2013 | Hansen | |
| 2013/0171328 A1 | 7/2013 | Kishore et al. | |
| 2014/0329281 A1 | 11/2014 | Houghton-Larsen et al. | |
| 2015/0159188 A1 | 6/2015 | Ono et al. | |
| 2015/0342234 A1 | 12/2015 | Hicks et al. | |
| 2016/0186225 A1 | 6/2016 | Mikkelsen et al. | |
| 2017/0247735 A1 | 8/2017 | Houghton-Larsen et al. | |
| 2021/0147815 A1 | 5/2021 | Boer et al. | |

FOREIGN PATENT DOCUMENTS

| | | |
|---|---|---|
| CN | 102216313 | 10/2011 |
| CN | 102559528 | 7/2012 |
| CN | 103397064 | 11/2013 |
| CN | 104845990 | 8/2015 |
| EP | 0955363 | 11/1999 |
| EP | 1072683 | 1/2001 |
| EP | 1171610 | 4/2007 |
| EP | 1198575 | 9/2007 |
| EP | 1383864 | 1/2008 |
| EP | 1897951 | 3/2008 |
| EP | 1947189 | 7/2008 |
| EP | 1392824 | 8/2008 |
| EP | 2575432 | 4/2013 |
| EP | 2902410 | 8/2015 |
| EP | 3034614 | 6/2016 |
| JP | 59101408 | 6/1984 |
| JP | 3-277275 | 12/1991 |
| JP | 05-115298 | 5/1993 |
| JP | 2005185101 | 7/2005 |
| JP | 2009034080 | 2/2009 |
| KR | 1020120088035 | 8/2012 |
| KR | 2015 0000258 | 1/2015 |
| WO | WO 1999/018224 | 4/1999 |
| WO | WO 2000/036081 | 6/2000 |
| WO | WO 2000/037663 | 6/2000 |
| WO | WO 2000/063400 | 10/2000 |
| WO | WO 2001/012828 | 2/2001 |
| WO | WO 2001/083769 | 11/2001 |
| WO | WO 2001/094561 | 12/2001 |
| WO | 2002/024865 | 3/2002 |
| WO | WO 2002/020728 | 3/2002 |
| WO | WO 2002/020815 | 3/2002 |
| WO | WO 2002/055709 | 7/2002 |
| WO | WO 2003/008540 | 1/2003 |
| WO | WO 2004/029255 | 4/2004 |
| WO | WO 2005/079183 | 9/2005 |
| WO | WO 2006/016395 | 2/2006 |
| WO | WO 2006069610 | 7/2006 |
| WO | WO 2006/093289 | 9/2006 |
| WO | WO 2006/096392 | 9/2006 |
| WO | WO 2007/136847 | 11/2007 |
| WO | WO 2008/008256 | 1/2008 |
| WO | WO 2008/034648 | 3/2008 |
| WO | WO 2008/039499 | 4/2008 |
| WO | WO 2008/051349 | 5/2008 |
| WO | WO 2008/091547 | 7/2008 |
| WO | WO 2009/005704 | 1/2009 |
| WO | WO 2009/037329 | 3/2009 |
| WO | WO 2009/071277 | 6/2009 |
| WO | WO 2009/086049 | 7/2009 |
| WO | WO 2009/105612 | 8/2009 |
| WO | WO 2009/108680 | 9/2009 |
| WO | WO 2009/111513 | 9/2009 |
| WO | 2009/140394 | 11/2009 |
| WO | WO 2009/140394 | 11/2009 |
| WO | WO 2010/021001 | 2/2010 |
| WO | WO 2010/038911 | 4/2010 |
| WO | WO 2010/044960 | 4/2010 |
| WO | 2010/142305 | 12/2010 |
| WO | WO 2010/146463 | 12/2010 |
| WO | WO 2011/028671 | 3/2011 |
| WO | WO 2011/037959 | 3/2011 |
| WO | WO 2011/046423 | 4/2011 |
| WO | WO 2011/056834 | 5/2011 |
| WO | WO 2011/060057 | 5/2011 |
| WO | WO 2011/153378 | 8/2011 |
| WO | 2011/140329 | 11/2011 |
| WO | 2011/151326 | 12/2011 |
| WO | 2011/153378 | 12/2011 |
| WO | WO 2011/151326 | 12/2011 |
| WO | WO 2011/153144 | 12/2011 |
| WO | WO 2012/075030 | 6/2012 |
| WO | 2013/022989 | 2/2013 |
| WO | WO 2013/019050 | 2/2013 |
| WO | WO 2013/022989 | 2/2013 |
| WO | WO 2013/021261 | 5/2013 |
| WO | WO 2013/076577 | 5/2013 |
| WO | WO 2013/096420 | 6/2013 |
| WO | WO 2013/102793 | 7/2013 |
| WO | WO 2013/110673 | 8/2013 |
| WO | WO 2013/176738 | 11/2013 |

(56) References Cited

FOREIGN PATENT DOCUMENTS

| | | |
|---|---|---|
| WO | WO 2014/086890 | 6/2014 |
| WO | WO 2014/122227 | 8/2014 |
| WO | WO 2014/122328 | 8/2014 |
| WO | 2014/191580 | 12/2014 |
| WO | 2014/191581 | 12/2014 |
| WO | WO2014/191580 | 12/2014 |
| WO | 2015/011209 | 1/2015 |
| WO | WO 2015/007748 | 1/2015 |
| WO | 2015/014959 | 2/2015 |
| WO | 2015/016393 | 2/2015 |
| WO | WO 2015/014969 | 2/2015 |
| WO | WO 2015/028324 | 3/2015 |
| WO | WO 2015051454 | 4/2015 |
| WO | WO 2015/132411 | 9/2015 |
| WO | 2016/023844 | 2/2016 |
| WO | WO 2016/038095 | 3/2016 |
| WO | WO 2016/120486 | 8/2016 |
| WO | WO 2017/025362 | 2/2017 |
| WO | WO 2017/098017 | 6/2017 |
| WO | WO 2017/178632 | 10/2017 |
| WO | WO 2018/083338 | 5/2018 |

OTHER PUBLICATIONS

Jewett et al. "An integrated cell-free metabolic platform for protein production and synthetic biology," Mol Syst Biol. 4:220 (2008).
Johnstone et al., "Cloning an Aspergillus nidulans developmental gene by transformation," EMBO J. 4(5):1307-11 (1985).
Khoury et al., "Computational design of Candida boidinii xylose reductase for altered cofactor specificity," Protein Sci. 18(10):2125-38 (Oct. 2009).
Kim et al., "Hydroxylation of ent-Kaurenoic Acid to Steviol in Stevia rebaudiana Bertoni-Purification and Partial Characterization of the Enzyme," Arch Biochem Biophys. 332(2):223-30 (1996).
Kim & Shibata, "Characterization of ent-kaurenoic acid 13-hydroxylase in steviol biosynthesis of Stevia rebaudiana Bertoni," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23-A (2003).
Kohda et al., "New Sweet Diterpene glucoside from Stevia Rebaudiana," Phytochemistry 15(6):981-3 (1976).
Kondo et al., "Preparation of high activity whole cell biocatalyst by permeabilization of recombinant flocculent yeast with alcohol," Enzyme Microb Technol. 27(10),806-11 (2000).
Kumar et al., "A comprehensive analysis of fifteen genes of steviol glycosides biosynthesis pathwayin Stevia rebaudiana (Bertoni)" Gene 492:276-84 (Epub Oct. 20, 2011).
Kusama et al., "Transglucosylation into stevioside by the enzyme system from *Streptomyces* sp.," Agric. Biol. Chem. 50(10):2445-51 (Oct. 1986).
Li et al., "Crystal structure of Medicago truncatula UGT85H2—insights into the structural basis of a multifunctional (iso) flavonoid glycosyltransferase," J Mol Biol 370(5):951-63 (2007).
Li et al., "Systematic Mutational Analysis of Peptide Inhibition of the p53-MDM2/MDMX," J Mol Biol. 398(2):200-13 (2010).
Li et al., "High-density cultivation of oleaginous yeast Rhodosporidium toruloides Y4 in fed-batch culture," Enzyme and Microbial Technology 41(3):312-7 (Aug. 2007).
Liu et al., "Preparation of high-activity whole cell biocatalysts by permeabilization of recombinant yeasts with alcohol," J Biosci Bioeng. 89(6):554-8 (2000).
Ma et al., "Molecular cloning and characterization of Stevia Rebaudiana UDP-glucosyltransferase," Acta Biologiae Expertmentalis Sinica 36(2):123-9 (2003).
Ma "Part 1. Molecular Cloning and Functional Analysis of UDPG Glucosyltransferase Gene. Part 2. Molecular Cloning, Sequence Analysis and Evolution of Actin and EF1a Genes in Stevia Rebaudiana." Chinese Doctor and Master Dissertations Full-Text Database, Agricultural Technology Part, vol. 2; pp. 1-74 (2004).

Madan et al., "Stevia rebaudiana (Bert.) Bertoni-A Review," Indian Journal of Natural Products and Resources 1 (3):267-86 (2010).
Madhav et al., "Functional and structural variation of uridine diphosphate glycosyltransferase (UGT) gene of Stevia rebaudiana-UGTSr involved in the synthesis of rebaudioside A," Plant Physiol. Biochem. 63:245-53 (Feb. 2013).
Malonek et al., "The NADPH-cytochrome P450 Reductase Gene from Gibberalla fujikuroi is Essential for Gibberellin Biosynthesis," J Bio Chem. 279(24):25075-84 (2004).
Mantovaneli et al., "The effect of temperature and flow rate on the clarification of the aqueous stevia-extract in a fixed bed column with zeolites," Braz J Chem Eng. 21(3):449-58 (2004).
Mattanovich et al., "Recombinant protein production in yeasts," Methods Mol Biol. 824:329-58 (2012).
Megeji et al., "Introducing Stevia rebaudiana, a natural zero-calorie sweetener," Current Science 88(5):801-4 (2005).
Mohamed et al., "UDP-dependent glycosyltransferases involved in the biosynthesis of steviol glycosides" Journal of Plant Physiology 168(10):1136-1141 (Jul. 2011; Epub Apr. 7, 2011).
Mumberg et al., "Yeast vectors for the controlled expression of heterologous proteins in different genetic backgrounds," Gene 156(1):119-22 (1995).
Naesby et al., "Yeast artificial chromosomes employed for random assembly of biosynthetic pathways and production of diverse compounds in *Saccharomyces cerevisiae*," Microb Cell Fact. 8:45 (2009).
Naglak & Wang, "Rapid protein release from *Escherichia coli* by chemical permeabilization under fermentation conditions," Biotechnol Bioeng. 39(7):732-40 (1991).
Nakagiri et al., "cDNA cloning, functional expression and characterization of ent-copalyl diphosphate synthase from *Scoparia dulcis* L.," Plant Sci. 169:760-7 (2005).
Nelson et al., "P450 superfamily: update on new sequences, gene mapping, accession numbers and nomenclature," Pharmacogenetics 6:1-42 (1996).
Newman et al., "High-level production of amorpha-4,11-diene in a two-phase partitioning bioreactor of metabolically engineered *Escherichia coli*," Biotechnol Bioeng 95(4):684-91 (2006).
Nicaud, "Yarrowia lipolytica," Yeast29(10):409-18 (Oct. 2012).
Nielsen et al., "Efficient PCR-based gene targeting with a recyclable marker for Aspergillus nidulans," Fungal Genet Biol. 43(1):54-64 (2006).
Nour-Eldin et al., "USER cloning and USER fusion: the ideal cloning techniques for small and big laboratories," Methods Mol Biol. 643:185-200 (2010).
Ohta et al., "Characterization of Novel Steviol Glycosides from Leaves of Stevia rebaudiana Morita," J. Applied Glycosides 57(3):199-209 (Mar. 2010).
Ohta et al., MassBank Accession No. FU000341 (May 2011).
Ohta et al., MassBank Accession No. FU000342 (May 2011).
Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka & Jigami, "Reconstruction of de novo pathway for synthesis of UDP-glucuronic acid and UDP-xylose from ntrinsic UDP-glucose in *Saccharomyces cerevisiae*," FEBS J. 273(12):2645-57 (2006).
Orihara et al., "Biotransformation of steviol by cultured cells of eucalyptus perriniana and Coffea Arabica," Phytochemistry 30(12):3989-92 (1991).
Paradise et al., "Redirection of flux through the FPP branch-point in *Saccharomyces cerevisiae* by down-regulating squalene synthase," Biotechnol Bioeng. 100(2):371-8 (2008).
Pearson & Lipman, "Improved tools for biological sequence comparison," Proc Natl Acad Sci. 85(8):2444-8 (1998).
Piirainen et al., "Glycoengineering of yeasts from the perspective of glycosylation efficiency," N Biotechnol. 31 (6):532-7 (Dec. 2014).
Pompon et al., "Yeast Expression of Animal and Plant P450s in Optimized RedoxEnvironments," Methods Enzymol 272:51-64 (1996).
Prelich, "Gene overexpression: uses, mechanisms, and interpretation," Genetics 190(3):841-54 (Mar. 2012).

(56) References Cited

OTHER PUBLICATIONS

Presecki & Vasic-Racki, "Production of L-malic acid by permeabilized cells of commercial *Saccharomyces* sp. strains," Biotechnol Lett. 27(23-24):1835-9 (2005).
Ro et al., "Production of the antimalarial drug precursor artemisinic acid in engineered yeast," Nature 440(7086):940-3 (2006).
Saenge et al., "Potential use of oleaginous red yeast Rhodotorula glutinis for the bioconversion of crude glycerol from biodiesel plant to lipids and carotenoids," Process Biochemistry 46(1):210-8 (Jan. 2011).
Schwab et al., Poster, "Watchmaker® —Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol.143 (3):212-23 (2007).
Senthilraja et al., "RNA secondary structure prediction: Analysis of *Saccharomyces cerevisiae* RNAs," Int. J. Pharm. Rev Res. 25(2):287-91 (Mar.-Apr. 2014).
GenBank Accession No. AAS07253.1, dated Jan. 31, 2004 (3 pages).
Gloster, "Advances in understanding glycosyltransferases from a structural perspective," Curr Opin Struct Biol. 28:131-41 (2014).
Guo et al., "Protein tolerance to random amino acid change", Proceedings of the National Academy of Sciences USA, vol. 101, No. 25, pp. 9205-9210 (2004).
Liu et al., "Biosynthesis of Rebaudioside A by Whole Cell of Recombinant *Saccharomyces cerevisiae*," Food and Fermentation Industries, 38(7): 6-10 (2012) (Abstract translation).
Ni et al., "Outer membrane mutation effects on UDP-glucose permeability and whole-cell catalysis rate," Appl Microbiol Biotechnol. 73(2):384-93 (2006).
Prisic et al., "Synergistic substrate inhibition of ent-copalyl diphosphate synthase: a potential feed-forward inhibition mechanism limiting gibberellin metabolism," Plant Physiol. 144(1):445-54 (2007).
Ünligil et al., "Glycosyltransferase structure and mechanism," Curr Opin Struct Biol. 10(5):510-7 (2000).
Wanchao et al., "Advances on the Stevoil Glycoside Biosynthesis and Its Key Enzymes," Biotechnology Bulletin, Feb. 2008 (English Abstract translation).
International Search Report by the International Searching Authority for International Application No. PCT/EP2015/070620; dated Mar. 29, 2016, pp. 1-10.
Written Opinion of the International Searching Authority for International Application No. PCT/EP2015/070620; dated Mar. 29, 2016, pp. 1-24.
Arnold, F. H. "Combinatorial and computational challenges for biocatalyst design," Nature 409(6817):253-257 (2001).
Bruyn et al., "Metabolic engineering of *Escherichia coli* into a versatile glycosylation platform: production of bio-active quercetin glycosides," Microb Cell Fact., 14:138 (2015).
Bruyn et al., "Development of an in vivo glucosylation platform by coupling production to growth: production of phenolic glucosides by a glycosyltransferase of Vitis vinifera," Biotechnol Bioeng., 112(8):1594-603 (2015).
Chen et al., "Synthesis of rebaudioside D using glycosyltransferase UGTSL2 and in situ UDP-glucoseregeneration," Food Chem. ;259:286-291 (2018).
Duetz, "Microtiter plates as mini-bioreactors: miniaturization offermentation methods," Trends Microbiol 15 (10):469-75 (2007).
François et al., "Reserve carbohydrates metabolism in the yeast *Saccharomyces cerevisiae*," FEMS Microbiol Rev., 25(1):125-45 (2001).
Jones et al., "UGT73C6 and UGT78D1, Glycosyltransferases Involved in Flavonol Glycoside Biosynthesis in *Arabidopsis thaliana*\*," J. Biol. Chem., vol. 278, No. 45, pp. 43910-43918 (2003).
Li et al., "Production of rebaudioside A from stevioside catalyzed by the engineered *Saccharomyces cerevisiae*," Appl Biochem Biotechnol., 178(8):1586-98 (2016).

Mikayama et al., "Molecular cloning and functional expression of a cDNA encoding glycosylation-inhibiting factor," Proc Natl Acad Sci U S A. 90(21):10056-60 (1993).
Popenberger et al., Heterologous Expression of Arabidopsis UDP-Glucosyltransferases in *Saccharomyces cerevisiae* for Production ofZearalenone-4-0-Glucoside, Appl. Environ. Microbial., vol. 72, pp. 4404-4410 (2006).
Rudinger et al., "Characteristics of the amino acids as components of a peptide hormone sequence," Peptide Hormones Biol. Council, pp. 5-7 (1976).
Sun et al., "Diterpenoid UDP-glycosyltransferases from Chinese sweet tea and ashitaba complete the biosynthesis of rubososide," Molecular Plant. 11(10):1308-1311 (plus Supplementary Information pp. 1-35)(2018).
Wang et al., "Glycosylation and Glycosyltransferase of Small Molecular Compounds of Plant," China Academic Journal, vol. 44-5, 997-1003 (2008).
GenBank Accession No. XM_004238649.2, dated Aug. 8, 2018 (2 pages).
International Preliminary Report on Patentability from the International Bureau for International Application PCT/EP2015/070620; dated Mar. 14, 2017 (pp. 1-25).
International Preliminary Report on Patentability from the International Bureau for International Application PCTEP2015/068314; dated Feb. 14, 2017 (pp. 1-10).
International Preliminary Report on Patentability from the International Bureau for International Application PCT/EP2015/052007; dated Aug. 1, 2017 (pp. 1-16).
International Search Report and Written Opinion of the International Searching Authority for International Application No. PCT/EP2016/068259; dated Jan. 24, 2017, pp. 1-18.
International Search Report and Written Opinion of International Search Authority for International Application No. PCTEP2016/080516; dated Mar. 15, 2017, pp. 1-22.
International Preliminary Report on Patentability from the International Bureau for International Application PCTEP2016/080516; dated Jun. 12, 2018 (pp. 1-11).
International Search Report and Written Opinion of the International Searching Authority for International Application No. PCT/EP2017/061775; dated Sep. 6, 2017, pp. 1-17.
International Preliminary Report on Patentability from the International Bureau for International Application PCT/EP2017/061775; dated Nov. 20, 2018 (pp. 1-9).
International Search Report and Written Opinion of International Search Authority for International Application No. PCTEP2017/059028; dated Jun. 27, 2017, pp. 1-15.
International Preliminary Report on Patentability from the International Bureau for International Application PCTEP2017/059028; dated Oct. 16, 2018 (pp. 1-7).
International Search Report of the International Searching Authority for International Application No. PCT/EP2017/061774; dated Aug. 30, 2017, pp. 1-20.
Written Opinion of the International Searching Authority for International Application No. PCT/EP2017/061774; dated Aug. 30, 2017, pp. 1-13.
International Preliminary Report on Patentability from then International Search Authority for International Application No. PCT/EP2017/061774; datefd Nov. 20, 2018, pp. 1-14.
Statement of Facts and Arguments In Support of Opposition for EP Application No. 12750513.9; dated Feb. 28, 2017 pp. 1-24.
Communication of Notice of Opposition against EP Application No. 12750513.9; dated Mar. 6, 2017 pp. 1-8.
Sequence alignment between the sequence of Uniprot database entry Q75183 version 31, updated Jul. 22, 2008 and Seq Id No. 152 (from European Patent No. 2742142) as cited in Notice of Opposition against EP Application No. 12750513.9; mailed Mar. 6, 2017; pp. 1-2.
Non-Final Office Action for U.S. Appl. No. 14/648,747, dated Mar. 23, 2017, pp. 1-20.
Third Party Observation in EP Application No. 13801569.8; dated Apr. 26, 2017, pp. 1-5.
Final Office Action for U.S. Appl. No. 14/648,747, dated Sep. 6, 2017 (pp. 1-19).

(56) References Cited

OTHER PUBLICATIONS

Third Party Observation in EP Application No. 13801569.8; dated Oct. 23, 2017, pp. 1-6.
Boer, "Strain and process development for fermentative production of Rebaudiosides" Abstract of Offered Oral from 33rd International Specialised Symposium on Yeasts; Jun. 26-29, 2017 University of College Cork, Ireland; pp. 1-2.
Non-Final Office Action for U.S. Appl. No. 14/761,629, dated Mar. 21, 2017 (pp. 1-19).
Final Office Action for U.S. Appl. No. 14/761,629, dated Aug. 11, 2017 (pp. 1-16).
Non-Final Office Action for U.S. Appl. No. 14/764,898, dated Mar. 30, 2017 (pp. 1-17).
Final Office Action for U.S. Appl. No. 14/764,898, dated Sep. 7, 2017 (pp. 1-16).
International Preliminary Report on Patentability from the International Bureau for International Application PCT/EP2016/068259; dated Feb. 13, 2018 (pp. 1-11).
GenBank Accession No. XM_001467423, dated Jul. 16, 2015 (2 pages).
GenBank Accession No. XP_002282091, dated Dec. 7, 2011 (1 page).
GenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
Gossen & Bujard, "Studying gene function in eukaryotes by conditional gene inactivation," Annu. Rev. Genet. 36:153-73 (Jun. 2002).
Gritz & Davies, "Plasmid-encoded hygromycin B resistance: the sequence of hygromycin B phosphotransferase gene and its expression in *Escherichia coli* and *Saccharomyces cerevisiae*," Gene 25(2-3):179-88 (Nov. 1983).
Hallstrom & Moye-Rowley, "Divergent transcriptional control of multidrug resistance genes in *Saccharomyces cerevisiae*," J. Biol. Chem. 273(4):2098-104 (Jan. 1998).
Katzmann et al., "Expression of an ATP-binding cassette transporter-encoding gene (YOR1) is required for oligomycin resistance in *Saccharomyces cerevisiae*," Mol. Cell Biol. 15(12):6875-83 (Dec. 1995).
Li et al., "Phylogenetic analysis of the UDP-glycosyltransferase multigene family of *Arabidopsis thaliana*," J. Biol. Chem. 276(6):4338-43 (Oct. 2000).
Masada et al., "An efficient chemoenzymatic production of small molecule glucosides with in situ UDP-glucose recycling," FEBS Lett. 581(13):2562-6 (May 2007).
Morita et al., "Japanese morning glory dusky mutants displaying reddish-brown or purplish-gray flowers are deficient n a novel glycosylation enzyme for anthocyanin biosynthesis, UDP-glucose:anthocyanidin 3-O-glucoside-2"-O-glucosyltransferase, due to 4-bp insertions in the gene," Plant J. 42(3):353-63 (May 2005).
Nagy et al., "Role of the yeast ABC transporter Yor1p in cadmium detoxification," Biochimie 88(11):1665-71 (Jun. 2006).
Nikaido & Takatsuk, "Mechanisms of RND multidrug efflux pumps," Biochim. Biophys. Acta. 1794(5):769-81 (May 2009).
Osmani et al., "Catalytic key amino acids and UDP-sugar donor specificity of a plant glucuronosyltransferase, UGT94B1: molecular modeling substantiated by site-specific mutagenesis and biochemical analyses," Plant Physiol. 148(3):1295-308 (Nov. 2008).
Osmani et al., "Substrate specificity of plant UDP-dependent glycosyltransferases predicted from crystal structures and homology modeling," Phytochemistry 70(3):325-47 (Feb. 2009).
Richman et al., "Functional genomics uncovers three glucosyltransferases involved in the synthesis of the major sweet glucosides of Stevia rebaudiana," Plant J 41(1):56-67 (Jan. 2005).
Riesmeier et al., "Isolation and characterization of a sucrose carrier cDNA from spinach by functional expression in yeast," EMBO J. 11(13):4705-13 (Dec. 1992).

Rodríguez-Concepción & Boronat, "Elucidation of the methylerythritol phosphate pathway for isoprenoid biosynthesis in bacteria and plastids. A metabolic milestone achieved through genomics," Plant Physiol 130(3):1079-89 (Nov. 2002).
Saier Jr et al., "The major facilitator superfamily," J. Mol. Microbiol. Biotechnol. 1 (2):257-79 (Nov. 1999).
Saier Jr et al., "The Transporter Classification Database: recent advances," Nucleic Acids Res. 37:D274-8 (Jan. 2009).
Sauer et al., "The soluble and membrane-bound transhydrogenases UdhA and PntAB have divergent functions in NADPH metabolism of *Escherichia coli*," J. Biol. Chem. 279(8):6613-9 (Dec. 2003).
Sawada et al., "UDP-glucuronic acid:anthocyanin glucuronosyltransferase from red daisy (Bellis perennis) flowers. Enzymology and phylogenetics of a novel glucuronosyltransferase involved in flower pigment biosynthesis," J. Biol. Chem. 280(2):899-906 (Jan. 2005).
Shao et al., "Enhanced production of alpha-galactosyl epitopes by metabolically engineered Pichia pastoris," Appl. Environ. Microbiol. 69(9):5238-42 (Sep. 2003).
Son et al., "Production of flavonoid O-glucoside using sucrose synthase and flavonoid O-glucosyltransferase fusion protein," J. Microbiol. Biotechnol. 19(7):709-12 (Jul. 2009).
Sonnhammer et al., "Pfam: a comprehensive database of protein domain families based on seed alignments," Proteins 28(3):405-20 (Jul. 1997).
Sonnhammer et al., "Pfam: multiple sequence alignments and HMM-profiles of protein domains," Nucleic Acids Res. 26(1):320-2 (Jan. 1998).
Yadav et al., "Steviol Glycosides from Stevia: Biosynthesis Pathway Review and their Application in Foods and Medicine", Critical Reviews in Food Science and Nutrition, vol. 52, No. 11, pp. 988-998; (2012).
International Search Report by the International Searching Authority for International Application No. PCT/EP2014/052675, dated Apr. 23, 2014 (5 pages).
Written Opinion of the International Searching Authority for International Application No. PCT/EP2014/052675, dated Apr. 23, 2014 (7 pages).
Chen et al., "Progress in the Application of Affinity Tags for the Expression and Purification of Recombinant Proteins," China Biotechnology, vol. 32, No. 12, pp. 93-103, Dec. 15, 2012 (English Abstract).
Ohta et al., MassBank Accession No. FU000299 (May 2016).
Ohta et al., MassBank Accession No. FU000332 (May 2016).
Tiwari et al., "Plant secondary metabolism linked glycosyltransferases: An update on expaning knowledge and scopes", Biotechnology Advances, 34:714-739 (May 2016).
Third Party Submission in U.S. Appl. No. 14/648,747; dated Mar. 28, 2016, pp. 1-231.
Liu et al., "Functional and Biochemical Characteritzation of *Escherichia coli* Sugar Efflux Transporters," JBC, 274 (33):22977-22984 (Aug. 1999).
Sun et al., "Regulation and Function of *Escherichia coli* Sugar Efflux Transporter A (Set A) during Glucose-Phosphate Stress," J of Bacteriology, 193(1):143-153 (Jan. 2011).
Bateman et al., "Pfam 3.1: 1313 multiple alignments and profile HMMs match the majority of proteins," Nucleic Acids Res. 27(1):260-2 (Jan. 1999).
Bay & Turner, "Diversity and evolution of the small multidrug resistance protein family," BMC Evol. Biol. 9:140 (Jun. 2009).
Brachmann et al., "Designer deletion strains derived from *Saccharomyces cerevisiae* S288C: a useful set of strains and plasmids for PCR-mediated gene disruption and other applications," Yeast 14:115-32 (1998).
Chen et al., "Transferring a biosynthetic cycle into a productive *Escherichia coli* strain: large-scale synthesis of galactosides," J. Am. Chem. Soc. 123(36):8866-7 (Sep. 2001).
Chenna et al., "Multiple sequence alignment with the Clustal series of programs," Nucleic Acids Res. 31 (13):3497-500 (Jul. 2003).
Del Sorbo et al., "Fungal transporters involved in efflux of natural toxic compounds and fungicides," Fungal. Genet. Biol. 30(1):1-15 (Jun. 2000).

(56) References Cited

OTHER PUBLICATIONS

Diener et al., "Arabidopsis ALF5, a multidrug efflux transporter gene family member, confers resistance to toxins," Plant Cell 13(7):1625-38 (Jul. 2001).
GenBank Accession No. AAB62280, dated Jul. 2, 1997 (2 pages).
GenBank Accession No. AAB87091, dated Mar. 22, 2000 (2 pages).
GenBank Accession No. AAC28895.1, dated Aug. 6, 1998 (2 pages).
GenBank Accession No. AAC39505, dated Jul. 26, 1998 (1 page).
GenBank Accession No. AAD34294, dated Mar. 22, 2000 (2 pages).
GenBank Accession No. AAD34295, dated Mar. 22, 2000 (2 pages).
GenBank Accession No. AAD47596, dated Aug. 9, 1999 (2 pages).
GenBank Accession No. AAH69913, dated Jul. 15, 2006 (2 pages).
GenBank Accession No. AEE36246, dated Oct. 6, 2014 (3 pages).
GenBank Accession No. AAR06912, dated Dec. 28, 2004 (2 pages).
GenBank Accession No. AAR06916.1, dated Dec. 28, 2004 (2 pages).
GenBank Accession No. AAR06920.1, dated Dec. 28, 2004 (2 pages).
GenBank Accession No. ABA42921, dated Jun. 21, 2006 (1 page).
GenBank Accession No. ABB88839, dated May 28, 2008 (2 pages).
GenBank Accession No. ABC59076, dated Jun. 6, 2007 (1 page).
GenBank Accession No. ABC98596, dated Jan. 31, 2014 (2 pages).
GenBank Accession No. ABD60225, dated May 28, 2008 (2 pages).
GenBank Accession No. ABD92926, dated Oct. 10, 2007 (2 pages).
GenBank Accession No. AC133334, dated Jan. 31, 2004 (44 pages).
GenBank Accession No. ACD93722, dated Jun. 10, 2008 (1 page).
GenBank Accession No. AF034774, dated Apr. 17, 1998 (2 pages).
GenBank Accession No. AY562490, dated May 23, 2006 (3 pages).
GenBank Accession No. BAA43200, dated Mar. 13, 1999 (2 pages).
GenBank Accession No. BAB59027, dated Jan. 30, 2002 (1 page).
GenBank Accession No. BAF61135, dated May 9, 2007 (2 pages).
GenBank Accession No. BAG30962, dated Nov. 12, 2012 (2 pages).
GenBank Accession No. BC153262, dated Oct. 4, 2007 (3 pages).
GenBank Accession No. CAA75568, dated Nov. 14, 2006 (2 pages).
GenBank Accession No. CAA76703, dated Nov. 14, 2006 (1 page).
GenBank Accession No. CAE09055, dated Nov. 14, 2006 (2 pages).
GenBank Accession No. CAG41604, dated Feb. 6, 2015 (2 pages).
GenBank Accession No. DQ398871.3, dated May 28, 2008 (2 pages).
GenBank Accession No. EDY51667, dated Sep. 2, 2008 (2 pages).
GenBank Accession No. EU263989, dated Jun. 11, 2008 (2 pages).
GenBank Accession No. NM_116512, dated Jan. 22, 2014 (3 pages).
GenBank Accession No. NP_001105097, dated Aug. 4, 2015 (2 pages).
GenBank Accession No. NP_013636.1 (YML075C), dated Jul. 16, 2015 (3 pages).
GenBank Accession No. NP_194183, dated Jan. 22, 2014 (4 pages).
GenBank Accession No. NP_195399, dated Jan. 22, 2014 (3 pages).
GenBank Accession No. NP_197872.1, dated Jan. 22, 2014 (2 pages).
GenBank Accession No. Q9UVY5.1, dated Apr. 1, 2015 (3 pages).
Shao et al., "Crystal structures of a multifunctional triterpene/flavonoid glycosyltransferase from Medicago truncatula," Plant Cell 17(11):3141-54 (2005).
Shibata et al., "Glucosylation of Steviol and Steviol-Glucosides in Extracts from Stevia rebaudiana Bertoni" Plant Physiol. 95(1):152-56 (1991).
Singh et al., "Compendium of Transgenic Crop Plants: Transgenic Sugar, Tuber and Fiber," Ed. Kole & Hall, Blackwell Publishing Ltd. pp. 97-115 (2008).
U.S. Food and Drug Administration GRAS Notice 323, "GRAS Assessment of High Purity Steviol Glycosides; Food Usage Conditions for General Recognition of Safety for PureCircle USA, Inc," pp. 1-262 (Feb. 2010).
U.S Food and Drug Administration GRAS Notice Notice 329, "Notice to the U.S. Food and Drug Administration that the use of RebpureTM (Rebaudioside A) derived from Stevia rebaudiana, as a Food Ingredient is Generally Recognized as Safe (GRAS)," pp. 1-275 (Mar. 2010).
Van Ooyen et al., "Heterologous protein production in the yeast Kluyveromyces lactis," FEMS Yeast Res. 6(3):381-92 (May 2006).
Vazquez De Aldana et al., "Nucleotide sequence of the exo-1,3-beta-glucanase-encoding gene, EXG1, of the yeast *Saccharomyces cerevisiae*," Gene 97(2):173-82 (1991).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol. 73 (13):4342-50 (2007).
Wallin, "Steviol Glycosides," Chem. Tech Assessment—63rd JECFA, pp. 1-5 (2004).
Wallin, "Steviol Glycosides," Chem. Tech Assessment—69th JECFA, pp. 1-7 (2007).
Wallner & Elofsson, "Can correct protein models be identified?," Protein Sci. 12(5):1073-86 (May 2003).
Wang, "Structure, mechanism and engineering of plant natural product glycosyltransferases," FEBS Letters 583 (20):3303-9 (2009).
Xu et al., "Generation of hepatitis B virus PreS2-S antigen in Hansenula polymorpha," Virol Sin. 29(6):403-9 (Dec. 2014).
Yadav et al., "A review on the improvement of stevia [Stevia rebaudiana (Bertoni)]," Can J Plant Sci. 91:1-27 (2011).
Yao et al., "A genetic linkage map for Stevia rebaudiana," Genome 42:657-61 (1999).
Yazaki, "ABC transporters involved in the transport of plant secondary metabolites," FEBS Lett. 580(4):1183-91 (Feb. 2006).
Yu et al., "Bioconversion of ethyl 4-chloro-3-oxobutanoate by permeabilized fresh brewer's yeast cells in the presence of allyl bromide," J Ind Microbiol Biotechnol. 34(2)151-6 (2007).
Yuan et al., "Kinetics and activation parameters for oxidations of styrene by Compounds I from the cytochrome P450 (BM-3) (CYP102A1) heme domain and from CYP119," Biochemistry 48(38):9140-6 (Sep. 2009).
Zheng et al. "An efficient one-step site-directed and site-saturation mutagenesis protocol," Nucleic Acids Res. 32(14):e115 (Aug. 2004).
Zhu et al., "A multi-omic map of the lipid-producing yeast Rhodosporidium toruloides," Nature Commun. 3:1112 (Oct. 2012).
GenBank Accession No. AAF61439.1, dated Sep. 25, 2000 (2 pages).
GenBank Accession No. AAM53963.1, dated Jun. 17, 2002 (2 pages).
GenBank Accession No. AAR06918.1, dated Dec. 28, 2004 (2 pages).
GenBank Accession No. AAT93110.1, dated Apr. 24, 2007 (2 pages).
GenBank Accession No. ACE87855.1, dated Jun. 24, 2008 (1 page).
GenBank Accession No. ACM4//34.1, dated Feb. 7, 2009 (1 page).
GenBank Accession No. ACT33422.1, dated Jul. 17, 2009 (1 page).
GenBank Accession No. AF515727.1, dated Jun. 17, 2002 (2 pages).
GenBank Accession No. AY345974.1, dated Dec. 28, 2004 (2 pages).
GenBank Accession No. AY345978.1, dated Dec. 28, 2004 (2 pages).
Genbank Accession No. AY345980.1, dated Dec. 28, 2004 (2 pages).
GenBank Accession No. AY345982.1, dated Dec. 28, 2004 (2 pages).
GenBank Accession No. BG521726.1, dated May 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. DQ269454.4, dated May 28, 2008 (2 pages).
GenBank Accession No. EU722415.1, dated Jun. 10, 2008 (2 pages).
GenBank Accession No. EU751291.1, dated Jun. 24, 2008 (2 pages).

(56) References Cited

OTHER PUBLICATIONS

EBI Accession No. AAY05902, "Jerusalem artichoke in-chain hydroxylase CYP81B1" (1 page), Jun. 15, 2009.
EBI Accession No. ABM86477, "Rice abiotic stress responsive polypeptide Seq Id No. 4723" (1 page), dated Jun. 2, 2005.
UniProt Accession No. F2DG34, May 2011 (pp. 1-4).
UniProt Accession No. Q6VAA8, 2004 (pp. 1-6).
UniProt Accession No. Q7FPQ4, 2004 (pp. 1-6).
Garber et al., "Computational methods for transcriptome annotation and quantification using RNA-seq," Nat Methods 8(6):469-77 (2011).
Kawai et al., "Transformation of Saccharomyces cerevisiae and other fungi: methods and possible underlying mechanism," Bioeng Bugs. 1(6):395-403 (2010).
Lin et al., "Arrestin-related ubiquitin-ligase adaptors regulate endocytosis and protein turnover at the cell surface," Cell 135(4):714-25 (2008).
Nagalakshmi et al., "The transcriptional landscape of the yeast genome defined by RNA sequencing," Science 320 (5881 ): 1344-9 (2008).
Nikko & Pelham, "Arrestin-mediated endocytosis of yeast plasma membrane transporters," Traffic 10(12):1856-67 (2009).
Nikko et al. "Arrestin-like proteins mediate ubiquitination and endocytosis of the yeast metal transporter Smf1," EMBO Rep. 9(12):1216-21 (2008).
Olsson et al., "Microbial production of next-generation stevia sweeteners," Microbial Cell Factories, 15:11-14 (2016).
Partow et al., "Characterization of different promoters for designing a new expression vector in Saccharomyces cerevisiae," Yeast 27:955-64 (2010).
Robinson & Oshlack et al., "A scaling normalization method for differential expression analysis of RNA-seq data," Genome Bioi. 11(3):R25 (2010).
Saier Jr. et al., "The transporter classification database," Nucl. Acids Res., 42(1):D251-258 (2014).
Wang et al., "RNA-Seq: a revolutionary tool for transcriptomics," Nat Rev Genet. 10(1):57-63 (2009).
Wilhelm et al., "Defining transcribed regions using RNA-seq," Nature Protocols 5:255-66 (2010).
Yang Quanhua et.al., "Analysis of the Chemical constituents of Stevia rebaudiana and its sweetness," Journal of Beijing University of Chemical Technology, vol. 39, No. 2., p. 28-32 (2012) (English Abstract).
Chen et al., "Sugar transporters for intercellular exchange and nutrition of pathogens," Nature 468(7323):527-32 (2010).
Chen et al., "Fusion protein linkers: Property, design, and functionality", Advanced Drug Delivery reviews, 65(0):1257-69 (2013).
Daran et al., "Genetic and biochemical characterization of the UGP1 gene encoding the UDP-glucose pyrophosphorylase from Saccharomyces cerevisiae," Eur J Biochem. 233(2):520-30 (Jul. 1995).
Husar et al., "Overexpression of the UGT73C6 alters brassinosteriod glucoside formation in Arabidopsis thaliana", BMC Plant Biology, 11:1-14 (2011).
Khan et al., "Physical and chemical mutagenesis in Stevia rebaudiana: variant generation with higher UGT expression and glycosidic profile but with low photosynthetic capabilities," Acta Physiologiae Plantarum 38(1) (2016).
Malonek et al., "The NADPH-cytochrome P450 Reductase Gene from Gibberalla fujikuroi is Essential for Gibberellin Biosynthesis", J Bio Chem. 279(24):25075-84 (Jun. 2004).
Mao et al., "Produce steviol glycosides in engineered yeast", 2015 Synthetic Biology: Engineering, Evolution & Design (SEED), Poster Abstract (Jun. 2015).
Nagatoshi et al., "UGT75L6 and UGT94E5 mediate sequential glucosylation of crocetin to crocin in Gardenia asminoides", FEBS Letters, 586:1055-1061 (2012).
Wang et al., "Pathway mining-based integration of critical enzyme parts for de novo biosynthesis of steviol glycoside sweetener in Escherichia coli", Cell Research, 26:258-261 (Sep. 2015).

Wang et al., " Efficient enzymatic production of rebaudioside A from stevioside". Bioscience, Biotechnology, and Biochemistry, 80:67-73 (Aug. 2015).
Wang et al., "Design and construction of artificial biological systems for complex natural products biosynthesis", Chinese Journal of Biotechnology, 29:1146-1160 (2013).
Warth et al., "Hydrophilic interaction liquid chromatography coupled with tandem mass spectrometry for the quantification of uridine diphosphate-glucose, uridine diphosphate-glucuronic acid, deoxynivalenol and its glucoside: In-house validation and application to wheat," Journal of Chromatography A, 1423, pp. 183-189 (2015).
Yang et al., "Base substitution mutations in uridinediphosphate-dependent glycosyltransferase 76G1 gene of Stevia rebaudioside A; Mustation in UGT76G1, a key gene of steviol glycoside synthesis", Plant Physiology and Biochemistry, 80:220-225 (2014).
Mahe et al., "The ATP Binding Cassette Transporters Pdr5 and Snq2 of Saccharomyces cerevisiae Can Mediate Transport of Steriods via in Vivo", JBC, 271(41):25167-25172. (Oct. 1996).
Starratt et al., "Rebaudioside F, a diterpene glycoside from Stevia redaudiana". Phytochemistry, 59(4):367-370. (Feb. 2002). Abstract.
Uniprot Accession No. Q75183, dated Jul. 5, 2004 (pp. 1-2).
Uniprot Accession No. Q75183, dated Jul. 22, 2008 (pp. 1-4).
Abraham & Bhat, "Permeabilization of baker's yeast with N-lauroyl sarcosine," J Ind Microbial Biotechnol. 35(8):1799-804 (2008).
Ageitos et al., "Oily yeasts as oleaginous cell factories," Appl Microbiol Biotechnol. 90(4):1219-27 (May 2011).
Agrawal, "NMR spectroscopy in the structural elucidation of oligosaccharides and glycosides," Phytochemistry 31(10):3307-30 (1992).
Ajikumar et al., "Terpenoids: opportunities for biosynthsis of natural product drugs using engineered microorganisms," Molecular Pharmaceuticals 5(2):167-90 (2008).
Alakomi et al., "Lactic acid permeabilizes gram-negative bacteria by disrupting the outer membrane," Appl Environ Microbiol. 66(5):2001-5 (2000).
Ali et al., "Biochemical investigation during different stages of in vitro propagation of Stevia rebaudiana," Pak J Bot. 42 (4):2827-37 (2010).
Bankar et al., "Environmental and industrial applications of Yarrowia lipolytica," Appl Microbiol Biotechnol. 84(5):847-65 (Oct. 2009).
Baykov et al., "A malachite green procedure for orthophosphate determination and its use in alkaline phosphatase-based enzyme immunoassay," Anal Biochem. 171(2):266-70 (Jun. 1988).
Beopoulos et al., "Yarrowia lipolytica: A model and a tool to understand the mechanisms implicated in lipid accumulation," Biochimie 91(6):692-6 (Jun. 2009).
Brandle et al., "Leaf ESTs from Stevia rebaudiana: A Resource for Gene Discovery in Diterpene Synthesis," Plant Mol Biol. 50(4-5):613-22 (2002).
Brandle & Telmer, "Steviol glycoside biosynthesis," Phytochemistry 68(14):1855-63 (2007).
Brochado et al. "Improved vanillin production in baker's yeast through in silico design," Microb Cell Fact. 9:84-98 (2010).
Carretero-Paulet et al.,"Expression and Molecular Analysis of the Arabidopsis DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).
Chemler et al., "Biosynthesis of isoprenoids, polyunsaturated fatty acids and flavonoids in Saccharomyces cerevisiae," Microb Cell Fact. 5:20 (2006).
Chen, "Summary on Study of Stevioside," China Pharmacist, 10(6):598-599 (2007).
Chen et al., "MolProbity: all-atom structure validation for macromolecular crystallography," Acta Crystallogr D Biol Crystallogr 66(Pt 1):12-21 (Jan. 2010).
Chica et al., "Semi-rational approaches to engineering enzyme activity: combining the benefits of directed evolution and rational design," Curr Opin Biotechnol.16(4):378-84 (2005).
Chow & Palecek, "Enzyme encapsulation in permeabilized Saccharomyces cerevisiae cells," Biotechnol Prog. 20(2):449-56 (2004).

(56) References Cited

OTHER PUBLICATIONS

Correa et al., "Genetic mapping of 1,3-beta-glucanase-encoding genes in *Saccharomyces cerevisiae*," Current Genet. 22(4):283-8 (1992).
Darise et al., "Enzymic Transglucosylation of Rubusoside and the Structure-Sweetness Relationship of Steviol-Bisglycosides," Agric. Biol. Chem. 48(10):2483-8 (Jan. 1984).
Davis et al., "MolProbity: all-atom contacts and structure validation for proteins and nucleic acids," Nucleic Acids Res. 35:W375-83 (Apr. 2007).
Dodhia et al., "Engineering human cytochrome P450 enzymes into catalytically self-sufficient chimeras using molecular Lego," J Biol Inorg Chem. 11(7):903-16 (Oct. 2006).
Dubey, et al., An overview of the non-mevalonate pathway for terpenoid biosynthesis in plants, J. Biosci. 28(5):637-46 (2003).
Dubois & Stephenson, "Diterpenoid sweeteners. Synthesis and sensory evaluation of stevioside analogues with improved organoleptic properties," J. Med. Chem. 28(1):93-8 (Jan. 1985).
EFSA Panel on Food Additives and Nutrient Sources added to Food (ANS), "Scientific Opinion on the safety of steviol glycosides for the proposed uses as a food additive," EFSA Journal 8(4):1537 (2010).
Eisenreich et al., "Biosynthesis of isoprenoids via the non-mevalonate pathway," Cell Mol Life Sci. 61(12):1401-6 (2004).
EMBOSS Needle results for Pairwise Sequence Alignment of UGT91D1 and UGT91D2; dated Apr. 4, 2016, 2 pages.
Emmerstorfer et al., "Over-expression of ICE2 stabilizes cytochrome P450 reductase in *Saccharomyces cerevisiae* and Pichia pastoris," Biotechnol J. 10(4):623-35 (Apr. 2015).
Estrada De Martin et al., "Ice2p is important for the distribution and structure of the cortical ER network in *Saccharomyces cerevisiae*," J Cell Sci. 118(Pt 1):65-77 (Oct. 2006).
Fernandez et al., "Activation of chitin synthetase in permeabilized cells of a *Saccharomyces cerevisiae* mutant lacking proteinase B," J Bacteriol. 152(3):1255-64 (1982).
Flores et al., "Permeabilization of yeast cells (Kluyveromyces lactis) with organic solvents," Enzyme Microb Technol. 16(4):340-6 (1994).
Fowler & Zabin, "Effects of Dimethylsulfoxide on the Lactose Operon in *Escherichia coli*," J Bacteriol. 92(2):353-7 (1966).
Freire, "Differential scanning calorimetry," Methods Mol Biol. 40:191-218 (1995).
Fukunaga et al., "Enzymatic transglucosylation products of stevioside: separation and sweetness-evaluation," Agric. Biol. Chem. 53(6):1603-7 (Jan. 1989).
Geuns, "Stevioside," Phytochemistry 64(5):913-21 (2003).
Giaever & Nislow, "The yeast deletion collection: a decade of functional genomics," Genetics 197(2):451-65 (Jun. 2014).
Gietz & Schiestl, "High-efficiency yeast transformation using the LiAc/SS carrier DNA/PEG method," Nat Protoc. 2(1):31-4 (2007).
Girvan et al., "Flavocytochrome P450 BM3 mutant W1046A is a NADH-dependent fatty acid hydroxylase: implications for the mechanism of electron transfer in the P450 BM3 dimer," Arch Biochem Biophys. 507(1):75-85 (Mar. 2011).
Goralczyk, "Compounds from Stevia for Improving and Maintaining Mental Performance," Stevia World Forum, Feb. 24-25, 2010, 17 pages.
Guleria & Yadav, "Insights into Steviol Glycoside Biosynthesis Pathway Enzymes Through Structural Homology Modeling," Am. J. Biochem. Molec. Biol. 3(1):1-19 (2013).
Gunel et al., "Metabolic Engineering for Production of Geranylgeranyl Pyrophosphate Synthase in Non-Carotenogenic Yeast Schizosaccharomyces Pombe," Biotechnol. & Biotechnol. Eq. 20(3):76-82 (2006).
Hansen et al., "De novo biosynthesis of vanillin in fission yeast (Schizosaccharomyces pombe) and baker's yeast (*Saccharomyces cerevisiae*)," Appl Environ Microbiol 75(9):2765-74 (2009).
Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9):3044-51 (2011).
Hellfritsch et al., "Human psychometric and taste receptor responses to steviol glycosides," J. Agric. Food Chem. 60(27):6782-93 (Jul. 2012).
Humphrey et al.," Spatial organisation of four enzymes from Stevia rebaudiana that are involved in steviol glycoside synthesis," Plant Mol Bio. 61(1-2):47-62 (2006).
Iandolino et al., "High-Quality RNA, cDNA, and Derived EST Libraries From Grapevine (*Vitis vinifera* L.)," Plant Mol Biol Reporter 22:269-78 (2004).
Irmler et al., "Indole alkaloid biosynthesis in Catharanthus roseus: new enzyme activities and identification of cytochrome P450 CYP72A1 as secologanin synthase," Plant J. 24(6):797-804 (2000).
Jennewein et al., "Taxol biosythesis: baxane 13 alpha-hydroxylase is a cytochrome P450-dependent monooxygenase," Proc Natl Acad Sci U S A 98(24):13595-600 (2001).
International Search Report issued by the International Searching Authority for International Application No. PCT/US2011/038967, dated Sep. 1, 2011 (10 pages).
Written Opinion of the International Searching Authority for International Application No. PCT/US2011/038967, dated Sep. 1, 2011 (12 pages).
International Preliminary Report on Patentability issued by the International Bureau for International Application No. PCT/US2011/038967, dated Dec. 4, 2012 (13 pages).
Third-Party Submission under 37 CFR 1.290 for U.S. Appl. No. 13/701,406, dated Mar. 7, 2014 (238 pages).
Extended European Search Report and Opinion issued by the European Patent Office for European Application No. 11790428.4, dated Dec. 20, 2013.
Non-Final Office Action for U.S. Appl. No. 14/237,540, datedd Dec. 30, 2015 (pp. 1-19).
International Search Report issued by the International Searching Authority for International Application No. PCT/US2012/050021, dated Apr. 12, 2013.
Written Opinion of the International Searching Authority for International Application No. PCT/US2012/050021, dated Apr. 12, 2013.
International Preliminary Report on Patentability issued by the International Bureau for International Application No. PCT/US2012/050021, dated Feb. 11, 2014.
Invitation to Pay Additional Fees and, Where Applicable, Protest Fee by the International Searching Authority for International Application No. PCT/EP2015/070620, dated Nov. 27, 2015 (pp. 1-14).
International Search Report from the International Searching Authority for International Application No. PCT/EP2014/052363, dated Sep. 22, 2014 (12 pages).
Written Opinion of the International Searching Authority for International Application No. PCT/EP2014/052363, dated Sep. 22, 2014 (10 pages).
International Preliminary Report on Patentability issued by the International Bureau for International Application No. PCT/EP2014/052363, dated Aug. 11, 2015 (11 pages).
International Preliminary Report on Patentability issued by the International Bureau for International Application No. PCT/EP2014/052675, dated Aug. 11, 2015 (8 pages).
International Search Report of the International Searching Authority for International Application No. PCT/EP2013/075587, dated Feb. 20, 2014 (pp. 1-5).
Written Opinion of the International Searching Authority for International Application No. PCT/EP2013/075587, dated Feb. 20, 2014 (pp. 1-9).
International Preliminary Report on Patentability from the International Bureau for International Application No. PCT/EP2013/075587, dated Jun. 9, 2015 (pp. 1-10).
International Search Report and Written Opinion of the International Searching Authority for International Application No. PCT/EP2015/068314, dated Jan. 20, 2016 (pp. 1-7).
Written Opinion of the International Searching Authority for International Application No. PCT/EP2015/068314, dated Jan. 20, 2016 (pp. 1-9).

(56) References Cited

OTHER PUBLICATIONS

Extended European Search Report issued in EP 15193074.0; dated Feb. 12, 2016, pp. 1-9.
Ceunen & Geuns, "Steviol glycosides: chemical diversity, metabolism, and function," J. Nat. Prod. 76(6):1201-28 (Jun. 2013).
Olsson et al., "Microbial production of next-generation stevia sweeteners," Microbial Cell Factories, 15:1-14 (2016).
Saier, "Families of transmembrane sugar transport proteins," Mol Microbiol., 35(4):699-710 (2000).
Song et al., "The Aspergillus fumigatus 1-29 damage resistance protein family coordinately regulates ergosterol biosynthesis and azole susceptibility," MBIO, 7:1-13 (2016).
GenBank Accession No. AZF53544, dated Apr. 14, 2011 (2 pages).
UniProt Accession No. B5MEX6, Nov. 4, 2008 (1 page).
UniProt Accession No. E4MW7, Feb. 8, 2011 (1 page).
UniProt Accession No. F6KWJ2, Jul. 27, 2011 (1 page).
UniProt Accession No. H9BYK3, May 16, 2012 (1 page).
Final Office Action issued in U.S. Appl. No. 14/237,540; dated Jul. 8, 2016, pp. 1-19.
International Search Report and Written Opinion of the International Searching Authority for International Application No. PCT/EP2015/052007; dated Jul. 4, 2016, pp. 1-24.
International Search Report and Written Opinion of the International Searching Authority for International Application No. PCT/EP2017/078473; dated Jan. 25, 2018, pp. 1-16.
International Preliminary Report on Patentability from then International Search Authority for International Application No. PCT/EP2017/078473; dated May 7, 2019, pp. 1-7.
Broun et al., "Catalytic plasticity of fatty acid modification enzymes underlying chemical diversity of plant lipids," Science, vol. 282: 1315-1317 (1998).
Cheng, "Food Biotechnology," Inner Mongolia Science and Technology Press (2008). (BOOK).
Devos et al., "Practical limits of function prediction," Proteins: Structure, Function, and Genetics, vol. 41: 98-107 (2000).
Seffernick et al., "Melamine deaminase and Atrazine chlorohydrolase: 98 percent identical but functionally different," J. Bacterial., vol. 183 (8): 2405-2410 (2001).
Whisstock et al., "Prediction of protein function from protein sequence," Q. Rev. Biophysics., vol. 36 (3): 307-340 (2003).
Witkowski et al., "Conversion of b-ketoacyl synthase to a Malonyl Decarboxylase by replacement of the active cysteine with glutamine," Biochemistry, vol. 38: 11643-11650 (1999).
Pearson, et al., "Improved tools for biological sequence comparison," Proc Natl Acad Sci. 85(8):2444-8 (1988).

\* cited by examiner

SEQUENCE LISTING

<160> NUMBER OF SEQ ID NOS: 120

<210> SEQ ID NO 1

<400> SEQUENCE: 1

000

<210> SEQ ID NO 2

<400> SEQUENCE: 2

000

<210> SEQ ID NO 3
<211> LENGTH: 1383
<212> TYPE: DNA
<213> ORGANISM: Stevia rebaudiana

<400> SEQUENCE: 3

```
atggcagagc aacaaaagat caaaaagtca cctcacgtct tacttattcc atttcctctg    60
caaggacata tcaacccatt catacaattt gggaaaagat tgattagtaa gggtgtaaag   120
acaacactgg taaccactat ccacactttg aattctactc tgaaccactc aaatactact   180
actacaagta tagaaattca agctatatca gacggatgcg atgagggtgg ctttatgtct   240
gccggtgaat cttacttgga aacattcaag caagtgggat ccaagtctct ggccgatcta   300
atcaaaaagt tacagagtga aggcaccaca attgacgcca taatctacga ttctatgaca   360
gagtgggttt tagacgttgc tatcgaattt ggtattgatg aggttccctt tttcacacaa   420
gcatgtgttg tgaattctct atactaccat gtgcataaag ggttaatctc tttaccattg   480
ggtgaaactg tttcagttcc aggttttcca gtgttacaac gttgggaaac cccattgatc   540
ttacaaaatc atgaacaaat acaatcacct tggtcccaga tgttgtttgg tcaattcgct   600
aacatcgatc aagcaagatg ggtctttact aattcattct ataagttaga ggaagaggta   660
attgaatgga ctaggaagat ctggaatttg aaagtcattg gtccaacatt gccatcaatg   720
```

-continued

```
tatttggaca aaagacttga tgatgataaa gataatggtt tcaatttgta caaggctaat    780
catcacgaat gtatgaattg gctggatgac aaaccaaagg aatcagttgt atatgttgct    840
ttcggctctc ttgttaaaca tggtccagaa caagttgagg agattacaag agcacttata    900
gactctgacg taaacttttt gtgggtcatt aagcacaaag aggagggaa actgccagaa    960
aacctttctg aagtgataaa gaccggaaaa ggtctaatcg ttgcttggtg taaacaattg   1020
gatgttttag ctcatgaatc tgtaggctgt tttgtaacac attgcggatt caactctaca   1080
ctagaagcca tttccttagg cgtacctgtc gttgcaatgc ctcagttctc cgatcagaca   1140
accaacgcta aacttttgga cgaaatacta ggggtgggtg tcagagttaa agcagacgag   1200
aatggtatcg tcagaagagg gaacctagct tcatgtatca aaatgatcat ggaagaggaa   1260
agaggagtta tcataaggaa aaacgcagtt aagtggaagg atcttgcaaa ggttgccgtc   1320
catgaaggcg gctcttcaga taatgatatt gttgaatttg tgtccgaact aatcaaagcc   1380
taa                                                                 1383
```

<210> SEQ ID NO 4
<211> LENGTH: 460
<212> TYPE: PRT
<213> ORGANISM: Stevia rebaudiana

<400> SEQUENCE: 4

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Lys Asp Asn Gly Phe Asn Leu
```

```
                245                 250                 255
Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
            275                 280                 285

Pro Glu Gln Val Glu Glu Ile Thr Arg Ala Leu Ile Asp Ser Asp Val
            290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
            325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
            355                 360                 365

Pro Val Val Ala Met Pro Gln Phe Ser Asp Gln Thr Thr Asn Ala Lys
            370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
            405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
            435                 440                 445

Asp Ile Val Glu Phe Val Ser Glu Leu Ile Lys Ala
450                 455                 460
```

<210> SEQ ID NO 5
<211> LENGTH: 1586
<212> TYPE: DNA
<213> ORGANISM: Stevia rebaudiana

<400> SEQUENCE: 5

```
atggatgcaa tggctacaac tgagaagaaa ccacacgtca tcttcatacc atttccagca    60
caaagccaca ttaaagccat gctcaaacta gcacaacttc tccaccacaa aggactccag   120
ataaccttcg tcaccaccga cttcatccac aaccagtttt tgaatcatc gggcccacat    180
tgtctagacg gtgcaccggg tttccggttc gaaaccattc cggatggtgt ttctcacagt   240
ccggaagcga gcatcccaat cagagaatca ctcttgagat ccattgaaac caacttcttg   300
gatcgtttca ttgatcttgt aaccaaactt ccggatcctc cgacttgtat tatctcagat   360
gggttcttgt cggttttcac aattgacgct gcaaaaaagc ttggaattcc ggtcatgatg   420
tattggacac ttgctgcctg tgggttcatg gttttttacc atattcattc tctcattgag   480
aaaggatttg caccacttaa agatgcaagt tacttgacaa tgggtatttt ggacaccgtc   540
attgattggg ttccgggaat ggaaggcatc cgtctcaagg atttcccgct ggactggagc   600
actgacctca tgacaaagt tttgatgttc actacggaag ctcctcaaag gtcacacaag   660
gtttcacatc atattttcca cacgttcgat gagttggagc ctagtattat aaaaactttg   720
tcattgaggt ataatcacat ttacaccatc ggcccactgc aattacttct tgatcaaata   780
cccgaagaga aaaagcaaac tggaattacg agtctccatg gatacagttt agtaaaagaa   840
gaaccagagt gtttccagtg gcttcagtct aaagaaccaa attccgtcgt ttatgtaaat   900
```

```
tttggaagta ctacagtaat gtctttagaa gacatgacgg aatttggttg gggacttgct        960
aatagcaacc attatttcct ttggatcatc cgatcaaact tggtgatagg ggaaaatgca       1020
gttttgcccc ctgaacttga ggaacatata agaaaagag gctttattgc tagctggtgt       1080
tcacaagaaa aggtcttgaa gcacccttcg gttggaggt tcttgactca ttgtgggtgg       1140
ggatcgacca tcgagagctt gtctgctggg gtgccaatga tatgctggcc ttattcgtgg       1200
gaccagctga ccaactgtag gtatatatgc aaagaatggg aggttgggct cgagatggga       1260
accaaagtga aacgagatga agtcaagagg cttgtacaag agttgatggg agaaggaggt       1320
cacaaaatga ggaacaaggc taaagattgg aaagaaaagg ctcgcattgc aatagctcct       1380
aacggttcat cttcttttgaa catagacaaa atggtcaagg aaatcaccgt gctagcaaga       1440
aactagttac aaagttgttt cacattgtgc tttctattta agatgtaact ttgttctaat       1500
ttaatattgt ctagatgtat tgaaccataa gtttagttgg tctcaggaat tgattttttaa       1560 tgaaataatg gtcattaggg gtgagt                                            1586

<210> SEQ ID NO 6
<211> LENGTH: 1446
<212> TYPE: DNA
<213> ORGANISM: Artificial Sequence
<220> FEATURE:
<223> OTHER INFORMATION: Codon-optimized UGT85C2

<400> SEQUENCE: 6
atggatgcaa tggcaactac tgagaaaaag cctcatgtga tcttcattcc atttcctgca         60
caatctcaca taaaggcaat gctaaagtta gcacaactat acaccataa gggattacag        120 ataactttcg tgaataccga cttcatccat aatcaatttc tggaatctag tggccctcat        180
tgtttggacg gagccccagg gtttagattc gaaacaattc ctgacggtgt ttcacattcc        240
ccagaggcct ccatcccaat aagagagagt ttactgaggt caatagaaac caacttttg        300 gatcgtttca ttgacttggt cacaaaactt ccagacccac caacttgcat aatctctgat        360
ggctttctgt cagtgtttac tatcgacgct gccaaaaagt gggtatccc agttatgatg        420 tactggactc ttgctgcatg cggtttcatg ggtttctatc acatccattc tcttatcgaa        480
aagggttttg ctccactgaa agatgcatca tacttaacca acggctacct ggatactgtt        540
attgactggg taccaggtat ggaaggtata agacttaaag attttcctttt ggattggtct       600 acagacctta tgataaagt attgatgttt actacagaag ctccacaaag atctcataag        660
gtttcacatc atatctttca cacctttgat gaattggaac catcaatcat caaaaccttg       720
tctctaagat acaatcatat ctacactatt ggtccattac aattacttct agatcaaatt        780
cctgaagaga aaaagcaaac tggtattaca tccttacacg ctactctttt agtgaaagag       840
gaaccagaat gttttcaatg gctacaaagt aaagagccta attctgtggt ctacgtcaac        900
ttcggaagta acagtcat gtccttggaa gatatgactg aatttggttg gggccttgct         960
aattcaaatc attactttct atggattatc aggtccaatt tggtaatagg ggaaaacgcc       1020
gtattacctc cagaattgga ggaacacatc aaaagagag gtttcattgc ttcctggtgt        1080
tctcaggaaa aggtattgaa acatccttct gttggtggtt tccttactca ttgcggttgg       1140
ggctctacaa tcgaatcact aagtgcagga gttccaatga tttgttggcc atattcatgg       1200
gaccaactta caaattgtag gtatatctgt aaagagtggg aagttggatt agaaatggga       1260
acaaaggtta aacgtgatga agtgaaaaga ttggttcagg agttgatggg ggaaggtggc       1320
cacaagatga gaaacaaggc caaagattgg aaggaaaaag ccagaattgc tattgctcct       1380
```

```
aacgggtcat cctctctaaa cattgataag atggtcaaag agattacagt cttagccaga    1440
aactaa                                                                1446

<210> SEQ ID NO 7
<211> LENGTH: 481
<212> TYPE: PRT
<213> ORGANISM: Stevia rebaudiana

<400> SEQUENCE: 7
```

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
210                 215                 220

Ile Phe His Thr Phe Asp Glu Leu Glu Pro Ser Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
            355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly His Lys Met Arg Asn Lys Ala Lys
            435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn

<210> SEQ ID NO 8
<211> LENGTH: 1377
<212> TYPE: DNA
<213> ORGANISM: Artificial Sequence
<220> FEATURE:
<223> OTHER INFORMATION: Codon-optimized UGT76G1

<400> SEQUENCE: 8

| | | | | | |
|---|---|---|---|---|---|
| atggaaaaca | agaccgaaac | aacagttaga | cgtaggcgta | gaatcattct | gtttccagta | 60 |
| ccttttcaag | ggcacatcaa | tccaatacta | caactagcca | acgttttgta | ctctaaaggt | 120 |
| ttttctatta | caatctttca | caccaatttc | aacaaaccaa | aaacatccaa | ttacccacat | 180 |
| ttcacattca | gattcatact | tgataatgat | ccacaagatg | aacgtatttc | aaacttacct | 240 |
| acccacggtc | ctttagctgg | aatgagaatt | ccaatcatca | tgaacatgg | tgccgatgag | 300 |
| cttagaagag | aattagagtt | acttatgttg | gcatccgaag | aggacgagga | agtctcttgt | 360 |
| ctgattactg | acgctctatg | gtactttgcc | caatctgtgg | ctgatagttt | gaatttgagg | 420 |
| agattggtac | taatgacatc | cagtctgttt | aactttcacg | ctcatgttag | tttaccacaa | 480 |
| tttgacgaat | gggatactt | ggaccctgat | gacaagacta | ggttagagga | acaggcctct | 540 |
| ggttttccta | tgttgaaagt | caaagatatc | aagtctgcct | attctaattg | gcaaatcttg | 600 |
| aaagagatct | taggaaagat | gatcaaacag | acaaaggctt | catctggagt | gatttggaac | 660 |
| agtttcaaag | agttagaaga | gtctgaattg | gagactgtaa | tcagagaaat | tccagcacct | 720 |
| tcattcctga | taccattacc | aaaacatttg | actgcttcct | cttcctcttt | gttggatcat | 780 |
| gacagaacag | ttttcaatg | gttggaccaa | caaccactta | gttctgtttt | gtacgtgtca | 840 |
| tttggtagta | cttctgaagt | cgatgaaaag | gacttccttg | aaatcgcaag | aggcttagtc | 900 |
| gatagtaagc | agtcattcct | ttgggtcgtg | cgtccaggtt | tcgtgaaagg | ctcaacatgg | 960 |
| gtcgaaccac | ttccagatgg | ttttctaggc | gaaagaggta | gaatagtcaa | atgggttcct | 1020 |
| caacaggaag | tttagctca | tggcgctatt | gggcattct | ggactcattc | cggatggaat | 1080 |
| tcaactttag | aatcagtatg | cgaaggggta | cctatgatct | tttcagattt | tggtcttgat | 1140 |
| caaccactga | acgcaagata | catgtctgat | gttttgaaag | tgggtgtata | tctagaaaat | 1200 |
| ggctgggaaa | ggggtgaaat | agctaatgca | ataagacgtg | ttatggttga | tgaagagggg | 1260 |
| gagtatatca | gacaaaacgc | aagagtgctg | aagcaaaagg | ccgacgtttc | tctaatgaag | 1320 |

-continued ggaggctctt catacgaatc cttagaatct cttgtttcct acatttcatc actgtaa     1377

<210> SEQ ID NO 9
<211> LENGTH: 458
<212> TYPE: PRT
<213> ORGANISM: Stevia rebaudiana

<400> SEQUENCE: 9

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
                35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                    85                  90                  95

Gly Ala Asp Glu Leu Arg Arg Glu Leu Glu Leu Leu Met Leu Ala Ser
                100                 105                 110

Glu Glu Asp Glu Glu Val Ser Cys Leu Ile Thr Asp Ala Leu Trp Tyr
            115                 120                 125

Phe Ala Gln Ser Val Ala Asp Ser Leu Asn Leu Arg Arg Leu Val Leu
        130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

```
Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
        450                 455

<210> SEQ ID NO 10
<211> LENGTH: 1422
<212> TYPE: DNA
<213> ORGANISM: Artificial Sequence
<220> FEATURE:
<223> OTHER INFORMATION: Codon-optimized UGT91D2e

<400> SEQUENCE: 10
atggctacat ctgattctat tgttgatgac aggaagcagt tgcatgtggc tactttccct      60
tggcttgctt tcggtcatat actgccttac ctacaactat caaaactgat agctgaaaaa     120
ggacataaag tgtcattcct ttcaacaact agaaacattc aaagattatc ttcccacata     180
tcaccattga ttaacgtcgt tcaattgaca cttccaagag tacaggaatt accagaagat     240
gctgaagcta acagatgtgt gcatcctgaa gatatccctt acttgaaaaa ggcatccgat     300
ggattacagc tgaggtcac  tagattcctt gagcaacaca gtccagattg gatcatatac     360
gactacactc actattggtt gccttcaatt gcagcatcac taggcatttc tagggcacat     420
ttcagtgtaa ccacaccttg gccattgct  tacatgggtc catccgctga tgctatgatt     480
aacggcagtg atggtagaac taccgttgaa gatttgacaa ccccaccaaa gtggtttcca     540
tttccaacta aagtctgttg gagaaaaacac gacttagcaa gactggttcc atacaaggca     600
ccaggaatct cagacggcta taaatgggt  ttagtcctta aagggtctga ctgcctattg     660
tctaagtgtt accatgagtt tgggacacaa tggctaccac ttttggaaac attacaccaa     720
gttcctgtcg taccagttgg tctattacct ccagaaatcc ctggtgatga aaggacgag      780 acttgggttt caatcaaaaa gtggttagac gggaagcaaa aaggctcagt ggtatatgtg     840
gcactgggtt ccgaagtttt agtatctcaa acagaagttg tggaacttgc cttaggtttg     900
gaactatctg gattgccatt tgtctgggcc tacagaaaac caaaggccct gcaaagtcc      960 gattcagttg aattgccaga cggctttgtc gagagaacta gagatagagg ttggtatgg     1020 acttcatggg ctccacaatt gagaatcctg agtcacgaat ctgtgtgcgg tttcctaaca    1080
cattgtggtt ctggttctat agttgaagga ctgatgtttg tcatccact  tatcatgttg    1140 ccaatctttg gtgaccagcc tttgaatgca cgtctgttag aagataaaca agttggaatt    1200
gaaatcccac gtaatgagga agatggatgt taaccaagg  agtctgtggc cagatcatta   1260
cgttccgttg tcgttgaaaa ggaaggcgaa atctacaagg ccaatgcccg tgaacttca    1320 aagatctaca atgacacaaa agtagagaag gaatatgttt ctcaatttgt agattaccta    1380
gagaaaaacg ctagagccgt agctattgat catgaatcct aa                       1422

<210> SEQ ID NO 11
```

```
<211> LENGTH: 473
<212> TYPE: PRT
<213> ORGANISM: Stevia rebaudiana

<400> SEQUENCE: 11

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Val Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
```

Glu Ile Pro Arg Asn Glu Glu Asp Gly Cys Leu Thr Lys Ser Val
        385             390             395             400

Ala Arg Ser Leu Arg Ser Val Val Glu Lys Glu Gly Glu Ile Tyr
            405             410             415

Lys Ala Asn Ala Arg Glu Leu Ser Lys Ile Tyr Asn Asp Thr Lys Val
        420             425             430

Glu Lys Glu Tyr Val Ser Gln Phe Val Asp Tyr Leu Glu Lys Asn Ala
    435             440             445

Arg Ala Val Ala Ile Asp His Glu Ser
450             455             460

465         470

<210> SEQ ID NO 12
<211> LENGTH: 1422
<212> TYPE: DNA
<213> ORGANISM: Artificial Sequence
<220> FEATURE:
<223> OTHER INFORMATION: Codon-optimized UGT91D2e-b

<400> SEQUENCE: 12
atggctactt ctgattccat cgttgacgat agaaagcaat tgcatgttgc tacttttcca      60
tggttggctt tcggtcatat tttgccatac ttgcaattgt ccaagttgat tgctgaaaag     120
ggtcacaagg tttcattctt gtctaccacc agaaacatcc aaagattgtc ctctcatatc     180
tccccattga tcaacgttgt tcaattgact ttgccaagag tccaagaatt gccagaagat     240
gctgaagcta ctactgatgt tcatccagaa gatatccctt acttgaaaaa ggcttccgat     300
ggtttacaac cagaagttac tagattcttg aacaacattc cccagattg gatcatctac      360
gattatactc attactggtt gccatccatt gctgcttcat gggtatttc tagagcccat      420
ttctctgtta ctactccatg gctattgct tatatgggtc catctgctga tgctatgatt     480
aacggttctg atggtagaac taccgttgaa gatttgacta ctccaccaaa gtggtttcca     540
tttccaacaa agtctgttg agaaaaacac gatttggcta gattggttcc atacaaagct      600
ccaggtattt ctgatggtta cagaatgggg atggttttga aaggttccga ttgcttgttg     660
tctaagtgct atcatgaatt cggtactcaa tggttgcctt tgttggaaac attgcatcaa     720
gttccagttg ttccagtagg tttgttgcca ccagaaaattc caggtgacga aaaagacgaa     780
acttgggttt ccatcaaaaa gtggttggat ggtaagcaaa agggttctgt tgtttatgtt     840
gctttgggtt ccgaagcttt ggtttctcaa accgaagttg ttgaattggc tttgggtttg     900
gaattgtctg gtttgccatt tgtttgggct tacagaaaaa ctaaaggtcc agctaagtct     960
gattctgttg aattgccaga tggtttcgtt gaaagaacta gagatagagg tttggtttgg    1020
acttcttggg ctccacaatt gagaattttg tctcatgaat ccgtctgtgg tttcttgact    1080
cattgtggtt ctggttctat cgttgaaggt ttgatgtttg gtcacccatt gattatgttg    1140
ccaatctttg gtgaccaacc attgaacgct agattattgg aagataagca agtcggtatc    1200
gaaatcccaa gaaatgaaga agatggttgc ttgaccaaag aatctgttgc tagatctttg    1260
agatccgttg tcgttgaaaa agaaggtgaa atctacaagg ctaacgctag agaattgtcc    1320
aagatctaca acgataccaa ggtcgaaaaa gaatacgttt cccaattcgt tgactacttg    1380
gaaaagaatg ctagagctgt tgccattgat catgaatctt ga                       1422

<210> SEQ ID NO 13
<211> LENGTH: 473
<212> TYPE: PRT

<213> ORGANISM: Artificial Sequence
<220> FEATURE:
<223> OTHER INFORMATION: UGT91D2e-b

<400> SEQUENCE: 13

```
Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Met Val Leu Lys Gly Ser Asp Cys Leu Leu Ser Lys Cys Tyr
210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Ala Leu Val
        275                 280                 285

Ser Gln Thr Glu Val Val Glu Leu Ala Leu Gly Leu Glu Leu Ser Gly
290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
370                 375                 380

Asp Gln Pro Leu Asn Ala Arg Leu Leu Glu Asp Lys Gln Val Gly Ile
```

```
                385              390              395              400
Glu Ile Pro Arg Asn Glu Glu Asp Gly Cys Leu Thr Lys Glu Ser Val
                    405              410              415

Ala Arg Ser Leu Arg Ser Val Val Glu Lys Glu Gly Glu Ile Tyr
                420              425              430

Lys Ala Asn Ala Arg Glu Leu Ser Lys Ile Tyr Asn Asp Thr Lys Val
            435              440              445

Glu Lys Glu Tyr Val Ser Gln Phe Val Asp Tyr Leu Glu Lys Asn Ala
    450              455              460

Arg Ala Val Ala Ile Asp His Glu Ser
465              470
```

<210> SEQ ID NO 14
<211> LENGTH: 1389
<212> TYPE: DNA
<213> ORGANISM: Oryza sativa

<400> SEQUENCE: 14

| | |
|---|---:|
| atggactccg gctactcctc ctcctacgcc gccgccgccg ggatgcacgt cgtgatctgc | 60 |
| ccgtggctcg ccttcggcca cctgctcccg tgcctcgacc tcgcccagcg cctcgcgtcg | 120 |
| cggggccacc gcgtgtcgtt cgtctccacg ccgcggaaca tatcccgcct cccgccggtg | 180 |
| cgccccgcgc tcgcgccgct cgtcgccttc gtggcgctgc cgctcccgcg cgtcgagggg | 240 |
| ctccccgacg gcgccgagtc caccaacgac gtccccacg acaggccgga catggtcgag | 300 |
| ctccaccgga gggccttcga cgggctcgcc gcgcccttct cggagttctt gggcaccgcg | 360 |
| tgcgccgact gggtcatcgt cgacgtcttc caccactggg ccgcagccgc cgctctcgag | 420 |
| cacaaggtgc catgtgcaat gatgttgttg ggctctgcac atatgatcgc ttccatagca | 480 |
| gacagacggc tcgagcgcgc ggagacagag tcgcctgcgg ctgccgggca gggacgccca | 540 |
| gcggcggcgc caacgttcga ggtggcgagg atgaagttga tacgaaccaa aggctcatcg | 600 |
| ggaatgtccc tcgccgagcg cttctccttg acgctctcga ggagcagcct cgtcgtcggg | 660 |
| cggagctgcg tggagttcga gccggagacc gtcccgctcc tgtcgacgct ccgcggtaag | 720 |
| cctattacct tccttggcct tatgccgccg ttgcatgaag gccgccgcga ggacggcgag | 780 |
| gatgccaccg tccgctggct cgacgcgcag ccggccaagt ccgtcgtgta cgtcgcgcta | 840 |
| ggcagcgagg tgccactggg agtggagaag gtccacgagc tcgcgctcgg gctgagctc | 900 |
| gccgggacgc gcttcctctg ggctcttagg aagcccactg gcgtctccga cgccgacctc | 960 |
| ctccccgccg gcttcgagga gcgcacgcgc ggccgcggcg tcgtggcgac gagatggggtt | 1020 |
| cctcagatga gcatactggc gcacgccgcc gtgggcgcgt tcctgaccca ctgcggctgg | 1080 |
| aactcgacca tcgaggggct catgttcggc caccgcttta tcatgctgcc gatcttcggc | 1140 |
| gaccagggac cgaacgcgcg gctaatcgag gcgaagaacg ccggattgca ggtggcaaga | 1200 |
| aacgacggcg atggatcgtt cgaccgagaa ggcgtcgcgg cggcgattcg tgcagtcgcg | 1260 |
| gtggaggaag aaagcagcaa agtgtttcaa gccaaagcca agaagctgca ggagatcgtc | 1320 |
| gcggacatgg cctgccatga gaggtacatc gacggattca ttcagcaatt gagatcttac | 1380 |
| aaggattga | 1389 |

<210> SEQ ID NO 15
<211> LENGTH: 1389
<212> TYPE: DNA
<213> ORGANISM: Artificial Sequence
<220> FEATURE:

<223> OTHER INFORMATION: Codon-optimized EUGT11

<400> SEQUENCE: 15

```
atggatagtg gctactcctc atcttatgct gctgccgctg gtatgcacgt tgtgatctgc      60
ccttggttgg cctttggtca cctgttacca tgtctggatt tagcccaaag actggcctca     120
agaggccata gagtatcatt tgtgtctact cctagaaata tctctcgttt accaccagtc     180
agacctgctc tagctcctct agttgcattc gttgctcttc cacttccaag agtagaagga     240
ttgccagacg gcgctgaatc tactaatgac gtaccacatg atagacctga catggtcgaa     300
ttgcatagaa gagcctttga tggattggca gctccatttt ctgagttcct gggcacagca     360
tgtgcagact gggttatagt cgatgtattt catcactggg ctgctgcagc cgcattggaa     420
cataaggtgc cttgtgctat gatgttgtta gggtcagcac acatgatcgc atccatagct     480
gatagaagat tggaaagagc tgaaacagaa tccccagccg cagcaggaca aggtaggcca     540
gctgccgccc aacctttga agtggctaga atgaaattga ttcgtactaa aggtagttca     600
gggatgagtc ttgctgaaag gttttctctg acattatcta gatcatcatt agttgtaggt     660
agatcctgcg tcgagttcga acctgaaaca gtacctttac tatctacttt gagaggcaaa     720
cctattactt tccttggtct aatgcctcca ttacatgaag aaggagaga agatggtgaa     780
gatgctactg ttaggtggtt agatgcccaa cctgctaagt ctgttgttta cgttgcattg     840
ggttctgagg taccactagg ggtggaaaag gtgcatgaat agcattagg acttgagctg     900
gccggaacaa gattcctttg gctttgaga aaaccaaccg tgtttctga cgccgacttg     960
ctaccagctg ggttcgaaga gagaacaaga ggccgtggtg tcgttgctac tagatgggtc    1020
ccacaaatga gtattctagc tcatgcagct gtaggggcct ttctaaccca ttgcggttgg    1080
aactcaacaa tagaaggact gatgtttggt catccactta ttatgttacc aatctttggc    1140
gatcagggac ctaacgcaag attgattgag caaagaacg caggtctgca ggttgcacgt    1200
aatgatggtg atggttcctt tgatagagaa ggcgttgcag ctgccatcag agcagtcgcc    1260
gttgaggaag agtcatctaa agttttccaa gctaaggcca aaaaattaca agagattgtg    1320
gctgacatgg cttgtcacga agatacatc gatggtttca tccaacaatt gagaagttat    1380
aaagactaa                                                            1389
```

<210> SEQ ID NO 16
<211> LENGTH: 462
<212> TYPE: PRT
<213> ORGANISM: Oryza sativa

<400> SEQUENCE: 16

```
Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
        35                  40                  45

Ser Thr Pro Arg Asn Ile Ser Arg Leu Pro Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
```

```
            100                 105                 110
Phe Ser Glu Phe Leu Gly Thr Ala Cys Ala Asp Trp Val Ile Val Asp
        115                 120                 125

Val Phe His His Trp Ala Ala Ala Ala Leu Glu His Lys Val Pro
130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Gly
            165                 170                 175

Gln Gly Arg Pro Ala Ala Pro Thr Phe Glu Val Ala Arg Met Lys
        180                 185                 190

Leu Ile Arg Thr Lys Gly Ser Ser Gly Met Ser Leu Ala Glu Arg Phe
        195                 200                 205

Ser Leu Thr Leu Ser Arg Ser Ser Leu Val Val Gly Arg Ser Cys Val
        210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
                245                 250                 255

Glu Asp Gly Glu Asp Ala Thr Val Arg Trp Leu Asp Ala Gln Pro Ala
                260                 265                 270

Lys Ser Val Val Tyr Val Ala Leu Gly Ser Glu Val Pro Leu Gly Val
            275                 280                 285

Glu Lys Val His Glu Leu Ala Leu Gly Leu Glu Leu Ala Gly Thr Arg
        290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
                325                 330                 335

Thr Arg Trp Val Pro Gln Met Ser Ile Leu Ala His Ala Ala Val Gly
            340                 345                 350

Ala Phe Leu Thr His Cys Gly Trp Asn Ser Thr Ile Glu Gly Leu Met
        355                 360                 365

Phe Gly His Pro Leu Ile Met Leu Pro Ile Phe Gly Asp Gln Gly Pro
        370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
                405                 410                 415

Arg Ala Val Ala Val Glu Glu Glu Ser Ser Lys Val Phe Gln Ala Lys
            420                 425                 430

Ala Lys Lys Leu Gln Glu Ile Val Ala Asp Met Ala Cys His Glu Arg
        435                 440                 445

Tyr Ile Asp Gly Phe Ile Gln Gln Leu Arg Ser Tyr Lys Asp
        450                 455                 460

<210> SEQ ID NO 17
<211> LENGTH: 465
<212> TYPE: PRT
<213> ORGANISM: Artificial Sequence
<220> FEATURE:
<223> OTHER INFORMATION: UGT91D2e-b-EUGT11 chimera 3

<400> SEQUENCE: 17

Met Asp Ser Gly Tyr Ser Ser Ser Tyr Ala Ala Ala Ala Gly Met His
```

```
1               5                   10                  15
Val Val Ile Cys Pro Trp Leu Ala Phe Gly His Leu Leu Pro Cys Leu
                20                  25                  30
Asp Leu Ala Gln Arg Leu Ala Ser Arg Gly His Arg Val Ser Phe Val
                35                  40                  45
Ser Thr Pro Arg Asn Ile Ser Arg Leu Pro Pro Val Arg Pro Ala Leu
                50                  55                  60
Ala Pro Leu Val Ala Phe Val Ala Leu Pro Leu Pro Arg Val Glu Gly
65                  70                  75                  80
Leu Pro Asp Gly Ala Glu Ser Thr Asn Asp Val Pro His Asp Arg Pro
                85                  90                  95
Asp Met Val Glu Leu His Arg Arg Ala Phe Asp Gly Leu Ala Ala Pro
                100                 105                 110
Phe Ser Glu Phe Leu Gly Thr Ala Cys Ala Asp Trp Val Ile Val Asp
                115                 120                 125
Val Phe His His Trp Ala Ala Ala Ala Leu Glu His Lys Val Pro
                130                 135                 140
Cys Ala Met Met Leu Leu Gly Ser Ala His Met Ile Ala Ser Ile Ala
145                 150                 155                 160
Asp Arg Arg Leu Glu Arg Ala Glu Thr Glu Ser Pro Ala Ala Gly
                165                 170                 175
Gln Gly Arg Pro Ala Ala Ala Pro Thr Phe Glu Val Ala Arg Met Lys
                180                 185                 190
Leu Ile Arg Thr Lys Gly Ser Ser Gly Met Ser Leu Ala Glu Arg Phe
                195                 200                 205
Ser Leu Thr Leu Ser Arg Ser Ser Leu Val Val Gly Arg Ser Cys Val
                210                 215                 220
Glu Phe Glu Pro Glu Thr Val Pro Leu Leu Ser Thr Leu Arg Gly Lys
225                 230                 235                 240
Pro Ile Thr Phe Leu Gly Leu Leu Pro Pro Glu Ile Pro Gly Asp Glu
                245                 250                 255
Lys Asp Glu Thr Trp Val Ser Ile Lys Lys Trp Leu Asp Gly Lys Gln
                260                 265                 270
Lys Gly Ser Val Val Tyr Val Ala Leu Gly Ser Glu Ala Leu Val Ser
                275                 280                 285
Gln Thr Glu Val Val Glu Leu Ala Leu Gly Leu Glu Leu Ser Gly Leu
                290                 295                 300
Pro Phe Val Trp Ala Tyr Arg Lys Pro Lys Gly Pro Ala Lys Ser Asp
305                 310                 315                 320
Ser Val Glu Leu Pro Asp Gly Phe Val Glu Arg Thr Arg Asp Arg Gly
                325                 330                 335
Leu Val Trp Thr Ser Trp Ala Pro Gln Leu Arg Ile Leu Ser His Glu
                340                 345                 350
Ser Val Cys Gly Phe Leu Thr His Cys Gly Ser Gly Ser Ile Val Glu
                355                 360                 365
Gly Leu Met Phe Gly His Pro Leu Ile Met Leu Pro Ile Phe Gly Asp
370                 375                 380
Gln Pro Leu Asn Ala Arg Leu Leu Glu Asp Lys Gln Val Gly Ile Glu
                385                 390                 395                 400
Ile Ala Arg Asn Asp Gly Asp Gly Ser Phe Asp Arg Glu Gly Val Ala
                405                 410                 415
Ala Ala Ile Arg Ala Val Ala Val Glu Glu Ser Ser Lys Val Phe
                420                 425                 430
```

```
Gln Ala Lys Ala Lys Lys Leu Gln Glu Ile Val Ala Asp Met Ala Cys
        435                 440                 445

His Glu Arg Tyr Ile Asp Gly Phe Ile Gln Gln Leu Arg Ser Tyr Lys
    450                 455                 460

Asp
465

<210> SEQ ID NO 18
<211> LENGTH: 470
<212> TYPE: PRT
<213> ORGANISM: Artificial Sequence
<220> FEATURE:
<223> OTHER INFORMATION: UGT91D2e-b-EUGT11 chimera 7

<400> SEQUENCE: 18

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Met Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Met Pro Pro Leu His Glu Gly Arg
                245                 250                 255

Arg Glu Asp Gly Glu Asp Ala Thr Val Arg Trp Leu Asp Ala Gln Pro
            260                 265                 270

Ala Lys Ser Val Val Tyr Val Ala Leu Gly Ser Glu Val Pro Leu Gly
        275                 280                 285

Val Glu Lys Val His Glu Leu Ala Leu Gly Leu Glu Leu Ala Gly Thr
    290                 295                 300

Arg Phe Leu Trp Ala Leu Arg Lys Pro Thr Gly Val Ser Asp Ala Asp
305                 310                 315                 320
```

```
Leu Leu Pro Ala Gly Phe Glu Glu Arg Thr Arg Gly Arg Gly Val Val
            325                 330                 335

Ala Thr Arg Trp Val Pro Gln Met Ser Ile Leu Ala His Ala Ala Val
            340                 345                 350

Gly Ala Phe Leu Thr His Cys Gly Trp Asn Ser Thr Ile Glu Gly Leu
            355                 360                 365

Met Phe Gly His Pro Leu Ile Met Leu Pro Ile Phe Gly Asp Gln Gly
            370                 375                 380

Pro Asn Ala Arg Leu Ile Glu Ala Lys Asn Ala Gly Leu Gln Val Pro
385                 390                 395                 400

Arg Asn Glu Glu Asp Gly Cys Leu Thr Lys Glu Ser Val Ala Arg Ser
                405                 410                 415

Leu Arg Ser Val Val Val Glu Lys Glu Gly Glu Ile Tyr Lys Ala Asn
            420                 425                 430

Ala Arg Glu Leu Ser Lys Ile Tyr Asn Asp Thr Lys Val Glu Lys Glu
            435                 440                 445

Tyr Val Ser Gln Phe Val Asp Tyr Leu Glu Lys Asn Ala Arg Ala Val
            450                 455                 460

Ala Ile Asp His Glu Ser
465                 470

<210> SEQ ID NO 19
<211> LENGTH: 1086
<212> TYPE: DNA
<213> ORGANISM: Artificial Sequence
<220> FEATURE:
<223> OTHER INFORMATION: Codon-optimized GGPPS

<400> SEQUENCE: 19
atggctttgg taaacccaac cgctctttc tatggtacct ctatcagaac aagacctaca      60
aacttactaa atccaactca aaagctaaga ccagtttcat catcttcctt accttctttc    120
tcatcagtta gtgcgattct tactgaaaaa catcaatcta atccttctga gaacaacaat    180
ttgcaaactc atctagaaac tcctttcaac tttgatagtt atatgttgga aaaagtcaac    240
atggttaacg aggcgcttga tgcatctgtc ccactaaaag acccaatcaa atccatgaa    300 tccatgagat actctttatt ggcaggcggt aagagaatca gaccaatgat gtgtattgca    360
gcctgcgaaa tagtcggagg taatatcctt aacgccatgc cagccgcatg tgccgtggaa    420
atgattcata ctatgtcttt ggtgcatgac gatcttccat gtatggataa tgatgacttc    480
agaagaggta aacctatttc acacaaggtc tacgggagg aaatggcagt attgaccggc    540
gatgctttac taagtttatc tttcgaacat atagctactg ctacaaaggg tgtatcaaag    600
gatagaatcg tcagagctat aggggagttg gcccgttcag ttggctccga aggtttagtg    660
gctggacaag ttgtagatat cttgtcagag ggtgctgatg ttggattaga tcacctagaa    720
tacattcaca tccacaaaac agcaatgttg cttgagtcct cagtagttat ggcgctatc    780 atgggaggag gatctgatca gcagatcgaa aagttgagaa aattcgctag atctattggt    840
ctactattcc aagttgtgga tgacattttg gatgttacaa atctaccga gagttgggg    900 aaaacagctg gtaaggattt gttgacagat aagacaactt acccaaagtt gttaggtata    960
gaaaagtcca gagaatttgc cgaaaaactt aacaaggaag cacagagca attaagtggc   1020 tttgatagac gtaaggcagc tcctttgatc gcgttagcca actacaatgc gtaccgtcaa   1080
aattga                                                              1086
```

```
<210> SEQ ID NO 20
<211> LENGTH: 361
<212> TYPE: PRT
<213> ORGANISM: Stevia rebaudiana

<400> SEQUENCE: 20

Met Ala Leu Val Asn Pro Thr Ala Leu Phe Tyr Gly Thr Ser Ile Arg
1               5                   10                  15

Thr Arg Pro Thr Asn Leu Leu Asn Pro Thr Gln Lys Leu Arg Pro Val
            20                  25                  30

Ser Ser Ser Ser Leu Pro Ser Phe Ser Val Ser Ala Ile Leu Thr
        35                  40                  45

Glu Lys His Gln Ser Asn Pro Ser Glu Asn Asn Leu Gln Thr His
    50                  55                  60

Leu Glu Thr Pro Phe Asn Phe Asp Ser Tyr Met Leu Glu Lys Val Asn
65                  70                  75                  80

Met Val Asn Glu Ala Leu Asp Ala Ser Val Pro Leu Lys Asp Pro Ile
                85                  90                  95

Lys Ile His Glu Ser Met Arg Tyr Ser Leu Leu Ala Gly Gly Lys Arg
                100                 105                 110

Ile Arg Pro Met Met Cys Ile Ala Ala Cys Glu Ile Val Gly Gly Asn
            115                 120                 125

Ile Leu Asn Ala Met Pro Ala Ala Cys Ala Val Glu Met Ile His Thr
        130                 135                 140

Met Ser Leu Val His Asp Asp Leu Pro Cys Met Asp Asn Asp Asp Phe
145                 150                 155                 160

Arg Arg Gly Lys Pro Ile Ser His Lys Val Tyr Gly Glu Glu Met Ala
                165                 170                 175

Val Leu Thr Gly Asp Ala Leu Leu Ser Leu Ser Phe Glu His Ile Ala
            180                 185                 190

Thr Ala Thr Lys Gly Val Ser Lys Asp Arg Ile Val Arg Ala Ile Gly
        195                 200                 205

Glu Leu Ala Arg Ser Val Gly Ser Glu Gly Leu Val Ala Gly Gln Val
    210                 215                 220

Val Asp Ile Leu Ser Glu Gly Ala Asp Val Gly Leu Asp His Leu Glu
225                 230                 235                 240

Tyr Ile His Ile His Lys Thr Ala Met Leu Leu Glu Ser Ser Val Val
                245                 250                 255

Ile Gly Ala Ile Met Gly Gly Gly Ser Asp Gln Gln Ile Glu Lys Leu
            260                 265                 270

Arg Lys Phe Ala Arg Ser Ile Gly Leu Leu Phe Gln Val Val Asp Asp
        275                 280                 285

Ile Leu Asp Val Thr Lys Ser Thr Glu Glu Leu Gly Lys Thr Ala Gly
    290                 295                 300

Lys Asp Leu Leu Thr Asp Lys Thr Thr Tyr Pro Lys Leu Leu Gly Ile
305                 310                 315                 320

Glu Lys Ser Arg Glu Phe Ala Glu Lys Leu Asn Lys Glu Ala Gln Glu
                325                 330                 335

Gln Leu Ser Gly Phe Asp Arg Arg Lys Ala Ala Pro Leu Ile Ala Leu
            340                 345                 350

Ala Asn Tyr Asn Ala Tyr Arg Gln Asn
        355                 360

<210> SEQ ID NO 21
```

<211> LENGTH: 1029
<212> TYPE: DNA
<213> ORGANISM: Artificial Sequence
<220> FEATURE:
<223> OTHER INFORMATION: Codon-optimized GGPPS

<400> SEQUENCE: 21

| | | |
|---|---|---|
| atggctgagc aacaaatatc taacttgctg tctatgtttg atgcttcaca tgctagtcag | 60 |
| aaattagaaa ttactgtcca aatgatggac ataccatt acagagaaac gcctccagat | 120 |
| tcctcatctt ctgaaggcgg ttcattgtct agatacgacg agagaagagt ctctttgcct | 180 |
| ctcagtcata tgctgcctc tccagatatt gtatcacaac tatgttttc cactgcaatg | 240 |
| tcttcagagt tgaatcacag atggaaatct caaagattaa aggtggccga ttctccttac | 300 |
| aactatatcc taacattacc atcaaaagga attagaggtg cctttatcga ttccctgaac | 360 |
| gtatggttgg aggttccaga ggatgaaaca tcagtcatca aggaagttat tggtatgctc | 420 |
| cacaactctt cattaatcat tgatgacttc aagataatt ctccacttag aagaggaaag | 480 |
| ccatctaccc atacagtctt cggccctgcc caggctatca atactgctac ttacgttata | 540 |
| gttaaagcaa tcgaaaagat acaagacata gtgggacacg atgcattggc agatgttacg | 600 |
| ggtactatta caactatttt ccaaggtcag gccatggact tgtggtggac agcaaatgca | 660 |
| atcgttccat caatacagga atacttactt atggtaaacg ataaaaccgg tgctctcttt | 720 |
| agactgagtt tggagttgtt agctctgaat tccgaagcca gtatttctga ctctgcttta | 780 |
| gaaagtttat ctagtgctgt tccttgcta ggtcaatact ccaaatcag agacgactat | 840 |
| atgaacttga tcgataacaa gtatacagat cagaaaggct tctgcgaaga tcttgatgaa | 900 |
| ggcaagtact cactaacact tattcatgcc ctccaaactg attcatccga tctactgacc | 960 |
| aacatccttt caatgagaag agtgcaagga aagttaacgg cacaaaagag atgttggttc | 1020 |
| tggaaatga | 1029 |

<210> SEQ ID NO 22
<211> LENGTH: 342
<212> TYPE: PRT
<213> ORGANISM: Gibberella fujikuroi

<400> SEQUENCE: 22

```
Met Ala Glu Gln Gln Ile Ser Asn Leu Leu Ser Met Phe Asp Ala Ser
1               5                   10                  15

His Ala Ser Gln Lys Leu Glu Ile Thr Val Gln Met Met Asp Thr Tyr
            20                  25                  30

His Tyr Arg Glu Thr Pro Pro Asp Ser Ser Ser Ser Glu Gly Gly Ser
        35                  40                  45

Leu Ser Arg Tyr Asp Glu Arg Arg Val Ser Leu Pro Leu Ser His Asn
    50                  55                  60

Ala Ala Ser Pro Asp Ile Val Ser Gln Leu Cys Phe Ser Thr Ala Met
65                  70                  75                  80

Ser Ser Glu Leu Asn His Arg Trp Lys Ser Gln Arg Leu Lys Val Ala
                85                  90                  95

Asp Ser Pro Tyr Asn Tyr Ile Leu Thr Leu Pro Ser Lys Gly Ile Arg
            100                 105                 110

Gly Ala Phe Ile Asp Ser Leu Asn Val Trp Leu Glu Val Pro Glu Asp
        115                 120                 125

Glu Thr Ser Val Ile Lys Glu Val Ile Gly Met Leu His Asn Ser Ser
    130                 135                 140
```

Leu Ile Ile Asp Asp Phe Gln Asp Asn Ser Pro Leu Arg Arg Gly Lys
145                 150                 155                 160

Pro Ser Thr His Thr Val Phe Gly Pro Ala Gln Ala Ile Asn Thr Ala
                165                 170                 175

Thr Tyr Val Ile Val Lys Ala Ile Glu Lys Ile Gln Asp Ile Val Gly
            180                 185                 190

His Asp Ala Leu Ala Asp Val Thr Gly Thr Ile Thr Thr Ile Phe Gln
        195                 200                 205

Gly Gln Ala Met Asp Leu Trp Trp Thr Ala Asn Ala Ile Val Pro Ser
    210                 215                 220

Ile Gln Glu Tyr Leu Leu Met Val Asn Asp Lys Thr Gly Ala Leu Phe
225                 230                 235                 240

Arg Leu Ser Leu Glu Leu Leu Ala Leu Asn Ser Glu Ala Ser Ile Ser
                245                 250                 255

Asp Ser Ala Leu Glu Ser Leu Ser Ser Ala Val Ser Leu Leu Gly Gln
            260                 265                 270

Tyr Phe Gln Ile Arg Asp Asp Tyr Met Asn Leu Ile Asp Asn Lys Tyr
        275                 280                 285

Thr Asp Gln Lys Gly Phe Cys Glu Asp Leu Asp Glu Gly Lys Tyr Ser
    290                 295                 300

Leu Thr Leu Ile His Ala Leu Gln Thr Asp Ser Ser Asp Leu Leu Thr
305                 310                 315                 320

Asn Ile Leu Ser Met Arg Arg Val Gln Gly Lys Leu Thr Ala Gln Lys
                325                 330                 335

Arg Cys Trp Phe Trp Lys
            340

<210> SEQ ID NO 23
<211> LENGTH: 903
<212> TYPE: DNA
<213> ORGANISM: Artificial Sequence
<220> FEATURE:
<223> OTHER INFORMATION: Codon-optimized GGPPS

<400> SEQUENCE: 23
atggaaaaga ctaaggagaa agcagaacgt atcttgctgg agccatacag atacttatta      60
caactaccag gaaagcaagt ccgttctaaa ctatcacaag cgttcaatca ctggttaaaa     120
gttcctgaag ataagttaca aatcattatt gaagtcacag aaatgctaca caatgcttct     180
ttactgatcg atgatataga ggattcttcc aaactgagaa gaggttttcc tgtcgctcat     240
tccatatacg gggtaccaag tgtaatcaac tcagctaatt acgtctactt cttgggattg     300
gaaaaagtat tgacattaga tcatccagac gctgtaaagc tattcaccag acaacttctt     360
gaattgcatc aaggtcaagg tttggatatc tattggagag acacttatac ttgcccaaca     420
gaagaggagt acaaagcaat ggttctacaa aagactggcg gtttgttcgg acttgccgtt     480
ggtctgatgc aacttttctc tgattacaag gaggacttaa agcctctgtt ggataccttg     540
ggcttgtttt tccagattag agatgactac gctaacttac attcaaagga atattcagaa     600
aacaaatcat tctgtgaaga tttgactgaa gggaagttta gttttccaac aatccacgcc     660
atttggtcaa gaccagaatc tactcaagtg caaaacattc tgcgtcagag aacagagaat     720
attgacatca aaagtattgt gttcagtac ttggaagatg ttggttcttt tgcttacaca     780
agacatacac ttagagaatt agaggcaaaa gcatacaagc aaatagaagc ctgtggaggc     840
aatccttctc tagtggcatt ggttaaacat ttgtccaaaa tgttcaccga ggaaaacaag     900
taa                                                              903

<210> SEQ ID NO 24
<211> LENGTH: 300
<212> TYPE: PRT
<213> ORGANISM: Mus musculus

<400> SEQUENCE: 24

Met Glu Lys Thr Lys Glu Lys Ala Glu Arg Ile Leu Leu Glu Pro Tyr
1               5                   10                  15

Arg Tyr Leu Leu Gln Leu Pro Gly Lys Gln Val Arg Ser Lys Leu Ser
            20                  25                  30

Gln Ala Phe Asn His Trp Leu Lys Val Pro Glu Asp Lys Leu Gln Ile
        35                  40                  45

Ile Ile Glu Val Thr Glu Met Leu His Asn Ala Ser Leu Leu Ile Asp
    50                  55                  60

Asp Ile Glu Asp Ser Ser Lys Leu Arg Arg Gly Phe Pro Val Ala His
65                  70                  75                  80

Ser Ile Tyr Gly Val Pro Ser Val Ile Asn Ser Ala Asn Tyr Val Tyr
                85                  90                  95

Phe Leu Gly Leu Glu Lys Val Leu Thr Leu Asp His Pro Asp Ala Val
            100                 105                 110

Lys Leu Phe Thr Arg Gln Leu Leu Glu Leu His Gln Gly Gln Gly Leu
        115                 120                 125

Asp Ile Tyr Trp Arg Asp Thr Tyr Thr Cys Pro Thr Glu Glu Glu Tyr
    130                 135                 140

Lys Ala Met Val Leu Gln Lys Thr Gly Gly Leu Phe Gly Leu Ala Val
145                 150                 155                 160

Gly Leu Met Gln Leu Phe Ser Asp Tyr Lys Glu Asp Leu Lys Pro Leu
                165                 170                 175

Leu Asp Thr Leu Gly Leu Phe Phe Gln Ile Arg Asp Asp Tyr Ala Asn
            180                 185                 190

Leu His Ser Lys Glu Tyr Ser Glu Asn Lys Ser Phe Cys Glu Asp Leu
        195                 200                 205

Thr Glu Gly Lys Phe Ser Phe Pro Thr Ile His Ala Ile Trp Ser Arg
    210                 215                 220

Pro Glu Ser Thr Gln Val Gln Asn Ile Leu Arg Gln Arg Thr Glu Asn
225                 230                 235                 240

Ile Asp Ile Lys Lys Tyr Cys Val Gln Tyr Leu Glu Asp Val Gly Ser
                245                 250                 255

Phe Ala Tyr Thr Arg His Thr Leu Arg Glu Leu Glu Ala Lys Ala Tyr
            260                 265                 270

Lys Gln Ile Glu Ala Cys Gly Gly Asn Pro Ser Leu Val Ala Leu Val
        275                 280                 285

Lys His Leu Ser Lys Met Phe Thr Glu Glu Asn Lys
    290                 295                 300

<210> SEQ ID NO 25
<211> LENGTH: 1020
<212> TYPE: DNA
<213> ORGANISM: Artificial Sequence
<220> FEATURE:
<223> OTHER INFORMATION: Codon-optimized GGPPS

<400> SEQUENCE: 25
atggcaagat ctcattttct taacgcacta ttgatggtta tctcattaca atcaactaca      60

-continued

```
gccttcactc cagctaaact tgcttatcca acaacaacaa cagctctaaa tgtcgcctcc      120
gccgaaactt ctttcagtct agatgaatac ttggcctcta agataggacc tatagagtct      180
gccttggaag catcagtcaa atccagaatt ccacagaccg ataagatctg cgaatctatg      240
gcctactctt tgatggcagg aggcaagaga attagaccag tgttgtgtat cgctgcatgt      300
gagatgttcg gtggatccca agatgtcgct atgcctactg ctgtggcatt agaaatgata      360
cacacaatgt ctttgattca tgatgatttg ccatccatgg ataacgatga cttgagaaga      420
ggtaaaccaa caaaccatgt cgttttcggc gaagatgtag ctattcttgc aggtgactct      480
ttattgtcaa cttccttcga gcacgtcgct agagaaacaa aaggagtgtc agcagaaaag      540
atcgtggatg ttatcgctag attaggcaaa tctgttggtg ccgagggcct tgctggcggt      600
caagttatgg acttagaatg tgaagctaaa ccaggtacca cattagacga cttgaaatgg      660
attcatatcc ataaaaccgc tacattgtta caagttgctg tagcttctgg tgcagttcta      720
ggtggtgcaa ctcctgaaga ggttgctgca tgcgagttgt ttgctatgaa ataggtctt      780 gcctttcaag ttgccgacga tatccttgat gtaaccgctt catcagaaga tttgggtaaa      840
actgcaggca agatgaagc tactgataag acaacttacc caaagttatt aggattagaa      900
gagagtaagg catacgcaag acaactaatc gatgaagcca aggaaagttt ggctcctttt      960
ggagatagag ctgccccttt attggccatt gcagatttca ttattgatag aaagaattga     1020
```

<210> SEQ ID NO 26
<211> LENGTH: 339
<212> TYPE: PRT
<213> ORGANISM: Thalassiosira pseudonana

<400> SEQUENCE: 26

```
Met Ala Arg Phe Tyr Phe Leu Asn Ala Leu Leu Met Val Ile Ser Leu
1               5                   10                  15

Gln Ser Thr Thr Ala Phe Thr Pro Ala Lys Leu Ala Tyr Pro Thr Thr
            20                  25                  30

Thr Thr Ala Leu Asn Val Ala Ser Ala Glu Thr Ser Phe Ser Leu Asp
        35                  40                  45

Glu Tyr Leu Ala Ser Lys Ile Gly Pro Ile Glu Ser Ala Leu Glu Ala
    50                  55                  60

Ser Val Lys Ser Arg Ile Pro Gln Thr Asp Lys Ile Cys Glu Ser Met
65                  70                  75                  80

Ala Tyr Ser Leu Met Ala Gly Gly Lys Arg Ile Arg Pro Val Leu Cys
                85                  90                  95

Ile Ala Ala Cys Glu Met Phe Gly Gly Ser Gln Asp Val Ala Met Pro
            100                 105                 110

Thr Ala Val Ala Leu Glu Met Ile His Thr Met Ser Leu Ile His Asp
        115                 120                 125

Asp Leu Pro Ser Met Asp Asn Asp Asp Leu Arg Arg Gly Lys Pro Thr
    130                 135                 140

Asn His Val Val Phe Gly Glu Asp Val Ala Ile Leu Ala Gly Asp Ser
145                 150                 155                 160

Leu Leu Ser Thr Ser Phe Glu His Val Ala Arg Glu Thr Lys Gly Val
                165                 170                 175

Ser Ala Glu Lys Ile Val Asp Val Ile Ala Arg Leu Gly Lys Ser Val
            180                 185                 190

Gly Ala Glu Gly Leu Ala Gly Gly Gln Val Met Asp Leu Glu Cys Glu
        195                 200                 205
```

```
Ala Lys Pro Gly Thr Thr Leu Asp Asp Leu Lys Trp Ile His Ile His
    210                 215                 220
Lys Thr Ala Thr Leu Leu Gln Val Ala Val Ala Ser Gly Ala Val Leu
225                 230                 235                 240
Gly Gly Ala Thr Pro Glu Glu Val Ala Ala Cys Glu Leu Phe Ala Met
                245                 250                 255
Asn Ile Gly Leu Ala Phe Gln Val Ala Asp Asp Ile Leu Asp Val Thr
            260                 265                 270
Ala Ser Ser Glu Asp Leu Gly Lys Thr Ala Gly Lys Asp Glu Ala Thr
        275                 280                 285
Asp Lys Thr Thr Tyr Pro Lys Leu Leu Gly Leu Glu Glu Ser Lys Ala
    290                 295                 300
Tyr Ala Arg Gln Leu Ile Asp Glu Ala Lys Glu Ser Leu Ala Pro Phe
305                 310                 315                 320
Gly Asp Arg Ala Ala Pro Leu Leu Ala Ile Ala Asp Phe Ile Ile Asp
                325                 330                 335
Arg Lys Asn
```

<210> SEQ ID NO 27
<211> LENGTH: 1068
<212> TYPE: DNA
<213> ORGANISM: Artificial Sequence
<220> FEATURE:
<223> OTHER INFORMATION: Codon-optimized GGPPS

<400> SEQUENCE: 27

```
atgcacttag caccacgtag agtccctaga ggtagaagat caccacctga cagagttcct    60
gaaagacaag gtgccttggg tagaagacgt ggagctggct ctactggctg tgcccgtgct   120
gctgctggtg ttcaccgtag aagaggagga ggcgaggctg atccatcagc tgctgtgcat   180
agaggctggc aagccggtgg tggcaccggt ttgcctgatg aggtggtgtc taccgcagcc   240
gccttagaaa tgtttcatgc ttttgcttta atccatgatg atatcatgga tgatagtgca   300
actagaagag gctccccaac tgttcacaga gccctagctg atcgtttagg cgctgctctg   360
gacccagatc aggccggtca actaggagtt tctactgcta tcttggttgg agatctggct   420
ttgacatggt ccgatgaatt gttatacgct ccattgactc acatagact ggcagcagta    480
ctaccattgg taacagctat gagagctgaa accgttcatg ccaatatct tgatataact    540
agtgctagaa gacctgggac cgatacttct cttgcattga gaatagccag atataagaca   600
gcagcttaca caatggaacg tccactgcac attggtgcag ccctggctgg ggcaagacca   660
gaactattag cagggctttc agcatacgcc ttgccagctg agaagcctt ccaattggca    720
gatgacctgc taggcgtctt cggtgatcca agacgtacag ggaaacctga cctagatgat   780
cttagaggtg gaaagcatac tgtcttagtc gccttggcaa gagaacatgc cactccagaa   840
cagagacaca cattggatac attattgggt acaccaggtc ttgatagaca aggcgcttca   900
agactaagat gcgtattggt agcaactggt gcaagagccg aagccgaaag acttattaca   960
gagagaagag atcaagcatt aactgcattg aacgcattaa cactgccacc tccttagct   1020
gaggcattag caagattgac attagggtct acagctcatc ctgcctaa              1068
```

<210> SEQ ID NO 28
<211> LENGTH: 355
<212> TYPE: PRT
<213> ORGANISM: Streptomyces clavuligerus

<400> SEQUENCE: 28

Met His Leu Ala Pro Arg Arg Val Pro Arg Gly Arg Ser Pro Pro
1               5                   10                  15

Asp Arg Val Pro Glu Arg Gln Gly Ala Leu Gly Arg Arg Gly Ala
            20                  25                  30

Gly Ser Thr Gly Cys Ala Arg Ala Ala Gly Val His Arg Arg Arg
        35                  40                  45

Gly Gly Gly Glu Ala Asp Pro Ser Ala Ala Val His Arg Gly Trp Gln
50                  55                  60

Ala Gly Gly Gly Thr Gly Leu Pro Asp Glu Val Val Ser Thr Ala Ala
65                  70                  75                  80

Ala Leu Glu Met Phe His Ala Phe Ala Leu Ile His Asp Asp Ile Met
                85                  90                  95

Asp Asp Ser Ala Thr Arg Arg Gly Ser Pro Thr Val His Arg Ala Leu
            100                 105                 110

Ala Asp Arg Leu Gly Ala Ala Leu Asp Pro Asp Gln Ala Gly Gln Leu
        115                 120                 125

Gly Val Ser Thr Ala Ile Leu Val Gly Asp Leu Ala Leu Thr Trp Ser
    130                 135                 140

Asp Glu Leu Leu Tyr Ala Pro Leu Thr Pro His Arg Leu Ala Ala Val
145                 150                 155                 160

Leu Pro Leu Val Thr Ala Met Arg Ala Glu Thr Val His Gly Gln Tyr
                165                 170                 175

Leu Asp Ile Thr Ser Ala Arg Arg Pro Gly Thr Asp Thr Ser Leu Ala
            180                 185                 190

Leu Arg Ile Ala Arg Tyr Lys Thr Ala Ala Tyr Thr Met Glu Arg Pro
        195                 200                 205

Leu His Ile Gly Ala Ala Leu Ala Gly Ala Arg Pro Glu Leu Leu Ala
    210                 215                 220

Gly Leu Ser Ala Tyr Ala Leu Pro Ala Gly Glu Ala Phe Gln Leu Ala
225                 230                 235                 240

Asp Asp Leu Leu Gly Val Phe Gly Asp Pro Arg Arg Thr Gly Lys Pro
                245                 250                 255

Asp Leu Asp Asp Leu Arg Gly Gly Lys His Thr Val Leu Val Ala Leu
            260                 265                 270

Ala Arg Glu His Ala Thr Pro Glu Gln Arg His Thr Leu Asp Thr Leu
        275                 280                 285

Leu Gly Thr Pro Gly Leu Asp Arg Gln Gly Ala Ser Arg Leu Arg Cys
    290                 295                 300

Val Leu Val Ala Thr Gly Ala Arg Ala Glu Ala Glu Arg Leu Ile Thr
305                 310                 315                 320

Glu Arg Arg Asp Gln Ala Leu Thr Ala Leu Asn Ala Leu Thr Leu Pro
                325                 330                 335

Pro Pro Leu Ala Glu Ala Leu Ala Arg Leu Thr Leu Gly Ser Thr Ala
            340                 345                 350

His Pro Ala
        355

<210> SEQ ID NO 29
<211> LENGTH: 993
<212> TYPE: DNA
<213> ORGANISM: Artificial Sequence
<220> FEATURE:
<223> OTHER INFORMATION: Codon-optimized GGPPS

<400> SEQUENCE: 29

```
atgtcatatt tcgataacta cttcaatgag atagttaatt ccgtgaacga catcattaag      60
tcttacatct ctggcgacgt accaaaacta tacgaagcct cctaccattt gtttacatca     120
ggaggaaaga gactaagacc attgatcctt acaatttctt ctgatctttt cggtggacag     180
agagaaagag catactatgc tggcgcagca atcgaagttt tgcacacatt cactttggtt     240
cacgatgata tcatggatca agataacatt cgtagaggtc ttcctactgt acatgtcaag     300
tatggcctac ctttggccat tttagctggt gacttattgc atgcaaaagc ctttcaattg     360
ttgactcagg cattgagagg tctaccatct gaaactatca tcaaggcgtt tgatatcttt     420
acaagatcta tcattatcat atcagaaggt caagctgtcg atatggaatt cgaagataga     480
attgatatca aggaacaaga gtatttggat atgatatctc gtaaaaccgc tgccttattc     540
tcagcttctt cttccattgg ggcgttgata gctggagcta atgataacga tgtgagatta     600
atgtccgatt tcggtacaaa tcttgggatc gcatttcaaa ttgtagatga tatacttggt     660
ttaacagctg atgaaaaaga gctaggaaaa cctgttttca gtgatatcag agaaggtaaa     720
aagaccatat tagtcattaa gactttagaa ttgtgtaagg aagacgagaa aaagattgtg     780
ttaaaagcgc taggcaacaa gtcagcatca aaggaagagt tgatgagttc tgctgacata     840
atcaaaaagt actcattgga ttacgcctac aacttagctg agaaatacta caaaaacgcc     900
atcgattctc taaatcaagt ttcaagtaaa agtgatattc cagggaaggc attgaaatat     960
cttgctgaat tcaccatcag aagacgtaag taa                                  993

<210> SEQ ID NO 30
<211> LENGTH: 330
<212> TYPE: PRT
<213> ORGANISM: Sulfolobus acidocaldarius

<400> SEQUENCE: 30

Met Ser Tyr Phe Asp Asn Tyr Phe Asn Glu Ile Val Asn Ser Val Asn
1               5                   10                  15

Asp Ile Ile Lys Ser Tyr Ile Ser Gly Asp Val Pro Lys Leu Tyr Glu
            20                  25                  30

Ala Ser Tyr His Leu Phe Thr Ser Gly Gly Lys Arg Leu Arg Pro Leu
        35                  40                  45

Ile Leu Thr Ile Ser Ser Asp Leu Phe Gly Gly Gln Arg Glu Arg Ala
    50                  55                  60

Tyr Tyr Ala Gly Ala Ala Ile Glu Val Leu His Thr Phe Thr Leu Val
65                  70                  75                  80

His Asp Asp Ile Met Asp Gln Asp Asn Ile Arg Arg Gly Leu Pro Thr
                85                  90                  95

Val His Val Lys Tyr Gly Leu Pro Leu Ala Ile Leu Ala Gly Asp Leu
            100                 105                 110

Leu His Ala Lys Ala Phe Gln Leu Leu Thr Gln Ala Leu Arg Gly Leu
        115                 120                 125

Pro Ser Glu Thr Ile Ile Lys Ala Phe Asp Ile Phe Thr Arg Ser Ile
    130                 135                 140

Ile Ile Ile Ser Glu Gly Gln Ala Val Asp Met Glu Phe Glu Asp Arg
145                 150                 155                 160

Ile Asp Ile Lys Glu Gln Glu Tyr Leu Asp Met Ile Ser Arg Lys Thr
                165                 170                 175

Ala Ala Leu Phe Ser Ala Ser Ser Ile Gly Ala Leu Ile Ala Gly
            180                 185                 190
```

Ala Asn Asp Asn Asp Val Arg Leu Met Ser Asp Phe Gly Thr Asn Leu
         195                 200                 205

Gly Ile Ala Phe Gln Ile Val Asp Asp Ile Leu Gly Leu Thr Ala Asp
    210                 215                 220

Glu Lys Glu Leu Gly Lys Pro Val Phe Ser Asp Ile Arg Glu Gly Lys
225                 230                 235                 240

Lys Thr Ile Leu Val Ile Lys Thr Leu Glu Leu Cys Lys Glu Asp Glu
                245                 250                 255

Lys Lys Ile Val Leu Lys Ala Leu Gly Asn Lys Ser Ala Ser Lys Glu
            260                 265                 270

Glu Leu Met Ser Ser Ala Asp Ile Ile Lys Lys Tyr Ser Leu Asp Tyr
        275                 280                 285

Ala Tyr Asn Leu Ala Glu Lys Tyr Tyr Lys Asn Ala Ile Asp Ser Leu
    290                 295                 300

Asn Gln Val Ser Ser Lys Ser Asp Ile Pro Gly Lys Ala Leu Lys Tyr
305                 310                 315                 320

Leu Ala Glu Phe Thr Ile Arg Arg Lys
                325                 330

<210> SEQ ID NO 31
<211> LENGTH: 894
<212> TYPE: DNA
<213> ORGANISM: Artificial Sequence
<220> FEATURE:
<223> OTHER INFORMATION: Codon-optimized GGPPS

<400> SEQUENCE: 31

```
atggtcgcac aaactttcaa cctggatacc tacttatccc aaagacaaca acaagttgaa      60
gaggccctaa gtgctgctct tgtgccagct tatcctgaga gaatatacga agctatgaga     120
tactccctcc tggcaggtgg caaaagatta agacctatct tatgtttagc tgcttgcgaa     180
ttggcaggtg ttctgttgga acaagccatg ccaactgcgt gtgcacttga atgatccat      240 acaatgtcac taattcatga tgacctgcca gccatggata cgatgatttt cagaagagga     300
aagccaacta atcacaaggt gttcggggaa gatatagcca tcttagcggg tgatgcgctt     360
ttagcttacg cttttgaaca tattgcttct caaacaagag gagtaccacc tcaattggtg     420
ctacaagtta ttgctagaat cggacacgcc gttgctgcaa caggcctcgt tggaggccaa     480
gtcgtagacc ttgaatctga aggtaaagct atttccttag aaacattgga gtatattcac     540
tcacataaga ctggagcctt gctggaagca tcagttgtct caggcggtat tctcgcaggg     600
gcagatgaag agctttttggc cagattgtct cattacgcta gagatatagg cttggctttt     660
caaatcgtcg atgatatcct ggatgttact gctacatctg aacagttggg gaaaaccgct     720
ggtaaagacc aggcagccgc aaaggcaact tatccaagtc tattgggttt agaagcctct     780
agacagaaag cggaagagtt gattcaatct gctaaggaag ccttaagacc ttacggttca     840
caagcagagc cactcctagc gctggcagac ttcatcacac gtcgtcagca ttaa            894
```

<210> SEQ ID NO 32
<211> LENGTH: 297
<212> TYPE: PRT
<213> ORGANISM: Synechococcus sp.

<400> SEQUENCE: 32

Met Val Ala Gln Thr Phe Asn Leu Asp Thr Tyr Leu Ser Gln Arg Gln
1               5                   10                  15

Gln Gln Val Glu Glu Ala Leu Ser Ala Ala Leu Val Pro Ala Tyr Pro

```
            20                  25                  30
Glu Arg Ile Tyr Glu Ala Met Arg Tyr Ser Leu Leu Ala Gly Gly Lys
        35                  40                  45

Arg Leu Arg Pro Ile Leu Cys Leu Ala Ala Cys Glu Leu Ala Gly Gly
    50                  55                  60

Ser Val Glu Gln Ala Met Pro Thr Ala Cys Ala Leu Glu Met Ile His
65                  70                  75                  80

Thr Met Ser Leu Ile His Asp Asp Leu Pro Ala Met Asp Asn Asp Asp
                85                  90                  95

Phe Arg Arg Gly Lys Pro Thr Asn His Lys Val Phe Gly Glu Asp Ile
            100                 105                 110

Ala Ile Leu Ala Gly Asp Ala Leu Leu Ala Tyr Ala Phe Glu His Ile
        115                 120                 125

Ala Ser Gln Thr Arg Gly Val Pro Pro Gln Leu Val Leu Gln Val Ile
    130                 135                 140

Ala Arg Ile Gly His Ala Val Ala Ala Thr Gly Leu Val Gly Gly Gln
145                 150                 155                 160

Val Val Asp Leu Glu Ser Glu Gly Lys Ala Ile Ser Leu Glu Thr Leu
                165                 170                 175

Glu Tyr Ile His Ser His Lys Thr Gly Ala Leu Leu Glu Ala Ser Val
            180                 185                 190

Val Ser Gly Gly Ile Leu Ala Gly Ala Asp Glu Glu Leu Leu Ala Arg
        195                 200                 205

Leu Ser His Tyr Ala Arg Asp Ile Gly Leu Ala Phe Gln Ile Val Asp
    210                 215                 220

Asp Ile Leu Asp Val Thr Ala Thr Ser Glu Gln Leu Gly Lys Thr Ala
225                 230                 235                 240

Gly Lys Asp Gln Ala Ala Ala Lys Ala Thr Tyr Pro Ser Leu Leu Gly
                245                 250                 255

Leu Glu Ala Ser Arg Gln Lys Ala Glu Glu Leu Ile Gln Ser Ala Lys
            260                 265                 270

Glu Ala Leu Arg Pro Tyr Gly Ser Gln Ala Glu Pro Leu Leu Ala Leu
        275                 280                 285

Ala Asp Phe Ile Thr Arg Arg Gln His
    290                 295
```

<210> SEQ ID NO 33
<211> LENGTH: 1680
<212> TYPE: DNA
<213> ORGANISM: Artificial Sequence
<220> FEATURE:
<223> OTHER INFORMATION: Codon-optimized CDPS

<400> SEQUENCE: 33
atgaaaaccg ggtttatctc accagcaaca gtatttcatc acagaatctc accagcgacc       60
actttcagac atcacttatc acctgctact acaaactcta caggcattgt cgccttaaga     120
gacatcaact tcagatgtaa agcagtttct aaagagtact ctgatctgtt cagaaagat      180 gaggcttctt tcacaaaatg gacgatgac aaggtgaaag atcatcttga taccaacaaa      240
aacttatacc caaatgatga gattaaggaa tttgttgaat cagtaaaggc tatgttcggt    300
agtatgaatg acggggagat aaacgtctct gcatacgata ctgcatgggt tgctttggtt    360
caagatgtcg atggatcagg tagtcctcag ttcccttctt ctttagaatg gattgccaac    420
aatcaattgt cagatggatc atggggagat catttgctgt tctcagctca cgatagaatc    480

-continued

```
atcaacacat tagcatgcgt tattgcactt acaagttgga atgttcatcc ttctaagtgt      540
gaaaaaggtt tgaattttct gagagaaaac atttgcaaat tagaagatga aaacgcagaa      600
catatgccaa ttggttttga agtaacattc ccatcactaa ttgatatcgc gaaaaagttg      660
aacattgaag tacctgagga tactccagca cttaaagaga tctacgcacg tagagatatc      720
aagttaacta agatcccaat ggaagttctt cacaaggtac ctactacttt gttacattct      780
ttggaaggaa tgcctgattt ggagtgggaa aaactgttaa agctacaatg taaagatggt      840
agtttcttgt tttccccatc tagtaccgca ttcgccctaa tgcaaacaaa agatgagaaa      900
tgcttacagt atctaacaaa tatcgtcact aagttcaacg gtggcgtgcc taatgtgtac      960
ccagtcgatt tgtttgaaca tatttgggtt gttgatagac tgcagagatt ggggattgcc     1020
agatacttca atcagagat aaagattgt gtagagtata tcaataagta ctggaccaaa      1080
aatggaattt gttgggctag aaatactcac gttcaagata tcgatgatac agccatggga     1140
ttcagagtgt tgagagcgca cggttatgac gtcactccag atgttttag acaatttgaa      1200 aaagatggta aattcgtttg ctttgcaggg caatcaacac aagccgtgac aggaatgttt     1260
aacgtttaca gagcctctca atgttgttc ccaggggaga gaattttgga agatgccaaa      1320
aagttctctt acaattactt aaaggaaaag caaagtacca acgaattgct ggataaatgg     1380
ataatcgcta aagatctacc tggtgaagtt ggttatgctc tggatatccc atggtatgct     1440
tccttaccaa gattggaaac tcgttattac cttgaacaat acggcggtga agatgatgtc     1500
tggataggca agacattata cagaatgggt tacgtgtcca ataacacata tctagaaatg     1560
gcaaagctgg attacaataa ctatgttgca gtccttcaat tagaatggta cacaatacaa     1620
caatggtacg tcgatattgg tatagagaag ttcgaatctg acaacatcaa gtcagtcctg     1680
```

<210> SEQ ID NO 34
<211> LENGTH: 787
<212> TYPE: PRT
<213> ORGANISM: Stevia rebaudiana

<400> SEQUENCE: 34

```
Met Lys Thr Gly Phe Ile Ser Pro Ala Thr Val Phe His His Arg Ile
1               5                   10                  15

Ser Pro Ala Thr Thr Phe Arg His His Leu Ser Pro Ala Thr Thr Asn
            20                  25                  30

Ser Thr Gly Ile Val Ala Leu Arg Asp Ile Asn Phe Arg Cys Lys Ala
        35                  40                  45

Val Ser Lys Glu Tyr Ser Asp Leu Leu Gln Lys Asp Glu Ala Ser Phe
    50                  55                  60

Thr Lys Trp Asp Asp Lys Val Lys Asp His Leu Asp Thr Asn Lys
65                  70                  75                  80

Asn Leu Tyr Pro Asn Asp Glu Ile Lys Glu Phe Val Glu Ser Val Lys
                85                  90                  95

Ala Met Phe Gly Ser Met Asn Asp Gly Glu Ile Asn Val Ser Ala Tyr
            100                 105                 110

Asp Thr Ala Trp Val Ala Leu Val Gln Asp Val Asp Gly Ser Gly Ser
        115                 120                 125

Pro Gln Phe Pro Ser Ser Leu Glu Trp Ile Ala Asn Gln Leu Ser
    130                 135                 140

Asp Gly Ser Trp Gly Asp His Leu Leu Phe Ser Ala His Asp Arg Ile
145                 150                 155                 160

Ile Asn Thr Leu Ala Cys Val Ile Ala Leu Thr Ser Trp Asn Val His
```

```
                    165                 170                 175
Pro Ser Lys Cys Glu Lys Gly Leu Asn Phe Leu Arg Glu Asn Ile Cys
                180                 185                 190

Lys Leu Glu Asp Glu Asn Ala Glu His Met Pro Ile Gly Phe Glu Val
            195                 200                 205

Thr Phe Pro Ser Leu Ile Asp Ile Ala Lys Lys Leu Asn Ile Glu Val
        210                 215                 220

Pro Glu Asp Thr Pro Ala Leu Lys Glu Ile Tyr Ala Arg Arg Asp Ile
225                 230                 235                 240

Lys Leu Thr Lys Ile Pro Met Glu Val Leu His Lys Val Pro Thr Thr
                245                 250                 255

Leu Leu His Ser Leu Glu Gly Met Pro Asp Leu Glu Trp Glu Lys Leu
            260                 265                 270

Leu Lys Leu Gln Cys Lys Asp Gly Ser Phe Leu Phe Ser Pro Ser Ser
        275                 280                 285

Thr Ala Phe Ala Leu Met Gln Thr Lys Asp Glu Lys Cys Leu Gln Tyr
        290                 295                 300

Leu Thr Asn Ile Val Thr Lys Phe Asn Gly Gly Val Pro Asn Val Tyr
305                 310                 315                 320

Pro Val Asp Leu Phe Glu His Ile Trp Val Asp Arg Leu Gln Arg
                325                 330                 335

Leu Gly Ile Ala Arg Tyr Phe Lys Ser Glu Ile Lys Asp Cys Val Glu
            340                 345                 350

Tyr Ile Asn Lys Tyr Trp Thr Lys Asn Gly Ile Cys Trp Ala Arg Asn
        355                 360                 365

Thr His Val Gln Asp Ile Asp Asp Thr Ala Met Gly Phe Arg Val Leu
        370                 375                 380

Arg Ala His Gly Tyr Asp Val Thr Pro Asp Val Phe Arg Gln Phe Glu
385                 390                 395                 400

Lys Asp Gly Lys Phe Val Cys Phe Ala Gly Gln Ser Thr Gln Ala Val
                405                 410                 415

Thr Gly Met Phe Asn Val Tyr Arg Ala Ser Gln Met Leu Phe Pro Gly
            420                 425                 430

Glu Arg Ile Leu Glu Asp Ala Lys Lys Phe Ser Tyr Asn Tyr Leu Lys
        435                 440                 445

Glu Lys Gln Ser Thr Asn Glu Leu Leu Asp Lys Trp Ile Ile Ala Lys
        450                 455                 460

Asp Leu Pro Gly Glu Val Gly Tyr Ala Leu Asp Ile Pro Trp Tyr Ala
465                 470                 475                 480

Ser Leu Pro Arg Leu Glu Thr Arg Tyr Tyr Leu Glu Gln Tyr Gly Gly
                485                 490                 495

Glu Asp Asp Val Trp Ile Gly Lys Thr Leu Tyr Arg Met Gly Tyr Val
            500                 505                 510

Ser Asn Asn Thr Tyr Leu Glu Met Ala Lys Leu Asp Tyr Asn Asn Tyr
        515                 520                 525

Val Ala Val Leu Gln Leu Glu Trp Tyr Thr Ile Gln Gln Trp Tyr Val
        530                 535                 540

Asp Ile Gly Ile Glu Lys Phe Glu Ser Asp Asn Ile Lys Ser Val Leu
545                 550                 555                 560

Val Ser Tyr Tyr Leu Ala Ala Ala Ser Ile Phe Glu Pro Glu Arg Ser
                565                 570                 575

Lys Glu Arg Ile Ala Trp Ala Lys Thr Thr Ile Leu Val Asp Lys Ile
            580                 585                 590
```

```
Thr Ser Ile Phe Asp Ser Ser Gln Ser Ser Lys Glu Asp Ile Thr Ala
        595                 600                 605
Phe Ile Asp Lys Phe Arg Asn Lys Ser Ser Lys Lys His Ser Ile
610                 615                 620
Asn Gly Glu Pro Trp His Glu Val Met Val Ala Leu Lys Lys Thr Leu
625                 630                 635                 640
His Gly Phe Ala Leu Asp Ala Leu Met Thr His Ser Gln Asp Ile His
                645                 650                 655
Pro Gln Leu His Gln Ala Trp Glu Met Trp Leu Thr Lys Leu Gln Asp
                660                 665                 670
Gly Val Asp Val Thr Ala Glu Leu Met Val Gln Met Ile Asn Met Thr
                675                 680                 685
Ala Gly Arg Trp Val Ser Lys Glu Leu Leu Thr His Pro Gln Tyr Gln
                690                 695                 700
Arg Leu Ser Thr Val Thr Asn Ser Val Cys His Asp Ile Thr Lys Leu
705                 710                 715                 720
His Asn Phe Lys Glu Asn Ser Thr Thr Val Asp Ser Lys Val Gln Glu
                725                 730                 735
Leu Val Gln Leu Val Phe Ser Asp Thr Pro Asp Leu Asp Gln Asp
                740                 745                 750
Met Lys Gln Thr Phe Leu Thr Val Met Lys Thr Phe Tyr Tyr Lys Ala
                755                 760                 765
Trp Cys Asp Pro Asn Thr Ile Asn Asp His Ile Ser Lys Val Phe Glu
        770                 775                 780
Ile Val Ile
785

<210> SEQ ID NO 35
<211> LENGTH: 1584
<212> TYPE: DNA
<213> ORGANISM: Artificial Sequence
<220> FEATURE:
<223> OTHER INFORMATION: Codon-optimized CDPS

<400> SEQUENCE: 35
atgcctgatg cacacgatgc tccacctcca caaataagac agagaacact agtagatgag     60
gctacccaac tgctaactga gtccgcagaa gatgcatggg gtgaagtcag tgtgtcagaa    120
tacgaaacag caaggctagt tgcccatgct acatggttag gtggacacgc cacaagagtg    180
gccttccttc tggagagaca acacgaagac gggtcatggg gtccaccagg tggatatagg    240
ttagtcccta cattatctgc tgttcacgca ttattgacat gtcttgcctc tcctgctcag    300
gatcatggcg ttccacatga tagacttttta agagctgttg acgcaggctt gactgccttg    360
agaagattgg ggacatctga ctcccccacct gatactatag cagttgagct ggttatccca    420
tctttgctag agggcattca acacttactg gaccctgctc atcctcatag tagaccagcc    480
ttctctcaac atagaggctc tcttgtttgt cctggtggac tagatgggag aactctagga    540
gctttgagat cacacgccgc agcaggtaca ccagtaccag aaaagtctg gcacgcttcc    600 gagactttgg gcttgagtac cgaagctgct tctcacttgc aaccagccca aggtataatc    660
ggtggctctg ctgctgccac agcaacatgg ctaaccaggg ttgcaccatc tcaacagtca    720
gattctgcca aagatacct tgaggaatta caacacagat actctggccc agttccttcc    780
attaccccta tcacatactt cgaaagagca tggttattga caattttgc agcagccggt    840 gttccttgtg aggctccagc tgctttgttg gattccttag aagcagcact tacaccacaa    900
```

```
ggtgctcctg ctggagcagg attgcctcca gatgctgatg atacagccgc tgtgttgctt    960
gcattggcaa cacatgggag aggtagaaga ccagaagtac tgatggatta caggactgac   1020
gggtatttcc aatgctttat tggggaaagg actccatcaa tttcaacaaa cgctcacgta   1080
ttggaaacat tagggcatca tgtgcccaa catccacaag atagagccag atacggatca    1140
gccatggata ccgcatcagc ttggctgctg gcagctcaaa agcaagatgg ctcttggtta   1200
gataaatggc atgcctcacc atactacgct actgtttgtt gcacacaagc cctagccgct   1260
catgcaagtc ctgcaactgc accagctaga cagagagctg tcagatgggt tttagccaca   1320
caaagatccg atggcggttg gggtctatgg cattcaactg ttgaagagac tgcttatgcc   1380
ttacagatct tggccccacc ttctggtggt ggcaatatcc cagtccaaca agcacttact   1440
agaggcagag caagattgtg tggagccttg ccactgactc ctttatggca tgataaggat   1500
tgtatactc cagtaagagt agtcagagct gccagagctg ctgctctgta cactaccaga    1560
gatctattgt taccaccatt gtaa                                          1584
```

<210> SEQ ID NO 36
<211> LENGTH: 527
<212> TYPE: PRT
<213> ORGANISM: Streptomyces clavuligerus

<400> SEQUENCE: 36

```
Met Pro Asp Ala His Asp Ala Pro Pro Gln Ile Arg Gln Arg Thr
1               5                   10                  15

Leu Val Asp Glu Ala Thr Gln Leu Leu Thr Glu Ser Ala Glu Asp Ala
            20                  25                  30

Trp Gly Glu Val Ser Val Ser Glu Tyr Glu Thr Ala Arg Leu Val Ala
        35                  40                  45

His Ala Thr Trp Leu Gly Gly His Ala Thr Arg Val Ala Phe Leu Leu
    50                  55                  60

Glu Arg Gln His Glu Asp Gly Ser Trp Gly Pro Gly Gly Tyr Arg
65                  70                  75                  80

Leu Val Pro Thr Leu Ser Ala Val His Ala Leu Leu Thr Cys Leu Ala
                85                  90                  95

Ser Pro Ala Gln Asp His Gly Val Pro His Asp Arg Leu Leu Arg Ala
            100                 105                 110

Val Asp Ala Gly Leu Thr Ala Leu Arg Arg Leu Gly Thr Ser Asp Ser
        115                 120                 125

Pro Pro Asp Thr Ile Ala Val Glu Leu Val Ile Pro Ser Leu Leu Glu
    130                 135                 140

Gly Ile Gln His Leu Leu Asp Pro Ala His Pro His Ser Arg Pro Ala
145                 150                 155                 160

Phe Ser Gln His Arg Gly Ser Leu Val Cys Pro Gly Gly Leu Asp Gly
                165                 170                 175

Arg Thr Leu Gly Ala Leu Arg Ser His Ala Ala Gly Thr Pro Val
            180                 185                 190

Pro Gly Lys Val Trp His Ala Ser Glu Thr Leu Gly Leu Ser Thr Glu
        195                 200                 205

Ala Ala Ser His Leu Gln Pro Ala Gln Gly Ile Ile Gly Gly Ser Ala
    210                 215                 220

Ala Ala Thr Ala Thr Trp Leu Thr Arg Val Ala Pro Ser Gln Gln Ser
225                 230                 235                 240

Asp Ser Ala Arg Arg Tyr Leu Glu Glu Leu Gln His Arg Tyr Ser Gly
```

```
                    245                 250                 255
Pro Val Pro Ser Ile Thr Pro Ile Thr Tyr Phe Glu Arg Ala Trp Leu
                260                 265                 270

Leu Asn Asn Phe Ala Ala Ala Gly Val Pro Cys Glu Ala Pro Ala Ala
                275                 280                 285

Leu Leu Asp Ser Leu Glu Ala Ala Leu Thr Pro Gln Gly Ala Pro Ala
            290                 295                 300

Gly Ala Gly Leu Pro Pro Asp Ala Asp Asp Thr Ala Ala Val Leu Leu
305                 310                 315                 320

Ala Leu Ala Thr His Gly Arg Gly Arg Arg Pro Glu Val Leu Met Asp
                325                 330                 335

Tyr Arg Thr Asp Gly Tyr Phe Gln Cys Phe Ile Gly Glu Arg Thr Pro
                340                 345                 350

Ser Ile Ser Thr Asn Ala His Val Leu Glu Thr Leu Gly His His Val
                355                 360                 365

Ala Gln His Pro Gln Asp Arg Ala Arg Tyr Gly Ser Ala Met Asp Thr
370                 375                 380

Ala Ser Ala Trp Leu Leu Ala Ala Gln Lys Gln Asp Gly Ser Trp Leu
385                 390                 395                 400

Asp Lys Trp His Ala Ser Pro Tyr Tyr Ala Thr Val Cys Cys Thr Gln
                405                 410                 415

Ala Leu Ala Ala His Ala Ser Pro Ala Thr Ala Pro Ala Arg Gln Arg
                420                 425                 430

Ala Val Arg Trp Val Leu Ala Thr Gln Arg Ser Asp Gly Gly Trp Gly
                435                 440                 445

Leu Trp His Ser Thr Val Glu Glu Thr Ala Tyr Ala Leu Gln Ile Leu
                450                 455                 460

Ala Pro Pro Ser Gly Gly Gly Asn Ile Pro Val Gln Gln Ala Leu Thr
465                 470                 475                 480

Arg Gly Arg Ala Arg Leu Cys Gly Ala Leu Pro Leu Thr Pro Leu Trp
                485                 490                 495

His Asp Lys Asp Leu Tyr Thr Pro Val Arg Val Val Arg Ala Ala Arg
                500                 505                 510

Ala Ala Ala Leu Tyr Thr Thr Arg Asp Leu Leu Leu Pro Pro Leu
                515                 520                 525
```

<210> SEQ ID NO 37
<211> LENGTH: 1551
<212> TYPE: DNA
<213> ORGANISM: Artificial Sequence
<220> FEATURE:
<223> OTHER INFORMATION: Codon-optimized CDPS

<400> SEQUENCE: 37

```
atgaacgccc tatccgaaca cattttgtct gaattgagaa gattattgtc tgaaatgagt      60
gatggcggat ctgttggtcc atctgtgtat gatacggccc aggccctaag attccacggt     120
aacgtaacag gtagacaaga tgcatatgct tggttgatcg cccagcaaca agcagatgga     180
ggttggggct ctgccgactt tccactcttt agacatgctc caacatgggc tgcacttctc     240
gcattacaaa gagctgatcc acttcctggc gcagcagacg cagttcagac cgcaacaaga     300
ttcttgcaaa gacaaccaga tccatacgct catgccgttc ctgaggatgc cctattggt      360 gctgaactga tcttgcctca gttttgtgga gaggctgctg gttgttggg aggtgtggcc      420 ttccctagac acccagccct attaccatta agacaggctt gtttagtcaa actgggtgca     480
```

-continued

```
gtcgccatgt tgccttcagg acacccattg ctccactcct gggaggcatg gggtacttct      540
ccaacaacag cctgtccaga cgatgatggt tctataggta tctcaccagc agctacagcc      600
gcctggagag cccaggctgt gaccagaggc tcaactcctc aagtgggcag agctgacgca      660
tacttacaaa tggcttcaag agcaacgaga tcaggcatag aaggagtctt ccctaatgtt      720
tggcctataa acgtattcga accatgctgg tcactgtaca ctctccatct tgccggtctg      780
ttcgcccatc cagcactggc tgaggctgta agagttatcg ttgctcaact tgaagcaaga      840 tgggagtgc atggcctcgg accagcttta cattttgctg ccgacgctga tgatactgca      900
gttgccttat gcgttctgca tttggctggc agagatcctg cagttgacgc attgagacat      960
tttgaaattg gtgagctctt tgttacattc ccaggagaga gaaatgctag tgtctctacg     1020
aacattcacg ctcttcatgc tttgagattg ttaggtaaac cagctgccgg agcaagtgca     1080
tacgtcgaag caaatagaaa tccacatggt ttgtgggaca acgaaaaatg gcacgtttca     1140
tggctttatc caactgcaca cgccgttgca gctctagctc aaggcaagcc tcaatggaga     1200
gatgaaagag cactagccgc tctactacaa gctcaaagag atgatggtgg ttggggagct     1260
ggtagaggat ccactttcga ggaaaccgcc tacgctcttt tcgctttaca cgttatggac     1320
ggatctgagg aagccacagg cagaagaaga atcgctcaag tcgtcgcaag agccttagaa     1380
tggatgctag ctagacatgc cgcacatgga ttaccacaaa caccactctg gattggtaag     1440
gaattgtact gtcctactag agtcgtaaga gtagctgagc tagctggcct gtggttagca     1500
ttaagatggg gtagaagagt attagctgaa ggtgctggtg ctgcacctta a              1551
```

<210> SEQ ID NO 38
<211> LENGTH: 516
<212> TYPE: PRT
<213> ORGANISM: Bradyrhizobium japonicum

<400> SEQUENCE: 38

```
Met Asn Ala Leu Ser Glu His Ile Leu Ser Glu Leu Arg Arg Leu Leu
1               5                   10                  15

Ser Glu Met Ser Asp Gly Gly Ser Val Gly Pro Ser Val Tyr Asp Thr
            20                  25                  30

Ala Gln Ala Leu Arg Phe His Gly Asn Val Thr Gly Arg Gln Asp Ala
        35                  40                  45

Tyr Ala Trp Leu Ile Ala Gln Gln Ala Asp Gly Gly Trp Gly Ser
    50                  55                  60

Ala Asp Phe Pro Leu Phe Arg His Ala Pro Thr Trp Ala Ala Leu Leu
65                  70                  75                  80

Ala Leu Gln Arg Ala Asp Pro Leu Pro Gly Ala Ala Asp Ala Val Gln
                85                  90                  95

Thr Ala Thr Arg Phe Leu Gln Arg Gln Pro Asp Pro Tyr Ala His Ala
            100                 105                 110

Val Pro Glu Asp Ala Pro Ile Gly Ala Glu Leu Ile Leu Pro Gln Phe
        115                 120                 125

Cys Gly Glu Ala Ala Trp Leu Leu Gly Gly Val Ala Phe Pro Arg His
    130                 135                 140

Pro Ala Leu Leu Pro Leu Arg Gln Ala Cys Leu Val Lys Leu Gly Ala
145                 150                 155                 160

Val Ala Met Leu Pro Ser Gly His Pro Leu Leu His Ser Trp Glu Ala
                165                 170                 175

Trp Gly Thr Ser Pro Thr Thr Ala Cys Pro Asp Asp Gly Ser Ile
            180                 185                 190
```

Gly Ile Ser Pro Ala Ala Thr Ala Ala Trp Arg Ala Gln Ala Val Thr
        195                 200                 205

Arg Gly Ser Thr Pro Gln Val Gly Arg Ala Asp Ala Tyr Leu Gln Met
    210                 215                 220

Ala Ser Arg Ala Thr Arg Ser Gly Ile Glu Gly Val Phe Pro Asn Val
225                 230                 235                 240

Trp Pro Ile Asn Val Phe Glu Pro Cys Trp Ser Leu Tyr Thr Leu His
                245                 250                 255

Leu Ala Gly Leu Phe Ala His Pro Ala Leu Ala Glu Ala Val Arg Val
            260                 265                 270

Ile Val Ala Gln Leu Glu Ala Arg Leu Gly Val His Gly Leu Gly Pro
        275                 280                 285

Ala Leu His Phe Ala Ala Asp Ala Asp Asp Thr Ala Val Ala Leu Cys
    290                 295                 300

Val Leu His Leu Ala Gly Arg Asp Pro Ala Val Asp Ala Leu Arg His
305                 310                 315                 320

Phe Glu Ile Gly Glu Leu Phe Val Thr Phe Pro Gly Glu Arg Asn Ala
                325                 330                 335

Ser Val Ser Thr Asn Ile His Ala Leu His Ala Leu Arg Leu Leu Gly
            340                 345                 350

Lys Pro Ala Ala Gly Ala Ser Ala Tyr Val Glu Ala Asn Arg Asn Pro
        355                 360                 365

His Gly Leu Trp Asp Asn Glu Lys Trp His Val Ser Trp Leu Tyr Pro
    370                 375                 380

Thr Ala His Ala Val Ala Ala Leu Ala Gln Gly Lys Pro Gln Trp Arg
385                 390                 395                 400

Asp Glu Arg Ala Leu Ala Leu Leu Gln Ala Gln Arg Asp Asp Gly
                405                 410                 415

Gly Trp Gly Ala Gly Arg Gly Ser Thr Phe Glu Glu Thr Ala Tyr Ala
            420                 425                 430

Leu Phe Ala Leu His Val Met Asp Gly Ser Glu Glu Ala Thr Gly Arg
        435                 440                 445

Arg Arg Ile Ala Gln Val Val Ala Arg Ala Leu Glu Trp Met Leu Ala
    450                 455                 460

Arg His Ala Ala His Gly Leu Pro Gln Thr Pro Leu Trp Ile Gly Lys
465                 470                 475                 480

Glu Leu Tyr Cys Pro Thr Arg Val Val Arg Val Ala Glu Leu Ala Gly
                485                 490                 495

Leu Trp Leu Ala Leu Arg Trp Gly Arg Arg Val Leu Ala Glu Gly Ala
            500                 505                 510

Gly Ala Ala Pro
        515

<210> SEQ ID NO 39
<211> LENGTH: 2490
<212> TYPE: DNA
<213> ORGANISM: Artificial Sequence
<220> FEATURE:
<223> OTHER INFORMATION: Codon-optimized CDPS

<400> SEQUENCE: 39
atggttttgt cttcttcttg tactacagta ccacacttat cttcattagc tgtcgtgcaa      60
cttggtcctt ggagcagtag gattaaaaag aaaaccgata ctgttgcagt accagccgct     120
gcaggaaggt ggagaagggc cttggctaga gcacagcaca catcagaatc cgcagctgtc     180

```
gcaaagggca gcagtttgac ccctatagtg agaactgacg ctgagtcaag gagaacaaga    240
tggccaaccg atgacgatga cgccgaacct ttagtggatg agatcagggc aatgcttact    300
tccatgtctg atggtgacat ttccgtgagc gcatacgata cagcctgggt cggattggtt    360
ccaagattag acgcggtga aggtcctcaa tttccagcag ctgtgagatg gataagaaat    420
aaccagttgc ctgacggaag ttggggcgat gccgcattat tctctgccta tgacaggctt    480
atcaataccc ttgcctgcgt tgtaactttg acaaggtggt ccctagaacc agagatgaga    540
ggtagaggac tatctttttt gggtaggaac atgtggaaat tagcaactga agatgaagag    600
tcaatgccta ttggcttcga attagcattt ccatctttga tagagcttgc taagagccta    660
ggtgtccatg acttcccttta tgatcaccag gccctacaag gaatctactc ttcaagagag    720
atcaaaatga gaggattcc aaaagaagtg atgcataccg ttccaacatc aatattgcac    780
agtttggagg gtatgcctgg cctagattgg gctaaactac ttaaactaca gagcagcgac    840
ggaagttttt tgttctcacc agctgccact gcatatgctt taatgaatac cggagatgac    900
aggtgtttta gctacatcga tagaacagta aagaaattca acggcggcgt ccctaatgtt    960
tatccagtgg atctatttga acatatttgg gccgttgata gacttgaaag attaggaatc   1020
tccaggtact tccaaaagga gatcgaacaa tgcatggatt atgtaaacag gcattggact   1080
gaggacggta tttgttgggc aaggaactct gatgtcaaag aggtggacga cacagctatg   1140
gcctttagac ttcttaggtt gcacggctac agcgtcagtc ctgatgtgtt taaaaacttc   1200
gaaaaggacg gtgaattttt cgcatttgtc ggacagtcta atcaagctgt taccggtatg   1260
tacaacttaa acagagcaag ccagatatcc ttcccaggcg aggatgtgct tcatagagct   1320
ggtgccttct catatgagtt cttgaggaga aaagaagcag agggagcttt gagggacaag   1380
tggatcattt ctaaagatct acctggtgaa gttgtgtata ctttggattt tccatggtac   1440
ggcaacttac ctagagtcga ggccagagac tacctagagc aatacggagg tggtgatgac   1500
gtttggattg gcaagacatt gtataggatg ccacttgtaa acaatgatgt atatttggaa   1560
ttggcaagaa tggatttcaa ccactgccag gctttgcatc agttagagtg caaggacta   1620 aaaagatggt atactgaaaa taggttgatg actttggtc tcgcccaaga agatgccctt   1680
agagcttatt tccttgcagc cgcatctgtt tacgagcctt gtagagctgc cgagaggctt   1740
gcatgggcta gagccgcaat actagctaac gccgtgagca cccacttaag aaatagccca   1800
tcattcagag aaaggttaga gcattctctt aggtgtagac ctagtgaaga gacagatggc   1860
tcctggttta actcctcaag tggctctgat gcagttttag taaaggctgt cttaagactt   1920
actgattcat tagccaggga agcacagcca atccatggag gtgacccaga agatattata   1980
cacaagttgt taagatctgc ttgggccgag tgggttaggg aaaaggcaga cgctgccgat   2040
agcgtgtgca atggtagttc tgcagtagaa caagagggat caagaatggt ccatgataaa   2100
cagacctgtc tattattggc tagaatgatc gaaatttctg ccggtagggc agctggtgaa   2160
gcagccagtg aggacggcga tagaagaata attcaattaa caggctccat ctgcgacagt   2220
cttaagcaaa aaatgctagt ttcacaggac cctgaaaaaa atgaagagat gatgtctcac   2280
gtggatgacg aattgaagtt gaggattaga gagttcgttc aatatttgct tagactaggt   2340
gaaaaaaaga ctggatctag cgaaaccagg caaacatttt taagtatagt gaaatcatgt   2400
tactatgctg ctcattgccc acctcatgtc gttgatagac acattagtag agtgattttc   2460
gagccagtaa gtgccgcaaa gtaaccgcgg                                     2490
```

<210> SEQ ID NO 40
<211> LENGTH: 827
<212> TYPE: PRT
<213> ORGANISM: Zea mays

<400> SEQUENCE: 40

```
Met Val Leu Ser Ser Cys Thr Thr Val Pro His Leu Ser Ser Leu
1               5                   10                  15

Ala Val Val Gln Leu Gly Pro Trp Ser Ser Arg Ile Lys Lys Lys Thr
            20                  25                  30

Asp Thr Val Ala Val Pro Ala Ala Gly Arg Trp Arg Arg Ala Leu
            35                  40                  45

Ala Arg Ala Gln His Thr Ser Glu Ser Ala Ala Val Ala Lys Gly Ser
50                  55                  60

Ser Leu Thr Pro Ile Val Arg Thr Asp Ala Glu Ser Arg Arg Thr Arg
65                  70                  75                  80

Trp Pro Thr Asp Asp Asp Ala Glu Pro Leu Val Asp Glu Ile Arg
                85                  90                  95

Ala Met Leu Thr Ser Met Ser Asp Gly Asp Ile Ser Val Ser Ala Tyr
            100                 105                 110

Asp Thr Ala Trp Val Gly Leu Val Pro Arg Leu Asp Gly Gly Glu Gly
            115                 120                 125

Pro Gln Phe Pro Ala Ala Val Arg Trp Ile Arg Asn Asn Gln Leu Pro
130                 135                 140

Asp Gly Ser Trp Gly Asp Ala Ala Leu Phe Ser Ala Tyr Asp Arg Leu
145                 150                 155                 160

Ile Asn Thr Leu Ala Cys Val Val Thr Leu Thr Arg Trp Ser Leu Glu
                165                 170                 175

Pro Glu Met Arg Gly Arg Gly Leu Ser Phe Leu Gly Arg Asn Met Trp
            180                 185                 190

Lys Leu Ala Thr Glu Asp Glu Glu Ser Met Pro Ile Gly Phe Glu Leu
            195                 200                 205

Ala Phe Pro Ser Leu Ile Glu Leu Ala Lys Ser Leu Gly Val His Asp
210                 215                 220

Phe Pro Tyr Asp His Gln Ala Leu Gln Gly Ile Tyr Ser Ser Arg Glu
225                 230                 235                 240

Ile Lys Met Lys Arg Ile Pro Lys Glu Val Met His Thr Val Pro Thr
                245                 250                 255

Ser Ile Leu His Ser Leu Glu Gly Met Pro Gly Leu Asp Trp Ala Lys
            260                 265                 270

Leu Leu Lys Leu Gln Ser Ser Asp Gly Ser Phe Leu Phe Ser Pro Ala
            275                 280                 285

Ala Thr Ala Tyr Ala Leu Met Asn Thr Gly Asp Asp Arg Cys Phe Ser
290                 295                 300

Tyr Ile Asp Arg Thr Val Lys Lys Phe Asn Gly Gly Val Pro Asn Val
305                 310                 315                 320

Tyr Pro Val Asp Leu Phe Glu His Ile Trp Ala Val Asp Arg Leu Glu
                325                 330                 335

Arg Leu Gly Ile Ser Arg Tyr Phe Gln Lys Glu Ile Glu Gln Cys Met
            340                 345                 350

Asp Tyr Val Asn Arg His Trp Thr Glu Asp Gly Ile Cys Trp Ala Arg
            355                 360                 365

Asn Ser Asp Val Lys Glu Val Asp Thr Ala Met Ala Phe Arg Leu
370                 375                 380
```

-continued

```
Leu Arg Leu His Gly Tyr Ser Val Ser Pro Asp Val Phe Lys Asn Phe
385                 390                 395                 400

Glu Lys Asp Gly Glu Phe Phe Ala Phe Val Gly Gln Ser Asn Gln Ala
            405                 410                 415

Val Thr Gly Met Tyr Asn Leu Asn Arg Ala Ser Gln Ile Ser Phe Pro
        420                 425                 430

Gly Glu Asp Val Leu His Arg Ala Gly Ala Phe Ser Tyr Glu Phe Leu
            435                 440                 445

Arg Arg Lys Glu Ala Glu Gly Ala Leu Arg Asp Lys Trp Ile Ile Ser
450                 455                 460

Lys Asp Leu Pro Gly Glu Val Val Tyr Thr Leu Asp Phe Pro Trp Tyr
465                 470                 475                 480

Gly Asn Leu Pro Arg Val Glu Ala Arg Asp Tyr Leu Glu Gln Tyr Gly
                485                 490                 495

Gly Gly Asp Asp Val Trp Ile Gly Lys Thr Leu Tyr Arg Met Pro Leu
            500                 505                 510

Val Asn Asn Asp Val Tyr Leu Glu Leu Ala Arg Met Asp Phe Asn His
            515                 520                 525

Cys Gln Ala Leu His Gln Leu Glu Trp Gln Gly Leu Lys Arg Trp Tyr
530                 535                 540

Thr Glu Asn Arg Leu Met Asp Phe Gly Val Ala Gln Glu Asp Ala Leu
545                 550                 555                 560

Arg Ala Tyr Phe Leu Ala Ala Ser Val Tyr Glu Pro Cys Arg Ala
                565                 570                 575

Ala Glu Arg Leu Ala Trp Ala Arg Ala Ile Leu Ala Asn Ala Val
            580                 585                 590

Ser Thr His Leu Arg Asn Ser Pro Ser Phe Arg Glu Arg Leu Glu His
            595                 600                 605

Ser Leu Arg Cys Arg Pro Ser Glu Gly Thr Asp Gly Ser Trp Phe Asn
610                 615                 620

Ser Ser Ser Gly Ser Asp Ala Val Leu Val Lys Ala Val Leu Arg Leu
625                 630                 635                 640

Thr Asp Ser Leu Ala Arg Glu Ala Gln Pro Ile His Gly Gly Asp Pro
                645                 650                 655

Glu Asp Ile Ile His Lys Leu Leu Arg Ser Ala Trp Ala Glu Trp Val
            660                 665                 670

Arg Glu Lys Ala Asp Ala Ala Asp Ser Val Cys Asn Gly Ser Ser Ala
            675                 680                 685

Val Glu Gln Glu Gly Ser Arg Met Val His Asp Lys Gln Thr Cys Leu
            690                 695                 700

Leu Leu Ala Arg Met Ile Glu Ile Ser Ala Gly Arg Ala Ala Gly Glu
705                 710                 715                 720

Ala Ala Ser Glu Asp Gly Asp Arg Arg Ile Ile Gln Leu Thr Gly Ser
                725                 730                 735

Ile Cys Asp Ser Leu Lys Gln Lys Met Leu Val Ser Gln Asp Pro Glu
            740                 745                 750

Lys Asn Glu Glu Met Met Ser His Val Asp Asp Glu Leu Lys Leu Arg
            755                 760                 765

Ile Arg Glu Phe Val Gln Tyr Leu Leu Arg Leu Gly Glu Lys Lys Thr
            770                 775                 780

Gly Ser Ser Glu Thr Arg Gln Thr Phe Leu Ser Ile Val Lys Ser Cys
785                 790                 795                 800
```

```
Tyr Tyr Ala Ala His Cys Pro Pro His Val Val Asp Arg His Ile Ser
            805                 810                 815

Arg Val Ile Phe Glu Pro Val Ser Ala Ala Lys
            820                 825

<210> SEQ ID NO 41
<211> LENGTH: 2570
<212> TYPE: DNA
<213> ORGANISM: Artificial Sequence
<220> FEATURE:
<223> OTHER INFORMATION: Codon-optimized CDPS

<400> SEQUENCE: 41
cttcttcact aaatacttag acagagaaaa cagagctttt taaagccatg tctcttcagt      60
atcatgttct aaactccatt ccaagtacaa cctttctcag ttctactaaa acaacaatat     120
cttcttcttt ccttaccatc tcaggatctc ctctcaatgt cgctagagac aaatccagaa     180
gcggttccat acattgttca aagcttcgaa ctcaagaata cattaattct caagaggttc     240
aacatgattt gcctctaata catgagtggc aacagcttca aggagaagat gctcctcaga     300
ttagtgttgg aagtaatagt aatgcattca agaagcagt gaagagtgtg aaaacgatct     360
tgagaaacct aacggacggg gaaattacga tatcggctta cgatacagct tgggttgcat     420
tgatcgatgc cggagataaa actccggcgt tccctccgc cgtgaaatgg atcgccgaga     480
accaactttc cgatggttct tggggagatg cgtatctctt ctcttatcat gatcgtctca     540
tcaataccct tgcatgcgtc gttgctctaa gatcatggaa tctctttcct catcaatgca     600
acaaaggaat cacgttttc cgggaaaata ttgggaagct agaagacgaa atgatgagc      660 atatgccaat cggattcgaa gtagcattcc catcgttgct tgagatagct cgaggaataa     720
acattgatgt accgtacgat tctccggtct taaaagatat atacgccaag aaagagctaa     780
agcttacaag gataccaaaa gagataatgc acaagatacc aacaacattg ttgcatagtt     840
tggaggggat gcgtgattta gattgggaaa agctcttgaa acttcaatct caagacggat     900
ctttcctctt ctctccttcc tctaccgctt ttgcattcat gcagacccga gacagtaact     960
gcctcgagta tttgcgaaat gccgtcaaac gtttcaatgg aggagttccc aatgtctttc    1020
ccgtggatct tttcgagcac atatggatag tggatcggtt acaacgttta gggatatcga    1080
gatactttga agaagagatt aaagagtgtc ttgactatgt ccacagatat ggaccgaca    1140 atggcatatg ttgggctaga tgttcccatg tccaagacat cgatgataca gccatggcat    1200
ttaggctctt aagacaacat ggataccaag tgtccgcaga tgtattcaag aactttgaga    1260
aagagggaga gttttttctgc tttgtggggc aatcaaacca agcagtaacc ggtatgttca    1320
acctataccg ggcatcacaa ttggcgtttc aagggaaga gatattgaaa acgccaaag    1380 agttttctta taattatctg ctagaaaaac gggagagaga ggagttgatt gataagtgga    1440
ttataatgaa agacttacct ggcgagattg ggtttgcgtt agagattcca tggtacgcaa    1500
gcttgcctcg agtagagacg agattctata ttgatcaata tggtggagaa aacgacgttt    1560
ggattggcaa gactctttat aggatgccat acgtgaacaa taatggatat ctggaattag    1620
caaaacaaga ttacaacaat tgccaagctc agcatcagct cgaatgggac atattccaaa    1680
agtggtatga agaaaatagg ttaagtgagt ggggtgtgcg cagaagtgag cttctcgagt    1740
gttactactt agcggctgca actatatttg aatcagaaag gtcacatgag agaatggttt    1800
gggctaagtc aagtgtattg gttaaagcca tttcttcttc ttttgggaa tcctctgact    1860 ccagaagaag cttctccgat cagtttcatg aatacattgc caatgctcga cgaagtgatc    1920
```

-continued

```
atcactttaa tgacaggaac atgagattgg accgaccagg atcggttcag gccagtcggc    1980
ttgccggagt gttaatcggg actttgaatc aaatgtcttt tgaccttttc atgtctcatg    2040
gccgtgacgt taacaatctc ctctatctat cgtggggaga ttggatggaa aaatggaaac    2100
tatatggaga tgaaggagaa ggagagctca tggtgaagat gataattcta atgaagaaca    2160
atgacctaac taacttcttc acccacactc acttcgttcg tctcgcggaa atcatcaatc    2220
gaatctgtct tcctcgccaa tacttaaagg caaggagaaa cgatgagaag gagaagacaa    2280
taaagagtat ggagaaggag atggggaaaa tggttgagtt agcattgtcg gagagtgaca    2340
catttcgtga cgtcagcatc acgtttcttg atgtagcaaa agcattttac tactttgctt    2400
tatgtggcga tcatctccaa actcacatct ccaaagtctt gtttcaaaaa gtctagtaac    2460
ctcatcatca tcatcgatcc attaacaatc agtggatcga tgtatccata gatgcgtgaa    2520
taatatttca tgtagagaag gagaacaaat tagatcatgt agggttatca                2570
```

<210> SEQ ID NO 42
<211> LENGTH: 802
<212> TYPE: PRT
<213> ORGANISM: Arabidopsis thaliana

<400> SEQUENCE: 42

```
Met Ser Leu Gln Tyr His Val Leu Asn Ser Ile Pro Ser Thr Thr Phe
1               5                   10                  15

Leu Ser Ser Thr Lys Thr Thr Ile Ser Ser Ser Phe Leu Thr Ile Ser
            20                  25                  30

Gly Ser Pro Leu Asn Val Ala Arg Asp Lys Ser Arg Ser Gly Ser Ile
        35                  40                  45

His Cys Ser Lys Leu Arg Thr Gln Glu Tyr Ile Asn Ser Gln Glu Val
    50                  55                  60

Gln His Asp Leu Pro Leu Ile His Glu Trp Gln Gln Leu Gln Gly Glu
65                  70                  75                  80

Asp Ala Pro Gln Ile Ser Val Gly Ser Asn Ser Asn Ala Phe Lys Glu
                85                  90                  95

Ala Val Lys Ser Val Lys Thr Ile Leu Arg Asn Leu Thr Asp Gly Glu
            100                 105                 110

Ile Thr Ile Ser Ala Tyr Asp Thr Ala Trp Val Ala Leu Ile Asp Ala
        115                 120                 125

Gly Asp Lys Thr Pro Ala Phe Pro Ser Ala Val Lys Trp Ile Ala Glu
    130                 135                 140

Asn Gln Leu Ser Asp Gly Ser Trp Gly Asp Ala Tyr Leu Phe Ser Tyr
145                 150                 155                 160

His Asp Arg Leu Ile Asn Thr Leu Ala Cys Val Val Ala Leu Arg Ser
                165                 170                 175

Trp Asn Leu Phe Pro His Gln Cys Asn Lys Gly Ile Thr Phe Phe Arg
            180                 185                 190

Glu Asn Ile Gly Lys Leu Glu Asp Glu Asn Asp Glu His Met Pro Ile
        195                 200                 205

Gly Phe Glu Val Ala Phe Pro Ser Leu Leu Glu Ile Ala Arg Gly Ile
    210                 215                 220

Asn Ile Asp Val Pro Tyr Asp Ser Pro Val Leu Lys Asp Ile Tyr Ala
225                 230                 235                 240

Lys Lys Glu Leu Lys Leu Thr Arg Ile Pro Lys Glu Ile Met His Lys
                245                 250                 255
```

```
Ile Pro Thr Thr Leu Leu His Ser Leu Glu Gly Met Arg Asp Leu Asp
            260                 265                 270

Trp Glu Lys Leu Leu Lys Leu Gln Ser Gln Asp Gly Ser Phe Leu Phe
        275                 280                 285

Ser Pro Ser Ser Thr Ala Phe Ala Phe Met Gln Thr Arg Asp Ser Asn
    290                 295                 300

Cys Leu Glu Tyr Leu Arg Asn Ala Val Lys Arg Phe Asn Gly Gly Val
305                 310                 315                 320

Pro Asn Val Phe Pro Val Asp Leu Phe Glu His Ile Trp Ile Val Asp
                325                 330                 335

Arg Leu Gln Arg Leu Gly Ile Ser Arg Tyr Phe Glu Glu Glu Ile Lys
            340                 345                 350

Glu Cys Leu Asp Tyr Val His Arg Tyr Trp Thr Asp Asn Gly Ile Cys
        355                 360                 365

Trp Ala Arg Cys Ser His Val Gln Asp Ile Asp Asp Thr Ala Met Ala
    370                 375                 380

Phe Arg Leu Leu Arg Gln His Gly Tyr Gln Val Ser Ala Asp Val Phe
385                 390                 395                 400

Lys Asn Phe Glu Lys Glu Gly Glu Phe Phe Cys Phe Val Gly Gln Ser
                405                 410                 415

Asn Gln Ala Val Thr Gly Met Phe Asn Leu Tyr Arg Ala Ser Gln Leu
            420                 425                 430

Ala Phe Pro Arg Glu Glu Ile Leu Lys Asn Ala Lys Glu Phe Ser Tyr
        435                 440                 445

Asn Tyr Leu Leu Glu Lys Arg Glu Arg Glu Leu Ile Asp Lys Trp
    450                 455                 460

Ile Ile Met Lys Asp Leu Pro Gly Glu Ile Gly Phe Ala Leu Glu Ile
465                 470                 475                 480

Pro Trp Tyr Ala Ser Leu Pro Arg Val Glu Thr Arg Phe Tyr Ile Asp
                485                 490                 495

Gln Tyr Gly Gly Glu Asn Asp Val Trp Ile Gly Lys Thr Leu Tyr Arg
            500                 505                 510

Met Pro Tyr Val Asn Asn Asn Gly Tyr Leu Glu Leu Ala Lys Gln Asp
        515                 520                 525

Tyr Asn Asn Cys Gln Ala Gln His Gln Leu Glu Trp Asp Ile Phe Gln
    530                 535                 540

Lys Trp Tyr Glu Glu Asn Arg Leu Ser Glu Trp Gly Val Arg Arg Ser
545                 550                 555                 560

Glu Leu Leu Glu Cys Tyr Tyr Leu Ala Ala Ala Thr Ile Phe Glu Ser
                565                 570                 575

Glu Arg Ser His Glu Arg Met Val Trp Ala Lys Ser Ser Val Leu Val
            580                 585                 590

Lys Ala Ile Ser Ser Ser Phe Gly Glu Ser Ser Asp Ser Arg Arg Ser
        595                 600                 605

Phe Ser Asp Gln Phe His Glu Tyr Ile Ala Asn Ala Arg Arg Ser Asp
    610                 615                 620

His His Phe Asn Asp Arg Asn Met Arg Leu Asp Arg Pro Gly Ser Val
625                 630                 635                 640

Gln Ala Ser Arg Leu Ala Gly Val Leu Ile Gly Thr Leu Asn Gln Met
                645                 650                 655

Ser Phe Asp Leu Phe Met Ser His Gly Arg Asp Val Asn Asn Leu Leu
            660                 665                 670

Tyr Leu Ser Trp Gly Asp Trp Met Glu Lys Trp Lys Leu Tyr Gly Asp
```

```
                675                 680                 685
Glu Gly Glu Gly Glu Leu Met Val Lys Met Ile Ile Leu Met Lys Asn
            690                 695                 700

Asn Asp Leu Thr Asn Phe Phe Thr His Thr His Phe Val Arg Leu Ala
705                 710                 715                 720

Glu Ile Ile Asn Arg Ile Cys Leu Pro Arg Gln Tyr Leu Lys Ala Arg
                725                 730                 735

Arg Asn Asp Glu Lys Glu Lys Thr Ile Lys Ser Met Glu Lys Glu Met
            740                 745                 750

Gly Lys Met Val Glu Leu Ala Leu Ser Glu Ser Asp Thr Phe Arg Asp
                755                 760                 765

Val Ser Ile Thr Phe Leu Asp Val Ala Lys Ala Phe Tyr Tyr Phe Ala
            770                 775                 780

Leu Cys Gly Asp His Leu Gln Thr His Ile Ser Lys Val Leu Phe Gln
785                 790                 795                 800

Lys Val

<210> SEQ ID NO 43
<211> LENGTH: 2355
<212> TYPE: DNA
<213> ORGANISM: Artificial Sequence
<220> FEATURE:
<223> OTHER INFORMATION: Codon-optimized KS

<400> SEQUENCE: 43
atgaatttga gtttgtgtat agcatctcca ctattgacca aatctaatag accagctgct      60
ttatcagcaa ttcatacagc tagtacatcc catggtggcc aaaccaaccc tacgaatctg     120
ataatcgata cgaccaagga gagaatacaa aaacaattca aaaatgttga aatttcagtt     180
tcttcttatg atactgcgtg ggttgccatg gttccatcac ctaattctcc aaagtctcca     240
tgtttcccag aatgtttgaa ttggctgatt aacaaccagt tgaatgatgg atcttggggt     300
ttagtcaatc acacgcacaa tcacaaccat ccacttttga agattctttt atcctcaact     360
ttggcttgca tcgtggccct aaagagatgg aacgtaggtg aggatcagat taacaagggg     420
cttagtttca ttgaatctaa cttggcttcc gcgactgaaa aatctcaacc atctccaata     480
ggattcgata tcatctttcc aggtctgtta gagtacgcca aaaatctaga tatcaactta     540
ctgtctaagc aaactgattt ctcactaatg ttacacaaga gagaattaga caaaagagaa     600
tgtcattcaa acgaaatgga tggttaccta gcttatatct ctgaaggtct tggtaatctt     660
tacgattgga atatggtgaa aaagtaccag atgaaaaatg gctcagtttt caattcccct     720
tctgcaactg cggcagcatt cattaaccat caaaatccag gatgcctgaa ctatttgaat     780
tcactactag acaaattcgg caacgcagtt ccaactgtat accctcacga tttgtttatc     840
agattgagta tggtggatac aattgaaaga cttggtatat cccaccactt tagagtcgag     900
atcaaaaatg ttttggatga acataccgt tgttgggtgg agagagatga acaaatcttt     960
atggatgttg tgacgtgcgc gttggccttt agattgttgc gtattaacgg ttacgaagtt    1020
agtccagatc cacttgccga aattacaaac gaattagctt taaaggatga atacgccgct    1080
cttgaaacat atcatgcgtc acatatcctt taccaagagg acttatcatc tggaaaacaa    1140
attcttaaat ctgctgattt cctgaaggaa atcatatcca ctgatagtaa tagactgtcc    1200
aaactgatcc ataagaggt tgaaaatgca cttaagttcc ctattaacac cggcttagaa    1260
cgtattaaca aagacgtaa catccagctt tacaacgtag acaatactag aatcttgaaa    1320
```

```
accacttacc attcttccaa catatcaaac actgattacc taagattagc tgttgaagat    1380
ttctacacat gtcagtctat ctatagagaa gagctgaaag gattagagag atgggtcgtt    1440
gagaataagc tagatcaatt gaaatttgcc agacaaaaga cagcttattg ttacttctca    1500
gttgccgcca ctttatcaag tccagaattg tcagatgcac gtatttcttg ggctaaaaac    1560
ggaattttga caactgttgt tgatgatttc tttgatattg gcgggacaat cgacgaattg    1620
acaaacctga ttcaatgcgt tgaaaagtgg aatgtcgatg tcgataaaga ctgttgctca    1680
gaacatgtta gaatactgtt cttggctctg aaagatgcta tctgttggat cggggatgag    1740
gctttcaaat ggcaagctag agatgtgacg tctcacgtca ttcaaacctg gctagaactg    1800
atgaactcta tgttgagaga agcaatttgg actagagatg catacgttcc tacattaaac    1860
gagtatatgg aaaacgctta tgtctccttt gctttgggtc ctatcgttaa gcctgccata    1920
tactttgtag gaccaaagct atccgaggaa atcgtcgaat catcagaata ccataacttg    1980
ttcaagttaa tgtccacaca aggcagatta cttaatgata ttcattcttt caaaagagag    2040
tttaaggaag gaaagttaaa tgctgttgct ctgcatcttt ctaatggcga aagtggtaaa    2100
gtcgaagagg aagtagttga ggaaatgatg atgatgatca aaaacaagag aaaggagttg    2160
atgaaactaa tcttcgaaga gaacggttca attgttccta gagcatgtaa ggatgcattt    2220
tggaacatgt gtcatgtgct aaactttttc tacgcaaacg acgatggttt tactgggaac    2280
acaatactag atacagtaaa agacatcata tacaacccct tggtcttagt aaacgaaaac    2340
gaggagcaaa gataa                                                    2355

<210> SEQ ID NO 44
<211> LENGTH: 784
<212> TYPE: PRT
<213> ORGANISM: Stevia rebaudiana

<400> SEQUENCE: 44

Met Asn Leu Ser Leu Cys Ile Ala Ser Pro Leu Leu Thr Lys Ser Asn
1               5                   10                  15

Arg Pro Ala Ala Leu Ser Ala Ile His Thr Ala Ser Thr Ser His Gly
            20                  25                  30

Gly Gln Thr Asn Pro Thr Asn Leu Ile Ile Asp Thr Thr Lys Glu Arg
        35                  40                  45

Ile Gln Lys Gln Phe Lys Asn Val Glu Ile Ser Val Ser Ser Tyr Asp
    50                  55                  60

Thr Ala Trp Val Ala Met Val Pro Ser Pro Asn Ser Pro Lys Ser Pro
65                  70                  75                  80

Cys Phe Pro Glu Cys Leu Asn Trp Leu Ile Asn Asn Gln Leu Asn Asp
                85                  90                  95

Gly Ser Trp Gly Leu Val Asn His Thr His Asn His Asn His Pro Leu
            100                 105                 110

Leu Lys Asp Ser Leu Ser Ser Thr Leu Ala Cys Ile Val Ala Leu Lys
        115                 120                 125

Arg Trp Asn Val Gly Glu Asp Gln Ile Asn Lys Gly Leu Ser Phe Ile
    130                 135                 140

Glu Ser Asn Leu Ala Ser Ala Thr Glu Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
            180                 185                 190
```

```
Lys Arg Glu Leu Glu Gln Lys Arg Cys His Ser Asn Glu Met Asp Gly
            195                 200                 205

Tyr Leu Ala Tyr Ile Ser Glu Gly Leu Gly Asn Leu Tyr Asp Trp Asn
    210                 215                 220

Met Val Lys Lys Tyr Gln Met Lys Asn Gly Ser Val Phe Asn Ser Pro
225                 230                 235                 240

Ser Ala Thr Ala Ala Phe Ile Asn His Gln Asn Pro Gly Cys Leu
                245                 250                 255

Asn Tyr Leu Asn Ser Leu Leu Asp Lys Phe Gly Asn Ala Val Pro Thr
            260                 265                 270

Val Tyr Pro His Asp Leu Phe Ile Arg Leu Ser Met Val Asp Thr Ile
        275                 280                 285

Glu Arg Leu Gly Ile Ser His His Phe Arg Val Glu Ile Lys Asn Val
    290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile Asn
                325                 330                 335

Gly Tyr Glu Val Ser Pro Asp Pro Leu Ala Glu Ile Thr Asn Glu Leu
            340                 345                 350

Ala Leu Lys Asp Glu Tyr Ala Ala Leu Glu Thr Tyr His Ala Ser His
        355                 360                 365

Ile Leu Tyr Gln Glu Asp Leu Ser Ser Gly Lys Gln Ile Leu Lys Ser
    370                 375                 380

Ala Asp Phe Leu Lys Glu Ile Ile Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
            420                 425                 430

Val Asp Asn Thr Arg Ile Leu Lys Thr Thr Tyr His Ser Ser Asn Ile
        435                 440                 445

Ser Asn Thr Asp Tyr Leu Arg Leu Ala Val Glu Asp Phe Tyr Thr Cys
    450                 455                 460

Gln Ser Ile Tyr Arg Glu Glu Leu Lys Gly Leu Glu Arg Trp Val Val
465                 470                 475                 480

Glu Asn Lys Leu Asp Gln Leu Lys Phe Ala Arg Gln Lys Thr Ala Tyr
                485                 490                 495

Cys Tyr Phe Ser Val Ala Ala Thr Leu Ser Ser Pro Glu Leu Ser Asp
            500                 505                 510

Ala Arg Ile Ser Trp Ala Lys Asn Gly Ile Leu Thr Thr Val Val Asp
        515                 520                 525

Asp Phe Phe Asp Ile Gly Gly Thr Ile Asp Glu Leu Thr Asn Leu Ile
    530                 535                 540

Gln Cys Val Glu Lys Trp Asn Val Asp Val Asp Lys Asp Cys Cys Ser
545                 550                 555                 560

Glu His Val Arg Ile Leu Phe Leu Ala Leu Lys Asp Ala Ile Cys Trp
                565                 570                 575

Ile Gly Asp Glu Ala Phe Lys Trp Gln Ala Arg Asp Val Thr Ser His
            580                 585                 590

Val Ile Gln Thr Trp Leu Glu Leu Met Asn Ser Met Leu Arg Glu Ala
        595                 600                 605
```

```
Ile Trp Thr Arg Asp Ala Tyr Val Pro Thr Leu Asn Glu Tyr Met Glu
            610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Glu Ile Val Glu Ser Ser Glu
                645                 650                 655

Tyr His Asn Leu Phe Lys Leu Met Ser Thr Gln Gly Arg Leu Leu Asn
            660                 665                 670

Asp Ile His Ser Phe Lys Arg Glu Phe Lys Glu Gly Lys Leu Asn Ala
                675                 680                 685

Val Ala Leu His Leu Ser Asn Gly Glu Ser Gly Lys Val Glu Glu Glu
690                 695                 700

Val Val Glu Glu Met Met Met Met Ile Lys Asn Lys Arg Lys Glu Leu
705                 710                 715                 720

Met Lys Leu Ile Phe Glu Asn Gly Ser Ile Val Pro Arg Ala Cys
                725                 730                 735

Lys Asp Ala Phe Trp Asn Met Cys His Val Leu Asn Phe Phe Tyr Ala
                740                 745                 750

Asn Asp Asp Gly Phe Thr Gly Asn Thr Ile Leu Asp Thr Val Lys Asp
                755                 760                 765

Ile Ile Tyr Asn Pro Leu Val Leu Val Asn Glu Asn Glu Glu Gln Arg
            770                 775                 780

<210> SEQ ID NO 45
<211> LENGTH: 2355
<212> TYPE: DNA
<213> ORGANISM: Artificial Sequence
<220> FEATURE:
<223> OTHER INFORMATION: Codon-optimized KS

<400> SEQUENCE: 45
atgaatctgt cccttttgtat agctagtcca ctgttgacaa atcttctag accaactgct      60 cttctgcaa ttcatactgc cagtactagt catggaggtc aaacaaaccc aacaaatttg     120
ataatcgata ctactaagga gagaatccaa aagctattca aaaatgttga atctcagta     180 tcatcttatg acaccgcatg ggttgcaatg gtgccatcac ctaattcccc aaaaagtcca     240
tgttttccag agtgcttgaa ttggttaatc aataatcagt taaacgatgg ttcttggggt     300
ttagtcaacc acactcataa ccacaatcat ccattattga aggactcttt atcatcaaca     360
ttagcctgta ttgttgcatt gaaaagatgg aatgtaggtg aagatcaaat caacaagggt     420
ttatcattca tagaatccaa tctagcttct gctaccgaca atcacaaacc atctccaatc     480
gggttcgaca taatcttccc tggtttgctg gagtatgcca aaaaccttga tatcaactta     540
ctgtctaaac aaacagattt ctctttgatg ctacacaaaa gagagttaga gcagaaaaga     600
tgccattcta acgaaattga cgggtactta gcatatatct cagaaggttt gggtaatttg     660
tatgactgga acatggtcaa aaagtatcag atgaaaaatg gatccgtatt caattctcct     720
tctgcaactg ccgcagcatt cattaatcat caaaaccctg ggtgtcttaa ctacttgaac     780
tcactattag ataagtttgg aaatgcagtt ccaacagtct atcctttgga cttgtacatc     840
agattatcta tggttgacac tatagagaga ttaggtattt ctcatcattt cagagttgag     900
atcaaaaatg ttttggacga gacatacaga tgttgggtcg aaagagatga gcaaatcttt     960
atggatgtcg tgacctgcgc tctggctttt agattgctaa ggatacacgg atacaaagta    1020
tctcctgatc aactggctga gattacaaac gaactggctt caaagacga atacgccgca    1080
```

```
ttagaaacat accatgcatc ccaaatactt taccaggaag acctaagttc aggaaaacaa    1140
atcttgaagt ctgcagattt cctgaaaggc attctgtcta cagatagtaa taggttgtct    1200
aaattgatac acaaggaagt agaaaacgca ctaaagtttc ctattaacac tggtttagag    1260
agaatcaata ctaggagaaa cattcagctg tacaacgtag ataatacaag gattcttaag    1320
accacctacc atagttcaaa catttccaac acctattact taagattagc tgtcgaagac    1380
ttttacactt gtcaatcaat ctacagagag gagttaaagg gcctagaaag atgggtagtt    1440
caaaacaagt tggatcaact gaagtttgct agacagaaga cagcatactg ttatttctct    1500
gttgctgcta ccctttcatc cccagaattg tctgatgcca gaataagttg ggccaaaaat    1560
ggtattctta caactgtagt cgatgatttc tttgatattg gaggtactat tgatgaactg    1620
acaaatctta ttcaatgtgt tgaaaagtgg aacgtggatg tagataagga ttgctgcagt    1680
gaacatgtga gaatactttt cctggctcta aaagatgcaa tatgttggat tggcgacgag    1740
gccttcaagt ggcaagctag agatgttaca tctcatgtca tccaaacttg gcttgaactg    1800
atgaactcaa tgctaagaga agcaatctgg acaagagatg catacgttcc aacattgaac    1860
gaatacatgg aaaacgctta cgtctcattt gccttgggtc ctattgttaa gccagccata    1920
tactttgttg ggccaaagtt atccgaagag attgttgagt cttccgaata tcataaccta    1980
ttcaagttaa tgtcaacaca aggcagactt ctgaacgata tccactcctt caaaagagaa    2040
ttcaaggaag gtaagctaaa cgctgttgct ttgcacttgt ctaatggtga atctggcaaa    2100
gtggaagagg aagtcgttga ggaaatgatg atgatgatca aaaacaagag aaaggaattg    2160
atgaaattga ttttcgagga aaatggttca atcgtaccta gagcttgtaa agatgctttt    2220
tggaatatgt gccatgttct taacttcttt tacgctaatg atgatggctt cactggaaat    2280
acaatattgg atacagttaa agatatcatc tacaacccac ttgttttggt caatgagaac    2340
gaggaacaaa gataa                                                      2355
```

<210> SEQ ID NO 46
<211> LENGTH: 784
<212> TYPE: PRT
<213> ORGANISM: Stevia rebaudiana

<400> SEQUENCE: 46

```
Met Asn Leu Ser Leu Cys Ile Ala Ser Pro Leu Leu Thr Lys Ser Ser
1               5                   10                  15

Arg Pro Thr Ala Leu Ser Ala Ile His Thr Ala Ser Thr Ser His Gly
            20                  25                  30

Gly Gln Thr Asn Pro Thr Asn Leu Ile Ile Asp Thr Thr Lys Glu Arg
        35                  40                  45

Ile Gln Lys Leu Phe Lys Asn Val Glu Ile Ser Val Ser Ser Tyr Asp
    50                  55                  60

Thr Ala Trp Val Ala Met Val Pro Ser Pro Asn Ser Pro Lys Ser Pro
65                  70                  75                  80

Cys Phe Pro Glu Cys Leu Asn Trp Leu Ile Asn Asn Gln Leu Asn Asp
                85                  90                  95

Gly Ser Trp Gly Leu Val Asn His Thr His Asn His Asn His Pro Leu
            100                 105                 110

Leu Lys Asp Ser Leu Ser Ser Thr Leu Ala Cys Ile Val Ala Leu Lys
        115                 120                 125

Arg Trp Asn Val Gly Glu Asp Gln Ile Asn Lys Gly Leu Ser Phe Ile
    130                 135                 140
```

```
Glu Ser Asn Leu Ala Ser Ala Thr Asp Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
            180                 185                 190

Lys Arg Glu Leu Glu Gln Lys Arg Cys His Ser Asn Glu Ile Asp Gly
        195                 200                 205

Tyr Leu Ala Tyr Ile Ser Glu Gly Leu Gly Asn Leu Tyr Asp Trp Asn
    210                 215                 220

Met Val Lys Lys Tyr Gln Met Lys Asn Gly Ser Val Phe Asn Ser Pro
225                 230                 235                 240

Ser Ala Thr Ala Ala Phe Ile Asn His Gln Asn Pro Gly Cys Leu
                245                 250                 255

Asn Tyr Leu Asn Ser Leu Leu Asp Lys Phe Gly Asn Ala Val Pro Thr
                260                 265                 270

Val Tyr Pro Leu Asp Leu Tyr Ile Arg Leu Ser Met Val Asp Thr Ile
        275                 280                 285

Glu Arg Leu Gly Ile Ser His His Phe Arg Val Glu Ile Lys Asn Val
    290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile His
                325                 330                 335

Gly Tyr Lys Val Ser Pro Asp Gln Leu Ala Glu Ile Thr Asn Glu Leu
            340                 345                 350

Ala Phe Lys Asp Glu Tyr Ala Ala Leu Glu Thr Tyr His Ala Ser Gln
        355                 360                 365

Ile Leu Tyr Gln Glu Asp Leu Ser Ser Gly Lys Gln Ile Leu Lys Ser
    370                 375                 380

Ala Asp Phe Leu Lys Gly Ile Leu Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
            420                 425                 430

Val Asp Asn Thr Arg Ile Leu Lys Thr Thr Tyr His Ser Ser Asn Ile
        435                 440                 445

Ser Asn Thr Tyr Tyr Leu Arg Leu Ala Val Glu Asp Phe Tyr Thr Cys
    450                 455                 460

Gln Ser Ile Tyr Arg Glu Glu Leu Lys Gly Leu Glu Arg Trp Val Val
465                 470                 475                 480

Gln Asn Lys Leu Asp Gln Leu Lys Phe Ala Arg Gln Lys Thr Ala Tyr
                485                 490                 495

Cys Tyr Phe Ser Val Ala Ala Thr Leu Ser Ser Pro Glu Leu Ser Asp
            500                 505                 510

Ala Arg Ile Ser Trp Ala Lys Asn Gly Ile Leu Thr Thr Val Val Asp
        515                 520                 525

Asp Phe Phe Asp Ile Gly Gly Thr Ile Asp Glu Leu Thr Asn Leu Ile
    530                 535                 540

Gln Cys Val Glu Lys Trp Asn Val Asp Val Asp Lys Asp Cys Cys Ser
545                 550                 555                 560

Glu His Val Arg Ile Leu Phe Leu Ala Leu Lys Asp Ala Ile Cys Trp
```

|  |  | 565 |  |  |  |  | 570 |  |  |  |  | 575 |  |
|--|--|--|--|--|--|--|--|--|--|--|--|--|--|

Ile Gly Asp Glu Ala Phe Lys Trp Gln Ala Arg Asp Val Thr Ser His
            580              585              590

Val Ile Gln Thr Trp Leu Glu Leu Met Asn Ser Met Leu Arg Glu Ala
        595              600              605

Ile Trp Thr Arg Asp Ala Tyr Val Pro Thr Leu Asn Glu Tyr Met Glu
610                615              620

Asn Ala Tyr Val Ser Phe Ala Leu Gly Pro Ile Val Lys Pro Ala Ile
625                630              635              640

Tyr Phe Val Gly Pro Lys Leu Ser Glu Glu Ile Val Glu Ser Ser Glu
        645              650              655

Tyr His Asn Leu Phe Lys Leu Met Ser Thr Gln Gly Arg Leu Leu Asn
            660              665              670

Asp Ile His Ser Phe Lys Arg Glu Phe Lys Glu Gly Lys Leu Asn Ala
              675              680              685

Val Ala Leu His Leu Ser Asn Gly Glu Ser Gly Lys Val Glu Glu Glu
690                695              700

Val Val Glu Glu Met Met Met Met Ile Lys Asn Lys Arg Lys Glu Leu
705                710              715              720

Met Lys Leu Ile Phe Glu Glu Asn Gly Ser Ile Val Pro Arg Ala Cys
              725              730              735

Lys Asp Ala Phe Trp Asn Met Cys His Val Leu Asn Phe Phe Tyr Ala
            740              745              750

Asn Asp Asp Gly Phe Thr Gly Asn Thr Ile Leu Asp Thr Val Lys Asp
        755              760              765

Ile Ile Tyr Asn Pro Leu Val Leu Val Asn Glu Asn Glu Glu Gln Arg
        770              775              780

<210> SEQ ID NO 47  
<211> LENGTH: 1773  
<212> TYPE: DNA  
<213> ORGANISM: Artificial Sequence  
<220> FEATURE:  
<223> OTHER INFORMATION: Codon-optimized KS

<400> SEQUENCE: 47

| | |
|---|---|
| atggctatgc cagtgaagct aacacctgcg tcattatcct taaaagctgt gtgctgcaga | 60 |
| ttctcatccg gtggccatgc tttgagattc gggagtagtc tgccatgttg agagaggacc | 120 |
| cctacccaaa gatctacttc ttcctctact actagaccag ctgccgaagt gtcatcaggt | 180 |
| aagagtaaac aacatgatca ggaagctagt gaagcgacta tcagacaaca attacaactt | 240 |
| gtggatgtcc tggagaatat gggaatatcc agacattttg ctgcagagat aaagtgcata | 300 |
| ctagacagaa cttacagatc ttggttacaa agacacgagg aaatcatgct ggacactatg | 360 |
| acatgtgcta tggcttttag aatcctaaga ttgaacggat acaacgtttc atcagatgaa | 420 |
| ctataccacg ttgtagaggc atctggtctg cataattctt gggtgggta tcttaacgat | 480 |
| accagaacac tacttgaatt acacaaggct tcaacagtta gtatctctga ggatgaatct | 540 |
| atcttagatt caattggctc tagatccaga acattgctta gaacaatt ggagtctggt | 600 |
| ggcgcactga gaaagccttc tttattcaaa gaggttgaac atgcactgga tggacctttt | 660 |
| tacaccacac ttgatagact tcatcatagg tggaatattg aaaacttcaa cattattgag | 720 |
| caacacatgt tggagactcc atacttatct aaccagcata catcaaggga tatcctagca | 780 |
| ttgtcaatta gagattttc ctcctcacaa ttcacttatc aacaagagct acagcatctg | 840 |

```
gagagttggg ttaaggaatg tagattagat caactacagt tcgcaagaca gaaattagcg    900
tacttttacc tatcagccgc aggcaccatg ttttctcctg agctttctga tgcgagaaca    960
ttatgggcca aaaacggggt gttgacaact attgttgatg atttctttga tgttgccggt   1020
tctaaagagg aattggaaaa cttagtcatg ctggtcgaaa tgtgggatga acatcacaaa   1080
gttgaattct attctgagca ggtcgaaatc atcttctctt ccatctacga ttctgtcaac   1140
caattgggtg agaaggcctc tttggttcaa gacagatcaa ttacaaaaca ccttgttgaa   1200
atatggttag acttgttaaa gtccatgatg acggaagttg aatggagact gtcaaaatac   1260
gtgcctacag aaaaggaata catgattaat gcctctctta tcttcggcct aggtccaatc   1320
gttttaccag ctttgtattt cgttggtcca aagatttcag aaagtatagt aaaggaccca   1380
gaatatgatg aattgttcaa actaatgtca acatgtggta gattgttgaa tgacgtgcaa   1440
acgttcgaaa gagaatacaa tgagggtaaa ctgaattctg tcagtctatt ggttcttcac   1500
ggaggcccaa tgtctatttc agacgcaaag aggaaattac aaaagcctat tgatacgtgt   1560
agaagagatc ttctttcttt ggtccttaga gaagagtctg tagtaccaag accatgtaag   1620
gaactattct ggaaaatgtg taaagtgtgc tatttctttt actcaacaac tgatgggttt   1680
tctagtcaag tcgaaagagc aaaagaggta gacgctgtca taaatgagcc actgaagttg   1740
caaggttctc atacactggt atctgatgtt taa                                1773
```

<210> SEQ ID NO 48
<211> LENGTH: 590
<212> TYPE: PRT
<213> ORGANISM: Zea mays

<400> SEQUENCE: 48

```
Met Ala Met Pro Val Lys Leu Thr Pro Ala Ser Leu Ser Leu Lys Ala
1               5                   10                  15

Val Cys Cys Arg Phe Ser Ser Gly Gly His Ala Leu Arg Phe Gly Ser
            20                  25                  30

Ser Leu Pro Cys Trp Arg Arg Thr Pro Thr Gln Arg Ser Thr Ser Ser
        35                  40                  45

Ser Thr Thr Arg Pro Ala Ala Glu Val Ser Ser Gly Lys Ser Lys Gln
    50                  55                  60

His Asp Gln Glu Ala Ser Glu Ala Thr Ile Arg Gln Gln Leu Gln Leu
65                  70                  75                  80

Val Asp Val Leu Glu Asn Met Gly Ile Ser Arg His Phe Ala Ala Glu
                85                  90                  95

Ile Lys Cys Ile Leu Asp Arg Thr Tyr Arg Ser Trp Leu Gln Arg His
            100                 105                 110

Glu Glu Ile Met Leu Asp Thr Met Thr Cys Ala Met Ala Phe Arg Ile
        115                 120                 125

Leu Arg Leu Asn Gly Tyr Asn Val Ser Ser Asp Glu Leu Tyr His Val
    130                 135                 140

Val Glu Ala Ser Gly Leu His Asn Ser Leu Gly Gly Tyr Leu Asn Asp
145                 150                 155                 160

Thr Arg Thr Leu Leu Glu Leu His Lys Ala Ser Thr Val Ser Ile Ser
                165                 170                 175

Glu Asp Glu Ser Ile Leu Asp Ser Ile Gly Ser Arg Ser Arg Thr Leu
            180                 185                 190

Leu Arg Glu Gln Leu Glu Ser Gly Gly Ala Leu Arg Lys Pro Ser Leu
        195                 200                 205
```

```
Phe Lys Glu Val Glu His Ala Leu Asp Gly Pro Phe Tyr Thr Thr Leu
    210                 215                 220

Asp Arg Leu His His Arg Trp Asn Ile Glu Asn Phe Asn Ile Ile Glu
225                 230                 235                 240

Gln His Met Leu Glu Thr Pro Tyr Leu Ser Asn Gln His Thr Ser Arg
                245                 250                 255

Asp Ile Leu Ala Leu Ser Ile Arg Asp Phe Ser Ser Gln Phe Thr
        260                 265                 270

Tyr Gln Gln Glu Leu Gln His Leu Glu Ser Trp Val Lys Glu Cys Arg
            275                 280                 285

Leu Asp Gln Leu Gln Phe Ala Arg Gln Lys Leu Ala Tyr Phe Tyr Leu
290                 295                 300

Ser Ala Ala Gly Thr Met Phe Ser Pro Glu Leu Ser Asp Ala Arg Thr
305                 310                 315                 320

Leu Trp Ala Lys Asn Gly Val Leu Thr Thr Ile Val Asp Asp Phe Phe
                325                 330                 335

Asp Val Ala Gly Ser Lys Glu Glu Leu Glu Asn Leu Val Met Leu Val
                340                 345                 350

Glu Met Trp Asp Glu His His Lys Val Glu Phe Tyr Ser Glu Gln Val
            355                 360                 365

Glu Ile Ile Phe Ser Ser Ile Tyr Asp Ser Val Asn Gln Leu Gly Glu
370                 375                 380

Lys Ala Ser Leu Val Gln Asp Arg Ser Ile Thr Lys His Leu Val Glu
385                 390                 395                 400

Ile Trp Leu Asp Leu Leu Lys Ser Met Met Thr Glu Val Glu Trp Arg
                405                 410                 415

Leu Ser Lys Tyr Val Pro Thr Glu Lys Glu Tyr Met Ile Asn Ala Ser
            420                 425                 430

Leu Ile Phe Gly Leu Gly Pro Ile Val Leu Pro Ala Leu Tyr Phe Val
            435                 440                 445

Gly Pro Lys Ile Ser Glu Ser Ile Val Lys Asp Pro Glu Tyr Asp Glu
    450                 455                 460

Leu Phe Lys Leu Met Ser Thr Cys Gly Arg Leu Leu Asn Asp Val Gln
465                 470                 475                 480

Thr Phe Glu Arg Glu Tyr Asn Glu Gly Lys Leu Asn Ser Val Ser Leu
                485                 490                 495

Leu Val Leu His Gly Gly Pro Met Ser Ile Ser Asp Ala Lys Arg Lys
            500                 505                 510

Leu Gln Lys Pro Ile Asp Thr Cys Arg Arg Asp Leu Leu Ser Leu Val
            515                 520                 525

Leu Arg Glu Glu Ser Val Val Pro Arg Pro Cys Lys Glu Leu Phe Trp
530                 535                 540

Lys Met Cys Lys Val Cys Tyr Phe Phe Tyr Ser Thr Thr Asp Gly Phe
545                 550                 555                 560

Ser Ser Gln Val Glu Arg Ala Lys Glu Val Asp Ala Val Ile Asn Glu
                565                 570                 575

Pro Leu Lys Leu Gln Gly Ser His Thr Leu Val Ser Asp Val
            580                 585                 590
```

<210> SEQ ID NO 49
<211> LENGTH: 2232
<212> TYPE: DNA
<213> ORGANISM: Artificial Sequence
<220> FEATURE:
<223> OTHER INFORMATION: Codon-optimized KS

<400> SEQUENCE: 49

```
atgcagaact tccatggtac aaaggaaagg atcaaaaaga tgtttgacaa gattgaattg      60
tccgtttctt cttatgatac agcctgggtt gcaatggtcc catcccctga ttgcccagaa     120
acaccttgtt ttccagaatg tactaaatgg atcctagaaa atcagttggg tgatggtagt     180
tggtcacttc ctcatggcaa tccacttcta gttaaagatg cattatcttc cactcttgct     240
tgtattctgg ctcttaaaag atggggaatc ggtgaggaac agattaacaa aggactgaga     300
ttcatagaac tcaactctgc tagtgtaacc gataacgaac aacacaaacc aattggattt     360
gacattatct ttccaggtat gattgaatac gctatagact tagacctgaa tctaccacta     420
aaaccaactg acattaactc catgttgcat cgtagagccc ttgaattgac atcaggtgga     480
ggcaaaaatc tagaaggtag aagagcttac ttggcctacg tctctgaagg aatcggtaag     540
ctgcaagatt gggaaatggc tatgaaatac caacgtaaaa acggatctct gttcaatagt     600
ccatcaacaa ctgcagctgc attcatccat atacaagatg ctgaatgcct ccactatatt     660
cgttctcttc tccagaaatt tggaaacgca gtccctacaa tatccctct cgatatctat      720
gccagacttt caatggtaga tgccctggaa cgtcttggta ttgatagaca tttcagaaag     780
gagagaaagt tcgttctgga tgaaacatac agattttggt tgcaaggaga gaggagatt      840
ttctccgata acgcaacctg tgctttggcc ttcagaatat tgagacttaa tggttacgat     900
gtctctcttg aagatcactt ctctaactct ctgggcggtt acttaaagga ctcaggagca     960
gctttagaac tgtacagagc cctccaattg tcttacccag acgagtccct cctggaaaag    1020
caaaattcta gaacttctta cttcttaaaa caaggtttat ccaatgtctc cctctgtggt    1080
gacagattgc gtaaaaacat aattggagag gtgcatgatg ctttaaactt ttccgaccac    1140
gctaacttac aaagattagc tattcgtaga aggattaagc attacgctac tgacgataca    1200
aggattctaa aaacttccta cagatgctca acaatcggta accagatttt tctaaaactt    1260
gcagtggaag atttcaatat ctgtcaatca atacaaagag aggaattcaa gcatattgaa    1320
agatgggtcg ttgaaagacg tctagacaag ttaaagttcg ctagacaaaa agaggcctat    1380
tgctatttct cagccgcagc aacattgttt gcccctgaat tgtctgatgc tagaatgtct    1440
tgggccaaaa atggtgtatt gacaactgtg gttgatgatt cttcgatgt cggaggctct     1500
gaagaggaat tagttaactt gatagaattg atcgagcgtt gggatgtgaa tggcagtgca    1560
gattttgta gtgaggaagt tgagattatc tattctgcta ccactcaac tatctctgaa      1620
ataggtgata agtcatttgg ctggcaaggt agagatgtaa agtctcaagt tatcaagatc    1680
tggctggact tattgaaatc aatgttaact gaagctcaat ggtcttcaaa caagtctgtt    1740
cctaccctag atgagtatat gacaaccgcc catgtttcat tcgcacttgg tccaattgta    1800
cttccagcct tatacttcgt tggcccaaag ttgtcagaag aggttgcagg tcatcctgaa    1860
ctactaaacc tctacaaagt cacatctact tgtggcagac tactgaatga ttggagaagt    1920
tttaagagag aatccgagga aggtaagctc aacgctatta gtttatacat gatccactcc    1980
ggtggtgctt ctacagaaga ggaaacaatc gaacatttca aaggttttgat tgattctcag    2040
agaaggcaac tgttacaatt ggtgttgcaa gagaaggata gtatcatacc tagaccatgt    2100
aaagatctat tttggaatat gattaagtta ttacacactt tctacatgaa agatgatggc    2160
ttcacctcaa atgagatgag gaatgtagtt aaggcaatca ttaacgaacc aatctcactg    2220
gatgaattat ga                                                         2232
```

<210> SEQ ID NO 50
<211> LENGTH: 775
<212> TYPE: PRT
<213> ORGANISM: Populus trichocarpa

<400> SEQUENCE: 50

```
Met Ser Cys Ile Arg Pro Trp Phe Cys Pro Ser Ser Ile Ser Ala Thr
1               5                   10                  15

Leu Thr Asp Pro Ala Ser Lys Leu Val Thr Gly Glu Phe Lys Thr Thr
            20                  25                  30

Ser Leu Asn Phe His Gly Thr Lys Glu Arg Ile Lys Lys Met Phe Asp
        35                  40                  45

Lys Ile Glu Leu Ser Val Ser Ser Tyr Asp Thr Ala Trp Val Ala Met
    50                  55                  60

Val Pro Ser Pro Asp Cys Pro Glu Thr Pro Cys Phe Pro Glu Cys Thr
65                  70                  75                  80

Lys Trp Ile Leu Glu Asn Gln Leu Gly Asp Gly Ser Trp Ser Leu Pro
                85                  90                  95

His Gly Asn Pro Leu Leu Val Lys Asp Ala Leu Ser Ser Thr Leu Ala
            100                 105                 110

Cys Ile Leu Ala Leu Lys Arg Trp Gly Ile Gly Glu Glu Gln Ile Asn
        115                 120                 125

Lys Gly Leu Arg Phe Ile Glu Leu Asn Ser Ala Ser Val Thr Asp Asn
    130                 135                 140

Glu Gln His Lys Pro Ile Gly Phe Asp Ile Ile Phe Pro Gly Met Ile
145                 150                 155                 160

Glu Tyr Ala Lys Asp Leu Asp Leu Asn Leu Pro Leu Lys Pro Thr Asp
                165                 170                 175

Ile Asn Ser Met Leu His Arg Arg Ala Leu Glu Leu Thr Ser Gly Gly
            180                 185                 190

Gly Lys Asn Leu Glu Gly Arg Arg Ala Tyr Leu Ala Tyr Val Ser Glu
        195                 200                 205

Gly Ile Gly Lys Leu Gln Asp Trp Glu Met Ala Met Lys Tyr Gln Arg
    210                 215                 220

Lys Asn Gly Ser Leu Phe Asn Ser Pro Ser Thr Thr Ala Ala Ala Phe
225                 230                 235                 240

Ile His Ile Gln Asp Ala Glu Cys Leu His Tyr Ile Arg Ser Leu Leu
                245                 250                 255

Gln Lys Phe Gly Asn Ala Val Pro Thr Ile Tyr Pro Leu Asp Ile Tyr
            260                 265                 270

Ala Arg Leu Ser Met Val Asp Ala Leu Glu Arg Leu Gly Ile Asp Arg
        275                 280                 285

His Phe Arg Lys Glu Arg Lys Phe Val Leu Asp Glu Thr Tyr Arg Phe
    290                 295                 300

Trp Leu Gln Gly Glu Glu Ile Phe Ser Asp Asn Ala Thr Cys Ala
305                 310                 315                 320

Leu Ala Phe Arg Ile Leu Arg Leu Asn Gly Tyr Asp Val Ser Leu Glu
                325                 330                 335

Asp His Phe Ser Asn Ser Leu Gly Gly Tyr Leu Lys Ser Gly Ala
            340                 345                 350

Ala Leu Glu Leu Tyr Arg Ala Leu Gln Leu Ser Tyr Pro Asp Glu Ser
        355                 360                 365

Leu Leu Glu Lys Gln Asn Ser Arg Thr Ser Tyr Phe Leu Lys Gln Gly
    370                 375                 380
```

Leu Ser Asn Val Ser Leu Cys Gly Asp Arg Leu Arg Lys Asn Ile Ile
385                 390                 395                 400

Gly Glu Val His Asp Ala Leu Asn Phe Pro Asp His Ala Asn Leu Gln
            405                 410                 415

Arg Leu Ala Ile Arg Arg Ile Lys His Tyr Ala Thr Asp Asp Thr
        420                 425                 430

Arg Ile Leu Lys Thr Ser Tyr Arg Cys Ser Thr Ile Gly Asn Gln Asp
            435                 440                 445

Phe Leu Lys Leu Ala Val Glu Asp Phe Asn Ile Cys Gln Ser Ile Gln
450                 455                 460

Arg Glu Glu Phe Lys His Ile Glu Arg Trp Val Glu Arg Arg Leu
465                 470                 475                 480

Asp Lys Leu Lys Phe Ala Arg Gln Lys Glu Ala Tyr Cys Tyr Phe Ser
            485                 490                 495

Ala Ala Ala Thr Leu Phe Ala Pro Glu Leu Ser Asp Ala Arg Met Ser
            500                 505                 510

Trp Ala Lys Asn Gly Val Leu Thr Thr Val Asp Asp Phe Phe Asp
            515                 520                 525

Val Gly Gly Ser Glu Glu Leu Val Asn Leu Ile Glu Leu Ile Glu
            530                 535                 540

Arg Trp Asp Val Asn Gly Ser Ala Asp Phe Cys Ser Glu Glu Val Glu
545                 550                 555                 560

Ile Ile Tyr Ser Ala Ile His Ser Thr Ile Ser Glu Ile Gly Asp Lys
            565                 570                 575

Ser Phe Gly Trp Gln Gly Arg Asp Val Lys Ser His Val Ile Lys Ile
            580                 585                 590

Trp Leu Asp Leu Leu Lys Ser Met Leu Thr Glu Ala Gln Trp Ser Ser
            595                 600                 605

Asn Lys Ser Val Pro Thr Leu Asp Glu Tyr Met Thr Thr Ala His Val
            610                 615                 620

Ser Phe Ala Leu Gly Pro Ile Val Leu Pro Ala Leu Tyr Phe Val Gly
625                 630                 635                 640

Pro Lys Leu Ser Glu Glu Val Ala Gly His Pro Glu Leu Leu Asn Leu
            645                 650                 655

Tyr Lys Val Met Ser Thr Cys Gly Arg Leu Leu Asn Asp Trp Arg Ser
            660                 665                 670

Phe Lys Arg Glu Ser Glu Glu Gly Lys Leu Asn Ala Ile Ser Leu Tyr
            675                 680                 685

Met Ile His Ser Gly Gly Ala Ser Thr Glu Glu Thr Ile Glu His
            690                 695                 700

Phe Lys Gly Leu Ile Asp Ser Gln Arg Arg Gln Leu Leu Gln Leu Val
705                 710                 715                 720

Leu Gln Glu Lys Asp Ser Ile Ile Pro Arg Pro Cys Lys Asp Leu Phe
            725                 730                 735

Trp Asn Met Ile Lys Leu Leu His Thr Phe Tyr Met Lys Asp Asp Gly
            740                 745                 750

Phe Thr Ser Asn Glu Met Arg Asn Val Val Lys Ala Ile Ile Asn Glu
            755                 760                 765

Pro Ile Ser Leu Asp Glu Leu
            770                 775

<210> SEQ ID NO 51
<211> LENGTH: 2358

```
<212> TYPE: DNA
<213> ORGANISM: Artificial Sequence
<220> FEATURE:
<223> OTHER INFORMATION: Codon-optimized KS

<400> SEQUENCE: 51
```

| | | | | | |
|---|---|---|---|---|---|
| atgtctatca | accttcgctc | ctccggttgt | tcgtctccga | tctcagctac | tttggaacga | 60 |
| ggattggact | cagaagtaca | gacaagagct | aacaatgtga | gctttgagca | aacaaaggag | 120 |
| aagattagga | gatgttgga | gaaagtggag | ctttctgttt | cggcctacga | tactagttgg | 180 |
| gtagcaatgg | ttccatcacc | gagctcccaa | aatgctccac | ttttcccaca | gtgtgtgaaa | 240 |
| tggttattgg | ataatcaaca | tgaagatgga | tcttggggac | ttgataacca | tgaccatcaa | 300 |
| tctcttaaga | aggatgtgtt | atcatctaca | ctggctagta | tcctcgcgtt | aaagaagtgg | 360 |
| ggaattggtg | aaagacaaat | aaacaagggt | ctccagttta | ttgagctgaa | ttctgcatta | 420 |
| gtcactgatg | aaaccataca | gaaaccaaca | gggtttgata | ttatatttcc | tgggatgatt | 480 |
| aaatatgcta | gagatttgaa | tctgacgatt | ccattgggct | cagaagtggt | ggatgacatg | 540 |
| atacgaaaaa | gagatctgga | tcttaaatgt | gatagtgaaa | agttttcaaa | gggaagagaa | 600 |
| gcatatctgg | cctatgtttt | agaggggaca | agaaacctaa | aagattggga | tttgatagtc | 660 |
| aaatatcaaa | ggaaaaatgg | gtcactgttt | gattctccag | ccacaacagc | agctgctttt | 720 |
| actcagtttg | ggaatgatgg | ttgtctccgt | tatctctgtt | ctctccttca | gaaattcgag | 780 |
| gctgcagttc | cttcagttta | tccatttgat | caatatgcac | gccttagtat | aattgtcact | 840 |
| cttgaaagct | taggaattga | tagagatttc | aaaaccgaaa | tcaaaagcat | attggatgaa | 900 |
| acctatagat | attggcttcg | tggggatgaa | gaaatatgtt | tggacttggc | cacttgtgct | 960 |
| ttggcttttc | cgattattgc | tgctcatggc | tatgatgtgt | cttacgatcc | gctaaaacca | 1020 |
| tttgcagaag | aatctggttt | ctctgatact | ttggaaggat | atgttaagaa | tacgttttct | 1080 |
| gtgttagaat | tatttaaggc | tgctcaaagt | tatccacatg | aatcagcttt | gaagaagcag | 1140 |
| tgttgttgga | ctaaacaata | tctggagatg | gaattgtcca | gctgggttaa | gacctctgtt | 1200 |
| cgagataaat | aacctcaagaa | agaggtcgag | gatgctcttg | cttttccctc | ctatgcaagc | 1260 |
| ctagaaagat | cagatcacag | gagaaaaata | ctcaatggtt | ctgctgtgga | aaacaccaga | 1320 |
| gttacaaaaa | cctcatatcg | tttgcacaat | atttgcacct | ctgatatcct | gaagttagct | 1380 |
| gtggatgact | tcaatttctg | ccagtccata | caccgtgaag | aaatgaaacg | tcttgatagg | 1440 |
| tggattgtgg | agaatagatt | gcaggaactg | aaatttgcca | gacagaagct | ggcttactgt | 1500 |
| tatttctctg | gggctgcaac | tttatttttct | ccagaactat | ctgatgctcg | tatatcgtgg | 1560 |
| gccaaaggtg | gagtacttac | aacggttgta | gacgacttct | tgatgttgg | agggtccaaa | 1620 |
| gaagaactga | aaaccctcat | acacttggtc | gaaaagtggg | atttgaacgg | tgttcctgag | 1680 |
| tacagctcag | aacatgttga | gatcatattc | tcagttctaa | gggacaccat | tctcgaaaca | 1740 |
| ggagacaaag | cattcaccta | tcaaggacgc | aatgtgacac | accacattgt | gaaaatttgg | 1800 |
| ttggatctgc | tcaagtctat | gttgagagaa | gccgagtggt | ccagtgacaa | gtcaacacca | 1860 |
| agcttggagg | attacatgga | aaatgcgtac | atatcatttg | cattaggacc | aattgtcctc | 1920 |
| ccagctacct | atctgatcgg | acctccactt | ccagagaaga | cagtcgatag | ccaccaatat | 1980 |
| aatcagctct | acaagctcgt | gagcactatg | ggtcgtcttc | taaatgacat | acaaggtttt | 2040 |
| aagagagaaa | gcgcggaagg | gaagctgaat | gcggtttcat | tgcacatgaa | acacgagaga | 2100 |
| gacaatcgca | gcaaagaagt | gatcatagaa | tcgatgaaag | gtttagcaga | gagaaagagg | 2160 |

```
gaagaattgc ataagctagt tttggaggag aaaggaagtg tggttccaag ggaatgcaaa    2220
gaagcgttct tgaaaatgag caaagtgttg aacttatttt acaggaagga cgatggattc    2280
acatcaaatg atctgatgag tcttgttaaa tcagtgatct acgagcctgt tagcttacag    2340
aaagaatctt taacttga                                                  2358
```

<210> SEQ ID NO 52
<211> LENGTH: 785
<212> TYPE: PRT
<213> ORGANISM: Arabidopsis thaliana

<400> SEQUENCE: 52

```
Met Ser Ile Asn Leu Arg Ser Gly Cys Ser Ser Pro Ile Ser Ala
1               5                   10                  15

Thr Leu Glu Arg Gly Leu Asp Ser Glu Val Gln Thr Arg Ala Asn Asn
            20                  25                  30

Val Ser Phe Glu Gln Thr Lys Glu Lys Ile Arg Lys Met Leu Glu Lys
        35                  40                  45

Val Glu Leu Ser Val Ser Ala Tyr Asp Thr Ser Trp Val Ala Met Val
    50                  55                  60

Pro Ser Pro Ser Ser Gln Asn Ala Pro Leu Phe Pro Gln Cys Val Lys
65                  70                  75                  80

Trp Leu Leu Asp Asn Gln His Glu Asp Gly Ser Trp Gly Leu Asp Asn
                85                  90                  95

His Asp His Gln Ser Leu Lys Lys Asp Val Leu Ser Ser Thr Leu Ala
            100                 105                 110

Ser Ile Leu Ala Leu Lys Lys Trp Gly Ile Gly Glu Arg Gln Ile Asn
        115                 120                 125

Lys Gly Leu Gln Phe Ile Glu Leu Asn Ser Ala Leu Val Thr Asp Glu
    130                 135                 140

Thr Ile Gln Lys Pro Thr Gly Phe Asp Ile Ile Phe Pro Gly Met Ile
145                 150                 155                 160

Lys Tyr Ala Arg Asp Leu Asn Leu Thr Ile Pro Leu Gly Ser Glu Val
                165                 170                 175

Val Asp Asp Met Ile Arg Lys Arg Asp Leu Asp Leu Lys Cys Asp Ser
            180                 185                 190

Glu Lys Phe Ser Lys Gly Arg Glu Ala Tyr Leu Ala Tyr Val Leu Glu
        195                 200                 205

Gly Thr Arg Asn Leu Lys Asp Trp Asp Leu Ile Val Lys Tyr Gln Arg
    210                 215                 220

Lys Asn Gly Ser Leu Phe Asp Ser Pro Ala Thr Ala Ala Ala Phe
225                 230                 235                 240

Thr Gln Phe Gly Asn Asp Gly Cys Leu Arg Tyr Leu Cys Ser Leu Leu
                245                 250                 255

Gln Lys Phe Glu Ala Ala Val Pro Ser Val Tyr Pro Phe Asp Gln Tyr
            260                 265                 270

Ala Arg Leu Ser Ile Ile Val Thr Leu Glu Ser Leu Gly Ile Asp Arg
        275                 280                 285

Asp Phe Lys Thr Glu Ile Lys Ser Ile Leu Asp Glu Thr Tyr Arg Tyr
    290                 295                 300

Trp Leu Arg Gly Asp Glu Glu Ile Cys Leu Asp Leu Ala Thr Cys Ala
305                 310                 315                 320

Leu Ala Phe Arg Leu Leu Leu Ala His Gly Tyr Asp Val Ser Tyr Asp
                325                 330                 335
```

```
Pro Leu Lys Pro Phe Ala Glu Glu Ser Gly Phe Ser Asp Thr Leu Glu
            340                 345                 350

Gly Tyr Val Lys Asn Thr Phe Ser Val Leu Glu Leu Phe Lys Ala Ala
        355                 360                 365

Gln Ser Tyr Pro His Glu Ser Ala Leu Lys Lys Gln Cys Cys Trp Thr
    370                 375                 380

Lys Gln Tyr Leu Glu Met Glu Leu Ser Ser Trp Val Lys Thr Ser Val
385                 390                 395                 400

Arg Asp Lys Tyr Leu Lys Lys Glu Val Glu Asp Ala Leu Ala Phe Pro
                405                 410                 415

Ser Tyr Ala Ser Leu Glu Arg Ser Asp His Arg Lys Ile Leu Asn
            420                 425                 430

Gly Ser Ala Val Glu Asn Thr Arg Val Thr Lys Thr Ser Tyr Arg Leu
        435                 440                 445

His Asn Ile Cys Thr Ser Asp Ile Leu Lys Leu Ala Val Asp Asp Phe
    450                 455                 460

Asn Phe Cys Gln Ser Ile His Arg Glu Glu Met Glu Arg Leu Asp Arg
465                 470                 475                 480

Trp Ile Val Glu Asn Arg Leu Gln Glu Leu Lys Phe Ala Arg Gln Lys
                485                 490                 495

Leu Ala Tyr Cys Tyr Phe Ser Gly Ala Ala Thr Leu Phe Ser Pro Glu
            500                 505                 510

Leu Ser Asp Ala Arg Ile Ser Trp Ala Lys Gly Gly Val Leu Thr Thr
        515                 520                 525

Val Val Asp Asp Phe Phe Asp Val Gly Gly Ser Lys Glu Glu Leu Glu
    530                 535                 540

Asn Leu Ile His Leu Val Glu Lys Trp Asp Leu Asn Gly Val Pro Glu
545                 550                 555                 560

Tyr Ser Ser Glu His Val Glu Ile Ile Phe Ser Val Leu Arg Asp Thr
                565                 570                 575

Ile Leu Glu Thr Gly Asp Lys Ala Phe Thr Tyr Gln Gly Arg Asn Val
            580                 585                 590

Thr His His Ile Val Lys Ile Trp Leu Asp Leu Leu Lys Ser Met Leu
        595                 600                 605

Arg Glu Ala Glu Trp Ser Ser Asp Lys Ser Thr Pro Ser Leu Glu Asp
    610                 615                 620

Tyr Met Glu Asn Ala Tyr Ile Ser Phe Ala Leu Gly Pro Ile Val Leu
625                 630                 635                 640

Pro Ala Thr Tyr Leu Ile Gly Pro Pro Leu Pro Glu Lys Thr Val Asp
                645                 650                 655

Ser His Gln Tyr Asn Gln Leu Tyr Lys Leu Val Ser Thr Met Gly Arg
            660                 665                 670

Leu Leu Asn Asp Ile Gln Gly Phe Lys Arg Glu Ser Ala Glu Gly Lys
        675                 680                 685

Leu Asn Ala Val Ser Leu His Met Lys His Glu Arg Asp Asn Arg Ser
    690                 695                 700

Lys Glu Val Ile Ile Glu Ser Met Lys Gly Leu Ala Glu Arg Lys Arg
705                 710                 715                 720

Glu Glu Leu His Lys Leu Val Leu Glu Glu Lys Gly Ser Val Val Pro
                725                 730                 735

Arg Glu Cys Lys Glu Ala Phe Leu Lys Met Ser Lys Val Leu Asn Leu
            740                 745                 750

Phe Tyr Arg Lys Asp Asp Gly Phe Thr Ser Asn Asp Leu Met Ser Leu
```

```
                755               760               765
Val Lys Ser Val Ile Tyr Glu Pro Val Ser Leu Gln Lys Glu Ser Leu
    770               775               780
Thr
785

<210> SEQ ID NO 53
<211> LENGTH: 2952
<212> TYPE: DNA
<213> ORGANISM: Artificial Sequence
<220> FEATURE:
<223> OTHER INFORMATION: Codon-optimized CDPS-KS

<400> SEQUENCE: 53
atggaatttg atgaaccatt ggttgacgaa gcaagatctt tagtgcagcg tactttacaa      60
gattatgatg acagatacgg cttcggtact atgtcatgtg ctgcttatga tacagcctgg     120
gtgtctttag ttacaaaaac agtcgatggg agaaaacaat ggcttttccc agagtgtttt     180
gaatttctac tagaaacaca atctgatgcc ggaggatggg aaatcgggaa ttcagccaca     240
atcgacggta tattgaatac agctgcatcc ttacttgctc taaaacgtca cgttcaaact     300
gagcaaatca tccaacctca acatgaccat aaggatctag caggtagagc tgaacgtgcc     360
gctgcatctt tgagagcaca attggctgca ttggatgtgt ctacaactga acacgtcggt     420
tttgagataa ttgttcctgc aatgctagac ccattagaag ccgaagatcc atctctagtt     480
ttcgattttc cagctaggaa acctttgatg aagattcatg atgctaagat gagtagattc     540
aggccagaat acttgtatgg caaacaacca atgaccgcct acattcatt  agaggctttc     600
ataggcaaaa tcgacttcga taaggtaaga caccaccgta cccatgggtc tatgatgggt     660
tctccttcat ctaccgcagc ctacttaatg cacgcttcac aatgggatgg tgactcagag     720
gcttacctta gacacgtgat taaacacgca gcagggcagg gaactggtgc tgtaccatct     780
gctttcccat caacacattt tgagtcatct tggattctta ccacattgtt tagagctgga     840
ttttcagctt ctcatcttgc ctgtgatgag ttgaacaagt tggtcgagat acttgagggc     900
tcattcgaga ggaaggtgg  ggcaatcggt tacgctccag ggtttcaagc agatgttgat     960
gatactgcta aaacaataag tacattagca gtccttggaa gagatgctac accaagacaa    1020
atgatcaagg tatttgaagc taatacacat tttagaacat accctggtga agagatcct    1080
tctttgacag ctaattgtaa tgctctatca gccttactac accaaccaga tgcagcaatg    1140
tatggatctc aaattcaaaa gattaccaaa tttgtctgtg actattggtg gaagtctgat    1200
ggtaagatta agataagtg  gaacacttgc tacttgtacc catctgtctt attagttgag    1260
gttttggttg atcttgttag tttattggag cagggtaaat tgcctgatgt tttggatcaa    1320
gagcttcaat acagagtcgc catcacattg ttccaagcat gtttaaggcc attactagac    1380
caagatgccg aaggatcatg gaacaagtct atcgaagcca cagcctacgg catccttatc    1440
ctaactgaag ctaggagagt tgtttcttc  gacagattgt ctgagccatt gaatgaggca    1500
atccgtagag gtatcgcttt cgccgactct atgtctggaa ctgaagctca gttgaactac    1560
atttggatcg aaaaggttag ttacgcacct gcattattga ctaaatccta tttgttagca    1620
gcaagatggg ctgctaagtc tccttaggc  gcttccgtag gctcttcttt gtggactcca    1680
ccaagagaag gattggataa gcatgtcaga ttattccatc aagctgagtt attcagatcc    1740
cttccagaat gggaattaag agcctccatg attgaagcag ctttgttcac accacttcta    1800
agagcacata gactagacgt tttccctaga caagatgtag gtgaagacaa atatcttgat    1860
```

```
gtagttccat tcttttggac tgccgctaac aacagagata gaacttacgc ttccactcta   1920
ttcctttacg atatgtgttt tatcgcaatg ttaaacttcc agttagacga attcatggag   1980
gccacagccg gtatcttatt cagagatcat atggatgatt tgaggcaatt gattcatgat   2040
cttttggcag agaaaacttc cccaaagagt tctggtagaa gtagtcaggg cacaaaagat   2100
gctgactcag gtatagagga agacgtgtca atgtccgatt cagcttcaga ttcccaggat   2160
agaagtccag aatacgactt ggttttcagt gcattgagta cctttacaaa acatgtcttg   2220
caacacccat ctatacaaag tgcctctgta tgggatagaa aactacttgc tagagagatg   2280
aaggcttact tacttgctca tatccaacaa gcagaagatt caactccatt gtctgaattg   2340
aaagatgtgc ctcaaaagac tgatgtaaca agagtttcta catctactac taccttcttt   2400
aactgggtta gaacaacttc cgcagaccat atatcctgcc catactcctt ccactttgta   2460
gcatgccatc taggcgcagc attgtcacct aaagggtcta acggtgattg ctatccttca   2520
gctggtgaga agttcttggc agctgcagtc tgcagacatt tggccaccat gtgtagaatg   2580
tacaacgatc ttggatcagc tgaacgtgat tctgatgaag gtaatttgaa ctccttggac   2640
ttccctgaat tcgccgattc cgcaggaaac ggagggatag aaattcagaa ggccgctcta   2700
ttaaggttag ctgagtttga gagagattca tacttagagg ccttccgtcg tttacaagat   2760
gaatccaata gagttcacgg tccagccggt ggtgatgaag ccagattgtc cagaaggaga   2820
atggcaatcc ttgaattctt cgcccagcag gtagatttgt acggtcaagt atacgtcatt   2880
agggatattt ccgctcgtat tcctaaaaac gaggttgaga aaagagaaa attggatgat   2940 gctttcaatt ga                                                       2952
```

<210> SEQ ID NO 54
<211> LENGTH: 983
<212> TYPE: PRT
<213> ORGANISM: Phomopsis amygdali

<400> SEQUENCE: 54

```
Met Glu Phe Asp Glu Pro Leu Val Asp Glu Ala Arg Ser Leu Val Gln
1               5                   10                  15

Arg Thr Leu Gln Asp Tyr Asp Asp Arg Tyr Gly Phe Gly Thr Met Ser
            20                  25                  30

Cys Ala Ala Tyr Asp Thr Ala Trp Val Ser Leu Val Thr Lys Thr Val
        35                  40                  45

Asp Gly Arg Lys Gln Trp Leu Phe Pro Glu Cys Phe Glu Phe Leu Leu
    50                  55                  60

Glu Thr Gln Ser Asp Ala Gly Gly Trp Glu Ile Gly Asn Ser Ala Pro
65                  70                  75                  80

Ile Asp Gly Ile Leu Asn Thr Ala Ala Ser Leu Leu Ala Leu Lys Arg
                85                  90                  95

His Val Gln Thr Glu Gln Ile Ile Gln Pro Gln His Asp His Lys Asp
            100                 105                 110

Leu Ala Gly Arg Ala Glu Arg Ala Ala Ser Leu Arg Ala Gln Leu
        115                 120                 125

Ala Ala Leu Asp Val Ser Thr Thr Glu His Val Gly Phe Glu Ile Ile
    130                 135                 140

Val Pro Ala Met Leu Asp Pro Leu Glu Ala Glu Asp Pro Ser Leu Val
145                 150                 155                 160

Phe Asp Phe Pro Ala Arg Lys Pro Leu Met Lys Ile His Asp Ala Lys
                165                 170                 175
```

```
Met Ser Arg Phe Arg Pro Glu Tyr Leu Tyr Gly Lys Gln Pro Met Thr
            180                 185                 190

Ala Leu His Ser Leu Glu Ala Phe Ile Gly Lys Ile Asp Phe Asp Lys
            195                 200                 205

Val Arg His His Arg Thr His Gly Ser Met Met Gly Ser Pro Ser Ser
210                 215                 220

Thr Ala Ala Tyr Leu Met His Ala Ser Gln Trp Asp Gly Asp Ser Glu
225                 230                 235                 240

Ala Tyr Leu Arg His Val Ile Lys His Ala Ala Gly Gln Gly Thr Gly
                245                 250                 255

Ala Val Pro Ser Ala Phe Pro Ser Thr His Phe Glu Ser Ser Trp Ile
            260                 265                 270

Leu Thr Thr Leu Phe Arg Ala Gly Phe Ser Ala Ser His Leu Ala Cys
            275                 280                 285

Asp Glu Leu Asn Lys Leu Val Glu Ile Leu Glu Gly Ser Phe Glu Lys
            290                 295                 300

Glu Gly Gly Ala Ile Gly Tyr Ala Pro Gly Phe Gln Ala Asp Val Asp
305                 310                 315                 320

Asp Thr Ala Lys Thr Ile Ser Thr Leu Ala Val Leu Gly Arg Asp Ala
                325                 330                 335

Thr Pro Arg Gln Met Ile Lys Val Phe Glu Ala Asn Thr His Phe Arg
            340                 345                 350

Thr Tyr Pro Gly Glu Arg Asp Pro Ser Leu Thr Ala Asn Cys Asn Ala
            355                 360                 365

Leu Ser Ala Leu Leu His Gln Pro Asp Ala Ala Met Tyr Gly Ser Gln
            370                 375                 380

Ile Gln Lys Ile Thr Lys Phe Val Cys Asp Tyr Trp Trp Lys Ser Asp
385                 390                 395                 400

Gly Lys Ile Lys Asp Lys Trp Asn Thr Cys Tyr Leu Tyr Pro Ser Val
                405                 410                 415

Leu Leu Val Glu Val Leu Val Asp Leu Val Ser Leu Leu Glu Gln Gly
            420                 425                 430

Lys Leu Pro Asp Val Leu Asp Gln Glu Leu Gln Tyr Arg Val Ala Ile
            435                 440                 445

Thr Leu Phe Gln Ala Cys Leu Arg Pro Leu Leu Asp Gln Asp Ala Glu
            450                 455                 460

Gly Ser Trp Asn Lys Ser Ile Glu Ala Thr Ala Tyr Gly Ile Leu Ile
465                 470                 475                 480

Leu Thr Glu Ala Arg Arg Val Cys Phe Phe Asp Arg Leu Ser Glu Pro
                485                 490                 495

Leu Asn Glu Ala Ile Arg Arg Gly Ile Ala Phe Ala Asp Ser Met Ser
            500                 505                 510

Gly Thr Glu Ala Gln Leu Asn Tyr Ile Trp Ile Glu Lys Val Ser Tyr
            515                 520                 525

Ala Pro Ala Leu Leu Thr Lys Ser Tyr Leu Leu Ala Ala Arg Trp Ala
            530                 535                 540

Ala Lys Ser Pro Leu Gly Ala Ser Val Gly Ser Ser Leu Trp Thr Pro
545                 550                 555                 560

Pro Arg Glu Gly Leu Asp Lys His Val Arg Leu Phe His Gln Ala Glu
                565                 570                 575

Leu Phe Arg Ser Leu Pro Glu Trp Glu Leu Arg Ala Ser Met Ile Glu
            580                 585                 590
```

-continued

Ala Ala Leu Phe Thr Pro Leu Leu Arg Ala His Arg Leu Asp Val Phe
            595                 600                 605

Pro Arg Gln Asp Val Gly Glu Asp Lys Tyr Leu Asp Val Val Pro Phe
610                 615                 620

Phe Trp Thr Ala Ala Asn Asn Arg Asp Arg Thr Tyr Ala Ser Thr Leu
625                 630                 635                 640

Phe Leu Tyr Asp Met Cys Phe Ile Ala Met Leu Asn Phe Gln Leu Asp
                645                 650                 655

Glu Phe Met Glu Ala Thr Ala Gly Ile Leu Phe Arg Asp His Met Asp
            660                 665                 670

Asp Leu Arg Gln Leu Ile His Asp Leu Leu Ala Glu Lys Thr Ser Pro
        675                 680                 685

Lys Ser Ser Gly Arg Ser Ser Gln Gly Thr Lys Asp Ala Asp Ser Gly
690                 695                 700

Ile Glu Glu Asp Val Ser Met Ser Asp Ser Ala Ser Asp Ser Gln Asp
705                 710                 715                 720

Arg Ser Pro Glu Tyr Asp Leu Val Phe Ser Ala Leu Ser Thr Phe Thr
                725                 730                 735

Lys His Val Leu Gln His Pro Ser Ile Gln Ser Ala Ser Val Trp Asp
            740                 745                 750

Arg Lys Leu Leu Ala Arg Glu Met Lys Ala Tyr Leu Leu Ala His Ile
        755                 760                 765

Gln Gln Ala Glu Asp Ser Thr Pro Leu Ser Glu Leu Lys Asp Val Pro
770                 775                 780

Gln Lys Thr Asp Val Thr Arg Val Ser Thr Ser Thr Thr Thr Phe Phe
785                 790                 795                 800

Asn Trp Val Arg Thr Thr Ser Ala Asp His Ile Ser Cys Pro Tyr Ser
                805                 810                 815

Phe His Phe Val Ala Cys His Leu Gly Ala Ala Leu Ser Pro Lys Gly
            820                 825                 830

Ser Asn Gly Asp Cys Tyr Pro Ser Ala Gly Lys Phe Leu Ala Ala
        835                 840                 845

Ala Val Cys Arg His Leu Ala Thr Met Cys Arg Met Tyr Asn Asp Leu
850                 855                 860

Gly Ser Ala Glu Arg Asp Ser Asp Glu Gly Asn Leu Asn Ser Leu Asp
865                 870                 875                 880

Phe Pro Glu Phe Ala Asp Ser Ala Gly Asn Gly Gly Ile Glu Ile Gln
                885                 890                 895

Lys Ala Ala Leu Leu Arg Leu Ala Glu Phe Glu Arg Asp Ser Tyr Leu
            900                 905                 910

Glu Ala Phe Arg Arg Leu Gln Asp Glu Ser Asn Arg Val His Gly Pro
        915                 920                 925

Ala Gly Gly Asp Glu Ala Arg Leu Ser Arg Arg Met Ala Ile Leu
930                 935                 940

Glu Phe Phe Ala Gln Gln Val Asp Leu Tyr Gly Gln Val Tyr Val Ile
945                 950                 955                 960

Arg Asp Ile Ser Ala Arg Ile Pro Lys Asn Glu Val Glu Lys Lys Arg
                965                 970                 975

Lys Leu Asp Asp Ala Phe Asn
            980

<210> SEQ ID NO 55
<211> LENGTH: 2646
<212> TYPE: DNA

<213> ORGANISM: Artificial Sequence
<220> FEATURE:
<223> OTHER INFORMATION: Codon-optimized CDPS-KS

<400> SEQUENCE: 55

```
atggcttcta gtacacttat ccaaaacaga tcatgtggcg tcacatcatc tatgtcaagt      60
tttcaaatct tcagaggtca accactaaga tttcctggca ctagaacccc agctgcagtt     120
caatgcttga aaagaggag atgccttagg ccaaccgaat ccgtactaga atcatctcct      180
ggctctggtt catatagaat agtaactggc ccttctggaa ttaacctag ttctaacggg      240
cacttgcaag agggttcctt gactcacagg ttaccaatac caatggaaaa atctatcgat     300
aacttccaat ctactctata tgtgtcagat atttggtctg aaacactaca gagaactgaa     360
tgtttgctac aagtaactga aaacgtccag atgaatgagt ggattgagga attagaatg     420
tactttagaa atatgacttt aggtgaaatt tccatgtccc cttacgacac tgcttgggtg    480
gctagagttc cagcgttgga cggttctcat gggcctcaat tccacagatc tttgcaatgg    540
attatcgaca accaattacc agatggggac tggggcgaac cttctctttt cttgggttac    600
gatagagttt gtaatacttt agcctgtgtg attgcgttga aaacatgggg tgttggggca    660
caaaacgttg aaagaggaat tcagttccta caatctaaca tatacaagat ggaggaagat    720
gacgctaatc atatgccaat aggattcgaa atcgtattcc ctgctatgat ggaagatgcc    780
aaagcattag gtttggattt gccatacgat gctactattt gcaacagat ttcagccgaa     840
agagagaaaa agatgaaaaa gatcccaatg gcaatggtgt acaaataccc aaccacttta    900
cttcactcct tagaaggctt gcatagaaaa gttgattgga ataagttgtt acaattacaa    960
tctgaaaatg gtagtttct ttattcacct gcttcaaccg catgcgcctt aatgtacact    1020
aaggacgtta aatgttttga ttacttaaac cagttgttga tcaagttcga ccacgcatgc   1080
ccaaatgtat atccagtcga tctattcgaa agattatgga tggttgacag attgcagaga   1140
ttagggatct ccagatactt tgaaagagag attagagatt gtttacaata cgtctacaga   1200
tattggaaag attgtggaat cggatgggct tctaactctt ccgtacaaga tgttgatgat   1260
acagccatgg cgtttagact tttaaggact catggtttcg acgtaaagga agattgcttt   1320
agacagttt tcaaggacgg agaattcttc tgcttcgcag gccaatcatc tcaagcagtt    1380
acaggcatgt taatctttc aagagccagt caaacattgt ttccaggaga atctttattg    1440
aaaaaggcta gaaccttctc tagaaacttc ttgagaacaa agcatgagaa caacgaatgt   1500
ttcgataaat ggatcattac taaagatttg gctggtgaag tcgagtataa cttgacccttc  1560
ccatggtatg cctcttttgcc tagattagaa cataggacat acttagatca atatggaatc   1620
gatgatatct ggataggcaa atctttatac aaaatgcctg ctgttaccaa cgaagttttc   1680
ctaaagttgg caaaggcaga ctttaacatg tgtcaagctc tacacaaaaa ggaattggaa  1740
caagtgataa agtggaacgc gtcctgtcaa ttcagagatc ttgaattcgc cagacaaaaa  1800
tcagtagaat gctattttgc tggtgcagcc acaatgttcg aaccagaaat ggttcaagct   1860
agattagtct gggcaagatg ttgtgtattg acaactgtct tagacgatta ctttgaccac  1920
gggacacctg ttgaggaact tagagtgttt gttcaagctg tcagaacatg gaatccagag  1980
ttgatcaacg gtttgccaga gcaagctaaa atcttgttta tgggcttata caaaacagtt  2040
aacacaattg cagaggaagc attcatggca cagaaaagag acgtccatca tcatttgaaa  2100
cactattggg acaagttgat aacaagtgcc ctaaggagg ccgaatgggc agagtcaggt  2160
tacgtcccaa catttgatga atacatggaa gtagctgaaa tttctgttgc tctagaacca  2220
```

-continued

```
attgtctgta gtaccttgtt ctttgcgggt catagactag atgaggatgt tctagatagt    2280
tacgattacc atctagttat gcatttggta acagagtcg gtagaatctt gaatgatata    2340
caaggcatga agagggaggc ttcacaaggt aagatctcat cagttcaaat ctacatggag    2400
gaacatccat ctgttccatc tgaggccatg gcgatcgctc atcttcaaga gttagttgat    2460
aattcaatgc agcaattgac atacgaagtt cttaggttca ctgcggttcc aaaaagttgt    2520
aagagaatcc acttgaatat ggctaaaatc atgcatgcct tctacaagga tactgatgga    2580
ttctcatccc ttactgcaat gacaggattc gtcaaaaagg ttcttttcga acctgtgcct    2640
gagtaa                                                               2646
```

<210> SEQ ID NO 56
<211> LENGTH: 881
<212> TYPE: PRT
<213> ORGANISM: Physcomitrella patens

<400> SEQUENCE: 56

```
Met Ala Ser Ser Thr Leu Ile Gln Asn Arg Ser Cys Gly Val Thr Ser
1               5                   10                  15

Ser Met Ser Ser Phe Gln Ile Phe Arg Gly Gln Pro Leu Arg Phe Pro
            20                  25                  30

Gly Thr Arg Thr Pro Ala Ala Val Gln Cys Leu Lys Lys Arg Arg Cys
        35                  40                  45

Leu Arg Pro Thr Glu Ser Val Leu Glu Ser Ser Pro Gly Ser Gly Ser
    50                  55                  60

Tyr Arg Ile Val Thr Gly Pro Ser Gly Ile Asn Pro Ser Ser Asn Gly
65                  70                  75                  80

His Leu Gln Glu Gly Ser Leu Thr His Arg Leu Pro Ile Pro Met Glu
                85                  90                  95

Lys Ser Ile Asp Asn Phe Gln Ser Thr Leu Tyr Val Ser Asp Ile Trp
            100                 105                 110

Ser Glu Thr Leu Gln Arg Thr Glu Cys Leu Leu Gln Val Thr Glu Asn
        115                 120                 125

Val Gln Met Asn Glu Trp Ile Glu Glu Ile Arg Met Tyr Phe Arg Asn
    130                 135                 140

Met Thr Leu Gly Glu Ile Ser Met Ser Pro Tyr Asp Thr Ala Trp Val
145                 150                 155                 160

Ala Arg Val Pro Ala Leu Asp Gly Ser His Gly Pro Gln Phe His Arg
                165                 170                 175

Ser Leu Gln Trp Ile Ile Asp Asn Gln Leu Pro Asp Gly Asp Trp Gly
            180                 185                 190

Glu Pro Ser Leu Phe Leu Gly Tyr Asp Arg Val Cys Asn Thr Leu Ala
        195                 200                 205

Cys Val Ile Ala Leu Lys Thr Trp Gly Val Gly Ala Gln Asn Val Glu
    210                 215                 220

Arg Gly Ile Gln Phe Leu Gln Ser Asn Ile Tyr Lys Met Glu Glu Asp
225                 230                 235                 240

Asp Ala Asn His Met Pro Ile Gly Phe Glu Ile Val Phe Pro Ala Met
                245                 250                 255

Met Glu Asp Ala Lys Ala Leu Gly Leu Asp Leu Pro Tyr Asp Ala Thr
            260                 265                 270

Ile Leu Gln Gln Ile Ser Ala Glu Arg Glu Lys Lys Met Lys Lys Ile
        275                 280                 285
```

```
Pro Met Ala Met Val Tyr Lys Tyr Pro Thr Thr Leu Leu His Ser Leu
290                 295                 300

Glu Gly Leu His Arg Glu Val Asp Trp Asn Lys Leu Leu Gln Leu Gln
305                 310                 315                 320

Ser Glu Asn Gly Ser Phe Leu Tyr Ser Pro Ala Ser Thr Ala Cys Ala
                325                 330                 335

Leu Met Tyr Thr Lys Asp Val Lys Cys Phe Asp Tyr Leu Asn Gln Leu
                340                 345                 350

Leu Ile Lys Phe Asp His Ala Cys Pro Asn Val Tyr Pro Val Asp Leu
            355                 360                 365

Phe Glu Arg Leu Trp Met Val Asp Arg Leu Gln Arg Leu Gly Ile Ser
370                 375                 380

Arg Tyr Phe Glu Arg Glu Ile Arg Asp Cys Leu Gln Tyr Val Tyr Arg
385                 390                 395                 400

Tyr Trp Lys Asp Cys Gly Ile Gly Trp Ala Ser Asn Ser Ser Val Gln
                405                 410                 415

Asp Val Asp Asp Thr Ala Met Ala Phe Arg Leu Leu Arg Thr His Gly
            420                 425                 430

Phe Asp Val Lys Glu Asp Cys Phe Arg Gln Phe Phe Lys Asp Gly Glu
                435                 440                 445

Phe Phe Cys Phe Ala Gly Gln Ser Ser Gln Ala Val Thr Gly Met Phe
450                 455                 460

Asn Leu Ser Arg Ala Ser Gln Thr Leu Phe Pro Gly Glu Ser Leu Leu
465                 470                 475                 480

Lys Lys Ala Arg Thr Phe Ser Arg Asn Phe Leu Arg Thr Lys His Glu
                485                 490                 495

Asn Asn Glu Cys Phe Asp Lys Trp Ile Ile Thr Lys Asp Leu Ala Gly
                500                 505                 510

Glu Val Glu Tyr Asn Leu Thr Phe Pro Trp Tyr Ala Ser Leu Pro Arg
            515                 520                 525

Leu Glu His Arg Thr Tyr Leu Asp Gln Tyr Gly Ile Asp Asp Ile Trp
530                 535                 540

Ile Gly Lys Ser Leu Tyr Lys Met Pro Ala Val Thr Asn Glu Val Phe
545                 550                 555                 560

Leu Lys Leu Ala Lys Ala Asp Phe Asn Met Cys Gln Ala Leu His Lys
                565                 570                 575

Lys Glu Leu Glu Gln Val Ile Lys Trp Asn Ala Ser Cys Gln Phe Arg
            580                 585                 590

Asp Leu Glu Phe Ala Arg Gln Lys Ser Val Glu Cys Tyr Phe Ala Gly
            595                 600                 605

Ala Ala Thr Met Phe Glu Pro Glu Met Val Gln Ala Arg Leu Val Trp
610                 615                 620

Ala Arg Cys Cys Val Leu Thr Thr Val Leu Asp Asp Tyr Phe Asp His
625                 630                 635                 640

Gly Thr Pro Val Glu Glu Leu Arg Val Phe Val Gln Ala Val Arg Thr
                645                 650                 655

Trp Asn Pro Glu Leu Ile Asn Gly Leu Pro Glu Gln Ala Lys Ile Leu
                660                 665                 670

Phe Met Gly Leu Tyr Lys Thr Val Asn Thr Ile Ala Glu Glu Ala Phe
            675                 680                 685

Met Ala Gln Lys Arg Asp Val His His Leu Lys His Tyr Trp Asp
690                 695                 700

Lys Leu Ile Thr Ser Ala Leu Lys Glu Ala Glu Trp Ala Glu Ser Gly
```

```
                705                 710                 715                 720
Tyr Val Pro Thr Phe Asp Glu Tyr Met Glu Val Ala Glu Ile Ser Val
                    725                 730                 735

Ala Leu Glu Pro Ile Val Cys Ser Thr Leu Phe Phe Ala Gly His Arg
                740                 745                 750

Leu Asp Glu Asp Val Leu Asp Ser Tyr Asp Tyr His Leu Val Met His
                755                 760                 765

Leu Val Asn Arg Val Gly Arg Ile Leu Asn Asp Ile Gln Gly Met Lys
                770                 775                 780

Arg Glu Ala Ser Gln Gly Lys Ile Ser Ser Val Gln Ile Tyr Met Glu
785                 790                 795                 800

Glu His Pro Ser Val Pro Ser Glu Ala Met Ala Ile Ala His Leu Gln
                805                 810                 815

Glu Leu Val Asp Asn Ser Met Gln Gln Leu Thr Tyr Glu Val Leu Arg
                820                 825                 830

Phe Thr Ala Val Pro Lys Ser Cys Lys Arg Ile His Leu Asn Met Ala
                835                 840                 845

Lys Ile Met His Ala Phe Tyr Lys Asp Thr Asp Gly Phe Ser Ser Leu
                850                 855                 860

Thr Ala Met Thr Gly Phe Val Lys Lys Val Leu Phe Glu Pro Val Pro
865                 870                 875                 880

Glu

<210> SEQ ID NO 57
<211> LENGTH: 2859
<212> TYPE: DNA
<213> ORGANISM: Artificial Sequence
<220> FEATURE:
<223> OTHER INFORMATION: Codon-optimized CDPS-KS

<400> SEQUENCE: 57
atgcctggta aaattgaaaa tggtacccca aaggacctca agactggaaa tgattttgtt      60
tctgctgcta agagtttact agatcgagct ttcaaaagtc atcattccta ctacggatta     120
tgctcaactt catgtcaagt ttatgataca gcttgggttg caatgattcc aaaaacaaga     180
gataatgtaa acagtggttg gtttccagaa tgtttccatt acctcttaaa aacacaagcc     240
gcagatggct catggggttc attgcctaca acacagacag cgggtatcct agatacagcc     300
tcagctgtgc tggcattatt gtgccacgca caagagcctt acaaatatt ggatgtatct      360 ccagatgaaa tggggttgag aatagaacac ggtgtcacat ccttgaaacg tcaattagca     420
gtttggaatg atgtggagga caccaaccat attggcgtcg agtttatcat accagcctta     480
ctttccatgc tagaaaagga attagatgtt ccatcttttg aatttccatg taggtccatc     540
ttagagagaa tgcacgggga gaaattaggt catttcgacc tggaacaagt ttacggcaag     600
ccaagctcat tgttgcactc attggaagca tttctcggta agctagattt tgatcgacta     660
tcacatcacc tataccacgg cagtatgatg gcatctccat cttcaacggc tgcttatctt     720 attgggcta caaaatggga tgacgaagcc gaagattacc taagacatgt aatgcgtaat      780
ggtgcaggac atgggaatgg aggtatttct ggtacatttc aactactca tttcgaatgt     840 agctggatta gcaacgtt gttaaaggtt ggctttactt tgaagcaaat tgacggcgat      900
ggcttaagag gttatcaac catcttactt gaggcgcttc gtgatgagaa tggtgtcata     960
ggctttgccc ctagaacagc agatgtagat gacacagcca agctctatt ggccttgtca     1020 ttggtaaacc agccagtgtc acctgatatc atgattaagg tctttgaggg caaagaccat    1080
```

```
tttaccactt ttggttcaga aagagatcca tcattgactt ccaacctgca cgtcctttta    1140
tctttactta aacaatctaa cttgtctcaa taccatcctc aaatcctcaa aacaacatta    1200
ttcacttgta gatggtggtg gggttccgat cattgtgtca aagacaaatg gaatttgagt    1260
cacctatatc caactatgtt gttggttgaa gccttcactg aagtgctcca tctcattgac    1320
ggtggtgaat tgtctagtct gtttgatgaa tcctttaagt gtaagattgg tcttagcatc    1380
tttcaagcgg tacttagaat aatcctcacc caagacaacg acggctcttg gagaggatac    1440
agagaacaga cgtgttacgc aatattggct ttagttcaag cgagacatgt atgctttttc    1500
actcacatgg ttgacagact gcaatcatgt gttgatcgag gtttctcatg gttgaaatct    1560 tgctctttc attctcaaga cctgacttgg acctctaaaa cagcttatga agtgggtttc    1620
gtagctgaag catataaact agctgcttta caatctgctt ccctggaggt tcctgctgcc    1680
accattggac attctgtcac gtctgccgtt ccatcaagtg atcttgaaaa atacatgaga    1740
ttggtgagaa aaactgcgtt attctctcca ctggatgagt ggggtctaat ggcttctatc    1800
atcgaatctt cattttccgt accattactg caggcacaaa gagttgaaat atacctaga    1860 gataatatca aggtggacga agataagtac ttgtctatta tcccattcac atgggtcgga    1920
tgcaataata ggtctagaac tttcgcaagt aacagatggc tatacgatat gatgtacctt    1980
tcattactcg gctatcaaac cgacgagtac atggaagctg tagctgggcc agtgtttggg    2040
gatgtttcct tgttacatca aacaattgat aaggtgattg ataatacaat gggtaacctt    2100
gcgagagcca atggaacagt acacagtggt aatggacatc agcacgaatc tcctaatata    2160
ggtcaagtcg aggacacctt gactcgtttc acaaattcag tcttgaatca caaagacgtc    2220
cttaactcta gctcatctga tcaagatact ttgagaagag agtttagaac attcatgcac    2280
gctcatataa cacaaatcga agataactca cgattcagta agcaagcctc atccgatgcg    2340
ttttcctctc ctgaacaatc ttactttcaa tgggtgaact caactggtgg ctcacatgtc    2400
gcttgcgcct attcatttgc cttctctaat tgcctcatgt ctgcaaattt gttgcagggt    2460
aaagacgcat ttccaagcgg aacgcaaaag tacttaatct cctctgttat gagacatgcc    2520
acaaacatgt gtagaatgta taacgacttt ggctctattg ccagagacaa cgctgagaga    2580
aatgttaata gtattcattt tcctgagttt actctctgta acggaacttc tcaaaaccta    2640
gatgaaagga aggaaagact tctgaaaatc gcaacttacg aacaagggta tttgatagaa    2700
gcactagagg ccttggaaag acagagtaga gatgatgccg gagacagagc tggatctaaa    2760
gatatgagaa agttgaaaat cgttaagtta ttctgtgatg ttacggactt atacgatcag    2820
ctctacgtta tcaaagattt gtcatcctct atgaagtaa                           2859
```

<210> SEQ ID NO 58
<211> LENGTH: 952
<212> TYPE: PRT
<213> ORGANISM: Gibberella fujikuroi

<400> SEQUENCE: 58

```
Met Pro Gly Lys Ile Glu Asn Gly Thr Pro Lys Asp Leu Lys Thr Gly
1               5                   10                  15

Asn Asp Phe Val Ser Ala Ala Lys Ser Leu Leu Asp Arg Ala Phe Lys
            20                  25                  30

Ser His His Ser Tyr Tyr Gly Leu Cys Ser Thr Ser Cys Gln Val Tyr
        35                  40                  45

Asp Thr Ala Trp Val Ala Met Ile Pro Lys Thr Arg Asp Asn Val Lys
```

-continued

```
                 50                  55                  60
Gln Trp Leu Phe Pro Glu Cys Phe His Tyr Leu Leu Lys Thr Gln Ala
 65                  70                  75                  80

Ala Asp Gly Ser Trp Gly Ser Leu Pro Thr Thr Gln Thr Ala Gly Ile
                 85                  90                  95

Leu Asp Thr Ala Ser Ala Val Leu Ala Leu Leu Cys His Ala Gln Glu
                100                 105                 110

Pro Leu Gln Ile Leu Asp Val Ser Pro Asp Glu Met Gly Leu Arg Ile
                115                 120                 125

Glu His Gly Val Thr Ser Leu Lys Arg Gln Leu Ala Val Trp Asn Asp
                130                 135                 140

Val Glu Asp Thr Asn His Ile Gly Val Glu Phe Ile Ile Pro Ala Leu
145                 150                 155                 160

Leu Ser Met Leu Glu Lys Glu Leu Asp Val Pro Ser Phe Glu Phe Pro
                165                 170                 175

Cys Arg Ser Ile Leu Glu Arg Met His Gly Glu Lys Leu Gly His Phe
                180                 185                 190

Asp Leu Glu Gln Val Tyr Gly Lys Pro Ser Ser Leu Leu His Ser Leu
                195                 200                 205

Glu Ala Phe Leu Gly Lys Leu Asp Phe Asp Arg Leu Ser His His Leu
                210                 215                 220

Tyr His Gly Ser Met Met Ala Ser Pro Ser Ser Thr Ala Ala Tyr Leu
225                 230                 235                 240

Ile Gly Ala Thr Lys Trp Asp Asp Glu Ala Glu Asp Tyr Leu Arg His
                245                 250                 255

Val Met Arg Asn Gly Ala Gly His Gly Asn Gly Gly Ile Ser Gly Thr
                260                 265                 270

Phe Pro Thr Thr His Phe Glu Cys Ser Trp Ile Ile Ala Thr Leu Leu
                275                 280                 285

Lys Val Gly Phe Thr Leu Lys Gln Ile Asp Gly Asp Gly Leu Arg Gly
                290                 295                 300

Leu Ser Thr Ile Leu Leu Glu Ala Leu Arg Asp Glu Asn Gly Val Ile
305                 310                 315                 320

Gly Phe Ala Pro Arg Thr Ala Asp Val Asp Thr Ala Lys Ala Leu
                325                 330                 335

Leu Ala Leu Ser Leu Val Asn Gln Pro Val Ser Pro Asp Ile Met Ile
                340                 345                 350

Lys Val Phe Glu Gly Lys Asp His Phe Thr Thr Phe Gly Ser Glu Arg
                355                 360                 365

Asp Pro Ser Leu Thr Ser Asn Leu His Val Leu Leu Ser Leu Leu Lys
370                 375                 380

Gln Ser Asn Leu Ser Gln Tyr His Pro Gln Ile Leu Lys Thr Thr Leu
385                 390                 395                 400

Phe Thr Cys Arg Trp Trp Trp Gly Ser Asp His Cys Val Lys Asp Lys
                405                 410                 415

Trp Asn Leu Ser His Leu Tyr Pro Thr Met Leu Leu Val Glu Ala Phe
                420                 425                 430

Thr Glu Val Leu His Leu Ile Asp Gly Glu Leu Ser Ser Leu Phe
                435                 440                 445

Asp Glu Ser Phe Lys Cys Lys Ile Gly Leu Ser Ile Phe Gln Ala Val
                450                 455                 460

Leu Arg Ile Ile Leu Thr Gln Asp Asn Asp Gly Ser Trp Arg Gly Tyr
465                 470                 475                 480
```

```
Arg Glu Gln Thr Cys Tyr Ala Ile Leu Ala Leu Val Gln Ala Arg His
                485                 490                 495

Val Cys Phe Phe Thr His Met Val Asp Arg Leu Gln Ser Cys Val Asp
                500                 505                 510

Arg Gly Phe Ser Trp Leu Lys Ser Cys Ser Phe His Ser Gln Asp Leu
                515                 520                 525

Thr Trp Thr Ser Lys Thr Ala Tyr Glu Val Gly Phe Val Ala Glu Ala
        530                 535                 540

Tyr Lys Leu Ala Ala Leu Gln Ser Ala Ser Leu Glu Val Pro Ala Ala
545                 550                 555                 560

Thr Ile Gly His Ser Val Thr Ser Ala Val Pro Ser Ser Asp Leu Glu
                565                 570                 575

Lys Tyr Met Arg Leu Val Arg Lys Thr Ala Leu Phe Ser Pro Leu Asp
                580                 585                 590

Glu Trp Gly Leu Met Ala Ser Ile Ile Glu Ser Ser Phe Phe Val Pro
                595                 600                 605

Leu Leu Gln Ala Gln Arg Val Glu Ile Tyr Pro Arg Asp Asn Ile Lys
        610                 615                 620

Val Asp Glu Asp Lys Tyr Leu Ser Ile Ile Pro Phe Thr Trp Val Gly
625                 630                 635                 640

Cys Asn Asn Arg Ser Arg Thr Phe Ala Ser Asn Arg Trp Leu Tyr Asp
                645                 650                 655

Met Met Tyr Leu Ser Leu Leu Gly Tyr Gln Thr Asp Glu Tyr Met Glu
                660                 665                 670

Ala Val Ala Gly Pro Val Phe Gly Asp Val Ser Leu Leu His Gln Thr
                675                 680                 685

Ile Asp Lys Val Ile Asp Asn Thr Met Gly Asn Leu Ala Arg Ala Asn
690                 695                 700

Gly Thr Val His Ser Gly Asn Gly His Gln His Glu Ser Pro Asn Ile
705                 710                 715                 720

Gly Gln Val Glu Asp Thr Leu Thr Arg Phe Thr Asn Ser Val Leu Asn
                725                 730                 735

His Lys Asp Val Leu Asn Ser Ser Ser Asp Gln Asp Thr Leu Arg
                740                 745                 750

Arg Glu Phe Arg Thr Phe Met His Ala His Ile Thr Gln Ile Glu Asp
        755                 760                 765

Asn Ser Arg Phe Ser Lys Gln Ala Ser Ser Asp Ala Phe Ser Ser Pro
770                 775                 780

Glu Gln Ser Tyr Phe Gln Trp Val Asn Ser Thr Gly Gly Ser His Val
785                 790                 795                 800

Ala Cys Ala Tyr Ser Phe Ala Phe Ser Asn Cys Leu Met Ser Ala Asn
                805                 810                 815

Leu Leu Gln Gly Lys Asp Ala Phe Pro Ser Gly Thr Gln Lys Tyr Leu
        820                 825                 830

Ile Ser Ser Val Met Arg His Ala Thr Asn Met Cys Arg Met Tyr Asn
        835                 840                 845

Asp Phe Gly Ser Ile Ala Arg Asp Asn Ala Glu Arg Asn Val Asn Ser
850                 855                 860

Ile His Phe Pro Glu Phe Thr Leu Cys Asn Gly Thr Ser Gln Asn Leu
865                 870                 875                 880

Asp Glu Arg Lys Glu Arg Leu Leu Lys Ile Ala Thr Tyr Glu Gln Gly
                885                 890                 895
```

Tyr Leu Asp Arg Ala Leu Glu Ala Leu Glu Arg Gln Ser Arg Asp Asp
            900                 905                 910

Ala Gly Asp Arg Ala Gly Ser Lys Asp Met Arg Lys Leu Lys Ile Val
        915                 920                 925

Lys Leu Phe Cys Asp Val Thr Asp Leu Tyr Asp Gln Leu Tyr Val Ile
    930                 935                 940

Lys Asp Leu Ser Ser Ser Met Lys
945                 950

<210> SEQ ID NO 59
<211> LENGTH: 1542
<212> TYPE: DNA
<213> ORGANISM: Artificial Sequence
<220> FEATURE:
<223> OTHER INFORMATION: Codon-optimized KO

<400> SEQUENCE: 59

```
atggatgctg tgacgggttt gttaactgtc ccagcaaccg ctataactat tggtggaact    60
gctgtagcat tggcggtagc gctaatcttt tggtacctga atcctacac atcagctaga   120
agatcccaat caaatcatct tccaagagtg cctgaagtcc caggtgttcc attgttagga   180
aatctgttac aattgaagga gaaaaagcca tacatgactt tacgagatgg gcagcgaca    240
tatggaccta tctatagtat caaaactggg gctacaagta tggttgtggt atcatctaat   300
gagatagcca aggaggcatt ggtgaccaga ttccaatcca tatctacaag gaacttatct   360
aaagccctga agtacttac agcagataag acaatggtcg caatgtcaga ttatgatgat   420
tatcataaaa cagttaagag acacatactg accgccgtct tgggtcctaa tgcacagaaa   480
aagcatagaa ttcacagaga tatcatgatg gataacatat ctactcaact tcatgaattc   540
gtgaaaaaca acccagaaca ggaagaggta gaccttagaa aaatctttca atctgagtta   600
ttcggcttag ctatgagaca agccttagga aaggatgttg aaagtttgta cgttgaagac   660
ctgaaaatca ctatgaatag agacgaaatc tttcaagtcc ttgttgttga tccaatgatg   720
ggagcaatcg atgttgattg gagagacttc tttccatacc taaagtgggt cccaaacaaa   780
aagttcgaaa atactattca acaaatgtac atcagaagag aagctgttat gaaatcttta   840
atcaaagagc acaaaaagag aatagcgtca ggcgaaaagc taaatagtta tatcgattac   900
cttttatctg aagctcaaac tttaaccgat cagcaactat tgatgtcctt gtgggaacca   960
atcattgaat cttcagatac aacaatggtc acaacagaat gggcaatgta cgaattagct  1020
aaaaaccctg aattgcaaga taggttgtac agagacatta gtccgtctg tggatctgaa  1080
aagataaccg aagagcatct atcacagctg ccttacatta cagctatttt ccacgaaaca  1140
ctgagaagac actcaccagt tcctatcatt cctctaagac atgtacatga agataccgtt  1200
ctaggcggct accatgttcc tgctggcaca gaacttgccg ttaacatcta cggttgcaac  1260
atggacaaaa acgtttggga aaatccagag gaatggaacc cagaaagatt catgaaagag  1320
aatgagacaa ttgattttca aaagacgatg gccttcggtg gtgtaagag agtttgtgct  1380
ggttccttgc aagccctttt aactgcatct attgggattg ggagaatggt tcaagagttc  1440
gaatggaaac tgaaggatat gactcaagag gaagtgaaca cgataggcct aactacacaa  1500
atgttaagac cattgagagc tattatcaaa cctaggatct aa                     1542
```

<210> SEQ ID NO 60
<211> LENGTH: 513
<212> TYPE: PRT
<213> ORGANISM: Stevia rebaudiana

<400> SEQUENCE: 60

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
210                 215                 220

Met Asn Arg Asp Glu Ile Phe Gln Val Leu Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365

Gln Leu Pro Tyr Ile Thr Ala Ile Phe His Glu Thr Leu Arg Arg His
370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile

```
            405                 410                 415
Tyr Gly Cys Asn Met Asp Lys Asn Val Trp Glu Asn Pro Glu Glu Trp
        420                 425                 430

Asn Pro Glu Arg Phe Met Lys Glu Asn Glu Thr Ile Asp Phe Gln Lys
        435                 440                 445

Thr Met Ala Phe Gly Gly Lys Arg Val Cys Ala Gly Ser Leu Gln
        450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
                500                 505                 510

Ile
```

<210> SEQ ID NO 61
<211> LENGTH: 1566
<212> TYPE: DNA
<213> ORGANISM: Artificial Sequence
<220> FEATURE:
<223> OTHER INFORMATION: Codon-optimized KO

<400> SEQUENCE: 61

```
aagcttacta gtaaaatgga cggtgtcatc gatatgcaaa ccattccatt gagaaccgct      60
attgctattg gtggtactgc tgttgctttg gttgttgcat tatactttg gttcttgaga     120
tcctacgctt ccccatctca tcattctaat catttgccac cagtacctga agttccaggt     180
gttccagttt tgggtaattt gttgcaattg aaagaaaaaa agccttacat gaccttcacc     240
aagtgggctg aaatgtatgg tccaatctac tctattagaa ctggtgctac ttccatggtt     300
gttgtctctt ctaacgaaat cgccaaagaa gttgttgtta ccagattccc atctatctct     360
accagaaaat tgtcttacgc cttgaaggtt ttgaccgaag ataagtctat ggttgccatg     420
tctgattatc acgattacca taagaccgtc aagagacata ttttgactgc tgttttgggt     480
ccaaacgccc aaaaaaagtt tagagcacat agagacacca tgatggaaaa cgtttccaat     540
gaattgcatg ccttcttcga aaagaaccca atcaagaag tcaacttgag aaagatcttc     600
caatcccaat tattcggttt ggctatgaag caagccttgg gtaaagatgt tgaatccatc     660
tacgttaagg atttggaaac caccatgaag agagaagaaa tcttcgaagt tttggttgtc     720
gatccaatga tgggtgctat tgaagttgat tggagagact ttttcccata cttgaaatgg     780
gttccaaaca gtccttcga aaacatcatc catagaatgt acactagaag agaagctgtt     840
atgaaggcct tgatccaaga acacaagaaa agaattgcct ccggtgaaaa cttgaactcc     900
tacattgatt acttgttgtc tgaagcccaa accttgaccg ataagcaatt attgatgtct     960
ttgtgggaac ctattatcga atcttctgat accactatgg ttactactga atgggctatg    1020
tacgaattgg ctaagaatcc aaacatgcaa gacagattat acgaagaaat ccaatccgtt    1080
tgcggttccg aaaagattac tgaagaaaac ttgtcccaat gccatactt gtacgctgtt    1140
ttccaagaaa ctttgagaaa gcactgtcca gttcctatta tgccattgag atatgttcac    1200
gaaaacaccg ttttgggtgg ttatcatgtt ccagctggta ctgaagttgc tattaacatc    1260
tacggttgca acatggataa gaaggtctgg gaaaatccag aagaatggaa tccagaaaga    1320
ttcttgtccg aaaagaatc catggacttg tacaaaacta tggcttttgg tggtggtaaa    1380
agagtttgcg ctggttcttt acaagccatg gttatttctt gcattggtat cggtagattg    1440
```

-continued

```
gtccaagatt ttgaatggaa gttgaaggat gatgccgaag aagatgttaa cactttgggt    1500
ttgactaccc aaaagttgca tccattattg gccttgatta acccaagaaa gtaactcgag    1560
ccgcgg                                                                1566
```

<210> SEQ ID NO 62
<211> LENGTH: 512
<212> TYPE: PRT
<213> ORGANISM: Lactuca sativa

<400> SEQUENCE: 62

```
Met Asp Gly Val Ile Asp Met Gln Thr Ile Pro Leu Arg Thr Ala Ile
1               5                   10                  15

Ala Ile Gly Gly Thr Ala Val Ala Leu Val Val Ala Leu Tyr Phe Trp
            20                  25                  30

Phe Leu Arg Ser Tyr Ala Ser Pro Ser His His Ser Asn His Leu Pro
        35                  40                  45

Pro Val Pro Glu Val Pro Gly Val Pro Val Leu Gly Asn Leu Leu Gln
    50                  55                  60

Leu Lys Glu Lys Lys Pro Tyr Met Thr Phe Thr Lys Trp Ala Glu Met
65                  70                  75                  80

Tyr Gly Pro Ile Tyr Ser Ile Arg Thr Gly Ala Thr Ser Met Val Val
                85                  90                  95

Val Ser Ser Asn Glu Ile Ala Lys Glu Val Val Thr Arg Phe Pro
            100                 105                 110

Ser Ile Ser Thr Arg Lys Leu Ser Tyr Ala Leu Lys Val Leu Thr Glu
        115                 120                 125

Asp Lys Ser Met Val Ala Met Ser Asp Tyr His Asp Tyr His Lys Thr
    130                 135                 140

Val Lys Arg His Ile Leu Thr Ala Val Leu Gly Pro Asn Ala Gln Lys
145                 150                 155                 160

Lys Phe Arg Ala His Arg Asp Thr Met Met Glu Asn Val Ser Asn Glu
                165                 170                 175

Leu His Ala Phe Phe Glu Lys Asn Pro Asn Gln Glu Val Asn Leu Arg
            180                 185                 190

Lys Ile Phe Gln Ser Gln Leu Phe Gly Leu Ala Met Lys Gln Ala Leu
        195                 200                 205

Gly Lys Asp Val Glu Ser Ile Tyr Val Lys Asp Leu Glu Thr Thr Met
    210                 215                 220

Lys Arg Glu Glu Ile Phe Glu Val Leu Val Asp Pro Met Met Gly
225                 230                 235                 240

Ala Ile Glu Val Asp Trp Arg Asp Phe Phe Pro Tyr Leu Lys Trp Val
                245                 250                 255

Pro Asn Lys Ser Phe Glu Asn Ile Ile His Arg Met Tyr Thr Arg Arg
            260                 265                 270

Glu Ala Val Met Lys Ala Leu Ile Gln Glu His Lys Lys Arg Ile Ala
        275                 280                 285

Ser Gly Glu Asn Leu Asn Ser Tyr Ile Asp Tyr Leu Leu Ser Glu Ala
    290                 295                 300

Gln Thr Leu Thr Asp Lys Gln Leu Leu Met Ser Leu Trp Glu Pro Ile
305                 310                 315                 320

Ile Glu Ser Ser Asp Thr Thr Met Val Thr Thr Glu Trp Ala Met Tyr
                325                 330                 335

Glu Leu Ala Lys Asn Pro Asn Met Gln Asp Arg Leu Tyr Glu Glu Ile
```

```
              340                 345                 350
Gln Ser Val Cys Gly Ser Glu Lys Ile Thr Glu Asn Leu Ser Gln
            355                 360                 365

Leu Pro Tyr Leu Tyr Ala Val Phe Gln Glu Thr Leu Arg Lys His Cys
        370                 375                 380

Pro Val Pro Ile Met Pro Leu Arg Tyr Val His Glu Asn Thr Val Leu
385                 390                 395                 400

Gly Gly Tyr His Val Pro Ala Gly Thr Glu Val Ala Ile Asn Ile Tyr
                405                 410                 415

Gly Cys Asn Met Asp Lys Lys Val Trp Glu Asn Pro Glu Glu Trp Asn
            420                 425                 430

Pro Glu Arg Phe Leu Ser Glu Lys Glu Ser Met Asp Leu Tyr Lys Thr
        435                 440                 445

Met Ala Phe Gly Gly Gly Lys Arg Val Cys Ala Gly Ser Leu Gln Ala
    450                 455                 460

Met Val Ile Ser Cys Ile Gly Ile Gly Arg Leu Val Gln Asp Phe Glu
465                 470                 475                 480

Trp Lys Leu Lys Asp Asp Ala Glu Glu Asp Val Asn Thr Leu Gly Leu
                485                 490                 495

Thr Thr Gln Lys Leu His Pro Leu Leu Ala Leu Ile Asn Pro Arg Lys
            500                 505                 510
```

<210> SEQ ID NO 63
<211> LENGTH: 1535
<212> TYPE: DNA
<213> ORGANISM: Rubus suavissimus

<400> SEQUENCE: 63

```
atggccaccc tccttgagca tttccaagct atgccctttg ccatccctat tgcactggct    60
gctctgtctt ggctgttcct cttttacatc aaagtttcat tcttttccaa caagagtgct   120
caggctaagc tccctcctgt gccagtggtt cctgggctgc cggtgattgg gaatttactg   180
caactcaagg agaagaaacc ctaccagact tttacaaggt gggctgagga gtatggacca   240
atctattcta tcaggactgg tgcttccacc atggtcgttc tcaataccac ccaagttgca   300
aaagaggcca tggtgaccag atatttatcc atctcaacca gaaagctatc aaacgcacta   360
aagattctta ctgctgataa atgtatggtt gcaataagtg actacaacga tttttcacaag   420
atgataaagc gatacatact ctcaaatgtt cttggaccta gtgctcagaa gcgtcaccgg   480
agcaacagag ataccttgag agctaatgtc tgcagccgat tgcattctca gtaaagaaac   540
tctcctcgag aagctgtgaa tttcagaaga gttttttgagt gggaactctt tggaattgca   600
ttgaagcaag cctttgggaaa ggacatagaa aagcccattt atgtggagga acttggcact   660
acactgtcaa gagatgagat ctttaaggtt ctagtgcttg acataatgga gggtgcaatt   720
gaggttgatt ggagagattt cttcccttac ctgagatgga ttccgaatac gcgcatggaa   780
acaaaaattc agcgactcta tttccgcagg aaagcagtga tgactgccct gatcaacgag   840
cagaagaagc gaattgcttc aggagaggaa atcaactgtt atatcgactt cttgcttaag   900
gaagggaaga cactgacaat ggaccaaata agtatgttgc tttgggagac ggttattgaa   960
acagcagata ctacaatggt aacgacagaa tgggctatgt atgaagttgc taaagactca  1020
aagcgtcagg atcgtctcta tcaggaaatc caaaaggttt gtggatcgga tggttaca    1080
gaggaatact tgtcccaact gccgtacctg aatgcagttt ccatgaaac gctaaggaag   1140
cacagtccgg ctgcgttagt tcctttaaga tatgcacatg aagatacccca actaggaggt  1200
```

```
tactacattc cagctggaac tgagattgct ataaacatat acgggtgtaa catggacaag    1260
catcaatggg aaagccctga ggaatggaaa ccggagagat ttttggaccc gaaatttgat    1320
cctatggatt tgtacaagac catggctttt ggggctggaa agagggtatg tgctggttct    1380
cttcaggcaa tgttaatagc gtgcccgacg attggtaggc tggtgcagga gtttgagtgg    1440
aagctgagag atggagaaga agaaaatgta gatactgttg ggctcaccac tcacaaacgc    1500
tatccaatgc atgcaatcct gaagccaaga agtta                              1535
```

<210> SEQ ID NO 64
<211> LENGTH: 1536
<212> TYPE: DNA
<213> ORGANISM: Artificial Sequence
<220> FEATURE:
<223> OTHER INFORMATION: Codon-optimized KO

<400> SEQUENCE: 64

```
atggctacct tgttggaaca ttttcaagct atgccattcg ctattccaat tgctttggct      60
gctttgtctt ggttgttttt gttctacatc aaggtttctt tcttctccaa caaatccgct    120
caagctaaat tgccaccagt tccagttgtt ccaggtttgc cagttattgg taatttgttg    180
caattgaaag aaaagaagcc ataccaaacc ttcactagat gggctgaaga atatggtcca    240
atctactcta ttagaactgg tgcttctact atggttgtct tgaacactac tcaagttgcc    300
aaagaagcta tggttaccag atacttgtct atctctacca gaaagttgtc caacgccttg    360
aaaattttga ccgctgataa gtgcatggtt gccatttctg attacaacga tttccacaag    420
atgatcaaga gatatatctt gtctaacgtt ttgggtccat ctgcccaaaa aagacataga    480
tctaacagag ataccttgag agccaacgtt tgttctagat tgcattccca agttaagaac    540
tctccaagag aagctgtcaa ctttagaaga gttttcgaat gggaattatt cggtatcgct    600
ttgaaacaag ccttcggtaa ggatattgaa aagccaatct acgtcgaaga attgggtact    660
actttgtcca gagatgaaat cttcaaggtt ttggtcttgg acattatgga aggtgccatt    720
gaagttgatt ggagagattt tttcccatac ttgcgttgga ttccaaacac cagaatggaa    780
actaagatcc aaagattata ctttagaaga aaggccgtta tgaccgcctt gattaacgaa    840
caaaagaaaa gaattgcctc cggtgaagaa atcaactgct acatcgattt cttgttgaaa    900
gaaggtaaga ccctgaccat ggaccaaatc tctatgttgt tgtgggaaac cgttattgaa    960
actgctgata ccacaatggt tactactgaa tgggctatgt acgaagttgc taaggattct    1020
aaaagacaag acagattata ccaagaaatc caaaggtct gcggttctga atggttaca     1080 gaagaatact tgtcccaatt gccatacttg aatgctgttt ccacgaaac tttgagaaaa    1140 cattctccag ctgctttggt tccattgaga tatgctcatg aagatactca attgggtggt    1200
tattacattc cagccggtac tgaaattgcc attaacatct acggttgcaa catggacaaa    1260
caccaatggg aatctccaga agaatggaag ccagaaagat tttggatcc taagtttgac     1320 ccaatggact tgtacaaaac tatggctttt ggtgctggta aaagagtttg cgctggttct    1380
ttacaagcta tgttgattgc ttgtccaacc atcggtagat ggttcaaga atttgaatgg     1440 aagttgagag atggtgaaga agaaaacgtt gatactgttg gtttgaccac ccataagaga    1500
tatccaatgc atgctatttt gaagccaaga tcttaa                              1536
```

<210> SEQ ID NO 65
<211> LENGTH: 1572
<212> TYPE: DNA

<213> ORGANISM: Artificial Sequence
<220> FEATURE:
<223> OTHER INFORMATION: Codon-optimized KO

<400> SEQUENCE: 65

```
aagcttacta gtaaaatggc ctccatcacc catttcttac aagattttca agctactcca      60
ttcgctactg cttttgctgt tggtggtgtt tctttgttga tattcttctt cttcatccgt     120
ggtttccact ctactaagaa aaacgaatat acaagttgc caccagttcc agttgttcca      180
ggtttgccag ttgttggtaa tttgttgcaa ttgaaagaaa gaagccata caagactttc      240
ttgagatggg ctgaaattca tggtccaatc tactctatta gaactggtgc ttctaccatg     300
gttgttgtta actctactca tgttgccaaa gaagctatgg ttaccagatt ctcttcaatc     360
tctaccagaa agttgtccaa ggctttggaa ttattgacct ccaacaaatc tatggttgcc     420
acctctgatt acaacgaatt tcacaagatg gtcaagaagt acatcttggc cgaattattg     480
ggtgctaatg ctcaaaagag acacagaatt catagacca ccttgatcga aacgtcttg      540
aacaaattgc atgcccatac caagaattct ccattgcaag ctgttaactt cagaaagatc     600
ttcgaatctg aattattcgg tttggctatg aagcaagcct tgggttatga tgttgattcc     660
ttgttcgttg aagaattggg tactaccttg tccagagaag aaatctacaa cgttttggtc     720
agtgacatgt gaagggtgc tattgaagtt gattggagag acttttttccc atacttgaaa     780
tggatcccaa acaagtcctt cgaaatgaag attcaaagat tggcctctag aagacaagcc     840
gttatgaact ctattgtcaa agaacaaaag aagtccattg cctctggtaa gggtgaaaac     900
tgttacttga attacttgtt gtccgaagct aagactttga ccgaaaagca aatttccatt     960
ttggcctggg aaaccattat tgaaactgct gatacaactg ttgttaccac tgaatgggct    1020
atgtacgaat tggctaaaaa cccaaagcaa caagacagat tatacaacga aatccaaaac    1080
gtctgcggta ctgataagat taccgaagaa catttgtcca gttgccttaa cttgtctgct    1140
gttttttcacg aaaccttgag aaagtattct ccatctccat tggttccatt gagatacgct    1200
catgaagata ctcaattggg tggttattat gttccagccg gtactgaaat tgctgttaat    1260
atctacggtt gcaacatgga caagaatcaa tgggaaactc cagaagaatg gaagccagaa    1320
agattttttgg acgaaaagta cgatccaatg gacatgtaca agactatgtc ttttggttcc    1380
ggtaaaagag tttgcgctgg ttctttacaa gctagtttga ttgcttgtac ctccatcggt    1440
agattggttc aagaatttga atggagattg aaagacggtg aagttgaaaa cgttgatacc    1500
ttgggtttga ctaccataa gttgtatcca atgcaagcta tcttgcaacc tagaaactga    1560
ctcgagccgc gg                                                        1572
```

<210> SEQ ID NO 66
<211> LENGTH: 514
<212> TYPE: PRT
<213> ORGANISM: Castanea mollissima

<400> SEQUENCE: 66

```
Met Ala Ser Ile Thr His Phe Leu Gln Asp Phe Gln Ala Thr Pro Phe
1               5                   10                  15

Ala Thr Ala Phe Ala Val Gly Gly Val Ser Leu Leu Ile Phe Phe Phe
            20                  25                  30

Phe Ile Arg Gly Phe His Ser Thr Lys Lys Asn Glu Tyr Tyr Lys Leu
        35                  40                  45

Pro Pro Val Pro Val Val Pro Gly Leu Pro Val Val Gly Asn Leu Leu
    50                  55                  60
```

-continued

```
Gln Leu Lys Glu Lys Lys Pro Tyr Lys Thr Phe Leu Arg Trp Ala Glu
 65                  70                  75                  80

Ile His Gly Pro Ile Tyr Ser Ile Arg Thr Gly Ala Ser Thr Met Val
                 85                  90                  95

Val Val Asn Ser Thr His Val Ala Lys Glu Ala Met Val Thr Arg Phe
            100                 105                 110

Ser Ser Ile Ser Thr Arg Lys Leu Ser Lys Ala Leu Glu Leu Leu Thr
        115                 120                 125

Ser Asn Lys Ser Met Val Ala Thr Ser Asp Tyr Asn Glu Phe His Lys
130                 135                 140

Met Val Lys Lys Tyr Ile Leu Ala Glu Leu Leu Gly Ala Asn Ala Gln
145                 150                 155                 160

Lys Arg His Arg Ile His Arg Asp Thr Leu Ile Glu Asn Val Leu Asn
                165                 170                 175

Lys Leu His Ala His Thr Lys Asn Ser Pro Leu Gln Ala Val Asn Phe
            180                 185                 190

Arg Lys Ile Phe Glu Ser Glu Leu Phe Gly Leu Ala Met Lys Gln Ala
        195                 200                 205

Leu Gly Tyr Asp Val Asp Ser Leu Phe Val Glu Glu Leu Gly Thr Thr
210                 215                 220

Leu Ser Arg Glu Glu Ile Tyr Asn Val Leu Val Ser Asp Met Leu Lys
225                 230                 235                 240

Gly Ala Ile Glu Val Asp Trp Arg Asp Phe Phe Pro Tyr Leu Lys Trp
                245                 250                 255

Ile Pro Asn Lys Ser Phe Glu Met Lys Ile Gln Arg Leu Ala Ser Arg
            260                 265                 270

Arg Gln Ala Val Met Asn Ser Ile Val Lys Glu Gln Lys Lys Ser Ile
        275                 280                 285

Ala Ser Gly Lys Gly Glu Asn Cys Tyr Leu Asn Tyr Leu Leu Ser Glu
290                 295                 300

Ala Lys Thr Leu Thr Glu Lys Gln Ile Ser Ile Leu Ala Trp Glu Thr
305                 310                 315                 320

Ile Ile Glu Thr Ala Asp Thr Thr Val Val Thr Thr Gly Trp Ala Met
                325                 330                 335

Tyr Glu Leu Ala Lys Asn Pro Lys Gln Gln Asp Arg Leu Tyr Asn Glu
            340                 345                 350

Ile Gln Asn Val Cys Gly Thr Asp Lys Ile Thr Glu Glu His Leu Ser
        355                 360                 365

Lys Leu Pro Tyr Leu Ser Ala Val Phe His Glu Thr Leu Arg Lys Tyr
370                 375                 380

Ser Pro Ser Pro Leu Val Pro Leu Arg Tyr Ala His Glu Asp Thr Gln
385                 390                 395                 400

Leu Gly Gly Tyr Tyr Val Pro Ala Gly Thr Glu Ile Ala Val Asn Ile
                405                 410                 415

Tyr Gly Cys Asn Met Asp Lys Asn Gln Trp Glu Thr Pro Glu Glu Trp
            420                 425                 430

Lys Pro Glu Arg Phe Leu Asp Glu Lys Tyr Asp Pro Met Asp Met Tyr
        435                 440                 445

Lys Thr Met Ser Phe Gly Ser Gly Lys Arg Val Cys Ala Gly Ser Leu
450                 455                 460

Gln Ala Ser Leu Ile Ala Cys Thr Ser Ile Gly Arg Leu Val Gln Glu
465                 470                 475                 480
```

Phe Glu Trp Arg Leu Lys Asp Gly Glu Val Glu Asn Val Asp Thr Leu
            485                 490                 495

Gly Leu Thr Thr His Lys Leu Tyr Pro Met Gln Ala Ile Leu Gln Pro
        500                 505                 510

Arg Asn

<210> SEQ ID NO 67
<211> LENGTH: 1512
<212> TYPE: DNA
<213> ORGANISM: Artificial Sequence
<220> FEATURE:
<223> OTHER INFORMATION: Codon-optimized KO

<400> SEQUENCE: 67

| | | | | | |
|---|---|---|---|---|---|
| atgatttcct | tgttgttggg | ttttgttgtc | tcctccttct | tgtttatctt | cttcttgaaa | 60 |
| aaattgttgt | tcttcttcag | tcgtcacaaa | atgtccgaag | tttctagatt | gccatctgtt | 120 |
| ccagttccag | gttttccatt | gattggtaac | ttgttgcaat | tgaaagaaaa | gaagccacac | 180 |
| aagactttca | ccaagtggtc | tgaattatat | ggtccaatct | actctatcaa | gatgggttcc | 240 |
| tcttctttga | tcgtcttgaa | ctctattgaa | accgccaaag | aagctatggt | cagtagattc | 300 |
| tcttcaatct | ctaccagaaa | gttgtctaac | gctttgactg | ttttgacctg | caacaaatct | 360 |
| atggttgcta | cctctgatta | cgatgacttt | cataagttcg | tcaagagatg | cttgttgaac | 420 |
| ggtttgttgg | gtgctaatgc | tcaagaaaga | aaaagacatt | acagagatgc | cttgatcgaa | 480 |
| aacgttacct | ctaaattgca | tgcccatacc | agaaatcatc | cacaagaacc | agttaacttc | 540 |
| agagccattt | tcgaacacga | attattcggt | gttgctttga | acaagccttt | cggtaaagat | 600 |
| gtcgaatcca | tctatgtaaa | agaattgggt | gtcaccttgt | ccagagatga | attttcaag | 660 |
| gttttggtcc | acgacatgat | ggaaggtgct | attgatgttg | attggagaga | tttcttccca | 720 |
| tacttgaaat | ggatcccaaa | caactctttc | gaagccagaa | ttcaacaaaa | gcacaagaga | 780 |
| agattggctg | ttatgaacgc | cttgatccaa | gacagattga | atcaaaacga | ttccgaatcc | 840 |
| gatgatgact | gctacttgaa | tttcttgatg | tctgaagcta | agaccttgac | catggaacaa | 900 |
| attgctatt | tggtttggga | aaccattatc | gaaactgctg | ataccacttt | ggttactact | 960 |
| gaatgggcta | tgtacgaatt | ggccaaacat | caatctgttc | aagatagatt | attcaaagaa | 1020 |
| atccaatccg | tctgcggtgg | tgaaaagatc | aagaagaac | aattgccaag | attgccttac | 1080 |
| gtcaatggtg | tttttcacga | aaccttgaga | agtattctc | cagctccatt | ggttccaatt | 1140 |
| agatacgctc | atgaagatac | ccaaattggt | ggttatcata | ttccagccgg | ttctgaaatt | 1200 |
| gccattaaca | tctacggttg | caacatggat | aagaagagat | gggaaagacc | tgaagaatgg | 1260 |
| tggccagaaa | gattttttgga | agatagatac | gaatcctccg | acttgcataa | gactatggct | 1320 |
| tttggtgctg | gtaaaagagt | ttgtgctggt | gctttacaag | ctagtttgat | ggctggtatt | 1380 |
| gctatcggta | gattggttca | agaattcgaa | tggaagttga | gagatggtga | agaagaaaac | 1440 |
| gttgatactt | acggtttgac | ctcccaaaag | ttgtatccat | tgatggccat | tatcaaccca | 1500 |
| agaagatctt | aa | | | | | 1512 |

<210> SEQ ID NO 68
<211> LENGTH: 506
<212> TYPE: PRT
<213> ORGANISM: Thellungiella halophila

<400> SEQUENCE: 68

Met Ala Ser Met Ile Ser Leu Leu Leu Gly Phe Val Val Ser Ser Phe

-continued

```
1               5                   10                  15
Leu Phe Ile Phe Phe Leu Lys Lys Leu Leu Phe Phe Ser Arg His
                20                  25                  30
Lys Met Ser Glu Val Ser Arg Leu Pro Ser Val Pro Val Pro Gly Phe
            35                  40                  45
Pro Leu Ile Gly Asn Leu Leu Gln Leu Lys Glu Lys Pro His Lys
    50                  55                  60
Thr Phe Thr Lys Trp Ser Glu Leu Tyr Gly Pro Ile Tyr Ser Ile Lys
65                  70                  75                  80
Met Gly Ser Ser Leu Ile Val Leu Asn Ser Ile Glu Thr Ala Lys
                85                  90                  95
Glu Ala Met Val Ser Arg Phe Ser Ser Ile Ser Thr Arg Lys Leu Ser
            100                 105                 110
Asn Ala Leu Thr Val Leu Thr Cys Asn Lys Ser Met Val Ala Thr Ser
                115                 120                 125
Asp Tyr Asp Asp Phe His Lys Phe Val Lys Arg Cys Leu Leu Asn Gly
            130                 135                 140
Leu Leu Gly Ala Asn Ala Gln Glu Arg Lys Arg His Tyr Arg Asp Ala
145                 150                 155                 160
Leu Ile Glu Asn Val Thr Ser Lys Leu His Ala His Thr Arg Asn His
                165                 170                 175
Pro Gln Glu Pro Val Asn Phe Arg Ala Ile Phe Glu His Glu Leu Phe
            180                 185                 190
Gly Val Ala Leu Lys Gln Ala Phe Gly Lys Asp Val Glu Ser Ile Tyr
            195                 200                 205
Val Lys Glu Leu Gly Val Thr Leu Ser Arg Asp Glu Ile Phe Lys Val
    210                 215                 220
Leu Val His Asp Met Met Glu Gly Ala Ile Asp Val Asp Trp Arg Asp
225                 230                 235                 240
Phe Phe Pro Tyr Leu Lys Trp Ile Pro Asn Asn Ser Phe Glu Ala Arg
                245                 250                 255
Ile Gln Gln Lys His Lys Arg Arg Leu Ala Val Met Asn Ala Leu Ile
                260                 265                 270
Gln Asp Arg Leu Asn Gln Asn Asp Ser Glu Ser Asp Asp Cys Tyr
            275                 280                 285
Leu Asn Phe Leu Met Ser Glu Ala Lys Thr Leu Thr Met Glu Gln Ile
            290                 295                 300
Ala Ile Leu Val Trp Glu Thr Ile Ile Glu Thr Ala Asp Thr Thr Leu
305                 310                 315                 320
Val Thr Thr Glu Trp Ala Met Tyr Glu Leu Ala Lys His Gln Ser Val
                325                 330                 335
Gln Asp Arg Leu Phe Lys Glu Ile Gln Ser Val Cys Gly Gly Glu Lys
            340                 345                 350
Ile Lys Glu Glu Gln Leu Pro Arg Leu Pro Tyr Val Asn Gly Val Phe
    355                 360                 365
His Glu Thr Leu Arg Lys Tyr Ser Pro Ala Pro Leu Val Pro Ile Arg
    370                 375                 380
Tyr Ala His Glu Asp Thr Gln Ile Gly Gly Tyr His Ile Pro Ala Gly
385                 390                 395                 400
Ser Glu Ile Ala Ile Asn Ile Tyr Gly Cys Asn Met Asp Lys Lys Arg
            405                 410                 415
Trp Glu Arg Pro Glu Glu Trp Trp Pro Glu Arg Phe Leu Glu Asp Arg
            420                 425                 430
```

```
Tyr Glu Ser Ser Asp Leu His Lys Thr Met Ala Phe Gly Ala Gly Lys
            435                 440                 445

Arg Val Cys Ala Gly Ala Leu Gln Ala Ser Leu Met Ala Gly Ile Ala
    450                 455                 460

Ile Gly Arg Leu Val Gln Glu Phe Glu Trp Lys Leu Arg Asp Gly Glu
465                 470                 475                 480

Glu Glu Asn Val Asp Thr Tyr Gly Leu Thr Ser Gln Lys Leu Tyr Pro
                485                 490                 495

Leu Met Ala Ile Ile Asn Pro Arg Arg Ser
            500                 505

<210> SEQ ID NO 69
<211> LENGTH: 1554
<212> TYPE: DNA
<213> ORGANISM: Artificial Sequence
<220> FEATURE:
<223> OTHER INFORMATION: Codon-optimized KO

<400> SEQUENCE: 69
aagcttacta gtaaaatgga catgatgggt attgaagctg ttccatttgc tactgctgtt        60
gttttgggtg gtatttcctt ggttgttttg atcttcatca gaagattcgt ttccaacaga      120
aagagatccg ttgaaggttt gccaccagtt ccagatattc aggtttacc attgattggt       180
aacttgttgc aattgaaaga aaagaagcca cataagacct tgctagatg ggctgaaact        240
tacggtccaa ttttctctat tagaactggt gcttctacca tgatcgtctt gaattcttct      300
gaagttgcca agaagctat ggtcactaga ttctcttcaa tctctaccag aaagttgtcc        360
aacgccttga agattttgac cttcgataag tgtatggttg ccacctctga ttacaacgat      420
tttcacaaaa tggtcaaggg tttcatcttg agaaacgttt aggtgctcc agcccaaaaa       480
agacatagat gtcatagaga taccttgatc gaaaacatct ctaagtactt gcatgcccat      540
gttaagactt ctccattgga accagttgtc ttgaagaaga ttttcgaatc cgaaattttc      600
ggtttggctt tgaaacaagc cttgggtaag gatatcgaat ccatctatgt tgaagaattg      660
ggtactacct tgtccagaga agaaattttt gccgttttgg ttgttgatcc aatggctggt      720
gctattgaag ttgattggag agattttttc ccatacttgt cctggattcc aaacaagtct      780
atggaaatga gatccaaag aatggatttt agaagaggtg ctttgatgaa ggccttgatt       840
ggtgaacaaa agaaaagaat cggttccggt gaagaaaaga ctcctacat tgatttcttg       900
ttgtctgaag ctaccacttt gaccgaaaag caaattgcta tgttgatctg gaaaccatc       960
atcgaaattt ccgatacaac tttggttacc tctgaatggg ctatgtacga attggctaaa     1020
gacccaaata gacaagaaat cttgtacaga gaaatccaca aggtttgcgg ttctaacaag     1080
ttgactgaag aaaacttgtc caagttgcca tacttgaact ctgttttcca cgaaaccttg     1140
agaaagtatt ctccagctcc aatggttcca gttagatatg ctcatgaaga tactcaattg     1200
ggtggttacc atattccagc tggttctcaa attgccatta acatctacgg ttgcaacatg     1260
aacaaaaagc aatgggaaaa tcctgaagaa tggaagccag aaagattctt ggacgaaaag     1320
tatgacttga tggacttgca taagactatg gcttttggtg gtggtaaaag agtttgtgct     1380
ggtgctttac aagcaatgtt gattgcttgc acttccatcg gtagattcgt tcaagaattt     1440
gaatggaagt tgatgggtgg tgaagaagaa aacgttgata ctgttgcttt gacctcccaa     1500
aaattgcatc caatgcaagc cattattaag gccagagaat gactcgagcc gcgg           1554
```

<210> SEQ ID NO 70
<211> LENGTH: 508
<212> TYPE: PRT
<213> ORGANISM: Vitis vinifera

<400> SEQUENCE: 70

```
Met Asp Met Met Gly Ile Glu Ala Val Pro Phe Ala Thr Ala Val Val
1               5                   10                  15

Leu Gly Gly Ile Ser Leu Val Val Leu Ile Phe Ile Arg Arg Phe Val
            20                  25                  30

Ser Asn Arg Lys Arg Ser Val Glu Gly Leu Pro Pro Val Pro Asp Ile
        35                  40                  45

Pro Gly Leu Pro Leu Ile Gly Asn Leu Leu Gln Leu Lys Glu Lys Lys
50                  55                  60

Pro His Lys Thr Phe Ala Arg Trp Ala Glu Thr Tyr Gly Pro Ile Phe
65                  70                  75                  80

Ser Ile Arg Thr Gly Ala Ser Thr Met Ile Val Leu Asn Ser Ser Glu
                85                  90                  95

Val Ala Lys Glu Ala Met Val Thr Arg Phe Ser Ser Ile Ser Thr Arg
            100                 105                 110

Lys Leu Ser Asn Ala Leu Lys Ile Leu Thr Phe Asp Lys Cys Met Val
        115                 120                 125

Ala Thr Ser Asp Tyr Asn Asp Phe His Lys Met Val Lys Gly Phe Ile
130                 135                 140

Leu Arg Asn Val Leu Gly Ala Pro Ala Gln Lys Arg His Arg Cys His
145                 150                 155                 160

Arg Asp Thr Leu Ile Glu Asn Ile Ser Lys Tyr Leu His Ala His Val
                165                 170                 175

Lys Thr Ser Pro Leu Glu Pro Val Val Leu Lys Lys Ile Phe Glu Ser
            180                 185                 190

Glu Ile Phe Gly Leu Ala Leu Lys Gln Ala Leu Gly Lys Asp Ile Glu
        195                 200                 205

Ser Ile Tyr Val Glu Glu Leu Gly Thr Thr Leu Ser Arg Glu Glu Ile
210                 215                 220

Phe Ala Val Leu Val Asp Pro Met Ala Gly Ala Ile Glu Val Asp
225                 230                 235                 240

Trp Arg Asp Phe Phe Pro Tyr Leu Ser Trp Ile Pro Asn Lys Ser Met
                245                 250                 255

Glu Met Lys Ile Gln Arg Met Asp Phe Arg Arg Gly Ala Leu Met Lys
            260                 265                 270

Ala Leu Ile Gly Glu Gln Lys Lys Arg Ile Gly Ser Gly Glu Lys
        275                 280                 285

Asn Ser Tyr Ile Asp Phe Leu Leu Ser Glu Ala Thr Thr Leu Thr Glu
290                 295                 300

Lys Gln Ile Ala Met Leu Ile Trp Glu Thr Ile Ile Glu Ile Ser Asp
305                 310                 315                 320

Thr Thr Leu Val Thr Ser Glu Trp Ala Met Tyr Glu Leu Ala Lys Asp
                325                 330                 335

Pro Asn Arg Gln Glu Ile Leu Tyr Arg Glu Ile His Lys Val Cys Gly
            340                 345                 350

Ser Asn Lys Leu Thr Glu Glu Asn Leu Ser Lys Leu Pro Tyr Leu Asn
        355                 360                 365

Ser Val Phe His Glu Thr Leu Arg Lys Tyr Ser Pro Ala Pro Met Val
370                 375                 380
```

```
Pro Val Arg Tyr Ala His Glu Asp Thr Gln Leu Gly Gly Tyr His Ile
385                 390                 395                 400

Pro Ala Gly Ser Gln Ile Ala Ile Asn Ile Tyr Gly Cys Asn Met Asn
                405                 410                 415

Lys Lys Gln Trp Glu Asn Pro Glu Trp Lys Pro Glu Arg Phe Leu
            420                 425                 430

Asp Glu Lys Tyr Asp Leu Met Asp Leu His Lys Thr Met Ala Phe Gly
        435                 440                 445

Gly Gly Lys Arg Val Cys Ala Gly Ala Leu Gln Ala Met Leu Ile Ala
    450                 455                 460

Cys Thr Ser Ile Gly Arg Phe Val Gln Glu Phe Glu Trp Lys Leu Met
465                 470                 475                 480

Gly Gly Glu Glu Glu Asn Val Asp Thr Val Ala Leu Thr Ser Gln Lys
                485                 490                 495

Leu His Pro Met Gln Ala Ile Ile Lys Ala Arg Glu
            500                 505
```

<210> SEQ ID NO 71
<211> LENGTH: 1593
<212> TYPE: DNA
<213> ORGANISM: Artificial Sequence
<220> FEATURE:
<223> OTHER INFORMATION: Codon-optimized KO

<400> SEQUENCE: 71

```
aagcttaaaa tgagtaagtc taatagtatg aattctacat cacacgaaac cctttttcaa      60
caattggtct tgggtttgga ccgtatgcca ttgatggatg ttcactggtt gatctacgtt     120
gctttcggcg catggttatg ttcttatgtg atacatgttt tatcatcttc ctctacagta     180
aaagtgccag ttgttggata caggtctgta ttcgaaccta catggttgct tagacttaga     240
ttcgtctggg aaggtggctc tatcataggt caagggtaca ataagtttaa agactctatt     300
ttccaagtta ggaaattggg aactgatatt gtcattatac cacctaacta tattgatgaa     360
gtgagaaaat tgtcacagga caagactaga tcagttgaac ctttcattaa tgattttgca     420
ggtcaataca caagaggcat ggttttcttg caatctgact acaaaaccg tgttatacaa     480
caaagactaa ctccaaaatt ggtttccttg accaaggtca tgaaggaaga gttggattat     540
gctttaacaa agagatgcc tgatatgaaa aatgacgaat gggtagaagt agatatcagt     600
agtataatgg tgagattgat ttccaggatc tccgccagag tctttctagg gcctgaacac     660
tgtcgtaacc aggaatggtt gactactaca gcagaatatt cagaatcact tttcattaca     720
gggtttatct taagagttgt acctcatatc ttaagaccat tcatcgcccc tctattacct     780
tcatacagga ctctacttag aaacgtttca agtggtagaa gagtcatcgg tgacatcata     840
agatctcagc aaggggatgg taacgaagat atactttcct ggatgagaga tgctgccaca     900
ggagaggaaa agcaaatcga taacattgct cagagaatgt taattctttc tttagcatca     960
atccacacta ctgcgatgac catgacacat gccatgtacg atctatgtgc ttgccctgag    1020
tacattgaac cattaagaga tgaagttaaa tctgttgttg gggcttctgg ctgggacaag    1080
acagcgttaa acagatttca taagttggac tccttcctaa agagtcaca agattcaac      1140
ccagtattct tattgacatt caatagaatc taccatcaat ctatgaccct tatcagatgcg   1200
actaacattc catctggaac acgtattgct gttccatcac acgcaatgtt gcaagattct    1260
gcacatgtcc caggtccaac cccacctact gaatttgatg gattcagata tagtaagata    1320
cgttctgata gtaactacgc acaaaagtac ctattctcca tgaccgattc ttcaaacatg    1380
```

-continued

```
gctttcggat acggcaagta tgcttgtcca ggtagatttt acgcgtctaa tgagatgaaa    1440
ctaacattag ccattttgtt gctacaattt gagttcaaac taccagatgg taaaggtcgt    1500
cctagaaata tcactatcga ttctgatatg attccagacc caagagctag actttgcgtc    1560
agaaaaagat cacttagaga tgaatgaccg cgg                                  1593
```

<210> SEQ ID NO 72
<211> LENGTH: 525
<212> TYPE: PRT
<213> ORGANISM: Gibberella fujikuroi

<400> SEQUENCE: 72

```
Met Ser Lys Ser Asn Ser Met Asn Ser Thr Ser His Glu Thr Leu Phe
 1               5                  10                  15

Gln Gln Leu Val Leu Gly Leu Asp Arg Met Pro Leu Met Asp Val His
            20                  25                  30

Trp Leu Ile Tyr Val Ala Phe Gly Ala Trp Leu Cys Ser Tyr Val Ile
        35                  40                  45

His Val Leu Ser Ser Ser Thr Val Lys Val Pro Val Val Gly Tyr
    50                  55                  60

Arg Ser Val Phe Glu Pro Thr Trp Leu Leu Arg Leu Arg Phe Val Trp
65                  70                  75                  80

Glu Gly Gly Ser Ile Ile Gly Gln Gly Tyr Asn Lys Phe Lys Asp Ser
                85                  90                  95

Ile Phe Gln Val Arg Lys Leu Gly Thr Asp Ile Val Ile Ile Pro Pro
            100                 105                 110

Asn Tyr Ile Asp Glu Val Arg Lys Leu Ser Gln Asp Lys Thr Arg Ser
        115                 120                 125

Val Glu Pro Phe Ile Asn Asp Phe Ala Gly Gln Tyr Thr Arg Gly Met
    130                 135                 140

Val Phe Leu Gln Ser Asp Leu Gln Asn Arg Val Ile Gln Gln Arg Leu
145                 150                 155                 160

Thr Pro Lys Leu Val Ser Leu Thr Lys Val Met Lys Glu Glu Leu Asp
                165                 170                 175

Tyr Ala Leu Thr Lys Glu Met Pro Asp Met Lys Asn Asp Glu Trp Val
            180                 185                 190

Glu Val Asp Ile Ser Ser Ile Met Val Arg Leu Ile Ser Arg Ile Ser
        195                 200                 205

Ala Arg Val Phe Leu Gly Pro Glu His Cys Arg Asn Gln Glu Trp Leu
    210                 215                 220

Thr Thr Thr Ala Glu Tyr Ser Glu Ser Leu Phe Ile Thr Gly Phe Ile
225                 230                 235                 240

Leu Arg Val Val Pro His Ile Leu Arg Pro Phe Ile Ala Pro Leu Leu
                245                 250                 255

Pro Ser Tyr Arg Thr Leu Leu Arg Asn Val Ser Ser Gly Arg Arg Val
            260                 265                 270

Ile Gly Asp Ile Ile Arg Ser Gln Gln Gly Asp Gly Asn Glu Asp Ile
        275                 280                 285

Leu Ser Trp Met Arg Asp Ala Ala Thr Gly Glu Glu Lys Gln Ile Asp
    290                 295                 300

Asn Ile Ala Gln Arg Met Leu Ile Leu Ser Leu Ala Ser Ile His Thr
305                 310                 315                 320

Thr Ala Met Thr Met Thr His Ala Met Tyr Asp Leu Cys Ala Cys Pro
                325                 330                 335
```

```
Glu Tyr Ile Glu Pro Leu Arg Asp Glu Val Lys Ser Val Val Gly Ala
            340                 345                 350

Ser Gly Trp Asp Lys Thr Ala Leu Asn Arg Phe His Lys Leu Asp Ser
        355                 360                 365

Phe Leu Lys Glu Ser Gln Arg Phe Asn Pro Val Phe Leu Leu Thr Phe
    370                 375                 380

Asn Arg Ile Tyr His Gln Ser Met Thr Leu Ser Asp Gly Thr Asn Ile
385                 390                 395                 400

Pro Ser Gly Thr Arg Ile Ala Val Pro Ser His Ala Met Leu Gln Asp
                405                 410                 415

Ser Ala His Val Pro Gly Pro Thr Pro Pro Thr Glu Phe Asp Gly Phe
            420                 425                 430

Arg Tyr Ser Lys Ile Arg Ser Asp Ser Asn Tyr Ala Gln Lys Tyr Leu
                435                 440                 445

Phe Ser Met Thr Asp Ser Ser Asn Met Ala Phe Gly Tyr Gly Lys Tyr
    450                 455                 460

Ala Cys Pro Gly Arg Phe Tyr Ala Ser Asn Glu Met Lys Leu Thr Leu
465                 470                 475                 480

Ala Ile Leu Leu Leu Gln Phe Glu Phe Lys Leu Pro Asp Gly Lys Gly
                485                 490                 495

Arg Pro Arg Asn Ile Thr Ile Asp Ser Asp Met Ile Pro Asp Pro Arg
                500                 505                 510

Ala Arg Leu Cys Val Arg Lys Arg Ser Leu Arg Asp Glu
                515                 520                 525

<210> SEQ ID NO 73
<211> LENGTH: 1515
<212> TYPE: DNA
<213> ORGANISM: Artificial Sequence
<220> FEATURE:
<223> OTHER INFORMATION: Codon-optimized KO

<400> SEQUENCE: 73
aagcttaaaa tggaagatcc tactgtctta tatgcttgtc ttgccattgc agttgcaact      60
ttcgttgtta gatggtacag agatccattg agatccatcc caacagttgg tggttccgat     120
ttgcctattc tatcttacat cggcgcacta gatggacaa gacgtggcag agagatactt      180
caagagggat atgatggcta cagaggatct acattcaaaa tcgcgatgtt agaccgttgg     240
atcgtgatcg caaatggtcc taaactagct gatgaagtca gacgtagacc agatgaagag     300 ttaaactta tggacggatt aggagcattc gtccaaacta gtacacctt aggtgaagct       360 attcataacg atccatacca tgtcgatatc ataagagaaa aactaacaag aggccttcca    420
gccgtgcttc ctgatgtcat tgaagagttg acacttgcgg ttagacagta cattccaaca    480
gaaggtgatg aatgggtgtc cgtaaactgt tcaaaggccg caagagatat tgttgctaga    540
gcttctaata gagtctttgt aggttttgcct gcttgcagaa accaaggtta cttagatttg     600
gcaatagact ttacattgtc tgttgtcaag gatagagcca tcatcaatat gtttccagaa     660
ttgttgaagc caatagttgg cagagttgta ggtaacgcca ccagaaatgt tcgtagagct    720 gttcctttg ttgctccatt ggtggaggaa agacgtagac ttatggaaga gtacggtgaa     780
gactggtctg aaaaacctaa tgatatgtta cagtggataa tggatgaagc tgcatccaga    840
gatagttcag tgaaggcaat cgcagagaga ttgttaatgg tgaacttcgc ggctattcat    900
acctcatcaa acactatcac tcatgctttg taccaccttc cgaaatgcc tgaaactttg    960
```

-continued

```
caaccactta gagaagagat cgaaccatta gtcaaagagg agggctggac caaggctgct    1020
atgggaaaaa tgtggtggtt agattcattt ctaagagaat ctcaaagata caatggcatt    1080
aacatcgtat ctttaactag aatggctgac aaagatatta cattgagtga tgcacacttt    1140
ttgccaaaag gtactctagt ggccgttcca gcgtattcta ctcatagaga tgatgctgtc    1200
tacgctgatg ccttagtatt cgatcctttc agattctcac gtatgagagc gagagaaggt    1260
gaaggtacaa agcaccagtt cgttaatact tcagtcgagt acgttccatt tggtcacgga    1320
aagcatgctt gtccaggaag attcttcgcc gcaaacgaat gaaagcaat gttggcttac    1380 attgttctaa actatgatgt aaagttgcct ggtgacggta acgtccatt gaacatgtat    1440 tggggtccaa cagttttgcc tgcaccagca ggccaagtat tgttcagaaa gagacaagtt    1500
agtctataac cgcgg                                                    1515
```

<210> SEQ ID NO 74
<211> LENGTH: 499
<212> TYPE: PRT
<213> ORGANISM: Trametes versicolor

<400> SEQUENCE: 74

```
Met Glu Asp Pro Thr Val Leu Tyr Ala Cys Leu Ala Ile Ala Val Ala
1               5                   10                  15

Thr Phe Val Val Arg Trp Tyr Arg Asp Pro Leu Arg Ser Ile Pro Thr
            20                  25                  30

Val Gly Gly Ser Asp Leu Pro Ile Leu Ser Tyr Ile Gly Ala Leu Arg
        35                  40                  45

Trp Thr Arg Arg Gly Arg Glu Ile Leu Gln Glu Gly Tyr Asp Gly Tyr
    50                  55                  60

Arg Gly Ser Thr Phe Lys Ile Ala Met Leu Asp Arg Trp Ile Val Ile
65                  70                  75                  80

Ala Asn Gly Pro Lys Leu Ala Asp Glu Val Arg Arg Pro Asp Glu
                85                  90                  95

Glu Leu Asn Phe Met Asp Gly Leu Gly Ala Phe Val Gln Thr Lys Tyr
            100                 105                 110

Thr Leu Gly Glu Ala Ile His Asn Asp Pro Tyr His Val Asp Ile Ile
        115                 120                 125

Arg Glu Lys Leu Thr Arg Gly Leu Pro Ala Val Leu Pro Asp Val Ile
130                 135                 140

Glu Glu Leu Thr Leu Ala Val Arg Gln Tyr Ile Pro Thr Glu Gly Asp
145                 150                 155                 160

Glu Trp Val Ser Val Asn Cys Ser Lys Ala Ala Arg Asp Ile Val Ala
                165                 170                 175

Arg Ala Ser Asn Arg Val Phe Val Gly Leu Pro Ala Cys Arg Asn Gln
            180                 185                 190

Gly Tyr Leu Asp Leu Ala Ile Asp Phe Thr Leu Ser Val Val Lys Asp
        195                 200                 205

Arg Ala Ile Ile Asn Met Phe Pro Glu Leu Leu Lys Pro Ile Val Gly
    210                 215                 220

Arg Val Val Gly Asn Ala Thr Arg Asn Val Arg Arg Ala Val Pro Phe
225                 230                 235                 240

Val Ala Pro Leu Val Glu Arg Arg Arg Leu Met Glu Glu Tyr Gly
                245                 250                 255

Glu Asp Trp Ser Glu Lys Pro Asn Asp Met Leu Gln Trp Ile Met Asp
            260                 265                 270
```

Glu Ala Ala Ser Arg Asp Ser Val Lys Ala Ile Ala Glu Arg Leu
            275                 280                 285

Leu Met Val Asn Phe Ala Ala Ile His Thr Ser Asn Thr Ile Thr
        290                 295                 300

His Ala Leu Tyr His Leu Ala Glu Met Pro Glu Thr Leu Gln Pro Leu
305                 310                 315                 320

Arg Glu Glu Ile Glu Pro Leu Val Lys Glu Glu Gly Trp Thr Lys Ala
                    325                 330                 335

Ala Met Gly Lys Met Trp Trp Leu Asp Ser Phe Leu Arg Glu Ser Gln
                340                 345                 350

Arg Tyr Asn Gly Ile Asn Ile Val Ser Leu Thr Arg Met Ala Asp Lys
            355                 360                 365

Asp Ile Thr Leu Ser Asp Gly Thr Phe Leu Pro Lys Gly Thr Leu Val
370                 375                 380

Ala Val Pro Ala Tyr Ser Thr His Arg Asp Asp Ala Val Tyr Ala Asp
385                 390                 395                 400

Ala Leu Val Phe Asp Pro Phe Arg Phe Ser Arg Met Arg Ala Arg Glu
                    405                 410                 415

Gly Glu Gly Thr Lys His Gln Phe Val Asn Thr Ser Val Glu Tyr Val
                420                 425                 430

Pro Phe Gly His Gly Lys His Ala Cys Pro Gly Arg Phe Phe Ala Ala
            435                 440                 445

Asn Glu Leu Lys Ala Met Leu Ala Tyr Ile Val Leu Asn Tyr Asp Val
            450                 455                 460

Lys Leu Pro Gly Asp Gly Lys Arg Pro Leu Asn Met Tyr Trp Gly Pro
465                 470                 475                 480

Thr Val Leu Pro Ala Pro Ala Gly Gln Val Leu Phe Arg Lys Arg Gln
                485                 490                 495

Val Ser Leu

<210> SEQ ID NO 75
<211> LENGTH: 1530
<212> TYPE: DNA
<213> ORGANISM: Artificial Sequence
<220> FEATURE:
<223> OTHER INFORMATION: Codon-optimized KO

<400> SEQUENCE: 75
atggcatttt tctctatgat ttcaattttg ttgggatttg ttatttcttc tttcatcttc     60 atcttttct tcaaaaagtt acttagtttt agtaggaaaa acatgtcaga agtttctact     120
ttgccaagtg ttccagtagt gcctggtttt ccagttattg ggaatttgtt gcaactaaag    180
gagaaaaagc tcataaaac tttcactaga tggtcagaga tatatggacc tatctactct    240
ataaagatgg ttcttcatc tcttattgta ttgaacagta cagaaactgc taaggaagca    300
atggtcacta gattttcatc aatatctacc agaaaattgt caaacgccct aacagttcta    360
acctgcgata agtctatggt cgccacttct gattatgatg acttccacaa attagttaag    420
agatgtttgc taaatggact tcttggtgct aatgctcaaa agagaaaaag acactacaga    480
gatgctttga ttgaaaatgt gagttccaag ctacatgcac acgctagaga tcatccacaa    540
gagccagtta actttagagc aatttttcgaa cacgaattgt ttggtgtagc attaaagcaa    600
gccttcggta agacgtaga atccatatac gtcaaggagt taggcgtaac attatcaaaa    660
gatgaaatct ttaaggtgct tgtacatgat atgatggagg gtgcaattga gtagattgg    720 agagatttct tcccatattt gaaatggatc cctaataagt cttttgaagc taggatacaa    780

-continued

```
caaaagcaca agagaagact agctgttatg aacgcactta tacaggacag attgaagcaa      840
aatgggtctg aatcagatga tgattgttac cttaacttct taatgtctga ggctaaaaca      900
ttgactaagg aacagatcgc aatccttgtc tgggaaacaa tcattgaaac agcagatact      960
accttagtca caactgaatg gccatatac gagctagcca acatccatc tgtgcaagat      1020
aggttgtgta aggagatcca gaacgtgtgt ggtggagaga aattcaagga gagcagttg      1080
tcacaagttc cttaccttaa cggcgttttc catgaaacct tgagaaaata ctcacctgca      1140
ccattagttc ctattagata cgcccacgaa gatacacaaa tcggtggcta ccatgttcca      1200
gctgggtccg aaattgctat aaacatctac gggtgcaaca tggacaaaaa gagatgggaa      1260
agaccagaag attggtggcc agaaagattc ttagatgatg caaatatga acatctgat      1320
ttgcataaaa caatggcttt cggagctggc aaaagagtgt gtgccggtgc tctacaagcc      1380
tccctaatgg ctggtatcgc tattggtaga ttggtccaag agttcgaatg gaaacttaga      1440
gatggtgaag aggaaaatgt cgatacttat gggttaacat ctcaaaagtt atacccacta      1500
atggcaatca tcaatcctag aagatcctaa                                      1530
```

<210> SEQ ID NO 76
<211> LENGTH: 509
<212> TYPE: PRT
<213> ORGANISM: Arabidopsis thaliana

<400> SEQUENCE: 76

```
Met Ala Phe Phe Ser Met Ile Ser Ile Leu Leu Gly Phe Val Ile Ser
1               5                   10                  15

Ser Phe Ile Phe Ile Phe Phe Lys Lys Leu Leu Ser Phe Ser Arg
                20                  25                  30

Lys Asn Met Ser Glu Val Ser Thr Leu Pro Ser Val Pro Val Pro
            35                  40                  45

Gly Phe Pro Val Ile Gly Asn Leu Leu Gln Leu Lys Glu Lys Pro
        50                  55                  60

His Lys Thr Phe Thr Arg Trp Ser Glu Ile Tyr Gly Pro Ile Tyr Ser
65                  70                  75                  80

Ile Lys Met Gly Ser Ser Leu Ile Val Leu Asn Ser Thr Glu Thr
                85                  90                  95

Ala Lys Glu Ala Met Val Thr Arg Phe Ser Ser Ile Ser Thr Arg Lys
            100                 105                 110

Leu Ser Asn Ala Leu Thr Val Leu Thr Cys Asp Lys Ser Met Val Ala
        115                 120                 125

Thr Ser Asp Tyr Asp Asp Phe His Lys Leu Val Lys Arg Cys Leu Leu
    130                 135                 140

Asn Gly Leu Leu Gly Ala Asn Ala Gln Lys Arg Lys Arg His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205

Ile Tyr Val Lys Glu Leu Gly Val Thr Leu Ser Lys Asp Glu Ile Phe
    210                 215                 220

Lys Val Leu Val His Asp Met Met Glu Gly Ala Ile Asp Val Asp Trp
225                 230                 235                 240
```

Arg Asp Phe Phe Pro Tyr Leu Lys Trp Ile Pro Asn Lys Ser Phe Glu
                245                 250                 255

Ala Arg Ile Gln Gln Lys His Lys Arg Arg Leu Ala Val Met Asn Ala
            260                 265                 270

Leu Ile Gln Asp Arg Leu Lys Gln Asn Gly Ser Glu Ser Asp Asp
        275                 280                 285

Cys Tyr Leu Asn Phe Leu Met Ser Glu Ala Lys Thr Leu Thr Lys Glu
    290                 295                 300

Gln Ile Ala Ile Leu Val Trp Glu Thr Ile Ile Glu Thr Ala Asp Thr
305                 310                 315                 320

Thr Leu Val Thr Thr Glu Trp Ala Ile Tyr Glu Leu Ala Lys His Pro
                325                 330                 335

Ser Val Gln Asp Arg Leu Cys Lys Glu Ile Gln Asn Val Cys Gly Gly
            340                 345                 350

Glu Lys Phe Lys Glu Glu Gln Leu Ser Gln Val Pro Tyr Leu Asn Gly
        355                 360                 365

Val Phe His Glu Thr Leu Arg Lys Tyr Ser Pro Ala Pro Leu Val Pro
    370                 375                 380

Ile Arg Tyr Ala His Glu Asp Thr Gln Ile Gly Gly Tyr His Val Pro
385                 390                 395                 400

Ala Gly Ser Glu Ile Ala Ile Asn Ile Tyr Gly Cys Asn Met Asp Lys
                405                 410                 415

Lys Arg Trp Glu Arg Pro Glu Asp Trp Trp Pro Glu Arg Phe Leu Asp
            420                 425                 430

Asp Gly Lys Tyr Glu Thr Ser Asp Leu His Lys Thr Met Ala Phe Gly
        435                 440                 445

Ala Gly Lys Arg Val Cys Ala Gly Ala Leu Gln Ala Ser Leu Met Ala
    450                 455                 460

Gly Ile Ala Ile Gly Arg Leu Val Gln Glu Phe Glu Trp Lys Leu Arg
465                 470                 475                 480

Asp Gly Glu Glu Glu Asn Val Asp Thr Tyr Gly Leu Thr Ser Gln Lys
                485                 490                 495

Leu Tyr Pro Leu Met Ala Ile Ile Asn Pro Arg Arg Ser
            500                 505

<210> SEQ ID NO 77
<211> LENGTH: 2133
<212> TYPE: DNA
<213> ORGANISM: Artificial Sequence
<220> FEATURE:
<223> OTHER INFORMATION: Codon-optimized CPR

<400> SEQUENCE: 77
atgcaatcag attcagtcaa agtctctcca tttgatttgg tttccgctgc tatgaatggc     60
aaggcaatgg aaaagttgaa cgctagtgaa tctgaagatc aacaacatt gcctgcacta    120 aagatgctag ttgaaaatag agaattgttg acactgttca caacttcctt cgcagttctt    180
attgggtgtc ttgtatttct aatgtggaga cgttcatcct ctaaaaagct ggtacaagat    240
ccagttccac aagttatcgt tgtaaagaag aagagaagg agtcagaggt tgatgacggg    300
aaaaagaaag tttctatttt ctacggcaca caaacaggaa ctgccgaagg ttttgctaaa    360
gcattagtcg aggaagcaaa agtgagatat gaaaagacct ctttcaaggt tatcgatcta    420
gatgactacg ctgcagatga tgatgaatat gaggaaaaac tgaaaaagga atccttagcc    480
ttcttcttct tggccacata cggtgatggt gaacctactg ataatgctgc taacttctac    540

-continued

```
aagtggttca cagaaggcga cgataaaggt gaatggctga aaaagttaca atacggagta    600
tttggtttag gtaacagaca atatgaacat ttcaacaaga tcgctattgt agttgatgat    660
aaacttactg aaatgggagc caaaagatta gtaccagtag gattagggga tgatgatcag    720
tgtatagaag atgacttcac cgcctggaag gaattggtat ggccagaatt ggatcaactt    780
ttaagggacg aagatgatac ttctgtgact accccataca ctgcagccgt attggagtac    840
agagtggttt accatgataa accagcagac tcatatgctg aagatcaaac ccatacaaac    900
ggtcatgttg ttcatgatgc acagcatcct tcaagatcta atgtggcttt caaaaaggaa    960
ctacacacct ctcaatcaga taggtcttgt actcacttag aattcgatat ttctcacaca   1020
ggactgtctt acgaaactgg cgatcacgtt ggcgtttatt ccgagaactt gtccgaagtt   1080
gtcgatgaag cactaaaact gttagggtta tcaccagaca catacttctc agtccatgct   1140
gataaggagg atgggacacc tatcggtggt gcttcactac caccaccttt tcctccttgc   1200
acattgagag acgctctaac cagatacgca gatgtcttat cctcacctaa aaaggtagct   1260
ttgctggcat tggctgctca tgctagtgat cctagtgaag ccgataggtt aaagttcctg   1320
gcttcaccag ccggaaaaga tgaatatgca caatggatcg tcgccaacca acgttctttg   1380
ctagaagtga tgcaaagttt tccatctgcc aagcctccat taggtgtgtt cttcgcagca   1440
gtagctccac gtttacaacc aagatactac tctatcagtt catctcctaa gatgtctcct   1500
aacagaatac atgttacatg tgctttggtg tacgagacta ctccagcagg cagaattcac   1560
agaggattgt gttcaacctg gatgaaaaat gctgtcccct taacagagtc acctgattgc   1620
tctcaagcat ccatttttcgt tagaacatca aatttcagac ttccagtgga tccaaaagtt   1680
ccagtcatta tgataggacc aggcactggt cttgccccat tcaggggctt tcttcaagag   1740
agattggcct tgaaggaatc tggtacagaa ttgggttctt ctatcttttt ctttggttgc   1800
cgtaatagaa aagttgactt tatctacgag gacgagctta acaattttgt tgagacagga   1860
gcattgtcag aattgatcgt cgcattttca agagaaggga ctgccaaaga gtacgttcag   1920
cacaagatga gtcaaaaagc ctccgatata tggaaacttc taagtgaagg tgcctatctt   1980
tatgtctgtg gcgatgcaaa gggcatggcc aaggatgtcc atagaactct gcatacaatt   2040
gttcaggaac aagggagtct ggattcttcc aaggctgaat tgtacgtcaa aaacttacag   2100
atgtctggaa gatacttaag agatgtttgg taa                                2133
```

<210> SEQ ID NO 78
<211> LENGTH: 710
<212> TYPE: PRT
<213> ORGANISM: Stevia rebaudiana

<400> SEQUENCE: 78

```
Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
            20                  25                  30

Asp Pro Thr Thr Leu Pro Ala Leu Lys Met Leu Val Glu Asn Arg Glu
        35                  40                  45

Leu Leu Thr Leu Phe Thr Thr Ser Phe Ala Val Leu Ile Gly Cys Leu
    50                  55                  60

Val Phe Leu Met Trp Arg Arg Ser Ser Lys Lys Leu Val Gln Asp
65                  70                  75                  80

Pro Val Pro Gln Val Ile Val Val Lys Lys Lys Glu Lys Glu Ser Glu
```

```
            85                  90                  95
Val Asp Asp Gly Lys Lys Val Ser Ile Phe Tyr Gly Thr Gln Thr
            100                 105                 110
Gly Thr Ala Glu Gly Phe Ala Lys Ala Leu Val Glu Glu Ala Lys Val
            115                 120                 125
Arg Tyr Glu Lys Thr Ser Phe Lys Val Ile Asp Leu Asp Asp Tyr Ala
            130                 135                 140
Ala Asp Asp Asp Glu Tyr Glu Glu Lys Leu Lys Lys Glu Ser Leu Ala
145                 150                 155                 160
Phe Phe Phe Leu Ala Thr Tyr Gly Asp Gly Glu Pro Thr Asp Asn Ala
                165                 170                 175
Ala Asn Phe Tyr Lys Trp Phe Thr Glu Gly Asp Asp Lys Gly Glu Trp
                180                 185                 190
Leu Lys Lys Leu Gln Tyr Gly Val Phe Gly Leu Gly Asn Arg Gln Tyr
                195                 200                 205
Glu His Phe Asn Lys Ile Ala Ile Val Val Asp Asp Lys Leu Thr Glu
                210                 215                 220
Met Gly Ala Lys Arg Leu Val Pro Val Gly Leu Gly Asp Asp Asp Gln
225                 230                 235                 240
Cys Ile Glu Asp Asp Phe Thr Ala Trp Lys Glu Leu Val Trp Pro Glu
                245                 250                 255
Leu Asp Gln Leu Leu Arg Asp Glu Asp Thr Ser Val Thr Thr Pro
                260                 265                 270
Tyr Thr Ala Ala Val Leu Glu Tyr Arg Val Val Tyr His Asp Lys Pro
                275                 280                 285
Ala Asp Ser Tyr Ala Glu Asp Gln Thr His Thr Asn Gly His Val Val
                290                 295                 300
His Asp Ala Gln His Pro Ser Arg Ser Asn Val Ala Phe Lys Lys Glu
305                 310                 315                 320
Leu His Thr Ser Gln Ser Asp Arg Ser Cys Thr His Leu Glu Phe Asp
                325                 330                 335
Ile Ser His Thr Gly Leu Ser Tyr Glu Thr Gly Asp His Val Gly Val
                340                 345                 350
Tyr Ser Glu Asn Leu Ser Glu Val Val Asp Glu Ala Leu Lys Leu Leu
                355                 360                 365
Gly Leu Ser Pro Asp Thr Tyr Phe Ser Val His Ala Asp Lys Glu Asp
                370                 375                 380
Gly Thr Pro Ile Gly Gly Ala Ser Leu Pro Pro Phe Pro Pro Cys
385                 390                 395                 400
Thr Leu Arg Asp Ala Leu Thr Arg Tyr Ala Asp Val Leu Ser Ser Pro
                405                 410                 415
Lys Lys Val Ala Leu Leu Ala Leu Ala His Ala Ser Asp Pro Ser
                420                 425                 430
Glu Ala Asp Arg Leu Lys Phe Leu Ala Ser Pro Ala Gly Lys Asp Glu
                435                 440                 445
Tyr Ala Gln Trp Ile Val Ala Asn Gln Arg Ser Leu Leu Glu Val Met
                450                 455                 460
Gln Ser Phe Pro Ser Ala Lys Pro Leu Gly Val Phe Phe Ala Ala
465                 470                 475                 480
Val Ala Pro Arg Leu Gln Pro Arg Tyr Tyr Ser Ile Ser Ser Ser Pro
                485                 490                 495
Lys Met Ser Pro Asn Arg Ile His Val Thr Cys Ala Leu Val Tyr Glu
                500                 505                 510
```

```
Thr Thr Pro Ala Gly Arg Ile His Arg Gly Leu Cys Ser Thr Trp Met
        515                 520                 525

Lys Asn Ala Val Pro Leu Thr Glu Ser Pro Asp Cys Ser Gln Ala Ser
    530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
                580                 585                 590

Ser Ser Ile Phe Phe Gly Cys Arg Asn Arg Lys Val Asp Phe Ile
            595                 600                 605

Tyr Glu Asp Glu Leu Asn Asn Phe Val Glu Thr Gly Ala Leu Ser Glu
        610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
                660                 665                 670

Val His Arg Thr Leu His Thr Ile Val Gln Glu Gln Gly Ser Leu Asp
            675                 680                 685

Ser Ser Lys Ala Glu Leu Tyr Val Lys Asn Leu Gln Met Ser Gly Arg
        690                 695                 700

Tyr Leu Arg Asp Val Trp
705                 710

<210> SEQ ID NO 79
<211> LENGTH: 2106
<212> TYPE: DNA
<213> ORGANISM: Siraitia grosvenorii

<400> SEQUENCE: 79
atgaaggtca gtccattcga attcatgtcc gctattatca agggtagaat ggacccatct      60
aactcctcat ttgaatctac tggtgaagtt gcctccgtta tctttgaaaa cagagaattg     120
gttgccatct tgaccacttc tattgctgtt atgattggtt gcttcgttgt cttgatgtgg     180
agaagagctg gttctagaaa ggttaagaat gtcgaattgc aaagccatt gattgtccat     240 gaaccagaac ctgaagttga agatggtaag aagaaggttt ccatcttctt cggtactcaa     300
actggtactg ctgaaggttt tgctaaggct ttggctgatg aagctaaagc tagatacgaa     360
aaggctacct tcagagttgt tgatttggat gattatgctg ccgatgatga ccaatacgaa     420
gaaaaattga gaacgaatc cttcgccgtt ttcttgttgg ctacttatgg tgatggtgaa     480
cctactgata tgctgctag attttacaag tggttcgccg aagtaaaga agaggtgaa      540 tggttgcaaa acttgcacta tgctgttttt ggtttgggta cagacaata cgaacacttc     600 aacaagattg ctaaggttgc cgacgaatta ttggaagctc aaggtggtaa tagattggtt     660
aaggttggtt taggtgatga cgatcaatgc atcgaagatg atttttctgc ttggagagaa     720
tctttgtggc cagaattgga tatgttgttg agagatgaag atgatgctac tactgttact     780
actccatata ctgctgctgt cttggaatac agagttgtct ttcatgattc tgctgatgtt     840 gctgctgaaag ataagtcttg gattaacgct aatggtcatg ctgttcatga tgctcaacat     900
ccattcagat ctaacgttgt cgtcagaaaa gaattgcata cttctgcctc tgatagatcc     960
```

```
tgttctcatt tggaattcaa catttccggt tccgctttga attacgaaac tggtgatcat    1020
gttggtgtct actgtgaaaa cttgactgaa actgttgatg aagccttgaa cttgttgggt    1080
ttgtctccag aaacttactt ctctatctac accgataacg aagatggtac tccattgggt    1140
ggttcttcat tgccaccacc atttccatca tgtactttga gaactgcttt gaccagatac    1200
gctgatttgt tgaactctcc aaaaaagtct gctttgttgg ctttagctgc tcatgcttct    1260
aatccagttg aagctgatag attgagatac ttggcttctc cagctggtaa agatgaatat    1320
gcccaatctg ttatcggttc ccaaaagtct ttgttggaag ttatggctga attcccatct    1380
gctaaaccac cattaggtgt ttttttttgct gctgttgctc caagattgca acctagattc    1440
tactccattt catcctctcc aagaatggct ccatctagaa tccatgttac ttgtgctttg    1500
gtttacgata gatgccaac tggtagaatt cataagggtg tttgttctac ctggatgaag    1560
aattctgttc aatggaaaa gtcccatgaa tgttcttggg ctccaatttt cgttagacaa    1620
tccaatttta agttgccagc cgaatccaag gttccaatta tcatggttgg tccaggtact    1680
ggtttggctc cttttagagg ttttttacaa gaaagattgg ccttgaaaga atccggtgtt    1740
gaattgggtc catccatttt gttttttcggt tgcagaaaca gaagaatgga ttacatctac    1800
gaagatgaat tgaacaactt cgttgaaacc ggtgctttgt ccgaattggt tattgctttt    1860
tctagagaag gtcctaccaa agaatacgtc aacataaga tggctgaaaa ggcttctgat    1920
atctggaact tgatttctga aggtgcttac ttgtacgttt gtggtgatgc taaaggtatg    1980 gctaaggat tcatagaac cttgcatacc atcatgcaag aacaaggttc tttggattct    2040
tccaaagctg aatccatggt caagaacttg caaatgaatg gtagatactt aagagatgtt    2100
tggtaa                                                              2106
```

<210> SEQ ID NO 80
<211> LENGTH: 701
<212> TYPE: PRT
<213> ORGANISM: Siraitia grosvenorii

<400> SEQUENCE: 80

```
Met Lys Val Ser Pro Phe Glu Phe Met Ser Ala Ile Ile Lys Gly Arg
1               5                   10                  15

Met Asp Pro Ser Asn Ser Ser Phe Glu Ser Thr Gly Glu Val Ala Ser
                20                  25                  30

Val Ile Phe Glu Asn Arg Glu Leu Val Ala Ile Leu Thr Thr Ser Ile
            35                  40                  45

Ala Val Met Ile Gly Cys Phe Val Val Leu Met Trp Arg Arg Ala Gly
        50                  55                  60

Ser Arg Lys Val Lys Asn Val Glu Leu Pro Lys Pro Leu Ile Val His
65                  70                  75                  80

Glu Pro Glu Pro Glu Val Glu Asp Gly Lys Lys Val Ser Ile Phe
                85                  90                  95

Phe Gly Thr Gln Thr Gly Thr Ala Glu Gly Phe Ala Lys Ala Leu Ala
            100                 105                 110

Asp Glu Ala Lys Ala Arg Tyr Glu Lys Ala Thr Phe Arg Val Val Asp
        115                 120                 125

Leu Asp Asp Tyr Ala Ala Asp Asp Gln Tyr Glu Glu Lys Leu Lys
    130                 135                 140

Asn Glu Ser Phe Ala Val Phe Leu Leu Ala Thr Tyr Gly Asp Gly Glu
145                 150                 155                 160
```

```
Pro Thr Asp Asn Ala Arg Phe Tyr Lys Trp Phe Ala Glu Gly Lys
            165                 170                 175

Glu Arg Gly Glu Trp Leu Gln Asn Leu His Tyr Ala Val Phe Gly Leu
        180                 185                 190

Gly Asn Arg Gln Tyr Glu His Phe Asn Lys Ile Ala Lys Val Ala Asp
        195                 200                 205

Glu Leu Leu Glu Ala Gln Gly Gly Asn Arg Leu Val Lys Val Gly Leu
        210                 215                 220

Gly Asp Asp Asp Gln Cys Ile Glu Asp Phe Ser Ala Trp Arg Glu
225                 230                 235                 240

Ser Leu Trp Pro Glu Leu Asp Met Leu Leu Arg Asp Glu Asp Ala
            245                 250                 255

Thr Thr Val Thr Thr Pro Tyr Thr Ala Ala Val Leu Glu Tyr Arg Val
            260                 265                 270

Val Phe His Asp Ser Ala Asp Val Ala Ala Glu Asp Lys Ser Trp Ile
        275                 280                 285

Asn Ala Asn Gly His Ala Val His Asp Ala Gln His Pro Phe Arg Ser
        290                 295                 300

Asn Val Val Arg Lys Glu Leu His Thr Ser Ala Ser Asp Arg Ser
305                 310                 315                 320

Cys Ser His Leu Glu Phe Asn Ile Ser Gly Ser Ala Leu Asn Tyr Glu
            325                 330                 335

Thr Gly Asp His Val Gly Val Tyr Cys Glu Asn Leu Thr Glu Thr Val
            340                 345                 350

Asp Glu Ala Leu Asn Leu Leu Gly Leu Ser Pro Glu Thr Tyr Phe Ser
        355                 360                 365

Ile Tyr Thr Asp Asn Glu Asp Gly Thr Pro Leu Gly Gly Ser Ser Leu
        370                 375                 380

Pro Pro Pro Phe Pro Ser Cys Thr Leu Arg Thr Ala Leu Thr Arg Tyr
385                 390                 395                 400

Ala Asp Leu Leu Asn Ser Pro Lys Lys Ser Ala Leu Leu Ala Leu Ala
            405                 410                 415

Ala His Ala Ser Asn Pro Val Glu Ala Asp Arg Leu Arg Tyr Leu Ala
            420                 425                 430

Ser Pro Ala Gly Lys Asp Glu Tyr Ala Gln Ser Val Ile Gly Ser Gln
            435                 440                 445

Lys Ser Leu Leu Glu Val Met Ala Glu Phe Pro Ser Ala Lys Pro Pro
    450                 455                 460

Leu Gly Val Phe Phe Ala Ala Val Ala Pro Arg Leu Gln Pro Arg Phe
465                 470                 475                 480

Tyr Ser Ile Ser Ser Ser Pro Arg Met Ala Pro Ser Arg Ile His Val
            485                 490                 495

Thr Cys Ala Leu Val Tyr Asp Lys Met Pro Thr Gly Arg Ile His Lys
            500                 505                 510

Gly Val Cys Ser Thr Trp Met Lys Asn Ser Val Pro Met Glu Lys Ser
        515                 520                 525

His Glu Cys Ser Trp Ala Pro Ile Phe Val Arg Gln Ser Asn Phe Lys
    530                 535                 540

Leu Pro Ala Glu Ser Lys Val Pro Ile Ile Met Val Gly Pro Gly Thr
545                 550                 555                 560

Gly Leu Ala Pro Phe Arg Gly Phe Leu Gln Glu Arg Leu Ala Leu Lys
            565                 570                 575

Glu Ser Gly Val Glu Leu Gly Pro Ser Ile Leu Phe Phe Gly Cys Arg
```

```
                580               585               590
Asn Arg Arg Met Asp Tyr Ile Tyr Glu Asp Glu Leu Asn Asn Phe Val
            595                   600               605

Glu Thr Gly Ala Leu Ser Glu Leu Val Ile Ala Phe Ser Arg Glu Gly
            610              615              620

Pro Thr Lys Glu Tyr Val Gln His Lys Met Ala Glu Lys Ala Ser Asp
625                 630              635              640

Ile Trp Asn Leu Ile Ser Glu Gly Ala Tyr Leu Tyr Val Cys Gly Asp
                645              650              655

Ala Lys Gly Met Ala Lys Asp Val His Arg Thr Leu His Thr Ile Met
            660              665              670

Gln Glu Gln Gly Ser Leu Asp Ser Ser Lys Ala Glu Ser Met Val Lys
        675              680              685

Asn Leu Gln Met Asn Gly Arg Tyr Leu Arg Asp Val Trp
        690              695              700

<210> SEQ ID NO 81
<211> LENGTH: 2142
<212> TYPE: DNA
<213> ORGANISM: Artificial Sequence
<220> FEATURE:
<223> OTHER INFORMATION: Codon-optimized CPR

<400> SEQUENCE: 81
```

| | | | | | |
|---|---|---|---|---|---|
| atggcagaat | tagatacact | tgatatagta | gtattaggtg | ttatctttt | gggtactgtg | 60 |
| gcatactta | ctaagggtaa | attgtggggt | gttaccaagg | atccatacgc | taacggattc | 120 |
| gctgcaggtg | gtgcttccaa | gcctggcaga | actagaaaca | tcgtcgaagc | tatggaggaa | 180 |
| tcaggtaaaa | actgtgttgt | tttctacggc | agtcaaacag | gtacagcgga | ggattacgca | 240 |
| tcaagacttg | caaaggaagg | aaagtccaga | ttcggtttga | cactatgat | cgccgatcta | 300 |
| gaagattatg | acttcgataa | cttagacact | gttccatctg | ataacatcgt | tatgtttgta | 360 |
| ttggctactt | acggtgaagg | cgaaccaaca | gataacgccg | tggatttcta | tgagttcatt | 420 |
| actggcgaag | atgcctcttt | caatgagggc | aacgatcctc | cactaggtaa | cttgaattac | 480 |
| gttgcgttcg | gtctgggcaa | caatacctac | gaacactaca | actcaatggt | caggaacgtt | 540 |
| aacaaggctc | tagaaaagtt | aggagctcat | agaattggag | aagcaggtga | gggtgacgac | 600 |
| ggagctggaa | ctatggaaga | ggactttta | gcttggaaag | atccaatgtg | gaagccttg | 660 |
| gctaaaaaga | tgggcttgga | ggaaagagaa | gctgtatatg | aacctatttt | cgctatcaat | 720 |
| gagagagatg | atttgaccccc | tgaagcgaat | gaggtatact | gggagaaacc | taataagcta | 780 |
| cacttggaag | gtacagcgaa | aggtccattc | aactcccaca | acccatatat | cgcaccaatt | 840 |
| gcagaatcat | acgaactttt | ctcagctaag | gatagaaatt | gtctgcatat | ggaaattgat | 900 |
| atttctggta | gtaatctaaa | gtatgaaaca | ggcgaccata | tcgcgatctg | gcctaccaac | 960 |
| ccaggtgaag | aggtcaacaa | atttcttgac | attctagatc | tgtctggtaa | gcaacattcc | 1020 |
| gtcgtaacag | tgaaagcctt | agaacctaca | gccaaagttc | cttttccaaa | tccaactacc | 1080 |
| tacgatgcta | tattgagata | ccatctggaa | atatgcgctc | cagtttctag | acagtttgtc | 1140 |
| tcaactttag | cagcattcgc | ccctaatgat | gatatcaaag | ctgagatgaa | ccgtttggga | 1200 |
| tcagacaaag | attacttcca | cgaaaagaca | ggaccacatt | actacaatat | cgctagattt | 1260 |
| ttggcctcag | tctctaaagg | tgaaaaatgg | acaaagatac | catttctgc | tttcatagaa | 1320 |
| ggccttacaa | aactacaacc | aagatactat | tctatctctt | cctctagttt | agttcagcct | 1380 |

```
aaaaagatta gtattactgc tgttgtcgaa tctcagcaaa ttccaggtag agatgaccca    1440
ttcagaggtg tagcgactaa ctacttgttc gctttgaagc agaaacaaaa cggtgatcca    1500
aatccagctc cttttggcca atcatacgag ttgacaggac caaggaataa gtatgatggt    1560
atacatgttc cagtccatgt aagacattct aactttaagc taccatctga tccaggcaaa    1620
cctattatca tgatcggtcc aggtaccggt gttgcccctt ttagaggctt cgtccaagag    1680
agggcaaaac aagccagaga tggtgtagaa gttggtaaaa cactgctgtt ctttggatgt    1740
agaaagagta cagaagattt catgtatcaa aaagagtggc aagagtacaa ggaagctctt    1800
ggcgacaaat tcgaaatgat tacagctttt tcaagagaag gatctaaaaa ggtttatgtt    1860
caacacagac tgaaggaaag atcaaaggaa gtttctgatc ttctatccca aaaagcatac    1920
ttctacgttt gcggagacgc cgcacatatg gcacgtgaag tgaacactgt gttagcacag    1980
atcatagcag aaggccgtgg tgtatcagaa gccaagggtg aggaaattgt caaaaacatg    2040
agatcagcaa atcaatacca agtgtgttct gatttcgtaa ctttacactg taaagagaca    2100
acatacgcga attcagaatt gcaagaggat gtctggagtt aa                       2142
```

<210> SEQ ID NO 82
<211> LENGTH: 713
<212> TYPE: PRT
<213> ORGANISM: Gibberella fujikuroi

<400> SEQUENCE: 82

```
Met Ala Glu Leu Asp Thr Leu Asp Ile Val Val Leu Gly Val Ile Phe
1               5                   10                  15

Leu Gly Thr Val Ala Tyr Phe Thr Lys Gly Lys Leu Trp Gly Val Thr
            20                  25                  30

Lys Asp Pro Tyr Ala Asn Gly Phe Ala Ala Gly Gly Ala Ser Lys Pro
        35                  40                  45

Gly Arg Thr Arg Asn Ile Val Glu Ala Met Glu Glu Ser Gly Lys Asn
    50                  55                  60

Cys Val Val Phe Tyr Gly Ser Gln Thr Gly Thr Ala Glu Asp Tyr Ala
65                  70                  75                  80

Ser Arg Leu Ala Lys Glu Gly Lys Ser Arg Phe Gly Leu Asn Thr Met
                85                  90                  95

Ile Ala Asp Leu Glu Asp Tyr Asp Phe Asp Asn Leu Asp Thr Val Pro
            100                 105                 110

Ser Asp Asn Ile Val Met Phe Val Leu Ala Thr Tyr Gly Glu Gly Glu
        115                 120                 125

Pro Thr Asp Asn Ala Val Asp Phe Tyr Glu Phe Ile Thr Gly Glu Asp
    130                 135                 140

Ala Ser Phe Asn Glu Gly Asn Asp Pro Pro Leu Gly Asn Leu Asn Tyr
145                 150                 155                 160

Val Ala Phe Gly Leu Gly Asn Asn Thr Tyr Glu His Tyr Asn Ser Met
                165                 170                 175

Val Arg Asn Val Asn Lys Ala Leu Glu Lys Leu Gly Ala His Arg Ile
            180                 185                 190

Gly Glu Ala Gly Glu Gly Asp Asp Gly Ala Gly Thr Met Glu Glu Asp
        195                 200                 205

Phe Leu Ala Trp Lys Asp Pro Met Trp Glu Ala Leu Ala Lys Lys Met
    210                 215                 220

Gly Leu Glu Glu Arg Glu Ala Val Tyr Glu Pro Ile Phe Ala Ile Asn
225                 230                 235                 240
```

```
Glu Arg Asp Asp Leu Thr Pro Glu Ala Asn Glu Val Tyr Leu Gly Glu
            245                 250                 255

Pro Asn Lys Leu His Leu Glu Gly Thr Ala Lys Gly Pro Phe Asn Ser
        260                 265                 270

His Asn Pro Tyr Ile Ala Pro Ile Ala Glu Ser Tyr Glu Leu Phe Ser
    275                 280                 285

Ala Lys Asp Arg Asn Cys Leu His Met Glu Ile Asp Ile Ser Gly Ser
290                 295                 300

Asn Leu Lys Tyr Glu Thr Gly Asp His Ile Ala Ile Trp Pro Thr Asn
305                 310                 315                 320

Pro Gly Glu Glu Val Asn Lys Phe Leu Asp Ile Leu Asp Leu Ser Gly
                325                 330                 335

Lys Gln His Ser Val Val Thr Val Lys Ala Leu Glu Pro Thr Ala Lys
            340                 345                 350

Val Pro Phe Pro Asn Pro Thr Thr Tyr Asp Ala Ile Leu Arg Tyr His
        355                 360                 365

Leu Glu Ile Cys Ala Pro Val Ser Arg Gln Phe Val Ser Thr Leu Ala
    370                 375                 380

Ala Phe Ala Pro Asn Asp Asp Ile Lys Ala Glu Met Asn Arg Leu Gly
385                 390                 395                 400

Ser Asp Lys Asp Tyr Phe His Glu Lys Thr Gly Pro His Tyr Tyr Asn
                405                 410                 415

Ile Ala Arg Phe Leu Ala Ser Val Ser Lys Gly Glu Lys Trp Thr Lys
            420                 425                 430

Ile Pro Phe Ser Ala Phe Ile Glu Gly Leu Thr Lys Leu Gln Pro Arg
        435                 440                 445

Tyr Tyr Ser Ile Ser Ser Ser Ser Leu Val Gln Pro Lys Lys Ile Ser
    450                 455                 460

Ile Thr Ala Val Val Glu Ser Gln Gln Ile Pro Gly Arg Asp Asp Pro
465                 470                 475                 480

Phe Arg Gly Val Ala Thr Asn Tyr Leu Phe Ala Leu Lys Gln Lys Gln
                485                 490                 495

Asn Gly Asp Pro Asn Pro Ala Pro Phe Gly Gln Ser Tyr Glu Leu Thr
            500                 505                 510

Gly Pro Arg Asn Lys Tyr Asp Gly Ile His Val Pro Val His Val Arg
        515                 520                 525

His Ser Asn Phe Lys Leu Pro Ser Asp Pro Gly Lys Pro Ile Ile Met
    530                 535                 540

Ile Gly Pro Gly Thr Gly Val Ala Pro Phe Arg Gly Phe Val Gln Glu
545                 550                 555                 560

Arg Ala Lys Gln Ala Arg Asp Gly Val Glu Val Gly Lys Thr Leu Leu
                565                 570                 575

Phe Phe Gly Cys Arg Lys Ser Thr Glu Asp Phe Met Tyr Gln Lys Glu
            580                 585                 590

Trp Gln Glu Tyr Lys Glu Ala Leu Gly Asp Lys Phe Glu Met Ile Thr
        595                 600                 605

Ala Phe Ser Arg Glu Gly Ser Lys Lys Val Tyr Val Gln His Arg Leu
    610                 615                 620

Lys Glu Arg Ser Lys Glu Val Ser Asp Leu Leu Ser Gln Lys Ala Tyr
625                 630                 635                 640

Phe Tyr Val Cys Gly Asp Ala Ala His Met Ala Arg Glu Val Asn Thr
                645                 650                 655

Val Leu Ala Gln Ile Ile Ala Glu Gly Arg Gly Val Ser Glu Ala Lys
```

```
                660               665               670
Gly Glu Glu Ile Val Lys Asn Met Arg Ser Ala Asn Gln Tyr Gln Val
            675               680               685

Cys Ser Asp Phe Val Thr Leu His Cys Lys Glu Thr Thr Tyr Ala Asn
        690               695               700

Ser Glu Leu Gln Glu Asp Val Trp Ser
705                 710

<210> SEQ ID NO 83
<211> LENGTH: 2130
<212> TYPE: DNA
<213> ORGANISM: Stevia rebaudiana

<400> SEQUENCE: 83
```

| | | | | | |
|---|---|---|---|---|---|
| atgcaatcgg | aatccgttga | agcatcgacg | attgatttga | tgactgctgt | tttgaaggac | 60 |
| acagtgatcg | atacagcgaa | cgcatctgat | aacggagact | caaagatgcc | gccggcgttg | 120 |
| gcgatgatgt | tcgaaattcg | tgatctgttg | ctgattttga | ctacgtcagt | tgctgttttg | 180 |
| gtcggatgtt | tcgttgtttt | ggtgtggaag | agatcgtccg | ggaagaagtc | cggcaaggaa | 240 |
| ttggagccgc | cgaagatcgt | tgtgccgaag | aggcggctgg | agcaggaggt | tgatgatggt | 300 |
| aagaagaagg | ttacgatttt | cttcggaaca | caaactggaa | cggctgaagg | tttcgctaag | 360 |
| gcacttttcg | aagaagcgaa | agcgcgatat | gaaaaggcag | cgtttaaagt | gattgatttg | 420 |
| gatgattatg | ctgctgattt | ggatgagtat | gcagagaagc | tgaagaagga | aacatatgct | 480 |
| ttcttcttct | tggctacata | tggagatggt | gagccaactg | ataatgctgc | caaattttat | 540 |
| aaatggttta | ctgagggaga | cgagaaaggc | gtttggcttc | aaaaacttca | atatggagta | 600 |
| tttggtcttg | gcaacagaca | atatgaacat | tcaacaagga | ttggaatagt | ggttgatgat | 660 |
| ggtctcaccg | agcagggtgc | aaaacgcatt | gttcccgttg | gtcttggaga | cgacgatcaa | 720 |
| tcaattgaag | acgatttttc | ggcatggaaa | gagttagtgt | ggcccgaatt | ggatctattg | 780 |
| cttcgcgatg | aagatgacaa | agctgctgca | actccttaca | cagctgcaat | ccctgaatac | 840 |
| cgcgtcgtat | tcatgacaaa | cccgatgcg | ttttctgatg | atcatactca | aaccaatggt | 900 |
| catgctgttc | atgatgctca | acatccatgc | agatccaatg | tggctgttaa | aaaagagctt | 960 |
| catactcctg | aatccgatcg | ttcatgcaca | catcttgaat | ttgacatttc | tcacactgga | 1020 |
| ttatcttatg | aaactgggga | tcatgttggt | gtatactgtg | aaaacctaat | tgaagtagtg | 1080 |
| gaagaagctg | ggaaattgtt | aggattatca | acagatactt | atttctcgtt | acatattgat | 1140 |
| aacgaagatg | gttcaccact | tggtggacct | tcattacaac | ctccttttcc | tccttgtact | 1200 |
| ttaagaaaag | cattgactaa | ttatgcagat | ctgttaagct | ctcccaaaaa | gtcaactttg | 1260 |
| cttgctctag | ctgctcatgc | ttccgatccc | actgaagctg | atcgtttaag | atttcttgca | 1320 |
| tctcgcgagg | gcaaggatga | atatgctgaa | tgggttgttg | caaaccaaag | aagtcttctt | 1380 |
| gaagtcatgg | aagctttccc | gtcagctaga | ccgccacttg | tgtttttctt | tgcagcggtt | 1440 |
| gcaccgcgtt | tacagcctcg | ttactactct | atttcttcct | ccccaaagat | ggaaccaaac | 1500 |
| aggattcatg | ttacttgcgc | gttggtttat | gaaaaaactc | ccgcaggtcg | tatccacaaa | 1560 |
| ggaatctgct | caacctggat | gaagaacgct | gtacctttga | ccgaaagtca | agattgcagt | 1620 |
| tgggcaccga | ttttgttag | aacatcaaac | ttcagacttc | caattgaccc | gaaagtcccg | 1680 |
| gttatcatga | ttggtcctgg | aaccggggttg | gctccattta | gggttttct | tcaagaagga | 1740 |
| ttggctctta | aagaatccgg | aaccgaactc | gggtcatcta | ttttattctt | cggttgtaga | 1800 |

```
aaccgcaaag tggattacat atatgagaat gaactcaaca actttgttga aaatggtgcg    1860
ctttctgagc ttgatgttgc tttctcccgc gatggcccga cgaaagaata cgtgcaacat    1920
aaaatgaccc aaaaggcttc tgaaatatgg aatatgcttt ctgagggagc atatttatat    1980
gtatgtggtg atgctaaagg catggctaaa gatgtacacc gtacacttca caccattgtg    2040
caagaacagg gaagtttgga ctcgtctaaa gcggagttgt atgtgaagaa tctacaaatg    2100
tcaggaagat acctccgtga tgtttggtaa                                      2130
```

```
<210> SEQ ID NO 84
<211> LENGTH: 709
<212> TYPE: PRT
<213> ORGANISM: Stevia rebaudiana

<400> SEQUENCE: 84
```

```
Met Gln Ser Glu Ser Val Glu Ala Ser Thr Ile Asp Leu Met Thr Ala
1               5                   10                  15

Val Leu Lys Asp Thr Val Ile Asp Thr Ala Asn Ala Ser Asp Asn Gly
            20                  25                  30

Asp Ser Lys Met Pro Pro Ala Leu Ala Met Met Phe Glu Ile Arg Asp
        35                  40                  45

Leu Leu Leu Ile Leu Thr Thr Ser Val Ala Val Leu Val Gly Cys Phe
    50                  55                  60

Val Val Leu Val Trp Lys Arg Ser Ser Gly Lys Lys Ser Gly Lys Glu
65                  70                  75                  80

Leu Glu Pro Pro Lys Ile Val Val Pro Lys Arg Arg Leu Glu Gln Glu
                85                  90                  95

Val Asp Asp Gly Lys Lys Lys Val Thr Ile Phe Phe Gly Thr Gln Thr
            100                 105                 110

Gly Thr Ala Glu Gly Phe Ala Lys Ala Leu Phe Glu Glu Ala Lys Ala
        115                 120                 125

Arg Tyr Glu Lys Ala Ala Phe Lys Val Ile Asp Leu Asp Asp Tyr Ala
    130                 135                 140

Ala Asp Leu Asp Glu Tyr Ala Glu Lys Leu Lys Lys Glu Thr Tyr Ala
145                 150                 155                 160

Phe Phe Phe Leu Ala Thr Tyr Gly Asp Gly Glu Pro Thr Asp Asn Ala
                165                 170                 175

Ala Lys Phe Tyr Lys Trp Phe Thr Glu Gly Asp Glu Lys Gly Val Trp
            180                 185                 190

Leu Gln Lys Leu Gln Tyr Gly Val Phe Gly Leu Gly Asn Arg Gln Tyr
        195                 200                 205

Glu His Phe Asn Lys Ile Gly Ile Val Val Asp Asp Gly Leu Thr Glu
    210                 215                 220

Gln Gly Ala Lys Arg Ile Val Pro Val Gly Leu Gly Asp Asp Asp Gln
225                 230                 235                 240

Ser Ile Glu Asp Asp Phe Ser Ala Trp Lys Glu Leu Val Trp Pro Glu
                245                 250                 255

Leu Asp Leu Leu Leu Arg Asp Glu Asp Asp Lys Ala Ala Ala Thr Pro
            260                 265                 270

Tyr Thr Ala Ala Ile Pro Glu Tyr Arg Val Val Phe His Asp Lys Pro
        275                 280                 285

Asp Ala Phe Ser Asp Asp His Thr Gln Thr Asn Gly His Ala Val His
    290                 295                 300

Asp Ala Gln His Pro Cys Arg Ser Asn Val Ala Val Lys Lys Glu Leu
305                 310                 315                 320
```

His Thr Pro Glu Ser Asp Arg Ser Cys Thr His Leu Glu Phe Asp Ile
            325                 330                 335

Ser His Thr Gly Leu Ser Tyr Glu Thr Gly Asp His Val Gly Val Tyr
        340                 345                 350

Cys Glu Asn Leu Ile Glu Val Val Glu Glu Ala Gly Lys Leu Leu Gly
        355                 360                 365

Leu Ser Thr Asp Thr Tyr Phe Ser Leu His Ile Asp Asn Glu Asp Gly
370                 375                 380

Ser Pro Leu Gly Gly Pro Ser Leu Gln Pro Pro Phe Pro Pro Cys Thr
385                 390                 395                 400

Leu Arg Lys Ala Leu Thr Asn Tyr Ala Asp Leu Leu Ser Ser Pro Lys
            405                 410                 415

Lys Ser Thr Leu Leu Ala Leu Ala Ala His Ala Ser Asp Pro Thr Glu
        420                 425                 430

Ala Asp Arg Leu Arg Phe Leu Ala Ser Arg Glu Gly Lys Asp Glu Tyr
        435                 440                 445

Ala Glu Trp Val Val Ala Asn Gln Arg Ser Leu Leu Glu Val Met Glu
        450                 455                 460

Ala Phe Pro Ser Ala Arg Pro Pro Leu Gly Val Phe Phe Ala Ala Val
465                 470                 475                 480

Ala Pro Arg Leu Gln Pro Arg Tyr Tyr Ser Ile Ser Ser Ser Pro Lys
            485                 490                 495

Met Glu Pro Asn Arg Ile His Val Thr Cys Ala Leu Val Tyr Glu Lys
        500                 505                 510

Thr Pro Ala Gly Arg Ile His Lys Gly Ile Cys Ser Thr Trp Met Lys
        515                 520                 525

Asn Ala Val Pro Leu Thr Glu Ser Gln Asp Cys Ser Trp Ala Pro Ile
530                 535                 540

Phe Val Arg Thr Ser Asn Phe Arg Leu Pro Ile Asp Pro Lys Val Pro
545                 550                 555                 560

Val Ile Met Ile Gly Pro Gly Thr Gly Leu Ala Pro Phe Arg Gly Phe
            565                 570                 575

Leu Gln Glu Arg Leu Ala Leu Lys Glu Ser Gly Thr Glu Leu Gly Ser
        580                 585                 590

Ser Ile Leu Phe Phe Gly Cys Arg Asn Arg Lys Val Asp Tyr Ile Tyr
        595                 600                 605

Glu Asn Glu Leu Asn Asn Phe Val Glu Asn Gly Ala Leu Ser Glu Leu
610                 615                 620

Asp Val Ala Phe Ser Arg Asp Gly Pro Thr Lys Glu Tyr Val Gln His
625                 630                 635                 640

Lys Met Thr Gln Lys Ala Ser Glu Ile Trp Asn Met Leu Ser Glu Gly
            645                 650                 655

Ala Tyr Leu Tyr Val Cys Gly Asp Ala Lys Gly Met Ala Lys Asp Val
        660                 665                 670

His Arg Thr Leu His Thr Ile Val Gln Glu Gln Gly Ser Leu Asp Ser
        675                 680                 685

Ser Lys Ala Glu Leu Tyr Val Lys Asn Leu Gln Met Ser Gly Arg Tyr
690                 695                 700

Leu Arg Asp Val Trp
705

<210> SEQ ID NO 85
<211> LENGTH: 2124

<212> TYPE: DNA
<213> ORGANISM: Artificial Sequence
<220> FEATURE:
<223> OTHER INFORMATION: Codon-optimized CPR

<400> SEQUENCE: 85

```
atgcaatcta actccgtgaa gatttcgccg cttgatctgg taactgcgct gtttagcggc      60
aaggttttgg acacatcgaa cgcatcggaa tcgggagaat ctgctatgct gccgactata     120
gcgatgatta tggagaatcg tgagctgttg atgatactca aacgtcggt tgctgtattg      180
atcggatgcg ttgtcgtttt ggtgtggcgg agatcgtcta cgaagaagtc ggcgttggag     240
ccaccggtga ttgtggttcc gaagagagtg caagaggagg aagttgatga tggtaagaag     300
aaagttacgg ttttcttcgg cacccaaact ggaacagctg aaggcttcgc taaggcactt     360
gttgaggaag ctaaagctcg atatgaaaag gctgtcttta agtaattga tttggatgat     420
tatgctgctg atgacgatga gtatgaggag aaactaaaga aagaatcttt ggcctttttc     480
tttttggcta cgtatggaga tggtgagcca acagataatg ctgccagatt ttataaatgg     540
tttactgagg gagatgcgaa aggagaatgg cttaataagc ttcaatatgg agtatttggt     600
ttgggtaaca gacaatatga acattttaac aagatcgcaa aagtggttga tgatggtctt     660
gtagaacagg gtgcaaagcg tcttgttcct gttggacttg agatgatga tcaatgtatt     720
gaagatgact tcaccgcatg gaaagagtta gtatggccgg agttggatca attacttcgt     780
gatgaggatg acacaactgt tgctactcca tacacagctg ctgttgcaga atatcgcgtt     840
gtttttcatg aaaaaccaga cgcgctttct gaagattata gttatacaaa tggccatgct     900
gttcatgatg ctcaacatcc atgcagatcc aacgtggctg tcaaaaagga acttcatagt     960
cctgaatctg accggtcttg cactcatctt gaatttgaca tctcgaacac cggactatca    1020
tatgaaactg gggaccatgt tggagtttac tgtgaaaact tgagtgaagt tgtgaatgat    1080
gctgaaagat tagtaggatt accaccagac acttactcct ccatccacac tgatagtgaa    1140
gacgggtcgc cacttggcgg agcctcattg ccgcctcctt tcccgccatg cactttaagg    1200
aaagcattga cgtgttatgc tgatgttttg agttctccca agaagtcggc tttgcttgca    1260
ctagctgctc atgccaccga tcccagtgaa gctgatagat tgaaatttct tgcatccccc    1320
gccggaaagg atgaatattc tcaatggata gttgcaagcc aaagaagtct ccttgaagtc    1380
atggaagcat tcccgtcagc taagccttca cttggtgttt tctttgcatc tgttgccccg    1440
cgcttacaac caagatacta ctctatttct tcctcaccca gatggcacc ggataggatt     1500
catgttacat gtgcattagt ctatgagaaa acacctgcag gccgcatcca caaggagtt    1560
tgttcaactt ggatgaagaa cgcagtgcct atgaccgaga gtcaagattg cagttgggcc    1620
ccaatatacg tccgaacatc caatttcaga ctaccatctg accctaaggt cccggttatc    1680
atgattggac ctggcactgg tttggctcct tttagaggtt ccttcaaga gcggttagct    1740
ttaaaggaag ccgaactga cctcggttta tccattttat tcttcggatg taggaatcgc    1800
aaagtggatt tcatatatga aaacgagctt aacaactttg tggagactgg tgctctttct    1860
gagcttattg ttgctttctc ccgtgaaggc ccgactaagg aatatgtgca acacaagatg    1920
agtgagaagg cttcggatat ctggaacttg ctttctgaag gagcatattt atacgtatgt    1980
ggtgatgcca aaggcatggc caaagatgta catcgaaccc tccacacaat tgtgcaagaa    2040
cagggatctc ttgactcgtc aaaggcagaa ctctacgtga agaatctaca aatgtcagga    2100
agataccctcc gtgacgtttg gtaa                                         2124
```

<210> SEQ ID NO 86
<211> LENGTH: 707
<212> TYPE: PRT
<213> ORGANISM: Stevia rebaudiana

<400> SEQUENCE: 86

Met Gln Ser Asn Ser Val Lys Ile Ser Pro Leu Asp Leu Val Thr Ala
1               5                   10                  15

Leu Phe Ser Gly Lys Val Leu Asp Thr Ser Asn Ala Ser Glu Ser Gly
            20                  25                  30

Glu Ser Ala Met Leu Pro Thr Ile Ala Met Ile Met Glu Asn Arg Glu
        35                  40                  45

Leu Leu Met Ile Leu Thr Thr Ser Val Ala Val Leu Ile Gly Cys Val
    50                  55                  60

Val Val Leu Val Trp Arg Arg Ser Ser Thr Lys Lys Ser Ala Leu Glu
65                  70                  75                  80

Pro Pro Val Ile Val Pro Lys Arg Val Gln Glu Glu Glu Val Asp
                85                  90                  95

Asp Gly Lys Lys Lys Val Thr Val Phe Phe Gly Thr Gln Thr Gly Thr
            100                 105                 110

Ala Glu Gly Phe Ala Lys Ala Leu Val Glu Glu Ala Lys Ala Arg Tyr
        115                 120                 125

Glu Lys Ala Val Phe Lys Val Ile Asp Leu Asp Asp Tyr Ala Ala Asp
    130                 135                 140

Asp Asp Glu Tyr Glu Glu Lys Leu Lys Lys Glu Ser Leu Ala Phe Phe
145                 150                 155                 160

Phe Leu Ala Thr Tyr Gly Asp Gly Glu Pro Thr Asp Asn Ala Ala Arg
                165                 170                 175

Phe Tyr Lys Trp Phe Thr Glu Gly Asp Ala Lys Gly Glu Trp Leu Asn
            180                 185                 190

Lys Leu Gln Tyr Gly Val Phe Gly Leu Gly Asn Arg Gln Tyr Glu His
        195                 200                 205

Phe Asn Lys Ile Ala Lys Val Val Asp Asp Gly Leu Val Glu Gln Gly
    210                 215                 220

Ala Lys Arg Leu Val Pro Val Gly Leu Gly Asp Asp Gln Cys Ile
225                 230                 235                 240

Glu Asp Asp Phe Thr Ala Trp Lys Glu Leu Val Trp Pro Glu Leu Asp
                245                 250                 255

Gln Leu Leu Arg Asp Glu Asp Thr Thr Val Ala Thr Pro Tyr Thr
            260                 265                 270

Ala Ala Val Ala Glu Tyr Arg Val Val Phe His Glu Lys Pro Asp Ala
        275                 280                 285

Leu Ser Glu Asp Tyr Ser Tyr Thr Asn Gly His Ala Val His Asp Ala
    290                 295                 300

Gln His Pro Cys Arg Ser Asn Val Ala Val Lys Lys Glu Leu His Ser
305                 310                 315                 320

Pro Glu Ser Asp Arg Ser Cys Thr His Leu Glu Phe Asp Ile Ser Asn
                325                 330                 335

Thr Gly Leu Ser Tyr Glu Thr Gly Asp His Val Gly Val Tyr Cys Glu
            340                 345                 350

Asn Leu Ser Glu Val Val Asn Asp Ala Glu Arg Leu Val Gly Leu Pro
        355                 360                 365

Pro Asp Thr Tyr Ser Ser Ile His Thr Asp Ser Glu Asp Gly Ser Pro
    370                 375                 380

Leu Gly Gly Ala Ser Leu Pro Pro Phe Pro Pro Cys Thr Leu Arg
385                 390                 395                 400

Lys Ala Leu Thr Cys Tyr Ala Asp Val Leu Ser Ser Pro Lys Lys Ser
            405                 410                 415

Ala Leu Leu Ala Leu Ala Ala His Ala Thr Asp Pro Ser Glu Ala Asp
            420                 425                 430

Arg Leu Lys Phe Leu Ala Ser Pro Ala Gly Lys Asp Glu Tyr Ser Gln
            435                 440                 445

Trp Ile Val Ala Ser Gln Arg Ser Leu Leu Glu Val Met Glu Ala Phe
            450                 455                 460

Pro Ser Ala Lys Pro Ser Leu Gly Val Phe Phe Ala Ser Val Ala Pro
465                 470                 475                 480

Arg Leu Gln Pro Arg Tyr Tyr Ser Ile Ser Ser Ser Pro Lys Met Ala
            485                 490                 495

Pro Asp Arg Ile His Val Thr Cys Ala Leu Val Tyr Glu Lys Thr Pro
            500                 505                 510

Ala Gly Arg Ile His Lys Gly Val Cys Ser Thr Trp Met Lys Asn Ala
            515                 520                 525

Val Pro Met Thr Glu Ser Gln Asp Cys Ser Trp Ala Pro Ile Tyr Val
530                 535                 540

Arg Thr Ser Asn Phe Arg Leu Pro Ser Asp Pro Lys Val Pro Val Ile
545                 550                 555                 560

Met Ile Gly Pro Gly Thr Gly Leu Ala Pro Phe Arg Gly Phe Leu Gln
            565                 570                 575

Glu Arg Leu Ala Leu Lys Glu Ala Gly Thr Asp Leu Gly Leu Ser Ile
            580                 585                 590

Leu Phe Phe Gly Cys Arg Asn Arg Lys Val Asp Phe Ile Tyr Glu Asn
            595                 600                 605

Glu Leu Asn Asn Phe Val Glu Thr Gly Ala Leu Ser Glu Leu Ile Val
610                 615                 620

Ala Phe Ser Arg Glu Gly Pro Thr Lys Glu Tyr Val Gln His Lys Met
625                 630                 635                 640

Ser Glu Lys Ala Ser Asp Ile Trp Asn Leu Leu Ser Glu Gly Ala Tyr
            645                 650                 655

Leu Tyr Val Cys Gly Asp Ala Lys Gly Met Ala Lys Asp Val His Arg
            660                 665                 670

Thr Leu His Thr Ile Val Gln Glu Gln Gly Ser Leu Asp Ser Ser Lys
            675                 680                 685

Ala Glu Leu Tyr Val Lys Asn Leu Gln Met Ser Gly Arg Tyr Leu Arg
            690                 695                 700

Asp Val Trp
705

<210> SEQ ID NO 87
<211> LENGTH: 2070
<212> TYPE: DNA
<213> ORGANISM: Artificial Sequence
<220> FEATURE:
<223> OTHER INFORMATION: Codon-optimized CPR

<400> SEQUENCE: 87
atgtcctcca actccgattt ggtcagaaga ttggaatctg ttttgggtgt tcttttcggt      60
ggttctgtta ctgattccgt tgttgttatt gctaccacct ctattgcttt ggttatcggt     120
gttttggttt tgttgtggag aagatcctct gacagatcta gagaagttaa gcaattggct     180

```
gttccaaagc cagttactat cgttgaagaa gaagatgaat tcgaagttgc ttctggtaag      240
accagagttt ctattttcta cggtactcaa actggtactg ctgaaggttt tgctaaggct      300
ttggctgaag aaatcaaagc cagatacgaa aaagctgccg ttaaggttat tgatttggat      360
gattacacag ccgaagatga caaatacggt gaaaagttga agaaagaaac tatggccttc      420
ttcatgttgg ctacttatgg tgatggtgaa cctactgata tgctgctag attttacaag       480 tggttcaccg aaggtactga tagaggtgtt tggttggaac atttgagata cggtgtattc      540
ggtttgggta acagacaata cgaacacttc aacaagattg ccaaggttgt tgatgatttg      600
ttggttgaac aaggtgccaa gagattggtt actgttggtt gggtgatga tgatcaatgc       660 atcgaagatg atttctccgc ttggaaagaa gccttgtggc cagaattgga tcaattattg      720
caagatgata ccaacaccgt ttctactcca tacactgctg ttattccaga atacagagtt      780
gttatccacg atccatctgt tacctcttat gaagatccat actctaacat ggctaacggt      840
aatgcctctt acgatattca tcatccatgt agagctaacg ttgccgtcca aaaagaattg      900
cataagccag aatctgacag aagttgcatc catttggaat tcgatatttt cgctactggt      960
ttgacttacg aaaccggtga tcatgttggt gtttacgctg ataattgtga tgatactgta    1020
gaagaagccg ctaagttgtt gggtcaacca ttggatttgt tgttctccat tcataccgat    1080
aacaacgacg gtacttcttt gggttcttct ttgccaccac catttccagg tccatgtact    1140
ttgagaactg ctttggctag atatgccgat tgttgaatc caccaaaaaa ggctgctttg     1200
attgctttag ctgctcatgc tgatgaacca tctgaagctg aaagattgaa gttcttgtca    1260
tctccacaag gtaaggacga atattctaaa tgggttgtcg gttcccaaag atccttggtt    1320
gaagttatgg ctgaatttcc atctgctaaa ccaccattgg gtgtattttt tgctgctgtt    1380
gttcctagat tgcaacctag atattactcc atctcttcca gtccaagatt tgctccacat    1440
agagttcatg ttacttgcgc tttggtttat ggtccaactc caactggtag aattcacaga    1500
ggtgtatgtt cattctggat gaagaatgtt gtcccattgg aaaagtctca aaactgttct    1560
tgggccccaa ttttcatcag acaatctaat ttcaagttgc cagccgatca ttctgttcca    1620
atagttatgg ttggtccagg tactggttta gctcctttta gaggtttctt acaagaaaga    1680
ttggccttga agaagaaggt tgctcaagtt ggtcctgctt tgttgttttt tggttgcaga    1740
aacagacaaa tggacttcat ctacgaagtc gaattgaaca ctttgtcga caaggtgct     1800 ttgtccgaat tgatcgttgc ttttttcaaga gaaggtccat ccaaagaata cgtccaacat    1860
aagatggttt aaaaggcagc ttacatgtgg aacttgattt ctcaaggtgg ttacttctac    1920
gtttgtggtg atgctaaagg tatggctaga gatgttcata gaacattgca taccatcgtc    1980
caacaagaag aaaaggttga ttctaccaag gccgaatcca tcgttaagaa attgcaaatg    2040
gacggtagat acttgagaga tgtttggtga                                    2070
```

<210> SEQ ID NO 88
<211> LENGTH: 689
<212> TYPE: PRT
<213> ORGANISM: Rubus suavissimus

<400> SEQUENCE: 88

Met Ser Ser Asn Ser Asp Leu Val Arg Arg Leu Glu Ser Val Leu Gly
1               5                   10                  15

Val Ser Phe Gly Gly Ser Val Thr Asp Ser Val Val Ile Ala Thr
            20                  25                  30

```
Thr Ser Ile Ala Leu Val Ile Gly Val Leu Val Leu Leu Trp Arg Arg
        35                  40                  45

Ser Ser Asp Arg Ser Arg Glu Val Lys Gln Leu Ala Val Pro Lys Pro
50                  55                  60

Val Thr Ile Val Glu Glu Asp Glu Phe Glu Val Ala Ser Gly Lys
65                  70                  75                  80

Thr Arg Val Ser Ile Phe Tyr Gly Thr Gln Thr Gly Thr Ala Glu Gly
                    85                  90                  95

Phe Ala Lys Ala Leu Ala Glu Glu Ile Lys Ala Arg Tyr Glu Lys Ala
                100                 105                 110

Ala Val Lys Val Ile Asp Leu Asp Asp Tyr Thr Ala Glu Asp Asp Lys
                115                 120                 125

Tyr Gly Glu Lys Leu Lys Lys Glu Thr Met Ala Phe Phe Met Leu Ala
130                 135                 140

Thr Tyr Gly Asp Gly Glu Pro Thr Asp Asn Ala Ala Arg Phe Tyr Lys
145                 150                 155                 160

Trp Phe Thr Glu Gly Thr Asp Arg Gly Val Trp Leu Glu His Leu Arg
                    165                 170                 175

Tyr Gly Val Phe Gly Leu Gly Asn Arg Gln Tyr Glu His Phe Asn Lys
                180                 185                 190

Ile Ala Lys Val Val Asp Asp Leu Leu Val Glu Gln Gly Ala Lys Arg
                195                 200                 205

Leu Val Thr Val Gly Leu Gly Asp Asp Asp Gln Cys Ile Glu Asp Asp
        210                 215                 220

Phe Ser Ala Trp Lys Glu Ala Leu Trp Pro Glu Leu Asp Gln Leu Leu
225                 230                 235                 240

Gln Asp Asp Thr Asn Thr Val Ser Thr Pro Tyr Thr Ala Val Ile Pro
                245                 250                 255

Glu Tyr Arg Val Val Ile His Asp Pro Ser Val Thr Ser Tyr Glu Asp
                260                 265                 270

Pro Tyr Ser Asn Met Ala Asn Gly Asn Ala Ser Tyr Asp Ile His His
        275                 280                 285

Pro Cys Arg Ala Asn Val Ala Val Gln Lys Glu Leu His Lys Pro Glu
        290                 295                 300

Ser Asp Arg Ser Cys Ile His Leu Glu Phe Asp Ile Phe Ala Thr Gly
305                 310                 315                 320

Leu Thr Tyr Glu Thr Gly Asp His Val Gly Val Tyr Ala Asp Asn Cys
                    325                 330                 335

Asp Asp Thr Val Glu Glu Ala Ala Lys Leu Leu Gly Gln Pro Leu Asp
                340                 345                 350

Leu Leu Phe Ser Ile His Thr Asp Asn Asn Asp Gly Thr Ser Leu Gly
                355                 360                 365

Ser Ser Leu Pro Pro Pro Phe Pro Gly Pro Cys Thr Leu Arg Thr Ala
370                 375                 380

Leu Ala Arg Tyr Ala Asp Leu Leu Asn Pro Pro Lys Lys Ala Ala Leu
385                 390                 395                 400

Ile Ala Leu Ala Ala His Ala Asp Glu Pro Ser Glu Ala Glu Arg Leu
                405                 410                 415

Lys Phe Leu Ser Ser Pro Gln Gly Lys Asp Glu Tyr Ser Lys Trp Val
                420                 425                 430

Val Gly Ser Gln Arg Ser Leu Val Glu Val Met Ala Glu Phe Pro Ser
                435                 440                 445

Ala Lys Pro Pro Leu Gly Val Phe Phe Ala Ala Val Val Pro Arg Leu
```

```
        450                 455                 460
Gln Pro Arg Tyr Tyr Ser Ile Ser Ser Ser Pro Arg Phe Ala Pro His
465                 470                 475                 480

Arg Val His Val Thr Cys Ala Leu Val Tyr Gly Pro Thr Pro Thr Gly
                485                 490                 495

Arg Ile His Arg Gly Val Cys Ser Phe Trp Met Lys Asn Val Val Pro
            500                 505                 510

Leu Glu Lys Ser Gln Asn Cys Ser Trp Ala Pro Ile Phe Ile Arg Gln
        515                 520                 525

Ser Asn Phe Lys Leu Pro Ala Asp His Ser Val Pro Ile Val Met Val
    530                 535                 540

Gly Pro Gly Thr Gly Leu Ala Pro Phe Arg Gly Phe Leu Gln Glu Arg
545                 550                 555                 560

Leu Ala Leu Lys Glu Glu Gly Ala Gln Val Gly Pro Ala Leu Leu Phe
                565                 570                 575

Phe Gly Cys Arg Asn Arg Gln Met Asp Phe Ile Tyr Glu Val Glu Leu
            580                 585                 590

Asn Asn Phe Val Glu Gln Gly Ala Leu Ser Glu Leu Ile Val Ala Phe
        595                 600                 605

Ser Arg Glu Gly Pro Ser Lys Glu Tyr Val Gln His Lys Met Val Glu
    610                 615                 620

Lys Ala Ala Tyr Met Trp Asn Leu Ile Ser Gln Gly Gly Tyr Phe Tyr
625                 630                 635                 640

Val Cys Gly Asp Ala Lys Gly Met Ala Arg Asp Val His Arg Thr Leu
                645                 650                 655

His Thr Ile Val Gln Gln Glu Glu Lys Val Asp Ser Thr Lys Ala Glu
            660                 665                 670

Ser Ile Val Lys Lys Leu Gln Met Asp Gly Arg Tyr Leu Arg Asp Val
        675                 680                 685

Trp

<210> SEQ ID NO 89
<211> LENGTH: 2079
<212> TYPE: DNA
<213> ORGANISM: Artificial Sequence
<220> FEATURE:
<223> OTHER INFORMATION: Codon-optimized CPR

<400> SEQUENCE: 89
atgacttctg cactttatgc ctccgatctt ttcaaacaat tgaaaagtat catgggaacg      60
gattctttgt ccgatgatgt tgtattagtt attgctacaa cttctctggc actggttgct     120
ggtttcgttg tcttattgtg gaaaaagacc acggcagatc gttccggcga gctaaagcca     180
ctaatgatcc ctaagtctct gatggcgaaa gatgaggatg atgacttaga tctaggttct     240
ggaaaaacga gagtctctat cttcttcggc acacaaaccg gaacagccga aggattcgct     300
aaagcacttt cagaagagat caagcaagaa tacgaaaagg cggctgtaaa agtaatcgat     360
ttggatgatt acgctgccga tgatgaccaa tatgaggaaa agttgaaaaa ggaaacattg     420
gctttctttt gtgtagccac gtatggtgat ggtgaaccaa ccgataacgc cgcaagattc     480
tacaagtggt ttactgaaga gaacgaaaga gatatcaagt gcagcaact tgcttacggc     540 gtttttgcct taggtaacag acaatacgag cactttaaca agataggtat tgtcttagat     600
gaagagttat gcaaaagggg tgcgaagaga ttgattgaag tcggtttagg agatgatgat     660
caatctatcg aggatgactt taatgcatgg aaggaatctt tgtggtctga attagataag     720
```

```
ttacttaagg acgaagatga taaatccgtt gccactccat acacagccgt cattccagaa    780
tatagagtag ttactcatga tccaagattc acaacacaga aatcaatgga aagtaatgtg    840
gctaatggta atactaccat cgatattcat catccatgta gagtagacgt tgcagttcaa    900
aaggaattgc acactcatga atcagacaga tcttgcatac atcttgaatt tgatatatca    960
cgtactggta tcacttacga aacaggtgat cacgtgggtg tctacgctga aaaccatgtt   1020
gaaattgtag aggaagctgg aaagttgttg ggcatagtt tagatcttgt tttctcaatt    1080
catgccgata agaggatgg ctcaccacta gaaagtgcag tgcctccacc atttccagga    1140
ccatgcaccc taggtaccgg tttagctcgt tacgcggatc tgttaaatcc tccacgtaaa   1200
tcagctctag tggccttggc tgcgtacgcc acagaacctt ctgaggcaga aaaactgaaa   1260
catctaactt caccagatgg taaggatgaa tactcacaat ggatagtagc tagtcaacgt   1320
tctttactag aagttatggc tgctttccca tccgctaaac ctcctttggg tgttttcttc   1380
gccgcaatag cgcctagact gcaaccaaga tactattcaa tttcatcctc acctagactg   1440
gcaccatcaa gagttcatgt cacatccgct ttagtgtacg gtccaactcc tactggtaga   1500
atccataagg gcgtttgttc aacatggatg aaaaacgcgg ttccagcaga gaagtctcac   1560
gaatgttctg gtgctccaat ctttatcaga gcctccaact tcaaactgcc ttccaatcct   1620
tctactccta ttgtcatggt cggtcctggt acaggtcttg ctccattcag aggtttctta   1680
caagagagaa tggccttaaa ggaggatggt gaagagttgg gatcttcttt gttgtttttc   1740
ggctgtagaa acagacaaat ggatttcatc tacgaagatg aactgaataa ctttgtagat   1800
caaggagtta tttcagagtt gataatggct ttttctagag aaggtgctca gaaggagtac   1860
gtccaacaca aaatgatgga aaaggccgca caagtttggg acttaatcaa agaggaaggc   1920
tatctatatg tctgtggtga tgcaaagggt atggcaagag atgttcacag aacacttcat   1980
actatagtcc aggaacagga aggcgttagt tcttctgaag cggaagcaat tgtgaaaaag   2040
ttacaaacag agggaagata cttgagagat gtgtggtaa                          2079
```

<210> SEQ ID NO 90
<211> LENGTH: 692
<212> TYPE: PRT
<213> ORGANISM: Arabidopsis thaliana

<400> SEQUENCE: 90

```
Met Thr Ser Ala Leu Tyr Ala Ser Asp Leu Phe Lys Gln Leu Lys Ser
1               5                   10                  15
Ile Met Gly Thr Asp Ser Leu Ser Asp Val Val Leu Val Ile Ala
            20                  25                  30
Thr Thr Ser Leu Ala Leu Val Ala Gly Phe Val Leu Leu Trp Lys
        35                  40                  45
Lys Thr Thr Ala Asp Arg Ser Gly Glu Leu Lys Pro Leu Met Ile Pro
    50                  55                  60
Lys Ser Leu Met Ala Lys Asp Glu Asp Asp Leu Asp Leu Gly Ser
65                  70                  75                  80
Gly Lys Thr Arg Val Ser Ile Phe Phe Gly Thr Gln Thr Gly Thr Ala
                85                  90                  95
Glu Gly Phe Ala Lys Ala Leu Ser Glu Glu Ile Lys Ala Arg Tyr Glu
            100                 105                 110
Lys Ala Ala Val Lys Val Ile Asp Leu Asp Asp Tyr Ala Ala Asp Asp
        115                 120                 125
```

```
Asp Gln Tyr Glu Glu Lys Leu Lys Lys Glu Thr Leu Ala Phe Phe Cys
    130                 135                 140
Val Ala Thr Tyr Gly Asp Gly Glu Pro Thr Asp Asn Ala Ala Arg Phe
145                 150                 155                 160
Tyr Lys Trp Phe Thr Glu Glu Asn Glu Arg Asp Ile Lys Leu Gln Gln
                165                 170                 175
Leu Ala Tyr Gly Val Phe Ala Leu Gly Asn Arg Gln Tyr Glu His Phe
            180                 185                 190
Asn Lys Ile Gly Ile Val Leu Asp Glu Glu Leu Cys Lys Lys Gly Ala
        195                 200                 205
Lys Arg Leu Ile Glu Val Gly Leu Gly Asp Asp Gln Ser Ile Glu
    210                 215                 220
Asp Asp Phe Asn Ala Trp Lys Glu Ser Leu Trp Ser Glu Leu Asp Lys
225                 230                 235                 240
Leu Leu Lys Asp Glu Asp Lys Ser Val Ala Thr Pro Tyr Thr Ala
                245                 250                 255
Val Ile Pro Glu Tyr Arg Val Val Thr His Asp Pro Arg Phe Thr Thr
                260                 265                 270
Gln Lys Ser Met Glu Ser Asn Val Ala Asn Gly Asn Thr Thr Ile Asp
            275                 280                 285
Ile His His Pro Cys Arg Val Asp Val Ala Val Gln Lys Glu Leu His
        290                 295                 300
Thr His Glu Ser Asp Arg Ser Cys Ile His Leu Glu Phe Asp Ile Ser
305                 310                 315                 320
Arg Thr Gly Ile Thr Tyr Glu Thr Gly Asp His Val Gly Val Tyr Ala
                325                 330                 335
Glu Asn His Val Glu Ile Val Glu Glu Ala Gly Lys Leu Leu Gly His
            340                 345                 350
Ser Leu Asp Leu Val Phe Ser Ile His Ala Asp Lys Glu Asp Gly Ser
    355                 360                 365
Pro Leu Glu Ser Ala Val Pro Pro Phe Pro Gly Pro Cys Thr Leu
370                 375                 380
Gly Thr Gly Leu Ala Arg Tyr Ala Asp Leu Leu Asn Pro Pro Arg Lys
385                 390                 395                 400
Ser Ala Leu Val Ala Leu Ala Ala Tyr Ala Thr Glu Pro Ser Glu Ala
                405                 410                 415
Glu Lys Leu Lys His Leu Thr Ser Pro Asp Gly Lys Asp Glu Tyr Ser
            420                 425                 430
Gln Trp Ile Val Ala Ser Gln Arg Ser Leu Leu Glu Val Met Ala Ala
        435                 440                 445
Phe Pro Ser Ala Lys Pro Pro Leu Gly Val Phe Phe Ala Ala Ile Ala
    450                 455                 460
Pro Arg Leu Gln Pro Arg Tyr Tyr Ser Ile Ser Ser Ser Pro Arg Leu
465                 470                 475                 480
Ala Pro Ser Arg Val His Val Thr Ser Ala Leu Val Tyr Gly Pro Thr
                485                 490                 495
Pro Thr Gly Arg Ile His Lys Gly Val Cys Ser Thr Trp Met Lys Asn
            500                 505                 510
Ala Val Pro Ala Glu Lys Ser His Glu Cys Ser Gly Ala Pro Ile Phe
        515                 520                 525
Ile Arg Ala Ser Asn Phe Lys Leu Pro Ser Asn Pro Ser Thr Pro Ile
    530                 535                 540
Val Met Val Gly Pro Gly Thr Gly Leu Ala Pro Phe Arg Gly Phe Leu
```

|    |     |     |     |     |     |     |     |     |     |     |     |     |     |     |     |
|----|-----|-----|-----|-----|-----|-----|-----|-----|-----|-----|-----|-----|-----|-----|-----|
| 545 | | | | | 550 | | | | | 555 | | | | | 560 |

Gln Glu Arg Met Ala Leu Lys Glu Asp Gly Glu Leu Gly Ser Ser
                     565                    570                 575

Leu Leu Phe Phe Gly Cys Arg Asn Arg Gln Met Asp Phe Ile Tyr Glu
           580                   585                  590

Asp Glu Leu Asn Asn Phe Val Asp Gln Gly Val Ile Ser Glu Leu Ile
           595                   600                605

Met Ala Phe Ser Arg Glu Gly Ala Gln Lys Glu Tyr Val Gln His Lys
   610                   615                   620

Met Met Glu Lys Ala Ala Gln Val Trp Asp Leu Ile Lys Glu Glu Gly
625                   630                   635              640

Tyr Leu Tyr Val Cys Gly Asp Ala Lys Gly Met Ala Arg Asp Val His
           645                   650                655

Arg Thr Leu His Thr Ile Val Gln Glu Gln Gly Val Ser Ser
          660                   665                670

Glu Ala Glu Ala Ile Val Lys Lys Leu Gln Thr Glu Gly Arg Tyr Leu
          675                   680                685

Arg Asp Val Trp
690

<210> SEQ ID NO 91
<211> LENGTH: 2139
<212> TYPE: DNA
<213> ORGANISM: Artificial Sequence
<220> FEATURE:
<223> OTHER INFORMATION: Codon-optimized CPR

<400> SEQUENCE: 91

| | | | | |
|---|---|---|---|---|
| atgtcttcct cttcctcttc cagtacctct atgattgatt tgatggctgc tattattaaa | | | | 60 |
| ggtgaaccag ttatcgtctc cgacccagca atgcctctg cttatgaatc agttgctgca | | | | 120 |
| gaattgtctt caatgttgat cgaaaacaga caattcgcca tgatcgtaac tacatcaatc | | | | 180 |
| gctgttttga tcggttgtat tgtcatgttg gtatggagaa gatccggtag tggtaattct | | | | 240 |
| aaaagagtcg aacctttgaa accattagta attaagccaa gagaagaaga aatagatgac | | | | 300 |
| ggtagaaaga aagttacaat attttcggt acccaaactg gtacagctga aggttttgca | | | | 360 |
| aaagccttag gtgaagaagc taaggcaaga tacgaaaaga ctagattcaa gatagtcgat | | | | 420 |
| ttggatgact atgccgctga tgacgatgaa tacgaagaaa agttgaagaa agaagatgtt | | | | 480 |
| gcatttttct ttttggcaac ctatggtgac ggtgaaccaa ctgacaatgc agccagattc | | | | 540 |
| tacaaatggt ttacagaggg taatgatcgt ggtgaatggt tgaaaaactt aaagtacggt | | | | 600 |
| gttttcggtt tgggtaacag acaatacgaa catttcaaca agttgcaaa ggttgtcgac | | | | 660 |
| gatatttggg tcgaacaagg tgctcaaaga ttagtccaag taggtttggg tgacgatgac | | | | 720 |
| caatgtatag aagatgactt tactgcctgg agagaagctt gtggcctga attagacaca | | | | 780 |
| atcttgagag aagaaggtga caccgccgtt gctaccccat atactgctgc agtattagaa | | | | 840 |
| tacagagttt ccatccatga tagtgaagac gcaaagttta tgatatcac tttggccaat | | | | 900 |
| ggtaacggtt atacagtttt cgatgcacaa caccccttaca aagctaacgt tgcagtcaag | | | | 960 |
| agagaattac atacaccaga atccgacaga agttgtatac acttggaatt tgatatcgct | | | | 1020 |
| ggttccggtt taaccatgaa gttgggtgac catgtaggtg ttttatgcga caatttgtct | | | | 1080 |
| gaaactgttg atgaagcatt gagattgttg gatatgtccc ctgacactta ttttagtttg | | | | 1140 |
| cacgctgaaa agaagatgg tacaccaatt tccagttct taccacctcc attccctcca | | | | 1200 |

-continued

```
tgtaacttaa gaacagcctt gaccagatac gcttgcttgt tatcatcccc taaaaagtcc    1260
gccttggttg ctttagccgc tcatgctagt gatcctactg aagcagaaag attgaaacac    1320
ttagcatctc cagccggtaa agatgaatat tcaaagtggg tagttgaatc tcaaagatca    1380
ttgttagaag ttatggcaga atttccatct gccaagcctc cattaggtgt cttctttgct    1440
ggtgtagcac ctagattgca accaagattc tactcaatca gttcttcacc taagatcgct    1500
gaaactagaa ttcatgttac atgtgcatta gtctacgaaa agatgccaac cggtagaatt    1560
cacaagggtg tatgctctac ttggatgaaa aatgctgttc cttacgaaaa atcagaaaag    1620
ttgttcttag gtagaccaat cttcgtaaga caatcaaact tcaagttgcc ttctgattca    1680
aaggttccaa taatcatgat aggtcctggt acaggtttag ccccattcag aggtttcttg    1740
caagaaagat tggctttagt tgaatctggt gtcgaattag gtccttcagt tttgttcttt    1800
ggttgtagaa acagaagaat ggatttcatc tatgaagaag aattgcaaag attcgtcgaa    1860
tctggtgcat tggccgaatt atctgtagct ttttcaagag aaggtccaac taaggaatac    1920
gttcaacata agatgatgga taaggcatcc gacatatgga acatgatcag tcaaggtgct    1980
tatttgtacg tttgcggtga cgcaaagggt atggccagag atgtccatag atctttgcac    2040
acaattgctc aagaacaagg ttccatggat agtaccaaag ctgaaggttt cgtaaagaac    2100
ttacaaactt ccggtagata cttgagagat gtctggtga                           2139
```

<210> SEQ ID NO 92
<211> LENGTH: 712
<212> TYPE: PRT
<213> ORGANISM: Arabidopsis thaliana

<400> SEQUENCE: 92

```
Met Ser Ser Ser Ser Ser Ser Thr Ser Met Ile Asp Leu Met Ala
1               5                  10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160

Ala Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205
```

```
Tyr Glu His Phe Asn Lys Val Ala Lys Val Val Asp Asp Ile Leu Val
    210                 215                 220
Glu Gln Gly Ala Gln Arg Leu Val Gln Val Gly Leu Gly Asp Asp
225                 230                 235                 240
Gln Cys Ile Glu Asp Asp Phe Thr Ala Trp Arg Glu Ala Leu Trp Pro
                245                 250                 255
Glu Leu Asp Thr Ile Leu Arg Glu Glu Gly Asp Thr Ala Val Ala Thr
                260                 265                 270
Pro Tyr Thr Ala Ala Val Leu Glu Tyr Arg Val Ser Ile His Asp Ser
        275                 280                 285
Glu Asp Ala Lys Phe Asn Asp Ile Thr Leu Ala Asn Gly Asn Gly Tyr
290                 295                 300
Thr Val Phe Asp Ala Gln His Pro Tyr Lys Ala Asn Val Ala Val Lys
305                 310                 315                 320
Arg Glu Leu His Thr Pro Glu Ser Asp Arg Ser Cys Ile His Leu Glu
                325                 330                 335
Phe Asp Ile Ala Gly Ser Gly Leu Thr Met Lys Leu Gly Asp His Val
                340                 345                 350
Gly Val Leu Cys Asp Asn Leu Ser Glu Thr Val Asp Glu Ala Leu Arg
                355                 360                 365
Leu Leu Asp Met Ser Pro Asp Thr Tyr Phe Ser Leu His Ala Glu Lys
        370                 375                 380
Glu Asp Gly Thr Pro Ile Ser Ser Ser Leu Pro Pro Phe Pro Pro
385                 390                 395                 400
Cys Asn Leu Arg Thr Ala Leu Thr Arg Tyr Ala Cys Leu Leu Ser Ser
                405                 410                 415
Pro Lys Lys Ser Ala Leu Val Ala Leu Ala Ala His Ala Ser Asp Pro
                420                 425                 430
Thr Glu Ala Glu Arg Leu Lys His Leu Ala Ser Pro Ala Gly Lys Asp
                435                 440                 445
Glu Tyr Ser Lys Trp Val Val Gly Ser Gln Arg Ser Leu Leu Glu Val
        450                 455                 460
Met Ala Glu Phe Pro Ser Ala Lys Pro Pro Leu Gly Val Phe Phe Ala
465                 470                 475                 480
Gly Val Ala Pro Arg Leu Gln Pro Arg Phe Tyr Ser Ile Ser Ser Ser
                485                 490                 495
Pro Lys Ile Ala Glu Thr Arg Ile His Val Thr Cys Ala Leu Val Tyr
                500                 505                 510
Glu Lys Met Pro Thr Gly Arg Ile His Lys Gly Val Cys Ser Thr Trp
        515                 520                 525
Met Lys Asn Ala Val Pro Tyr Glu Lys Ser Glu Lys Leu Phe Leu Gly
        530                 535                 540
Arg Pro Ile Phe Val Arg Gln Ser Asn Phe Lys Leu Pro Ser Asp Ser
545                 550                 555                 560
Lys Val Pro Ile Ile Met Ile Gly Pro Gly Thr Gly Leu Ala Pro Phe
                565                 570                 575
Arg Gly Phe Leu Gln Glu Arg Leu Ala Leu Val Glu Ser Gly Val Glu
                580                 585                 590
Leu Gly Pro Ser Val Leu Phe Phe Gly Cys Arg Asn Arg Arg Met Asp
                595                 600                 605
Phe Ile Tyr Glu Glu Glu Leu Gln Arg Phe Val Glu Ser Gly Ala Leu
        610                 615                 620
Ala Glu Leu Ser Val Ala Phe Ser Arg Glu Gly Pro Thr Lys Glu Tyr
```

```
                    625                 630                 635                 640
Val Gln His Lys Met Met Asp Lys Ala Ser Asp Ile Trp Asn Met Ile
                        645                 650                 655

Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
                675                 680                 685

Met Asp Ser Thr Lys Ala Glu Gly Phe Val Lys Asn Leu Gln Thr Ser
    690                 695                 700

Gly Arg Tyr Leu Arg Asp Val Trp
705                 710

<210> SEQ ID NO 93
<211> LENGTH: 1503
<212> TYPE: DNA
<213> ORGANISM: Artificial Sequence
<220> FEATURE:
<223> OTHER INFORMATION: Codon-optimized KAH

<400> SEQUENCE: 93
atggaagcct cttacctata catttctatt ttgcttttac tggcatcata cctgttcacc      60
actcaactta aaggaagag cgctaatcta ccaccaaccg tgtttccatc aataccaatc     120
attggacact tatacttact caaaaagcct ctttatagaa ctttagcaaa aattgccgct     180
aagtacggac caatactgca attacaactc ggctacagac gtgttctggt gatttcctca     240
ccatcagcag cagaagagtg ctttaccaat aacgatgtaa tcttcgcaaa tagacctaag     300
acattgtttg gcaaaatagt gggtggaaca tcccttggca gtttatccta cggcgatcaa     360
tggcgtaatc taaggagagt agcttctatc gaatcctat cagttcatag gttgaacgaa     420
tttcatgata tcagagtgga tgagaacaga ttgttaatta gaaaacttag aagttcatct     480
tctcctgtta ctcttataac agtcttttat gctctaacat gaacgtcat tatgagaatg     540
atctctggca aagatatttt cgacagtggg gatagagaat ggaggagga aggtaagaga     600
tttcgagaaa tcttagacga aacgttgctt ctagccggtg cttctaatgt tggcgactac     660
ttaccaatat tgaactggtt gggagttaag tctcttgaaa agaaattgat cgcttttgcag     720
aaaaagagag atgacttttt ccagggtttg attgaacagg ttagaaaatc tcgtggtgct     780
aaagtaggca aaggtagaaa aacgatgatc gaactcttat tatctttgca agagtcagaa     840
cctgagtact atacagatgc tatgataaga tcttttgtcc taggtctgct ggctgcaggt     900
agtgatactt cagcgggcac tatggaatgg gccatgagct actggtcaa tcacccacat     960
gtattgaaga aagctcaagc tgaaatcgat agagttatcg gtaataacag attgattgac    1020
gagtcagaca ttgaaaatat cccttacatc gggtgtatta tcaatgaaac tctaagactc    1080
tatccagcag ggccattgtt gttcccacat gaaagttctg ccgactgcgt tatttccggt    1140
tacaatatac ctagaggtac aatgttaatc gtaaaccaat gggcgattca tcacgatcct    1200
aaagtctggg atgatcctga aacctttaaa cctgaaagat tcaaggatt agaaggaact    1260
agagatggtt tcaaacttat gccattcggt tctgggagaa aggatgtcc aggtgaaggt    1320
ttggcaataa ggctgttagg gatgacacta ggctcagtga tccaatgttt tgattgggag    1380
agagtaggag atgagatggt tgacatgaca gaaggtttgg gtgtcacact tcctaaggcc    1440
gttccattag ttgccaaatg taagccacgt tccgaaatga ctaatctcct atccgaactt    1500
taa                                                                  1503
```

<210> SEQ ID NO 94
<211> LENGTH: 500
<212> TYPE: PRT
<213> ORGANISM: Stevia rebaudiana

<400> SEQUENCE: 94

```
Met Glu Ala Ser Tyr Leu Tyr Ile Ser Ile Leu Leu Leu Ala Ser
1               5                   10                  15

Tyr Leu Phe Thr Thr Gln Leu Arg Arg Lys Ser Ala Asn Leu Pro Pro
            20                  25                  30

Thr Val Phe Pro Ser Ile Pro Ile Gly His Leu Tyr Leu Leu Lys
            35                  40                  45

Lys Pro Leu Tyr Arg Thr Leu Ala Lys Ile Ala Ala Lys Tyr Gly Pro
50                  55                  60

Ile Leu Gln Leu Gln Leu Gly Tyr Arg Arg Val Leu Val Ile Ser Ser
65                  70                  75                  80

Pro Ser Ala Ala Glu Glu Cys Phe Thr Asn Asn Asp Val Ile Phe Ala
                85                  90                  95

Asn Arg Pro Lys Thr Leu Phe Gly Lys Ile Val Gly Gly Thr Ser Leu
            100                 105                 110

Gly Ser Leu Ser Tyr Gly Asp Gln Trp Arg Asn Leu Arg Arg Val Ala
        115                 120                 125

Ser Ile Glu Ile Leu Ser Val His Arg Leu Asn Glu Phe His Asp Ile
130                 135                 140

Arg Val Asp Glu Asn Arg Leu Leu Ile Arg Lys Leu Arg Ser Ser Ser
145                 150                 155                 160

Ser Pro Val Thr Leu Ile Thr Val Phe Tyr Ala Leu Thr Leu Asn Val
                165                 170                 175

Ile Met Arg Met Ile Ser Gly Lys Arg Tyr Phe Asp Ser Gly Asp Arg
            180                 185                 190

Glu Leu Glu Glu Gly Lys Arg Phe Arg Glu Ile Leu Asp Glu Thr
        195                 200                 205

Leu Leu Leu Ala Gly Ala Ser Asn Val Gly Asp Tyr Leu Pro Ile Leu
210                 215                 220

Asn Trp Leu Gly Val Lys Ser Leu Glu Lys Lys Leu Ile Ala Leu Gln
225                 230                 235                 240

Lys Lys Arg Asp Asp Phe Phe Gln Gly Leu Ile Glu Gln Val Arg Lys
                245                 250                 255

Ser Arg Gly Ala Lys Val Gly Lys Gly Arg Lys Thr Met Ile Glu Leu
            260                 265                 270

Leu Leu Ser Leu Gln Glu Ser Glu Pro Glu Tyr Tyr Thr Asp Ala Met
        275                 280                 285

Ile Arg Ser Phe Val Leu Gly Leu Leu Ala Ala Gly Ser Asp Thr Ser
290                 295                 300

Ala Gly Thr Met Glu Trp Ala Met Ser Leu Leu Val Asn His Pro His
305                 310                 315                 320

Val Leu Lys Lys Ala Gln Ala Glu Ile Asp Arg Val Ile Gly Asn Asn
                325                 330                 335

Arg Leu Ile Asp Glu Ser Asp Ile Gly Asn Ile Pro Tyr Ile Gly Cys
            340                 345                 350

Ile Ile Asn Glu Thr Leu Arg Leu Tyr Pro Ala Gly Pro Leu Leu Phe
        355                 360                 365

Pro His Glu Ser Ser Ala Asp Cys Val Ile Ser Gly Tyr Asn Ile Pro
370                 375                 380
```

```
Arg Gly Thr Met Leu Ile Val Asn Gln Trp Ala Ile His His Asp Pro
385                 390                 395                 400

Lys Val Trp Asp Asp Pro Glu Thr Phe Lys Pro Glu Arg Phe Gln Gly
            405                 410                 415

Leu Glu Gly Thr Arg Asp Gly Phe Lys Leu Met Pro Phe Gly Ser Gly
                420                 425                 430

Arg Arg Gly Cys Pro Gly Glu Gly Leu Ala Ile Arg Leu Leu Gly Met
            435                 440                 445

Thr Leu Gly Ser Val Ile Gln Cys Phe Asp Trp Glu Arg Val Gly Asp
450                 455                 460

Glu Met Val Asp Met Thr Glu Gly Leu Gly Val Thr Leu Pro Lys Ala
465                 470                 475                 480

Val Pro Leu Val Ala Lys Cys Lys Pro Arg Ser Glu Met Thr Asn Leu
                485                 490                 495

Leu Ser Glu Leu
            500

<210> SEQ ID NO 95
<211> LENGTH: 1572
<212> TYPE: DNA
<213> ORGANISM: Rubus suavissimus

<400> SEQUENCE: 95
atggaagtaa cagtagctag tagtgtagcc ctgagcctgg tctttattag catagtagta     60
agatgggcat ggagtgtggt gaattgggtg tggtttaagc cgaagaagct ggaaagattt    120
ttgagggagc aaggccttaa aggcaattcc tacaggtttt tatatggaga catgaaggag    180
aactctatcc tgctcaaaca agcaagatcc aaacccatga acctctccac ctcccatgac    240
atagcacctc aagtcacccc ttttgtcgac caaaccgtga agcttacgg taagaactct     300 tttaattggg ttggcccat accaagggtg aacataatga atccagaaga tttgaaggac    360
gtcttaacaa aaaatgttga ctttgttaag ccaatatcaa cccacttat caagttgcta     420 gctacaggta ttgcaatcta tgaaggtgag aaatggacta acacagaag gattatcaac    480 ccaacattcc attcggagag gctaaagcgt atgttacctt catttcacca agttgtaat    540 gagatggtca aggaatggga gagcttggtg tcaaaagagg ttcatcatg tgagttggat     600 gtctggcctt ttcttgaaaa atatgtcggca gatgtgatct cgagaacagc atttggaact    660
agctacaaaa aaggacagaa aatctttgaa ctcttgagag agcaagtaat atatgtaacg    720
aaaggctttc aaagttttta cattccagga tggaggtttc tcccaactaa gatgaacaag    780
aggatgaatg agattaacga agaaataaaa ggattaatca ggggtattat aattgacaga    840
gagcaaatca ttaaggcagg tgaagaaacc aacgatgact tattaggtgc acttatggag    900
tcaaacttga aggacattcg ggaacatggg aaaaacaaca aaaatgttgg gatgagtatt    960
gaagatgtaa ttcaggagtg taagctgttt tactttgctg gcaagaaaac cacttcagtg   1020
ttgctggctt ggacaatggt tttacttggt caaaatcaga actggcaaga tcgagcaaga   1080
caagaggttt tgcaagtctt tggaagcagc aagccagatt ttgatggtct agctcacctt   1140
aaagtcgtaa ccatgatttt gcttgaagtt cttcgattat acccaccagt cattgaactt   1200
attcgaacca ttcacaagaa aacacaactt gggaagctct cactaccaga aggagttgaa   1260
gtccgcttac caacactgct cattcaccat gacaaggaac tgtggggtga tgatgcaaac   1320
cagttcaatc cagagaggtt ttcggaagga gtttccaaag caacaaagaa ccgactctca   1380
```

```
ttcttcccct tcggagccgg tccacgcatt tgcattggac agaactttc tatgatggaa    1440 gcaaagttgg ccttagcatt gatcttgcaa cacttcacct ttgagctttc tccatctcat    1500
gcacatgctc cttcccatcg tataacctt caaccacagt atggtgttcg tatcatttta    1560
catcgacgtt ag                                                        1572

<210> SEQ ID NO 96
<211> LENGTH: 1572
<212> TYPE: DNA
<213> ORGANISM: Artificial Sequence
<220> FEATURE:
<223> OTHER INFORMATION: Codon-optimized KAH

<400> SEQUENCE: 96
atggaagtca ctgtcgcctc ttctgtcgct ttatccttag tcttcatttc cattgtcgtc      60
agatgggctt ggtccgttgt caactgggtt tggttcaaac caagaagtt ggaaagattc      120 ttgagagagc aaggtttgaa gggtaattct tatagattct tgtacggtga catgaaggaa     180
aattctattt tgttgaagca agccagatcc aaaccaatga acttgtctac ctctcatgat     240
attgctccac aagttactcc attcgtcgat caaactgtta agcctacgg taagaactct      300 ttcaattggg ttggtccaat tcctagagtt aacatcatga cccgaaga tttgaaggat      360 gtcttgacca agaacgttga cttcgttaag ccaatttcca acccattgat taaattgttg    420
gctactggta ttgccatta cgaaggtgaa agtggacta agcatagaag aatcatcaac      480
cctaccttcc actctgaaag attgaagaga atgttaccat ctttccatca atcctgtaat    540
gaaatggtta aggaatggga atccttggtt tctaaagaag ttcttcttg cgaattggat     600 gtttggccat tcttggaaaa tatgtctgct gatgtcattt ccagaaccgc tttcggtacc    660
tcctacaaga agggtcaaaa gattttcgaa ttgttgagag agcaagttat ttacgttacc    720
aagggtttcc aatccttcta catcccaggt tggagattct tgccaactaa atgaacaag    780 cgtatgaacg agatcaacga agaaattaaa ggtttgatca gaggtattat tatcgacaga    840
gaacaaatta ttaaagctgg tgaagaaacc aacgatgatt tgttgggtgc tttgatggag    900
tccaacttga aggatattag agaacatggt aagaacaaca gaatgttgg tatgtctatt     960 gaagatgtta ttcaagaatg taagttattc tacttcgctg gtcaagagac cacttctgtt    1020
ttgttagcct ggactatggt cttgttaggt caaaaccaaa attggcaaga tagagctaga   1080
caagaagttt tgcaagtctt cggttcttcc aagccagact tgatggtttt ggcccacttg   1140
aaggttgtta ctatgatttt gttagaagtt ttgagattgt acccaccagt cattgagtta   1200
atcagaacca ttcataaaaa gactcaattg gtaaattat ctttgccaga aggtgttgaa    1260
gtcagattac aaccttgtt gattcaccac gataaggaat tatgggggtga cgacgctaat   1320 caatttaatc agaaagatt ttccgaaggt gtttccaagg ctaccaaaaa ccgtttgtcc    1380
ttcttcccat tggtgctgg tccacgtatt tgtatcggtc aaaacttttc catgatggaa    1440
gccaagttgg ctttggcttt aatcttgcaa cacttcactt tcgaattgtc tccatcccat   1500
gcccacgctc cttctcatag aatcactta caaccacaat acggtgtcag aatcatctta    1560
cacagaagat aa                                                        1572

<210> SEQ ID NO 97
<211> LENGTH: 523
<212> TYPE: PRT
<213> ORGANISM: Rubus suavissimus

<400> SEQUENCE: 97
```

```
Met Glu Val Thr Val Ala Ser Ser Val Ala Leu Ser Leu Val Phe Ile
1               5                   10                  15

Ser Ile Val Val Arg Trp Ala Trp Ser Val Val Asn Trp Val Trp Phe
            20                  25                  30

Lys Pro Lys Lys Leu Glu Arg Phe Leu Arg Glu Gln Gly Leu Lys Gly
            35                  40                  45

Asn Ser Tyr Arg Phe Leu Tyr Gly Asp Met Lys Glu Asn Ser Ile Leu
50                      55                  60

Leu Lys Gln Ala Arg Ser Lys Pro Met Asn Leu Ser Thr Ser His Asp
65                  70                  75                  80

Ile Ala Pro Gln Val Thr Pro Phe Val Asp Gln Thr Val Lys Ala Tyr
                85                  90                  95

Gly Lys Asn Ser Phe Asn Trp Val Gly Pro Ile Pro Arg Val Asn Ile
            100                 105                 110

Met Asn Pro Glu Asp Leu Lys Asp Val Leu Thr Lys Asn Val Asp Phe
            115                 120                 125

Val Lys Pro Ile Ser Asn Pro Leu Ile Lys Leu Leu Ala Thr Gly Ile
            130                 135                 140

Ala Ile Tyr Glu Gly Glu Lys Trp Thr Lys His Arg Arg Ile Ile Asn
145                 150                 155                 160

Pro Thr Phe His Ser Glu Arg Leu Lys Arg Met Leu Pro Ser Phe His
                165                 170                 175

Gln Ser Cys Asn Glu Met Val Lys Glu Trp Glu Ser Leu Val Ser Lys
            180                 185                 190

Glu Gly Ser Ser Cys Glu Leu Asp Val Trp Pro Phe Leu Glu Asn Met
            195                 200                 205

Ser Ala Asp Val Ile Ser Arg Thr Ala Phe Gly Thr Ser Tyr Lys Lys
210                 215                 220

Gly Gln Lys Ile Phe Glu Leu Leu Arg Glu Gln Val Ile Tyr Val Thr
225                 230                 235                 240

Lys Gly Phe Gln Ser Phe Tyr Ile Pro Gly Trp Arg Phe Leu Pro Thr
            245                 250                 255

Lys Met Asn Lys Arg Met Asn Glu Ile Asn Glu Ile Lys Gly Leu
            260                 265                 270

Ile Arg Gly Ile Ile Ile Asp Arg Glu Gln Ile Ile Lys Ala Gly Glu
            275                 280                 285

Glu Thr Asn Asp Asp Leu Leu Gly Ala Leu Met Glu Ser Asn Leu Lys
            290                 295                 300

Asp Ile Arg Glu His Gly Lys Asn Asn Lys Asn Val Gly Met Ser Ile
305                 310                 315                 320

Glu Asp Val Ile Gln Glu Cys Lys Leu Phe Tyr Phe Ala Gly Gln Glu
                325                 330                 335

Thr Thr Ser Val Leu Leu Ala Trp Thr Met Val Leu Leu Gly Gln Asn
            340                 345                 350

Gln Asn Trp Gln Asp Arg Ala Arg Gln Glu Val Leu Gln Val Phe Gly
            355                 360                 365

Ser Ser Lys Pro Asp Phe Asp Gly Leu Ala His Leu Lys Val Val Thr
370                 375                 380

Met Ile Leu Leu Glu Val Leu Arg Leu Tyr Pro Pro Val Ile Glu Leu
385                 390                 395                 400

Ile Arg Thr Ile His Lys Lys Thr Gln Leu Gly Lys Leu Ser Leu Pro
                405                 410                 415
```

| Glu | Gly | Val | Glu | Val | Arg | Leu | Pro | Thr | Leu | Leu | Ile | His | His | Asp | Lys |
|---|---|---|---|---|---|---|---|---|---|---|---|---|---|---|---|
| | | | 420 | | | | | 425 | | | | | 430 | | |

| Glu | Leu | Trp | Gly | Asp | Asp | Ala | Asn | Gln | Phe | Asn | Pro | Glu | Arg | Phe | Ser |
|---|---|---|---|---|---|---|---|---|---|---|---|---|---|---|---|
| | | | 435 | | | | | 440 | | | | | 445 | | |

| Glu | Gly | Val | Ser | Lys | Ala | Thr | Lys | Asn | Arg | Leu | Ser | Phe | Phe | Pro | Phe |
|---|---|---|---|---|---|---|---|---|---|---|---|---|---|---|---|
| | | | 450 | | | | | 455 | | | | | 460 | | |

| Gly | Ala | Gly | Pro | Arg | Ile | Cys | Ile | Gly | Gln | Asn | Phe | Ser | Met | Met | Glu |
|---|---|---|---|---|---|---|---|---|---|---|---|---|---|---|---|
| 465 | | | | | 470 | | | | | 475 | | | | | 480 |

| Ala | Lys | Leu | Ala | Leu | Ala | Leu | Ile | Leu | Gln | His | Phe | Thr | Phe | Glu | Leu |
|---|---|---|---|---|---|---|---|---|---|---|---|---|---|---|---|
| | | | | 485 | | | | | 490 | | | | | 495 | |

| Ser | Pro | Ser | His | Ala | His | Ala | Pro | Ser | His | Arg | Ile | Thr | Leu | Gln | Pro |
|---|---|---|---|---|---|---|---|---|---|---|---|---|---|---|---|
| | | | 500 | | | | | 505 | | | | | 510 | | |

| Gln | Tyr | Gly | Val | Arg | Ile | Ile | Leu | His | Arg | Arg |
|---|---|---|---|---|---|---|---|---|---|---|
| | | | 515 | | | | | 520 | | |

<210> SEQ ID NO 98
<211> LENGTH: 1566
<212> TYPE: DNA
<213> ORGANISM: Prunus avium

<400> SEQUENCE: 98

| | |
|---|---|
| atggaagcat caagggctag ttgtgttgcg ctatgtgttg tttgggtgag catagtaatt | 60 |
| acattggcat ggagggtgct gaattgggtg tggttgaggc caagaaaact agaaagatgc | 120 |
| ttgagggagc aaggccttac aggcaattct acaggctttt gtttggaga caccaaggat | 180 |
| ctctcgaaga tgctggaaca acacaatcc aaacccatca aactctccac ctcccatgat | 240 |
| atagcgccac gagtcacccc attttccat cgaactgtga actctaatgg caagaattct | 300 |
| tttgtttgga tgggccctat accaagagtg cacatcatga atccagaaga tttgaaagat | 360 |
| gccttcaaca gacatgatga ttttcataag acagtaaaaa atcctatcat gaagtctcca | 420 |
| ccaccgggca ttgtaggcat tgaaggtgag caatgggcta acacagaaa gattatcaac | 480 |
| ccagcattcc atttagagaa gctaaagggt atggtaccaa tatttaccca agttgtagc | 540 |
| gagatgatta caaatgggga gagcttggtg tccaaagaga gttcatgtga gttggatgtg | 600 |
| tggccttatc ttgaaaattt taccagcgat gtgatttccc gagctgcatt tggaagtagc | 660 |
| tatgaagagg gaaggaaaat atttcaacta ctaagagagg aagcaaaagt ttattcggta | 720 |
| gctctacgaa gtgtttacat tccaggatgg aggtttctac caaccaagca gaacaagaag | 780 |
| acgaaggaaa ttcacaatga aattaaaggc ttacttaagg cattataaa taaaagggaa | 840 |
| gaggcgatga aggcagggga agccactaaa gatgacttac taggaatact tatggagtcc | 900 |
| aacttcaggg aaattcagga acatgggaac aacaaaaatg ctggaatgag tattgaagat | 960 |
| gtaattggag agtgtaagtt gttttacttt gctgggcaag agaccacttc ggtgttgctt | 1020 |
| gtttggacaa tgatttact aagccaaaat caggattggc aagctcgtgc aagagaagag | 1080 |
| gtcttgaaag tctttggaag caacatccca acctatgaag agctaagtca cctaaaagtt | 1140 |
| gtgaccatga ttttacttga agttcttcga ttatacccat cagtcgttgc gcttcctcga | 1200 |
| accactcaca gaaaacaca gcttggaaaa ttatcattac cagctggagt ggaagtctcc | 1260 |
| ttgcccatac tgcttgttca ccatgacaaa gagtgtgggg gtgaggatgc aaatgagttc | 1320 |
| aagccagaga ggttttcaga gggagtttca aaggcaacaa gaacaaatt tacatactta | 1380 |
| cctttcggag ggggtccaag gatttgcatt ggacaaaact tgccatggt ggaagctaaa | 1440 |
| ttggccttgg ccctgatttt acaacacttt gcctttgagc tttctccatc ctatgctcat | 1500 |

```
gctccttctg cagttataac ccttcaacct caatttggtg ctcatatcat tttgcataaa    1560
cgttga                                                              1566
```

<210> SEQ ID NO 99
<211> LENGTH: 1567
<212> TYPE: DNA
<213> ORGANISM: Artificial Sequence
<220> FEATURE:
<223> OTHER INFORMATION: Codon-optimized KAH

<400> SEQUENCE: 99

```
atggaagctt ctagagcatc ttgtgttgct ttgtgtgttg tttgggtttc catcgttatt      60
actttggctt ggagagtttt gaattgggtc tggttaagac caaaaaagtt ggaaagatgc     120
ttgagagaac aaggtttgac tggtaactct tacagattgt tgttcggtga taccaaggac     180
ttgtctaaga tgttggaaca aactcaatcc aagcctatca agttgtctac ctctcatgat     240
attgctccaa gagttactcc attcttccat agaactgtta actccaacgg taagaactct     300
tttgttggga tgggtccaat ccaagagtc catattatga accctgaaga tttgaaggac     360
gctttcaaca gacatgatga tttccataag accgtcaaga acccaattat gaagtctcca     420
ccaccaggta tagttggtat tgaaggtgaa caatgggcca acatagaaa gattattaac     480 ccagccttcc acttggaaaa gttgaaaggt atggttccaa tcttctacca atcctgctct     540
gaaatgatta caagtgggga atccttggtt tccaaagaat cttcctgtga attggatgtc     600
tggccatatt tggaaaactt cacctccgat gttatttcca gagctgcttt tggttcttct     660
tacgaagaag gtgaaaagat cttccaatta ttgagaaag aagccaaggt ttactccgtt     720
gctttgagat ctgtttacat tccaggttgg agattcttgc aactaagca aaacaaaaag     780 accaaagaaa tccacaacga aatcaagggt tgttgaagg tatcatcaa caagagagaa     840 gaagctatga aggctggtga agctacaaaa gatgatttgt tgggtatctt gatggaatcc     900
aacttcagag aaatccaaga acacggtaac aacaagaatg ccggtatgtc tattgaagat     960
gttatcggtg aatgcaagtt gttctacttt gctggtcaag aaactaccta cgttttgttg    1020
gtttggacca tgatttgttt gtcccaaaat caagattggc aagctagagc tagagaagaa    1080
gtcttgaaag ttttcggttc taacatccca acctacgaag aattgtctca cttgaaggtt    1140
gtcactatga tcttgttgga agtattgaga ttatacccat ccgttgttgc attgccaaga    1200
actactcata gaaaaactca attgggtaaa ttgtccttgc agctggtgt tgaagttctt    1260 ttgccaattt tgttagtcca ccacgacaaa gaattgtggg gtgaagatgc taatgaattc    1320
aagccagaaa gattctccga aggtgtttct aaagctacca gaacaagtt cacttacttg    1380 ccatttggtg tggtccaag aatatgtatt ggtcaaaatt cgctatggt cgaagctaaa    1440 ttggcttttg gctttgatctt gcaacatttc gctttcgaat tgtcaccatc ttatgctcat    1500
gctccatctg ctgttattac attgcaacca caatttggtg cccatatcat cttgcataag    1560
agataac                                                             1567
```

<210> SEQ ID NO 100
<211> LENGTH: 521
<212> TYPE: PRT
<213> ORGANISM: Prunus avium

<400> SEQUENCE: 100

```
Met Glu Ala Ser Arg Ala Ser Cys Val Ala Leu Cys Val Val Trp Val
1               5                   10                  15
```

-continued

Ser Ile Val Ile Thr Leu Ala Trp Arg Val Leu Asn Trp Val Trp Leu
            20                  25                  30

Arg Pro Lys Lys Leu Glu Arg Cys Leu Arg Glu Gln Gly Leu Thr Gly
            35                  40                  45

Asn Ser Tyr Arg Leu Leu Phe Gly Asp Thr Lys Asp Leu Ser Lys Met
 50                  55                  60

Leu Glu Gln Thr Gln Ser Lys Pro Ile Lys Leu Ser Thr Ser His Asp
65                   70                  75                  80

Ile Ala Pro Arg Val Thr Pro Phe Phe His Arg Thr Val Asn Ser Asn
                85                  90                  95

Gly Lys Asn Ser Phe Val Trp Met Gly Pro Ile Pro Arg Val His Ile
            100                 105                 110

Met Asn Pro Glu Asp Leu Lys Asp Ala Phe Asn Arg His Asp Asp Phe
            115                 120                 125

His Lys Thr Val Lys Asn Pro Ile Met Lys Ser Pro Pro Gly Ile
            130                 135                 140

Val Gly Ile Glu Gly Glu Gln Trp Ala Lys His Arg Lys Ile Ile Asn
145                 150                 155                 160

Pro Ala Phe His Leu Glu Lys Leu Lys Gly Met Val Pro Ile Phe Tyr
                165                 170                 175

Gln Ser Cys Ser Glu Met Ile Asn Lys Trp Glu Ser Leu Val Ser Lys
            180                 185                 190

Glu Ser Cys Glu Leu Asp Val Trp Pro Tyr Leu Glu Asn Phe Thr
            195                 200                 205

Ser Asp Val Ile Ser Arg Ala Ala Phe Gly Ser Ser Tyr Glu Glu Gly
210                 215                 220

Arg Lys Ile Phe Gln Leu Leu Arg Glu Glu Ala Lys Val Tyr Ser Val
225                 230                 235                 240

Ala Leu Arg Ser Val Tyr Ile Pro Gly Trp Arg Phe Leu Pro Thr Lys
                245                 250                 255

Gln Asn Lys Lys Thr Lys Glu Ile His Asn Glu Ile Lys Gly Leu Leu
            260                 265                 270

Lys Gly Ile Ile Asn Lys Arg Glu Glu Ala Met Lys Ala Gly Glu Ala
            275                 280                 285

Thr Lys Asp Asp Leu Leu Gly Ile Leu Met Glu Ser Asn Phe Arg Glu
290                 295                 300

Ile Gln Glu His Gly Asn Asn Lys Asn Ala Gly Met Ser Ile Glu Asp
305                 310                 315                 320

Val Ile Gly Glu Cys Lys Leu Phe Tyr Phe Ala Gly Gln Glu Thr Thr
                325                 330                 335

Ser Val Leu Leu Val Trp Thr Met Ile Leu Leu Ser Gln Asn Gln Asp
            340                 345                 350

Trp Gln Ala Arg Ala Arg Glu Glu Val Leu Lys Val Phe Gly Ser Asn
            355                 360                 365

Ile Pro Thr Tyr Glu Glu Leu Ser His Leu Lys Val Val Thr Met Ile
            370                 375                 380

Leu Leu Glu Val Leu Arg Leu Tyr Pro Ser Val Val Ala Leu Pro Arg
385                 390                 395                 400

Thr Thr His Lys Lys Thr Gln Leu Gly Lys Leu Ser Leu Pro Ala Gly
                405                 410                 415

Val Glu Val Ser Leu Pro Ile Leu Leu Val His His Asp Lys Glu Leu
            420                 425                 430

Trp Gly Glu Asp Ala Asn Glu Phe Lys Pro Glu Arg Phe Ser Glu Gly

```
                435                 440                 445
Val Ser Lys Ala Thr Lys Asn Lys Phe Thr Tyr Leu Pro Phe Gly Gly
    450                 455                 460

Gly Pro Arg Ile Cys Ile Gly Gln Asn Phe Ala Met Val Glu Ala Lys
465                 470                 475                 480

Leu Ala Leu Ala Leu Ile Leu Gln His Phe Ala Phe Glu Leu Ser Pro
                485                 490                 495

Ser Tyr Ala His Ala Pro Ser Ala Val Ile Thr Leu Gln Pro Gln Phe
            500                 505                 510

Gly Ala His Ile Ile Leu His Lys Arg
        515                 520

<210> SEQ ID NO 101
<211> LENGTH: 517
<212> TYPE: PRT
<213> ORGANISM: Prunus mume

<400> SEQUENCE: 101

Ala Ser Trp Val Ala Val Leu Ser Val Val Trp Ser Met Val Ile
1               5                   10                  15

Ala Trp Ala Trp Arg Val Leu Asn Trp Val Trp Leu Arg Pro Lys Lys
            20                  25                  30

Leu Glu Lys Cys Leu Arg Glu Gln Gly Leu Ala Gly Asn Ser Tyr Arg
        35                  40                  45

Leu Leu Phe Gly Asp Thr Lys Asp Leu Ser Lys Met Leu Glu Gln Thr
    50                  55                  60

Gln Ser Lys Pro Ile Lys Leu Ser Thr Ser His Asp Ile Ala Pro His
65                  70                  75                  80

Val Thr Pro Phe Phe His Gln Thr Val Asn Ser Tyr Gly Lys Asn Ser
                85                  90                  95

Phe Val Trp Met Gly Pro Ile Pro Arg Val His Ile Met Asn Pro Glu
            100                 105                 110

Asp Leu Lys Asp Thr Phe Asn Arg His Asp Phe His Lys Val Val
        115                 120                 125

Lys Asn Pro Ile Met Lys Ser Leu Pro Gln Gly Ile Val Gly Ile Glu
    130                 135                 140

Gly Glu Gln Trp Ala Lys His Arg Lys Ile Ile Asn Pro Ala Phe His
145                 150                 155                 160

Leu Glu Lys Leu Lys Gly Met Val Pro Ile Phe Tyr Arg Ser Cys Ser
                165                 170                 175

Glu Met Ile Asn Lys Trp Glu Ser Leu Val Ser Lys Glu Ser Ser Cys
            180                 185                 190

Glu Leu Asp Val Trp Pro Tyr Leu Glu Asn Phe Thr Ser Asp Val Ile
        195                 200                 205

Ser Arg Ala Ala Phe Gly Ser Ser Tyr Glu Glu Gly Arg Lys Ile Phe
    210                 215                 220

Gln Leu Leu Arg Glu Glu Ala Lys Ile Tyr Thr Val Ala Met Arg Ser
225                 230                 235                 240

Val Tyr Ile Pro Gly Trp Arg Phe Leu Pro Thr Lys Gln Asn Lys Lys
                245                 250                 255

Ala Lys Glu Ile His Asn Glu Ile Lys Gly Leu Leu Lys Gly Ile Ile
            260                 265                 270

Asn Lys Arg Glu Glu Ala Met Lys Ala Gly Glu Ala Thr Lys Asp Asp
        275                 280                 285
```

```
Leu Leu Gly Ile Leu Met Glu Ser Asn Phe Arg Glu Ile Gln Glu His
    290                 295                 300

Gly Asn Asn Lys Asn Ala Gly Met Ser Ile Glu Asp Val Ile Gly Glu
305                 310                 315                 320

Cys Lys Leu Phe Tyr Phe Ala Gly Gln Glu Thr Thr Ser Val Leu Leu
                325                 330                 335

Val Trp Thr Met Val Leu Leu Ser Gln Asn Gln Asp Trp Gln Ala Arg
            340                 345                 350

Ala Arg Glu Val Leu Gln Val Phe Gly Ser Asn Ile Pro Thr Tyr
        355                 360                 365

Glu Glu Leu Ser Gln Leu Lys Val Val Thr Met Ile Leu Leu Glu Val
370                 375                 380

Leu Arg Leu Tyr Pro Ser Val Ala Leu Pro Arg Thr Thr His Lys
385                 390                 395                 400

Lys Thr Gln Leu Gly Lys Leu Ser Leu Pro Ala Gly Val Glu Val Ser
                405                 410                 415

Leu Pro Ile Leu Leu Val His His Asp Lys Glu Leu Trp Gly Glu Asp
            420                 425                 430

Ala Asn Glu Phe Lys Pro Glu Arg Phe Ser Glu Gly Val Ser Lys Ala
        435                 440                 445

Thr Lys Asn Gln Phe Thr Tyr Phe Pro Phe Gly Gly Pro Arg Ile
450                 455                 460

Cys Ile Gly Gln Asn Phe Ala Met Met Glu Ala Lys Leu Ala Leu Ser
465                 470                 475                 480

Leu Ile Leu Arg His Phe Ala Leu Glu Leu Ser Pro Leu Tyr Ala His
                485                 490                 495

Ala Pro Ser Val Thr Ile Thr Leu Gln Pro Gln Tyr Gly Ala His Ile
            500                 505                 510

Ile Leu His Lys Arg
        515

<210> SEQ ID NO 102
<211> LENGTH: 521
<212> TYPE: PRT
<213> ORGANISM: Prunus mume

<400> SEQUENCE: 102

Met Glu Ala Ser Arg Pro Ser Cys Val Ala Leu Ser Val Val Leu Val
1               5                   10                  15

Ser Ile Val Ile Ala Trp Ala Trp Arg Val Leu Asn Trp Val Trp Leu
            20                  25                  30

Arg Pro Asn Lys Leu Glu Arg Cys Leu Arg Glu Gln Gly Leu Thr Gly
        35                  40                  45

Asn Ser Tyr Arg Leu Leu Phe Gly Asp Thr Lys Glu Ile Ser Met Met
50                  55                  60

Val Glu Gln Ala Gln Ser Lys Pro Ile Lys Leu Ser Thr Thr His Asp
65                  70                  75                  80

Ile Ala Pro Arg Val Ile Pro Phe Ser His Gln Ile Val Tyr Thr Tyr
                85                  90                  95

Gly Arg Asn Ser Phe Val Trp Met Gly Pro Thr Pro Val Thr Ile
            100                 105                 110

Met Asn Pro Glu Asp Leu Lys Asp Ala Phe Asn Lys Ser Asp Glu Phe
        115                 120                 125

Gln Arg Ala Ile Ser Asn Pro Ile Val Lys Ser Ile Ser Gln Gly Leu
130                 135                 140
```

-continued

Ser Ser Leu Glu Gly Glu Lys Trp Ala Lys His Arg Lys Ile Ile Asn
145                 150                 155                 160

Pro Ala Phe His Leu Glu Lys Leu Lys Gly Met Leu Pro Thr Phe Tyr
            165                 170                 175

Gln Ser Cys Ser Glu Met Ile Asn Lys Trp Glu Ser Leu Val Phe Lys
        180                 185                 190

Glu Gly Ser Arg Glu Met Asp Val Trp Pro Tyr Leu Glu Asn Leu Thr
    195                 200                 205

Ser Asp Val Ile Ser Arg Ala Ala Phe Gly Ser Ser Tyr Glu Glu Gly
210                 215                 220

Arg Lys Ile Phe Gln Leu Leu Arg Glu Glu Ala Lys Phe Tyr Thr Ile
225                 230                 235                 240

Ala Ala Arg Ser Val Tyr Ile Pro Gly Trp Arg Phe Leu Pro Thr Lys
            245                 250                 255

Gln Asn Lys Arg Met Lys Glu Ile His Lys Glu Val Arg Gly Leu Leu
        260                 265                 270

Lys Gly Ile Ile Asn Lys Arg Glu Asp Ala Ile Lys Ala Gly Glu Ala
    275                 280                 285

Ala Lys Gly Asn Leu Leu Gly Ile Leu Met Glu Ser Asn Phe Arg Glu
290                 295                 300

Ile Gln Glu His Gly Asn Asn Lys Asn Ala Gly Met Ser Ile Glu Asp
305                 310                 315                 320

Val Ile Gly Glu Cys Lys Leu Phe Tyr Phe Ala Gly Gln Glu Thr Thr
            325                 330                 335

Ser Val Leu Leu Val Trp Thr Leu Val Leu Leu Ser Gln Asn Gln Asp
        340                 345                 350

Trp Gln Ala Arg Ala Arg Glu Glu Val Leu Gln Val Phe Gly Thr Asn
    355                 360                 365

Ile Pro Thr Tyr Asp Gln Leu Ser His Leu Lys Val Val Thr Met Ile
370                 375                 380

Leu Leu Glu Val Leu Arg Leu Tyr Pro Ala Val Val Glu Leu Pro Arg
385                 390                 395                 400

Thr Thr Tyr Lys Lys Thr Gln Leu Gly Lys Phe Leu Leu Pro Ala Gly
            405                 410                 415

Val Glu Val Ser Leu His Ile Met Leu Ala His His Asp Lys Glu Leu
        420                 425                 430

Trp Gly Glu Asp Ala Lys Glu Phe Lys Pro Glu Arg Phe Ser Glu Gly
    435                 440                 445

Val Ser Lys Ala Thr Lys Asn Gln Phe Thr Tyr Phe Pro Phe Gly Ala
450                 455                 460

Gly Pro Arg Ile Cys Ile Gly Gln Asn Phe Ala Met Leu Glu Ala Lys
465                 470                 475                 480

Leu Ala Leu Ser Leu Ile Leu Gln His Phe Thr Phe Glu Leu Ser Pro
            485                 490                 495

Ser Tyr Ala His Ala Pro Ser Val Thr Ile Thr Leu His Pro Gln Phe
        500                 505                 510

Gly Ala His Phe Ile Leu His Lys Arg
    515                 520

<210> SEQ ID NO 103
<211> LENGTH: 514
<212> TYPE: PRT
<213> ORGANISM: Prunus mume

```
<400> SEQUENCE: 103

Cys Val Ala Leu Ser Val Val Leu Val Ser Ile Val Ile Ala Trp Ala
1               5                   10                  15

Trp Arg Val Leu Asn Trp Val Trp Leu Arg Pro Asn Lys Leu Glu Arg
            20                  25                  30

Cys Leu Arg Glu Gln Gly Leu Thr Gly Asn Ser Tyr Arg Leu Leu Phe
        35                  40                  45

Gly Asp Thr Lys Glu Ile Ser Met Met Val Glu Gln Ala Gln Ser Lys
    50                  55                  60

Pro Ile Lys Leu Ser Thr Thr His Asp Ile Ala Pro Arg Val Ile Pro
65                  70                  75                  80

Phe Ser His Gln Ile Val Tyr Thr Tyr Gly Arg Asn Ser Phe Val Trp
                85                  90                  95

Met Gly Pro Thr Pro Arg Val Thr Ile Met Asn Pro Glu Asp Leu Lys
            100                 105                 110

Asp Ala Phe Asn Lys Ser Asp Glu Phe Gln Arg Ala Ile Ser Asn Pro
        115                 120                 125

Ile Val Lys Ser Ile Ser Gln Gly Leu Ser Ser Leu Glu Gly Glu Lys
    130                 135                 140

Trp Ala Lys His Arg Lys Ile Ile Asn Pro Ala Phe His Leu Glu Lys
145                 150                 155                 160

Leu Lys Gly Met Leu Pro Thr Phe Tyr Gln Ser Cys Ser Glu Met Ile
                165                 170                 175

Asn Lys Trp Glu Ser Leu Val Phe Lys Glu Gly Ser Arg Glu Met Asp
            180                 185                 190

Val Trp Pro Tyr Leu Glu Asn Leu Thr Ser Asp Val Ile Ser Arg Ala
        195                 200                 205

Ala Phe Gly Ser Ser Tyr Glu Glu Gly Arg Lys Ile Phe Gln Leu Leu
    210                 215                 220

Arg Glu Glu Ala Lys Phe Tyr Thr Ile Ala Ala Arg Ser Val Tyr Ile
225                 230                 235                 240

Pro Gly Trp Arg Phe Leu Pro Thr Lys Gln Asn Lys Arg Met Lys Glu
                245                 250                 255

Ile His Lys Glu Val Arg Gly Leu Leu Lys Gly Ile Ile Asn Lys Arg
            260                 265                 270

Glu Asp Ala Ile Lys Ala Gly Glu Ala Lys Gly Asn Leu Leu Gly
        275                 280                 285

Ile Leu Met Glu Ser Asn Phe Arg Glu Ile Gln Glu His Gly Asn Asn
    290                 295                 300

Lys Asn Ala Gly Met Ser Ile Glu Asp Val Ile Gly Glu Cys Lys Leu
305                 310                 315                 320

Phe Tyr Phe Ala Gly Gln Glu Thr Thr Ser Val Leu Leu Val Trp Thr
                325                 330                 335

Leu Val Leu Leu Ser Gln Asn Gln Asp Trp Gln Ala Arg Ala Arg Glu
            340                 345                 350

Glu Val Leu Gln Val Phe Gly Thr Asn Ile Pro Thr Tyr Asp Gln Leu
        355                 360                 365

Ser His Leu Lys Val Val Thr Met Ile Leu Leu Glu Val Leu Arg Leu
    370                 375                 380

Tyr Pro Ala Val Val Glu Leu Pro Arg Thr Thr Tyr Lys Lys Thr Gln
385                 390                 395                 400

Leu Gly Lys Phe Leu Leu Pro Ala Gly Val Glu Val Ser Leu His Ile
                405                 410                 415
```

```
Met Leu Ala His His Asp Lys Glu Leu Trp Gly Glu Asp Ala Lys Glu
            420                 425                 430

Phe Lys Pro Glu Arg Phe Ser Glu Gly Val Ser Lys Ala Thr Lys Asn
        435                 440                 445

Gln Phe Thr Tyr Phe Pro Phe Gly Ala Gly Pro Arg Ile Cys Ile Gly
    450                 455                 460

Gln Asn Phe Ala Met Leu Glu Ala Lys Leu Ala Leu Ser Leu Ile Leu
465                 470                 475                 480

Gln His Phe Thr Phe Glu Leu Ser Pro Ser Tyr Ala His Ala Pro Ser
                485                 490                 495

Val Thr Ile Thr Leu His Pro Gln Phe Gly Ala His Phe Ile Leu His
            500                 505                 510

Lys Arg

<210> SEQ ID NO 104
<211> LENGTH: 418
<212> TYPE: PRT
<213> ORGANISM: Prunus persica

<400> SEQUENCE: 104

Met Gly Pro Ile Pro Arg Val His Ile Met Asn Pro Glu Asp Leu Lys
1               5                   10                  15

Asp Thr Phe Asn Arg His Asp Phe His Lys Val Val Lys Asn Pro
            20                  25                  30

Ile Met Lys Ser Leu Pro Gln Gly Ile Val Gly Ile Glu Gly Asp Gln
            35                  40                  45

Trp Ala Lys His Arg Lys Ile Ile Asn Pro Ala Phe His Leu Glu Lys
    50                  55                  60

Leu Lys Gly Met Val Pro Ile Phe Tyr Gln Ser Cys Ser Glu Met Ile
65                  70                  75                  80

Asn Ile Trp Lys Ser Leu Val Ser Lys Glu Ser Ser Cys Glu Leu Asp
                85                  90                  95

Val Trp Pro Tyr Leu Glu Asn Phe Thr Ser Asp Val Ile Ser Arg Ala
            100                 105                 110

Ala Phe Gly Ser Ser Tyr Glu Glu Gly Arg Lys Ile Phe Gln Leu Leu
        115                 120                 125

Arg Glu Glu Ala Lys Val Tyr Thr Val Ala Val Arg Ser Val Tyr Ile
    130                 135                 140

Pro Gly Trp Arg Phe Leu Pro Thr Lys Gln Asn Lys Lys Thr Lys Glu
145                 150                 155                 160

Ile His Asn Glu Ile Lys Gly Leu Leu Lys Gly Ile Ile Asn Lys Arg
                165                 170                 175

Glu Glu Ala Met Lys Ala Gly Glu Ala Thr Lys Asp Asp Leu Leu Gly
            180                 185                 190

Ile Leu Met Glu Ser Asn Phe Arg Glu Ile Gln Glu His Gly Asn Asn
        195                 200                 205

Lys Asn Ala Gly Met Ser Ile Glu Asp Val Ile Gly Glu Cys Lys Leu
    210                 215                 220

Phe Tyr Phe Ala Gly Gln Glu Thr Thr Ser Val Leu Leu Val Trp Thr
225                 230                 235                 240

Met Val Leu Leu Ser Gln Asn Gln Asp Trp Gln Ala Arg Ala Arg Glu
                245                 250                 255

Glu Val Leu Gln Val Phe Gly Ser Asn Ile Pro Thr Tyr Glu Glu Leu
            260                 265                 270
```

```
Ser His Leu Lys Val Val Thr Met Ile Leu Leu Glu Val Leu Arg Leu
        275                 280                 285

Tyr Pro Ser Val Val Ala Leu Pro Arg Thr Thr His Lys Lys Thr Gln
        290                 295                 300

Leu Gly Lys Leu Ser Leu Pro Ala Gly Val Glu Val Ser Leu Pro Ile
305                 310                 315                 320

Leu Leu Val His His Asp Lys Glu Leu Trp Gly Glu Asp Ala Asn Glu
                325                 330                 335

Phe Lys Pro Glu Arg Phe Ser Glu Gly Val Ser Lys Ala Thr Lys Asn
                340                 345                 350

Gln Phe Thr Tyr Phe Pro Phe Gly Gly Gly Pro Arg Ile Cys Ile Gly
            355                 360                 365

Gln Asn Phe Ala Met Met Glu Ala Lys Leu Ala Leu Ser Leu Ile Leu
        370                 375                 380

Gln His Phe Thr Phe Glu Leu Ser Pro Gln Tyr Ser His Ala Pro Ser
385                 390                 395                 400

Val Thr Ile Thr Leu Gln Pro Gln Tyr Gly Ala His Leu Ile Leu His
                405                 410                 415

Lys Arg

<210> SEQ ID NO 105
<211> LENGTH: 1578
<212> TYPE: DNA
<213> ORGANISM: Artificial Sequence
<220> FEATURE:
<223> OTHER INFORMATION: Codon-optimized KAH

<400> SEQUENCE: 105
atgggtttgt tcccattaga ggattcctac gcgctggtct ttgaaggact agcaataaca      60
ctggctttgt actatctact gtctttcatc tacaaaacat ctaaaagac atgtacacct     120 cctaaagcat ctggtgaaat cattccaatt acaggaatca tattgaatct gctatctggc     180
tcaagtggtc tacctattat cttagcactt gcctctttag cagacagatg tggtcctatt     240
ttcaccatta ggctgggtat taggagagtg ctagtagtat caaattggga aatcgctaag     300
gagattttca ctacccacga tttgatagtt tctaatagac aaaatactt agccgctaag     360 attcttggtt tcaattatgt ttcattctct ttcgctccat acggcccata ttgggtcgga     420
atcagaaaga ttattgctac aaaactaatg tcttcttcca gacttcagaa gttgcaattt     480
gtaagagttt tgaactaga aaactctatg aaatctatca gagaatcatg gaaggagaaa     540
aaggatgaag agggaaaggt attagttgag atgaaaaagt ggttctggga actgaatatg     600
aacatagtgt taaggacagt tgctggtaaa caatacactg gtacagttga tgatgccgat     660
gcaaagcgta tctccgagtt attcagagaa tggtttcact acactggcag atttgtcgtt     720
ggagacgctt ttccttttct aggttggttg gacctgggcg gatacaaaaa gacaatggaa     780
ttagttgcta gtagattgga ctcaatggtc agtaaatggt tagatgagca tcgtaaaaag     840
caagctaacg atgacaaaaa ggaggatatg gatttcatgg atatcatgat ctccatgaca     900
gaagcaaatt caccacttga aggatacggc actgatacta ttatcaagac acatgtatg      960 actttgattg tttcaggagt tgatacaacc tcaatcgtac ttacttgggc cttatcactt    1020
ttgttaaaca acagagatac tttgaaaaag gcacaagagg aattagatat gtgcgtaggt    1080 aaggaagac aagtcaacga gtctgatctt gttaacttga tacttggaa agcagtgctt    1140 aaagaggctt taagacttta cccagcagcg ttcttaggcg gaccaagagc attcttggaa    1200
```

```
gattgtactg ttgctggtta tagaattcca aagggcacct gcttgttgat taacatgtgg    1260
aaactgcata gagatccaaa catttggagt gatccttgcg aattcaagcc agaaagattt    1320
ttgacaccta atcaaaagga tgttgatgtg atcggtatgg atttcgaatt gataccattt    1380
ggtgccggca aagatattg tccaggtact agattggctt tacagatgtt gcatatcgta     1440
ttagcgacat tgctgcaaaa cttcgaaatg tcaacaccaa acgatgcgcc agtcgatatg    1500
actgcttctg ttggcatgac aaatgccaaa gcatcacctt tagaagtctt gctatcacct    1560
cgtgttaaat ggtcctaa                                                  1578
```

<210> SEQ ID NO 106
<211> LENGTH: 522
<212> TYPE: PRT
<213> ORGANISM: Stevia rebaudiana

<400> SEQUENCE: 106

```
Met Gly Leu Phe Pro Leu Glu Asp Ser Tyr Ala Leu Val Phe Glu Gly
 1               5                  10                  15

Leu Ala Ile Thr Leu Ala Leu Tyr Tyr Leu Leu Ser Phe Ile Tyr Lys
            20                  25                  30

Thr Ser Lys Lys Thr Cys Thr Pro Lys Ala Ser Gly Glu His Pro
        35                  40                  45

Ile Thr Gly His Leu Asn Leu Leu Ser Gly Ser Gly Leu Pro His
    50                  55                  60

Leu Ala Leu Ala Ser Leu Ala Asp Arg Cys Gly Pro Ile Phe Thr Ile
65                  70                  75                  80

Arg Leu Gly Ile Arg Arg Val Leu Val Val Ser Asn Trp Glu Ile Ala
                85                  90                  95

Lys Glu Ile Phe Thr Thr His Asp Leu Ile Val Ser Asn Arg Pro Lys
            100                 105                 110

Tyr Leu Ala Ala Lys Ile Leu Gly Phe Asn Tyr Val Ser Phe Ser Phe
        115                 120                 125

Ala Pro Tyr Gly Pro Tyr Trp Val Gly Ile Arg Lys Ile Ile Ala Thr
    130                 135                 140

Lys Leu Met Ser Ser Ser Arg Leu Gln Lys Leu Gln Phe Val Arg Val
145                 150                 155                 160

Phe Glu Leu Glu Asn Ser Met Lys Ser Ile Arg Glu Ser Trp Lys Glu
                165                 170                 175

Lys Lys Asp Glu Glu Gly Lys Val Leu Val Glu Met Lys Lys Trp Phe
            180                 185                 190

Trp Glu Leu Asn Met Asn Ile Val Leu Arg Thr Val Ala Gly Lys Gln
        195                 200                 205

Tyr Thr Gly Thr Val Asp Asp Ala Asp Ala Lys Arg Ile Ser Glu Leu
    210                 215                 220

Phe Arg Glu Trp Phe His Tyr Thr Gly Arg Phe Val Val Gly Asp Ala
225                 230                 235                 240

Phe Pro Phe Leu Gly Trp Leu Asp Leu Gly Gly Tyr Lys Lys Thr Met
                245                 250                 255

Glu Leu Val Ala Ser Arg Leu Asp Ser Met Val Ser Lys Trp Leu Asp
            260                 265                 270

Glu His Arg Lys Lys Gln Ala Asn Asp Lys Lys Glu Asp Met Asp
        275                 280                 285

Phe Met Asp Ile Met Ile Ser Met Thr Glu Ala Asn Ser Pro Leu Glu
    290                 295                 300
```

```
Gly Tyr Gly Thr Asp Thr Ile Ile Lys Thr Thr Cys Met Thr Leu Ile
305                 310                 315                 320

Val Ser Gly Val Asp Thr Thr Ser Ile Val Leu Thr Trp Ala Leu Ser
            325                 330                 335

Leu Leu Leu Asn Asn Arg Asp Thr Leu Lys Lys Ala Gln Glu Glu Leu
        340                 345                 350

Asp Met Cys Val Gly Lys Gly Arg Gln Val Asn Glu Ser Asp Leu Val
    355                 360                 365

Asn Leu Ile Tyr Leu Glu Ala Val Leu Lys Glu Ala Leu Arg Leu Tyr
370                 375                 380

Pro Ala Ala Phe Leu Gly Gly Pro Arg Ala Phe Leu Glu Asp Cys Thr
385                 390                 395                 400

Val Ala Gly Tyr Arg Ile Pro Lys Gly Thr Cys Leu Leu Ile Asn Met
            405                 410                 415

Trp Lys Leu His Arg Asp Pro Asn Ile Trp Ser Asp Pro Cys Glu Phe
        420                 425                 430

Lys Pro Glu Arg Phe Leu Thr Pro Asn Gln Lys Asp Val Asp Val Ile
    435                 440                 445

Gly Met Asp Phe Glu Leu Ile Pro Phe Gly Ala Gly Arg Arg Tyr Cys
450                 455                 460

Pro Gly Thr Arg Leu Ala Leu Gln Met Leu His Ile Val Leu Ala Thr
465                 470                 475                 480

Leu Leu Gln Asn Phe Glu Met Ser Thr Pro Asn Asp Ala Pro Val Asp
            485                 490                 495

Met Thr Ala Ser Val Gly Met Thr Asn Ala Lys Ala Ser Pro Leu Glu
        500                 505                 510

Val Leu Leu Ser Pro Arg Val Lys Trp Ser
    515                 520
```

<210> SEQ ID NO 107
<211> LENGTH: 1431
<212> TYPE: DNA
<213> ORGANISM: Artificial Sequence
<220> FEATURE:
<223> OTHER INFORMATION: Codon-optimized KAH

<400> SEQUENCE: 107

```
atgatacaag ttttaactcc aattctactc ttcctcatct tcttcgtttt ctggaaagtc      60
tacaaacatc aaaagactaa aatcaatcta ccaccaggtt ccttcggctg ccattttttg     120
ggtgaaacct tagccttact tagagcaggc tgggattctg agccagaaag attcgtaaga     180
gagcgtatca aaaagcatgg atctccactt gttttcaaga catcactatt tggagacaga     240
ttcgctgttc tttgcggtcc agctggtaat aagttttttgt tctgcaacga aaacaaatta     300
gtggcatctt ggtggccagt ccctgtaagg aagttgttcg gtaaaagttt actcacaata     360
agaggagatg aagcaaaatg gatgagaaaa atgctattgt cttacttggg tccagatgca     420
tttgccacac attatgccgt tactatggat gttgtaacac gtagacatat tgatgtccat     480 tggagggggca aggaggaagt taatgtattt caaacagtta agttgtacgc attcgaatta     540
gcttgtagat tattcatgaa cctagatgac ccaaaccaca tcgcgaaact cggtagtctt     600
ttcaacattt tcctcaaagg gatcatcgag cttcctatag acgttcctgg aactagattt     660
tactccagta aaaaggccgc agctgccatt agaattgaat tgaaaaagct cattaaagct     720
agaaaactcg aattgaagga gggtaaggcg tcttcttcac aggacttgct ttctcatcta     780
```

```
ttaacatcac ctgatgagaa tgggatgttc ttgacagaag aggaaatagt cgataacatt    840
ctacttttgt tattcgctgg tcacgatacc tctgcactat caataacact tttgatgaaa    900
accttaggtg aacacagtga tgtgtacgac aaggttttga aggaacaatt agaaatttcc    960
aaaacaaagg aggcttggga atcactaaag tgggaagata tccagaagat gaagtactca   1020
tggtcagtaa tctgtgaagt catgagattg aatcctcctg tcataggggac atacagagag   1080 gcgttggttg atatcgacta tgctggttac actatcccaa aaggatggaa gttgcattgg   1140
tcagctgttt ctactcaaag agacgaagcc aatttcgaag atgtaactag attcgatcca   1200
tccagatttg aaggggcagg ccctactcca ttcacatttg tgcctttcgg tggaggtcct   1260
agaatgtgtt taggcaaaga gtttgccagg ttagaagtgt tagcatttct ccacaacatt   1320
gttaccaact ttaagtggga tcttctaatc cctgatgaga agatcgaata tgatccaatg   1380
gctactccag ctaagggctt gccaattaga cttcatccac accaagtcta a            1431
```

<210> SEQ ID NO 108
<211> LENGTH: 476
<212> TYPE: PRT
<213> ORGANISM: Stevia rebaudiana

<400> SEQUENCE: 108

```
Met Ile Gln Val Leu Thr Pro Ile Leu Leu Phe Leu Ile Phe Phe Val
1               5                   10                  15

Phe Trp Lys Val Tyr Lys His Gln Lys Thr Lys Ile Asn Leu Pro Pro
                20                  25                  30

Gly Ser Phe Gly Trp Pro Phe Leu Gly Glu Thr Leu Ala Leu Leu Arg
            35                  40                  45

Ala Gly Trp Asp Ser Glu Pro Glu Arg Phe Val Arg Glu Arg Ile Lys
        50                  55                  60

Lys His Gly Ser Pro Leu Val Phe Lys Thr Ser Leu Phe Gly Asp Arg
65                  70                  75                  80

Phe Ala Val Leu Cys Gly Pro Ala Gly Asn Lys Phe Leu Phe Cys Asn
                85                  90                  95

Glu Asn Lys Leu Val Ala Ser Trp Trp Pro Val Pro Val Arg Lys Leu
                100                 105                 110

Phe Gly Lys Ser Leu Leu Thr Ile Arg Gly Asp Glu Ala Lys Trp Met
            115                 120                 125

Arg Lys Met Leu Leu Ser Tyr Leu Gly Pro Asp Ala Phe Ala Thr His
        130                 135                 140

Tyr Ala Val Thr Met Asp Val Val Thr Arg Arg His Ile Asp Val His
145                 150                 155                 160

Trp Arg Gly Lys Glu Glu Val Asn Val Phe Gln Thr Val Lys Leu Tyr
                165                 170                 175

Ala Phe Glu Leu Ala Cys Arg Leu Phe Met Asn Leu Asp Asp Pro Asn
                180                 185                 190

His Ile Ala Lys Leu Gly Ser Leu Phe Asn Ile Phe Leu Lys Gly Ile
            195                 200                 205

Ile Glu Leu Pro Ile Asp Val Pro Gly Thr Arg Phe Tyr Ser Ser Lys
        210                 215                 220

Lys Ala Ala Ala Ala Ile Arg Ile Glu Leu Lys Leu Ile Lys Ala
225                 230                 235                 240

Arg Lys Leu Glu Leu Lys Glu Gly Lys Ala Ser Ser Ser Gln Asp Leu
                245                 250                 255

Leu Ser His Leu Leu Thr Ser Pro Asp Glu Asn Gly Met Phe Leu Thr
```

```
                  260                 265                 270
Glu Glu Glu Ile Val Asp Asn Ile Leu Leu Leu Phe Ala Gly His
            275                 280                 285
Asp Thr Ser Ala Leu Ser Ile Thr Leu Leu Met Lys Thr Leu Gly Glu
            290                 295                 300
His Ser Asp Val Tyr Asp Lys Val Leu Lys Glu Gln Leu Glu Ile Ser
305                 310                 315                 320
Lys Thr Lys Glu Ala Trp Glu Ser Leu Lys Trp Glu Asp Ile Gln Lys
                325                 330                 335
Met Lys Tyr Ser Trp Ser Val Ile Cys Glu Val Met Arg Leu Asn Pro
                340                 345                 350
Pro Val Ile Gly Thr Tyr Arg Glu Ala Leu Val Asp Ile Asp Tyr Ala
            355                 360                 365
Gly Tyr Thr Ile Pro Lys Gly Trp Lys Leu His Trp Ser Ala Val Ser
            370                 375                 380
Thr Gln Arg Asp Glu Ala Asn Phe Glu Asp Val Thr Arg Phe Asp Pro
385                 390                 395                 400
Ser Arg Phe Glu Gly Ala Gly Pro Thr Pro Phe Thr Phe Val Pro Phe
                405                 410                 415
Gly Gly Gly Pro Arg Met Cys Leu Gly Lys Glu Phe Ala Arg Leu Glu
                420                 425                 430
Val Leu Ala Phe Leu His Asn Ile Val Thr Asn Phe Lys Trp Asp Leu
            435                 440                 445
Leu Ile Pro Asp Glu Lys Ile Glu Tyr Asp Pro Met Ala Thr Pro Ala
            450                 455                 460
Lys Gly Leu Pro Ile Arg Leu His Pro His Gln Val
465                 470                 475

<210> SEQ ID NO 109
<211> LENGTH: 1578
<212> TYPE: DNA
<213> ORGANISM: Artificial Sequence
<220> FEATURE:
<223> OTHER INFORMATION: Codon-optimized KAH

<400> SEQUENCE: 109
atggagtctt tagtggttca tacagtaaat gctatctggt gtattgtaat cgtcgggatt    60
ttctcagttg ttatcacgt ttacggtaga gctgtggtcg aacaatggag aatgagaaga   120
tcactgaagc tacaaggtgt taaaggccca ccaccatcca tcttcaatgg taacgtctca   180
gaaatgcaac gtatccaatc cgaagctaaa cactgctctg cgataacat tatctcacat   240 gattattctt cttcattatt cccacacttc gatcactgga gaaaacagta cggcagaatc   300
tacacatact ctactggatt aaagcaacac ttgtacatca atcatccaga aatggtgaag   360
gagctatctc agactaacac attgaacttg gtagaatca cccatataac caaaagattg   420
aatcctatct taggtaacgg aatcataacc tctaatggtc tcattgggc ccatcagcgt   480 agaattatcg cctacgagtt tactcatgat aagatcaagg gtatggttgg tttgatggtt   540
gagtctgcta tgcctatgtt gaataagtgg gaggagatgg taaagagagg cggagaaatg   600
ggatgcgaca taagagttga tgaggacttg aaagatgttt cagcagatgt gattgcaaaa   660
gcctgtttcg gatcctcatt ttctaaaggt aaggctattt tctctatgat aagagatttg   720
cttacagcta tcacaaagag aagtgttcta ttcagattca acggattcac tgatatggtc   780
tttgggagta aaaagcatgg tgacgttgat atagacgctt tagaaatgga attggaatca   840
```

```
tccatttggg aaactgtcaa ggaacgtgaa atagaatgta aagatactca caaaaaggat    900
ctgatgcaat tgattttgga aggggcaatg cgttcatgtg acggtaacct ttgggataaa    960
tcagcatata gaagatttgt tgtagataat tgtaaatcta tctacttcgc agggcatgat   1020
agtacagctg tctcagtgtc atggtgtttg atgttactgg ccctaaaccc atcatggcaa   1080
gttaagatcc gtgatgaaat ctgtcttct  tgcaaaaatg gtattccaga tgccgaaagt   1140
atcccaaacc ttaaaacagt gactatggtt attcaagaga caatgagatt ataccctcca   1200
gcaccaatcg tcgggagaga agcctctaaa gatatcagat tgggcgatct agttgttcct   1260
aaaggcgtct gtatatggac actaatacca gctttacaca gagatcctga gatttgggga   1320
ccagatgcaa acgatttcaa accagaaaga ttttctgaag gaatttcaaa ggcttgtaag   1380
tatcctcaaa gttacattcc atttggtctg ggtcctagaa catgcgttgg taaaaacttt   1440
ggcatgatgg aagtaaaggt tcttgttttcc ctgattgtct ccaagttctc tttcactcta   1500
tctcctacct accaacatag tcctagtcac aaacttttag tagaaccaca acatggggtg   1560
gtaattagag tggtttaa                                                 1578
```

<210> SEQ ID NO 110
<211> LENGTH: 525
<212> TYPE: PRT
<213> ORGANISM: Arabidopsis thaliana

<400> SEQUENCE: 110

```
Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
            20                  25                  30

Val Glu Gln Trp Arg Met Arg Arg Ser Leu Lys Leu Gln Gly Val Lys
        35                  40                  45

Gly Pro Pro Pro Ser Ile Phe Asn Gly Asn Val Ser Glu Met Gln Arg
    50                  55                  60

Ile Gln Ser Glu Ala Lys His Cys Ser Gly Asp Asn Ile Ile Ser His
65                  70                  75                  80

Asp Tyr Ser Ser Ser Leu Phe Pro His Phe Asp His Trp Arg Lys Gln
                85                  90                  95

Tyr Gly Arg Ile Tyr Thr Tyr Ser Thr Gly Leu Lys Gln His Leu Tyr
            100                 105                 110

Ile Asn His Pro Glu Met Val Lys Glu Leu Ser Gln Thr Asn Thr Leu
        115                 120                 125

Asn Leu Gly Arg Ile Thr His Ile Thr Lys Arg Leu Asn Pro Ile Leu
    130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Ile Lys Gly Met Val
                165                 170                 175

Gly Leu Met Val Glu Ser Ala Met Pro Met Leu Asn Lys Trp Glu Glu
            180                 185                 190

Met Val Lys Arg Gly Gly Glu Met Gly Cys Asp Ile Arg Val Asp Glu
        195                 200                 205

Asp Leu Lys Asp Val Ser Ala Asp Val Ile Ala Lys Ala Cys Phe Gly
    210                 215                 220

Ser Ser Phe Ser Lys Gly Lys Ala Ile Phe Ser Met Ile Arg Asp Leu
225                 230                 235                 240
```

Leu Thr Ala Ile Thr Lys Arg Ser Val Leu Phe Arg Phe Asn Gly Phe
                245                 250                 255

Thr Asp Met Val Phe Gly Ser Lys Lys His Gly Asp Val Asp Ile Asp
            260                 265                 270

Ala Leu Glu Met Glu Leu Glu Ser Ser Ile Trp Glu Thr Val Lys Glu
            275                 280                 285

Arg Glu Ile Glu Cys Lys Asp Thr His Lys Lys Asp Leu Met Gln Leu
        290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Phe
                325                 330                 335

Ala Gly His Asp Ser Thr Ala Val Ser Val Ser Trp Cys Leu Met Leu
            340                 345                 350

Leu Ala Leu Asn Pro Ser Trp Gln Val Lys Ile Arg Asp Glu Ile Leu
        355                 360                 365

Ser Ser Cys Lys Asn Gly Ile Pro Asp Ala Glu Ser Ile Pro Asn Leu
        370                 375                 380

Lys Thr Val Thr Met Val Ile Gln Glu Thr Met Arg Leu Tyr Pro Pro
385                 390                 395                 400

Ala Pro Ile Val Gly Arg Glu Ala Ser Lys Asp Ile Arg Leu Gly Asp
                405                 410                 415

Leu Val Val Pro Lys Gly Val Cys Ile Trp Thr Leu Ile Pro Ala Leu
            420                 425                 430

His Arg Asp Pro Glu Ile Trp Gly Pro Asp Ala Asn Asp Phe Lys Pro
        435                 440                 445

Glu Arg Phe Ser Glu Gly Ile Ser Lys Ala Cys Lys Tyr Pro Gln Ser
        450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
                485                 490                 495

Ser Phe Thr Leu Ser Pro Thr Tyr Gln His Ser Pro Ser His Lys Leu
            500                 505                 510

Leu Val Glu Pro Gln His Gly Val Val Ile Arg Val Val
        515                 520                 525

<210> SEQ ID NO 111
<211> LENGTH: 1590
<212> TYPE: DNA
<213> ORGANISM: Artificial Sequence
<220> FEATURE:
<223> OTHER INFORMATION: Codon-optimized KAH

<400> SEQUENCE: 111
atgtacttcc tactacaata cctcaacatc acaaccgttg gtgtctttgc cacattgttt      60
ctctcttatt gtttacttct ctggagaagt agagcgggta acaaaaagat tgccccagaa     120
gctgccgctg catggcctat tatcggccac ctccacttac ttgcaggtgg atcccatcaa     180
ctaccacata ttcacattgg taacatggca gataagtacg gtcctgtatt cacaatcaga     240
ataggcttgc atagagctgt agttgtctca tcttgggaaa tggcaaagga atgttcaaca     300
gctaatgatc aagtgtcttc ttcaagacct gaactattag cttctaagtt gttgggttat     360
aactacgcca tgtttggttt ttcaccatac ggttcatact ggagagaaat gagaaagatc     420
atctctctcg aattactatc taattccaga ttggaactat tgaaagatgt tagagcctca     480

```
gaagttgtca catctattaa ggaactatac aaattgtggg cggaaaagaa gaatgagtca    540
ggattggttt ctgtcgagat gaaacaatgg ttcggagatt tgactttaaa cgtgatcttg    600
agaatggtgg ctggtaaaag atacttctcc gcgagtgacg cttcagaaaa caaacaggcc    660
cagcgttgta gaagagtctt cagagaattc ttccatctct ccggcttgtt tgtggttgct    720
gatgctatac ctttcttgg atggctcgat tggggaagac acgagaagac cttgaaaaag      780
accgccatag aaatggattc catcgcccag gagtggcttg aggaacatag acgtagaaaa    840
gattctggag atgataattc tacccaagat tcatggacg ttatgcaatc tgtgctagat      900
ggcaaaaatc taggcggata cgatgctgat acgattaaca aggctacatg cttaactctt    960
atatcaggtg gcagtgatac tactgtagtt tctttgacat gggctcttag tcttgtgtta    1020
aacaatagag atactttgaa aaaggcacag gaagagttag acatccaagt cggtaaggaa    1080
agattggtta acgagcaaga catcagtaag ttagtttact tgcaagcaat agtaaaagag    1140
acactcagac tttatccacc aggtcctttg ggtggtttga acaattcac tgaagattgt      1200 acactaggtg gctatcacgt ttcaaaagga actagattaa tcatgaactt atccaagatt    1260
caaaaagatc cacgtatttg gtctgatcct actgaattcc aaccagagag attccttacg    1320
actcataaag atgtcgatcc acgtggtaaa cactttgaat tcattccatt cggtgcagga    1380
agacgtgcat gtcctggtat cacattcgga ttacaagtac tacatctaac attggcatct    1440
ttcttgcatg cgtttgaatt ttcaacacca tcaaatgagc aggttaacat gagagaatca    1500
ttaggtctta cgaatatgaa atctacccca ttagaagttt tgatttctcc aagactatcc    1560
cttaattgct tcaaccttat gaaaatttga                                      1590
```

<210> SEQ ID NO 112
<211> LENGTH: 526
<212> TYPE: PRT
<213> ORGANISM: Vitis vinifera

<400> SEQUENCE: 112

```
Met Tyr Phe Leu Leu Gln Tyr Leu Asn Ile Thr Thr Val Gly Val Phe
1               5                   10                  15

Ala Thr Leu Phe Leu Ser Tyr Cys Leu Leu Trp Arg Ser Arg Ala
            20                  25                  30

Gly Asn Lys Lys Ile Ala Pro Glu Ala Ala Ala Trp Pro Ile Ile
        35                  40                  45

Gly His Leu His Leu Leu Ala Gly Gly Ser His Gln Leu Pro His Ile
    50                  55                  60

Thr Leu Gly Asn Met Ala Asp Lys Tyr Gly Pro Val Phe Thr Ile Arg
65                  70                  75                  80

Ile Gly Leu His Arg Ala Val Val Val Ser Ser Trp Glu Met Ala Lys
                85                  90                  95

Glu Cys Ser Thr Ala Asn Asp Gln Val Ser Ser Arg Pro Glu Leu
            100                 105                 110

Leu Ala Ser Lys Leu Leu Gly Tyr Asn Tyr Ala Met Phe Gly Phe Ser
        115                 120                 125

Pro Tyr Gly Ser Tyr Trp Arg Glu Met Arg Lys Ile Ile Ser Leu Glu
    130                 135                 140

Leu Leu Ser Asn Ser Arg Leu Glu Leu Leu Lys Asp Val Arg Ala Ser
145                 150                 155                 160

Glu Val Val Thr Ser Ile Lys Glu Leu Tyr Lys Leu Trp Ala Glu Lys
                165                 170                 175
```

```
Lys Asn Glu Ser Gly Leu Val Ser Val Glu Met Lys Gln Trp Phe Gly
            180                 185                 190

Asp Leu Thr Leu Asn Val Ile Leu Arg Met Val Ala Gly Lys Arg Tyr
        195                 200                 205

Phe Ser Ala Ser Asp Ala Ser Glu Asn Lys Gln Ala Gln Arg Cys Arg
    210                 215                 220

Arg Val Phe Arg Glu Phe Phe His Leu Ser Gly Leu Phe Val Val Ala
225                 230                 235                 240

Asp Ala Ile Pro Phe Leu Gly Trp Leu Asp Trp Gly Arg His Glu Lys
                245                 250                 255

Thr Leu Lys Lys Thr Ala Ile Glu Met Asp Ser Ile Ala Gln Glu Trp
            260                 265                 270

Leu Glu Glu His Arg Arg Arg Lys Asp Ser Gly Asp Asp Asn Ser Thr
        275                 280                 285

Gln Asp Phe Met Asp Val Met Gln Ser Val Leu Asp Gly Lys Asn Leu
    290                 295                 300

Gly Gly Tyr Asp Ala Asp Thr Ile Asn Lys Ala Thr Cys Leu Thr Leu
305                 310                 315                 320

Ile Ser Gly Gly Ser Asp Thr Thr Val Val Ser Leu Thr Trp Ala Leu
                325                 330                 335

Ser Leu Val Leu Asn Asn Arg Asp Thr Leu Lys Lys Ala Gln Glu Glu
            340                 345                 350

Leu Asp Ile Gln Val Gly Lys Glu Arg Leu Val Asn Glu Gln Asp Ile
        355                 360                 365

Ser Lys Leu Val Tyr Leu Gln Ala Ile Val Lys Glu Thr Leu Arg Leu
    370                 375                 380

Tyr Pro Pro Gly Pro Leu Gly Gly Leu Arg Gln Phe Thr Glu Asp Cys
385                 390                 395                 400

Thr Leu Gly Gly Tyr His Val Ser Lys Gly Thr Arg Leu Ile Met Asn
                405                 410                 415

Leu Ser Lys Ile Gln Lys Asp Pro Arg Ile Trp Ser Asp Pro Thr Glu
            420                 425                 430

Phe Gln Pro Glu Arg Phe Leu Thr Thr His Lys Asp Val Asp Pro Arg
        435                 440                 445

Gly Lys His Phe Glu Phe Ile Pro Phe Gly Ala Gly Arg Arg Ala Cys
    450                 455                 460

Pro Gly Ile Thr Phe Gly Leu Gln Val Leu His Leu Thr Leu Ala Ser
465                 470                 475                 480

Phe Leu His Ala Phe Glu Phe Ser Thr Pro Ser Asn Glu Gln Val Asn
                485                 490                 495

Met Arg Glu Ser Leu Gly Leu Thr Asn Met Lys Ser Thr Pro Leu Glu
            500                 505                 510

Val Leu Ile Ser Pro Arg Leu Ser Ser Cys Ser Leu Tyr Asn
        515                 520                 525

<210> SEQ ID NO 113
<211> LENGTH: 1440
<212> TYPE: DNA
<213> ORGANISM: Artificial Sequence
<220> FEATURE:
<223> OTHER INFORMATION: Codon-optimized KAH

<400> SEQUENCE: 113
atggaaccta actttactt gtcattacta ttgttgttcg tgaccttcat ttctttaagt    60
```

```
ctgtttttca tcttttacaa acaaaagtcc ccattgaatt tgccaccagg gaaaatgggt    120
taccctatca taggtgaaag tttagaattc ctatccacag gctggaaggg acatcctgaa    180
aagttcatat ttgatagaat gcgtaagtac agtagtgagt tattcaagac ttctattgta    240
ggcgaatcca cagttgtttg ctgtggggca gctagtaaca aattcctatt ctctaacgaa    300
aacaaactgg taactgcctg gtggccagat tctgttaaca aaatcttccc aacaacttca    360
ctggattcta atttgaagga ggaatctata aagatgagaa agttgctgcc acagttcttc    420
aaaccagaag cacttcaaag atacgtcggc gttatggatg taatcgcaca agacattt     480 gtcactcact gggacaacaa aaatgagatc acagtttatc cacttgctaa agatacact     540 ttcttgcttg cgtgtagact gttcatgtct gttgaggatg aaaatcatgt ggcgaaattc    600
tcagacccat ccaactaat cgctgcaggc atcatttcac ttcctatcga tcttcctggt     660
actccattca acaaggccat aaaggcttca aatttcatta gaaagagct gataaagatt     720 atcaaacaaa gacgtgttga tctggcagag ggtacagcat ctccaaccca ggatatcttg    780
tcacatatgc tattaacatc tgatgaaaac ggtaaatcta tgaacgagtt gaacattgcc    840
gacaagattc ttggactatt gataggaggc cacgatacag cttcagtagc ttgcacattt    900
ctagtgaagt acttaggaga attaccacat atctacgata aagtctacca agagcaaatg    960
gaaattgcca gtccaaacc tgctggggaa ttgttgaatt gggatgactt gaaaaagatg    1020
aagtattcat ggaatgtggc atgtgaggta atgagattgt caccaccttt acaaggtggg    1080
tttagagagg ctataactga ctttatgttt aacggtttct ctattccaaa agggtggaag    1140
ttatactggt ccgccaactc tacacacaaa atgcagaat gtttcccaat gcctgagaaa    1200
ttcgatccta ccagatttga aggtaatggt ccagcgcctt atacatttgt accattcggt    1260
ggaggcccta gaatgtgtcc tggaaaggaa tacgctagat tagaaatctt ggttttcatg    1320
cataatctgg tcaaacgttt taagtgggaa aaggttattc cagacgaaaa gattattgtc    1380
gatccattcc caatcccagc taaagatctt ccaatccgtt tgtatcctca caaagcttaa   1440
```

<210> SEQ ID NO 114
<211> LENGTH: 479
<212> TYPE: PRT
<213> ORGANISM: Medicago truncatula

<400> SEQUENCE: 114

```
Met Glu Pro Asn Phe Tyr Leu Ser Leu Leu Leu Phe Val Thr Phe
 1               5                  10                  15

Ile Ser Leu Ser Leu Phe Phe Ile Phe Tyr Lys Gln Lys Ser Pro Leu
                20                  25                  30

Asn Leu Pro Pro Gly Lys Met Gly Tyr Pro Ile Ile Gly Glu Ser Leu
            35                  40                  45

Glu Phe Leu Ser Thr Gly Trp Lys Gly His Pro Glu Lys Phe Ile Phe
    50                  55                  60

Asp Arg Met Arg Lys Tyr Ser Ser Glu Leu Phe Lys Thr Ser Ile Val
65                  70                  75                  80

Gly Glu Ser Thr Val Val Cys Cys Gly Ala Ala Ser Asn Lys Phe Leu
                85                  90                  95

Phe Ser Asn Glu Asn Lys Leu Val Thr Ala Trp Trp Pro Asp Ser Val
                100                 105                 110

Asn Lys Ile Phe Pro Thr Thr Ser Leu Asp Ser Asn Leu Lys Glu Glu
            115                 120                 125

Ser Ile Lys Met Arg Lys Leu Leu Pro Gln Phe Phe Lys Pro Glu Ala
```

```
                130                 135                 140
Leu Gln Arg Tyr Val Gly Val Met Asp Val Ile Ala Gln Arg His Phe
145                 150                 155                 160

Val Thr His Trp Asp Asn Lys Asn Glu Ile Thr Val Tyr Pro Leu Ala
                165                 170                 175

Lys Arg Tyr Thr Phe Leu Leu Ala Cys Arg Leu Phe Met Ser Val Glu
            180                 185                 190

Asp Glu Asn His Val Ala Lys Phe Ser Asp Pro Phe Gln Leu Ile Ala
            195                 200                 205

Ala Gly Ile Ile Ser Leu Pro Ile Asp Leu Pro Gly Thr Pro Phe Asn
        210                 215                 220

Lys Ala Ile Lys Ala Ser Asn Phe Ile Arg Lys Glu Leu Ile Lys Ile
225                 230                 235                 240

Ile Lys Gln Arg Arg Val Asp Leu Ala Glu Gly Thr Ala Ser Pro Thr
                245                 250                 255

Gln Asp Ile Leu Ser His Met Leu Leu Thr Ser Asp Glu Asn Gly Lys
            260                 265                 270

Ser Met Asn Glu Leu Asn Ile Ala Asp Lys Ile Leu Gly Leu Leu Ile
        275                 280                 285

Gly Gly His Asp Thr Ala Ser Val Ala Cys Thr Phe Leu Val Lys Tyr
    290                 295                 300

Leu Gly Glu Leu Pro His Ile Tyr Asp Lys Val Tyr Gln Glu Gln Met
305                 310                 315                 320

Glu Ile Ala Lys Ser Lys Pro Ala Gly Glu Leu Leu Asn Trp Asp Asp
                325                 330                 335

Leu Lys Lys Met Lys Tyr Ser Trp Asn Val Ala Cys Glu Val Met Arg
            340                 345                 350

Leu Ser Pro Pro Leu Gln Gly Gly Phe Arg Glu Ala Ile Thr Asp Phe
        355                 360                 365

Met Phe Asn Gly Phe Ser Ile Pro Lys Gly Trp Lys Leu Tyr Trp Ser
    370                 375                 380

Ala Asn Ser Thr His Lys Asn Ala Glu Cys Phe Pro Met Pro Glu Lys
385                 390                 395                 400

Phe Asp Pro Thr Arg Phe Glu Gly Asn Gly Pro Ala Pro Tyr Thr Phe
                405                 410                 415

Val Pro Phe Gly Gly Gly Pro Arg Met Cys Pro Gly Lys Glu Tyr Ala
            420                 425                 430

Arg Leu Glu Ile Leu Val Phe Met His Asn Leu Val Lys Arg Phe Lys
        435                 440                 445

Trp Glu Lys Val Ile Pro Asp Glu Lys Ile Ile Val Asp Pro Phe Pro
    450                 455                 460

Ile Pro Ala Lys Asp Leu Pro Ile Arg Leu Tyr Pro His Lys Ala
465                 470                 475

<210> SEQ ID NO 115
<211> LENGTH: 1116
<212> TYPE: DNA
<213> ORGANISM: Artificial Sequence
<220> FEATURE:
<223> OTHER INFORMATION: Codon-optimized GGPPS

<400> SEQUENCE: 115
atggcctctg ttactttggg ttcctggatc gtcgtccacc accataacca tcaccatcca      60
tcatctatcc taactaaatc tcgttcaaga tcctgtccta ttacactaac caaaccaatc     120
```

```
tcttttcgtt caaagagaac agtttcctct agtagttcta tcgtgtcctc tagtgtcgtc    180
actaaggaag acaatctgag acagtctgaa ccttcttcct ttgatttcat gtcatatatc    240
attactaagg cagaactagt gaataaggct cttgattcag cagttccatt aagagagcca    300
ttgaaaatcc atgaagcaat gagatactct cttctagctg gcgggaagag agtcagacct    360
gtactctgca tagcagcgtg cgaattagtt ggtggcgagg aatcaaccgc tatgcctgcc    420
gcttgtgctg tagaaatgat tcatacaatg tcactgatac acgatgattt gccatgtatg    480
gataacgatg atctgagaag ggtaagcca actaaccata aggttttcgg cgaagatgtt    540
gccgtcttag ctggtgatgc tttgttatct ttcgcgttcg aacatttggc atccgcaaca    600
tcaagtgatg ttgtgtcacc agtaagagta gttagagcag ttggagaact ggctaaagct    660
attggaactg agggtttagt tgcaggtcaa gtcgtcgata tctcttccga aggtcttgat    720
ttgaatgatg taggtcttga acatctcgaa ttcatccatc ttcacaagac agctgcactt    780
ttagaagcca gtgcggttct cggcgcaatt gttggcggag ggagtgatga cgaaattgag    840
agattgagga agtttgctag atgtatagga ttactgttcc aagtagtaga cgatatacta    900
gatgtgacaa gtcttccaa agagttggga aaaacagctg gtaaagattt gattgccgac    960
aaattgacct acccctaagat tatggggcta gaaaaatcaa gagaatttgc cgagaaactc   1020
aatagagagg cgcgtgatca actgttgggt ttcgattctg ataaagttgc accactctta   1080
gccttagcca actacatcgc ttacagacaa aactaa                              1116
```

<210> SEQ ID NO 116
<211> LENGTH: 371
<212> TYPE: PRT
<213> ORGANISM: Arabidopsis thaliana

<400> SEQUENCE: 116

```
Met Ala Ser Val Thr Leu Gly Ser Trp Ile Val His His Asn
1               5                   10                  15

His His Pro Ser Ser Ile Leu Thr Lys Ser Arg Ser Arg Ser Cys
            20                  25                  30

Pro Ile Thr Leu Thr Lys Pro Ile Ser Phe Arg Ser Lys Arg Thr Val
            35                  40                  45

Ser Ser Ser Ser Ser Ile Val Ser Ser Val Val Thr Lys Glu Asp
    50                  55                  60

Asn Leu Arg Gln Ser Glu Pro Ser Ser Phe Asp Phe Met Ser Tyr Ile
65                  70                  75                  80

Ile Thr Lys Ala Glu Leu Val Asn Lys Ala Leu Asp Ser Ala Val Pro
                85                  90                  95

Leu Arg Glu Pro Leu Lys Ile His Glu Ala Met Arg Tyr Ser Leu Leu
            100                 105                 110

Ala Gly Gly Lys Arg Val Arg Pro Val Leu Cys Ile Ala Ala Cys Glu
        115                 120                 125

Leu Val Gly Gly Glu Glu Ser Thr Ala Met Pro Ala Ala Cys Ala Val
    130                 135                 140

Glu Met Ile His Thr Met Ser Leu Ile His Asp Asp Leu Pro Cys Met
145                 150                 155                 160

Asp Asn Asp Asp Leu Arg Arg Gly Lys Pro Thr Asn His Lys Val Phe
                165                 170                 175

Gly Glu Asp Val Ala Val Leu Ala Gly Asp Ala Leu Leu Ser Phe Ala
            180                 185                 190

Phe Glu His Leu Ala Ser Ala Thr Ser Ser Asp Val Val Ser Pro Val
```

```
                195                 200                 205
Arg Val Val Arg Ala Val Gly Glu Leu Ala Lys Ala Ile Gly Thr Glu
210                 215                 220

Gly Leu Val Ala Gly Gln Val Val Asp Ile Ser Ser Glu Gly Leu Asp
225                 230                 235                 240

Leu Asn Asp Val Gly Leu Glu His Leu Glu Phe Ile His Leu His Lys
                245                 250                 255

Thr Ala Ala Leu Leu Glu Ala Ser Ala Val Leu Gly Ala Ile Val Gly
                260                 265                 270

Gly Gly Ser Asp Asp Glu Ile Glu Arg Leu Arg Lys Phe Ala Arg Cys
                275                 280                 285

Ile Gly Leu Leu Phe Gln Val Val Asp Asp Ile Leu Asp Val Thr Lys
290                 295                 300

Ser Ser Lys Glu Leu Gly Lys Thr Ala Gly Lys Asp Leu Ile Ala Asp
305                 310                 315                 320

Lys Leu Thr Tyr Pro Lys Ile Met Gly Leu Glu Lys Ser Arg Glu Phe
                325                 330                 335

Ala Glu Lys Leu Asn Arg Glu Ala Arg Asp Gln Leu Leu Gly Phe Asp
                340                 345                 350

Ser Asp Lys Val Ala Pro Leu Leu Ala Leu Ala Asn Tyr Ile Ala Tyr
                355                 360                 365

Arg Gln Asn
    370

<210> SEQ ID NO 117
<211> LENGTH: 511
<212> TYPE: PRT
<213> ORGANISM: Rubus suavissimus

<400> SEQUENCE: 117

Met Ala Thr Leu Leu Glu His Phe Gln Ala Met Pro Phe Ala Ile Pro
1               5                   10                  15

Ile Ala Leu Ala Ala Leu Ser Trp Leu Phe Leu Phe Tyr Ile Lys Val
                20                  25                  30

Ser Phe Phe Ser Asn Lys Ser Ala Gln Ala Lys Leu Pro Pro Val Pro
            35                  40                  45

Val Val Pro Gly Leu Pro Val Ile Gly Asn Leu Leu Gln Leu Lys Glu
        50                  55                  60

Lys Lys Pro Tyr Gln Thr Phe Thr Arg Trp Ala Glu Glu Tyr Gly Pro
65                  70                  75                  80

Ile Tyr Ser Ile Arg Thr Gly Ala Ser Thr Met Val Val Leu Asn Thr
                85                  90                  95

Thr Gln Val Ala Lys Glu Ala Met Val Thr Arg Tyr Leu Ser Ile Ser
                100                 105                 110

Thr Arg Lys Leu Ser Asn Ala Leu Lys Ile Leu Thr Ala Asp Lys Cys
            115                 120                 125

Met Val Ala Ile Ser Asp Tyr Asn Asp Phe His Lys Met Ile Lys Arg
        130                 135                 140

Tyr Ile Leu Ser Asn Val Leu Gly Pro Ser Ala Gln Lys Arg His Arg
145                 150                 155                 160

Ser Asn Arg Asp Thr Leu Arg Ala Asn Val Cys Ser Arg Leu His Ser
                165                 170                 175

Gln Val Lys Asn Ser Pro Arg Glu Ala Val Asn Phe Arg Arg Val Phe
                180                 185                 190
```

```
Glu Trp Glu Leu Phe Gly Ile Ala Leu Lys Gln Ala Phe Gly Lys Asp
            195                 200                 205

Ile Glu Lys Pro Ile Tyr Val Glu Glu Leu Gly Thr Thr Leu Ser Arg
    210                 215                 220

Asp Glu Ile Phe Lys Val Leu Val Leu Asp Ile Met Glu Gly Ala Ile
225                 230                 235                 240

Glu Val Asp Trp Arg Asp Phe Phe Pro Tyr Leu Arg Trp Ile Pro Asn
                245                 250                 255

Thr Arg Met Glu Thr Lys Ile Gln Arg Leu Tyr Phe Arg Arg Lys Ala
            260                 265                 270

Val Met Thr Ala Leu Ile Asn Glu Gln Lys Lys Arg Ile Ala Ser Gly
        275                 280                 285

Glu Glu Ile Asn Cys Tyr Ile Asp Phe Leu Leu Lys Glu Gly Lys Thr
    290                 295                 300

Leu Thr Met Asp Gln Ile Ser Met Leu Leu Trp Glu Thr Val Ile Glu
305                 310                 315                 320

Thr Ala Asp Thr Thr Met Val Thr Thr Glu Trp Ala Met Tyr Glu Val
                325                 330                 335

Ala Lys Asp Ser Lys Arg Gln Asp Arg Leu Tyr Gln Glu Ile Gln Lys
            340                 345                 350

Val Cys Gly Ser Glu Met Val Thr Glu Glu Tyr Leu Ser Gln Leu Pro
        355                 360                 365

Tyr Leu Asn Ala Val Phe His Glu Thr Leu Arg Lys His Ser Pro Ala
    370                 375                 380

Ala Leu Val Pro Leu Arg Tyr Ala His Glu Asp Thr Gln Leu Gly Gly
385                 390                 395                 400

Tyr Tyr Ile Pro Ala Gly Thr Glu Ile Ala Ile Asn Ile Tyr Gly Cys
                405                 410                 415

Asn Met Asp Lys His Gln Trp Glu Ser Pro Glu Glu Trp Lys Pro Glu
            420                 425                 430

Arg Phe Leu Asp Pro Lys Phe Asp Pro Met Asp Leu Tyr Lys Thr Met
        435                 440                 445

Ala Phe Gly Ala Gly Lys Arg Val Cys Ala Gly Ser Leu Gln Ala Met
450                 455                 460

Leu Ile Ala Cys Pro Thr Ile Gly Arg Leu Val Gln Glu Phe Glu Trp
465                 470                 475                 480

Lys Leu Arg Asp Gly Glu Glu Asn Val Asp Thr Val Gly Leu Thr
                485                 490                 495

Thr His Lys Arg Tyr Pro Met His Ala Ile Leu Lys Pro Arg Ser
            500                 505                 510

<210> SEQ ID NO 118
<211> LENGTH: 1383
<212> TYPE: DNA
<213> ORGANISM: Artificial Sequence
<220> FEATURE:
<223> OTHER INFORMATION: Codon-optimized Stevia rebaudiana UGT74G1

<400> SEQUENCE: 118
atggctgaac aacaaaagat caagaagtct ccacacgttt tgttgattcc atttccattg      60
caaggtcaca tcaacccatt cattcaattc ggtaagagat tgatttccaa gggtgttaag     120
actactttgg ttactaccat ccataccttg aactctacct tgaaccattc taacactacc     180
accacctcca ttgaaattca agctatttcc gatggttgtg atgaaggtgg ttttatgtct     240
gctggtgaat cttacttgga aacctttaag caagttggtt ctaagtcctt ggccgatttg     300
```

```
attaagaagt tgcaatctga aggtactacc attgatgcca ttatctacga ttctatgacc    360
gaatgggttt tggatgttgc tattgaattc ggtattgatg gtggttcatt cttcactcaa    420
gcttgtgttg ttaactcctt gtactaccat gttcacaagg gtttgatctc attgccattg    480
ggtgaaactg tttctgttcc aggtttccca gttttacaaa gatgggaaac tccattgatc    540
ttgcaaaacc acgaacaaat tcaatctcca tggtcccaaa tgttgtttgg tcaattcgcc    600
aacattgatc aagctagatg ggttttacc aactccttct acaagttgga agaagaagtt    660
atcgaatgga ccagaaagat ctggaacttg aaagttattg gtccaaccct tgccatctatg   720
tacttggata agagattgga tgacgataag gacaacggtt tcaacttgta caaggctaac    780
catcatgaat gcatgaattg gttggacgac aagccaaaag aatccgttgt ttatgttgct    840
ttcggttctt tggtcaaaca tggtccagaa caagttgaag aaattaccag gccttgatc     900
gattccgatg ttaatttctt gtgggtcatc aagcacaaag aagaaggtaa attgccagaa    960
aacttgtccg aagttatcaa aactggtaag ggtttgattg tcgcttggtg taaacaattg   1020
gatgttttgg ctcatgaatc cgttggttgt ttcgttactc attgtggttt caactccacc   1080
ttggaagcta tttctttggg tgttccagtt gttgctatgc cacaattttc tgatcaaact   1140
accaacgcta agttgttgga cgaaattttg ggtgttggtg ttagagttaa ggctgacgaa   1200
aatggtatcg ttagaagagg taacttggct tcttgcatca agatgatcat ggaagaagaa   1260
agaggtgtca tcattagaaa gaacgctgtt aagtggaagg atttggctaa agttgctgtt   1320
catgaaggtg gtagttccga taatgatatc gttgaattcg tttccgaatt gatcaaggcc   1380
taa                                                                  1383

<210> SEQ ID NO 119
<211> LENGTH: 2340
<212> TYPE: DNA
<213> ORGANISM: Artificial Sequence
<220> FEATURE:
<223> OTHER INFORMATION: Truncated Zea Mays CDPS

<400> SEQUENCE: 119
gcacagcaca catcagaatc cgcagctgtc gcaaagggca gcagtttgac ccctatagtg     60
agaactgacg ctgagtcaag gagaacaaga tggccaaccg atgacgatga cgccgaacct    120
ttagtggatg agatcagggc aatgcttact tccatgtctg atggtgacat ttccgtgagc    180
gcatacgata cagcctgggt cggattggtt ccaagattag acggcggtga aggtcctcaa    240
tttccagcag ctgtgagatg gataagaaat aaccagttgc ctgacggaag ttggggcgat    300
gccgcattat tctctgccta tgacaggctt atcaataccc ttgcctgcgt tgtaactttg    360
acaaggtggt ccctagaacc agagatgaga ggtagaggac tatcttttt gggtaggaac    420
atgtggaaat tagcaactga agatgaagag tcaatgccta ttggcttcga attagcattt    480
ccatctttga tagagcttgc taagagccta ggtgtccatg acttccctta tgatcaccag    540
gccctacaag gaatctactc ttcaagagag atcaaaatga gaggattcc aaaagaagtg    600
atgcataccg ttccaacatc aatattgcac agtttggagg gtatgcctgg cctagattgg    660
gctaaactac ttaaactaca gagcagcgac ggaagttttt tgttctcacc agctgccact    720
gcatatgctt taatgaatac cggagatgac aggtgtttta gctacatcga tagaacagta    780
aagaaattca acggcggcgt ccctaatgtt tatccagtgg atctatttga acatatttgg    840
gccgttgata gacttgaaag attaggaatc tccaggtact tccaaaagga gatcgaacaa    900
```

| | | | | |
|---|---|---|---|---|
| tgcatggatt atgtaaacag gcattggact gaggacggta tttgttgggc aaggaactct | | | | 960 |
| gatgtcaaag aggtggacga cacagctatg gcctttagac ttcttaggtt gcacggctac | | | | 1020 |
| agcgtcagtc ctgatgtgtt taaaaacttc gaaaaggacg gtgaattttt cgcatttgtc | | | | 1080 |
| ggacagtcta atcaagctgt taccggtatg tacaacttaa acagagcaag ccagatatcc | | | | 1140 |
| ttcccaggcg aggatgtgct tcatagagct ggtgccttct catatgagtt cttgaggaga | | | | 1200 |
| aaagaagcag agggagcttt gagggacaag tggatcattt ctaaagatct acctggtgaa | | | | 1260 |
| gttgtgtata ctttggattt tccatggtac ggcaacttac ctagagtcga ggccagagac | | | | 1320 |
| tacctagagc aatacggagg tggtgatgac gtttggattg caagacatt gtataggatg | | | | 1380 |
| ccacttgtaa acaatgatgt atatttggaa ttggcaagaa tggatttcaa ccactgccag | | | | 1440 |
| gctttgcatc agttagagtg gcaaggacta aaaagatggt atactgaaaa taggttgatg | | | | 1500 |
| gactttggtg tcgcccaaga agatgccctt agagcttatt ttcttgcagc cgcatctgtt | | | | 1560 |
| tacgagcctt gtagagctgc cgagaggctt gcatgggcta gagccgcaat actagctaac | | | | 1620 |
| gccgtgagca cccacttaag aaatagccca tcattcagag aaaggttaga gcattctctt | | | | 1680 |
| aggtgtagac ctagtgaaga gacagatggc tcctggttta actcctcaag tggctctgat | | | | 1740 |
| gcagttttag taaaggctgt cttaagactt actgattcat tagccaggga agcacagcca | | | | 1800 |
| atccatggag gtgacccaga agatattata cacaagttgt taagatctgc ttgggccgag | | | | 1860 |
| tgggttaggg aaaaggcaga cgctgccgat agcgtgtgca atggtagttc tgcagtagaa | | | | 1920 |
| caagagggat caagaatggt ccatgataaa cagacctgtc tattattggc tagaatgatc | | | | 1980 |
| gaaatttctg ccgttagggc agctggtgaa gcagccagtg aggacggcga tagaagaata | | | | 2040 |
| attcaattaa caggctccat ctgcgacagt cttaagcaaa aaatgctagt ttcacaggac | | | | 2100 |
| cctgaaaaaa atgaagagat gatgtctcac gtggatgacg aattgaagtt gaggattaga | | | | 2160 |
| gagttcgttc aatatttgct tagactaggt gaaaaaaaga ctggatctag cgaaaccagg | | | | 2220 |
| caaacatttt taagtatagt gaaatcatgt tactatgctg ctcattgccc acctcatgtc | | | | 2280 |
| gttgatagac acattagtag agtgattttc gagccagtaa gtgccgcaaa gtaaccgcgg | | | | 2340 |

<210> SEQ ID NO 120
<211> LENGTH: 777
<212> TYPE: PRT
<213> ORGANISM: Zea mays

<400> SEQUENCE: 120

Ala Gln His Thr Ser Glu Ser Ala Ala Val Ala Lys Gly Ser Ser Leu
1               5                   10                  15

Thr Pro Ile Val Arg Thr Asp Ala Glu Ser Arg Arg Thr Arg Trp Pro
            20                  25                  30

Thr Asp Asp Asp Ala Glu Pro Leu Val Asp Glu Ile Arg Ala Met
        35                  40                  45

Leu Thr Ser Met Ser Asp Gly Asp Ile Ser Val Ser Ala Tyr Asp Thr
    50                  55                  60

Ala Trp Val Gly Leu Val Pro Arg Leu Asp Gly Glu Gly Pro Gln
65                  70                  75                  80

Phe Pro Ala Ala Val Arg Trp Ile Arg Asn Asn Gln Leu Pro Asp Gly
                85                  90                  95

Ser Trp Gly Asp Ala Ala Leu Phe Ser Ala Tyr Asp Arg Leu Ile Asn
            100                 105                 110

Thr Leu Ala Cys Val Val Thr Leu Thr Arg Trp Ser Leu Glu Pro Glu
        115                 120                 125

Met Arg Gly Arg Gly Leu Ser Phe Leu Gly Arg Asn Met Trp Lys Leu
130                 135                 140

Ala Thr Glu Asp Glu Glu Ser Met Pro Ile Gly Phe Glu Leu Ala Phe
145                 150                 155                 160

Pro Ser Leu Ile Glu Leu Ala Lys Ser Leu Gly Val His Asp Phe Pro
                165                 170                 175

Tyr Asp His Gln Ala Leu Gln Gly Ile Tyr Ser Ser Arg Glu Ile Lys
            180                 185                 190

Met Lys Arg Ile Pro Lys Glu Val Met His Thr Val Pro Thr Ser Ile
        195                 200                 205

Leu His Ser Leu Glu Gly Met Pro Gly Leu Asp Trp Ala Lys Leu Leu
210                 215                 220

Lys Leu Gln Ser Ser Asp Gly Ser Phe Leu Phe Ser Pro Ala Ala Thr
225                 230                 235                 240

Ala Tyr Ala Leu Met Asn Thr Gly Asp Asp Arg Cys Phe Ser Tyr Ile
                245                 250                 255

Asp Arg Thr Val Lys Lys Phe Asn Gly Gly Val Pro Asn Val Tyr Pro
            260                 265                 270

Val Asp Leu Phe Glu His Ile Trp Ala Val Asp Arg Leu Glu Arg Leu
        275                 280                 285

Gly Ile Ser Arg Tyr Phe Gln Lys Glu Ile Glu Gln Cys Met Asp Tyr
290                 295                 300

Val Asn Arg His Trp Thr Glu Asp Gly Ile Cys Trp Ala Arg Asn Ser
305                 310                 315                 320

Asp Val Lys Glu Val Asp Thr Ala Met Ala Phe Arg Leu Leu Arg
                325                 330                 335

Leu His Gly Tyr Ser Val Ser Pro Asp Val Phe Lys Asn Phe Glu Lys
            340                 345                 350

Asp Gly Glu Phe Phe Ala Phe Val Gly Gln Ser Asn Gln Ala Val Thr
        355                 360                 365

Gly Met Tyr Asn Leu Asn Arg Ala Ser Gln Ile Ser Phe Pro Gly Glu
370                 375                 380

Asp Val Leu His Arg Ala Gly Ala Phe Ser Tyr Glu Phe Leu Arg Arg
385                 390                 395                 400

Lys Glu Ala Glu Gly Ala Leu Arg Asp Lys Trp Ile Ile Ser Lys Asp
                405                 410                 415

Leu Pro Gly Glu Val Val Tyr Thr Leu Asp Phe Pro Trp Tyr Gly Asn
            420                 425                 430

Leu Pro Arg Val Glu Ala Arg Asp Tyr Leu Glu Gln Tyr Gly Gly Gly
        435                 440                 445

Asp Asp Val Trp Ile Gly Lys Thr Leu Tyr Arg Met Pro Leu Val Asn
450                 455                 460

Asn Asp Val Tyr Leu Glu Leu Ala Arg Met Asp Phe Asn His Cys Gln
465                 470                 475                 480

Ala Leu His Gln Leu Glu Trp Gln Gly Leu Lys Arg Trp Tyr Thr Glu
                485                 490                 495

Asn Arg Leu Met Asp Phe Gly Val Ala Gln Glu Asp Ala Leu Arg Ala
            500                 505                 510

Tyr Phe Leu Ala Ala Ala Ser Val Tyr Glu Pro Cys Arg Ala Ala Glu
        515                 520                 525

Arg Leu Ala Trp Ala Arg Ala Ala Ile Leu Ala Asn Ala Val Ser Thr
530                 535                 540

```
His Leu Arg Asn Ser Pro Ser Phe Arg Glu Arg Leu Glu His Ser Leu
545                 550                 555                 560

Arg Cys Arg Pro Ser Glu Glu Thr Asp Gly Ser Trp Phe Asn Ser Ser
            565                 570                 575

Ser Gly Ser Asp Ala Val Leu Val Lys Ala Val Leu Arg Leu Thr Asp
            580                 585                 590

Ser Leu Ala Arg Glu Ala Gln Pro Ile His Gly Gly Asp Pro Glu Asp
        595                 600                 605

Ile Ile His Lys Leu Leu Arg Ser Ala Trp Ala Glu Trp Val Arg Glu
        610                 615                 620

Lys Ala Asp Ala Ala Asp Ser Val Cys Asn Gly Ser Ser Ala Val Glu
625                 630                 635                 640

Gln Glu Gly Ser Arg Met Val His Asp Lys Gln Thr Cys Leu Leu Leu
            645                 650                 655

Ala Arg Met Ile Glu Ile Ser Ala Gly Arg Ala Ala Gly Glu Ala Ala
            660                 665                 670

Ser Glu Asp Gly Asp Arg Arg Ile Ile Gln Leu Thr Gly Ser Ile Cys
        675                 680                 685

Asp Ser Leu Lys Gln Lys Met Leu Val Ser Gln Asp Pro Glu Lys Asn
        690                 695                 700

Glu Glu Met Met Ser His Val Asp Asp Glu Leu Lys Leu Arg Ile Arg
705                 710                 715                 720

Glu Phe Val Gln Tyr Leu Leu Arg Leu Gly Glu Lys Lys Thr Gly Ser
            725                 730                 735

Ser Glu Thr Arg Gln Thr Phe Leu Ser Ile Val Lys Ser Cys Tyr Tyr
            740                 745                 750

Ala Ala His Cys Pro Pro His Val Val Asp Arg His Ile Ser Arg Val
        755                 760                 765

Ile Phe Glu Pro Val Ser Ala Ala Lys
770                 775
```

PRODUCTION OF STEVIOL GLYCOSIDES IN RECOMBINANT HOSTS

This application is a U.S. National Phase application under 35 U.S.C. § 371 of PCT/EP2017/078473, filed on Nov. 7, 2017, which claims priority from and the benefit of U.S. Provisional Application No. 62/418,584, filed on Nov. 7, 2016, the specifications of which are hereby incorporated by reference in their entireties.

BACKGROUND OF THE INVENTION

Field of the Invention

This disclosure relates to recombinant production of steviol glycosides, glycosides of steviol precursors, and steviol glycoside precursors in recombinant hosts. In particular, this disclosure relates to production of steviol glycosides comprising steviol-13-O-glucoside (13-SMG), steviol-19-O-glucoside (19-SMG), steviol-1,2-bioside, steviol-1,3-bioside, 1,2-stevioside, 1,3-stevioside, rubusoside, Rebaudioside A (RebA), Rebaudioside B (RebB), Rebaudioside C (RebC), Rebaudioside D (RebD), Rebaudioside E (RebE), Rebaudioside F (RebF), Rebaudioside M (RebM), Rebaudioside Q (RebQ), Rebaudioside I (RebI), dulcoside A, mono-glycosylated ent-kaurenoic acids, di-glycosylated ent-kaurenoic acids, tri-glycosylated ent-kaurenoic acids, mono-glycosylated ent-kaurenols (e.g., kaurenoate-19-O-glucoside or 19-KMG), di-glycosylated ent-kaurenols, tri-glycosylated ent-kaurenols, tri-glycosylated steviol glycosides, tetra-glycosylated steviol glycosides, penta-glycosylated steviol glycosides, hexa-glycosylated steviol glycosides, hepta-glycosylated steviol glycosides, or isomers thereof in recombinant hosts.

Description of Related Art

Sweeteners are well known as ingredients used most commonly in the food, beverage, or confectionary industries. The sweetener can either be incorporated into a final food product during production or for stand-alone use, when appropriately diluted, as a tabletop sweetener or an at-home replacement for sugars in baking. Sweeteners include natural sweeteners such as sucrose, high fructose corn syrup, molasses, maple syrup, and honey and artificial sweeteners such as aspartame, saccharine, and sucralose. Stevia extract is a natural sweetener that can be isolated and extracted from a perennial shrub, *Stevia rebaudiana*. Stevia is commonly grown in South America and Asia for commercial production of stevia extract. Stevia extract, purified to various degrees, is used commercially as a high intensity sweetener in foods and in blends or alone as a tabletop sweetener.

Chemical structures for several steviol glycosides are shown in FIG. 1, including the diterpene steviol and various steviol glycosides. Extracts of the Stevia plant generally comprise steviol glycosides that contribute to the sweet flavor, although the amount of each steviol glycoside often varies, inter alia, among different production batches.

Recovery and purification of steviol glycosides from the Stevia plant have proven to be labor intensive and inefficient. Moreover, steviol glycoside compositions obtained from a plant-derived Stevia extract generally contain Stevia plant-derived components that can contribute to off-flavors. As such, there remains a need for a recombinant production system that can accumulate high yields of desired steviol glycosides, such as RebD and RebM and produce steviol glycoside compositions that are enriched for a one or more desired steviol glycosides relative to a steviol glycoside composition of Stevia plant with a reduced level of Stevia plant-derived components relative to a steviol glycoside composition obtained from a plant-derived Stevia extract. There also remains a need for improved production of steviol glycosides in recombinant hosts for commercial uses. As well, there remains a need for identifying enzymes selective towards particular substrates to produce one or more specific steviol glycosides. In some aspects, there remains a need to increase the catalytic capability of enzymes with 19-0 glycosylation activity in order to produce higher yields of steviol glycosides.

SUMMARY OF THE INVENTION

It is against the above background that the present invention provides certain advantages and advancements over the prior art.

Although this invention as disclosed herein is not limited to specific advantages or functionalities (such for example, the ability to scale up production of a one or more steviol glycosides or glycosides of a steviol precursor, purify the one or more steviol glycosides or glycosides of the steviol precursor, and produce steviol glycoside compositions where the different proportions of the various steviol glycosides provide the advantage of having a reduced level of Stevia plant-derived components relative to a steviol glycoside composition obtained from a plant-derived Stevia extract), the invention provides a recombinant host cell capable of producing one or more steviol glycosides or glycosides of a steviol precursor, comprising a recombinant gene encoding a polypeptide capable of glycosylating steviol or a steviol glycoside at its C-19 carboxyl group having at least 80% sequence identity to the amino acid sequence set forth in SEQ ID NO:4 and having one or more amino acid substitutions of residues 15, 16, 18, 20, 27, 28, 30, 31, 49, 51, 67, 68, 73, 75, 79, 81, 83, 84, 86-88, 90, 91, 96, 99, 107, 110, 111, 113, 115, 119-121, 123, 128, 129, 135, 136, 140, 141, 143, 146, 147, 156, 162, 166, 169, 173, 176, 179-181, 183-189, 191-195, 200, 204, 209, 211, 212, 215, 221, 222, 224, 232, 237, 247, 252, 255, 257, 259, 263, 265, 266, 269, 274, 280, 284, 285, 287, 292, 295-298, 300, 301, 303, 310, 311, 313, 315, 316, 320, 322, 325, 326, 328, 329, 332, 333, 335, 338, 341, 346, 347, 357, 364, 370, 371, 373, 375-377, 380, 385, 387-391, 396, 401, 407-411, 415, 416, 419, 424, 426, 427, 434, 448, 449, 455, 456, or 458 of SEQ ID NO:4.

In one aspect of the recombinant host cells disclosed herein, the polypeptide comprises at least one amino acid substitution of SEQ ID NO:4 that is L15V, I16L, F18Y, L20A, F27M, I28L, F30L, G31S, G31A, T49I, N51K, Q67E, A68T, C73F, E75D, M79A, E83D, E83K, S84A, L86I, E87D, T88R, K90W, Q91E, S96T, D99E, E107S, T110P, I111V, A113C, I115V, M119F, T120L, E121P, V123A, I128K, E129Q, G135A, S136A, Q140N, A141S, V143A, S146N, L147I, I156L, E162T, V166L, F169L, Q173E, E176D, L179S, I180F, L181V, N183D, H184P, E185G, Q186S, I187Y, Q188P, S189A, W191F, S192D, Q193M, M194V, L195V, A200S, Q204K, F209L, N211H, S212T, K215E, I221V, E222D, T224M, V232T, L237I, D247E, N252Y, N255S, Y257F, A259P, E263A, M265I, N266K, N266E, D269N, E274G, A280S, L284M, V285A, H287L, V292M, I295L, I295M, T296A, R297W, A298G, I300K, D301N, D303N, I310V, K311R, K313S, E315Q, G316A, E320K, L322F, V325E, I326T, T328S, G329E, L332I, I333V, A335S, K338P, D341E, E346P, E346K, S347A, F357W, I364L, V370M, V371I, M373V, Q375L, F376W, S377T, T380S, L385F, D387E, E388D, I389V, L390W, G391K, V396A, N401K, G407E, N408E, L409I, A410E, S411D, M415E, I416V, E419G, I424E, R426K, K427E, D434E, N448K, D449N, S455A, E456K, or I458V.

In one aspect, the recombinant host cells disclosed herein further comprise:
(a) a gene encoding a polypeptide capable of synthesizing geranylgeranyl pyrophosphate (GGPP) from farnesyl diphosphate (FPP) and isopentenyl diphosphate (IPP);
(b) a gene encoding a polypeptide capable of synthesizing ent-copalyl diphosphate from GGPP;
(c) a gene encoding an a polypeptide capable of synthesizing ent-kaurene from ent-copalyl diphosphate;
(d) a gene encoding a polypeptide capable of synthesizing ent-kaurenoic acid from ent-kaurene;
(e) a gene encoding a polypeptide capable of synthesizing steviol from ent-kaurenoic acid;
(f) a gene encoding a polypeptide capable of reducing cytochrome P450 complex;
(g) a gene encoding a polypeptide capable of glycosylating steviol or a steviol glycoside at its C-13 hydroxyl group;
(h) a gene encoding a polypeptide capable of beta 1,3 glycosylation of the C3' of the 13-O-glucose, 19-O-glucose, or both 13-O-glucose and 19-O-glucose of a steviol glycoside; and/or
(i) a gene encoding a polypeptide capable of beta 1,2 glycosylation of the C2' of the 13-O-glucose, 19-O-glucose, or both 13-O-glucose and 19-O-glucose of a steviol glycoside;
wherein at least one of the genes is a recombinant gene.

In one aspect of the recombinant host cells disclosed herein:
(a) the polypeptide capable of synthesizing GGPP comprises a polypeptide having at least 70% sequence identity to the amino acid sequence set forth in any one of SEQ ID NOs:20, 22, 24, 26, 28, 30, 32, or 116;
(b) the polypeptide capable of synthesizing ent-copalyl diphosphate comprises a polypeptide having at least 70% sequence identity to the amino acid sequence set forth in any one of SEQ ID NOs:34, 36, 38, 40, or 42;
(c) the polypeptide capable of synthesizing ent-kaurene comprises a polypeptide having at least 70% sequence identity to the amino acid sequence set forth in any one of SEQ ID NOs:44, 46, 48, 50, or 52;
(d) the polypeptide capable of synthesizing ent-kaurenoic acid comprises a polypeptide having at least 70% sequence identity to the amino acid sequence set forth in any one of SEQ ID NOs:60, 62, 66, 68, 70, 72, 74, 76, or 117;
(e) the polypeptide capable of reducing cytochrome P450 complex comprises a polypeptide having at least 70% sequence identity to the amino acid sequence set forth in any one of SEQ ID NOs:78, 80, 82, 84, 86, 88, 90, or 92;
(f) the polypeptide capable of synthesizing steviol comprises a polypeptide having at least 70% sequence identity to the amino acid sequence set forth in any one of SEQ ID NOs:94, 97, 100, 101, 102, 103, 104, 106, 108, 110, 112, or 114;
(g) the polypeptide capable of glycosylating steviol or a steviol glycoside at its C-13 hydroxyl group comprises a polypeptide having at least 55% sequence identity to the amino acid sequence set forth in SEQ ID NO:7;
(h) the polypeptide capable of beta 1,3 glycosylation of the C3' of the 13-O-glucose, 19-O-glucose, or both 13-O-glucose and 19-O-glucose of a steviol glycoside comprises a polypeptide having at least 50% sequence identity to the amino acid sequence set forth in SEQ ID NO:9;
(i) the polypeptide capable of beta 1,2 glycosylation of the C2' of the 13-O-glucose, 19-O-glucose, or both 13-O-glucose and 19-O-glucose of a steviol glycoside comprises a polypeptide having at least 80% sequence identity to the amino acid sequence set forth in SEQ ID NO:11, a polypeptide having at least 80% sequence identity to the amino acid sequence set forth in SEQ ID NO:13; or a polypeptide having at least 65% sequence identity to the amino acid sequence set forth in SEQ ID NO:16.

In one aspect of the recombinant host cells disclosed herein, the one or more steviol glycosides or glycosides of the steviol precursor comprises kaurenoate-19-O-glucoside (19-KMG), steviol-13-O-glucoside (13-SMG), steviol-1,2-Bioside, steviol-1,3-Bioside, steviol-19-O-glucoside (19-SMG), 1,2-Stevioside, 1,3-stevioside (RebG), rubusoside, rebaudioside A (RebA), rebaudioside B (RebB), rebaudioside C (RebC), rebaudioside D (RebD), rebaudioside E (RebE), rebaudioside F (RebF), rebaudioside M (RebM), rebaudioside Q (RebQ), rebaudioside I (RebI), dulcoside A, a mono-glycosylated ent-kaurenoic acid, a di-glycosylated ent-kaurenoic acid, a tri-glycosylated ent-kaurenoic acid, a mono-glycosylated ent-kaurenols, a di-glycosylated ent-kaurenol, a tri-glycosylated ent-kaurenol, a tri-glycosylated steviol glycoside, a tetra-glycosylated steviol glycoside, a penta-glycosylated steviol glycoside, a hexa-glycosylated steviol glycoside, a hepta-glycosylated steviol glycoside, and/or an isomer thereof.

In one aspect of the recombinant host cells disclosed herein, the expression of the polypeptide capable of glycosylating steviol or a steviol glycoside at its C-19 carboxyl group, having at least 80% sequence identity to the amino acid sequence set forth in SEQ ID NO:4 and having the one or more amino acid substitutions, increases or decreases the amount of 19-KMG, 19-SMG, and/or rubusoside produced by the cell by at least about 5%, 10%, 25%, 50%, or 100% relative to a corresponding host expressing a polypeptide capable of glycosylating steviol or a steviol glycoside at its C-19 carboxyl group lacking the one or more amino acid substitutions.

In one aspect of the recombinant host cells disclosed herein, the recombinant host cell comprises a plant cell, a mammalian cell, an insect cell, a fungal cell, an algal cell, an archaeal cell, or a bacterial cell.

In one aspect of the recombinant host cells disclosed herein, the recombinant host cell is a *Saccharomyces cerevisiae* cell.

In one aspect of the recombinant host cells disclosed herein, the recombinant host cell is a *Yarrowia lipolytica* cell.

The invention also provides a method of producing one or more steviol glycosides or glycosides of a steviol precursor in a cell culture, comprising culturing the recombinant host cells disclosed herein in the cell culture, under conditions in which the genes are expressed; and wherein the one or more steviol glycosides or glycosides of the steviol precursor is produced by the recombinant host cell.

In one aspect of the methods disclosed herein, the genes are constitutively expressed.

In one aspect of the methods disclosed herein, the expression of the genes is induced.

In one aspect, the methods disclosed herein further comprise isolating the produced one or more steviol glycosides or glycosides of the steviol precursor from the cell culture.

In one aspect of the methods disclosed herein, the isolating step comprises separating a liquid phase of the cell culture from a solid phase of the cell culture to obtain a supernatant comprising the produced one or more steviol glycosides or glycosides of the steviol precursor, and:
- (a) contacting the supernatant with one or more adsorbent resins in order to obtain at least a portion of the produced one or more steviol glycosides or glycosides of the steviol precursor; or
- (b) contacting the supernatant with one or more ion exchange or reversed-phase chromatography columns in order to obtain at least a portion of the produced one or more steviol glycosides or glycosides of the steviol precursor; or
- (c) crystallizing or extracting the produced one or more steviol glycosides or glycosides of the steviol precursor;

thereby isolating the produced one or more steviol glycosides or glycosides of the steviol precursor.

In one aspect, the methods disclosed herein further comprise recovering the one or more steviol glycosides or glycosides of the steviol precursor from the cell culture.

In one aspect of the methods disclosed herein, the recovered one or more steviol glycosides or glycosides of the steviol precursor is enriched for the one or more steviol glycosides or glycosides of the steviol precursor relative to a steviol glycoside composition of Stevia plant and has a reduced level of Stevia plant-derived components relative to a steviol glycoside composition obtained from a plant-derived Stevia extract.

The invention also provides a method for producing one or more steviol glycosides or glycosides of a steviol precursor, comprising whole-cell bioconversion of a plant-derived or synthetic steviol, steviol precursors, and/or steviol glycosides in a cell culture of a recombinant host cell using a polypeptide capable of glycosylating steviol or a steviol glycoside at its C-19 carboxyl group having at least 80% sequence identity to the amino acid sequence set forth in SEQ ID NO:4 and having one or more amino acid substitutions of residues 15, 16, 18, 20, 27, 28, 30, 31, 49, 51, 67, 68, 73, 75, 79, 81, 83, 84, 86-88, 90, 91, 96, 99, 107, 110, 111, 113, 115, 119-121, 123, 128, 129, 135, 136, 140, 141, 143, 146, 147, 156, 162, 166, 169, 173, 176, 179-181, 183-189, 191-195, 200, 204, 209, 211, 212, 215, 221, 222, 224, 232, 237, 247, 252, 255, 257, 259, 263, 265, 266, 269, 274, 280, 284, 285, 287, 292, 295-298, 300, 301, 303, 310, 311, 313, 315, 316, 320, 322, 325, 326, 328, 329, 332, 333, 335, 338, 341, 346, 347, 357, 364, 370, 371, 373, 375-377, 380, 385, 387-391, 396, 401, 407-411, 415, 416, 419, 424, 426, 427, 434, 448, 449, 455, 456, or 458 of SEQ ID NO:4; and, optionally, one or more of:
- (a) a polypeptide capable of glycosylating steviol or a steviol glycoside at its C-13 hydroxyl group, comprising a polypeptide having at least 55% sequence identity to the amino acid sequence set forth in SEQ ID NO:7;
- (b) the polypeptide capable of beta 1,3 glycosylation of the C3' of the 13-O-glucose, 19-O-glucose, or both 13-O-glucose and 19-O-glucose of a steviol glycoside, comprising a polypeptide having at least 50% sequence identity to the amino acid sequence set forth in SEQ ID NO:9;
- (c) the polypeptide capable of beta 1,2 glycosylation of the C2' of the 13-O-glucose, 19-O-glucose, or both 13-O-glucose and 19-O-glucose of a steviol glycoside, comprising a polypeptide having at least 80% sequence identity to the amino acid sequence set forth in SEQ ID NO:11, a polypeptide having at least 80% sequence identity to the amino acid sequence set forth in SEQ ID NO:13; or a polypeptide having at least 65% sequence identity to the amino acid sequence set forth in SEQ ID NO:16;

wherein at least one of the polypeptide is a recombinant polypeptide; and producing the one or more steviol glycosides or glycosides of the steviol precursor thereby.

In one aspect of the methods disclosed herein, the polypeptide capable of glycosylating steviol or a steviol glycoside at its C-19 carboxyl group comprises at least one amino acid substitution of SEQ ID NO:4 that is L15V, I16L, F18Y, L20A, F27M, I28L, F30L, G31S, G31A, T49I, N51K, Q67E, A68T, C73F, E75D, M79A, E83D, E83K, S84A, L86I, E87D, T88R, K90W, Q91E, S96T, D99E, E107S, T110P, I111V, A113C, I115V, M119F, T120L, E121P, V123A, I128K, E129Q, G135A, S136A, Q140N, A141S, V143A, S146N, L147I, I156L, E162T, V166L, F169L, Q173E, E176D, L179S, I180F, L181V, N183D, H184P, E185G, Q186S, I187Y, Q188P, S189A, W191F, S192D, Q193M, M194V, L195A, A200S, Q204K, F209L, N211H, S212T, K215E, I221V, E222D, T224M, V232L, L237I, D247E, N252Y, N255S, Y257F, A259P, E263A, M265I, N266K, N266E, D269N, E274G, A280S, L284M, V285A, H287E, V292M, I295L, I295M, T296A, R297W, A298G, I300K, D301N, D303N, I310V, K311R, K313S, E315Q, G316A, E320K, L322F, V325E, I326T, T328S, G329E, L332I, I333V, A335S, K338P, D341E, E346P, E346K, S347A, F357W, I364L, V370M, V371I, M373V, Q375L, F376W, S377T, T380S, L385P, D387E, E388D, I389V, L390W, G391K, V396A, N401K, G407E, N408E, L409I, A410E, S411D, M415E, I416V, E419G, I424E, R426K, K427E, D434E, N448K, D449N, S455A, E456K, or I458V.

In one aspect of the methods disclosed herein, the recombinant host cell comprises a plant cell, a mammalian cell, an insect cell, a fungal cell, an algal cell, an archaeal cell or a bacterial cell.

In one aspect of the methods disclosed herein, the recombinant host cell is a *Saccharomyces cerevisiae* cell.

In one aspect of the methods disclosed herein, the recombinant host cell is a *Yarrowia lipolytica* cell.

The invention also provides an in vitro method for producing one or more steviol glycosides or glycosides of a steviol precursor comprising adding a polypeptide capable of glycosylating steviol or a steviol glycoside at its C-19 carboxyl group having at least 80% sequence identity to the amino acid sequence set forth in SEQ ID NO:4 and having one or more amino acid substitutions of residues 15, 16, 18, 20, 27, 28, 30, 31, 49, 51, 67, 68, 73, 75, 79, 81, 83, 84, 86-88, 90, 91, 96, 99, 107, 110, 111, 113, 115, 119-121, 123, 128, 129, 135, 136, 140, 141, 143, 146, 147, 156, 162, 166, 169, 173, 176, 179-181, 183-189, 191-195, 200, 204, 209, 211, 212, 215, 221, 222, 224, 232, 237, 247, 252, 255, 257, 259, 263, 265, 266, 269, 274, 280, 284, 285, 287, 292, 295-298, 300, 301, 303, 310, 311, 313, 315, 316, 320, 322, 325, 326, 328, 329, 332, 333, 335, 338, 341, 346, 347, 357, 364, 370, 371, 373, 375-377, 380, 385, 387-391, 396, 401, 407-411, 415, 416, 419, 424, 426, 427, 434, 448, 449, 455, 456, or 458 of SEQ ID NO:4; and, optionally, one or more of:
- (a) a polypeptide capable of glycosylating steviol or a steviol glycoside at its C-13 hydroxyl group, comprising a polypeptide having at least 55% sequence identity to the amino acid sequence set forth in SEQ ID NO:7;
- (b) the polypeptide capable of beta 1,3 glycosylation of the C3' of the 13-O-glucose, 19-O-glucose, or both 13-O-glucose and 19-O-glucose of a steviol glycoside, comprising a polypeptide having at least 50% sequence identity to the amino acid sequence set forth in SEQ ID NO:9;

(c) the polypeptide capable of beta 1,2 glycosylation of the C2' of the 13-O-glucose, 19-O-glucose, or both 13-O-glucose and 19-O-glucose of a steviol glycoside, comprising a polypeptide having at least 80% sequence identity to the amino acid sequence set forth in SEQ ID NO:11, a polypeptide having at least 80% sequence identity to the amino acid sequence set forth in SEQ ID NO:13; or a polypeptide having at least 65% sequence identity to the amino acid sequence set forth in SEQ ID NO:16;

and a plant-derived or synthetic steviol, steviol precursors, and/or steviol glycosides to a reaction mixture;

wherein at least one of the polypeptide is a recombinant polypeptide; and producing the one or more steviol glycosides or glycosides of the steviol precursor thereby.

In one aspect of the methods disclosed herein, the polypeptide capable of glycosylating steviol or a steviol glycoside at its C-19 carboxyl group comprises at least one amino acid substitution of SEQ ID NO:4 that is L15V, I16L, F18Y, L20A, F27M, I28L, F30L, G31S, G31A, T49I, N51K, Q67E, A68T, C73F, E75D, M79A, E83D, E83K, S84A, L86I, E87D, T88R, K90W, Q91E, S96T, D99E, E107S, T110P, I111V, A113C, I115V, M119F, T120L, E121P, V123A, I128K, E129Q, G135A, S136A, Q140N, A141S, V143A, S146N, L147I, I156L, E162T, V166L, F169L, Q173E, E176D, L179S, I180F, L181V, N183D, H184P, E185G, Q186S, I187Y, Q188P, S189A, W191F, S192D, Q193M, M194V, L195V, A200S, Q204K, F209L, N211H, S212T, K215E, I221V, E222D, T224M, V232T, L237I, D247E, N252Y, N255S, Y257F, A259P, E263A, M265I, N266K, N266E, D269N, E274G, A280S, L284M, V285A, H287L, V292M, I295L, I295M, T296A, R297W, A298G, I300K, D301N, D303N, I310V, K311R, K313S, E315Q, G316A, E320K, L322F, V325E, I326T, T328S, G329E, L332I, I333V, A335S, K338P, D341E, E346P, E346K, S347A, F357W, I364L, V370M, V371I, M373V, Q375L, F376W, S377T, T380S, L385F, D387E, E388D, I389V, L390W, G391K, V396A, N401K, G407E, N408E, L409I, A410E, S411D, M415E, I416V, E419G, I424E, R426K, K427E, D434E, N448K, D449N, S455A, E456K, or I458V.

In one aspect of the methods disclosed herein, the reaction mixture comprises:

(a) one or more steviol glycosides or glycosides of the steviol precursor;
(b) a UGT polypeptide;
(c) uridine diphosphate (UDP)-glucose, UDP-rhamnose, UDP-xylose, and/or N-acetyl-glucosamine; and/or
(d) reaction buffer and/or salts.

In one aspect of the methods disclosed herein, the one or more steviol glycosides or glycosides of the steviol precursor comprises 19-KMG, 13-SMG, steviol-1,2-Bioside, steviol-1,3-Bioside, 19-SMG, 1,2-Stevioside, RebG, rubusoside, RebA, RebB, RebC, RebD, RebE, RebF, RebM, RebQ, RebI, dulcoside A, a mono-glycosylated ent-kaurenoic acid, a di-glycosylated ent-kaurenoic acid, a tri-glycosylated ent-kaurenoic acid, a mono-glycosylated ent-kaurenols, a di-glycosylated ent-kaurenol, a tri-glycosylated ent-kaurenol, a tri-glycosylated steviol glycoside, a tetra-glycosylated steviol glycoside, a penta-glycosylated steviol glycoside, a hexa-glycosylated steviol glycoside, a hepta-glycosylated steviol glycoside, and/or an isomer thereof.

The invention also provides a cell culture, comprising the recombinant host cells disclosed herein, the cell culture further comprising:

(a) the one or more steviol glycosides or glycosides of the steviol precursor produced by the recombinant host cell;
(b) glucose, fructose, sucrose, xylose, rhamnose, UDP-glucose, UDP-rhamnose, UDP-xylose, and/or N-acetyl-glucosamine; and
(c) supplemental nutrients comprising trace metals, vitamins, salts, YNB, and/or amino acids;

wherein the one or more steviol glycosides or glycosides of the steviol precursor are present at a concentration of at least 1 mg/liter of the cell culture;

wherein the cell culture is enriched for the one or more steviol glycosides or glycosides of the steviol precursor relative to a steviol glycoside composition from a Stevia plant and has a reduced level of Stevia plant-derived components relative to a plant-derived Stevia extract.

The invention also provides a cell lysate from the recombinant host cells disclosed herein grown in the cell culture, comprising:

(a) the one or more steviol glycosides or glycosides of the steviol precursor produced by the recombinant host cell;
(b) glucose, fructose, sucrose, xylose, rhamnose, UDP-glucose, UDP-rhamnose, UDP-xylose, and/or N-acetyl-glucosamine; and/or
(c) supplemental nutrients comprising trace metals, vitamins, salts, yeast nitrogen base, YNB, and/or amino acids;

wherein the one or more steviol glycosides or glycosides of the steviol precursor produced by the recombinant host cell is present at a concentration of at least 1 mg/liter of the cell culture.

The invention also provides one or more steviol glycosides or glycosides of the steviol precursor produced by the recombinant host cells disclosed herein; wherein the one or more steviol glycosides or glycosides of the steviol precursor produced by the recombinant host cell are present in relative amounts that are different from a steviol glycoside composition from a Stevia plant and have a reduced level of Stevia plant-derived components relative to a plant-derived Stevia extract.

The invention also provides one or more steviol glycosides or glycosides of the steviol precursor produced by the methods disclosed herein; wherein the one or more steviol glycosides or glycosides of the steviol precursor produced by the recombinant host cell are present in relative amounts that are different from a steviol glycoside composition from a Stevia plant and have a reduced level of Stevia plant-derived components relative to a plant-derived Stevia extract.

The invention also provides sweetener compositions, comprising the one or more steviol glycosides or glycosides of the steviol precursor produced by the recombinant host cell or the methods disclosed herein.

The invention also provides a food product, comprising the sweetener compositions disclosed herein.

The invention also provides a beverage or a beverage concentrate, comprising the sweetener compositions disclosed herein.

The invention also provides an isolated nucleic acid molecule encoding a polypeptide or a catalytically active portion thereof capable of glycosylating steviol or a steviol glycoside at its C-19 carboxyl group, wherein the encoded polypeptide or the catalytically active portion thereof comprises a polypeptide having at least 80% sequence identity to the amino acid sequence set forth in SEQ ID NO:4 and having one or more amino acid substitutions of residues 15, 16, 18, 20, 27, 28, 30, 31, 49, 51, 67, 68, 73, 75, 79, 81, 83, 84, 86-88, 90, 91, 96, 99, 107, 110, 111, 113, 115, 119-121, 123, 128, 129, 135, 136, 140, 141, 143, 146, 147, 156, 162, 166, 169, 173, 176, 179-181, 183-189, 191-195, 200, 204, 209, 211, 212, 215, 221, 222, 224, 232, 237, 247, 252, 255, 257, 259, 263, 265, 266, 269, 274, 280, 284, 285, 287, 292, 295-298, 300, 301, 303, 310, 311, 313, 315, 316, 320, 322, 325, 326, 328, 329, 332, 333, 335, 338, 341, 346, 347, 357, 364, 370, 371, 373, 375-377, 380, 385, 387-391, 396, 401, 407-411, 415, 416, 419, 424, 426, 427, 434, 448, 449, 455, 456, or 458 of SEQ ID NO:4.

The invention also provides an isolated nucleic acid molecule encoding a polypeptide or a catalytically active portion thereof capable of glycosylating steviol or a steviol glycoside at its C-19 carboxyl group, wherein the encoded polypeptide or the catalytically active portion thereof comprises a polypeptide having at least 80% sequence identity to the amino acid sequence set forth in SEQ ID NO:4 and having at least one amino acid substitution of SEQ ID NO:4 that is L15V, I16L, F18Y, L20A, F27M, I28L, F30L, G31S, G31A, T49I, N51K, Q67E, A68T, C73F, E75D, M79A, E83D, E83K, S84A, L86I, E87D, T88R, K90W, Q91E, S96T, D99E, E107S, T110P, I111V, A113C, I115V, M119F, T120L, E121P, V123A, I128K, E129Q, G135A, S136A, Q140N, A141S, V143A, S146N, L147I, I156L, E162T, V166L, F169L, Q173E, E176D, L179S, I180F, L181V, N183D, H184P, E185G, Q186S, I187Y, Q188P, S189A, W191F, S192D, Q193M, M194V, L195V, A200S, Q204K, F209L, N211H, S212T, K215E, I221V, E222D, T224M, V232T, L237I, D247E, N252Y, N255S, Y257F, A259P, E263A, M265I, N266K, N266E, D269N, E274G, A280S, L284M, V285A, H287L, V292M, I295L, 1295M, T296A, R297W, A298G, I300K, D301N, D303N, I310V, K311R, K313S, E315Q, G316A, E320K, L322F, V325E, I326T, T328S, G329E, L332I, I333V, A335S, K338P, D341E, E346P, E346K, S347A, F357W, I364L, V370M, V371I, M373V, Q375L, F376W, S377T, T380S, L385F, D387E, E388D, I389V, L390W, G391K, V396A, N401K, G407E, N408E, L409I, A410E, S411D, M415E, I416V, E419G, I424E, R426K, K427E, D434E, N448K, D449N, S455A, E456K, or I458V.

In one aspect of the polypeptides or the catalytically active portions thereof, wherein the polypeptide or the catalytically active portion thereof is a purified polypeptide or a catalytically active portion thereof.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
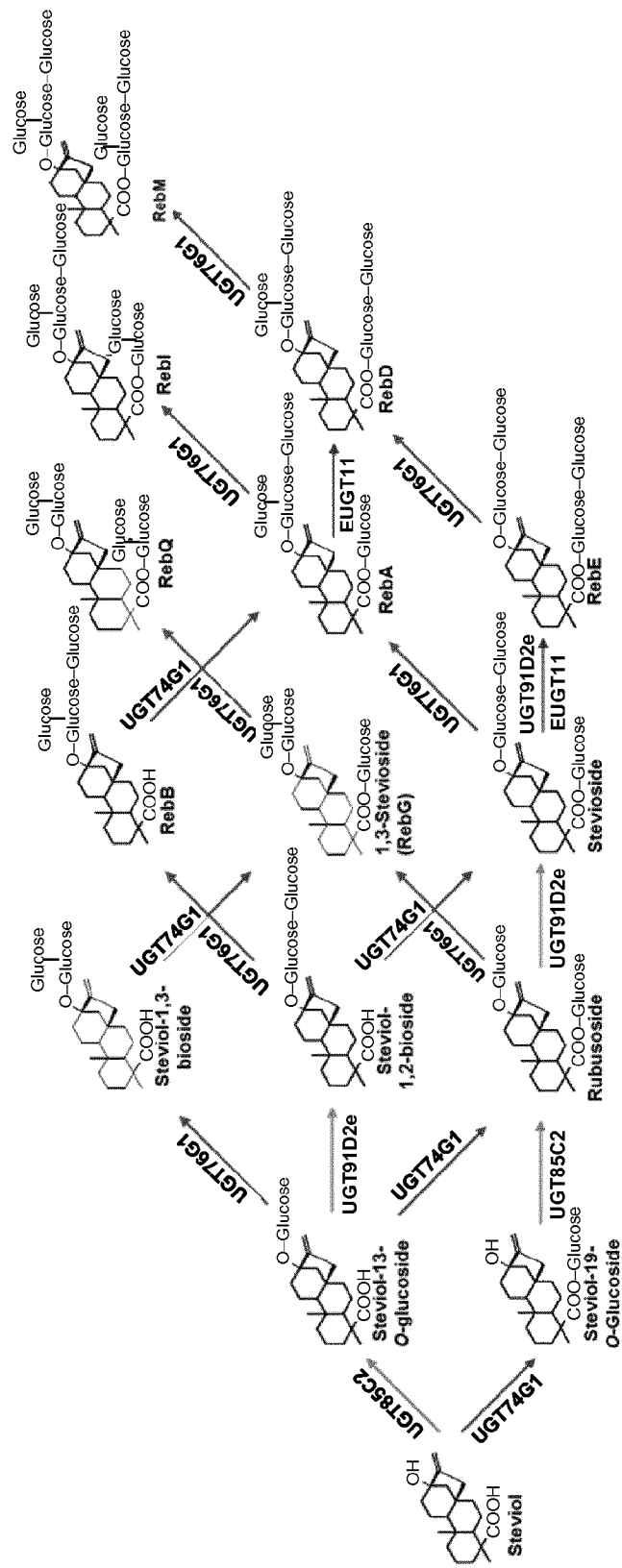
FIG. 1 shows representative primary steviol glycoside glycosylation reactions catalyzed by suitable UGT enzymes and chemical structures for several steviol glycoside compounds.

Skilled artisans will appreciate that elements in the Figures are illustrated for simplicity and clarity and have not necessarily been drawn to scale. For example, the dimensions of some of the elements in the Figures can be exaggerated relative to other elements to help improve understanding of the embodiment(s) of the present invention.

DETAILED DESCRIPTION OF THE INVENTION

All publications, patents and patent applications cited herein are hereby expressly incorporated by reference for all purposes.

Before describing the present invention in detail, a number of terms will be defined. As used herein, the singular forms "a," "an," and "the" include plural referents unless the context clearly dictates otherwise. For example, reference to a "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Green & Sambrook, 2012, MOLECULAR CLONING: A LABORATORY MANUAL, Fourth Edition, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

As used herein, the terms "polynucleotide," "nucleotide," "oligonucleotide," and "nucleic acid" can be used interchangeably to refer to nucleic acid comprising DNA, RNA, derivatives thereof, or combinations thereof, in either single-stranded or double-stranded embodiments depending on context as understood by the skilled worker.

As used herein, the terms "microorganism," "microorganism host," "microorganism host cell," "recombinant host," and "recombinant host cell" can be used interchangeably. As used herein, the term "recombinant host" is intended to refer to a host, the genome of which has been augmented by at least one DNA sequence. Such DNA sequences include but are not limited to genes that are not naturally present, DNA sequences that are not normally transcribed into RNA or translated into a protein ("expressed"), and other genes or DNA sequences which one desires to introduce into a host. It will be appreciated that typically the genome of a recombinant host described herein is augmented through stable introduction of one or more recombinant genes. Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "cell culture" refers to a culture medium comprising one or more recombinant hosts. A cell culture may comprise a single strain of recombinant host, or may comprise two or more distinct host strains. The culture medium may be any medium that may comprise a recombinant host, e.g., a liquid medium (i.e., a culture broth) or a semi-solid medium, and may comprise additional components, e.g., UDP-glucose, UDP-rhamnose, UDP-xylose, N-acetyl-glucosamine, glucose, fructose, sucrose, trace metals, vitamins, salts, yeast nitrogen base (YNB), etc.

As used herein, the term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene can be a DNA sequence from another species or can be a DNA sequence that originated from or is present in the same species but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. In some aspects, said recombinant genes are encoded by cDNA. In other embodiments, recombinant genes are synthetic and/or codon-optimized for expression in S. cerevisiae.

As used herein, the term "engineered biosynthetic pathway" refers to a biosynthetic pathway that occurs in a recombinant host, as described herein. In some aspects, one or more steps of the biosynthetic pathway do not naturally occur in an unmodified host. In some embodiments, a heterologous version of a gene is introduced into a host that comprises an endogenous version of the gene.

As used herein, the term "endogenous" gene refers to a gene that originates from and is produced or synthesized within a particular organism, tissue, or cell. In some embodiments, the endogenous gene is a yeast gene. In some embodiments, the gene is endogenous to S. cerevisiae, including, but not limited to S. cerevisiae strain S288C. In some embodiments, an endogenous yeast gene is overexpressed. As used herein, the term "overexpress" is used to refer to the expression of a gene in an organism at levels higher than the level of gene expression in a wild type organism. See, e.g., Prelich, 2012, Genetics 190:841-54. In some embodiments, an endogenous yeast gene is deleted. See, e.g., Giaever & Nislow, 2014, Genetics 197(2):451-65. As used herein, the terms "deletion," "deleted," "knockout," and "knocked out" can be used interchangeably to refer to an endogenous gene that has been manipulated to no longer be expressed in an organism, including, but not limited to, S. cerevisiae.

As used herein, the terms "heterologous sequence" and "heterologous coding sequence" are used to describe a sequence derived from a species other than the recombinant host. In some embodiments, the recombinant host is an S. cerevisiae cell, and a heterologous sequence is derived from an organism other than S. cerevisiae. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

As used herein, the terms "heterologous sequence" and "heterologous coding sequence" are used to describe a sequence derived from a species other than the recombinant host. In some embodiments, the recombinant host is an S. cerevisiae cell, and a heterologous sequence is derived from an organism other than *S. cerevisiae*. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

As used herein, the term "constitutive," "constitutive expression," or "constitutively expressed" refers to a continuous transcription of a gene resulting in the continuous expression of a protein.

As used herein, the term "inducible," "inducible expression," or "inducibly expressed" refers to the expression of a gene in response to a stumuli. Stimuli include, but are not limited to, chemicals, stress, or biotic stimuli.

A "selectable marker" can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, PCR or Southern blot analysis. Subsequent to its use in selection, a selectable marker can be removed from the genome of the host cell by, e.g., Cre-LoxP systems (see, e.g., Gossen et al., 2002, *Ann. Rev. Genetics* 36:153-173 and U.S. 2006/0014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

As used herein, the terms "variant" and "mutant" are used to describe a protein sequence that has been modified at one or more amino acids, compared to the wild-type sequence of a particular protein.

As used herein, the term "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of a gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene with inactivation thereof.

As used herein, the term "steviol glycoside" refers to Rebaudioside A (RebA) (CAS #58543-16-1), Rebaudioside B (RebB) (CAS #58543-17-2), Rebaudioside C (RebC) (CAS #63550-99-2), Rebaudioside D (RebD) (CAS #63279-13-0), Rebaudioside E (RebE) (CAS #63279-14-1), Rebaudioside F (RebF) (CAS #438045-89-7), Rebaudioside M (RebM) (CAS #1220616-44-3), rubusoside (CAS #63849-39-4), Dulcoside A (CAS #64432-06-0), Rebaudioside I (RebI) (MassBank Record: FU000332), Rebaudioside Q (RebQ), 1,2-Stevioside (CAS #57817-89-7), 1,3-Stevioside (RebG), Steviol-1,2-Bioside (MassBank Record: FU000299), Steviol-1,3-Bioside, Steviol-13-O-glucoside (13-SMG), Steviol-19-O-glucoside (19-SMG), a tri-glycosylated steviol glycoside, a tetra-glycosylated steviol glycoside, a penta-glycosylated steviol glycoside, a hexa-glycosylated steviol glycoside, a hepta-glycosylated steviol glycoside, and isomers thereof. See FIG. 1; see also, Steviol Glycosides Chemical and Technical Assessment 69th JECFA, 2007, prepared by Harriet Wallin, Food Agric. Org.

Figure 2:
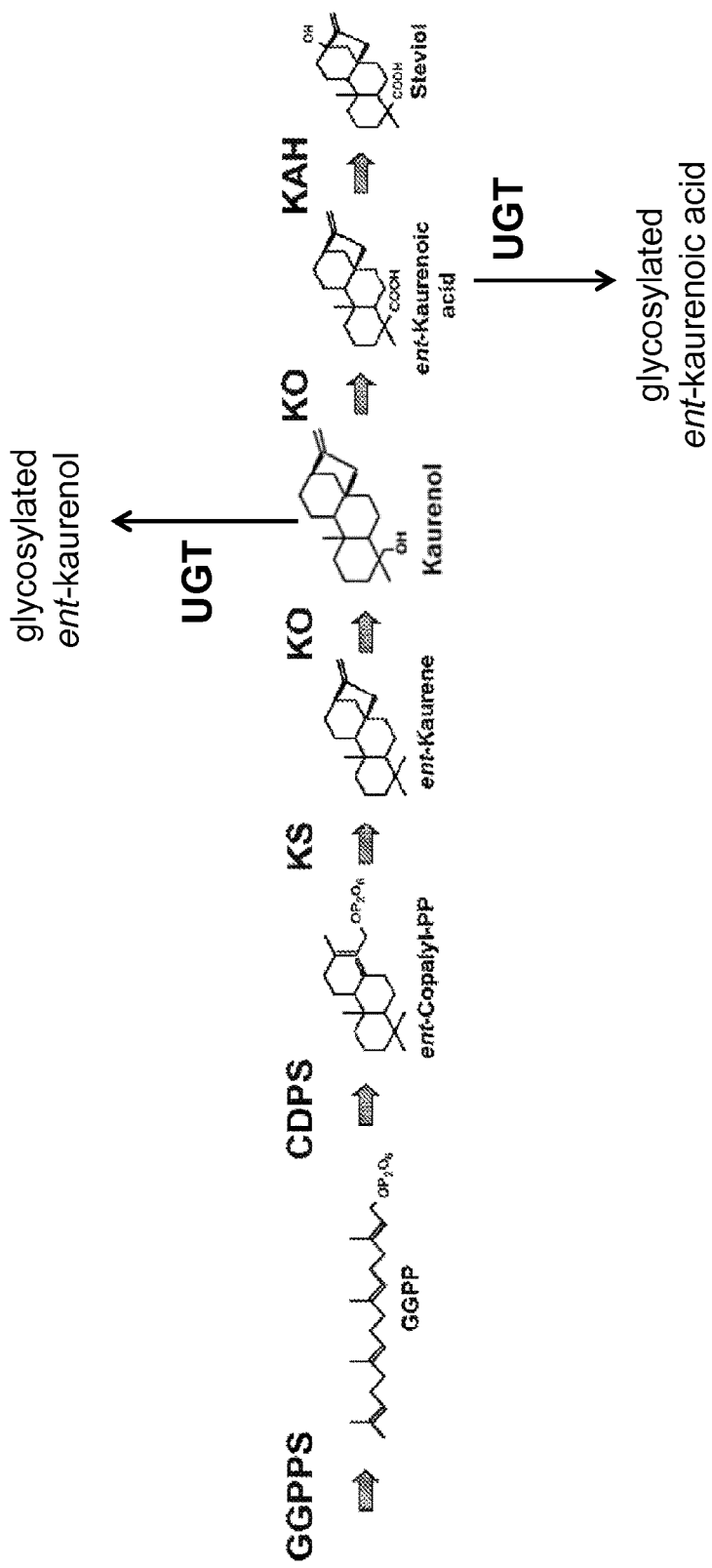
FIG. 2 shows the biochemical pathway for the production of steviol, glycosylated ent-kaurenoic acid, and glycosylated ent-kaurenol from prenyl phosphates.

As used herein, the terms "steviol glycoside precursor" and "steviol glycoside precursor compound" are used to refer to intermediate compounds in the steviol glycoside biosynthetic pathway. Steviol glycoside precursors include, but are not limited to, geranylgeranyl diphosphate (GGPP), ent-copalyl-diphosphate, ent-kaurene, ent-kaurenol, ent-kaurenal, ent-kaurenoic acid, and steviol. See FIG. 2. Also as used herein, the terms "steviol precursor" and "steviol precursor compound" are used to refer to intermediate compounds in the steviol biosynthetic pathway. Steviol precursors may also be steviol glycoside precursors, and include, but are not limited to, geranylgeranyl diphosphate (GGPP), ent-copalyl-diphosphate, ent-kaurene, ent-kaurenol, ent-kaurenal, and ent-kaurenoic acid. Also as used herein, the terms "steviol precursor" and "steviol precursor compound" are used to refer to intermediate compounds in the steviol biosynthetic pathway.

Also as used herein, the term "glycosides of a steviol precursor" is used to refer to steviol precursors that can be glycosylated, e.g., tri-glycosylated ent-kaurenoic acid (ent-kaurenoic acid+3Glc), di-glycosylated ent-kaurenoic acid, mono-glycosylated ent-kaurenoic acid, tri-glycosylated ent-kaurenol, di-glycosylated ent-kaurenol (ent-kaurenol+2Glc), or mono-glycosylated ent-kaurenol (ent-kaurenol+1Glc; e.g., kaurenoate-19-O-glucoside or 19-KMG). In some embodiments, steviol glycoside precursors are themselves steviol glycoside compounds. For example, 19-SMG, rubusoside, stevioside, and RebE are steviol glycoside precursors of RebM. See FIG. 1.

As used herein, the term "contact" is used to refer to any physical interaction between two objects. For example, the term "contact" may refer to the interaction between an enzyme and a substrate. In another example, the term "contact" may refer to the interaction between a liquid (e.g., a supernatant) and an adsorbent resin.

Steviol precursors may also be steviol glycoside precursors, and include, but are not limited to, geranylgeranyl diphosphate (GGPP), ent-copalyl-diphosphate, ent-kaurene, ent-kaurenol, ent-kaurenal, and ent-kaurenoic acid. Steviol glycosides and/or steviol glycoside precursors, or glycosides of a steviol precursor can be produced in vivo (i.e., in a recombinant host), in vitro (i.e., enzymatically), or by whole cell bioconversion.

As used herein, the terms "produce" and "accumulate" can be used interchangeably to describe synthesis of steviol glycosides and steviol glycoside precursors in vivo, in vitro, or by whole cell bioconversion.

As used herein, the terms "culture broth," "culture medium," and "growth medium" can be used interchangeably to refer to a liquid or solid that supports growth of a cell. A culture broth can comprise glucose, fructose, sucrose, trace metals, vitamins, salts, yeast nitrogen base (YNB), and/or amino acids. The trace metals can be divalent cations, including, but not limited to, $Mn^{2+}$ and/or $Mg^{2+}$. In some embodiments, $Mn^{2+}$ can be in the form of $MnCl_2$ dihydrate and range from approximately 0.01 g/L to 100 g/L. In some embodiments, $Mg^{2+}$ can be in the form of $MgSO_4$ heptahydrate and range from approximately 0.01 g/L to 100 g/L. For example, a culture broth can comprise i) approximately 0.02-0.03 g/L $MnCl_2$ dihydrate and approximately 0.5-3.8 g/L $MgSO_4$ heptahydrate, ii) approximately 0.03-0.06 g/L $MnCl_2$ dihydrate and approximately 0.5-3.8 g/L $MgSO_4$ heptahydrate, and/or iii) approximately 0.03-0.17 g/L MnCl$_2$ dihydrate and approximately 0.5-7.3 g/L MgSO$_4$ heptahydrate. Additionally, a culture broth can comprise one or more steviol glycosides produced by a recombinant host, as described herein.

Recombinant steviol glycoside-producing *Saccharomyces cerevisiae* (*S. cerevisiae*) strains are described in WO 2011/153378, WO 2013/022989, WO 2014/122227, and WO 2014/122328, each of which is incorporated by reference in their entirety. Methods of producing steviol glycosides in recombinant hosts, by whole cell bio-conversion, and in vitro are also described in WO 2011/153378, WO 2013/022989, WO 2014/122227, and WO 2014/122328.

In some embodiments, a recombinant host comprising a gene encoding a polypeptide capable of synthesizing geranylgeranyl pyrophosphate (GGPP) from farnesyl diphosphate (FPP) and isopentenyl diphosphate (IPP) (e.g., a geranylgeranyl diphosphate synthase (GGPPS) polypeptide); a gene encoding a polypeptide capable of synthesizing ent-copalyl diphosphate from GGPP (e.g., a ent-copalyl diphosphate synthase (CDPS) polypeptide); a gene encoding a polypeptide capable of synthesizing ent-kaurene from ent-copalyl diphosphate (e.g., a kaurene synthase (KS) polypeptide); a gene encoding a polypeptide capable of synthesizing ent-kaurenoic acid, ent-kaurenol, and/or ent-kaurenal from ent-kaurene (e.g., a kaurene oxidase (KO) polypeptide); a gene encoding a polypeptide capable of reducing cytochrome P450 complex (e.g., a cytochrome P450 reductase (CPR) polypeptide or a P450 oxidoreductase (POR) polypeptide; for example, but not limited to a polypeptide capable of capable of reducing cytochrome P450 complex (e.g., an electron transfer from NADPH to cytochrome P450 complex during conversion of NADPH to NADP$^+$), which is utilized as a cofactor for terpenoid biosynthesis); a gene encoding a polypeptide capable of synthesizing steviol from ent-kaurenoic acid (e.g., a steviol synthase (KAH) polypeptide); and/or a gene encoding a bifunctional polypeptide capable of synthesizing ent-copalyl diphosphate from GGPP and synthesizing ent-kaurene from ent-copalyl diphosphate (e.g., an ent-copalyl diphosphate synthase (CDPS)-ent-kaurene synthase (KS) polypeptide) can produce steviol in vivo. See, e.g., FIG. 1. The skilled worker will appreciate that one or more of these genes can be endogenous to the host provided that at least one (and in some embodiments, all) of these genes is a recombinant gene introduced into the recombinant host.

In some embodiments, a recombinant host comprising a gene encoding a polypeptide capable of glycosylating steviol or a steviol glycoside at its C-13 hydroxyl group (e.g., a UGT85C2 polypeptide); a gene encoding a polypeptide capable of beta 1,3 glycosylation of the C3' of the 13-O-glucose, 19-O-glucose, or both 13-O-glucose and 19-O-glucose of a steviol glycoside (e.g., a UGT76G1 polypeptide); a gene encoding a polypeptide capable of glycosylating steviol or a steviol glycoside at its C-19 carboxyl group (e.g., a UGT74G1 polypeptide); and/or a gene encoding a polypeptide capable of beta 1,2 glycosylation of the C2' of the 13-O-glucose, 19-O-glucose, or both 13-O-glucose and 19-O-glucose of a steviol glycoside (e.g., a UGT91D2 or a EUGT11 polypeptide) can produce a steviol glycoside in vivo. The skilled worker will appreciate that one or more of these genes can be endogenous to the host provided that at least one (and in some embodiments, all) of these genes is a recombinant gene introduced into the recombinant host.

In some embodiments, steviol glycosides and/or steviol glycoside precursors are produced in vivo through expression of one or more enzymes involved in the steviol glycoside biosynthetic pathway in a recombinant host. For example, a recombinant host comprising a gene encoding a polypeptide capable of synthesizing GGPP from FPP and IPP; a gene encoding a polypeptide capable of synthesizing ent-copalyl diphosphate from GGPP; a gene encoding a polypeptide capable of synthesizing ent-kaurene from ent-copalyl diphosphate; a gene encoding a polypeptide capable of synthesizing ent-kaurenoic acid, ent-kaurenol, and/or ent-kaurenal from ent-kaurene; a gene encoding a polypeptide capable of reducing cytochrome P450 complex; a gene encoding a bifunctional polypeptide capable of synthesizing ent-copalyl diphosphate from GGPP and synthesizing ent-kaurene from ent-copalyl diphosphate; a gene encoding a polypeptide capable of glycosylating steviol or a steviol glycoside at its C-13 hydroxyl group; a gene encoding a polypeptide capable of beta 1,3 glycosylation of the C3' of the 13-O-glucose, 19-O-glucose, or both 13-O-glucose and 19-O-glucose of a steviol glycoside; a gene encoding a polypeptide capable of glycosylating steviol or a steviol glycoside at its C-19 carboxyl group; and/or a gene encoding a polypeptide capable of beta 1,2 glycosylation of the C2' of the 13-O-glucose, 19-O-glucose, or both 13-O-glucose and 19-O-glucose of a steviol glycoside can produce a steviol glycoside and/or steviol glycoside precursors in vivo. See, e.g., FIGS. 1 and 2. The skilled worker will appreciate that one or more of these genes can be endogenous to the host provided that at least one (and in some embodiments, all) of these genes is a recombinant gene introduced into the recombinant host.

In some embodiments, a steviol-producing recombinant microorganism comprises heterologous nucleic acids encoding a polypeptide capable of glycosylating steviol or a steviol glycoside at its C-13 hydroxyl group; a polypeptide capable of beta 1,3 glycosylation of the C3' of the 13-O-glucose, 19-O-glucose, or both 13-O-glucose and 19-O-glucose of a steviol glycoside; a polypeptide capable of glycosylating steviol or a steviol glycoside at its C-19 carboxyl group; and a polypeptide capable of beta 1,2 glycosylation of the C2' of the 13-O-glucose, 19-O-glucose, or both 13-O-glucose and 19-O-glucose of a steviol glycoside.

In some embodiments, a steviol-producing recombinant microorganism comprises heterologous nucleic acids encoding a polypeptide capable of glycosylating steviol or a steviol glycoside at its C-13 hydroxyl group, a polypeptide capable of beta 1,3 glycosylation of the C3' of the 13-O-glucose, 19-O-glucose, or both 13-O-glucose and 19-O-glucose of a steviol glycoside, and a polypeptide capable of beta 1,2 glycosylation of the C2' of the 13-O-glucose, 19-O-glucose, or both 13-O-glucose and 19-O-glucose of a steviol glycoside.

In some aspects, a polypeptide capable of glycosylating steviol or a steviol glycoside at its C-13 hydroxyl group, a polypeptide capable of beta 1,3 glycosylation of the C3' of the 13-0-glucose, 19-O-glucose, or both 13-O-glucose and 19-O-glucose of a steviol glycoside, a polypeptide capable of glycosylating steviol or a steviol glycoside at its C-19 carboxyl group, and/or a polypeptide capable of beta 1,2 glycosylation of the C2' of the 13-O-glucose, 19-O-glucose, or both 13-O-glucose and 19-O-glucose of a steviol glycoside, transfers a glucose molecule from uridine diphosphate glucose (UDP-glucose) to steviol and/or a steviol glycoside.

In some aspects, the polypeptide capable of synthesizing geranylgeranyl pyrophosphate (GGPP) from farnesyl diphosphate (FPP) and isopentenyl diphosphate (IPP) comprises a polypeptide having the amino acid sequence set forth in SEQ ID NO:20 (which can be encoded by the nucleotide sequence set forth in SEQ ID NO:19), SEQ ID NO:22 (encoded by the nucleotide sequence set forth in SEQ ID NO:21), SEQ ID NO:24 (encoded by the nucleotide sequence set forth in SEQ ID NO:23), SEQ ID NO:26 (encoded by the nucleotide sequence set forth in SEQ ID NO:25), SEQ ID NO:28 (encoded by the nucleotide sequence set forth in SEQ ID NO:27), SEQ ID NO:30 (encoded by the nucleotide sequence set forth in SEQ ID NO:29), SEQ ID NO:32 (encoded by the nucleotide sequence set forth in SEQ ID NO:31), or SEQ ID NO:116 (which can be encoded by the nucleotide sequence set forth in SEQ ID NO:115).

In some aspects, the polypeptide capable of synthesizing ent-copalyl diphosphate from GGPP comprises a polypeptide having an amino acid sequence set forth in SEQ ID NO:34 (which can be encoded by the nucleotide sequence set forth in SEQ ID NO:33), SEQ ID NO:36 (encoded by the nucleotide sequence set forth in SEQ ID NO:35), SEQ ID NO:38 (encoded by the nucleotide sequence set forth in SEQ ID NO:37), SEQ ID NO:40 (encoded by the nucleotide sequence set forth in SEQ ID NO:39), or SEQ ID NO:42 (encoded by the nucleotide sequence set forth in SEQ ID NO:41). In some embodiments, the polypeptide capable of synthesizing ent-copalyl diphosphate from GGPP lacks a chloroplast transit peptide. For example, the polypeptide capable of synthesizing ent-copalyl diphosphate from GGPP lacking a chloroplast transit polypeptide can comprise a polypeptide having an amino acid sequence set forth in SEQ ID NO:120 (encoded by the nucleotide sequence set forth in SEQ ID NO:119).

In some aspects, the polypeptide capable of synthesizing ent-kaurene from ent-copalyl pyrophosphate comprises a polypeptide having an amino acid sequence set forth in SEQ ID NO:44 (which can be encoded by the nucleotide sequence set forth in SEQ ID NO:43), SEQ ID NO:46 (encoded by the nucleotide sequence set forth in SEQ ID NO:45), SEQ ID NO:48 (encoded by the nucleotide sequence set forth in SEQ ID NO:47), SEQ ID NO:50 (encoded by the nucleotide sequence set forth in SEQ ID NO:49), or SEQ ID NO:52 (encoded by the nucleotide sequence set forth in SEQ ID NO:51).

In some aspects, the polypeptide capable of synthesizing ent-kaurenoic acid from ent-kaurene comprises a polypeptide having an amino acid sequence set forth in SEQ ID NO:60 (which can be encoded by the nucleotide sequence set forth in SEQ ID NO:59), SEQ ID NO:62 (encoded by the nucleotide sequence set forth in SEQ ID NO:61), SEQ ID NO:117 (encoded by the nucleotide sequence set forth in SEQ ID NO:63 or SEQ ID NO:64), SEQ ID NO:66 (encoded by the nucleotide sequence set forth in SEQ ID NO:65), SEQ ID NO:68 (encoded by the nucleotide sequence set forth in SEQ ID NO:67), SEQ ID NO:70 (encoded by the nucleotide sequence set forth in SEQ ID NO:69), SEQ ID NO:72 (encoded by the nucleotide sequence set forth in SEQ ID NO:71), SEQ ID NO:74 (encoded by the nucleotide sequence set forth in SEQ ID NO:73), or SEQ ID NO:76 (encoded by the nucleotide sequence set forth in SEQ ID NO:75).

In some aspects, the polypeptide capable of reducing cytochrome P450 complex comprises a polypeptide having an amino acid sequence set forth in SEQ ID NO:78 (which can be encoded by the nucleotide sequence set forth in SEQ ID NO:77), SEQ ID NO:80 (encoded by the nucleotide sequence set forth in SEQ ID NO:79), SEQ ID NO:82 (encoded by the nucleotide sequence set forth in SEQ ID NO:81), SEQ ID NO:84 (encoded by the nucleotide sequence set forth in SEQ ID NO:83), SEQ ID NO:86 (encoded by the nucleotide sequence set forth in SEQ ID NO:85), SEQ ID NO:88 (encoded by the nucleotide sequence set forth in SEQ ID NO:87), SEQ ID NO:90 (encoded by the nucleotide sequence set forth in SEQ ID NO:89), or SEQ ID NO:92 (encoded by the nucleotide sequence set forth in SEQ ID NO:91).

In some aspects, the polypeptide capable of synthesizing steviol from ent-kaurenoic acid comprises a polypeptide having an amino acid sequence set forth in SEQ ID NO:94 (which can be encoded by the nucleotide sequence set forth in SEQ ID NO:93), SEQ ID NO:97 (encoded by the nucleotide sequence set forth in SEQ ID NO:95 or SEQ ID NO:96), SEQ ID NO:100 (encoded by the nucleotide sequence set forth in SEQ ID NO:98 or SEQ ID NO:99), SEQ ID NO:101, SEQ ID NO:102, SEQ ID NO:103, SEQ ID NO:104, SEQ ID NO:106 (encoded by the nucleotide sequence set forth in SEQ ID NO:105), SEQ ID NO:108 (encoded by the nucleotide sequence set forth in SEQ ID NO:107), SEQ ID NO:110 (encoded by the nucleotide sequence set forth in SEQ ID NO:109), SEQ ID NO:112 (encoded by the nucleotide sequence set forth in SEQ ID NO:111), or SEQ ID NO:114 (encoded by the nucleotide sequence set forth in SEQ ID NO:113).

In some embodiments, a recombinant host comprises a nucleic acid encoding a polypeptide capable of glycosylating steviol or a steviol glycoside at its C-13 hydroxyl group (SEQ ID NO:7), a nucleic acid encoding a polypeptide capable of beta 1,3 glycosylation of the C3' of the 13-O-glucose, 19-O-glucose, or both 13-O-glucose and 19-O-glucose of a steviol glycoside (SEQ ID NO:9), a nucleic acid encoding a polypeptide capable of glycosylating steviol or a steviol glycoside at its C-19 carboxyl group (SEQ ID NO:4), a nucleic acid encoding a polypeptide capable of beta 1,2 glycosylation of the C2' of the 13-O-glucose, 19-O-glucose, or both 13-O-glucose and 19-O-glucose of a steviol glycoside (SEQ ID NO:16, SEQ ID NO:11, SEQ ID NO:13). In some aspects, the polypeptide capable of glycosylating steviol or a steviol glycoside at its C-13 hydroxyl group is encoded by the nucleotide sequence set forth in SEQ ID NO:5 or SEQ ID NO:6, the polypeptide capable of beta 1,3 glycosylation of the C3' of the 13-O-glucose, 19-O-glucose, or both 13-O-glucose and 19-O-glucose of a steviol glycoside is encoded by the nucleotide sequence set forth in SEQ ID NO:8, the polypeptide capable of glycosylating steviol or a steviol glycoside at its C-19 carboxyl group is encoded by the nucleotide sequence set forth in SEQ ID NO:118 or SEQ ID NO:3, the polypeptide capable of beta 1,2 glycosylation of the C2' of the 13-O-glucose, 19-O-glucose, or both 13-O-glucose and 19-O-glucose of a steviol glycoside is encoded by the nucleotide sequence set forth in any one of SEQ ID NOs:10, 12, 14, or 15.

In certain embodiments, the steviol glycoside produced is RebA, RebB, RebD, and/or RebM. RebA can be synthesized in a steviol-producing recombinant microorganism expressing a polypeptide capable of glycosylating steviol or a steviol glycoside at its C-13 hydroxyl group; a polypeptide capable of beta 1,3 glycosylation of the C3' of the 13-O-glucose, 19-O-glucose, or both 13-O-glucose and 19-O-glucose of a steviol glycoside; a polypeptide capable of glycosylating steviol or a steviol glycoside at its C-19 carboxyl group; and a polypeptide capable of beta 1,2 glycosylation of the C2' of the 13-O-glucose, 19-O-glucose, or both 13-O-glucose and 19-O-glucose of a steviol glycoside. RebB can be synthesized in a steviol-producing recombinant microorganism expressing a polypeptide capable of glycosylating steviol or a steviol glycoside at its C-13 hydroxyl group; a polypeptide capable of beta 1,3 glycosylation of the C3' of the 13-O-glucose, 19-O-glucose, or both 13-O-glucose and 19-O-glucose of a steviol glycoside; and a polypeptide capable of beta 1,2 glycosylation of the C2' of the 13-O-glucose, 19-O-glucose, or both 13-O-glucose and 19-O-glucose of a steviol glycoside. RebD can be synthesized in a steviol-producing recombinant microorganism expressing a polypeptide capable of glycosylating steviol or a steviol glycoside at its C-13 hydroxyl group; a polypeptide capable of beta 1,3 glycosylation of the C3' of the 13-O-glucose, 19-O-glucose, or both 13-O-glucose and 19-O-glucose of a steviol glycoside; a polypeptide capable of glycosylating steviol or a steviol glycoside at its C-19 carboxyl group; and a polypeptide capable of beta 1,2 glycosylation of the C2' of the 13-O-glucose, 19-O-glucose, or both 13-O-glucose and 19-O-glucose of a steviol glycoside. RebM can be synthesized in a steviol-producing recombinant microorganism expressing a polypeptide capable of glycosylating steviol or a steviol glycoside at its C-13 hydroxyl group; a polypeptide capable of beta 1,3 glycosylation of the C3' of the 13-O-glucose, 19-O-glucose, or both 13-O-glucose and 19-O-glucose of a steviol glycoside; a polypeptide capable of glycosylating steviol or a steviol glycoside at its C-19 carboxyl group; and a polypeptide capable of beta 1,2 glycosylation of the C2' of the 13-O-glucose, 19-O-glucose, or both 13-O-glucose and 19-O-glucose of a steviol glycoside (see FIG. 2).

In some embodiments, one or more steviol glycosides or glycosides of a steviol precursor is produced by whole cell bioconversion. For whole cell bioconversion to occur, a host cell expressing one or more enzymes involved in the steviol glycoside pathway takes up and modifies a steviol glycoside precursor in the cell; following modification in vivo, a steviol glycoside remains in the cell and/or is excreted into the culture medium. For example, a host cell expressing a gene encoding a polypeptide capable of glycosylating steviol or a steviol glycoside at its C-13 hydroxyl group; a gene encoding a polypeptide capable of beta 1,3 glycosylation of the C3' of the 13-O-glucose, 19-O-glucose, or both 13-O-glucose and 19-O-glucose of a steviol glycoside; a gene encoding a polypeptide capable of glycosylating steviol or a steviol glycoside at its C-19 carboxyl group; and/or a gene encoding a polypeptide capable of beta 1,2 glycosylation of the C2' of the 13-O-glucose, 19-O-glucose, or both 13-O-glucose and 19-O-glucose of a steviol glycoside can take up steviol and glycosylate steviol in the cell; following glycosylation in vivo, a steviol glycoside can be excreted into the culture medium.

In some embodiments, the method of producing one or more steviol glycosides or glycosides of a steviol precursor disclosed herein comprises whole-cell bioconversion of plant-derived or synthetic steviol and/or steviol glycosides in a cell culture medium of a recombinant host cell using a polypeptide capable of glycosylating steviol or a steviol glycoside at its C-19 carboxyl group having at least 80% sequence identity to the amino acid sequence set forth in SEQ ID NO:4 and having one or more amino acid substitutions of residues 15, 16, 18, 20, 27, 28, 30, 31, 49, 51, 67, 68, 73, 75, 79, 81, 83, 84, 86-88, 90, 91, 96, 99, 107, 110, 111, 113, 115, 119-121, 123, 128, 129, 135, 136, 140, 141, 143, 146, 147, 156, 162, 166, 169, 173, 176, 179-181, 183-189, 191-195, 200, 204, 209, 211, 212, 215, 221, 222, 224, 232, 237, 247, 252, 255, 257, 259, 263, 265, 266, 269, 274, 280, 284, 285, 287, 292, 295-298, 300, 301, 303, 310, 311, 313, 315, 316, 320, 322, 325, 326, 328, 329, 332, 333, 335, 338, 341, 346, 347, 357, 364, 370, 371, 373, 375-377, 380, 385, 387-391, 396, 401, 407-411, 415, 416, 419, 424, 426, 427, 434, 448, 449, 455, 456, or 458 of SEQ ID NO:4; wherein the polypeptides is a recombinant polypeptide; and synthesizing the one or more steviol glycosides or the steviol glycoside composition thereby.

In some embodiments of the methods of producing one or more steviol glycosides or glycosides of a steviol precursor disclosed herein comprises whole-cell bioconversion of plant-derived or synthetic steviol and/or steviol glycosides in a cell culture medium of a recombinant host cell disclosed herein, the polypeptide capable of glycosylating steviol or a steviol glycoside at its C-19 carboxyl group comprises at least one amino acid substitution of SEQ ID NO:4 that is L15V, I16L, F18Y, L20A, F27M, I28L, F30L, G31S, G31A, T49I, N51K, Q67E, A68T, C73F, E75D, M79A, E83D, E83K, S84A, L86I, E87D, T88R, K90W, Q91E, S96T, D99E, E107S, T110P, I111V, A113C, I115V, M119F, T120L, E121P, V123A, I128K, E129Q, G135A, S136A, Q140N, A141S, V143A, S146N, L147I, I156L, E162T, V166L, F169L, Q173E, E176D, L179S, I180F, L181V, N183D, H184P, E185G, Q186S, 1187Y, Q188P, S189A, W191F, S192D, Q193M, M194V, L195V, A200S, Q204K, F209L, N211H, S212T, K215E, I221V, E222D, T224M, V232T, L237I, D247E, N252Y, N255S, Y257F, A259P, E263A, M265I, N266K, N266E, D269N, E274G, A280S, L284M, V285A, H287L, V292M, I295L, 1295M, T296A, R297W, A298G, I300K, D301N, D303N, I310V, K311R, K313S, E315Q, G316A, E320K, L322F, V325E, I326T, T328S, G329E, L332I, I333V, A335S, K338P, D341E, E346P, E346K, S347A, F357W, I364L, V370M, V371I, M373V, Q375L, F376W, S377T, T380S, L385F, D387E, E388D, I389V, L390W, G391K, V396A, N401K, G407E, N408E, L409I, A410E, S411D, M415E, I416V, E419G, I424E, R426K, K427E, D434E, N448K, D449N, S455A, E456K, or I458V.

In some embodiments, the cell is permeabilized to take up a substrate to be modified or to excrete a modified product. In some embodiments, a permeabilizing agent can be added to aid the feedstock entering into the host and product getting out. In some embodiments, the cells are permeabilized with a solvent such as toluene, or with a detergent such as Triton-X or Tween. In some embodiments, the cells are permeabilized with a surfactant, for example a cationic surfactant such as cetyltrimethylammonium bromide (CTAB). In some embodiments, the cells are permeabilized with periodic mechanical shock such as electroporation or a slight osmotic shock. For example, a crude lysate of the cultured microorganism can be centrifuged to obtain a supernatant. The resulting supernatant can then be applied to a chromatography column, e.g., a C18 column, and washed with water to remove hydrophilic compounds, followed by elution of the compound(s) of interest with a solvent such as methanol. The compound(s) can then be further purified by preparative HPLC. See also, WO 2009/140394.

In some embodiments, steviol, one or more steviol glycoside precursors, and/or one or more steviol glycosides are produced by co-culturing of two or more hosts. In some embodiments, one or more hosts, each expressing one or more enzymes involved in the steviol glycoside pathway, produce steviol, one or more steviol glycoside precursors, and/or one or more steviol glycosides. For example, a host expressing a gene encoding a polypeptide capable of synthesizing GGPP from FPP and IPP; a gene encoding a polypeptide capable of synthesizing ent-copalyl diphosphate from GGPP; a gene encoding a polypeptide capable of synthesizing ent-kaurene from ent-copalyl diphosphate; a gene encoding a polypeptide capable of synthesizing ent-kaurenoic acid, ent-kaurenol, and/or ent-kaurenal from ent-kaurene; a gene encoding a polypeptide capable of reducing cytochrome P450 complex; a gene encoding a polypeptide capable of synthesizing steviol from ent-kaurenoic acid; and/or a gene encoding a bifunctional polypeptide capable of synthesizing ent-copalyl diphosphate from GGPP and synthesizing ent-kaurene from ent-copalyl diphosphate and a host expressing a gene encoding a polypeptide capable of glycosylating steviol or a steviol glycoside at its C-13 hydroxyl group; a gene encoding a polypeptide capable of beta 1,3 glycosylation of the C3' of the 13-O-glucose, 19-O-glucose, or both 13-O-glucose and 19-O-glucose of a steviol glycoside; a gene encoding a polypeptide capable of glycosylating steviol or a steviol glycoside at its C-19 carboxyl group; and/or a gene encoding a polypeptide capable of beta 1,2 glycosylation of the C2' of the 13-O-glucose, 19-O-glucose, or both 13-O-glucose and 19-O-glucose of a steviol glycoside, produce one or more steviol glycosides.

In some embodiments, the steviol glycoside comprises, for example, but not limited to, steviol-13-O-glucoside (13-SMG), steviol-19-O-glucoside (19-SMG), steviol-1,2-bioside, steviol-1,3-bioside, 1,2-stevioside, 1,3-stevioside, rubusoside, Rebaudioside A (RebA), Rebaudioside B (RebB), Rebaudioside C (RebC), Rebaudioside D (RebD), Rebaudioside E (RebE), Rebaudioside F (RebF), Rebaudioside M (RebM), Rebaudioside Q (RebQ), Rebaudioside I (RebI), dulcoside A, mono-glycosylated ent-kaurenoic acids, di-glycosylated ent-kaurenoic acids, tri-glycosylated ent-kaurenoic acids, mono-glycosylated ent-kaurenols (e.g., kaurenoate-19-O-glucoside or 19-KMG), di-glycosylated ent-kaurenols, tri-glycosylated ent-kaurenols, tri-glycosylated steviol glycosides, tetra-glycosylated steviol glycosides, penta-glycosylated steviol glycosides, hexa-glycosylated steviol glycosides, hepta-glycosylated steviol glycosides, or isomers thereof.

In some embodiments, polypeptides suitable for producing steviol glycosides or glycosides of steviol precursors, such as kaurenoate-19-O-glucoside (19-KMG), steviol-19-O-glucoside (19-SMG), and rubusoside, in vitro, in a recombinant host, or by whole cell bioconversion include a polypeptide capable of glycosylating steviol or a steviol glycoside at its C-19 carboxyl group, such as a functional homolog of UGT74G1 (SEQ ID NO:4). As described in section "Functional Homologs" below, functional homologs disclosed herein can include, for example but not limited to, conservative amino acid substitutions, such as, for example, substitution of one hydrophobic residue for another or substitution of one polar residue for another.

In some embodiments, a useful UGT74G1 homolog can have one or more amino acid substitutions at residues 15, 16, 18, 20, 27, 28, 30, 31, 49, 51, 67, 68, 73, 75, 79, 81, 83, 84, 86-88, 90, 91, 96, 99, 107, 110, 111, 113, 115, 119-121, 123, 128, 129, 135, 136, 140, 141, 143, 146, 147, 156, 162, 166, 169, 173, 176, 179-181, 183-189, 191-195, 200, 204, 209, 211, 212, 215, 221, 222, 224, 232, 237, 247, 252, 255, 257, 259, 263, 265, 266, 269, 274, 280, 284, 285, 287, 292, 295-298, 300, 301, 303, 310, 311, 313, 315, 316, 320, 322, 325, 326, 328, 329, 332, 333, 335, 338, 341, 346, 347, 357, 364, 370, 371, 373, 375-377, 380, 385, 387-391, 396, 401, 407-411, 415, 416, 419, 424, 426, 427, 434, 448, 449, 455, 456, or 458. See, Table 1.

Non-limiting examples of useful UGT74G1 homologs include polypeptides having substitutions (with respect to SEQ ID NO:4) at residue 15 (e.g., a valine at residue 15); 16 (e.g., a leucine at reside 16); 18 (e.g., a tyrosine at residue 18); 20 (e.g., an alanine at residue 20); 27 (e.g., a methionine at residue 27); 28 (e.g., a leucine at residue 28); 30 (e.g., a leucine at residue 30); 31 (e.g., a serine or an alanine at residue 31); 49 (e.g., an isoleucine at residue 49); 51 (e.g., a lysine at residue 51); 67 (e.g., a glutamic acid at residue 67); 68 (e.g., a threonine at residue 68); 73 (e.g., a phenylalanine at residue 73); 75 (e.g., an aspartic acid at residue 75); 79 (e.g., an alanine at residue 79); 81 (e.g., a tryptophan at residue 81); 83 (e.g., an aspartic acid or a lysine at residue 83); 84 (e.g., an alanine at residue 84); 86 (e.g., an isoleucine at residue 86); 87 (e.g., an aspartic acid at residue 87); 88 (e.g., an arginine at residue 88); 90 (e.g., a tryptophan at residue 90); 91 (e.g., a glutamic acid at residue 91); 96 (e.g., a threonine at residue 96); 99 (e.g., a glutamic acid at residue 99); 107 (e.g., a serine at residue 107); 110 (e.g., a proline at residue 110); 111 (e.g., a valine at residue 111); 113 (e.g., a cysteine at residue 113); 115 (e.g., a valine at residue 115); 119 (e.g., a phenylalanine at residue 119); 120 (e.g., a leucine at residue 120); 121 (e.g., a proline at residue 121); 123 (e.g., an alanine at residue 123); 128 (e.g., a lysine at residue 128); 129 (e.g., a glutamine at residue 129); 135 (e.g., an alanine at residue 135); 136 (e.g., an alanine at residue 136); 140 (e.g., an asparagine at residue 140); 141 (e.g., a serine at residue 141); 143 (e.g., an alanine at residue 143); 146 (e.g., an asparagine at residue 146); 147 (e.g., an isoleucine at residue 147); 156 (e.g., a leucine at residue 156); 162 (e.g., a threonine at residue 162); 166 (e.g., a leucine at residue 166); 169 (e.g., a leucine at residue 169); 173 (e.g., a glutamic acid at residue 173); 176 (e.g., an aspartic acid at residue 176); 179 (e.g., a serine at residue 179); 180 (e.g., a phenylalanine at residue 180); 181 (e.g., a valine at residue 181); 183 (e.g., an aspartic acid at residue 183); 184 (e.g., a proline at residue 184); 185 (e.g., a glycine at residue 185); 186 (e.g., a serine at residue 186); 187 (e.g., a tyrosine at residue 187); 188 (e.g., a proline at residue 188); 189 (e.g., an alanine at residue 189); 191 (e.g., a phenylalanine at residue 191); 192 (e.g., an aspartic acid at residue 192); 193 (e.g., a methionine at residue 193); 194 (e.g., a valine at residue 194); 195 (e.g., a valine at residue 195); 200 (e.g., a serine at residue 200); 204 (e.g., a lysine at residue 204); 209 (e.g., a leucine at residue 209); 211 (e.g., a histidine at residue 211); 212 (e.g., a threonine at residue 212); 215 (e.g., a glutamic acid at residue 215); 221 (e.g., a valine at residue 221); 222 (e.g., an aspartic acid at residue 222); 224 (e.g., a methionine at residue 224); 232 (e.g., a threonine at residue 232); 237 (e.g., an isoleucine at residue 237); 247 (e.g., a glutamic acid at residue 247); 252 (e.g., a tyrosine at residue 252); 255 (e.g., a serine at residue 255); 257 (e.g., a phenylalanine at residue 257); 259 (e.g., a proline at residue 259); 263 (e.g., an alanine at residue 263); 265 (e.g., an isoleucine at residue 265); 266 (e.g., a lysine or a glutamic acid at residue 266); 269 (e.g., an asparagine at residue 269); 274 (e.g., a glycine at residue 274); 280 (e.g., a serine at residue 280); 284 (e.g., a methionine at residue 284); 285 (e.g., an alanine at residue 285); 287 (e.g., a leucine at residue 287); 292 (e.g., a methionine at residue 292); 295 (e.g., a leucine or a methionine at residue 295); 296 (e.g., an alanine at residue 296); 297 (e.g., a tryptophan at residue 297); 298 (e.g., a glycine at residue 298); 300 (e.g., a lysine at residue 300); 301 (e.g., an asparagine at residue 301); 303 (e.g., an asparagine at residue 303); 310 (e.g., a valine at residue 310); 311 (e.g., an arginine at residue 311); 313 (e.g., a serine at residue 313); 315 (e.g., a glutamine at residue 315); 316 (e.g., an alanine at residue 316); 320 (e.g., a lysine at residue 320); 322 (e.g., a phenylalanine at residue 322); 325 (e.g., a glutamic acid at residue 325); 326 (e.g., a threonine at residue 326); 328 (e.g., a serine at residue 328); 329 (e.g., a glutamic acid at residue 329); 332 (e.g., isoleucine at residue 332); 333 (e.g., a valine at residue 333); 335 (e.g., a serine at residue 335); 338 (e.g., a proline at residue 338); 341 (e.g., a glutamic acid at residue 341); 346 (e.g., a lysine or a proline at residue 346); 347 (e.g., an alanine at residue 347); 357 (e.g., tryptophan at residue 357); 364 (e.g., a leucine at residue 364); 370 (e.g., a methionine at residue 370); 371 (e.g., an isoleucine at residue 371); 373 (e.g., a valine at residue 373); 375 (e.g., a leucine at residue 375); 376 (e.g., a tryptophan at residue 376); 377 (e.g., a threonine at residue 377); 380 (e.g., a serine at residue 380); 385 (e.g., a phenylalanine at residue 385); 387 (e.g., a glutamic acid at residue 387); 388 (e.g., an aspartic acid at residue 388); 389 (e.g., a valine at residue 389); 390 (e.g., a tryptophan at residue 390); 391 (e.g., a lysine at residue 391); 396 (e.g., an alanine at residue 396); 401 (e.g., a lysine at residue 401); 407 (e.g., a glutamic acid at residue 407); 408 (e.g., a glutamic acid at residue 408); 409 (e.g., an isoleucine at residue 409); 410 (e.g., a glutamic acid at residue 410); 411 (e.g., an aspartic acid at residue 411); 415 (e.g., a glutamic acid at residue 415); 416 (e.g., a valine at residue 416); 419 (e.g., a glycine at residue 419); 424 (e.g., a glutamic acid at residue 424); 426 (e.g., a lysine at residue 426); 427 (e.g., a glutamic acid at residue 427); 434 (e.g., a glutamic acid at residue 434); 448 (e.g., a lysine at residue 448); 449 (e.g., an asparagine at residue 449); 455 (e.g., a alanine at residue 455); 456 (e.g., a lysine at residue 456); or 458 (e.g., a valine at residue 458).

In some embodiments, UGT74G1 variants having one substitution (with respect to SEQ ID NO:4), e.g., L15V, F18Y, M79A, E87D, G31S, E83D, N51K, E75D, T49I, D99E, S96T, C73F, S84A, A68T, Q67E, I16L, I28L, G31A, S377T, M119F, E456K, L181V, L385F, N183D, E176D, F209L, N211H, V143A, R297W, A410E, L390W, N252Y, S212T, V232T, I115V, G329E, T224M, I295L, T328S, L409I, D387E, D449N, V123A, M373V, V285A, Q204K, S189A, D247E, G135A, I111V, T120L, G316A, Q173E, V166L, I221V, L147I, F376W, L284M, E162T, Q375L, S136A, E315Q, I333V, M265I, A141S, E107S, E185G, V396A, L237I, Q186S, E320K, A200S, L195V, Q188P, Y257F, D269N, D341E, D434E, K313S, L179S, S455A, E263A, K311R, A259P, T110P, V292M, I326T, T296A, E222D, G391K, K215E, I310V, I156L, D303N, E121P, V370M, K427E, I180F, E274G, I458V, A335S, S411D, or F169L, accumulate rubusoside, 19-SMG, and/or 19-KMG.

In some embodiments, UGT74G1 variants having two substitutions (with respect to SEQ ID NO:4), e.g., E176D and F357W, accumulate rubusoside, 19-SMG, and/or 19-KMG. In some embodiments, UGT74G1 variants having three substitutions (with respect to SEQ ID NO:4), e.g., F18Y, I416V, and F27M; E87D, Q91E, and I300K; E274G, L86I, and F30L; E83D, R426K, and Q91E; S96T, V325E, and T88R; D99E, L322F, and S192D; C73F, S146N, and T380S; A259P, V371I, and K90W; T49I, A280S, and A113C; V123A, M194V, and T88R; L181V, A280S, and L86I; N252Y, E129Q, and F30L; A68T, L322F, and A113C; S212T, F357W, and F30L; E75D, I300K, and F357W; A335S, G407E, and Q91E; I16L, A113C, and M415E; G31S, N255S, and I295M; S377T, E388D, and L86I; I180F, H184P, and E83K; Q188P, N408E, and E83K; K311R, W191F, and F27M; L195V, L20A, and E346P; M79A, V325E, and M415E; Q67E, N401K, and D301N; S84A, S347A, and I295M; A141S, F27M, and V371I; L179S, N266K, and E83K; Q186S, W191F, and T88R; A410E, A298G, and L20A; K311R, W191F, and F27M; V285A, E388D, and L20A; E176D, L322F, and K90W; F169L, K90W, and N266E; E456K, N255S, and N401K; V370M, N448K, and M194V; A200S, E129Q, and Q140N; L390W, N266K, and S192D; E320K, N266K, and M194V; M265I, I364L, and I187Y; E315Q, E129Q, and S192D; E222D, N408E, and Q140N; M119F, N255S, and A298G; D269N, R426K, and S146N; E185G, A298G, and Q193M; V232T, E388D, and Q140N; G316A, V325E, and I187Y; L409I, D301N, and H184P; S189A, S146N, and I389V; V143A, I416V, and H184P; S455A, Q193M, and E346K; R297W, S347A, and E346K; D341E, Q193M, and L332I; D434E, T380S, and I389V; T328S, A280S, and L332I; Q375L, E419G, and R426K; I221V, K338P, and I295M; T296A, I128K, and L332I; D449N, G407E, and H287L; T110P, K338P, and E346P; E121P, I416V, and H287L; L284M, I424E, and E346K; K427E, K338P, and I424E; D303N, N408E, and I300K; D247E, D301N, and E346P; F376W, N448K, and I128K; K313S, I187Y, I128K; G329E, G407E, and N266E; I111V, M415E, and H287L; G391K, T380S, and I389V; V396A, N448K, and S347A; I310V, V371I, and N266E; Y257F, N401K, and W191F; S136A, I364L, and I424E; or V292M, E419G, and I364L, accumulate rubusoside, 19-SMG, and/or 19-KMG. See, Tables 2 and 3.

In some embodiments, expression of UGT74G1 variants as otherwise described herein in steviol glycoside producing *S. cerevisiae* strains (See, WO 2014/122227, which is hereby incorporated herein by reference in its entirety) increases accumulation of rubusoside, 19-SMG, and/or 19-KMG relative to steviol glycoside producing *S. cerevisiae* strains expressing, e.g., a UGT74G1 polypeptide having the amino acid sequence set forth in SEQ ID NO:4. In some embodiments, inclusion of UGT74G1 variants as otherwise described herein in an in vitro reaction mixture also comprising ent-kaurenoic acid, steviol, and/or 13-SMG increases accumulation of rubusoside, 19-SMG, and/or 19-KMG relative to a reaction mixture comprising, e.g., a UGT74G1 polypeptide having the amino acid sequence set forth in SEQ ID NO:4. In some embodiments, expression of UGT74G1 variants that increase accumulation of rubusoside also results in increased accumulation of 19-SMG and 19-KMG. In some embodiments, expression of UGT74G1 variants that increase accumulation of rubusoside also results in increased accumulation of 19-SMG, but decreased accumulation of 19-KMG. In some embodiments, expression of UGT74G1 variants that increase accumulation of rubusoside also results in increased accumulation of 19-KMG, but decreased accumulation of 19-SMG. In some embodiments, expression of UGT74G1 variants that increase accumulation of rubusoside also results in decreased accumulation of 19-SMG and 19-KMG.

In some embodiments, expression of UGT74G1 variants that increase accumulation of 19-SMG also results in increased accumulation of rubusoside and 19-KMG. In some embodiments, expression of UGT74G1 variants that increase accumulation of 19-SMG also results in increased accumulation of rubusoside, but decreased accumulation of 19-KMG. In some embodiments, expression of UGT74G1 variants that increase accumulation of 19-SMG also results in increased accumulation of 19-KMG, but decreased accumulation of rubusoside. In some embodiments, expression of UGT74G1 variants that increase accumulation of 19-SMG also results in decreased accumulation of rubusoside and 19-KMG.

In some embodiments, expression of UGT74G1 variants that increase accumulation of 19-KMG also results in increased accumulation of rubusoside and 19-SMG. In some embodiments, expression of UGT74G1 variants that increase accumulation of 19-KMG also results in increased accumulation of rubusoside, but decreased accumulation of 19-SMG. In some embodiments, expression of UGT74G1 variants that increase accumulation of 19-KMG also results in increased accumulation of 19-SMG, but decreased accumulation of rubusoside. In some embodiments, expression of UGT74G1 variants that increase accumulation of 19-KMG also results in decreased accumulation of rubusoside and 19-SMG.

In some embodiments, expression of a UGT74G1 variant having one substitution (with respect to SEQ ID NO:4), e.g., N183D, D387E, L409I, G316A, T224M, V143A, A410E, L390W, S212T, Q204K, T120L, M79A, L237I, I295L, S136A, V285A, N211H, V232T, or L181V, results in increased rubusoside. In some embodiments, expression of a UGT74G1 variant having more than one substitution (with respect to SEQ ID NO:4), e.g., A335S, G407E, and Q91E; D99E, L322F, and S192D; C73F, S146N, and T380S; E83D, R426K, and Q91E; D434E, T380S, and I389V; or G361A, V325E, and I187Y, results in increased rubusoside.

In some embodiments, expression of a UGT74G1 variant having one substitution (with respect to SEQ ID NO:4), e.g., F169L, E176D, E456K, M119F, S377T, L15V, L385F, F18Y, L181V, N183D, F209L, V166L, R297W, C73F, D449N, E107S, N252Y, G135A, S189A, G31A, T49I, I180F, Q375L, Q186S, F376W, S411D, V370M, I111V, I221V, I458V, E87D, G31S, V123A, K427E, L179S, I28L, I156L, S84A, 116L, D303N, E274G, Q188P, L284M, Q173E, I115V, V143A, I310V, N211H, E222D, E83D, A335S, V292M, D99E, T296A, E162T, E263A, A68T, S96T, A259P, A141S, V285A, E320K, G391K, K311R, M79A, L195V, E320K, T110P, K215E, or I333V, results in increased 19-KMG. In some embodiments, expression of a UGT74G1 variant having more than one substitution (with respect to SEQ ID NO:4), e.g., V232T, E388D, and Q140N; E222D, N408E, and Q140N; S189A, S146N, and I389V; M119F, N255S, and A298G; A200S, E129Q, and Q140N; L181V, A280S, and L86I; S377T, E388D, and L86I; E456K, N255S, and N401K; V123A, M194V, and T88R; C73F, S146N, and T380S; V370M, N448K, and M194V; D99E, L322F, and S192D; A259P, V371I, and K90W; E315Q, E129Q, and S192D; M265I, I364L, and I187Y; T49I, A280S, and A113C; E320K, N266K, and M194V; L390W, N266K, and S192D; D269N, R426K, and S146N; E185G, A298G, and Q193M; S212T, F357W, and F30L; N252Y, E129Q, and F30L; V143A, I416V, and H184P; L409I, D301N, and H184P; R297W, S347A, and E346K; 116L, A113C, and M415E; A68T, L322F, and A113C; Q188P, N408E, and E83K; G31S, N255S, and 1295M; E75D, I300K, and F357W; G316A, V325E, and I187Y; S455A, Q193M, and E346K; E274G, L86I, and F30L; D341E, Q193M, and L332I; E176D and F357W; I180F, H184P, and E83K; T328S, A280S, and L332I; D449N, G407E, and H287L; K313S, I187Y, and I128K; S96T, V325E, and T88R; V396A, N448K, and S347A; F18Y, I416V, and F27M; I221V, K338P, and I295M; K427E, K338P, and 1424E; V292M, E419G, and I364L; G391K, T380S, and I389V; G329E, G407E, and N266E; I310V, V371I, and N266E; M79A, V325E, and M415E; Q67E, N401K, and D301N; S84A, S347A, and 1295M; L179S, N266K, and E83K; I111V, M415E, and H287L; Q186S, W191F, and T88R; V285A, E388D, and L20A; F376W, N448K, and I128K; Y257F, N401K, and W191F; D247E, D301N, and E346P; D303N, N408E, and I300K; A141S, F27M, and V371I; S136A, I364L, and 1424E; K311R, W191F, and F27M; Q375L, E419G, and R426K; L195V, L20A, and E346P; A410E, A298G, and L20A; T110P, K338P, and E346P; E121P, I416V, and H287L; K311R, W191F, and F27M; E87D, Q91E, and I300K; or L284M, I424E, and E346K, results in increased 19-KMG.

In some embodiments, expression of a UGT74G1 variant having one substitution (with respect to SEQ ID NO:4), e.g., G316A, Q204K, S212T, A410E, I295L, T328S, T224M, L409I, D387E, T120L, S136A, A200S, M373V, E315Q, V143A, L390W, or M79A, results in increased 19-SMG. In some embodiments, expression of a UGT74G1 variant having more than one substitution (with respect to SEQ ID NO:4), e.g., A335S, G407E, and Q91E; T296A, I128K, and I332I; D434E, T380S, and 1389V; or E87D, Q91E, and I300K, results in increased 19-SMG.

In some embodiments, one or more steviol glycosides or glycosides of a steviol precursor produced in vivo, in vitro, or by whole cell bioconversion does not comprise or comprises a reduced amount or reduced level of plant-derived components than a Stevia extract from, inter alia, a Stevia plant. Plant-derived components can contribute to off-flavors and include pigments, lipids, proteins, phenolics, saccharides, spathulenol and other sesquiterpenes, labdane diterpenes, monoterpenes, decanoic acid, 8,11,14-eicosatrienoic acid, 2-methyloctadecane, pentacosane, octacosane, tetracosane, octadecanol, stigmasterol, β-sitosterol, α- and β-amyrin, lupeol, β-amryin acetate, pentacyclic triterpenes, centauredin, quercitin, epi-alpha-cadinol, carophyllenes and derivatives, beta-pinene, beta-sitosterol, and gibberellin. In some embodiments, the plant-derived components referred to herein are non-glycoside compounds.

As used herein, the terms "detectable amount," "detectable concentration," "measurable amount," and "measurable concentration" refer to a level of steviol glycosides measured in AUC, $\mu M/OD_{600}$, mg/L, $\mu M$, or mM. Steviol glycoside production (i.e., total, supernatant, and/or intracellular steviol glycoside levels) can be detected and/or analyzed by techniques generally available to one skilled in the art, for example, but not limited to, liquid chromatography-mass spectrometry (LC-MS), thin layer chromatography (TLC), high-performance liquid chromatography (HPLC), ultraviolet-visible spectroscopy/spectrophotometry (UV-Vis), mass spectrometry (MS), and nuclear magnetic resonance spectroscopy (NMR).

As used herein, the term "undetectable concentration" refers to a level of a compound that is too low to be measured and/or analyzed by techniques such as TLC, HPLC, UV-Vis, MS, or NMR. In some embodiments, a compound of an "undetectable concentration" is not present in one or more steviol glycosides or glycosides of a steviol precursor.

After the recombinant microorganism has been grown in culture for the period of time, wherein the temperature and period of time facilitate the production of a steviol glycoside, steviol and/or one or more steviol glycosides can then be recovered from the culture using various techniques known in the art. Steviol glycosides can be isolated using a method described herein. For example, following fermentation, a culture broth can be centrifuged for 30 min at 7000 rpm at 4° C. to remove cells, or cells can be removed by filtration. The cell-free lysate can be obtained, for example, by mechanical disruption or enzymatic disruption of the host cells and additional centrifugation to remove cell debris. Mechanical disruption of the dried broth materials can also be performed, such as by sonication. The dissolved or suspended broth materials can be filtered using a micron or sub-micron prior to further purification, such as by preparative chromatography. The fermentation media or cell-free lysate can optionally be treated to remove low molecular weight compounds such as salt; and can optionally be dried prior to purification and re-dissolved in a mixture of water and solvent.

The supernatant or cell-free lysate can be purified as follows: a column can be filled with, for example, HP20

Diaion resin (aromatic type Synthetic Adsorbent; Supelco) or other suitable non-polar adsorbent or reversed-phase chromatography resin, and an aliquot of supernatant or cell-free lysate can be loaded on to the column and washed with water to remove the hydrophilic components. The steviol glycoside product can be eluted by stepwise incremental increases in the solvent concentration in water or a gradient from, e. g., 0%→100% methanol). The levels of steviol glycosides, glycosylated ent-kaurenol, and/or glycosylated ent-kaurenoic acid in each fraction, including the flow-through, can then be analyzed by LC-MS. Fractions can then be combined and reduced in volume using a vacuum evaporator. Additional purification steps can be utilized, if desired, such as additional chromatography steps and crystallization. For example, steviol glycosides can be isolated by methods not limited to ion exchange chromatography, reversed-phase chromatography (i.e., using a C18 column), extraction, crystallization, and carbon columns and/or decoloring steps.

As used herein, the terms "or" and "and/or" is utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." In some embodiments, "and/or" is used to refer to the exogenous nucleic acids that a recombinant cell comprises, wherein a recombinant cell comprises one or more exogenous nucleic acids selected from a group. In some embodiments, "and/or" is used to refer to production of steviol glycosides and/or steviol glycoside precursors. In some embodiments, "and/or" is used to refer to production of steviol glycosides, wherein one or more steviol glycosides are produced. In some embodiments, "and/or" is used to refer to production of steviol glycosides, wherein one or more steviol glycosides are produced through the following steps: culturing a recombinant microorganism, synthesizing one or more steviol glycosides in a recombinant microorganism, and/or isolating one or more steviol glycosides.

Functional Homologs

Functional homologs of the polypeptides described above are also suitable for use in producing steviol glycosides in a recombinant host. A functional homolog is a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of steviol glycoside biosynthesis polypeptides. Sequence analysis can involve BLAST, Reciprocal BLAST, or PSI-BLAST analysis of non-redundant databases using a UGT amino acid sequence as the reference sequence. Amino acid sequence is, in some instances, deduced from the nucleotide sequence. Those polypeptides in the database that have greater than 40% sequence identity are candidates for further evaluation for suitability as a steviol glycoside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in steviol glycoside biosynthesis polypeptides, e.g., conserved functional domains. In some embodiments, nucleic acids and polypeptides are identified from transcriptome data based on expression levels rather than by using BLAST analysis.

Conserved regions can be identified by locating a region within the primary amino acid sequence of a steviol glycoside biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., Nud. Acids Res., 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some embodiments, alignment of sequences from two different species is adequate to identify such homologs.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing steviol in a recombinant host include functional homologs of UGTs.

Methods to modify the substrate specificity of, for example, a UGT, are known to those skilled in the art, and include without limitation site-directed/rational mutagenesis approaches, random directed evolution approaches and combinations in which random mutagenesis/saturation techniques are performed near the active site of the enzyme. For example see Osmani et al., 2009, *Phytochemistry* 70: 325-347.

A candidate sequence typically has a length that is from 80% to 250% of the length of the reference sequence, e.g., 82, 85, 87, 89, 90, 93, 95, 97, 99, 100, 105, 110, 115, 120, 130, 140, 150, 160, 170, 180, 190, 200, 210, 220, 230, 240, or 250% of the length of the reference sequence. A functional homolog polypeptide typically has a length that is from 95% to 105% of the length of the reference sequence, e.g., 90, 93, 95, 97, 99, 100, 105, 110, 115, or 120% of the length of the reference sequence, or any range between. A % sequence identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program Clustal Omega (version 1.2.1, default parameters), which allows alignments of nucleic acid or polypeptide sequences to be carried out across their entire length (global alignment). Chenna et al., 2003, *Nucleic Acids Res.* 31(13):3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: % age; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method:% age; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine a % sequence identity of a candidate nucleic acid or amino acid sequence to a reference sequence, the sequences are aligned using Clustal Omega, the number of identical matches in the alignment is divided by the length of the reference sequence, and the result is multiplied by 100. It is noted that the % sequence identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional UGT proteins can include additional amino acids that are not involved in the enzymatic activities carried out by the enzymes. In some embodiments, UGT proteins are fusion proteins. The terms "chimera," "fusion polypeptide," "fusion protein," "fusion enzyme," "fusion construct," "chimeric protein," "chimeric polypeptide," "chimeric construct," and "chimeric enzyme" can be used interchangeably herein to refer to proteins engineered through the joining of two or more genes that code for different proteins.

In some embodiments, a chimeric enzyme is constructed by joining the C-terminal of a first polypeptide ProteinA to the N-terminal of a second polypeptide ProteinB through a linker "b," i.e., "ProteinA-b-ProteinB." In some aspects, the linker of a chimeric enzyme may be the amino acid sequence "KLVK." In some aspects, the linker of a chimeric enzyme may be the amino acid sequence "RASSTKLVK." In some aspects, the linker of a chimeric enzyme may be the amino acid sequence "GGGGS." In some aspects, the linker of a chimeric enzyme may be two repeats of the amino acid sequence "GGGGS" "GGGGSGGGGS"). In some aspects, the linker of a chimeric enzyme may be three repeats of the amino acid sequence "GGGGS." In some aspects, the linker of a chimeric enzyme is a direct bond between the C-terminal of a first polypeptide and the N-terminal of a second polypeptide. In some embodiments, a chimeric enzyme is constructed by joining the C-terminal of a first polypeptide ProteinA to the N-terminal of a second polypeptide ProteinB through a linker "b," i.e., "ProteinA-b-ProteinB" and by joining the C-terminal of the second polypeptide ProteinB to the N-terminal of a third polypeptide ProteinC through a second linker "d," i.e., "ProteinA-b-ProteinB-d-ProteinC.

In some embodiments, a nucleic acid sequence encoding a UGT polypeptide (e.g., a polypeptide capable of glycosylating steviol or a steviol glycoside at its C-19 carboxyl group) can include a tag sequence that encodes a "tag" designed to facilitate subsequent manipulation (e.g., to facilitate purification or detection), secretion, or localization of the encoded polypeptide. Tag sequences can be inserted in the nucleic acid sequence encoding the polypeptide such that the encoded tag is located at either the carboxyl or amino terminus of the polypeptide. Non-limiting examples of encoded tags include green fluorescent protein (GFP), human influenza hemagglutinin (HA), glutathione S transferase (GST), polyhistidine-tag (HIS tag), and Flag™ tag (Kodak, New Haven, Conn.). Other examples of tags include a chloroplast transit peptide, a mitochondrial transit peptide, an amyloplast peptide, signal peptide, or a secretion tag.

In some embodiments, a fusion protein is a protein altered by domain swapping. As used herein, the term "domain swapping" is used to describe the process of replacing a domain of a first protein with a domain of a second protein. In some embodiments, the domain of the first protein and the domain of the second protein are functionally identical or functionally similar. In some embodiments, the structure and/or sequence of the domain of the second protein differs from the structure and/or sequence of the domain of the first protein. In some embodiments, a UGT polypeptide (e.g., a polypeptide capable of glycosylating steviol or a steviol glycoside at its C-19 carboxyl group) is altered by domain swapping.

In some embodiments, a fusion protein is a protein altered by circular permutation, which consists in the covalent attachment of the ends of a protein that would be opened elsewhere afterwards. Thus, the order of the sequence is altered without causing changes in the amino acids of the protein. In some embodiments, a targeted circular permutation can be produced, for example but not limited to, by designing a spacer to join the ends of the original protein. Once the spacer has been defined, there are several possibilities to generate permutations through generally accepted molecular biology techniques, for example but not limited to, by producing concatemers by means of PCR and subsequent amplification of specific permutations inside the concatemer or by amplifying discrete fragments of the protein to exchange to join them in a different order. The step of generating permutations can be followed by creating a circular gene by binding the fragment ends and cutting back at random, thus forming collections of permutations from a unique construct.

Steviol and Steviol Glycoside Biosynthesis Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes can be combined in a recombinant nucleic acid construct in "modules" useful for a discrete aspect of steviol and/or steviol glycoside production. Combining a plurality of genes in a module, particularly a polycistronic module, facilitates the use of the module in a variety of species. For example, a steviol biosynthesis gene cluster, or a UGT gene cluster, can be combined in a polycistronic module such that, after insertion of a suitable regulatory region, the module can be introduced into a wide variety of species. As another example, a UGT gene cluster can be combined such that each UGT coding sequence is operably linked to a separate regulatory region, to form a UGT module. Such a module can be used in those species for which monocistronic expression is necessary or desirable. In addition to genes useful for steviol or steviol glycoside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards steviol or steviol glycoside biosynthesis. For example, it may be desirable to downregulate synthesis of sterols in a yeast strain in order to further increase steviol or steviol glycoside production, e.g., by downregulating squalene epoxidase. As another example, it may be desirable to inhibit degradative functions of certain endogenous gene products, e.g., glycohydrolases that remove glucose moieties from secondary metabolites or phosphatases as discussed herein. In such cases, a nucleic acid that overexpresses the polypeptide or gene product may be included in a recombinant construct that is transformed into the strain. Alternatively, mutagenesis can be used to generate mutants in genes for which it is desired to increase or enhance function.

Host Microorganisms

Recombinant hosts can be used to express polypeptides for producing steviol glycosides, including, but not limited to, a plant cell, comprising a plant cell that is grown in a plant, a mammalian cell, an insect cell, a fungal cell, an algal cell, an archaeal cell or a bacterial cell.

A number of prokaryotes and eukaryotes are also suitable for use in constructing the recombinant microorganisms described herein, e.g., gram-negative bacteria, yeast, and fungi. A species and strain selected for use as a steviol glycoside production strain is first analyzed to determine which production genes are endogenous to the strain and which genes are not present. Genes for which an endogenous counterpart is not present in the strain are advantageously assembled in one or more recombinant constructs, which are then transformed into the strain in order to supply the missing function(s).

Typically, the recombinant microorganism is grown in a fermenter at a temperature(s) for a period of time, wherein the temperature and period of time facilitate the production of a steviol glycoside. The constructed and genetically engineered microorganisms provided by the invention can be cultivated using conventional fermentation processes, including, inter alia, chemostat, batch, fed-batch cultivations, semi-continuous fermentations such as draw and fill, continuous perfusion fermentation, and continuous perfusion cell culture. Depending on the particular microorganism used in the method, other recombinant genes such as isopentenyl biosynthesis genes and terpene synthase and cyclase genes may also be present and expressed. Levels of substrates and intermediates, e.g., isopentenyl diphosphate, dimethylallyl diphosphate, GGPP, ent-kaurene and ent-kaurenoic acid, can be determined by extracting samples from culture media for analysis according to published methods.

In some aspects, the recombinant microorganism is grown in a deep well plate. It will be understood that while data on production of steviol glycosides by the recombinant microorganism grown in deep well cultures, in some aspects, may be more easily collected than that in fermentation cultures, the small culture volume of the deep well (e.g., 1 ml or 0.5 ml) can effect differences in the environment of the microorganism and, therefore its efficiency and effectiveness in producing steviol glycosides. For example, nutrient availability, cellular waste product buildup, pH, temperature, agitation, and aeration may differ significantly between fermentation and deep well cultures. Accordingly, uptake of nutrients or other enzyme substrates may vary, affecting the cellular metabolism (e.g., changing the amount and/or profile of products accumulated by a recombinant microorganism). See, e.g., Duetz, *Trends Microbiol* 15(10):469-75 (2007).

Carbon sources of use in the instant method include any molecule that can be metabolized by the recombinant host cell to facilitate growth and/or production of the steviol glycosides. Examples of suitable carbon sources include, but are not limited to, sucrose (e.g., as found in molasses), fructose, xylose, ethanol, glycerol, glucose, cellulose, starch, cellobiose or other glucose-comprising polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

It will be appreciated that the various genes and modules discussed herein can be present in two or more recombinant hosts rather than a single host. When a plurality of recombinant hosts is used, they can be grown in a mixed culture to accumulate steviol and/or steviol glycosides.

Alternatively, the two or more hosts each can be grown in a separate culture medium and the product of the first culture medium, e.g., steviol, can be introduced into second culture medium to be converted into a subsequent intermediate, or into an end product such as, for example, RebA. The product produced by the second, or final host is then recovered. It will also be appreciated that in some embodiments, a recombinant host is grown using nutrient sources other than a culture medium and utilizing a system other than a fermenter.

Exemplary prokaryotic and eukaryotic species are described in more detail below. However, it will be appreciated that other species can be suitable. However, it will be appreciated that other species can be suitable to express polypeptides for the producing steviol glycosides.

For example, suitable species can be in a genus such as *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia* (formally known as *Hansuela*), *Scheffersomyces, Physcomitrella, Rhodoturula, Saccharomyces, Schizosaccharomyces, Sphaceloma, Xanthophyllomyces, Humicola, Issatchenkia, Brettanomyces, Yamadazyma, Lachancea, Zygosaccharomyces, Komagataella, Kazachstania, Xanthophyllomyces, Geotrichum, Blakeslea, Dunaliella, Haematococcus, Chlorella, Undaria, Sargassum, Laminaria, Scenedesmus, Pachysolen, Trichosporon, Acremonium, Aureobasidium, Cryptococcus, Corynascus, Chrysosporium, Filibasidium, Fusarium, Magnaporthe, Monascus, Mucor, Myceliophthora, Mortierella, Neocallimastix, Neurospora, Paecilomyces, Penicillium, Piromyces, Pachysolen, Phanerochaete, Podospora, Pycnoporus, Rhizopus, Schizophyllum, Sordaria, Talaromyces, Rasmsonia, Thermoascus, Thielavia, Tolypocladium, Kloeckera, Pachysolen, Schwanniomyces, Trametes, Trichoderma, Acinetobacter, Nocardia, Xanthobacter, Streptomyces, Erwinia, Klebsiella, Serratia, Pseudomonas, Salmonella, Choroflexus, Chloronema, Chlorobium, Pelodictyon, Chromatium, Rhode-spirillum, Rhodobacter, Rhodomicrobium,* or *Yarrowia.*

Exemplary species from such genera include *Lentinus tigrinus, Laetiporus sulphureus, Phanerochaete chrysosporium, Pichia pastoris, Pichia kudriavzevii, Cyberlindnera jadinii, Physcomitrella patens, Rhodoturula glutinis, Rhodoturula mucilaginosa, Phaffia rhodozyma, Xanthophyllomyces dendrorhous, Issatchenkia orientalis, Saccharomyces cerevisiae, Saccharomyces bayanus, Saccharomyces pastorianus, Saccharomyces carlsbergensis, Hansuela polymorpha, Brettanomyces anomalus, Yamadazyma philogaea, Fusarium fujikuroi/Gibberella fujikuroi, Candida utilis, Candida glabrata, Candida krusei, Candida revkaufi, Candida pulcherrima, Candida tropicalis, Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla, Candida albicans, Bacillus subtilis, Bacillus amyloliquefaciens, Baciilius licheniformis, Bacillus puntis, Baciilius megaterium, Baciilius halofurans, Baciilius punilus, Serratia marcessans, Pseudomonas aeruginosa, Salmonella typhimurium, Blakeslea trispora, Dunaliella salina, Haematococcus pluvialis, Chlorella* sp., *Undaria pinnatifida, Sargassum, Laminaria japonica, Scenedesmus almeriensis, Salmonella typhi, Choroflexus aurantiacus, Chloronema gigateum, Chlorobium limicola, Pelodictyon luteolum, Chromatium okenii, Rhode-spirillum rubrum, Rhodobacter spaeroides, Rhodobacter capsulatus, Rhodomicrobium vaneffii, Pachysolen tannophilus, Trichosporon beigelii,* and *Yarrowia lipolytica.*

In some embodiments, a microorganism can be a prokaryote such as *Escherichia* bacteria cells, for example, *Escherichia coli* cells; *Lactobacillus* bacteria cells; *Lactococcus* bacteria cells; *Comebacterium* bacteria cells; *Acetobacter* bacteria cells; *Acinetobacter* bacteria cells; or *Pseudomonas* bacterial cells.

In some embodiments, a microorganism can be an algal cell such as *Blakeslea trispora, Dunaliella salina, Haematococcus pluvialis, Chlorella* sp., *Undaria pinnatifida, Sargassum, Laminaria japonica, Scenedesmus almeriensis* species.

In some embodiments, a microorganism can be a fungi from the genera including but not limited to *Acremonium, Arxula, Agaricus, Aspergillus, Agaricus, Aureobasidium, Brettanomyces, Candida, Cryptococcus, Corynascus, Chrysosporium, Debaromyces, Filibasidium, Fusarium,*

*Gibberella, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus, Rhizopus, Schizophyllum, Schizosaccharomyces, Sordaria, Scheffersomyces, Talaromyces, Rhodotorula, Rhodosporidium, Rasmsonia, Zygosaccharomyces, Thermoascus, Thielavia, Trichosporon, Tolypocladium, Trametes,* and *Trichoderma.* Fungal species include, but are not limited to, *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla.*

In some embodiments, a microorganism can be an *Ascomycete* such as *Gibberella fujikuroi, Kluyveromyces lactis, Schizosaccharomyces pombe, Geotrichum Aspergillus niger, Yarrowia lipolytica, Ashbya gossypii, Yamadazyma philogaea, Lachancea kluyveri, Kodamaea ohmeri,* or *S. cerevisiae.*

*Agaricus, Gibberella,* and *Phanerochaete* spp.

*Agaricus, Gibberella,* and *Phanerochaete* spp. can be useful because they are known to produce large amounts of isoprenoids in culture. Thus, the terpene precursors for producing large amounts of steviol glycosides are already produced by endogenous genes. Thus, modules comprising recombinant genes for steviol glycoside biosynthesis polypeptides can be introduced into species from such genera without the necessity of introducing mevalonate or MEP pathway genes.

*Arxula adeninivorans* (*Blastobotrys adeninivorans*)

*Arxula adeninivorans* is dimorphic yeast (it grows as budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Rhodotorula* sp.

*Rhodotorula* is unicellular, pigmented yeast. The oleaginous red yeast, *Rhodotorula glutinis*, has been shown to produce lipids and carotenoids from crude glycerol (Saenge et al., 2011, Process Biochemistry 46(1):210-8). *Rhodotorula* toruloides strains have been shown to be an efficient fed-batch fermentation system for improved biomass and lipid productivity (Li et al., 2007, Enzyme and Microbial Technology 41:312-7).

*Schizosaccharomyces* spp.

*Schizosaccharomyces* is a genus of fission yeasts. Similar to *S. cerevisiae, Schizosaccharomyces* is a model organism in the study of eukaryotic cell biology. It provides an evolutionary distant comparison to *S. cerevisiae.* Species include but are not limited to *S. cryophilius* and *S. pombe.* (See Hoffman et al., 2015, Genetics. 201(2):403-23).

*Humicola* spp.

*Humicola* is a genus of filamentous fungi. Species include but are not limited to *H. alopallonella* and *H. siamensis.*

*Brettanomyces* spp.

*Brettanomyces* is a non-spore forming genus of yeast. It is from the Saccharomycetaceae family and commonly used in the brewing and wine industries. *Brettanomyces* produces several sensory compounds that contribute to the complexity of wine, specifically red wine. *Brettanomyces* species include but are not limited to *B. bruxellensis* and *B. claussenii.* See, e.g., Fugelsang et al., 1997, Wine Microbiology.

*Trichosporon* spp.

*Trichosporon* is a genus of the fungi family. *Trichosporon* species are yeast commonly isolated from the soil, but can also be found in the skin microbiota of humans and animals. Species include, for example but are not limited to, *T. aquatile, T. beigelii,* and *T. dermatis.*

*Debaromyces* spp.

*Debaromyces* is a genus of the ascomycetous yeast family, in which species are characterized as a salt-tolerant marine species. Species include but are not limited to *D. hansenii* and *D. hansenius.*

*Physcomitrella* spp.

*Physcomitrella* mosses, when grown in suspension culture, have characteristics similar to yeast or other fungal cultures. This genera can be used for producing plant secondary metabolites, which can be difficult to produce in other types of cells.

*Saccharomyces* spp.

*Saccharomyces* is a widely used chassis organism in synthetic biology, and can be used as the recombinant microorganism platform. For example, there are libraries of mutants, plasmids, detailed computer models of metabolism and other information available for *S. cerevisiae,* allowing for rational design of various modules to enhance product yield. Methods are known for making recombinant microorganisms. Examples of *Saccharomyces* species include *S. casteffii,* also known as *Naumovozyma castelli.*

*Zygosaccharomyces* spp.

*Zygosaccharomyces* is a genus of yeast. Originally classified under the *Saccharomyces* genus it has since been reclassified. It is widely known in the food industry because several species are extremely resistant to commercially used food preservation techniques. Species include but are not limited to *Z. bisporus* and *Z. cidri.* (See Barnett et al, Yeasts: Characteristics and Identification, 1983).

*Geotrichum* spp.

*Geotrichum* is a fungi commonly found in soil, water and sewage worldwide. It's often identified in plants, cereal and diary products. Species include, for example but are not limited to, *G. candidum* and *G. klebahnii* (see Carmichael et al., Mycologica, 1957, 49(6):820-830).

*Kazachstania* sp

*Kazachstania* is a yeast genus in the family Sacchromycetaceae.

*Torulaspora* spp.

*Torulaspora* is a genus of yeasts and species include but are not limited to *T. franciscae* and *T. globosa.*

*Aspergillus* spp.

*Aspergillus* species such as *A. oryzae, A. niger* and *A. sojae* are widely used microorganisms in food production and can also be used as the recombinant microorganism platform. Nucleotide sequences are available for genomes of *A. nidulans, A. fumigatus, A. oryzae, A. clavatus, A. flavus, A. niger,* and *A. terreus,* allowing rational design and modification of endogenous pathways to enhance flux and increase product yield. Metabolic models have been developed for *Aspergillus,* as well as transcriptomic studies and proteomics studies. *A. niger* is cultured for the industrial production of a number of food ingredients such as citric acid and gluconic acid, and thus species such as *A. niger* are generally suitable for producing steviol glycosides.

*Yarrowia lipolytica*

*Yarrowia lipolytica* is dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g., alkanes, fatty acids, and oils) and can grow on sugars. It has a high potential for industrial applications and is an oleaginous microorgamism. *Yarrowia lipolyptica* can accumulate lipid content to approximately 40% of its dry cell weight and is a model organism for lipid accumulation and remobilization. See e.g., Nicaud, 2012, Yeast 29(10):409-18; Beopoulos et al., 2009, *Biochimie* 91(6):692-6; Bankar et al., 2009, *Appl Microbiol Biotechnol.* 84(5):847-65.

*Rhodosporidium toruloides*

*Rhodosporidium toruloides* is oleaginous yeast and useful for engineering lipid-production pathways (See e.g. Zhu et al., 2013, *Nature Commun.* 3:1112; Ageitos et al., 2011, *Applied Microbiology and Biotechnology* 90(4):1219-27).

*Candida boidinii*

*Candida boidinii* is methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. See, e.g., Mattanovich et al., 2012, Methods Mol Biol. 824:329-58; Khoury et al., 2009, Protein Sci. 18(10):2125-38.

*Hansenula polymorpha (Pichia angusta)*

*Hansenula polymorpha* is methylotrophic yeast (see *Candida boidinii*). It can furthermore grow on a wide range of other substrates; it is thermo-tolerant and can assimilate nitrate (see also, *Kluyveromyces lactis*). It has been applied to producing hepatitis B vaccines, insulin and interferon alpha-2a for the treatment of hepatitis C, furthermore to a range of technical enzymes. See, e.g., Xu et al., 2014, *Virol Sin.* 29(6):403-9.

*Candida krusei (Issatchenkia orientalis)*

*Candida krusei*, scientific name *Issatchenkia orientalis*, is widely used in chocolate production. *C. krusei* is used to remove the bitter taste of and break down cacao beans. In addition to this species involvement in chocolate production, *C. krusei* is commonly found in the immunocompromised as a fungal nosocomial pathogen (see Mastromarino et al., New Microbiolgica, 36:229-238; 2013)

*Kluyveromyces lactis*

*Kluyveromyces lactis* is yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, FEMS Yeast Res. 6(3):381-92.

*Pichia pastoris*

*Pichia pastoris* is methylotrophic yeast (see *Candida boidinii* and *Hansenula polymorpha*). It is also commonly referred to as *Komagataella pastoris*. It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et al., 2014, *N Biotechnol.* 31(6):532-7.

*Scheffersomyces stipitis*

*Scheffersomyces stipitis* also known as *Pichia stipitis* is a homothallic yeast found in haploid form. Commonly used instead of *S. cerevisiae* due to its enhanced respiratory capacity that results from and alternative respiratory system. (See Papini et al., Microbial Cell Factories, 11:136 (2012)).

In some embodiments, a microorganism can be an insect cell such as *Drosophilia*, specifically, *Drosophilia melanogaster*.

In some embodiments, a microorganism can be an algal cell such as, for example but not limited to, *Blakeslee trispora, Dunaliella saline, Haematococcus pluvialis, Chlorella* sp., In some embodiments, a microorganism can be a cyanobacterial cell such as, for example but not limited to, *Blakeslee trispora, Dunaliella saline, Haematococcus pluvialis, Chlorella* sp., *Undaria pinnatifida, Sargassum, Laminaria japonica*, and *Scenedesmus almeriensis*.

In some embodiments, a microorganism can be a bacterial cell. Examples of bacteria include, but are not limited to, the genera *Bacillus* (e.g., *B. subtilis, B. amyloliquefaciens, B. licheniformis, B. puntis, B. megaterium, B. halodurans, B. pumilus*), *Acinetobacter, Nocardia, Xanthobacter, Escherichia* (e.g., *E. coli*), *Streptomyces, Erwinia, Klebsiella, Serratia* (e.g., *S. marcessans*), *Pseudomonas* (e.g., *P. aeruginosa*), *Salmonella* (e.g., *S. typhimurium*, and *S. typhi*). Bacterial cells may also include, but are not limited to, photosynthetic bacteria (e.g., green non-sulfur bacteria (e.g., *Choroflexus* bacteria (e.g., *C. aurantiacus*), *Chloronema* (e.g., *C. gigateum*), green sulfur bacteria (e.g., *Chlorobium* bacteria (e.g., *C. limicola*), *Pelodictyon* (e.g., *P. luteolum*), purple sulfur bacteria (e.g., *Chromatium* (e.g., *C. okenii*)), and purple non-sulfur bacteria (e.g., *Rhode-spirillum* (e.g., *R. rubrum*), *Rhodobacter* (e.g., *R. sphaeroides, R. capsulatus*), and *Rhodomicrobium* bacteria (e.g., *R. vanellii*)).

*E. coli*

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

It can be appreciated that the recombinant host cell disclosed herein can comprise a plant cell, comprising a plant cell that is grown in a plant, a mammalian cell, an insect cell, a fungal cell from *Aspergillus* genus; a yeast cell from *Saccharomyces* (e.g., *S. cerevisiae, S. bayanus, S. pastorianus*, and *S. carlsbergensis*), *Schizosaccharomyces* (e.g., *S. pombe*), *Yarrowia* (e.g., *Y. lipolytica*), *Candida* (e.g., *C. glabrata, C. albicans, C. krusei, C. revkaufi, C. pulcherrima, Candida tropicalis, C. utilis*, and *C. boidinii*), *Ashbya* (e.g., *A. gossypii*), *Cyberlindnera* (e.g., *C. jadinii*), *Pichia* (e.g., *P. pastoris* and *P. kudriavzevii*), *Kluyveromyces* (e.g., *K. lactis*), Hansenual (e.g., *H. polymorpha*), *Arxula* (e.g., *A. adeninivorans*), *Xanthophyllomyces* (e.g., *X. dendrorhous*), *Issatchenkia* (e.g., *I. orientali*), *Toruslaspora* (e.g., *T. franciscae* and *T. globosa*), *Geotrichum* (e.g., *G. candidum* and *G. klebahni*), *Zygosaccharomyces* (e.g., *Z. bisporus* and *Z. cidri*), *Yamadazyma* (e.g., *Y. philogaea*), *Lanchancea* (e.g., *L. kluyven*), *Kodamaea* (e.g., *K. ohmen*), *Brettanomyces* (e.g., *B. anomalus*), *Trichosporon* (e.g., *T. aquatile, T. beigelii*, and *T. dermatis*), *Debaromyces* (e.g., *D. hansenuis* and *D. hansenii*), *Scheffersomyces* (e.g., *S. stipis*), *Rhodosporidium* (e.g., *R. toruloides*), *Pachysolen* (e.g., *P. tannophilus*), and *Physcomitrella, Rhodotorula, Kazachstania, Gibberella, Agaricus*, and *Phanerochaete* genera; an insect cell including, but not limited to, *Drosophilia melanogaster*, an algal cell including, but not limited to, *Blakeslea trispora, Dunaliella Haematococcus pluvialis, Chlorella* sp., *Undaria pinnatifida, Sargassum, Laminaria japonica*, and *Scenedes-*

*mus almeriensis* species; or a bacterial cell from *Bacillus* genus (e.g., *B. subtilis, B. amyloliquefaciens, B. licheniformis, B. puntis, B. megaterium, B. halodurans,* and *B. pumilus*) *Acinetobacter, Nocardia, Xanthobacter* genera, *Escherichia* (e.g., *E. coli*), *Streptomyces, Erwinia, Klebsiella, Serratia* (e.g., *S. marcessans*), *Pseudomonas* (e.g., *P. aeruginosa*), *Salmonella* (e.g., *S. typhimurium* and *S. typhi*), and further including, *Choroflexus* bacteria (e.g., *C. aurantiacus*), *Chloronema* (e.g., *C. gigateum*), green sulfur bacteria (e.g., *Chlorobium* bacteria (e.g., *C. limicola*), *Pelodictyon* (e.g., *P. luteolum*)), purple sulfur bacteria (e.g., *Chromatium* (e.g., *C. okenii*)), and purple non-sulfur bacteria (e.g., *Rhode-spirillum* (e.g., *R. rubrum*), *Rhodobacter* (e.g., *R. sphaeroides* and *R. capsulatus*), and *Rhodomicrobium* bacteria (e.g., *R. vanellii*).

Steviol Glycoside Compositions

Steviol glycosides do not necessarily have equivalent performance in different food systems. It is therefore desirable to have the ability to direct the synthesis to steviol glycoside compositions of choice. Recombinant hosts described herein can produce compositions that are selectively enriched for specific steviol glycosides (e.g., RebD or RebM) and have a consistent taste profile. As used herein, the term "enriched" is used to describe a steviol glycoside composition with an increased proportion of a particular steviol glycoside, compared to a steviol glycoside composition (extract) from a stevia plant. Thus, the recombinant hosts described herein can facilitate the production of compositions that are tailored to meet the sweetening profile desired for a given food product and that have a proportion of each steviol glycoside that is consistent from batch to batch. In some embodiments, hosts described herein do not produce or produce a reduced amount of undesired plant by-products found in Stevia extracts. Thus, steviol glycoside compositions produced by the recombinant hosts described herein are distinguishable from compositions derived from Stevia plants.

The amount of an individual steviol glycoside (e.g., RebA, RebB, RebD, or RebM) accumulated can be from about 1 to about 7,000 mg/L, e.g., about 1 to about 10 mg/L, about 3 to about 10 mg/L, about 5 to about 20 mg/L, about 10 to about 50 mg/L, about 10 to about 100 mg/L, about 25 to about 500 mg/L, about 100 to about 1,500 mg/L, or about 200 to about 1,000 mg/L, at least about 1,000 mg/L, at least about 1,200 mg/L, at least about at least 1,400 mg/L, at least about 1,600 mg/L, at least about 1,800 mg/L, at least about 2,800 mg/L, or at least about 7,000 mg/L. In some aspects, the amount of an individual steviol glycoside can exceed 7,000 mg/L. The amount of a combination of steviol glycosides (e.g., RebA, RebB, RebD, or RebM) accumulated can be from about 1 mg/L to about 7,000 mg/L, e.g., about 200 to about 1,500, at least about 2,000 mg/L, at least about 3,000 mg/L, at least about 4,000 mg/L, at least about 5,000 mg/L, at least about 6,000 mg/L, or at least about 7,000 mg/L. In some aspects, the amount of a combination of steviol glycosides can exceed 7,000 mg/L. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce steviol and/or steviol glycosides. For example, a first microorganism can comprise one or more biosynthesis genes for producing a steviol glycoside precursor, while a second microorganism comprises steviol glycoside biosynthesis genes. The product produced by the second, or final microorganism is then recovered. It will also be appreciated that in some embodiments, a recombinant microorganism is grown using nutrient sources other than a culture medium and utilizing a system other than a fermenter.

Alternatively, the two or more microorganisms each can be grown in a separate culture medium and the product of the first culture medium, e.g., steviol, can be introduced into second culture medium to be converted into a subsequent intermediate, or into an end product such as RebA. The product produced by the second, or final microorganism is then recovered. It will also be appreciated that in some embodiments, a recombinant microorganism is grown using nutrient sources other than a culture medium and utilizing a system other than a fermenter.

Steviol glycosides and compositions obtained by the methods disclosed herein can be used to make food products, dietary supplements and sweetener compositions. See, e.g., WO 2011/153378, WO 2013/022989, WO 2014/122227, and WO 2014/122328.

For example, substantially pure steviol or steviol glycoside such as RebM or RebD can be included in food products such as ice cream, carbonated 2s, fruit juices, yogurts, baked goods, chewing gums, hard and soft candies, and sauces. Substantially pure steviol or steviol glycoside can also be included in non-food products such as pharmaceutical products, medicinal products, dietary supplements and nutritional supplements. Substantially pure steviol or steviol glycosides may also be included in animal feed products for both the agriculture industry and the companion animal industry. Alternatively, a mixture of steviol and/or steviol glycosides can be made by culturing recombinant microorganisms separately, each producing a specific steviol or steviol glycoside, recovering the steviol or steviol glycoside in substantially pure form from each microorganism and then combining the compounds to obtain a mixture comprising each compound in the desired proportion. The recombinant microorganisms described herein permit more precise and consistent mixtures to be obtained compared to current Stevia products.

In another alternative, a substantially pure steviol or steviol glycoside can be incorporated into a food product along with other sweeteners, e.g., saccharin, dextrose, sucrose, fructose, erythritol, aspartame, sucralose, monatin, or acesulfame potassium. The weight ratio of steviol or steviol glycoside relative to other sweeteners can be varied as desired to achieve a satisfactory taste in the final food product. See, e.g., U.S. 2007/0128311. In some embodiments, the steviol or steviol glycoside may be provided with a flavor (e.g., citrus) as a flavor modulator.

Compositions produced by a recombinant microorganism described herein can be incorporated into food products. For example, a steviol glycoside composition produced by a recombinant microorganism can be incorporated into a food product in an amount ranging from about 20 mg steviol glycoside/kg food product to about 1800 mg steviol glycoside/kg food product on a dry weight basis, depending on the type of steviol glycoside and food product. For example, a steviol glycoside composition produced by a recombinant microorganism can be incorporated into a dessert, cold confectionary (e.g., ice cream), dairy product (e.g., yogurt), or beverage (e.g., a carbonated beverage) such that the food product has a maximum of 500 mg steviol glycoside/kg food on a dry weight basis. A steviol glycoside composition produced by a recombinant microorganism can be incorporated into a baked good (e.g., a biscuit) such that the food product has a maximum of 300 mg steviol glycoside/kg food on a dry weight basis. A steviol glycoside composition produced by a recombinant microorganism can be incorporated into a sauce (e.g., chocolate syrup) or vegetable product (e.g., pickles) such that the food product has a maximum of 1000 mg steviol glycoside/kg food on a dry weight basis. A steviol glycoside composition produced by a recombinant microorganism can be incorporated into bread such that the food product has a maximum of 160 mg steviol glycoside/kg food on a dry weight basis. A steviol glycoside composition produced by a recombinant microorganism, plant, or plant cell can be incorporated into a hard or soft candy such that the food product has a maximum of 1600 mg steviol glycoside/kg food on a dry weight basis. A steviol glycoside composition produced by a recombinant microorganism, plant, or plant cell can be incorporated into a processed fruit product (e.g., fruit juices, fruit filling, jams, and jellies) such that the food product has a maximum of 1000 mg steviol glycoside/kg food on a dry weight basis. In some embodiments, a steviol glycoside composition produced herein is a component of a pharmaceutical composition. See, e.g., Steviol Glycosides Chemical and Technical Assessment 69th JECFA, 2007, prepared by Harriet Wallin, Food Agric. Org.; EFSA Panel on Food Additives and Nutrient Sources added to Food (ANS), "Scientific Opinion on the safety of steviol glycosides for the proposed uses as a food additive," 2010, EFSA Journal 8(4):1537; U.S. Food and Drug Administration GRAS Notice 323; U.S Food and Drug Administration GRAS Notice 329; WO 2011/037959; WO 2010/146463; WO 2011/046423; and WO 2011/056834.

For example, such a steviol glycoside composition can have from 90-99 weight % RebA and an undetectable amount of stevia plant-derived contaminants, and be incorporated into a food product at from 25-1600 mg/kg, e.g., 100-500 mg/kg, 25-100 mg/kg, 250-1000 mg/kg, 50-500 mg/kg or 500-1000 mg/kg on a dry weight basis.

Such a steviol glycoside composition can be a RebB-enriched composition having greater than 3 weight % RebB and be incorporated into the food product such that the amount of RebB in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebB-enriched composition has an undetectable amount of stevia plant-derived contaminants.

Such a steviol glycoside composition can be a RebD-enriched composition having greater than 3 weight % RebD and be incorporated into the food product such that the amount of RebD in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebD-enriched composition has an undetectable amount of stevia plant-derived contaminants.

Such a steviol glycoside composition can be a RebE-enriched composition having greater than 3 weight % RebE and be incorporated into the food product such that the amount of RebE in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebE-enriched composition has an undetectable amount of stevia plant-derived contaminants.

Such a steviol glycoside composition can be a RebM-enriched composition having greater than 3 weight % RebM and be incorporated into the food product such that the amount of RebM in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebM-enriched composition has an undetectable amount of stevia plant-derived contaminants.

In some embodiments, a substantially pure steviol or steviol glycoside is incorporated into a tabletop sweetener or "cup-for-cup" product. Such products typically are diluted to the appropriate sweetness level with one or more bulking agents, e.g., maltodextrins, known to those skilled in the art. Steviol glycoside compositions enriched for RebA, RebB, RebD, RebE, or RebM, can be package in a sachet, for example, at from 10,000 to 30,000 mg steviol glycoside/kg product on a dry weight basis, for tabletop use. In some embodiments, a steviol glycoside produced in vitro, in vivo, or by whole cell bioconversion The invention will be further described in the following examples, which do not limit the scope of the invention described in the claims.

EXAMPLES

The Examples that follow are illustrative of specific embodiments of the invention, and various uses thereof. They are set forth for explanatory purposes only, and are not to be taken as limiting the invention.

Example 1. UGT74G1 Variant Expression

A set of 154 possible mutations at 149 positions of the UGT74G1 polypeptide of SEQ ID NO:4 was identified through modeling as described above in "Functional Homologs" (See Table 1). A library of 179 UGT74G1 variants (i.e., functional homologs) including one or more identified mutations was prepared (SEQ ID NO:3, SEQ ID NO:4). See Table 2.

TABLE 1

UGT74G1 Mutation Set

| | | | |
|---|---|---|---|
| L15V | Q140N | Y257F | F357W |
| I16L | A141S | A259P | E357W |
| F18Y | V143A | E263A | I364L |
| L20A | S146N | M265I | V370M |
| F27M | L147I | N266K | V371I |
| I28L | I156L | N266E | M373V |
| F30L | E162T | D269N | Q375L |
| G31S | V166L | E274G | F376W |
| G31A | F169L | A280S | S377T |
| T49I | Q173E | L284M | T380S |
| N51K | E176D | V285A | L385F |
| Q67E | L179S | H287L | D387E |
| A68T | I180F | V292M | E388D |
| C73F | L181V | I295L | I389V |
| E75D | N183D | I295M | L390W |
| M79A | H184P | T296A | G391K |
| E83D | E185G | R297W | V396A |
| E83K | Q186S | A298G | N401K |
| S84A | I187Y | I300K | G407E |
| L86I | Q188P | D301N | N408E |
| E87D | S189A | D303N | L409I |
| T88R | W191F | I310V | A410E |
| K90W | S192D | K311R | S411D |
| Q91E | Q193M | K313S | M415E |
| S96T | M194V | E315Q | I416V |
| D99E | L195V | G316A | E419G |
| E107S | A200S | E320K | I424E |
| T110P | Q204K | L322F | R426K |
| I111V | F209L | V325E | K427E |
| A113C | N211H | I326T | D434E |
| I115V | S212T | T328S | N448K |
| M119F | K215E | G329E | D449N |
| T120L | I221V | L332I | S455A |
| E121P | E222D | I333V | E456K |

TABLE 1-continued

UGT74G1 Mutation Set

| | | | |
|---|---|---|---|
| V123A | T224M | A335S | I458V |
| I128K | V232T | K338P | |
| E129Q | L237I | D341E | |
| G135A | D247E | E346P | |
| S136A | N252Y | E346K | |
| | N255S | S347A | |

TABLE 2

UGT74G1 Variant Library

| Variant No. | Mutation 1 | Mutation 2 | Mutation 3 |
|---|---|---|---|
| 1 | E456K | N255S | N401K |
| 2 | V370M | N448K | M194V |
| 3 | A200S | E129Q | Q140N |
| 4 | L390W | N266K | S192D |
| 5 | E320K | N266K | M194V |
| 6 | M265I | I364L | I187Y |
| 7 | E315Q | E129Q | S192D |
| 8 | E222D | N408E | Q140N |
| 9 | M119F | N255S | A298G |
| 10 | D269N | R426K | S146N |
| 11 | E185G | A298G | Q193M |
| 12 | V232T | E388D | Q140N |
| 13 | G316A | V325E | I187Y |
| 14 | L409I | D301N | H184P |
| 15 | S189A | S146N | I389V |
| 16 | V143A | I416V | H184P |
| 17 | S455A | Q193M | E346K |
| 18 | R297W | S347A | E346K |
| 19 | D341E | Q193M | L332I |
| 20 | D434E | T380S | I389V |
| 21 | T328S | A280S | L332I |
| 22 | Q375L | E419G | R426K |
| 23 | I221V | K338P | I295M |
| 24 | T296A | I128K | L332I |
| 25 | D449N | G407E | H287L |
| 26 | T110P | K338P | E346P |
| 27 | E121P | I416V | H287L |
| 28 | L284M | I424E | E346K |
| 29 | K427E | K338P | I424E |
| 30 | D303N | N408E | I300K |
| 31 | D247E | D301N | E346P |
| 32 | F376W | N448K | I128K |
| 33 | K313S | I187Y | I128K |
| 34 | G329E | G407E | N266E |
| 35 | I111V | M415E | H287L |
| 36 | G391K | T380S | I389V |
| 37 | V396A | N448K | S347A |
| 38 | I310V | V371I | N266E |
| 39 | Y257F | N401K | W191F |
| 40 | S136A | I364L | I424E |
| 41 | V292M | E419G | I364L |
| 42 | D99E | L322F | S192D |
| 43 | C73F | S146N | T380S |
| 44 | A259P | V371I | K90W |
| 45 | T49I | A280S | A113C |
| 46 | V123A | M194V | T88R |
| 47 | L181V | A280S | L86I |
| 48 | N252Y | E129Q | F30L |
| 49 | A68T | L322F | A113C |
| 50 | S212T | F357W | F30L |
| 51 | E75D | I300K | F357W |
| 52 | A335S | G407E | Q91E |
| 53 | I16L | A113C | M415E |
| 54 | G31S | N255S | I295M |
| 55 | S377T | E388D | L86I |
| 56 | I180F | H184P | E83K |
| 57 | Q188P | N408E | E83K |
| 58 | K311R | W191F | F27M |
| 59 | L195V | L20A | E346P |
| 60 | M79A | V325E | M415E |
| 61 | Q67E | N401K | D301N |
| 62 | S84A | S347A | I295M |
| 63 | A141S | F27M | V371I |
| 64 | L179S | N266K | E83K |
| 65 | Q186S | W191F | T88R |
| 66 | A410E | A298G | L20A |
| 67 | K311R | W191F | F27M |
| 68 | V285A | E388D | L20A |
| 69 | E176D | L322F | K90W |
| 70 | F169L | K90W | N266E |
| 71 | F18Y | I416V | F27M |
| 72 | E87D | Q91E | I300K |
| 73 | E274G | L86I | F30L |
| 74 | E83D | R426K | Q91E |
| 75 | S96T | V325E | T88R |
| 76 | E176D | F357W | |
| 77 | S377T | | |
| 78 | M119F | | |
| 79 | E456K | | |
| 80 | L181V | | |
| 81 | L385F | | |
| 82 | N183D | | |
| 83 | E176D | | |
| 84 | F209L | | |
| 85 | N211H | | |
| 86 | V143A | | |
| 87 | R297W | | |
| 88 | A410E | | |
| 89 | L390W | | |
| 90 | N252Y | | |
| 91 | S212T | | |
| 92 | V232T | | |
| 93 | I115V | | |
| 94 | G329E | | |
| 95 | T224M | | |
| 96 | I295L | | |
| 97 | T328S | | |
| 98 | L409I | | |
| 99 | D387E | | |
| 100 | D449N | | |
| 101 | V123A | | |
| 102 | M373V | | |
| 103 | V285A | | |
| 104 | Q204K | | |
| 105 | S189A | | |
| 106 | D247E | | |
| 107 | G135A | | |
| 108 | I111V | | |
| 109 | T120L | | |
| 110 | G316A | | |
| 111 | Q173E | | |
| 112 | V166L | | |
| 113 | I221V | | |
| 114 | L147I | | |
| 115 | F376W | | |
| 116 | L284M | | |
| 117 | E162T | | |
| 118 | Q375L | | |
| 119 | S136A | | |
| 120 | E315Q | | |
| 121 | I333V | | |
| 122 | M265I | | |
| 123 | A141S | | |
| 124 | E107S | | |
| 125 | E185G | | |
| 126 | V396A | | |
| 127 | L237I | | |
| 128 | Q186S | | |
| 129 | E320K | | |
| 130 | A200S | | |
| 131 | L195V | | |
| 132 | Q188P | | |
| 133 | Y257F | | |
| 134 | D269N | | |
| 135 | D341E | | |
| 136 | D434E | | |
| 137 | K313S | | |
| 138 | L179S | | |

TABLE 2-continued

UGT74G1 Variant Library

| Variant No. | Mutation 1 | Mutation 2 | Mutation 3 |
|---|---|---|---|
| 139 | S455A | | |
| 140 | E263A | | |
| 141 | K311R | | |
| 142 | A259P | | |
| 143 | T110P | | |
| 144 | V292M | | |
| 145 | I326T | | |
| 146 | T296A | | |
| 147 | E222D | | |
| 148 | G391K | | |
| 149 | K215E | | |
| 150 | I310V | | |
| 151 | I156L | | |
| 152 | D303N | | |
| 153 | E121P | | |
| 154 | V370M | | |
| 155 | K427E | | |
| 156 | I180F | | |
| 157 | E274G | | |
| 158 | I458V | | |
| 159 | A335S | | |
| 160 | S411D | | |
| 161 | F169L | | |
| 162 | L15V | | |
| 163 | F18Y | | |
| 164 | M79A | | |
| 165 | E87D | | |
| 166 | G31S | | |
| 167 | E83D | | |
| 168 | N51K | | |
| 169 | E75D | | |
| 170 | T49I | | |
| 171 | D99E | | |
| 172 | S96T | | |
| 173 | C73F | | |
| 174 | S84A | | |
| 175 | A68T | | |
| 176 | Q67E | | |
| 177 | I16L | | |
| 178 | I28L | | |
| 179 | G31A | | |

Competent *E. coli* cells were transformed with vectors expressing the UGT74G1 variants of Table 2. After transformation, 80 μL of each culture was transferred into 800 μL of standard lysogeny broth (LB) medium containing 100 μg/mL ampicillin and 50 μg/mL chloramphenicol and incubated at 37° C. for 18 hours, shaking at 300 rpm. Glycerol stocks of the transformed cells (25% glycerol) were prepared and stored at −80° C.

1 mL of auto-induction pre-culture medium containing 100 μg/mL ampicillin and 50 μg/mL chloramphenicol was inoculated with 10 μL of a glycerol stock prepared as described in the previous paragraph and incubated in a 96-well plate for 20 hours at 25° C., shaking at 300 rpm. 1 mL of auto-induction medium containing 100 μg/mL ampicillin and 50 μg/mL chloramphenicol was then inoculated with an amount of pre-culture sample sufficient to provide an initial OD of 0.2 (~20-25 μL of pre-culture) and incubated for 18 hours at 25° C., shaking at 300 rpm. Cells were then pelleted by centrifugation at 3500 rpm for 15 minutes at 4° C. The supernatant was discarded by inverting the plate and subsequently tapping the inverted plate on tissue paper. Pellets were then frozen at −80° C. for at least 15 minutes.

After thawing cell pellets in a water bath at room temperature, binding and lysozyme buffer with protease inhibitor (Tris-HCl 20 mM pH8, NaCl 0.5 M, Imidazole 20 mM, Lysozyme 0.2 mg/ml, DNase I 20 μg/ml, $MgCl_2$ 1 mM, protease inhibitor complete mini-tablet 1×) was added to the wells in an amount of 1 mL per 100 mg cells (~250 μL). Cells were resuspended on an orbital shaker at 300 rpm for 15 minutes at 20° C., and then incubated for 2 hours at 4° C. After incubation, cells were lysed via one or more freeze-thaw cycles, and then clarified by centrifugation at 3000 g for 15 minutes at 4° C. The supernatant was transferred to a clean 96-well plate and diluted with glycerol (40% glycerol). Samples were stored at −20° C.

Example 2. UGT74G1 Variant Activity Assay

60 μL of reaction mixtures in 96-well plates prepared according to Table 3 were incubated at 30° C., shaking at 75-100 rpm for 2h. The reaction was then quenched by diluting the mixture 1:5 in pure methanol and centrifuged at 3500 rpm for 15 minutes. The supernatant was isolated and stored at −80° C. until LC-MS analysis.

TABLE 3

Activity Assay Reaction Mixture

| Component | Concentration |
|---|---|
| Potassium Phosphate Buffer (pH 7.5) | 50 mM |
| UDP-glucose | 1 mM |
| ent-kaurenoic acid | 0.1 mM |
| Steviol-13-O-glucoside | 0.03 mM |
| Steviol | 0.03 mM |
| Clarified cell lysate | 20% (v/v) |
| Alkaline phosphatase enzyme | 1% (v/v) |
| DMSO | 4% (v/v) |
| Triton X-100 | 0.1% (v/v) |

A 5 μL sample of the quenched reaction mixture was injected into a Water Acquity UPLC system (Milford, USA) coupled to a Bruker mictoTOF-Q II mass detector (Bremen, Germany). Separation of the compounds was achieved on a Waters Acquity UPLC® BEH C18 column (1.7 μm, 2.1 mm×50 mm) kept at 55° C., using a gradient of two mobile phases: A (water with 5 mM ammonium formate, pH 9.0) and B (acetonitrile) at a flow of 0.6 mL/min. The gradient profile consisted of 25% B for 0.3 minutes, a linear gradient from 25% B to 85% B over 2 minutes, a 100% B wash for 1 minute, and finally 35% B for 0.6 minutes. The mass analyzer was equipped with electrospray ionization (ESI) source and operated in negative mode. The capillary voltage was 3.5 kV, the source was kept at 180° C., and the desolvation gas flow and nebulizer pressure were 8 L/min and 1.6 bar, respectively.

Compounds of interest were tracked in MS full scan mode (120-800 m/z range) and quantification was performed post-acquisition by extracting ions from the total ion chromatogram. Extracted-ion chromatograms (EICs) provided semi-quantification of steviol-13-O-glucoside (13-SMG) (525.3 m/z [M+Fa-H]$^-$), kaurenoic acid (KA) (301.2 m/z [M-H]$^-$), rubusoside (rubu) (687.3 m/z [M+Fa-H]$^-$), and steviol (317.2 m/z [M-H]), using one-point calibration with 10 μM authentic standards using Bruker QuantAnalysis software. Steviol-19-O-glucoside (19-SMG) (525.3 [M+Fa-H]$^-$) and kaurenoate-19-O-glucoside (19-KMG) (509.3 m/z [M+Fa-H]$^-$) concentrations were estimated as 13-SMG equivalents, using corrected response factors. Results are shown in Table 4.

TABLE 4

UGT74G1 Variant Activity

| Variant No. | 13-SMG | Steviol | KA | Rubu | 19-SMG* | 19-KMG* |
|---|---|---|---|---|---|---|
| 4 | 2.34 | 9.99 | 61.34 | 25.56 | 17.55 | 34.71 |
| 6 | 3.73 | 12.77 | 63.41 | 24.43 | 14.96 | 29.65 |
| 7 | 3.01 | 12.23 | 59.29 | 23.83 | 14.96 | 26.88 |
| 8 | 13.10 | 24.74 | 97.94 | 14.75 | 1.57 | 2.08 |
| 9 | 13.59 | 23.08 | 87.98 | 14.01 | 2.15 | 2.71 |
| 11 | 2.52 | 8.33 | 48.34 | 23.16 | 19.58 | 42.29 |
| 12 | 16.26 | 25.48 | 94.98 | 10.87 | 1.23 | 1.33 |
| 15 | 14.99 | 22.83 | 89.16 | 10.54 | 1.78 | 2.45 |
| 16 | 2.88 | 5.13 | 36.77 | 21.15 | 20.05 | 52.82 |
| 20 | 4.59 | 4.26 | 19.32 | 26.21 | 25.46 | 87.90 |
| 23 | 3.57 | 4.26 | 19.96 | 23.28 | 23.89 | 75.21 |
| 26 | 4.69 | 4.76 | 18.63 | 24.10 | 23.66 | 82.00 |
| 28 | 3.65 | 4.05 | 17.03 | 24.58 | 24.72 | 83.14 |
| 29 | 4.58 | 5.18 | 19.70 | 22.30 | 22.28 | 75.43 |
| 32 | 4.25 | 4.76 | 17.13 | 21.99 | 23.24 | 78.66 |
| 38 | 2.62 | 2.80 | 14.66 | 21.82 | 21.81 | 77.28 |
| 39 | 2.53 | 2.52 | 12.91 | 22.32 | 23.86 | 79.53 |
| 42 | 3.38 | 19.73 | 82.66 | 28.77 | 11.20 | 18.37 |
| 43 | 3.24 | 18.61 | 82.21 | 27.82 | 9.52 | 17.38 |
| 44 | 2.89 | 14.60 | 71.56 | 24.54 | 12.04 | 21.30 |
| 45 | 3.06 | 11.95 | 61.62 | 23.70 | 15.42 | 29.74 |
| 46 | 3.18 | 17.69 | 72.26 | 22.07 | 7.72 | 15.17 |
| 50 | 2.34 | 6.37 | 44.47 | 22.18 | 18.63 | 43.54 |
| 52 | 5.95 | 6.00 | 22.43 | 32.80 | 32.29 | 110.42 |
| 55 | 13.51 | 18.39 | 73.61 | 10.63 | 5.78 | 9.68 |
| 56 | 3.04 | 4.34 | 26.78 | 23.23 | 22.25 | 67.34 |
| 60 | 4.24 | 4.61 | 18.73 | 21.98 | 21.98 | 77.35 |
| 61 | 3.44 | 3.82 | 15.99 | 22.99 | 22.50 | 77.44 |
| 62 | 3.12 | 3.68 | 17.19 | 21.93 | 22.94 | 77.94 |
| 63 | 3.37 | 3.08 | 15.05 | 23.00 | 23.67 | 79.82 |
| 64 | 3.06 | 3.34 | 16.67 | 21.64 | 23.09 | 78.07 |
| 65 | 2.81 | 3.43 | 13.66 | 23.56 | 23.68 | 78.43 |
| 66 | 2.68 | 2.91 | 14.22 | 22.88 | 22.18 | 81.72 |
| 67 | 2.92 | 2.61 | 13.09 | 23.06 | 23.23 | 82.22 |
| 68 | 3.20 | 3.13 | 13.73 | 22.02 | 22.86 | 78.44 |
| 69 | 28.66 | 28.17 | 99.32 | 0.00 | 0.00 | 0.00 |
| 70 | 27.93 | 25.44 | 99.83 | 0.00 | 0.00 | 0.00 |
| 71 | 4.46 | 5.17 | 26.51 | 24.49 | 24.73 | 75.00 |
| 72 | 5.38 | 5.13 | 22.50 | 25.62 | 25.30 | 82.77 |
| 73 | 3.05 | 3.73 | 26.10 | 22.31 | 21.39 | 63.87 |
| 74 | 3.57 | 3.32 | 15.94 | 27.46 | 25.24 | 90.20 |
| 75 | 4.15 | 3.93 | 19.42 | 22.87 | 22.67 | 74.63 |
| 76 | 4.02 | 4.59 | 26.21 | 21.32 | 22.61 | 64.74 |
| 77 | 9.43 | 21.10 | 89.01 | 21.77 | 7.56 | 9.77 |
| 78 | 7.50 | 22.54 | 88.99 | 20.52 | 3.98 | 6.03 |
| 79 | 7.72 | 22.20 | 89.16 | 18.67 | 3.73 | 5.41 |
| 80 | 2.79 | 7.03 | 51.82 | 25.74 | 20.71 | 47.77 |
| 81 | 2.40 | 6.90 | 50.09 | 23.24 | 18.63 | 41.50 |
| 82 | 7.18 | 6.97 | 27.31 | 34.42 | 17.24 | 53.56 |
| 83 | 16.67 | 23.33 | 86.84 | 11.50 | 1.54 | 2.24 |
| 84 | 4.09 | 4.23 | 27.50 | 22.93 | 23.07 | 64.68 |
| 87 | 5.04 | 4.95 | 22.57 | 24.34 | 22.85 | 71.84 |
| 88 | 4.71 | 5.05 | 19.64 | 26.62 | 26.73 | 91.63 |
| 89 | 5.02 | 5.06 | 19.78 | 26.61 | 25.35 | 88.49 |
| 90 | 4.01 | 3.94 | 22.04 | 24.12 | 22.94 | 74.25 |
| 94 | 4.55 | 5.01 | 20.99 | 24.69 | 24.73 | 83.53 |
| 95 | 3.96 | 4.28 | 17.84 | 26.80 | 26.00 | 88.13 |
| 98 | 3.36 | 4.07 | 17.02 | 27.03 | 25.99 | 88.04 |
| 99 | 3.59 | 3.80 | 16.11 | 27.60 | 25.94 | 89.85 |
| 100 | 3.98 | 4.26 | 21.80 | 22.37 | 23.52 | 72.60 |
| 103 | 4.01 | 4.34 | 17.46 | 25.87 | 24.72 | 83.42 |
| 104 | 3.72 | 4.08 | 16.68 | 26.42 | 27.23 | 91.74 |
| 107 | 4.22 | 4.65 | 20.34 | 23.72 | 22.30 | 75.33 |
| 108 | 4.05 | 4.21 | 19.38 | 24.24 | 23.42 | 79.05 |
| 110 | 3.05 | 3.42 | 15.34 | 26.99 | 27.24 | 92.27 |
| 111 | 4.62 | 4.91 | 19.76 | 23.59 | 23.89 | 81.07 |
| 113 | 2.82 | 3.65 | 18.67 | 24.09 | 23.54 | 79.07 |
| 114 | 4.14 | 4.22 | 18.60 | 24.32 | 24.90 | 85.59 |
| 115 | 5.16 | 5.09 | 18.96 | 23.57 | 23.45 | 77.95 |
| 116 | 3.02 | 3.65 | 17.47 | 24.52 | 24.33 | 81.05 |
| 117 | 4.27 | 4.26 | 18.71 | 23.66 | 24.46 | 82.38 |
| 118 | 3.36 | 3.28 | 16.53 | 24.74 | 23.83 | 77.63 |
| 121 | 4.46 | 4.73 | 18.35 | 24.31 | 23.66 | 84.87 |
| 122 | 3.04 | 3.96 | 16.01 | 25.28 | 25.16 | 86.71 |
| 123 | 3.69 | 3.63 | 17.05 | 24.57 | 23.66 | 83.40 |
| 124 | 3.55 | 4.26 | 19.29 | 22.12 | 22.58 | 73.14 |
| 129 | 3.04 | 3.15 | 15.76 | 25.55 | 23.29 | 84.24 |
| 130 | 3.78 | 3.88 | 15.91 | 24.18 | 25.77 | 86.22 |
| 131 | 3.63 | 4.00 | 16.07 | 24.11 | 24.95 | 84.21 |
| 132 | 3.18 | 3.42 | 16.69 | 23.65 | 23.83 | 80.85 |
| 137 | 2.51 | 2.85 | 14.32 | 25.23 | 24.84 | 85.27 |
| 138 | 3.40 | 3.36 | 16.04 | 23.90 | 23.14 | 80.14 |
| 139 | 2.78 | 3.10 | 14.81 | 25.22 | 24.64 | 87.95 |
| 143 | 3.05 | 3.45 | 15.39 | 24.22 | 23.43 | 84.29 |
| 144 | 4.01 | 4.42 | 16.59 | 22.99 | 23.26 | 81.73 |
| 145 | 3.17 | 3.58 | 15.45 | 23.43 | 25.04 | 86.51 |
| 146 | 3.18 | 3.53 | 14.27 | 23.86 | 24.50 | 82.34 |
| 150 | 2.99 | 3.81 | 15.75 | 22.67 | 23.64 | 81.30 |
| 151 | 3.03 | 3.85 | 16.03 | 22.54 | 22.73 | 80.26 |
| 152 | 3.44 | 3.65 | 15.70 | 22.86 | 22.64 | 80.63 |
| 153 | 2.83 | 2.72 | 13.74 | 24.30 | 23.98 | 86.19 |
| 154 | 2.97 | 3.38 | 15.64 | 22.23 | 22.64 | 78.53 |
| 155 | 3.02 | 3.75 | 15.35 | 22.32 | 23.06 | 80.09 |
| 156 | 2.89 | 3.03 | 14.86 | 22.44 | 22.67 | 77.55 |
| 161 | 26.48 | 25.52 | 95.94 | 1.21 | 0.21 | 0.18 |
| 162 | 1.96 | 14.27 | 69.61 | 23.43 | 10.27 | 16.84 |
| 164 | 4.01 | 4.05 | 17.63 | 26.21 | 25.30 | 84.15 |
| 166 | 3.03 | 3.43 | 18.76 | 23.88 | 23.38 | 79.46 |
| 167 | 2.87 | 3.35 | 15.12 | 25.15 | 24.54 | 81.59 |
| 169 | 3.30 | 3.58 | 15.76 | 25.05 | 24.19 | 86.24 |
| 170 | 3.69 | 3.62 | 16.20 | 23.60 | 23.22 | 76.74 |
| 173 | 4.48 | 4.43 | 18.75 | 21.11 | 21.51 | 72.60 |
| 174 | 2.71 | 2.89 | 14.68 | 23.55 | 24.16 | 80.31 |
| 176 | 3.70 | 3.68 | 16.07 | 22.98 | 24.34 | 87.92 |
| 177 | 3.06 | 3.01 | 14.09 | 23.47 | 22.76 | 80.44 |
| 178 | 3.25 | 3.31 | 15.04 | 21.65 | 24.07 | 80.23 |
| 179 | 2.75 | 3.04 | 14.06 | 21.89 | 22.67 | 76.74 |

*estimated as 13-SMG equivalents.

The results, provided in Table 4, show that UGT74G1 variants produce one or more steviol glycosides or glycosides of a steviol precursor in relative amounts different than those of a wild-type UGT74G1 polypeptide. For example, several of the variants of Table 4 produce rubusoside and 19-SMG in relative amounts different than those of a wild-type UGT74G1 polypeptide (see e.g., Example 21 of WO 2011/153378).

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

TABLE 5

Sequences disclosed herein.

SEQ ID NO: 3
*S. rebaudiana*

TABLE 5-continued

Sequences disclosed herein.

```
atggcagagc aacaaaagat caaaaagtca cctcacgtct tacttattcc atttcctctg    60
caaggacata tcaacccatt catacaattt gggaaaagat tgattagtaa gggtgtaaag   120
acaacactgg taaccactat ccacactttg aattctactc tgaaccactc aaatactact   180
actacaagta tagaaattca agctatatca gacggatgcg atgagggtgg ctttatgtct   240
gccggtgaat cttacttgga aacattcaag caagtgggat ccaagtctct ggccgatcta   300
atcaaaaagt tacagagtga aggcaccaca attgacgcca taatctacga ttctatgaca   360
gagtgggttt tagacgttgc tatcgaattt ggtattgatg gaggttcctt tttcacacaa   420
gcatgtgttg tgaattctct atactaccat gtgcataaag ggttaatctc tttaccattg   480
ggtgaaactg tttcagttcc aggttttcca gtgttacaac gttgggaaac cccattgatc   540
ttacaaaatc atgaacaaat acaatcacct tggtcccaga tgttgtttgg tcaattcgct   600
aacatcgatc aagcaagatg ggtctttact aattcattct ataagttaga ggaagaggta   660
attgaatgga ctaggaagat ctggaatttg aaagtcattg gtccaacatt gccatcaatg   720
tatttggaca aaagacttga tgatgataaa gataatggtt caatttgta caaggctaat   780
catcacgaat gtatgaattg gctggatgac aaaccaaagg aatcagttgt atatgttgct   840
ttcggctctc ttgttaaaca tggtccagaa caagttgagg agattacaag agcacttata   900
gactctgacg taaactttt gtgggtcatt aagcacaaag aggagggaa actgccagaa    960
aaccttctg aagtgataaa gaccggaaaa ggtctaatcg ttgcttggtg taaacaattg  1020
gatgtttag ctcatgaatc tgtaggctgt tttgtaacac attgcggatt caactctaca   1080
ctagaagcca tttccttagg cgtacctgtc gttgcaatgc ctcagtttc cgatcagaca   1140
accaacgcta aacttttgga cgaaatacta ggggtgggtg tcagagttaa agcagacgag  1200
aatggtatcg tcagaagagg gaacctagct tcatgtatca aaatgatcat ggaagaggaa  1260
agaggagtta tcataaggaa aaacgcagtt aagtggaagg atcttgcaaa ggttgccgtc  1320
catgaaggcg gctcttcaga taatgatatt gttgaatttg tgtccgaact aatcaaagcc  1380
taa                                                                1383
```

SEQ ID NO: 4
S. rebaudiana
```
MAEQQKIKKS PHVLLIPFPL QGHINPFIQF GKRLISKGVK TTLVITIHTL NSTLNHSNTT    60
TTSIEIQAIS DGCDEGGFMS AGESYLETFK QVGSKSLADL IKKLQSEGTT IDAIIYDSMT   120
EWVLDVAIEF GIDGGSFFTQ ACVVNSLYYH VHKGLISLPL GETVSVPGFP VLQRWETPLI   180
LQNHEQIQSP WSQMLFGQFA NIDQARWVFT NSFYKLEEEV IEWTRKIWNL KVIGPTLPSM   240
YLDKRLDDDK DNGFNLYKAN HHECMNWLDD KPKESVVYVA FGSLVKHGPE QVEEITRALI   300
DSDVNFLWVI KHKEEGKLPE NLSEVIKTGK GLIVAWCKQL DVLAHESVGC FVTHCGFNST   360
LEAISLGVPV VAMPQFSDQT TNAKLLDEIL GVGVRVKADE NGIVRRGNLA SCIKMIMEEE   420
RGVIIRKNAV KWKDLAKVAV HEGGSSDNDI VEFVSELIKA                         460
```

SEQ ID NO: 5
S. rebaudiana
```
atggatgcaa tggctacaac tgagaagaaa ccacacgtca tcttcatacc atttccagca    60
caaagccaca ttaaagccat gctcaaacta cgacaacctc tccaccacaa aggactccag   120
ataaccttcg tcaacaccga cttcatccac aaccagtttc ttgaatcatc gggcccacat   180
tgtctagacg tgcaccgggg tttccggttc gaaaccattc cggatggtgt ttctcacagt   240
ccggaagcga gcatcccaat cagagaatca ctcttgagat ccattgaaac caacttcttg   300
gatcgtttca ttgatcttgt aaccaaactt ccggatcctc cgacttgtat tatctcagat   360
gggttcttgt cggttttcac aattgacgct gcaaaaaagc ttggaattcc ggtcatgatg   420
tattggacac ttgctgcctg tgggttcatg ggttttacc atattcattc tctcattgag   480
aaaggatttg caccacttaa agatgcaagt tacttgacaa tgggtattt ggacaccgtc    540
attgattggg ttccgggaat ggaaggcatc gtctcaaagg atttcccgct ggactgggac   600
actgacctca atgacaaagt tttgatgttc actacgaag ctcctcaaag gtcacacaag    660
gtttcacatc atattttcca cacgttcgat gagttggagc ctagtattat aaaaactttg   720
tcattgaggt ataatcacat ttacaccatc ggcccactgc aattacttct tgatcaaata   780
cccgaagaga aaaagcaaac tggaattacg agtctccatg gatacagttt agtaaaagaa   840
gaaccagagt gtttccagtg gcttcagtct aaagaaccaa attccgtcgt ttatgtaaat   900
tttgaagta ctacagtaat gtctttaaga gacatgacgg aatttggttg gggacttgct   960
aatagcaacc attatttcct ttggatcatc cgatcaaact ggtgatagg ggaaaatgca   1020
gttttgcccc ctgaacttga ggaacatata aagaaaagag ctttattgc tagctggtgt   1080
tcacaagaaa aggtcttgaa gcacccttcg gttggaggt tcttgactca ttgtgggtgg   1140
ggatcgacca tcgagagctt gtctgctggg gtgccaatga tatgctggcc ttattcgtgg   1200
gaccagctga ccaactgtag gtatatatgc aaagaatggg aggttgggct cgagatggga   1260
accaaagtga aacgagatga agtcaagagg cttgtacaag agttgatggg agaaggaggt   1320
cacaaaatga ggaacaaggc taaagattgg aagaaaagg ctcgcattgc aatagctcct    1380
aacggttcat cttctttgaa catagacaaa atggtcaagg aaatcaccgt gctagcaaga   1440
aactagttac aaagttgttt cacattgtgc tttctattta agatgtaact tgttctaat    1500
ttaatattgt ctagatgtat tgaaccctaaa gtttagttgg tctcaggaat tgattttaa   1560
tgaaataatg gtcattaggg gtgagt                                        1586
```

SEQ ID NO: 6
S. rebaudiana
```
atggatgcaa tggcaactac tgagaaaaag cctcatgtga tcttcattcc atttcctgca    60
caatctcaca taaaggcaat gctaaagtta gcacaactat acaccataa gggattacag    120
ataactttcg tgaataccga cttcatccat aatcaatttc tggaatctag tggccctcat   180
tgtttggacg gagccccagg gtttagattc gaaacaattc ctgacggtgt tcacattcc    240
ccagaggcct ccatcccaat aagagagagt tactgaggt caatagaaac caactttttg    300
gatcgtttca ttgactggt cacaaaactt ccagacccac caacttgcat aatctctgat   360
ggctttctgt cagtgtttac tatcgacgct gccaaaagt tgggtatccc agttatgatg   420
tactggactc ttgctgcatg cggtttcatg ggtttctatc acatccattc tcttatcgaa   480
aagggttttg ctccactgaa agatgcatca tacttaacca acggctacct ggatactgtt   540
attgactggg taccaggtat ggaaggtata agacttaaag attttccttt ggattggtct   600
```

TABLE 5-continued

Sequences disclosed herein.

```
acagacctta atgataaagt attgatgttt actacagaag ctccacaaag atctcataag    660
gtttcacatc atatctttca caccctttgat gaattggaac catcaatcat caaaaccttg   720
tctctaagat acaatcatat ctacactatt ggtccattac aattacttct agatcaaatt    780
cctgaagaga aaaagcaaac tggtattaca tccttacacg gctactcttt agtgaaagag    840
gaaccagaat gttttcaatg gctacaaagt aaagagccta attctgtggt ctacgtcaac    900
ttcggaagta caacagtcat gtccttggaa gatatgactg aatttggttg gggccttgct    960
aattcaaatc attacttct atggattatc aggtccaatt tggtaatagg ggaaaacgaa    1020
gtattacctc cagaattgga ggaacacatc aaaaagagag gtttcattgc ttcctggtgt    1080
tctcaggaaa aggtattgaa acatccttct gttggtggtt tccttactca ttgcggttgg    1140
ggctctacaa tcgaatcact aagtgcagga gttccaatga tttgttggcc atattcatgg    1200
gaccaactta caattgtag gtatatctgt aaagagtggg aagttggatt agaaatggga    1260
acaaaggtta aacgtgatga agtgaaaaga ttggttcagg agttgatggg ggaaggtggc    1320
cacaagatga gaaacaaggc caagattgg aaggaaaaag ccagaattgc tattgctcct    1380
aacgggtcat cctctctaaa cattgataag atggtcaaag agattacagt cttagccaga    1440
aactaa                                                              1446

SEQ ID NO: 7
S. rebaudiana
MDAMATTEKK PHVIFIPFPA QSHIKAMLKL AQLLHHKGLQ ITFVNTDFIH NQFLESSGPH    60
CLDGAPGFRF ETIPDGVSHS PEASIPIRES LLRSIETNFL DRFIDLVTKL PDPPTCIISD   120
GELSVFTIDA AKKLGIPVMM YWTLAACGFM GFYIHSLIE KGFAPLKDAS YLTNGYLDTV    180
IDWVPGMEGI RLKDFPLDWS TDLNDKVLMF TTEAPQRSHK VSHHIFHTFD ELEPSIIKTL   240
SLRYNHIYTI GPLQLLLDQI PEEKKQTGIT SLHGYSLVKE EPECFQWLQS KEPNSVVYVN   300
FGSTTVMSLE DMTEFGWGLA NSNHYFLWII RSNLVIGENA VLPPELEEHI KKRGFIASWC   360
SQEKVLKHPS VGGFLTHCGW GSTIESLSAG VPMICWPYSW DQLTNCRYIC KEWEVGLEMG   420
TKVKRDEVKR LVQELMGEGG HKMRNKAKDW KEKARIAIAP NGSSSLNIDK MVKEITVLAR   480
N                                                                  481

SEQ ID NO: 8
S. rebaudiana
atggaaaaca agaccgaaac aacagttaga cgtaggcgta gaatcattct gtttccagta    60
ccttttcaag ggcacatcaa tccaatacta caactagcca acgttttgta ctctaaaggt   120
ttttctatta caatctttca caccaatttc aacaaaccaa aaacatccaa ttacccacat   180
ttcacattca gattcatact tgataatgat ccacaagatg aacgtatttc aaacttacct   240
acccacggtc ctttagctgg aatgagaatt ccaatcatca tgaacatgg tgccgatgag   300
cttagaagag aattagagtt acttatgttg gcatccgaaa aggacgagga agtctcttgt   360
ctgattactg acgctctatg gtactttgcc caatctgtgg ctgatagttt gaatttgagg   420
agattggtac taatgacatc cagtctgttt aactttcacg ctcatgttag tttaccacaa   480
tttgacgaat gggatacttt ggaccctgat gacaagacta ggtagagga acaggcctct    540
ggttttccta tgttgaaagt caaagatatc aagtctgcct attctaattg gcaaatcttg   600
aaagagatct taggaaagat gatcaaacag acaaaggctt catctggagt gatttggaac   660
agtttcaaag agttagaaga gtctgaattg gagactgtaa tcagagaaat tccagcacct   720
tcattcctga taccattacc aaaacatttg actgcttcct cttcctcttt gttggatcat   780
gacagaacag ttttttcaatg gttggaccaa caaccaccta gttctgttttt gtacgtgtca   840
tttggtagta cttctgaagt cgatgaaaag gacttccttg aaatcgcaag aggcttagtc   900
gatagtaagc agtcattcct ttgggtcgtg cgtccaggtt tcgtgaaagg ctcaacatgg   960
gtcgaaccac ttccagatgg ttttctaggc gaaagaggta gatagtcaa atgggttcct  1020
caacaggaag ttttagctca tgcgctatt ggggcattct ggactcattc ggatgggaat  1080
tcaactttag aatcagtatg cgaagggta cctatgatct tttcagattt tggtcttgat  1140
caaccactga acgcaagata catgtctgat gttttgaaag tgggtgtata tctagaaaat  1200
ggctgggaaa ggggtgaaat agctaatgca ataagacgtg ttatggttga tgaagagggg  1260
gagtatatca gacaaaacgc aagagtgctg aagcaaaagg ccgacgtttc tctaatgaag  1320
ggaggctctt catacgaatc cttagaatct cttgtttcct acatttcatc actgtaa     1377

SEQ ID NO: 9
S. rebaudiana
MENKTETTVR RRRRIILFPV PFQGHINPIL QLANVLYSKG FSITIFHTNF NKPKTSNYPH    60
FTFRFILDND PQDERISNLP THGPLAGMRI PIINEHGADE LRRELELLML ASEEDEEVSC   120
LITDALWYFA QSVADSLNLR RLVLMTSSLF NFHAHVSLPQ FDELGYLDPD DKTRLEEQAS   180
GFPMLKVKDI KSAYSNWQIL KEILGKMIKQ TKASSGVIWN SFKELEESEL ETVIREIPAP   240
SFLIPLPKHL TASSSSLLDH DRTVFQWLDQ QPPSSVLYVS FGSTSEVDEK DFLEIARGLV   300
DSKQSFLWVV RPGFVKGSTW VEPLPDGFLG ERGRIVKWVP QQEVLAHGAI GAFWTHSGWN   360
STLESVCEGV PMIFSDFGLD QPLNARYMSD VLKVGVYLEN GWERGEIANA IRRVMVDEEG   420
EYIRQNARVL KQKADVSLMK GGSSYESLES LVSYISSL                           458

SEQ ID NO: 10
atggctacat ctgattctat tgttgatgac aggaagcagt tgcatgtggc tacttccct    60
tggcttgctt tcggtcatat actgcctac ctacaactat caaaactgat agctgaaaaa   120
ggacataaag tgtcattcct ttcaacaact agaaacattc aagattatc ttcccacata   180
tcaccattga ttaacgtcgt tcaattgaca cttccaagag tacaggaatt accagaagat   240
gctgaagcta aacagatgt gcatcctgaa gatatccctt acttgaaaaa ggcatccgat   300
ggattacagc ctgaggtcac tagattcctt gagcaacaca gtccagattg atcatatac   360
gactacatc actattggtt gccttcaatt gcagcatat taggcattta tagggcacat   420
ttcagtgtaa ccacaccttg ggcattgct tacatgggtc catccgctga tgctatgatt   480
aacggcagtg atggtagaac taccgttgaa gatttgacaa ccccaccaaa gtggtttcca   540
tttccaacta aagtctgttg gagaaaacac gacttagcaa gactggttcc atacaaggca   600
ccaggaatct cagacggcta tagaatgggt ttagtcctta aagggtctga ctgcctattg   660
tctaagtgtt accatgagtt tgggacacaa tggctaccac ttttggaaac attacaccaa   720
```

TABLE 5-continued

Sequences disclosed herein.

```
gttcctgtcg taccagttgg tctattacct ccagaaatcc ctggtgatga aaggacgag    780
acttgggttt caatcaaaaa gtggttagac gggaagcaaa aaggctcagt ggtatatgtg    840
gcactgggtt ccgaagtttt agtatctcaa acagaagttg tggaacttgc cttaggtttg    900
gaactatctg gattgccatt tgtctgggcc tacagaaaac caaaaggccc tgcaaagtcc    960
gattcagttg aattgccaga cggctttgtc gagagaacta gagatagagg ttggtatgg   1020
acttcatggg ctccacaatt gagaatcctg agtcacgaat ctgtgtgcgg tttcctaaca  1080
cattgtgggtt ctggttctat agttgaagga ctgatgtttg gtcatccact tatcatgttg  1140
ccaatctttg gtgaccagcc tttgaatgca cgtctgttag aagataaaca agttggaatt  1200
gaaatcccac gtaatgagga agatggatgt taaccaagg agtctgtggc cagatcatta   1260
cgttccgttg tcgttgaaaa ggaaggcgaa atctacaagg ccaatgcccg tgaactttca   1320
aagatctaca atgacacaaa agtagagaag gaatatgttt tcaatttgt agattaccta   1380
gagaaaaacg ctagagccgt agctattgat catgaatcct aa                     1422

SEQ ID NO: 11
S. rebaudiana
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY   120
DYTHYWLPSI AASLGISRAH FSVTTPWAIA YMGPSDAMI NGSDGRTTVE DLTTPPKWFP    180
FPTKVCWRKH DLARLVPYKA PGISDGYRMG LVLKGSDCLL SKCYHEFGTQ WLPLLETLHQ   240
VPVVPVGLLP PEIPGDEKDE TWVSIKKWLD GKQKGSVVYV ALGSEVLVSQ TEVVELALGL   300
ELSGLPFVWA YRKPKGPAKS DSVELPDGFV ERTRDRGLVW TSWAPQLRIL SHESVCGFLT   360
HCGSGSIVEG LMFGHPLIML PIFGDQPLNA RLLEDKQVGI EIPRNEEDGC LTKESVARSL   420
RSVVVEKEGE IYKANARELS KIYNDTKVEK EYVSQFVDYL EKNARAVAID HES          473

SEQ ID NO: 12
atggctactt ctgattccat cgttgacgat agaaagcaat tgcatgttgc tacttttcca    60
tggttggctt tcggtcatat tttgccatac ttgcaattgt ccaagttgat tgctgaaaag   120
ggtcacaagg tttcattctt gtctaccacc agaaacatcc aaagattgtc ctctcatatc   180
tccccattga tcaacgttgt tcaattgact ttgccaagag tccaagaatt gccagaagat   240
gctgaagcta ctactgatgt tcatccagaa gatatccctt acttgaaaaa ggcttccgat   300
ggtttacaac cagaagttac tagattcttg gaacaacatt ccccagattg gatcatctac   360
gattatactc attactggtt gccatccatt gctgcttcat tgggtatttc tagagccat   420
ttctctgtta ctactccatg ggctattgct tatatgggtc catctgctga tgctatgatt   480
aacggttctg atggtagaac taccgttgaa gatttgacta ctccaccaaa gtggtttcca   540
tttccaacaa agtctgttg gagaaaacac gatttggcta gattggttcc atacaaagct   600
ccaggtattt ctgatggtta cagaatgggt atggttttga aaggttccga ttgcttgttg   660
tctaagtgct atcatgaatt cggtactcaa tggttgcctt tgttggaaac attgcatcaa   720
gttccagttg ttccagtagg tttgttgcca ccagaaattc caggtgacga aaaagacgaa   780
acttgggttt ccatcaaaaa gtggttggat ggtaagcaaa agggttctgt tgtttatgtt   840
gctttggtt ccgaagcttt ggtttctcaa accgaagttg ttgaattggc tttgggtttg   900
gaattgtctg gtttgccatt tgtttgggct tacagaaaac ctaaaggtcc agctaagtct   960
gattctgttg aattgccaga tggtttcgtt gaaagaacta gagatagagg tttggttgg   1020
acttcttggg ctccacaatt gagaattttg tctcatgaat ccgtctgtgg tttcttgact  1080
cattgtgggt ctggttctat cgttgaaggt ttgatgtttg gtcacccatt gattatgttg   1140
ccaatctttg gtgaccaacc attgaacgct agattattgg aagataagca agtcggtatc  1200
gaaatcccaa gaaatgaaga agatggttgc ttgaccaaag aatctgttgc tagatctttg  1260
agatccgttg tcgttgaaaa agaaggtgaa atctacaagg ctaacgctag agaattgtcc  1320
aagatctaca acgataccaa ggtcgaaaaa gaatacgttt cccaattcgt tgactacttg  1380
gaaaagaatg ctagagctgt tgccattgat catgaatctt ga                     1422

SEQ ID NO: 13
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY   120
DYTHYWLPSI AASLGISRAH FSVTTPWAIA YMGPSDAMI NGSDGRTTVE DLTTPPKWFP    180
FPTKVCWRKH DLARLVPYKA PGISDGYRMG MVLKGSDCLL SKCYHEFGTQ WLPLLETLHQ   240
VPVVPVGLLP PEIPGDEKDE TWVSIKKWLD GKQKGSVVYV ALGSEALVSQ TEVVELALGL   300
ELSGLPFVWA YRKPKGPAKS DSVELPDGFV ERTRDRGLVW TSWAPQLRIL SHESVCGFLT   360
HCGSGSIVEG LMFGHPLIML PIFGDQPLNA RLLEDKQVGI EIPRNEEDGC LTKESVARSL   420
RSVVVEKEGE IYKANARELS KIYNDTKVEK EYVSQFVDYL EKNARAVAID HES          473

SEQ ID NO: 14
O. sativa
atggactccg gctactcctc ctcctacgcc gccgccgccg ggatgcacgt cgtgatctgc    60
ccgtggctcc ccttcggcca cctgctcccg tgcctcgacc tcgcccagcg cctcgcgtcg   120
cgggcgcacc gcgtgtcgtt cgtctccacg ccgcggaaca tcccgcgcct cgcgccggtg   180
cgccccgcgc tcgcgccgct cgtcgccttc gtgcgcgctgc cgctcccgcg cgtcgagggg   240
ctccccgacg cgccgagtc caccaacgac gtccccacg acaggccgga catggtcgag   300
ctccaccgga gggccttcga cgggctcgcc gcgcccttct cggagttctt gggcaccgcg   360
tgcgcgact gggtcatcgt cgacgtcttc caccactggg cgcagccgc gctctcgag   420
cacaaggtgc catgtgcaat gatgttgttg ggctctgcac atatgatcgc ttccatagca   480
gacagacggc tcgagcgcgc ggagacagag tcgcctgcgg ctgccgggca gggacgccca   540
gcggcggcgc caacgttcga ggtggcgagg atgaagttga tacgaaccaa aggctcatcg   600
ggaatgtccc tcgccgagcg cttctccttg acgctctcaa gctctccgac cgtcgtcggg   660
cggagctgcg tggagttcga gccgagacc gtcccgctcc tgtcgacgct ccgcggtaag   720
cctattacct tcctttggcct tatgccgccg ttgcatgaag gccgccgcga ggacggcgag   780
gatgccaccg tccgctggct cgacgcgcag ccggccaagt ccgtcgtgta cgtcgcgcta   840
ggcagcgagg tgccactggg agtggagaag gtccacgagc tcgcgctcgg gctggagctc   900
gccgggacgc gcttcctctg ggctcttagg aagcccactg gcgtctccga cgccgacctc   960
```

TABLE 5-continued

Sequences disclosed herein.

```
ctccccgccg gcttcgagga gcgcacgcgc ggccgcggcg tcgtggcgac gagatggggt    1020
cctcagatga gcatactggc gcacgccgcc gtgggcgcgt tcctgacgca ctgcggctgg    1080
aactcgacca tcgagggggct catgttcggc cacccgctta tcatgctgcc gatcttcggc    1140
gaccagggac cgaacgcgcg gctaatcgag gcgaagaacg ccggattgca ggtggcaaga    1200
aacgacggca tggatcgttc gaccgagaa ggcgtcgcgg cggcgattcg tgcagtcgcg    1260
gtggaggaag aaagcagcaa agtgtttcaa gccaaagcca agaagctgca ggagatcgtc    1320
gcggacatgg cctgccatga gaggtacatc gacggattca ttcagcaatt gagatcttac    1380
aaggattga                                                             1389

SEQ ID NO: 15
O. sativa
atggatagtg gctactcctc atcttatgct gctgccgctg gtatgcacgt tgtgatctgc     60
ccttggttgg ccttttggtca cctgttacca tgtctggatt tagcccaaag actggcctca    120
agaggccata gagtatcatt tgtgtctact cctagaaata tctctcgttt accaccagtc    180
agacctgctc tagctcctct agttgcattc gttgctcttc cacttccaag agtagaagga    240
ttgccagacg gcgctgaatc tactaatgac gtaccacatg atagacctga catggtcgaa    300
ttgcatagaa gagcctttga tggattggca gctccatttt ctgagttcct gggcacagca    360
tgtgcagact gggttatagt cgatgtattt catcactggg ctgctgcagc cgcattggaa    420
cataaggtgc cttgtgctat gatgttgtta gggtcagcac acatgatcgc atccatagct    480
gatagaagat tggaaagagc tgaaacagaa tccccagccg cagcaggaca aggtaggcca    540
gctgccgccc aacctttga agtggctaga atgaaattga ttcgtactaa aggtagttca    600
gggatgagtc ttgctgaaag gttttctctg acattatcta gatcatcatt agttgtaggt    660
agatcctgcg tcgagttcga acctgaaaca gtaccttttac tatctacttt gagaggcaaa    720
cctattactt tccttggtct aatgcctcca ttacatgaag gaaggagaga agatggtgaa    780
gatgctactg ttaggtggtt agatgcccaa cctgctaagt ctgttgttta cgttgcattg    840
ggttctgagg taccactagg ggtggaaaag gtgcatgaat tagcattagg acttgagctg    900
gccggaacaa gattcctttg ggcttttgaga aaaccaaccg gtgtttctga cgccgacttg    960
ctaccagctg ggttcgaaga gagaacaaga ggccgtggtg tcgttgctac tagatgggtc   1020
ccacaaatga gtattctagc tcatgcagct gtaggggcct ttcaacccca ttgcggttgg   1080
aactcaacaa tagaaggact gatgtttggt catccactta ttatgttacc aatctttggc   1140
gatcagggac ctaacgcaag attgattgag caaagaacg caggtctgca ggttgcacgt   1200
aatgatggta tggttccctt tgatagaaa ggcgttgcag ctgccatcag acagagattg   1260
gttgaggaag agtcatctaa agttttccaa gctaaggcca aaaaattaca agagattgtg   1320
gctgacatgg cttgtcacga aagatacatc gatggtttca tccaacaatt gagaagttat   1380
aaagactaa                                                            1389

SEQ ID NO: 16
O. sativa
MDSGYSSSYA AAAGMHVVIC PWLAFGHLLP CLDLAQRLAS RGHRVSFVST PRNISRLPPV     60
RPALAPLVAF VALPLPRVEG LPDGAESTND VPHDRPDMVE LHRRAFDGLA APFSEFLGTA    120
CADWVIVDVF HHWAAAAALE HKVPCAMMLL GSAHMIASIA DRRLERAETE SPAAAGQGRP    180
AAAPTFEVAR MKLIRTKGSS GMSLAERFSL TLSRSSLVVG RSCVEFEPET VPLLSTLRGK    240
PITFLGLMPP LHEGRREDGE DATVRWLDAQ PAKSVVYVAL GSEVPLGVEK VHELALGLEL    300
AGTRFLWALR KPTGVSDADL LPAGFEERTR GRGVVATRWV PQMSILAHAA VGAFLTHCGW    360
NSTIEGLMFG HPLIMLPIFG DQGPNARLIE AKNAGLQVAR NDGDGSFDRE GVAAAIRAVA    420
VEEESSKVFQ AKAKKLQEIV ADMACHERYI DGFIQQLRSY KD                      462

SEQ ID NO: 17
MDSGYSSSYA AAAGMHVVIC PWLAFGHLLP CLDLAQRLAS RGHRVSFVST PRNISRLPPV     60
RPALAPLVAF VALPLPRVEG LPDGAESTND VPHDRPDMVE LHRRAFDGLA APFSEFLGTA    120
CADWVIVDVF HHWAAAAALE HKVPCAMMLL GSAHMIASIA DRRLERAETE SPAAAGQGRP    180
AAAPTFEVAR MKLIRTKGSS GMSLAERFSL TLSRSSLVVG RSCVEFEPET VPLLSTLRGK    240
PITFLGLLPP EIPGDEKDET WVSIKKWLDG KQKGSVVYVA LGSEALVSQT EVVELALGLE    300
LSGLPFVWAY RKPKGPAKSD SVELPDGFVE RTRDRGLVWT SWAPQLRILS HESVCGFLTH    360
CGSGSIVEGL MFGHPLIMLP IFGDQPLNAR LLEDKQVGIE IARNDGDGSF DREGVAAAIR    420
AVAVEEESSK VFQAKAKKLQ EIVADMACHE RYIDGFIQQL RSYKD                   465

SEQ ID NO: 18
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG MVLKGSDCLL SKCYHEFGTQ WLPLLETLHQ    240
VPVVPVGLMP PLHEGRREDG EDATVRWLDA QPAKSVVYVA LGSEVPLGVE KVHELALGLE    300
LAGTRFLWAL RKPTGVSDAD LLPAGFEERT RGRGVVATRW VPQMSILAHA AVGAFLTHCG    360
WNSTIEGLMF GHPLIMLPIF GDQGPNARLI EAKNAGLQVP RNEEDGCLTK ESVARSLRSV    420
VVEKEGEIYK ANARELSKIY NDTKVEKEYV SQFVDYLEKN ARAVAIDHES              470

SEQ ID NO: 19
Synechococcus sp.
atggctttgg taaacccaac cgctctttc tatggtacct ctatcagaac aagacctaca     60
aactactaa atccaactca aaagctaaga ccagtttcat catcttcctt accttctttc    120
tcatcagtta gtgcgattct tactgaaaaa catcaatcta atccttctga gaacaacaat    180
ttgcaaactc atctagaaac tccttttcaac tttgatagtt atatgttgga aaaagtcaac    240
atggttaacg aggcgcttga tgcatctgtc ccactaaaag acccaatcaa atccatggaa    300
tccatgagat actcttttatt ggcaggcggt aagagaatca gaccaatgat gtgtattgca    360
gcctgcgaaa tagtcggagg taatatcctt aacgccatgc cagccgcatg tgccgtggaa    420
atgattcata ctatgtcttt ggtgcatgac gatcttccat gtatggataa tgatgacttc    480
agaagaggta aacctatttc acacaaggtc tacgggggag aaatgcagt attgaccggc    540
```

TABLE 5-continued

Sequences disclosed herein.

```
gatgctttac taagtttatc tttcgaacat atagctactg ctacaaaggg tgtatcaaag    600
gatagaatcg tcagagctat aggggagttg gcccgttcga ttggctccga aggtttagtg    660
gctggacaag ttgtagatat cttgtcagag ggtgctgatg ttggattaga tcacctagaa    720
tacattcaca tccacaaaac agcaatgttg cttgagtcct cagtagttat tggcgctatc    780
atgggaggag gatctgatca gcagatcgaa aagttgagaa aattcgctag atctattggt    840
ctactattcc aagttgtgga tgacattttg gatgttacaa aatctaccga agagttgggg    900
aaaacagctg gtaaggattt gttgacagat aagacaactt acccaaagtt gttaggtata    960
gaaaagtcca gagaatttgc cgaaaaactt aacaaggaag cacaagagca attaagtggc   1020
tttgatagac gtaaggcagc tccttttgatc gcgttagcca actacaatgc gtaccgtcaa   1080
aattga                                                              1086

SEQ ID NO: 20
Synechococcus sp.
MALVNPTALF YGTSIRTRPT NLLNPTQKLR PVSSSSLPSF SSVSAILTEK HQSNPSENNN     60
LQTHLETPFN FDSYMLEKVN MVNEALDASV PLKDPIKIHE SMRYSLLAGG KRIRPMMCIA    120
ACEIVGGNIL NAMPAACAVE MIHTMSLVHD DLPCMDNDDF RRGKPISHKV YGEEMAVLTG    180
DALLSLSFEH IATATKGVSK DRIVRAIGEL ARSVGSEGLV AGQVVDILSE GADVGLDHLE    240
YIHIHKTAML LESSVVIGAI MGGGSDQQIE KLRKFARSIG LLFQVVDDIL DVTKSTEELG    300
KTAGKDLLTD KTTYPKLLGI EKSREFAEKL NKEAQEQLSG FDRRKAAPLI ALANYNAYRQ    360
N                                                                   361

SEQ ID NO: 21
atggctgagc aacaaatatc taacttgctg tctatgtttg atgcttcaca tgctagtcag     60
aaattagaaa ttactgtcca aatgatggac atataccatt acagagaaac gcctccagat    120
tcctcatctt ctgaaggcgg ttcattgtct agatacgacg agagaagagt ctctttgcct    180
ctcagtcata atgctgcctc tccagatatt gtatcacaac tatgtttttc cactgcaatg    240
tcttcagagt tgaatcacag atggaaatct caaagattaa aggtggccga ttctccttac    300
aactatatcc taacattacc atcaaaagga attagaggtg cctttatcga ttccctgaac    360
gtatggttgg aggttccaga ggatgaaaca tcagtcatca aggaagttat tggtatgctc    420
cacaactctt cattaatcat tgatgacttc aagataatt ctccacttag aagaggaaag    480
ccatctaccc atacagtctt cggccctgcc caggctcaca atactgctac ttacgttata    540
gttaaagcaa tcgaaaagat acaagacata gtgggacacg atgcattggc agatgttacg    600
ggtactatta caactatttt ccaaggtcag gccatggact tgtggtggac agcaaatgca    660
atcgttccat caatacagga atacttactt atggtaaacg ataaaaccgg tgctctcttt    720
agactgagtt tggagttgtt agctctgaat tccgaagcca gtatttctga ctctgcttta    780
gaaagtttat ctagtgctgt ttccttgcta ggtcaatact tccaaatcag agacgactat    840
atgaacttga tcgataacaa gtatacagat cagaaaggct tctgcgaaga tcttgatgaa    900
ggcaagtact cactaacact tattcatgcc ctccaaactg attcatccga tctactgacc    960
aacatccttt caatgagaag agtgcaagga agttaacgg cacaaaagag atgttggttc   1020
tggaaatga                                                          1029

SEQ ID NO: 22
Gibberella fujikuroi
MAEQQISNLL SMFDASHASQ KLEITVQMMD TYHYRETPPD SSSSEGGSLS RYDERRVSLP     60
LSHNAASPDI VSQLCFSTAM SSELNHRWKS QRLKVADSPY NYILTLPSKG IRGAFIDSLN    120
VWLEVPEDET SVIKEVIGML HNSSLIIDDF QDNSPLRRGK PSTHTVFGPA QAINTATYVI    180
VKAIEKIQDI VGHDALADVT GTITTIFQGQ AMDLWWTANA IVPSIQEYLL MVNDKTGALF    240
RLSLELLALN SEASISDSAL ESLSSAVSLL GQYFQIRDDY MNLIDNKYTD QKGFCEDLDE    300
GKYSLTLIHA LQTDSSDLLT NILSMRRVQG KLTAQKRCWF WK                      342

SEQ ID NO: 23
atggaaaaga ctaaggagaa agcagaacgt atcttgctgg agccatacag atacttatta     60
caactaccag gaaagcaagt ccgttctaaa ctatcacaag cgttcaatca ctggttaaaa    120
gttcctgaag ataagttaca aatcattatt gaagtcacag aaatgctaca caatgcttct    180
ttactgatcg atgatataga ggattcttcc aaactgagaa gaggttttcc tgtcgctcat    240
tccatatacg gggtaccaag tgtaatcaac tcagctaatt acgtctactt cttgggattg    300
gaaaaagtat tgacattaga tcatccagac gctgtaaagc tattcaccag acaacttctt    360
gaattgcatc aaggtcaagg tttggatatc tattggagag acacttatac ttgcccaaca    420
gaagaggagt acaaagcaat ggttctacaa aagactggcg gtttgttcgg acttgccgtt    480
ggtctgatgc aacttttctc tgattacaag gaggacttaa agcctctgtt ggataccttg    540
ggcttgtttt tccagattag agatgactac gctaacttac attcaaagga atattcagaa    600
aacaaatcat tctgtgaaga tttgactgaa gggaagttta gttttccaac aatccacgcc    660
atttggtcaa gaccagaatc tactcaagtg caaaacattc tgcgtcagag aacagagaat    720
attgacatca aaaagtattg tgttcagtac ttggaagatg tggttctttt gcttacaca    780
agacatacac ttagagaatt agaggcaaaa gcatacaagc aaatagaagc ctgtggaggc    840
aatccttctc tagtggcatt ggttaaacat ttgtccaaaa tgttcaccga ggaaaacaag    900
taa                                                                 903

SEQ ID NO: 24
Mus musculus
MEKTKEKAER ILLEPYRYLL QLPGKQVRSK LSQAFNHWLK VPEDKLQIII EVTEMLHNAS     60
LLIDDIEDSS KLRRGFPVAH SIYGVPSVIN SANYVYFLGL EKVLTLDHPD AVKLFTRQLL    120
ELHQGQLDI YWRDTYTCPT EEEYKAMVLQ KIGGLFGLAV GLMQLFSDYK EDLKPLLDTL    180
GLFFQIRDDY ANLHSKEYSE NKSFCEDLTE GKFSFPTIHA IWSRPESTQV QNILRQRTEN    240
IDIKKYCVQY LEDVGSFAYT RHTLRELEAK AYKQIEACGG NPSLVALVKH LSKMFTEENK    300

SEQ ID NO: 25
atggcaagat tctatttct taacgcacta ttgatggtta tctcattaca atcaactaca      60
```

TABLE 5-continued

Sequences disclosed herein.

```
gccttcactc cagctaaact tgcttatcca acaacaacaa cagctctaaa tgtcgcctcc    120
gccgaaactt ctttcagtct agatgaatac ttggcctcta agataggacc tatagagtct    180
gccttggaag catcagtcaa atccagaatt ccacagaccg ataagatctg cgaatctatg    240
gcctactctt tgatggcagg aggcaagaga attagaccag tgttgtgtat cgctgcatgt    300
gagatgttcg gtggatccca agatgtcgct atgcctactg ctgtggcatt agaaatgata    360
cacacaatgt ctttgattca tgatgatttg ccatccatgg ataacgatga cttgagaaga    420
ggtaaaccaa caaaccatgt cgttttcggc gaagatgtag ctattcttgc aggtgactct    480
ttattgtcaa cttccttcga gcacgtcgct agagaaacaa aaggagtgtc agcagaaaag    540
atcgtggatg ttatcgctag attaggcaaa tctgttggtg ccgagggcct tgctggcggt    600
caagttatgg acttagaatg tgaagctaaa ccaggtacca cattgacga cttgaaatgg     660
attcatatcc ataaaaccgc tacattgtta caagttgctg tagcttctgg tgcagttcta    720
ggtggtgcaa ctcctgaaga ggttgctgca tgcgagttgt ttgctatgaa tataggtctt    780
gcctttcaag ttgccgacga tatccttgat gtaaccgctt catcagaaga tttgggtaaa    840
actgcaggca aagatgaagc tactgataag acaacttacc caaagttatt aggattagaa    900
gagagtaagg catacgcaag acaactaatc gatgaagcca aggaaagttt ggctccttt     960
ggagatagag ctgcccttt attggccatt gcagatttca ttattgatag aaagaattga   1020
```

SEQ ID NO: 26
*Thalassiosira pseudonana*

```
MARFYFLNAL LMVISLQSTT AFTPAKLAYP TTTTALNVAS AETSFSLDEY LASKIGPIES    60
ALEASVKSRI PQTDKICESM AYSLMAGGKR IRPVLCIAAC EMFGGSQDVA MPTAVALEMI   120
HTMSLIHDDL PSMDNDDLRR GKPTNHVVFG EDVAILAGDS LLSTSFEHVA RETKGVSAEK   180
IVDVIARLGK SVGAEGLAGG QVMDLECEAK PGTTLDDLKW IHIHKTATLL QVAVASGAVL   240
GGATPEEVAA CELFAMNIGL AFQVADDILD VTASSEDLGK TAGKDEATDK TTYPKLLGLE   300
ESKAYARQLI DEAKESLAPF GDRAAPLLAI ADFIIDRKN                          339
```

SEQ ID NO: 27

```
atgcacttag caccacgtag agtccctaga ggtagaagat caccacctga cagagttcct    60
gaaagacaag gtgccttggg tagaagacgt ggagctggct ctactggctg tgcccgtgct   120
gctgctggtg ttcaccgtag aagaggagga ggcgaggctg atccatcagc tgctgtgcat   180
agaggctggc aagccggtgg tggcaccggt ttgcctgatg aggtggtgtc taccgcagcc   240
gccttagaaa tgtttcatgc ttttgcttta atccatgatg atatcatgga tgatagtgca   300
actagaagag gctccccaac tgttcacaga gccctagctg atcgtttagg cgctgctctg   360
gacccagatc aggccggtca actaggagtt ctactgctca tcttggttgg agatctggct   420
ttgacatggt ccgatgaatt gttatacgct ccattgactc acatagact ggcagcagta    480
ctaccattgg taacagctat gagagctgaa accgttcatg gccaatatct tgatataact   540
agtgctagaa gacctgggac cgatacttct cttgcattga gaatagccag atataagaca   600
gcagcttaca caatggaacg tccactgcac attggtgcag ccctggctgg ggcaagacca   660
gaactattag cagggctttc agcatacgcc ttgccagctg gagaagcctt ccaattggca   720
gatgacctgc taggcgtctt cggtgatcca agacgtacag gaaacctga cctagatgat   780
cttagaggtg gaaagcatac tgtcttagtc gccttggcaa gagaacatgc cactccagaa   840
cagagacaca cattggatac attattgggt acaccaggtc ttgatagaca aggcgcttca   900
agactaagat gcgtattggt agcaactggt gcaagagccg aagccgaaag acttattaca   960
gagagaaag atcaagcatt aactgcattg aacgcattaa cactgccacc tcctttagct   1020
gaggcattag caagattgac attagggtct acagctcatc ctgcctaa               1068
```

SEQ ID NO: 28
*Streptomyces clavuligerus*

```
MHLAPRRVPR GRRSPPDRVP ERQGALGRRR GAGSTGCARA AAGVHRRRGG GEADPSAAVH    60
RGWQAGGGTG LPDEVVSTAA ALEMFHAFAL IHDDIMDDSA TRRGSPTVHR ALADRLGAAL   120
DPDQAGQLGV STAILVGDLA LTWSDELLYA PLTPHRLAAV LPLVTAMRAE TVHGQYLDIT   180
SARRPGTDTS LALRIARYKT AAYTMERPLH IGAALAGARP ELLAGLSAYA LPAGEAFQLA   240
DDLLGVFGDP RRTGKPDLDD LRGGKHTVLV ALAREHATPE QRHTLDTLLG TPGLDRQGAS   300
RLRCVLVATG ARAEAERLIT ERRDQALTAL NALTLPPPLA EALARLTLGS TAHPA        355
```

SEQ ID NO: 29

```
atgtcatatt tcgataacta cttcaatgag atagttaatt ccgtgaacga catcattaag    60
tcttacatct ctggcgacgt accaaaacta tacgaagcct cctaccctt gtttacatca    120
ggaggaaaga gactaagacc attgatcctt acaatttctt ctgatctttt cggtggacag   180
agagaaaagag catactatgc tggcgcagca atcgaagttt gcacacatt cactttggtt    240
cacgatgata tcatggatca agataacatt cgtagagctg ttcctactgt acatgtcaag   300
tatggcctac ctttgccat tttagctggt gacttattga tgcaaaagc cttcaattg    360
ttgactcagg cattgagagg tctaccatct gaaactatca tcaaggcgtt tgatatcttt   420
acaagatcta tcattatcat atcagaaggt caagctgtcg atatggaatt cgaagataga   480
attgatatca aggaacaaga tgatttggat atgatatctc gtaaaaccgc tgccttattc   540
tcagcttctt cttccattgg ggcgttgata gctggagcta atgataacga tgtgagatta   600
atgtccgatt tcggtacaaa tcttgggatc gcatttcaaa ttgtagatga tatacttggt   660
ttaacagctg atgaaaaaga gctaggaaaa cctgtttca gtgatatcag agaaggtaaa    720
aagaccatat tagtcattaa gactttagaa ttgtgtaagg aagacgagaa aaagattgta   780
ttaaaagcgc taggcaacaa gtcagcatca aaggaagagt tgatgagttc tgctgacata   840
atcaaaagt actcattgga ttacgcctac aacttagctg agaaatacta caaaaacgcc   900
atcgattctc taaatcaagt ttcaagtaaa agtgatattc cagggaaggc attgaaatat   960
cttgctgaat tcaccatcag aagacgtaag taa                                 993
```

SEQ ID NO: 30
*Sulfolobus acidocaldarius*

```
MSYFDNYFNE IVNSVNDIIK SYISGDVPKL YEASYHLFTS GGKRLRPLIL TISSDLFGGQ    60
RERAYYAGAA IEVLHTFTLV HDDIMDQDNI RRGLPTVHVK YGLPLAILAG DLLHAKAFQL   120
```

TABLE 5-continued

Sequences disclosed herein.

```
LTQALRGLPS ETIIKAFDIF TRSIIIISEG QAVDMEFEDR IDIKEQEYLD MISRKTAALF    180
SASSSIGALI AGANDNDVRL MSDFGTNLGI AFQIVDDILG LTADEKELGK PVFSDIREGK    240
KTILVIKTLE LCKEDEKKIV LKALGNKSAS KEELMSSADI IKKYSLDYAY NLAEKYYKNA    300
IDSLNQVSSK SDIPGKALKY LAEFTIRRRK                                    330

SEQ ID NO: 31
atggtcgcac aaactttcaa cctggatacc tacttatccc aaagacaaca acaagttgaa     60
gaggccctaa gtgctgctct tgtgccagct tatcctgaga gaatatacga agctatgaga    120
tactccctcc tggcaggtgg caaaagatta agacctatct tatgtttagc tgcttgcgaa    180
ttggcaggtg gttctgttga acaagccatg ccaactgcgt gtgcacttga aatgatccat    240
acaatgtcac taattcatga tgacctgcca gccatggata acgatgattt cagaagagga    300
aagccaacta atcacaaggt gttcggggaa gatatagcca tcttagcggg tgatgcgctt    360
ttagcttacg cttttgaaca tattgcttct caaacaagag gagtaccacc tcaattggtg    420
ctacaagtta ttgctagaat cggacacgcc gttgctgcaa caggcctcgt tggaggccaa    480
gtcgtagacc ttgaatctga aggtaaagct atttccttag aaacattgga gtatattcac    540
tcacataaga ctggagcctt gctgaagca tcagttgtct caggcggtat tctcgcaggg     600
gcagatgaag agcttttggc cagattgtct cattacgcta gagatatagg cttggctttt    660
caaatcgtcg atgatatcct ggatgttact gctacatctg aacagttggg gaaaaccgct    720
ggtaaagacc aggcagccgc aaaggcaact tatccaagtc tattgggttt agaagcctct    780
agacagaaag cggaagagtt gattcaatct gctaaggaag ccttaagacc ttacggttca    840
caagcagagc cactcctagc gctggcagac ttcatcacac gtcgtcagca ttaa           894

SEQ ID NO: 32
Synechococcus sp.
MVAQTFNLDT YLSQRQQQVE EALSAALVPA YPERIYEAMR YSLLAGGKRL RPILCLAACE     60
LAGGSVEQAM PTACALEMIH TMSLIHDDLP AMDNDDFRRG KPTNHKVFGE DIAILAGDAL    120
LAYAFEHIAS QTRGVPPQLV LQVIARIGHA VAATGLVGGQ VVDLESEGKA ISLETLEYIH    180
SHKTGALLEA SVVSGGILAG ADEELLARLS HYARDIGLAF QIVDDILDVT ATSEQLGKTA    240
GKDQAAAKAT YPSLLGLEAS RQKAEEELIQS AKEALRPYGS QAEPLLALAD FITRRQH     297

SEQ ID NO: 33
atgaaaaccg gtttatctc caccagcaaca gtatttcatc acagaatctc accagcgacc     60
actttcagac atcacttatc acctgctact acaaactcta caggcattgt cgccttaaga    120
gacatcaact tcagatgtaa agcagtttct aaagagtact ctgatctgtt gcagaaagat    180
gaggcttctt tcacaaaatg ggacgatgac aaggtgaaag atcatcttga taccaacaaa    240
aacttatacc caaatgatga gattaaggaa tttgttgaat cagtaaaggc tatgttcggt    300
agtatgaatg acggggagat aaacgtctct gcatacgata ctgcatgggt tgcctttggtt   360
caagatgtcg atggatcagg tagtcctcag ttcccttctt ctttagaatg gattgccaac    420
aatcaattgt cagatggatc atgggagat catttgctgt tctcagctca cgatagaatc     480
atcaacacat tagcatgcgt tattgcactt acaagttgga atgttcatcc ttctaagtgt    540
gaaaaaggtt tgaattttct gagagaaaac atttgcaaat tagaagatga aacgcagaa     600
catatgccaa ttggttttga agtaacattc ccatcactaa ttgatatcgc gaaaagttg     660
aacattgaag tacctgagga tactccagca cttaaagaga tctacgcacg tagagatatc    720
aagttaacta agatcccaat ggaagttctt cacaaggtac ctactacttt gttacattct    780
ttggaaggaa tgcctgattt ggagtgggaa aaactgttaa agtacaatg taaagatggt    840
agtttcttgt tttccccatc tagtaccgca ttcgccctaa tgcaaacaaa agatgagaaa    900
tgcttacagt atctaacaaa tatcgtcact aagttcaacg gtgcgtgcc taatgtgtac    960
ccagtcgatt gtttgaaaca tatttgggtt gttgatagac tgcagagatt ggggattgcc   1020
agatacttca aatcagagat aaaagattgt gtagagatata caataagta ctggaccaaa   1080
aatggaattt gttgggctag aaatactcac gttcaagata tcgatgatac agccatggaa   1140
ttcagagtgt tgagagcgca cggttatgac gtcactccag atgttttag acaatttgaa    1200
aaagatggta aattcgtttg ctttgcaggg caatcaacac aagccgtgac aggaatgttt    1260
aacgtttaca gagcctctca aatgttgttc ccaggggaga gaattttgga agatgccaaa   1320
aagttctctt acaattactt aaaggaaaag caaagtacca acgaattgct ggataaatgg   1380
ataatcgcta aagatctacc tggtgaagtt ggttatgctc tgtagtatccc atggtatgt   1440
tccttaccaa gattggaaac tcgttattac cttgaacaat acggcggtga agatgatgtc   1500
tggatagagca agacattata cagaatgggt acgtgtcca ataacacata tctagaaatg    1560
gcaaagctgg attacaataa ctatgttgca gtccttcaat tagaatggta cacaatacaa   1620
caatggtacg tcgatattgg tatagagaag ttcgaatctg acaacatcaa gtcagtcctg   1680

SEQ ID NO: 34
Stevia rebaudiana
MKTGFISPAT VFHHRISPAT TFRHHLSPAT TNSTGIVALR DINFRCKAVS KEYSDLLQKD     60
EASFTKWDDD KVKDHLDTNK NLYPNDEIKE FVESVKAMFG SMNDGEINVS AYDTAWVALV    120
QDVDGSGSPQ FPSSLEWIAN NQLSDGSWGD HLLFSAHDRI INTLACVIAL TSWNVHPSKC    180
EKGLNFLREN ICKLEDENAE HMPIGFEVTF PSLIDIAKKL NIEVPEDTPA LKEIYARRDI    240
KLTKIPMEVL HKVPTTLLHS LEGMPDLEWE KLLKLQCKDG SFLFSPSSTA FALMQTKDEK    300
CLQYLTNIVT KFNGGVPNVY PVDLFEHIWV VDRLQRLGIA RYFKSEIKDC VEYINKYWTK    360
NGICWARNTH VQDIDDTAMG FRVLRAHGYD VTPDVFRQFE KDGKFVCFAG QSTQAVTGMF    420
NVYRASQMLF PGERILEDAK KFSYNYLKEK QSTNELLDKW IIAKDLPGEV GYALDIPWYA    480
SLPRLETRYY LEQYGGEDDV WIGKTLYRMG YVSNNTYLEM AKLDYNNYVA VLQLEWYTIQ    540
QWYVDIGIEK FESDNIKSVL VSYYLAAASI FEPERSKERI AWAKTTILVD KITSIFDSSQ    600
SSKEDITAFI DKFRNKSSSK KHSINGEPWH EVMVALKKTL HGFALDALMT HSQDIHPQLH    660
QAWEMWLTKL QDGVDVTAEL MVQMINMTAG RWVSKELLTH PQYQRLSTVT NSVCHDITKL    720
HNFKENSTTV DSKVQELVQL VFSDTPDDLD QDMKQTFLTV MKTFYYKAWC DPNTINDHIS    780
KVFEIVI                                                              787
```

TABLE 5-continued

Sequences disclosed herein.

```
SEQ ID NO: 35
atgcctgatg cacacgatgc tccacctcca caaataagac agagaacact agtagatgag    60
gctacccaac tgctaactga gtccgcagaa gatgcatggg gtgaagtcag tgtgtcagaa   120
tacgaaacag caaggctagt tgcccatgct acatggttag gtggacacgc cacaagagtg   180
gccttccttc tggagagaca acacgaagac gggtcatggg gtccaccagg tggatatagg   240
ttagtcccta cattatctgc tgttcacgca ttattgacat gtcttgcctc tcctgctcag   300
gatcatggcg ttccacatga tagactttta agagctgttg acgcaggctt gactgccttg   360
agaagattgg ggacatctga ctcccccacct gatactatag cagttgagct ggttatccca   420
tctttgctag agggcattca acacttactg gaccctgctc atcctcatag tagaccagcc   480
ttctctcaac atagaggctc tcttgtttgt cctggtggac tagatgggaa aactctagga   540
gctttgagat cacacgccgc agcaggtaca ccagtaccag gaaaagtctg gcacgcttcc   600
gagactttgg gcttgagtac cgaagctgct tctcacttgc aaccagccca aggtataatc   660
ggtggctctg ctgctgccac agcaacatgg ctaaccaggg ttgcaccatc tcaacagtca   720
gattctgcca gaagatacct tgaggaatta caacacagat actctggccc agttccttcc   780
attacccta tcacatactt cgaaagagca tggttattga caaattttgc agcagccggt   840
gttccttgtg aggctccagc tgctttgttg gattccttag aagcagcact tacaccacaa   900
ggtgctcctg ctggagcagg attgcctcca gatgctgatg atacagccgc tgtgttgctt   960
gcattggcaa cacatgggag aggtagaaga ccagaagtac tgatggatta caggactgac  1020
gggtatttcc aatgctttat tggggaaagg actccatcaa tttcaacaaa cgctcacgta  1080
ttggaaacat tagggcatca tgtgggccaa catccacaag atagagccag atacggatca  1140
gccatggata ccgcatcagc ttggctgctg gcagctcaaa agcaagatgg ctcttggtta  1200
gataaatggc atgcctcacc atactacgct actgtttgtt gcacacaagc tctagccgct  1260
catgcaagtc ctgcaactgc accagctaga cagagagctg tcagatgggt tttagccaca  1320
caaagatccg atggcggttg gggtctatgg cattcaactg ttgaagagac tgcttatgcc  1380
ttacagatct tggccccacc ttctggtggt ggcaatatcc cagtccaaca agcacttact  1440
agaggcagag caagattgtg tggagccttg ccactgactc ctttatggca tgataaggat  1500
ttgtatactc cagtaagagt agtcagagct gccagagctg ctgctctgta cactaccaga  1560
gatctattgt taccaccatt gtaa                                          1584

SEQ ID NO: 36
Streptomyces clavuligerus
MPDAHDAPPP QIRQRTLVDE ATQLLTESAE DAWGEVSVSE YETARLVAHA TWLGGHATRV    60
AFLLERQHED GSWGPPGGYR LVPTLSAVHA LLTCLASPAQ DHGVPHDRLL RAVDAGLTAI   120
RRLGTSDSPP DTIAVELVIP SLLEGIQHLL DPAHPHSRPA FSQHRGSLVC PGGLDGRTLG   180
ALRSHAAAGT PVPGKVWHAS ETLGLSTEAA SHLQPAQGII GGSAAATATW LTRVAPSQQS   240
DSARRYLEEL QHRYSGPVPS ITPITYFERA WLLNNFAAAG VPCEAPAALL DSLEAALTPQ   300
GAPAGAGLPP DADDTAAVLL ALATHGRGRR PEVLMDYRTD GYFQCFIGER TPSISTNAHV   360
LETLGHHVAQ HPQDRARYGS AMDTASAWLL AAQKQDGSWL DKWHASPYYA TVCCTQALAA   420
HASPATAPAR QRAVRWVLAT QRSDGGWGLW HSTVEETAYA LQILAPPSGG GNIPVQQALT   480
RGRARLCGAL PLTPLWHDKD LYTPVRVVRA ARAAALYTTR DLLLPPL                 527

SEQ ID NO: 37
atgaacgccc tatccgaaca cattttgtct gaattgagaa gattattgtc tgaaatgagt    60
gatggcggat ctgttggtcc atctgtgtat gatacggccc aggccctaag attccacggt   120
aacgtaacag gtagacaaga tgcatatgct tggttgatcg cccagcaaca agcagatgga   180
ggttggggct ctgccgactt tccactcttt agacatgctc caacatgggc tgcacttctc   240
gcattacaaa gagctgatcc acttcctggc gcagcagacg cagttcagac cgcaacaaga   300
ttcttgcaaa gacaaccaga tccatacgct catgccgttc ctgaggatgc ccctattggt   360
gctgaactga tcttgcctca gttttgtgga gaggctgctt ggttgttggg aggtgtggcc   420
ttccctagac acccagccct attaccatta agacaggctt gtttagtcaa actgggtgca   480
gtcgccatgt tgccttcagg cacccccattg ctccactcct gggaggcagg gggtacttct   540
ccaacaacag cctgtccaga cgatgatggt tctataggta tctcaccagc agctacagcc   600
gcctggagag cccaggctgt gaccagaggc tcaactcctc aagtgggcag agctgacgca   660
tacttacaaa tggcttcaag agcaacgaga tcaggcatag aaggagtctt ccctaatgtt   720
tggcctataa acgtattcga accatgctgg tcactgtaca ctctccatct tgccggtctg   780
ttcgcccatc cagcactggc tgaggctgta agagttatcg ttgctcaact tgaagcaaga   840
ttgggagtgc atggcctcgg accagcttta cattttgctg ccgacgctga tgatactgca   900
gttgccttat gcgttctgca tttggctggc agagatcctg cagttgacgc attgagacat   960
tttgaaattg gtgagctctt tgttacattc ccaggagaga gaaatgctag tgtctctacg  1020
aacattcacg ctcttcatgc tttgagattg ttaggtaaac cagctgccgg agcaagtgca  1080
tacgtcgaag caaatagaaa tccacatggt ttgtgggaca cgaaaaatg gcacgtttca   1140
tggctttatc caactgcaca cgccgttgca gctctagctc aaggcaagcc tcaatggaga  1200
gatgaaagag cactagccgc tctactacaa gctcaaagag atgatggtgg ttggggagct  1260
ggtagaggat ccactttcga ggaaaccgcc tacgctcctt tcgctttaca cgttatggac  1320
ggatctgagg aagccacagg cagaagaaga atcgctcaag tcgtcgcaag agccttagaa  1380
tggatgctag ctagacatgc cgcacatgga ttaccacaaa caccactctg gattggtaag  1440
gaattgtact gtcctactag agtcgtaaga gtagctgagc tagctggcct gtggttagca  1500
ttaagatggg gtagaagagt attagctgaa ggtgctggtg ctgcacctta a            1551

SEQ ID NO: 38
Bradyrhizobium japonicum
MNALSEHILS ELRRLLSEMS DGGSVGPSVY DTAQAIRFHG NVTGRQDAYA WLIAQQQADG    60
GWGSADFPLF RHAPTWAALL ALQRADPLPG AADAVQTATR FLQRQPDPYA HAVPEDAPIG   120
AELILPQFCG EAAWLLGGVA FPRHPALLPL RQACLVKLGA VAMLPSGHPL LHSWEAWGTS   180
PTTACPDDDG SIGISPAATA AWRAQAVTRG STPQVGRADA YLQMSRATRR SGIEGVFPNV   240
WPINVFEPCW SLYTLHLAGL FAHPALAEAV RVIVAQLEAR LGVHGLGPAL HFAADADDTA   300
VALCVLHLAG RDPAVDAIRH FEIGELFVTF PGERNASVST NIHALHALRL LGKPAAGASA   360
```

TABLE 5-continued

Sequences disclosed herein.

| | | | | | |
|---|---|---|---|---|---|
| YVEANRNPHG | LWDNEKWHVS | WLYPTAHAVA | ALAQGKPQWR | DERALAALLQ | AQRDDGWGA 420 |
| GRGSTFEETA | YALFALHVMD | GSEEATGRRR | IAQVVARALE | WMLARHAAHG | LPQTPLWIGK 480 |
| ELYCPTRVVR | VAELAGLWLA | LRWGRRVLAE | GAGAAP | | 516 |

SEQ ID NO: 39
Z. mays

| | | | | | |
|---|---|---|---|---|---|
| atggttttgt | cttcttcttg | tactacagta | ccacacttat | cttcattagc | tgtcgtgcaa | 60 |
| cttggtcctt | ggagcagtag | gattaaaaag | aaaaccgata | ctgttgcagt | accagccgct | 120 |
| gcaggaaggt | ggagaagggc | cttggctaga | gcacagcaca | catcagaatc | cgcagctgtc | 180 |
| gcaaagggca | gcagtttgac | ccctatagtg | agaactgacg | ctgagtcaag | gagaacaaga | 240 |
| tggccaaccg | atgacgatga | cgccgaacct | ttagtggatg | agatcagggc | aatgcttact | 300 |
| tccatgtctg | atggtgacat | ttccgtgagc | gcatacgata | cagcctgggt | cggattggtt | 360 |
| ccaagattag | acggcggtga | aggtcctcaa | tttccagcag | ctgtgagatg | gataagaaat | 420 |
| aaccagttgc | ctgacggaag | ttggggcgat | gccgcattat | tctctgccta | tgacaggctt | 480 |
| atcaataccc | ttgcctcgct | tgtaaactttg | acaaggtggt | ccctagaaac | agagatgaga | 540 |
| ggtagaggac | tatcttttt | gggtaggaac | atgtggaaat | tagcaactga | agatgaagag | 600 |
| tcaatgccta | ttggcttcga | attagcatttt | ccatctttga | tagagcttgc | taagagccta | 660 |
| ggtgtccatg | acttccctta | tgatcaccag | gcccacaag | gaatctactc | ttcaagagag | 720 |
| atcaaaatga | agaggattcc | aaaagaagtg | atgcatacg | ttccaacatc | aatattgcac | 780 |
| agtttggagg | gtatgcctgg | cctagattgg | gctaaactac | ttaaactaca | gagcagcgac | 840 |
| ggaagttttt | tgttctcacc | agctgccact | gcatatgctt | taatgaatac | cggagatgac | 900 |
| aggtgtttta | gctacatcga | tagaacagta | aagaaattca | acggcggcgt | ccctaatgtt | 960 |
| tatccagtgg | atctatttga | acatatttgg | gccgttgata | gacttgaaag | attaggaatc | 1020 |
| tccaggtact | tccaaaagga | gatcgaacaa | tgcatggatt | atgtaaacag | gcattggact | 1080 |
| gaggacggta | tttgttgggc | aaggaactct | gatgtcaaag | aggtgaccga | cacagctatg | 1140 |
| gcctttagac | ttcttaggtt | gcacggctac | agcgtcagtc | ctgatgtgtt | taaaaacttc | 1200 |
| gaaaaggacg | gtgaattttt | cgcatttgtc | ggacagtcta | atcaagctgt | taccggtatg | 1260 |
| tacaacttaa | acagagcaag | ccagatatcc | ttcccaggcg | aggatgtgct | tcatagagct | 1320 |
| ggtgccttct | catatgagtt | cttgaggaga | aaagaagcag | agggagcttt | gagggacaag | 1380 |
| tggatcattt | ctaaagatct | acctggtgaa | gttgtgtata | ctttggattt | tccatggtac | 1440 |
| ggcaacttac | ctagagtcga | ggccagagac | tacctagagc | aatacggagg | tggtgatgac | 1500 |
| gtttggattg | gcaagacatt | gtataggatg | ccacttgtaa | acaatgatgt | atatttggaa | 1560 |
| ttggcaagaa | tggatttcaa | ccactgccag | gctttgcatc | agttagagtg | gcaaggacta | 1620 |
| aaaagatggt | atactgaaaa | taggttgatg | gactttggtg | tcgcccaaga | agatgccctt | 1680 |
| agagcttatt | ttcttgcagc | cgcatctgtt | tacgagcctt | gtagagctgc | cgagaggctt | 1740 |
| gcatgggcta | gagccgcaat | actagctaac | gccgtgagca | cccacttaag | aaatagccca | 1800 |
| tcattcagag | aaaggttaga | gcattctctt | aggtgtagac | ctagtgaaga | gacagatggc | 1860 |
| tcctggttta | actcctcaag | tggctctgat | gcagttttag | taaaggctgt | cttaagactt | 1920 |
| actgattcat | tagccaggga | agcacagcca | atccatggag | gtgacccaga | agatattata | 1980 |
| cacaagttgt | taagatctgc | ttgggccgag | tgggttaggg | aaaaggcaga | cgctgccgat | 2040 |
| agcgtgtgca | atggtagttc | tgcagtagaa | caagagggat | caagaatggt | ccatgataaa | 2100 |
| cagacctgtc | tattattggc | tagaatgatc | gaaatttctg | ccgtagggc | agctggtgaa | 2160 |
| gcagccagtg | aggacggcga | tagaagaata | attcaattaa | caggctccat | ctgcgacagt | 2220 |
| cttaagcaaa | aaatgctagt | ttcacaggac | cctgaaaaaa | atgaagagat | gatgtctcac | 2280 |
| gtggatgacg | aattgaagtt | gaggattaga | gagttcgttc | aatatttgct | tagactaggt | 2340 |
| gaaaaaaaga | ctggatctag | cgaaaccagg | caaacatttt | taagtatagt | gaaatcatgt | 2400 |
| tactatgctg | ctcattgccc | acctcatgtc | gttgatagac | acattagtag | agtgattttc | 2460 |
| gagccagtaa | gtgccgcaaa | gtaaccgcgg | | | | 2490 |

SEQ ID NO: 40
Z. mays

| | | | | | |
|---|---|---|---|---|---|
| MVLSSSCTTV | PHLSSLAVVQ | LGPWSSRIKK | KTDTVAVPAA | AGRWRRALAR | AQHTSESAAV | 60 |
| AKGSSLTPIV | RTDAESRRTR | WPTDDDDAEP | LVDEIRAMLT | SMSDGDISVS | AYDTAWVGLV | 120 |
| PRLDGGEGPQ | FPAAVRWIRN | NQLPDGSWGD | AALFSAYDRL | INTLACVVTL | TRWSLEPEMR | 180 |
| GRGLSFLGRN | MWKLATEDEE | SMPIGFELAF | PSLIELAKSL | GVHDFPYDHQ | ALQGIYSSRE | 240 |
| IKMKRIPKEV | MHTVPTSILH | SLEGMPGLDW | AKLLKLQSSD | GSFLFSPAAT | AYALMNTGDD | 300 |
| RCFSYIDRTV | KKFNGGVPNV | YPVDLFEHIW | AVDRLERLGI | SRYFQKEIEQ | CMDYVNRHWT | 360 |
| EDGICWARNS | DVKEVDDTAM | AFRLLRLHGY | SVSPDVFKNF | EKDGEFFAFV | GQSNQAVTGM | 420 |
| YNLNRASQIS | FPGEDVLHRA | GAFSYEFLRR | KEAEGALRDK | WIISKDLPGE | VVYTLDFPWY | 480 |
| GNLPRVEARD | YLEQYGGGDD | VWIGKTLYRM | PLVNNDVYLE | LARMDFNHCQ | ALHQLEWQGL | 540 |
| KRWYTENRLM | DFGVAQEDAL | RAYFLAAASV | YEPCRAAERL | AWARAAILAN | AVSTHLRNSP | 600 |
| SFRERLEHSL | RCRPSEETDG | SWFNSSSGSD | AVLVKAVLRL | TDSLAREAQP | IHGGDPEDII | 660 |
| HKLLRSAWAE | WVREKADAAD | SVCNGSSAVE | QEGSRMVHDK | QTCLLLARMI | EISAGRAAGE | 720 |
| AASEDGDRRI | IQLTGSICDS | LKQKMLVSQD | PEKNEEMMSH | VDDELKLRIR | EFVQYLLRLG | 780 |
| EKKTGSSETR | QTFLSIVKSC | YYAAHCPPHV | VDRHISRVIF | EPVSAAK | | 827 |

SEQ ID NO: 41

| | | | | | |
|---|---|---|---|---|---|
| cttcttcact | aaatacttag | acagagaaaa | cagagctttt | taaagccatg | tctcttcagt | 60 |
| atcatgttct | aaactccatt | ccaagtacaa | cctttctcag | ttctactaaa | acaacaatat | 120 |
| cttcttcttt | ccttaccatc | tcaggatctc | ctctcaatgt | cgctagagac | aaatccagaa | 180 |
| gcggttccat | acattgttca | aagcttcgaa | ctcaagaata | cattaattct | caagaggttc | 240 |
| aacatgattt | gcctctaata | catgagtggc | aacagcttca | aggagaagat | gctcctcaga | 300 |
| ttagtgttgg | aagtaaatagt | aatgcattca | aagaagcagt | agagagtgtg | aaaacgatct | 360 |
| tgagaaacct | aacggacggg | gaaattacga | tatcggctta | cgatacagct | tgggttcat | 420 |
| tgatcgatgc | cggagataaa | actccggcgt | ttccctccgc | cgtgaaatgg | atcgccgaga | 480 |
| accaactttc | cgatggttct | tggggagatg | cgtatctctt | ctcttatcat | gatcgtctca | 540 |
| tcaataccct | tgcatgcgtc | gttgctctaa | gatcatggaa | tctctttcct | catcaatgca | 600 |
| acaaaggaat | cacgttttc | cgggaaaata | ttgggaagct | agaagacgaa | aatgatgagc | 660 |

TABLE 5-continued

Sequences disclosed herein.

| | | | | |
|---|---|---|---|---|
| atatgccaat | cggattcgaa | gtagcattcc | catcgttgct | tgagatagct cgaggaataa 720 |
| acattgatgt | accgtacgat | tctccggtct | taaaagatat | atacgccaag aaagagctaa 780 |
| agcttacaag | gataccaaaa | gagataatgc | acaagatacc | aacaacattg ttgcatagtt 840 |
| tggaggggat | gcgtgattta | gattgggaaa | agctcttgaa | acttcaatct caagacggat 900 |
| cttcctctt | ctctccttcc | tctaccgctt | ttgcattcat | gcagacccga gacagtaact 960 |
| gcctcgagta | tttgcgaaat | gccgtcaaac | gtttcaatgg | aggagttccc aatgtctttc 1020 |
| ccgtggatct | tttcgagcac | atatggatag | tggatcggtt | acaacgttta gggatatcga 1080 |
| gatactttga | agaagagatt | aaagagtgtc | ttgactatgt | ccacagatat tggaccgaca 1140 |
| atggcatatg | ttgggctaga | tgttccatg | tccaagacat | cgatgataca gccatggcat 1200 |
| ttaggctctt | aagacaacat | ggataccaag | tgtccgcaga | tgtattcaag aactttgaga 1260 |
| aagagggaga | gttttctgc | tttgtggggc | aatcaaacca | agcagtaacc ggtatgttca 1320 |
| acctataccg | ggcatcacaa | ttggcgtttc | caagggaaga | gatattgaaa acgccaaag 1380 |
| agttttctta | taattatctg | ctagaaaaac | gggagagaga | ggagttgatt gataagtgga 1440 |
| ttataatgaa | agacttacct | ggcgagattg | ggtttgcgtt | agagattcca tggtacgcaa 1500 |
| gcttgcctcg | agtagagacg | agattctata | ttgatcaata | tggtggagaa aacgacgttt 1560 |
| ggattggcaa | gactctttat | aggatgccat | acgtgaacaa | taatggatat ctggaattag 1620 |
| caaaacaaga | ttcaacaat | tgccaagctc | agcatcagct | cgaatgggac atattccaaa 1680 |
| agtggtatga | agaaaatagg | ttaagtgagt | ggggtgtgcg | cagaagtgag cttctcgagt 1740 |
| gttactactt | agcggctgca | actatatttg | aatcagaaag | gtcacatgag agaatggttt 1800 |
| gggctaagtc | aagtgtattg | gttaaagcca | tttcttcttc | ttttggggaa tcctctgact 1860 |
| ccagaagaag | cttctccgat | cagtttcatg | aatacattgc | caatgctcga cgaagtgatc 1920 |
| atcactttaa | tgacaggaac | atgagattgg | accgaccagg | atcggttcag gccagtcggc 1980 |
| ttgccggagt | gttaatcggg | actttgaatc | aaatgtcttt | tgaccttttc atgtctcatg 2040 |
| gccgtgacgt | taacaatctc | ctctatctat | cgtggggaga | ttggatggaa aaatggaaac 2100 |
| tatatggaga | tgaaggagaa | ggagagctca | tggtgaagat | gataattcta atgaagaaca 2160 |
| atgacctaac | taacttcttc | acccacactc | acttcgttcg | tctcgcgaa atcatcaatc 2220 |
| gaatctgtct | tcctcgccaa | tacttaaagg | caaggagaa | cgatgagaag gagaagacaa 2280 |
| taaagagtat | ggagaaggag | atggggaaaa | tggttgagtt | agcattgtcg gagagtgaca 2340 |
| catttcgtga | cgtcagcatc | acgtttcttg | atgtagcaaa | agcattttac tactttgctt 2400 |
| tatgtggcga | tcatctccaa | actcacatct | ccaaagtctt | gtttcaaaaa gtctagtaac 2460 |
| ctcatcatca | tcatcgatcc | attaacaatc | agtggatcga | tgtatccata gatgcgtgaa 2520 |
| taatatttca | tgtagagaag | gagaacaaat | tagatcatgt | agggttatca 2570 |

SEQ ID NO: 42
Arabidopsis thaliana

| | | | | | |
|---|---|---|---|---|---|
| MSLQYHVLNS | IPSTTFLSST | KTTISSSFLT | ISGSPLNVAR | DKSRSGSIHC | SKLRTQEYIN 60 |
| SQEVQHDLPL | IHEWQQLQGE | DAPQISVGSN | SNAFKEAVKS | VKTILRNLTD | GEITISAYDT 120 |
| AWVALIDAGD | KTPAFPSAVK | WIAENQLSDG | SWGDAYLFSY | HDRLINTLAC | VVALRSWNLF 180 |
| PHQCNKGITF | FRENIGKLED | ENDEHMPIGF | EVAFPSLLEI | ARGINIDVPY | DSPVLKDIYA 240 |
| KKELKLTRIP | KEIMHKIPTT | LLHSLEGMRD | LDWEKLLKLQ | SQDGSFLFSP | SSTAFAFMQT 300 |
| RDSNCLEYLR | NAVKRFNGGV | PNVFPVDLFE | HIWIVDRLQR | LGISRYFEEE | IKECLDYVHR 360 |
| YWTDNGICWA | RCSHVQDIDD | TAMAFRLLRQ | HGYQVSADVF | KNFEKEGEFF | CFVGQSNQAV 420 |
| TGMFNLYRAS | QLAFPREEIL | KNAKEFSYNY | LLEKREREEL | IDKWIIMKDL | PGEIGFALEI 480 |
| PWYASLPRVE | TRFYIDQYGG | ENDVWIGKTL | YRMPYVNNNG | YLELAKQDYN | NCQAQHQLEW 540 |
| DIFQKWYEEN | RLSEWGVRRS | ELLECYYLAA | ATIFESERSH | ERMVWAKSSV | LVKAISSSFG 600 |
| ESSDSRRSFS | DQFHEYIANA | RRSDHHFNDR | NMRLDRPGSV | QASRLAGVLI | GTLNQMSFDL 660 |
| FMSHGRDVNN | LLYLSWGDWM | EKWKLYGDEG | EGELMVKMII | LMKNNDLTNF | FTHTHFVRLA 720 |
| EIINRICLPR | QYLKARRNDE | KEKTIKSMEK | EMGKMVELAL | SESDTFRDVS | ITFLDVAKAF 780 |
| YYFALCGDHL | QTHISKVLFQ | KV | | | 802 |

SEQ ID NO: 43

| | | | | |
|---|---|---|---|---|
| atgaatttga | gtttgtgtat | agcatctcca | ctattgacca | aatctaatag accagctgct 60 |
| ttatcagcaa | ttcatacagc | tagtacatcc | catggtggcc | aaaccaaccc tacgaatctg 120 |
| ataatcgata | cgaccaagga | gagaataca | aaacaattca | aaatgttga atttcagtt 180 |
| tcttctatg | atactgcgtg | ggttgccatg | gttccatcac | ctaattctcc aaagtctcca 240 |
| tgtttccag | aatgtttgaa | ttggctgatt | aacaaccagt | tgaatgatgg atcttgggt 300 |
| ttagtcaatc | acacgcacaa | tcacaaccat | ccacttttga | agattcttt atcctcaact 360 |
| ttggctttgca | tcgtgccct | aaagagatgg | aacgtaggtg | aggatcagat taacaagggg 420 |
| cttagtttca | ttgaatctaa | cttggcttcc | gcgactgaaa | atctcaacc atctccaata 480 |
| ggattcgata | tcatctttcc | aggtctgtta | gagtacgcca | aaaatctaga tatcaactta 540 |
| ctgtctaagc | aaactgattt | ctcactaatg | ttacacaaga | gagaattgaa acaaaagaga 600 |
| tgtcattcaa | acgaaatgga | tggttaccta | gcttatatct | ctgaaggtct tggtaatctt 660 |
| tacgattgga | atatggtgaa | aaagtaccag | atgaaaatg | gctcagtttt caattcccct 720 |
| tctgcaactg | cggcagcatt | cattaaccat | caaaatccag | gatgcctgaa ctatttgaat 780 |
| tcactactag | acaaattcgg | caacgcagtt | ccaactgtca | accctcacga tttgtttatc 840 |
| agattgagta | tggtggatac | aattgaaaga | cttggtatat | cccaccactt tagagtcgag 900 |
| atcaaaaatg | ttttggatga | gacataccgt | tgttgggtgg | agagagatga acaaatctt 960 |
| atggatgttg | tgacgtgcgc | gttggccttt | agattgttgc | gtattaacgg ttacgaagtt 1020 |
| agtccagatc | cacttgccga | aattacaaac | gaattagctt | taaaggatga atacgccgct 1080 |
| cttgaaacat | atcatgcgtc | acatatcctt | taccaagagg | acttatcatc tggaaaacaa 1140 |
| attcttaaat | ctgctgattt | cctgaaggaa | atcatatcca | ctgatagtaa tagactgtcc 1200 |
| aaactgatcc | ataagaggt | tgaaaatgca | cttaagttcc | ctattaacac cggcttagaa 1260 |
| cgtattaaca | caagacgtaa | catccgcctt | tacaacgtaa | acaatactaa attcttgaaa 1320 |
| accttaccc | attcttccaa | catatcaaac | actgttgatc | taagattagc tgttgaagat 1380 |
| ttctacacat | gtcagtctat | ctatagaaa | gagctgaaaag | gattagagag atgggtcgtt 1440 |
| gagaataagc | tagatcaatt | gaaatttgcc | agacaaaaga | cagcttattg ttacttctca 1500 |
| gttgccgcca | ctttatcaag | tccagaattg | tcagatgcac | gtatttcttg ggctaaaaac 1560 |
| ggaattttga | caactgttgt | tgatgatttc | tttgatattg | gcgggacaat cgacgaattg 1620 |

TABLE 5-continued

Sequences disclosed herein.

```
acaaacctga ttcaatgcgt tgaaaagtgg aatgtcgatg tcgataaaga ctgttgctca   1680
gaacatgtta gaatactgtt cttggctctg aaagatgcta tctgttggat cggggatgag   1740
gcttcaaat  ggcaagctag agatgtgacg tctcacgtca ttcaaacctg gctagaactg   1800
atgaactcta tgttgagaga agcaatttgg actagagatg catacgttcc tacattaaac   1860
gagtatatgg aaaacgctta tgtctccttt gctttgggtc ctatcgttaa gcctgccata   1920
tactttgtag gaccaaagct atccgaggaa atcgtcgaat catcagaata ccataacttg   1980
ttcaagttaa tgtccacaca aggcagatta cttaatgata ttcattcttt caaaagagag   2040
tttaaggaag gaaagttaaa tgctgttgct ctgcatcttt ctaatggcga agtggtaaa    2100
gtcgaagagg aagtagttga ggaaatgatg atgatcaaaa aaacaagag aaaggagttg     2160
atgaaactaa tcttcgaaga aacggttca attgttccta gagcatgtaa ggatgcattt    2220
tggaacatgt gtcatgtgct aaactttttc tacgcaaacg acgatggttt tactgggaac   2280
acaatactag atacagtaaa agacatcata tacaacccct tggtcttagt aaacgaaaac   2340
gaggagcaaa gataa                                                    2355

SEQ ID NO: 44
Stevia rebaudiana
MNLSLCIASP LLTKSNRPAA LSAIHTASTS HGGQTNPTNL IIDTTKERIQ KQFKNVEISV    60
SSYDTAWVAM VPSPNSPKSP CFPECLNWLI NNQLNDGSWG LVNHTHNHNH PLLKDSLSST   120
LACIVALKRW NVGEDQINKG LSFIESNLAS ATEKSQPSPI GFDIIFPGLL EYAKNLDINL   180
LSKQTDFSLM LHKRELEQKR CHSNEMDGYL AYISEGLGNL YDWNMVKKYQ MKNGSVFNSP   240
SATAAAFINH QNPGCLNYLN SLLDKFGNAV PTVYPHDLFI RLSMVDTIER LGISHHFRVE   300
IKNVLDETYR CWVERDEQIF MDVVTCALAF RLLRINGYEV SPDPLAEITN ELALKDEYAA   360
LETYHASHIL YQEDLSSGKQ ILKSADFLKE IISTDSNRLS KLIHKEVENA LKFPINTGLE   420
RINTRRNIQL YNVDNTRILK TTYHSSNISN TDYLRLAVED FYTCQSIYRE ELKGLERWVV   480
ENKLDQLKFA RQKTAYCYFS VAATLSSPEL SDARISWAKN GILTTVVDDF FDIGGTIDEL   540
TNLIQCVEKW NVDVDKDCCS EHVRILFLAL KDAICWIGDE AFKWQARDVT SHVIQTWLEL   600
MNSMLREAIW TRDAYVPTLN EYMENAYVSF ALGPIVKPAI YFVGPKLSEE IVESSEYHNL   660
FKLMSTQGRL LNDIHSFKRE FKEGKLNAVA LHLSNGESGK VEEEVVEEMM MMIKNKRKEL   720
MKLIFEENGS IVPRACKDAF WNMCHVLNFF YANDDGFTGN TILDTVKDII YNPLVLVNEN   780
EEQR                                                                784

SEQ ID NO: 45
atgaatctgt ccctttgtat agctagtcca ctgttgacaa atcttctag  accaactgct    60
ctttctgcaa ttcatactgc cagtactagt catggaggtc aaacaaaccc aacaaatttg   120
ataatcgata ctactaagga gagaatccaa aagctattca aaaatgttga atctcagta    180
tcatcttatg acaccgcatg ggttgcaatg gtgccatcca ttaattcccc aaaaagtcca   240
tgttttccag agtgcttgaa ttggttaatc aataatcagt taaacgatgg ttcttggggt   300
ttagtcaacc acactcataa ccacaatcat ccattattga aggactcttt atcatcaaca   360
ttagcctgta ttgttgcatt gaaagatggg aatgtaggtg aagatcaaat caacaagggt   420
ttatcattca tagaatccaa tctagcttct gctaccgaca aatcacaacc atctccaatc   480
gggttcgaca taatcttccc tggtttgctg gagtatgcca aaaaccttga tatcaactta   540
ctgtctaaac aaacagattt ctctttgatg ctacacaaaa gagagttaga gcagaaaaga   600
tgccattcta acgaaattga cgggtactta gcatatatct cagaaggttt gggtaattt g   660
tatgactgga acatggtcaa aaagtatcag atgaaaaatg gatccgtatt caattctcgt   720
tctgcaactg ccgcagcatt cattaatcat caaaaccctg ggtgtcttaa ctacttgaac   780
tcactattag ataagtttgg aaatgcagtt ccaacagtct atcctttgga cttgtacatc   840
agattatcta tggttgacac tatagagaga ttaggtattt ctcatcattt cagagttgag   900
atcaaaaatg ttttggacga gacatacaga tgttgggtcg aaagagatga gcaaatcttt  960
atggatgtcg tgacctgcgc tctggccttt agattgctaa ggatacacgg atacaaagta  1020
tctcctgatc aactggctga gattacaaac gaactggctt caaagacga  atacgccgca  1080
ttagaaacat accatgcatc ccaaatactt taccaggaag acctaagttc aggaaaacaa  1140
atcttgaagt ctgcagattt cctgaaaggc atttctgtta agatagtaa taggttgtct  1200
aaattgatac acaaggaagt agaaaacgca ctaaagtttc ctattagtaac tggtttagag  1260
agaatcaata ctaggagaaa cattcagctg tacaacgtag ataatacaag gattcttaag  1320
accacctacc atagttcaaa cattcccaac acctattact taagattagc tgtcgaagac  1380
ttttacactt gtcaatcaat ctacagagag gagttaaagg gcctagaaag atgggtagtt  1440
caaaacaagt tggatcaact gaagtttgct agacagaaga cagcatactg ttatttctct  1500
gttgctgcta cccttcatc cccagaattg tctgatgcca gaataagttg ggccaaaaat  1560
ggtattctta caactgtagt cgatgatttc tttgatattg gaggtactat tgatgaactg  1620
acaaatctta ttcaatgtgt tgaaaagtgg aacgtggatg tagataagga ttgctgcagt  1680
gaacatgtga gaatactttt cctggctcta aaagatgcaa tatgttggat tggcgacgag  1740
gccttcaagt ggcaagctag agatgttaca tctcatgtca tccaaacttg cttgaactg  1800
atgaactcaa tgctaagaga agcaatctgg acaagagatg catacgttcc aacattgaac  1860
gaatacatgg aaaacgctta cgtctcattt gccttgggtc ctattgttaa gccagccata  1920
tactttgttg ggccaaagtt atccgaagag attgttgagt cttccgaata tcataaccta  1980
ttcaagttaa tgtcaacaca aggcagactt ctgaacgata tccactcctt caaaagagaa  2040
ttcaaggaag gtaagctaaa cgctgttgct ttgcacttgt ctaatggtga atctggcaaa  2100
gtggaagagg aagtcgttga ggaaatgatg atgatcaaaa aacaagag aaaggaattg     2160
atgaaattga ttttcgagga aaatggttca atcgtaccta gacttgtaa agatgcttt     2220
tggaatatgt gccatgttct taacttcttt tacgctaatg atgatggctt cactgggaat  2280
acaatattgg atacagttaa agatatcatc tacaacccac ttgttttggt caatgagaac  2340
gaggaacaaa gataa                                                    2355

SEQ ID NO: 46
Stevia rebaudiana
MNLSLCIASP LLTKSSRPTA LSAIHTASTS HGGQTNPTNL IIDTTKERIQ KLFKNVEISV    60
SSYDTAWVAM VPSPNSPKSP CFPECLNWLI NNQLNDGSWG LVNHTHNHNH PLLKDSLSST   120
LACIVALKRW NVGEDQINKG LSFIESNLAS ATDKSQPSPI GFDIIFPGLL EYAKNLDINL   180
```

TABLE 5-continued

Sequences disclosed herein.

```
LSKQTDFSLM LHKRELEQKR CHSNEIDGYL AYISEGLGNL YDWNMVKKYQ MKNGSVFNSP     240
SATAAAFINH QNPGCLNYLN SLLDKFGNAV PTVYPLDLYI RLSMVDTIER LGISHHFRVE     300
IKNVLDETYR CWVERDEQIF MDVVTCALAF RLLRIHGYKV SPDQLAEITN ELAFKDEYAA     360
LETYHASQIL YQEDLSSGKQ ILKSADFLKG ILSTDSNRLS KLIHKEVENA LKFPINTGLE     420
RINTRRNIQL YNVDNTRILK TTYHSSNISN TYYLRLAVED FYTCQSIYRE ELKGLERWVV     480
QNKLDQLKFA RQKTAYCYFS VAATLSSPEL SDARISWAKN GILTTVVDDF FDIGGTIDEL     540
TNLIQCVEKW NVDVDKDCCS EHVRILFLAL KDAICWIGDE AFKWQARDVT SHVIQTWLEL     600
MNSMLREAIW TRDAYVPTLN EYMENAYVSF ALGPIVKPAI YFVGPKLSEE IVESSEYHNL     660
FKLMSTQGRL LNDIHSFKRE FKEGKLNAVA LHLSNGESGK VEEEVVEEMM MMIKNKRKEL     720
MKLIFEENGS IVPRACKDAF WNMCHVLNFF YANDDGFTGN TILDTVKDII YNPLVLVNEN     780
EEQR                                                                 784

SEQ ID NO: 47
atggctatgc cagtgaagct aacacctgcg tcattatcct taaaagctgt gtgctgcaga     60
ttctcatccg gtggccatgc tttgagattc gggagtagtc tgccatgttg gagaaggacc    120
cctacccaaa gatctacttc ttcctctact actagaccag ctgccgaagt gtcatcaggt    180
aagagtaaac aacatgatca ggaagctagt gaagcgacta tcagacaaca attacaactt    240
gtggatgtcc tggagaatat gggaatatcc agacattttg ctgcagagat aaagtgcata    300
ctagacagaa cttacagatc ttggttacaa agacacgaag aaatcatgct ggacactatg    360
acatgtgcta tggcttttag aatcctaaga ttgaacggat acaacgtttc atcagatgaa    420
ctataccacg ttgtagaggc atctggtctg cataattctt gggtgggta tcttaacgat     480
accagaacac tacttgaatt acacaaggct tcaacagtta gtatctctga ggatgaatct    540
atcttagatt caattggctc tagatccaga acattgctta gagaacaatt ggagtctgtt    600
ggcgcactga gaaagccttc tttattcaaa gaggttgaac atgcactgga tggaccttt     660
tacaccacac ttgatagact tcatcatagg tggaatattg aaaacttcaa cattattgag    720
caacacatgt tggagactcc atacttatct aaccagcata catcaaggga tatcctagca    780
ttgtcaatta gagattttc ctcctcacaa ttcacttatc acaagagact acagcatctg     840
gagagttggg ttaaggaatg tagattagat caactacagt tcgcaaagaca gaaattagcg    900
tacttttacc tatcagccgc aggcaccatg ttttctcctg agctttctga tgcgagaaca    960
ttatgggcca aaaacggggt gttgacaact attgttgatg atttctttga tgttgccggt   1020
tctaaagagg aattggaaaa cttagtcatg ctggtcgaaa tgtgggatga acatcacaaa   1080
gttgaattct attctgagca ggtcgaaatc atcttctctt ccatctacga ttctgtcaac   1140
caattgggtg agaaggcctc tttggttcaa gacagatcaa ttacaaaaca ccttgttgaa   1200
atatggttag acttgttaaa gtccatgatg acggaagttg aatggagact gtcaaaatac   1260
gtgcctacag aaaaggaata catgattaat gcctctctta tcttcggcct aggtccaatc   1320
gttttaccag cttttgtattt cgttggtcca aagatttcaa aagtatagt aaaggaccca   1380
gaatatgatg aattgttcaa actaatgtca acatgtggta gattgttgaa tgacgtgcaa   1440
acgttcgaaa gagaatacaa tgagggtaaa ctgaattctg tcagtctatt ggttcttcac   1500
ggaggcccaa tgtctatttc agacgcaaag aggaaattac aaaaagccta tgatacgtgt   1560
agaagagatc ttctttcttt ggtccttaga gaagagtctg tagtaccaag accatgtaag   1620
gaactattct ggaaaatgtg taaagtgtgc tatttctttt actcaacaac tgatgggttt   1680
tctagtcaag tcgaaagagc aaaagaggta gacgctgtca taaatgagcc actgaagttg   1740
caaggttctc atacactggt atctgatgtt taa                                1773

SEQ ID NO: 48
Zea mays
MAMPVKLTPA SLSLKAVCCR FSSGGHALRF GSSLPCWRRT PTQRSTSSST TRPAAEVSSG     60
KSKQHDQEAS EATIRQQLQL VDVLENMGIS RHFAAEIKCI LDRTYRSWLQ RHEEIMLDTM    120
TCAMAFRILR LNGYNVSSDE LYHVVEASGL HNSLGGYLND TRTLLELHKA STVSISEDES    180
ILDSIGSRSR TLLREQLESG GALRKPSLFK EVEHALDGPF YTTLDRLHHR WNIENFNIIE    240
QHMLETPYLS NQHTSRDILA LSIRDFSSSQ FTYQQELQHL ESWVKECRLD QLQFARQKLA    300
YFYLSAAGTM FSPELSDART LWAKNGVLTT IVDDFFDVAG SKEELENLVM LVEMWDEHHK    360
VEFYSEQVEI IFSSIYDSVN QLGEKASLVQ DRSITKHLVE IWLDLLKSMM TEVEWRLSKY    420
VPTEKEYMIN ASLIFGLGPI VLPALYFVGP KISESIVKDP EYDELFKLMS TCGRLLNDVQ    480
TFEREYNEGK LNSVSLLVLH GGPMSISDAK RKLQKPIDTC RRDLLSLVLR EESVVPRPCK    540
ELFWKMCKVC YFFYSTTDGF SSQVERAKEV DAVINEPLKL QGSHTLVSDV               590

SEQ ID NO: 49
atgcagaact ccatggtac aaaggaaagg atcaaaaaga tgtttgacaa gattgaattg     60
tccgtttctt cttatgatac agcctgggtt gcaatggtcc catccctga ttgcccagaa    120
acaccttgtt ttccagaatg tactaaatgg atcctagaaa atcagttggg tgatggtagt    180
tggtcacttc ctcatggcaa tccacttcta gttaaagatg cattatcttc cactcttgct    240
tgtattctgg ctcttaaaag atggggaatc ggtgaggaac agattaacaa aggactgaga    300
ttcatagaac tcaactctgc tagtgtaacc gataacgaac aacacaaacc aattggattt    360
gacattatct ttccaggtat gattgaatac gctatagact tagacctgaa tctaccacta    420
aaaccaactg acattaactc catgttgcat cgtagagccc ttgaattgac atcaggtgga    480
ggcaaaaatc tagaaggtag aagagcttac ttggcctacg tctctgaagg aatcggtaag    540
ctgcaagatt gggaaatggc tatgaaatac aacgtaaaa acggatctct gttcaatagt    600
ccatcaacaa ctgcagctgc attcatccat atacaagatg ctgaatgcct ccactatgtc    660
cgttctcttc tccagaaatt tggaaacgca gtccctacaa tataccctct cgatatctat    720
gccagacttt caatggtaga tgcctggaa cgtcttggta ttgatagaca tttcagaaag    780
gagagaaagt tcgttctgga tgaaacatac agattttggt gcaaggaga agaggagatt    840
ttctccgata acgcaacctg tgctttggcc ttcaaatat tgagacttaa tggttacgat    900
gtctctcttg aagatcactt ctctaactct ctgggcggtt acttaaagga ctcaggagca    960
gctttagaac tgtacagagc cctccaattg tcttacccag acgagtccct cctgaaaag   1020
caaaattcta gaacttctta cttccttaaaa caaggttat ccaatgtctc cctctgtggt  1080
gacagattgc gtaaaaacat aattggagag gtgcatgatg ctttaaactt ttccgaccac  1140
gctaacttac aaagattagc tattcgtaga aggattaagc attacgctac tgacgataca  1200
```

TABLE 5-continued

Sequences disclosed herein.

```
aggattctaa aaacttccta cagatgctca acaatcggta accaagattt tctaaaactt   1260
gcagtggaag atttcaatat ctgtcaatca atacaaagag aggaattcaa gcatattgaa   1320
agatgggtcg ttgaaagacg tctagacaag ttaaagttcg ctagacaaaa agaggcctat   1380
tgctatttct cagccgcagc aacattgttt gccccctgaat tgtctgatgc tagaatgtct   1440
tgggccaaaa atggtgtatt gacaactgtg gttgatgatt tcttcgatgt cggaggctct   1500
gaagaggaat tagttaactt gatagaattg atcgagcgtt gggatgtgaa tggcagtgca   1560
gattttgta gtgaggaagt tgagattatc tattctgcta tccactcaac tatctctgaa   1620
ataggtgata agtcatttgg ctggcaaggt agagatgtaa agtctcaagt tatcaagatc   1680
tggctggact tattgaaatc aatgttaact gaagctcaat ggtcttcaaa caagtctgtt   1740
cctaccctag atgagtatat gacaaccgcc catgtttcat tcgcacttgg tccaattgta   1800
cttccagcct tatacttcgt tggcccaaag ttgtcagaag aggttgcagg tcatcctgaa   1860
ctactaaacc tctacaaagt cacatctact tgtggcagaa tactgaatga ttggagaagt   1920
tttaagagag aatccgagga aggtaagctc aacgctatta gtttatacat gatccactcc   1980
ggtggtgctt ctacagaaga ggaaacaatc gaacatttca aaggtttgat tgattctcag   2040
agaaggcaac tgttacaatt ggtgttgcaa gagaaggata gtatcatacc tagaccatgt   2100
aaagatctat tttggaatat gattaagtta ttacacactt tctacatgaa agatgatggc   2160
ttcacctcaa atgagatgag gaatgtagtt aaggcaatca ttaacgaacc aatctcactg   2220
gatgaattat ga                                                       2232

SEQ ID NO: 50
Populus trichocarpa
MSCIRPWFCP SSISATLTDP ASKLVTGEFK TTSLNFHGTK ERIKKMFDKI ELSVSSYDTA    60
WVAMVPSPDC PETPCFPECT KWILENQLGD GSWSLPHGNP LLVKDALSST LACILALKRW   120
GIGEEQINKG LRFIELNSAS VTDNEQHKPI GFDIIFPGMI EYAKDLDLNL PLKPTDINSM   180
LHRRALELTS GGGKNLEGRR AYLAYVSEGI GKLQDWEMAM KYQRKNGSLF NSPSTTAAAF   240
IHIQDAECLH YIRSLLQKFG NAVPTIYPLD IYARLSMVDA LERLGIDRHF RKERKFVLDE   300
TYRFWLQGEE EIFSDNATCA LAFRILRLNG YDVSLEDHFS NSLGGYLKDS GAALELYRAL   360
QLSYPDESLL EKQNSRTSYF LKQGLSNVSL CGDRLRKNII GEVHDALNFP DHANLQRLAI   420
RRRIKHYATD DTRILKTSYR CSTIGNQDFL KLAVEDFNIC QSIQREEFKH IERWVVERRL   480
DKLKFARQKE AYCYFSAAAT LFAPELSDAR MSWAKNGVLT TVVDDFFDVG GSEEELVNLI   540
ELIERWDVNG SADFCSEEVE IIYSAIHSTI SEIGDKSFGW QGRDVKSHVI KIWLDLLKSM   600
LTEAQWSSNK SVPTLDEYMT TAHVSFALGP IVLPALYFVG PKLSEEVAGH PELLNLYKVM   660
STCGRLLNDW RSFKRESEEG KLNAISLYMI HSGGASTEEE TIEHFKGLID SQRRQLLQLV   720
LQEKDSIIPR PCKDLFWNMI KLLHTFYMKD DGFTSNEMRN VVKAIINEPI SLDEL        775

SEQ ID NO: 51
A. thaliana
atgtctatca accttcgctc ctccggttgt tcgtctccga tctcagctac tttggaacga    60
ggattggact cagaagtaca gacaagagct aacaatgtga gctttgagca aacaaaggag   120
aagattagga agatgttgga gaaagtggag cttttctgttt cggcctacga tactagttgg   180
gtagcaatgg ttccatcacc gagctcccaa aatgctccac ttttcccaca gtgtgtgaaa   240
tggttattgg ataatcaaca tgaagatgga tcttggggac ttgataacca tgaccatcaa   300
tctcttaaga aggatgtgtt atcatctaca ctggctagta tcctcgcgtt aaagaagtgg   360
ggaattggtg aaagacaaat aaacaagggt ctccagttta ttgagctgaa ttctgcatta   420
gtcactgatg aaaccataca gaaaccaaca gggtttgata ttatatttcc tgggatgatt   480
aaatatgcta gagatttgaa tctgacgatt ccattgggct cagaagtggt ggatgacatg   540
atacgaaaaa gagatctgga tcttaaatgt gatagtgaaa gttttcaaa gggaagagaa   600
gcatatctgg cctatgtttt agaggggaca agaaacctaa agaattggga tttgatagtc   660
aaatatcaaa ggaaaaatgg gtcactgttt gattctccag ccacaacagc agctgctttt   720
actcagtttg ggaatgatgg ttgtctccgt tatctctgtt ctctccttca gaaattcgag   780
gctgcagttc cttcagttta tccatttgat caatatgcac gccttagtat aattgtcact   840
cttgaaagct taggaattga tagagatttc aaaaccgaaa tcaaaagcat attgatgaa   900
acctatagat attggcttcg tggggatgaa gaaatatgtt tggacttggc cacttgtgct   960
ttggcttttcc gattattgct tgctcatggc tatgatgtgt cttacgatcc gctaaaacca  1020
tttgcagaag aatctggttt ctctgatact ttggaaggat atgttaagaa tacgttttct  1080
gtgttagaat tatttaaggc tgctcaaagt tatccacatg aatcagcttt gaagaagcag  1140
tgttgttgga ctaaacaata tctggagatg gaattgtcca gctgggttaa gacctctgtt  1200
cgagataaat acctcaagaa agaggtcgag gatgctcttg cttttccctc ctatgcaagc  1260
ctagaaagat cagatcacag gagaaaaata tcaatggtt ctgctgtgga aaacaccaga  1320
gttacaaaaa cctcatatcg tttgcacaat atttgcacct ctgatatcct gaagttagct  1380
gtggatgact tcaatttctg ccagtccata caccgtgaag aaatggaacg tcttgatagg  1440
tggattgtgg agaatagatt gcaggaactg aaatttgcca gacagaagct ggcttactgt  1500
tatttctctg ggctgcaac tttatttttct ccagaactat ctgatgctcg tatatcgtgg  1560
gccaaaggtg gagtacttac aacggttgta gacgacttct ttgatgttgg agggtccaaa  1620
gaagaactgg aaaacctcat acacttggtc gaaaagtggg atttgaaggt tgttcctgag  1680
tacagctcag aacatgttga gatcatattc tcagttctaa gggacaccat tctcgaaaca  1740
ggagacaaag cattcccta tcaaggacgc aatgtgacac accacattgt gaaaatttgg  1800
ttggatctgc tcaagtctat gttgagagaa ccgagtggg ccagtgacaa gtcaacacca  1860
agcttggagg attacatgga aaatgcgtac atatcatttg cattaggacc aattgtccct  1920
ccagctacct atctgatcgg acctccactt ccagagaaga cagtcgatag ccaccaatat  1980
aatcagctct acaagctcgt gagcactatg ggtcgtcttc taaatgacat acaaggtttt  2040
aagagagaaa gcgcggaagg gaagctgaat gcggtttcat tgcacatgaa acacgagaga  2100
gacaatcgca gcaaagaagt gatcatagaa tcgatgaaag gtttagcaga gagaagagg  2160
gaagaattgc ataagctagt tttggaggag aaaggaagtg tggttccaag ggaatgcaaa  2220
gaagcgttct tgaaaatgag caaagtgttg aacttatttt acaggaagga cgatggattc  2280
acatcaaatg atctgatgag tcttgttaaa tcagtgatct acgagcctgt tagcttacag  2340
aaagaatctt taacttga                                                2358
```

TABLE 5-continued

Sequences disclosed herein.

SEQ ID NO: 52
A. thaliana
```
MSINLRSSGC SSPISATLER GLDSEVQTRA NNVSFEQTKE KIRKMLEKVE LSVSAYDTSW    60
VAMVPSPSSQ NAPLFPQCVK WLLDNQHEDG SWGLDNHDHQ SLKKDVLSST LASILALKKW   120
GIGERQINKG LQFIELNSAL VIDETIQKPT GFDIIFPGMI KYARDLNLTI PLGSEVVDDM   180
IRKRDLDLKC DSEKFSKGRE AYLAYVLEGT RNLKDWDLIV KYQRKNGSLF DSPATTAAAF   240
TQFGNDGCLR YLCSLLQKFE AAVPSVYPFD QYARLSIIVT LESLGIDRDF KTEIKSILDE   300
TYRYWLRGDE EICLDLATCA LAFRLLLAHG YDVSYDPLKP FAEESGFSDT LEGYVKNTFS   360
VLELFKAAQS YPHESALKKQ CCWTKQYLEM ELSSWVKTSV RDKYLKKEVE DALAFPSYAS   420
LERSDHRRKI LNGSAVENTR VTKTSYRLHN ICTSDILKLA VDDFNFCQSI HREEMERLDR   480
WIVENRLQEL KFARQKLAYC YFSGAATLFS PELSDARISW AKGGVLTTVV DDFFDVGGSK   540
EELENLIHLV EKWDLNGVPE YSSEHVEIIF SVLRDTILET GDKAFTYQGR NVTHHIVKIW   600
LDLLKSMLRE AEWSSDKSTP SLEDYMENAY ISFALGPIVL PATYLIGPPL PEKTVDSHQY   660
NQLYKLVSTM GRLLNDIQGF KRESAEGKLN AVSLHMKHER DNRSKEVIIE SMKGLAERKR   720
EELHKLVLEE KGSVVPRECK EAFLKMSKVL NLFYRKDDGF TSNDLMSLVK SVIYEPVSLQ   780
KESLT                                                              785
```

SEQ ID NO: 53
```
atggaatttg atgaaccatt ggttgacgaa gcaagatctt tagtgcagcg tactttacaa    60
gattatgatg acagatacgg cttcggtact atgtcatgtg ctgcttatga tacagcctgg   120
gtgtctttag ttacaaaaac agtcgatggg agaaaacaat ggcttttccc agagtgtttt   180
gaatttctac tagaaacaca atctgatgcc ggaggatggg aaatcggaa ttcagcacca    240
atcgacggta tattgaatac agctgcatcc ttacttgctc taaaacgtca cgttcaaact   300
gagcaaatca tccaacctca acatgaccat aaggatctag caggtagagc tgaacgtgcc   360
gctgcatctt tgagagcaca attggctgca ttggatgtgt ctacaactga acacgtcggt   420
tttgagataa ttgttcctgc aatgctagac ccattagaag ccgaagatcc atctctagtt   480
ttcgattttc cagctaggaa acctttgatg aagattcatg atgctaagat gagtagattc   540
aggccagaat acttgtatgg caaacaacca atgaccgcct tacattcatt agaggctttc   600
ataggcaaaa tcgacttcga taaggtaaga caccaccgta cccatgggtc tatgatgggt   660
tctccttcat ctaccgcagc ctacttaatg cacgcttcac aatgggatgg tgactcagag   720
gcttacctta gacacgtgat taaacacgca gcagggcagg aactggtgc tgtaccatct    780
gctttcccat caacacattt tgagtcatct tggattctta ccacattgtt tagagctgga   840
ttttcagctt ctcatcttgc ctgtgatgag ttgaacaagt tggtcgagat acttgaggc    900
tcattcgaga aggaaggtgg ggcaatcggt tacgctccag ggtttcaagc agatgttgat   960
gatactgcta aaacaataag tacattagca gtccttggaa gagatgctac accaagacaa  1020
atgatcaagg tatttgaagc taatacacat tttagaacat accctggtga aagagatcct  1080
tctttgacag ctaattgtaa tgctctatca gccttactac accaaccaga tgcagcaatg  1140
tatggatctc aaattcaaaa gattaccaaa tttgtctgtg actattggtg gaagtctgat  1200
ggtaagatta agataagtg gaacacttgc tacttgtacc catctgtctt attagttgag   1260
gttttggttg atcttgttag tttattggag cagggtaaat tgcctgatgt tttggatcaa  1320
gagcttcaat acagagtcgc catcacattg ttccaagcat gtttaaggcc attactagac  1380
caagatgccg aaggatcatg gaacaagtct atcgaagcca cagcctacgg catccttatc  1440
ctaactgaag ctaggagagt ttgtttcttc gacagattgt ctgagccatt gaatgaggca  1500
atccgtagag gtatcgcttt cgccgactct atgtctggaa ctgaagctca gttgaactac  1560
atttggatcg aaaaggttag ttacgcacct gcattattga ctaaatccta tttgttagca  1620
gcaagatggg ctgctaagtc tccttttaggc gcttccgtag gctcttcttt gtggactcca  1680
ccaagagaag gattggataa gcatgtcaga ttattccatc aagctgagtt attcagatcc  1740
cttccagaat gggaattaag agcctccatg attgaagcag ctttgttcac accacttcta  1800
agagcacata gactgacgt tttccctaga caagatgtag gtgaagacaa atatcttgat   1860
gtagttccat tcttttggac tgccgctaac aacagagata gaacttacgc ttccactcta  1920
ttcctttacg atatgtgttt tatcgcaatg ttaaacttcc agttagacga attcatggag  1980
gccacagccg gtatcttatt cagagatcat atggatgatt tgaggcaatt gattcatgat  2040
cttttggcag agaaaacttc cccaaagagt tctggtagaa gtagtcaggg cacaaaagat  2100
gctgactcag gtatagagga agacgtgtca atgtccgatt cagcttcaga ttcccaggat  2160
agaagtccag aatacgactt ggttttcagt gcattgagta cctttacaaa acatgtcttg  2220
caacacccat ctatacaaag tgcctctgta tgggataaga aactacttgc tagagagatg  2280
aaggcttact tacttgctca tatccaacaa gcagaagatt caatccatt gtctgaattg   2340
aaagatgtgc ctcaaaagac tgatgtaaca agagtttcta catctactac taccttcttt  2400
aactggttta gaacaacttc cgcagaccat atatcctgcc catactcctt ccactttgta  2460
gcatgccatc taggcgcagc attgtcacct aaagggtcta acgtgattg ctatccttca   2520
gctggtgaga agttcttggc agctgcagtc tgcagacatt tggccaccat gtgtagaatg  2580
tacaacgatc ttggatcagc tgaacgtgat tctgatgaag gtaatttgaa ctccttggac  2640
ttccctgaat cgccgattc cgcaggaaac ggagggata aaattcagaa ggccgctcta   2700
ttaaggttag ctgagtttga gagagattca tacttagagg ccttccgtcg tttacaagat  2760
gaatccaata gagttcacgg tccagccggt ggtgatgaag ccagattgtc cagaaggaga  2820
atggcaatcc ttgaattctt cgcccagcag gtagatttgt acggtcaagt atacgtcatt  2880
agggatattt ccgctcgtat tcctaaaaac gaggttgaga aaagagaaa attggatgat   2940
gctttcaatt ga                                                      2952
```

SEQ ID NO: 54
Phomopsis amygdali
```
MEFDEPLVDE ARSLVQRTLQ DYDDRYGFGT MSCAAYDTAW VSLVTKTVDG RKQWLFPECF    60
EPLLETQSDA GGWEIGNSAP IDGILNTAAS LLALKRHVQT EQIIQPQHDH KDLAGRAERA   120
AASLRAQLAA LDVSTTEHVG FEIIVPAMLD PLEAEDPSLV FDFPARKPLM KIHDAKMSRF   180
RPEYLYGKQP MTALHSLEAF IGKIDFDKVR HHRTHGSMMG SPSSTAAYLM HASQWDGDSE   240
AYLRHVIKHA AGQGTGAVPS AFPSTHFESS WILTTLFRAG FSASHLACDE LNKLVEILEG   300
SFEKEGGAIG YAPGFQADVD DTAKTISTLA VLGRDATPRQ MIKVFEANTH FRTYPGERDP   360
SLTANCNALS ALLHQPDAAM YGSQIQKITK FVCDYWWKSD GKIKDKWNTC YLYPSVLLVE   420
```

TABLE 5-continued

Sequences disclosed herein.

```
VLVDLVSLLE QGKLPDVLDQ ELQYRVAITL FQACLRPLLD QDAEGSWNKS IEATAYGILI    480
LTEARRVCFF DRLSEPLNEA IRRGIAFADS MSGTEAQLNY IWIEKVSYAP ALLTKSYLLA    540
ARWAAKSPLG ASVGSSLWTP PREGLDKHVR LFHQAELFRS LPEWELRASM IEAALFTPLL    600
RAHRLDVFPR QDVGEDKYLD VVPFFWTAAN NRDRTYASTL FLYDMCFIAM LNFQLDEFME    660
ATAGILFRDH MDDLRQLIHD LLAEKTSPKS SGRSSQGTKD ADSGIEEDVS MSDSASDSQD    720
RSPEYDLVFS ALSTFTKHVL QHPSIQSASV WDRKLLAREM KAYLLAHIQQ AEDSTPLSEL    780
KDVPQKTDVT RVSTSTTTFF NWVRTTSADH ISCPYSFHFV ACHLGAALSP KGSNGDCYPS    840
AGEKFLAAAV CRHLATMCRM YNDLGSAERD SDEGNLNSLD FPEFADSAGN GGIEIQKAAL    900
LRLAEFERDS YLEAFRRLQD ESNRVHGPAG GDEARLSRRR MAILEFFAQQ VDLYGQVYVI    960
RDISARIPKN EVEKKRKLDD AFN                                            983

SEQ ID NO: 55
atggcttcta gtacacttat ccaaaacaga tcatgtggcg tcacatcatc tatgtcaagt     60
tttcaaatct tcagaggtca accactaaga tttcctggca ctagaacccc agctgcagtt    120
caatgcttga aaaagaggag atgccttagg ccaaccgaat ccgtactaga atcatctcct    180
ggctctggtt catatagaat agtaactggc ccttctggaa ttaaccctag ttctaacggg    240
cacttgcaag agggttcctt gactcacagg ttaccaatac aatggaaaaa atctatcgat    300
aacttccaat ctactctata tgtgtcagat atttggtctg aaacactaca gagaactgaa    360
tgtttgctac aagtaactga aaacgtccag atgaatgagt ggattgagga aattagaatg    420
tactttagaa atatgacttt aggtgaaatt tccatgtccc cttacgcac tgcttgggtg    480
gctagagttc cagcgttgga cggttctcat gggcctcaat tccacagatc tttgcaatgg    540
attatcgaca accaattacc agatggggac tggggcgaac cttctctttt cttgggttac    600
gatagagttt gtaatacttt agcctgtgtg attgcgttga aacatgggg tgttggggca    660
caaaacgttg aaagaggaat tcagttccta caatctaaca tatacaagat ggaggaagat    720
gacgctaatc atatgccaat aggattcgaa atcgtattcc ctgctatgat ggaagatgcc    780
aaaagcattag gtttggattt gccatacgat gctactattt tgcaacagat ttcagccgaa    840
agagaaaaa agatgaaaaa gatcccaatg gcaatggtgt acaaataccc aaccacttta    900
cttcactcct tagaaggctt gcatagagaa gttgattgga ataagttgtt acaattacaa    960
tctgaaaatg gtagtttttct ttattcacct gcttcaaccg catgcgcctt aatgtacact   1020
aaggacgtta aatgttttga ttacttaaac cagttgttga tcaagttcga ccacgcatgc   1080
ccaaatgtat atccagtcga tctattcgaa agattatgga tggttgacag attgcagaga   1140
ttagggatct ccagatactt tgaaagagag attagagatt gtttacaata cgtctacaga   1200
tattggaaag attgtggaat cggatgggct tctaactctt ccgtacaaga tgttgatgat   1260
acagccatgg cgtttagact tttaaggact catggtttcg acgtaaagga agattgcttt   1320
agacagtttt tcaaggacgg agaattcttc tgcttcgcag ccaatcatc tcaagcagtt   1380
acaggcatgt ttaatctttc aagagccagt caaacattgt ttccaggaga atcttttattg   1440
aaaaaggcta gaaccttctc tagaaacttc ttgagaacaa agcatgagaa caacgaatgt   1500
ttcgataaat ggatcattac taaagatttg gctggtgaag tcgagtataa cttgaccttc   1560
ccatggtatg cctctttgcc tagattagaa cataggacat acttagatca atatggaatc   1620
gatgatatct ggataggcaa atcttttatac aaaatgcctg ctgttaccaa cgaagtttc   1680
ctaaagttgg caaaggcaga ctttaacatg tgtcaagctc tacacaaaaa ggaattggaa   1740
caagtgataa agtggaacgc gtccgtcaa ttcagagatc ttgaattcgc cagacaaaaa   1800
tcagtagaat gctattttgc tggtgcagcc acaatgttcg aaccagaaat ggttcaagct   1860
agattagtct gggcaagatg ttgtgtattg acaactgtct tagacgatta cttgaccac   1920
gggacacctg ttgaggaact tagagtgttt gttcaagctg tcagaacatg gaatccagag   1980
ttgatcaacg gtttgccaga gcaagctaaa atcttgttta tgggcttata caaaacagtt   2040
aacacaattg cagaggaagc attcatggca cagaaaagag acgtccatca tcatttgaaa   2100
cactattggg acaagttgat aacaagtgcc ctaaaggagg ccgaatgggc agagtcaggt   2160
tacgtcccaa catttgatga atacatgaa gtagctgaaa tttctgttgc tctagaacca   2220
attgtctgta gtaccttgtt ctttgcgggt catagactag atgaggatgt tctagatagt   2280
tacgattacc atctagttat gcatttggta aacagagtcg gtagaatctt gaatgatata   2340
caaggcatga agaggagc ttcacaaggt aagatctcat cagttcaaat ctacctggag   2400
gaacatccat ctgttccatc tgaggccatg gcgatcgctc atcttcaaga gttagttgaa   2460
aattcaatgc agcaattgac atacgaagtt cttaggttca ctgcggttcc aaaaagttgt   2520
aagagaatcc acttgaatat ggctaaaatc atgcatgcct tctacaagga tactgatgga   2580
ttctcatccc ttactgcaat gacaggattc gtcaaaaagg ttcttttcga acctgtgcct   2640
gagtaa                                                              2646

SEQ ID NO: 56
Physcomitrella patens
MASSTLIQNR SCGVTSSMSS FQIFRGQPLR FPGTRTPAAV QCLKKRRCLR PTESVLESSP     60
GSGSYRIVTG PSGINPSSNG HLQEGSLTHR LPIPMEKSID NFQSTLYVSD IWSETLQRTE    120
CLLQVTENVQ MNEWIEEIRM YFRNMTLGEI SMSPYDTAWV ARVPALDGSH GPQFHRSLQW    180
IIDNQLPDGD WGEPSLFLGY DRVCNTLACV IALKTWGVGA QNVERGIQFL QSNIYKMEED    240
DANHMPIGFE IVFPAMMEDA KALGLDLPYD ATILQQISAE REKKMKKIPM AMVYKYPTTL    300
LHSLEGLHRE VDWNKLLQLQ SENGSFLYSP ASTACALMYT KDVKCFDYLN QLLIKFDHAC    360
PNVYPVDLFE RLWMVDRLQR LGISRYFERE IRDCLQYVYR YWKDCGIGWA SNSSVQDVDD    420
TAMAFRLLRT HGFDVKEDCF RQFFKDGEFF CFAGQSSQAV TGMFNLSRAS QTLFPGESLL    480
KKARTFSRNF LRTKHENNEC FDKWIITKDL AGEVEYNLTF PWYASLPRLE HRTYLDQYGI    540
DDIWIGKSLY KMPAVTNEVF LKLAKADFNM CQALHKKELE QVIKWNASCQ FRDLEFARQK    600
SVECYFAGAA TMFEPEMVQA RLVWARCCVL TTVLDDYFDH GTPVEELRVF QAVRTWNPE    660
LINGLPEQAK ILFMGLYKTV NTIAEEEAFMA QKRDVHHHLK HYWDKLITSA LKEAEWAESG    720
YVPTFDEYME VAEISVALEP IVCSTLFFAG HRLDEDVLDS YDYHLVMHLV NRVGRILNDI    780
QGMKREASQG KISSVQIYME EHPSVPSEAM AIAHLQELVD NSMQQLTYEV LRFTAVPKSC    840
KRIHLNMAKI MHAFYKDTDG FSSLTAMTGF VKKVLFEPVP E                        881

SEQ ID NO: 57
atgcctggta aaattgaaaa tggtaccccca aaggacctca agactggaaa tgattttgtt     60
```

TABLE 5-continued

Sequences disclosed herein.

```
tctgctgcta agagtttact agatcgagct ttcaaaagtc atcattccta ctacggatta    120
tgctcaactt catgtcaagt ttatgataca gcttgggttg caatgattcc aaaaacaaga    180
gataatgtaa aacagtggtt gtttccagaa tgtttccatt acctcttaaa aacacaagcc    240
gcagatggct catggggttc attgcctaca acacagacag cgggtatcct agatacagcc    300
tcagctgtgc tggcattatt gtgccacgca caagagcctt tacaaatatt ggatgtatct    360
ccagatgaaa tgggggttgag aatagaacac ggtgtcacat ccttgaaacg tcaattagca    420
gtttggaatg atgtggagga caccaaccat attggcgtcg agtttatcat accagcctta    480
ctttccatgc tagaaaagga attagatgtt ccatctttg aatttccatg taggtccatc    540
ttagagagaa tgcacgggga gaaattaggt catttcgacc tggaacaagt ttacggcaag    600
ccaagctcat tgttgcactc attggaagca tttctcggta agctagattt tgatcgacta    660
tcacatcacc tataccacgg cagtatgatg gcatctccat cttcaacggc tgcttatctt    720
attgggctta caaatggga tgacgaagcc gaagattacc taagacatgt aatgcgtaat    780
ggtgcaggac atgggaatgg aggtatttct ggtacatttc caactactca tttcgaatgt    840
agctggatta tagcaacgtt gttaaaggtt ggctttactt tgaagcaaat tgacggcgat    900
ggcttaagag gtttatcaac catcttactt gaggcgctca gtgatgagaa tggtgtcata    960
ggctttgccc ctagaacagc agatgtagat gacacagcca aagctctatt ggccttgtca   1020
ttggtaaacc agccagtgtc acctgatatc atgattaagg tctttgaggg caaagaccat   1080
tttaccactt ttggttcaga aagagatcca tcattgactt ccaacctgca cgtccttta   1140
tcttactta aacaatctaa cttgtctcaa taccatccte aaatcctcaa aacaacatta   1200
ttcacttgta gatggtggtg gggttccgat cattgtgtca aagacaaatg gaatttgagt   1260
cacctatatc caactatgtt gttggttgaa gccttcactg aagtgctcca tctcattgac   1320
ggtggtgaat tgtctagtct gtttgatgaa tcctttaagt gtaagattgg tcttagcatc   1380
tttcaagcgg tacttagaat aatcctcacc caagacaacg gggctcttg gagaggatac   1440
agagaacaga cgtgttacgc aatattggct ttagttcaag cgagacatgt atgcttttc   1500
actcacatgt tgacagact gcaatcatgt gttgatcgag gtttctcatg gttgaaatct   1560
tgctcttttc attctcaaga cctgacttgg acctctaaaa cagcttatga agtgggttc   1620
gtagctgaag catataaact agctgcttta caatctgctc ccctggaggt tcctgctgcc   1680
accattggac attctgtcac gtctgccgtt ccatcaagtg atcttgaaaa atacatgaga   1740
ttggtgagaa aaactgcgtt attctctcca ctggatgagt gggtctaat ggcttctatc   1800
atcgaatctt catttttcgt accattactg caggcacaaa gagttgaaat atacccctaga   1860
gataatatca aggtggacga agataagtac ttgtctatta tcccattcac atgggtcgga   1920
tgcaataata ggtctagaac tttcgcaagt aacagatgc tatacgatat gatgtacctt   1980
tcattactcg gctatcaaac cgacgagtac atggaagctg tagctgggcc agtgtttggg   2040
gatgtttcct tgttacatca aacaattgat aaggtgattg ataatacaat gggtaacctt   2100
gcgagagcca atgaacagt acacagtggt aatggacatc agcacgaatc tcctaatata   2160
ggtcaagtcg aggacacctt gactcgtttc acaaattcag tcttgaatca caaagacgtc   2220
cttaactcta gctcatctga tcaagatact ttgagaagag agtttagaac attcatgcac   2280
gctcatataa cacaaatcga agataactca cgattcagta agcaagcctc atccgatgcg   2340
ttttcctctc ctgaacaatc ttactttcaa tgggtgaact caactggtgg ctcacatgtc   2400
gcttcgcct attcatttgc cttctctaat tgcctcatgt ctgcaaattt gttgcagggt   2460
aaagacgcat ttccaagcgg aacgcaaaag tacttaatct cctctgttat gagacatgca   2520
acaaacatgt gtagaatgta taacgacttt ggctctattg ccagagacaa cgctgagaga   2580
aatgttaata gtattcattt tcctgagttt actctctgta acggaacttc tcaaaaccta   2640
gatgaaagga aggaaagact tctgaaaatc gcaacttacg acaagggta tttggataga   2700
gcactagagg ccttggaaag acagagtaga gatgatgccg gagacagagc tggatctaaa   2760
gatatgagaa agttgaaaat cgttaagtta ttctgtgatg ttacggactt atacgatcag   2820
ctctacgtta tcaaagattt gtcatcctct atgaagtaa                           2859
```

SEQ ID NO: 58
Gibberella fujikuroi

```
MPGKIENGTP KDLKTGNDFV SAAKSLLDRA FKSHHSYYGL CSTSCQVYDT AWVAMIPKTR     60
DNVKQWLFPE CFHYLLKTQA ADGSWGSLPT TQTAGILDTA SAVLALLCHA QEPLQILDVS    120
PDEMGLRIEH GVTSLKRQLA VWNDVEDTNH IGVEFIIPAL LSMLEKELDV PSFEFPCRSI    180
LERMHGEKLG HFDLEQVYGK PSSLLHSLEA FLGKLDFDRL SHHLYHGSMM ASPSSTAAYL    240
IGATKWDDEA EDYLRHVMRN GAGHGNGGIS GTFPTTHFEC SWIIATLLKV GFTLKQIDGD    300
GLRGLSTILL EALRDENGVI GFAPRTADVD DTAKALLALS LVNQPVSPDI MIKVFEGKDH    360
FTTFGSERDP SLTSNLHVLL SLLKQSNLSQ YHPQILKTTL FTCRWWWGSD HCVKDKWNLS    420
HLYPTMLLVE AFTEVLHLID GGELSSLFDE SFKCKIGLSI FQAVLRIILT QDNDGSWRGY    480
REQTCYAILA LVQARHVCFF THMVDRLQSC VDRGFSWLKS CSFHSQDLTW TSKTAYEVGF    540
VAEAYKLAAL QSASLEVPAA TIGHSVTSAV PSSDLEKYMR LVRKTALFSP LDEWGLMASI    600
IESSFFVPLL QAQRVEIYPR DNIKVDEDKY LSIIPFTWVG CNNRSRTFAS NRWLYDMMYL    660
SLLGYQTDEY MEAVAGPVFG DVSLLHQTID KVIDNTMGNL ARANGTVHSG NGHQHESPNI    720
GQVEDTLTRF TNSVLNHKDV LNSSSSDQDT LRREFRTFMH AHITQIEDNS RFSKQASSDA    780
FSSPEQSYFQ WVNSTGGSHV ACAYSFAFSN CLMSANLLQG KDAFPSGTQK YLISSVMRHA    840
TNMCRMYNDF GSIARDNAER NVNSIHFPEF TLCNGTSQNL DERKERLLKI ATYEQGYLDR    900
ALEALERQSR DDAGDRAGSK DMRKLKIVKL FCDVTDLYDQ LYVIKDLSSS MK             952
```

SEQ ID NO: 59
S. rebaudiana

```
atggatgctg tgacgggttt gttaactgtc ccagcaaccg ctataactat tggtggaact     60
gctgtagcat tggcggtagc gctaatcttt tggtacctga atcctacac atcagctaga    120
agatcccaat caaatcatct tccaagagtg cctgaagtcc aggtgttcc attgttagga    180
aatctgttac aattgaagga gaaaaagcca tacatgacgt ttacgagatg ggcagcgaca    240
tatggaccta tctatagtat caaaactggg gctacaagta tggtgtggt atcatctaat    300
gagatagcca aggaggcatt ggtgaccaga ttccaatcca tatctacaag gaacttatct    360
aaagccctga agtacttac agcagataag acaatggtcg caatgtcaga ttatgatgat    420
tatcataaaa cagttaagag acacatactg accgccgtct gggtcctaa tgcacagaaa    480
aagcatgaaa ttcacagaga tatcatgatg gataacatat ctactcaact tcatgaattc    540
```

TABLE 5-continued

Sequences disclosed herein.

```
gtgaaaaaca acccagaaca ggaagaggta gaccttagaa aaatctttca atctgagtta    600
ttcggcttag ctatgagaca agccttagga aaggatgttg aaagtttgta cgttgaaagc    660
ctgaaaatca ctatgaatag agacgaaatc tttcaagtcc ttgttgttga tccaatgatg    720
ggagcaatcg atgttgattg gagagacttc tttccatacc taaagtgggt cccaaacaaa    780
aagttcgaaa atactattca acaaatgtac atcagaagag aagctgttat gaaatcttta    840
atcaaagagc acaaaaagag aatagcgtca ggcgaaaagc taaatagtta tatcgattac    900
cttttatctg aagctcaaac tttaaccgat cagcaactta tgatgtcctt gtgggaacca    960
atcattgaat cttcagatac aacaatggtc acaacagaat gggcaatgta cgaattagct   1020
aaaaaccctaa aattgcaaga taggttgtac agagacatta gtccgtctg tggatctgaa   1080
aagataaccg aagagcatct atcacagctg ccttacatta cagctatttt ccacgaaaca   1140
ctgagaagac actcaccagt tcctatcatt cctctaagac atgtacatga agataccgtt   1200
ctaggcggct accatgttcc tgctggcaca gaacttgccg ttaacatcta cggttgcaac   1260
atggacaaaa acgtttggga aaatccagag aatggaacc cagaaagatt catgaaagag   1320
aatgagacaa ttgattttca aaagacgatg gccttcggtg gtggtaagag agtttgtgct   1380
ggttccttgc aagccctttt aactgcatct atttgggattg ggagaatggt tcaagagttc   1440
gaatggaaac tgaaggatat gactcaagag gaagtgaaca cgataggcct aactacacaa   1500
atgttaagac cattgagagc tattatcaaa cctaggatct aa                      1542

SEQ ID NO: 60
S. rebaudiana
MDAVTGLLTV PATAITIGGT AVALAVALIF WYLKSYTSAR RSQSNHLPRV PEVPGVPLLG     60
NLLQLKEKKP YMTFTRWAAT YGPIYSIKTG ATSMVVVSSN EIAKEALVTR FQSISTRNLS    120
KALKVLTADK TMVAMSDYDD YHKTVKRHIL TAVLGPNAQK KHRIHRDIMM DNISTQLHEF    180
VKNNPEQEEV DLRKIFQSEL FGLAMRQALG KDVESLYVED LKITMNRDEI FQVLVVDPMM    240
GAIDVDWRDF FPYLKWVPNK KFENTIQQMY IRREAVMKSL IKEHKKRIAS GEKLNSYIDY    300
LLSEAQTLTD QQLLMSLWEP IIESSDTTMV TTEWAMYELA KNPKLQDRLY RDIKSVCGSE    360
KITEEHLSQL PYITAIFHET LRRHSPVPII PLRHVHDTV LGGYHVPAGT ELAVNIYGCN    420
MDKNVWENPE EWNPERFMKE NETIDFQKTM AFGGGKRVCA GSLQALLTAS IGIGRMVQEF    480
EWKLKDMTQE EVNTIGLTTQ MLRPLRAIIK PRI                                 513

SEQ ID NO: 61
aagcttacta gtaaaatgga cggtgtcatc gatatgcaaa ccattccatt gagaaccgct     60
attgctattg gtggtactgc tgttgctttg gttgttgcat atacttttg gttcttgaga    120
tcctacgctt cccccatctca tcattctaat catttgccac cagtacctga agttccaggt   180
gttccagttt tgggtaattt gttgcaattg aaagaaaaaa agccttacat gaccttcacc    240
aagtgggctg aaatgtatgg tccaatctac tcattagaa ctggtgctac ttccatggtt    300
gttgtctctt ctaacgaaat cgccaaagaa gttgttgtta ccagattccc atctatctct    360
accagaaaat tgtcttacgc cttgaaggtt ttgaccgaag ataagtctat ggttgccatg    420
tctgattatc acgattacca taagaccgtc aagagacata ttttgactgc tgttttgggt    480
ccaaacgccc aaaaaagtt tagagcacat agagcaccca tgatgaaaa cgtttccaat    540
gaattgcatg ccttcttcga aaagaaccca aatcaagaag tcaacttgag aaagatcttc    600
caatcccaat tattcggttt ggctatgaag caagccttgg gtaaagatgt tgaatccatc    660
tacgttaagg atttggaaac caccatgaag agagaagaaa tcttcgaagt ttgagttgtc    720
gatccaatga tgggtgctat tgaagttgat tggagagaat ttttcccata cttgaaatgg    780
gttccaaaca agtccttcga aaacatcatc catagaatgt acactagaag agaagctgtt    840
atgaaggcct tgatccaaga aacaagaaa agaattgcc ccggtgaaaa cttgaactcc    900
tacattgatt acttgttgtc tgaagcccaa accttgaccg ataagcaatt attgatgtct    960
ttgtgggaac ctattatcga atcttctgat accactatgg ttactacaga atgggctatg   1020
tacgaattgg ctaagaatcc aaacatgcaa gacagattat acgaagaaat ccaatccgtt   1080
tgcggttccg aaaagattac tgaagaaaac ttgtcccaat gccatactt gtacgctgtt   1140
ttccaagaaa ctttgagaaa gcactgtcca gttcctatta tgccattgag atatgttcac   1200
gaaacaccgg ttttgggtgg ttatcatgtt ccagctggta ctgaagttgc tattaacatc   1260
tacggttgca acatggataa gaaggtctgg gaaaatccag aagaatggaa tccagaaaga   1320
ttcttgtccg aaaagaatc catggacttg tacaaaacta tggcttttgg tggtggtaaa   1380
agagtttgcg ctggttcttt acaagccatg gttatttctt gcattggtat cggtagattg   1440
gtccaagatt tgaatggaa gttgaaggat gatgccgaag aagatgttaa cactttgggt   1500
ttgactaccc aaaaagttgca tccattattg gccttgatta cccaagaaa gtaactcgag   1560
ccgcgg                                                              1566

SEQ ID NO: 62
Lactuca sativa
MDGVIDMQTI PLRTAIAIGG TAVALVVALY FWFLRSYASP SHHSNHLPPV PEVPGVPVLG     60
NLLQLKEKKP YMTFTKWAEM YGPIYSIRTG ATSMVVVSSN EIAKEVVVTR FPSISTRKLS    120
YALKVLTEDK SMVAMSDYHD YHKTVKRHIL TAVLGPNAQK KFRAHRDTMM ENVSNELHAF    180
FEKNPNQEVN LRKIFQSQLF GLAMKQALGK DVESIYVKDL ETTMKREEIF EVLVVDPMMG    240
AIEVDWRDFF PYLKWVPNKS FENIIHRMYT RREAVMKALI QEHKKRIASG ENLNSYIDYL    300
LSEAQTLTDK QLLMSLWEPI IESSDTTMVT TEWAMYELAK NPNMQDRLYE EIQSVCGSEK    360
ITEENLSQLP YLYAVFQETL RKHCPVPIMP LRYVHENTVL GGYHVPAGTE VAINIYGCNM    420
DKKVWENPEE WNPERFLSEK ESMDLYKTMA FGGGKRVCAG SLQAMVISCI GIGRLVQDFE    480
WKLKDDAEED VNTLGLTTQK LHPLLALINP RK                                  512

SEQ ID NO: 63
R. suavissimus
atggccaccc tccttgagca tttccaagct atgcccttg ccatccctat tgcactggct     60
gctctgtctt ggctgttcct cttttacatc aaagtttcat tctttttcaa caagagtgct    120
caggctaagc tccctcctgt gccagtggtt cctgggctgc cggtgattgg gaatttactg    180
caactcaagg agaagaaacc ctaccagact tttacaaggt gggctgagga gtatggacca    240
atctattcta tcaggactgg tgcttccacc atggtcgttc tcaataccac ccaagttgca    300
```

TABLE 5-continued

Sequences disclosed herein.

```
aaagaggcca tggtgaccag atatttatcc atctcaacca gaaagctatc aaacgcacta    360
aagattctta ctgctgataa atgtatggtt gcaataagtg actacaacga ttttcacaag    420
atgataaagc gatacatact ctcaaatgtt cttggaccta gtgctcagaa gcgtcaccgg    480
agcaacagag ataccttgag agctaatgtc tgcagccgat tgcattctca agtaaagaac    540
tctcctcgag aagctgtgaa tttcagaaga gttttgagt gggaactctt tggaattgca     600
ttgaagcaag cctttggaaa ggacatagaa aagcccattt atgtggagga acttggcact    660
acactgtcaa gagatgagat cttaaggtt ctagtgcttg acataatgga gggtgcaatt     720
gaggttgatt ggagagattt cttcccttac ctgagatgga ttccgaatac gcgcatggaa    780
acaaaaattc agcgactcta tttccgcagg aaagcagtga tgactgccct gatcaacgag    840
cagaagaagc gaattgcttc aggagaggaa atcaactgtt atatcgactt cttgcttaag    900
gaagggaaga cactgacaat ggaccaaata agtatgttgc tttgggagac ggttattgaa    960
acagcagata ctacaatggt aacgacagaa tgggctatgt atgaagttgc taaagactca   1020
aagcgtcagg atcgtctcta tcaggaaatc caaaaggttt gtggatcgga gatggttaca   1080
gaggaatact tgtcccaact gccgtacctg aatgcagttt ccatgaaaac gctaaggaag   1140
cacagtccgg ctgcgttagt tccttaaga tatgcacatg aagatacca actaggaggt     1200
tactacattc cagctggaac tgagattgct ataaacatat acgggtgtaa catggacaag   1260
catcaatggg aaagccctga ggaatggaaa ccggagagat ttttggaccc gaaatttgat   1320
cctatggatt tgtacaagac catggctttt ggggctggaa agagggtatg tgctggttct   1380
cttcaggcaa tgttaatagc gtgcccgacg attggtaggc tggtgcagga gtttgagtgg   1440
aagctgagag atggagaaga agaaaatgta gatactgttg ggctcaccac tcacaaacgc   1500
tatccaatgc atgcaatcct gaagccaaga agtta                              1535

SEQ ID NO: 64
R. suavissimus
atggctacct tgttggaaca ttttcaagct atgccattcg ctattccaat tgctttggct     60
gctttgtctt ggttgttttt gttctacatc aaggtttctt tcttctccaa caaatccgct    120
caagctaaat tgccaccagt tccagttgtt ccaggttttgc cagttattgg taatttgttg    180
caattgaaag aaaagaagcc ataccaaacc ttcactagat gggctgaaga atatggtcca    240
atctactcta ttagaactgg tgcttctact atggttgtct gaacactac tcaagttgcc     300
aaagaagcta tggttaccag atacttgtct atctctacca gaaagttgtc caacgccttg    360
aaaattttga ccgctgataa gtgcatggtt gccatttctg attacaacga tttccacaag    420
atgatcaaga gatatatctt gtctaacgtt tgggtccat ctgcccaaaa aagacataga     480
tctaacagag ataccttgag agccaacgtt tgttctagat tgcattccca agttaagaac    540
tctccaagag aagctgtcaa ctttagaaga gttttcgaat gggaattatt cggtatcgct    600
ttgaaacaag ccttcggtaa ggatattgaa aagccaatct acgtcgaaga attgggtact    660
actttgtcca gagatgaaat cttcaaggtt ttggtcttga acattatgga aggtgccatt    720
gaagttgatt ggagagattt tttcccctac ttgcgttgga ttccaaacac cagaatggaa    780
actaagatcc aaagattata ctttagaaga aaggccgtta tgaccgcctt gattaacgaa    840
caaaagaaaa gaattgcctc cggtgaagaa atcaactgct catcgatttt cttgttgaaa    900
gaaggtaaga ccttgaccat ggaccaaatc tctatgtgt tgtgggaaac cgttattgaa     960
actgctgata ccacaatggt tactactgaa tgggctatgt acgaagttgc taaggattcc   1020
aaaagacaag acagattata ccaagaaatc caaaaggtct gcggttctga atggttaca    1080
gaagaatact tgtcccaatt gccatacttg aatgctgttt ccacgaaaac tttgagaaaa   1140
cattctccag ctgcttcatt gttccattgaga tatgctcatg aagatactca attgggtggt   1200
tattacattc cagccggtac tgaaattgcc attaacatct acggttgcaa catggacaaa   1260
caccaatggg aatctccaga agaatggaag ccagaaagat ttttggatcc taagtttgac   1320
ccaatggact tgtacaaaac tatggctttt ggtgctggta aaagagtttg cgctggttct   1380
ttacaagcta tgttgattgc ttgtccaacc atcggtagat tggttcaaga atttgaatgg   1440
aagttgagag atggtgaaga gaaaaacgtt gatactgttg gtttgaccac ccataagaga   1500
tatccaatgc atgctatttt gaagccaaga tcttaa                              1536

SEQ ID NO: 65
aagcttacta gtaaaatggc ctccatcacc catttcttac aagattttca agctactcca     60
ttcgctactg cttttgctgt tggtggtgtt tctttgttga tattcttctt cttcatccgt    120
ggtttccact ctactaagaa aaacgaatat tacaagttgc caccagttcc agttgttcca    180
ggtttgccag ttgttggtaa tttgttgcaa ttgaaagaaa agaagccata caagactttc    240
ttgagatggg ctgaaattca tggtccaatc tactctatta gaactggtag ttctactatg    300
gttgttgtta actctactca tgttgccaaa gaagctatgg ttaccagatt ctcttcaatc    360
tctaccagaa agttgtccaa ggctttgaa ttattgacct ccaacaaatc tatggttgcc    420
acctctgatt acaacgaatt tcacaagatg gtcaagaagt acatcttggc cgaattattg    480
ggtgctaatg ctcaaaagag acacagaatt catagagaca ccttgatcga aaacgtcttg    540
aacaaattgc atgcccatac caagaattct ccattgcaag ctgttaactt cagaaagatc    600
ttcgaatctg aattattcgg tttggcctatg aagcaagcct tgggttatga tgttgattcc    660
ttgttcgttg aagaattggg tactaccttg tccagaaag aaatctacaa cgttttggtc    720
agtgacatgt tgaagggtgc tattgaagtt gattggagag actttttccc atacttgaaa   780
tggatcccaa acagtcctt cgaaatgaag attcaaagat tggcctctag aagacaagcc    840
gttatgaact ctattgtcaa agaacaaaag aagtccattg cctctggtaa gggtgaaaac    900
tgttacttga attacttgtt gtccgaagct aagactttga ccgaaaagca aatttccatt    960
ttggcctggg aaaccattat tgaaactgct gatacaactg ttgttaccac tgaatgggct   1020
atgtacgaat tggctaaaaa cccaaagcaa aagacagat tatacaacga atccaaaac    1080
gtctgcggta ctgataagat taccgaagaa catttgtcca gttgcctta cttgtctgct   1140
gttttcacg aaaagtattct ccatctccat tgttccatt gagatacgct   1200
catgaagata ctcaattggg tggttattat gttccagccg gtactgaaat tgctgttaat   1260
atctacggtt gcaacatgga caagaatcaa tgggaaactc agaagaatg gaagccagaa   1320
agattttggg cgaaaagta cgatccaatg gacatgtaca agactatgtc ttttggttcc   1380
ggtaaaagag tttgcgctgg ttcttttacaa gctagttga ttgcttgtac ctccatcggt   1440
agattggttc aagaatttga atggagattg aaagacggta agttgaaaaa cgttgatacc   1500
```

TABLE 5-continued

| Sequences disclosed herein. | | | | | |
|---|---|---|---|---|---|
| ttgggtttga | ctaccataa | gttgtatcca | atgcaagcta | tcttgcaacc | tagaaactga | 1560 |
| ctcgagccgc | gg | | | | | 1572 |

SEQ ID NO: 66
*Castanea mollissima*

```
MASITHFLQD FQATPPFATAF AVGGVSLLIF FFFIRGFHST KKNEYYKLPP VPVVPGLPVV    60
GNLLQLKEKK PYKTFLRWAE IHGPIYSIRT GASTMVVVNS THVAKEAMVT RFSSISTRKL   120
SKALELLTSN KSMVATSDYN EFHKMVKKYI LAELLGANAQ KRHRIHRDTL IENVLNKLHA   180
HTKNSPLQAV NFRKIFESEL FGLAMKQALG YDVDSLFVEE LGTTLSREEI YNVLVSDMLK   240
GAIEVDWRDF FPYLKWIPNK SFEMKIQRLA SRRQAVMNSI VKEQKKSIAS GKGENCYLNY   300
LLSEAKTLTE KQISILAWET IIETADTTVV TTEWAMYELA KNPKQQDRLY NEIQNVCGTD   360
KITEEHLSKL PYLSAVFHET LRKYSPSPLV PLRYAHEDTQ LGGYYVPAGT EIAVNIYGCN   420
MDKNQWETPE EWKPERFLDE KYDPMDMYKT MSFGSGKRVC AGSLQASLIA CTSIGRLVQE   480
FEWRLKDGEV ENVDTLGLTT HKLYPMQAIL QPRN                              514
```

SEQ ID NO: 67

```
atgatttcct tgttgttggg ttttgttgtc tcctccttct tgtttatctt cttcttgaaa    60
aaattgttgt tcttcttcag tcgtcacaaa atgtccgaag tttctagatt gccatctgtt   120
ccagttccag gttttccatt gattggtaac ttgttgcaat tgaaagaaaa gaagccacac   180
aagactttca ccaagtggtc tgaattatat ggtccaatct actctatcaa gatgggttcc   240
tcttctttga tcgtcttgaa ctctattgaa accgccaaag aagctatggt cagtagattc   300
tcttcaatct ctaccagaaa gttgtctaac gctttgactg ttttgacctg caacaaatct   360
atggttgcta cctctgatta cgatgacttt cataagttcg tcaagagatg cttgttgaac   420
ggtttgttgg gtgctaatgc tcaagaaaga aaaagacatt acagagatgc cttgatcgaa   480
aacgttacct ctaaattgca tgcccatacc agaaatcatc cacaagaacc agttaacttc   540
agagccattt tcgaacacga attattcggt gttgctttga acaagccttt cggtaaagat   600
gtcgaatcca tctatgtaaa agaattgggt gtcacccttgt ccagagatga aattttcaag   660
gttttggtcc acgacatgat ggaaggtgct attgatgttg attggagaga tttcttccca   720
tacttgaaat ggatcccaaa caactctttc gaagccagaa ttcaacaaaa gcacaagaga   780
agattggctg ttatgaacgc cttgatccaa gacagattga atcaaaacga ttccgaatcc   840
gatgatgact gctacttgaa tttcttgatg tctgaagcta agaccttgac catggaacaa   900
attgctattt tggttttggga aaccattatc gaaactgctg ataccacttt ggttactact   960
gaatgggcta tgtacgaatt ggccaaacat caatctgttc aagatagatt attcaaagaa  1020
atccaatccg tctgcggtgg tgaaaagatc aagaagaac aattgccaag attgccttac  1080
gtcaatggtg tttttcacga aaccttgaga agtattctc cagctccatt ggttccaatt  1140
agatacgctc atgaagatac ccaaattggt ggttatcata ttccagccgg ttctgaaatt  1200
gccattaaca tctacggttg caacatggat aagaagagat gggaaagacc tgaagaatgg  1260
tggccagaaa gatttttgga agatagatac gaatcctccg acttgcataa gactatggct  1320
tttggtgctg gtaaaagagt ttgtgctggt gcttacaag ctagtttgat ggctggtatt  1380
gctatcggta gattggttca agaattcgaa tggaagttga gagatggtga agaagaaaac  1440
gttgatactt acggtttgac ctcccaaaag ttgtatccat tgatggccat tatcaaccca  1500
agaagatctt aa                                                      1512
```

SEQ ID NO: 68
*Thellungiella halophila*

```
MASMISLLLG FVVSSFLFIF FLKKLLFFFS RHKMSEVSRL PSVPVPGFPL IGNLLQLKEK    60
KPHKTFTKWS ELYGPIYSIK MGSSSLIVLN SIETAKEAMV SRFSSISTRK LSNALTVLTC   120
NKSMVATSDY DDFHKFVKRC LLNGLLGANA QERKRHYRDA LIENVTSKLH AHTRNHPQEP   180
VNFRAIFEHE LFGVALKQAF GKDVESIYVK ELGVTLSRDE IFKVLVHDMM EGAIDVDWRD   240
FFPYLKWIPN NSFEARIQQK HKRRLAVMNA LIQDRLNQND SESDDDCYLN FLMSEAKTLT   300
MEQIAILVWE TIIETADTTL VTTEWAMYEL AKHQSVQDRL FKEIQSVCGG EKIKEEQLPR   360
LPYVNGVFHE TLRKYSPAPL VPIRYAHEDT QIGGYHIPAG SEIAINIYGC NMDKKRWERP   420
EEWWPERFLE DRYESSDLHK TMAFGAGKRV CAGALQASLM AGIAIGRLVQ EFEWKLRDGE   480
EENVDTYGLT SQKLYPLMAI INPRRS                                       506
```

SEQ ID NO: 69

```
aagcttacta gtaaaatgga catgatgggt attgaagctg ttccatttgc tactgctgtt    60
gttttgggtg gtatttcctt ggttgttttg atcttcatca gaagattcgt ttccaacaga   120
aagagatccg ttgaaggttt gccaccagtt ccagatattc aggtttacc attgattggt   180
aacttgttgc aattgaaaga aaagaagcca cataagacct tgctagatgg gctgaaaact   240
tacggtccaa ttttctctat tagaactggt gcttctacat ctgtcgtctt gaattcttcc   300
gaagttgcca aagaagctat ggtcactaga ttctcttcaa tctctaccag aaagttgtcc   360
aacgccttga gattttgac cttcgataag tgtatggttg ccacctctga ttacaacgat   420
tttcacaaaa tggtcaaggg tttcatcttg agaaacgttt taggtgctcc agcccaaaaa   480
agacatagat gtcatagaga taccttgatc gaaaacatct ctaagtacct gcatgcccat   540
gttaagactt tctccattgg accagttgtc ttgaagaaga ttttcgaatc cgaaattttc   600
ggtttggctt tgaacaagc cttgggtaag gatatcgaat ccatctatgt tgaagaattg   660
ggtactacct tgtccagaga agaaattttt gccgttttgg ttgttgatcc aatggctggt   720
gctattgaag ttgattggag agattttttc ccatacttgt cctggattcc aaacaagtct   780
atggaaatga agatccaaag aatggatttt agaagaggtg ctttgatgaa ggccttgatt   840
ggtgaacaaa agaaaagaat cggttccggt gaagaaagat actcctacat tgattcttg   900
ttgtctgaag ctaccacttt gaccgaaaag caaattgcta tgttgatctg ggaaccatc   960
atgaaaattt ccgatacaac tttggttacc tctgaatggg ctatgtacga tgctaaa   1020
gacccaaata gacaagaaat cttgtacaga gaaatccaaa aggttgcgg ttctaacaag  1080
ttgactgaag aaaacttgtc caagttgcca tacttgaact ctgttttcca cgaaaccttg  1140
agaaagtatt ctccagctcc aatggttcca gttagatatg ctcatgaaga tactcaattg  1200
ggtggttacc atattccagc tggttctcaa attgccatta acatctacgg ttgcaacatg  1260
aacaaaaagc aatgggaaaa tcctgaagaa tggaagccaa agagattctt ggacgaaaag  1320
```

TABLE 5-continued

Sequences disclosed herein.

```
tatgacttga tggacttgca taagactatg gcttttggtg gtggtaaaag agtttgtgct    1380
ggtgctttac aagcaatgtt gattgcttgc acttccatcg gtagattcgt tcaagaattt    1440
gaatggaagt tgatgggtgg tgaagaagaa aacgttgata ctgttgcttt gacctcccaa    1500
aaattgcatc caatgcaagc cattattaag gccagagaat gactcgagcc gcgg          1554

SEQ ID NO: 70
Vitis vinifera
MDMMGIEAVP FATAVVLGGI SLVVLIFIRR FVSNRKRSVE GLPPVPDIPG LPLIGNLLQL     60
KEKKPHKTFA RWAETYGPIF SIRTGASTMI VLNSSEVAKE AMVTRFSSIS TRKLSNALKI    120
LTFDKCMVAT SDYNDFHKMV KGFILRNVLG APAQKRHRCH RDTLIENISK YLHAHVKTSP    180
LEPVVLKKIF ESEIFGLALK QALGKDIESI YVEELGTTLS REEIFAVLVV DPMAGAIEVD    240
WRDFFPYLSW IPNKSMEMKI QRMDFRRGAL MKALIGEQKK RIGSGEEKNS YIDFLLSEAT    300
TLTEKQIAML IWETIIEISD TTLVTSEWAM YELAKDPNRQ EILYREIHKV CGSNKLTEEN    360
LSKLPYLNSV FHETLRKYSP APMVPVRYAH EDTQLGGYHI PAGSQIAINI YGCNMNKKQW    420
ENPEEWKPER FLDEKYDLMD LHKTMAFGGG KRVCAGALQA MLIACTSIGR FVQEFEWKLM    480
GGEEENVDTV ALTSQKLHPM QAIIKARE                                       508

SEQ ID NO: 71
aagcttaaaa tgagtaagtc taatagtatg aattctacat cacacgaaac ccttttttcaa    60
caattggtct tgggtttgga ccgtatgcca ttgatggatg ttcactggtt gatctacgtt   120
gctttcggcg catggttatg ttcttatgtg atacatgttt tatcatcttc ctctacagta   180
aaagtgccag ttgttggata caggtctgta ttcgaaccta catggttgct tagacttaga   240
ttcgtctggg aaggtggctc tatcataggt caagggtaca ataagtttaa agactctatt   300
ttccaagtta ggaaattggg aactgatatt gtcattatac cacctaacta tattgatgaa   360
gtgagaaaat tgtcacagga caagactaga tcagttgaac ctttcattaa tgattttgca   420
ggtcaataca caagaggcat ggttttcttg caatctgact acaaaaccg tgttatacaa   480
caaagactaa ctccaaaatt ggttttccttg accaaggtca tgaaggaaga gttgattat   540
gctttaacaa aagagatgcc tgatatgaaa aatgacgaat gggtagaagt agatatcagt   600
agtataatgg tgagattgat ttccaggatc tccgccagag tctttctagg gcctgaacac   660
tgtcgtaacc aggaatggtt gactactaca gcagaatatt cagaatcact tttcattaca   720
gggtttatct taagagttgt acctcatatc ttaagaccat tcatcgcccc tctattacct   780
tcatacagga ctctacttag aaacgtttca agtggtagaa gagtcatcgg tgacatcata   840
agatctcagc aaggggatgg taacgaagat atactttcct ggatgagaga tgctgccaca   900
ggagaggaaa agcaaatcga taacattgct cagagaatgt taattcttc tttagcatca   960
atccacacta ctgcgatgac catgacacat gccatgtacg atctatgtgc ttgccctgag  1020
tacattgaac cattaagaga tgaagttaaa tctgttgttg gggcttctgg ctgggacaag  1080
acagcgttaa acagatttca taagttggac tccttcctaa aagagtcaca aagattcaac  1140
ccagtattct tattgacatt caatagaatc taccatcaat ctatgacctt atcagatggc  1200
actaacattc catctggaac acgtattgct gttccatcac acgcaatgtt gcaagattct  1260
gcacatgtcc caggtccaac cccacctact gaatttgata gattcagata gtaagata  1320
cgttctgata gtaactacgc acaaaagtac ctattctcca tgaccgattc ttcaaacatg  1380
gctttcggat acgcaagta tgcttgtcca ggtagatttt acgcgtctaa tgagatgaaa  1440
ctaacattag ccattttgtt gctacaattt gagttcaaac taccagatgg taaaggtcgt  1500
cctagaaata tcactatcga ttctgatatg attccagacc caagagctag actttgcgtc  1560
agaaaaagat cacttagaga tgaatgaccg cgg                                1593

SEQ ID NO: 72
Gibberella fujikuroi
MSKSNSMNST SHETLFQQLV LGLDRMPLMD VHWLIYVAFG AWLCSYVIHV LSSSSTVKVP     60
VVGYRSVFEP TWLLRLRFVW EGGSIIGQGY NKFKDSIFQV RKLGTDIVII PPNYIDEVRK    120
LSQDKTRSVE PFINDFAGQY TRGMVFLQSD LQNRVIQQRL TPKLVSLTKV MKEELDYALT    180
KEMPDMKNDE WVEVDISSIM VRLISRISAR VFLGPEHCRN QEWLTTTAEY SESLFITGFI    240
LRVVPHILRP FIAPLLPSYR TLLRNVSSGR RVIGDIIRSQ QGDGNEDILS WMRDAATGEE    300
KQIDNIAQRM LILSLASIHT TAMTMTHAMY DLCACPEYIE PLRDEVKSVV GASGWDKTAL    360
NRFHKLDSFL KESQRFNPVF LLTFNRIYHQ SMTLSDGTNI PSGTRIAVPS HAMLQDSAHV    420
PGPTPPTEFD GFRYSKIRSD SNYAQKYLFS MTDSSNMAFG YGKYACPGRF YASNEMKLTL    480
AILLLQFEFK LPDGKGRPRN ITIDSDMIPD PRARLCVRKR SLRDE                    525

SEQ ID NO: 73
aagcttaaaa tggaagatcc tactgtctta tatgcttgtc ttgccattgc agttgcaact     60
ttcgttgtta gatggtacag agatccattg agatcctcc caacagttgg tggttcgtat   120
ttgcctattc tatcttacat cggcgcacta agatggacaa gacgtggcag agagatactt   180
caagagggat atgatggcta cagaggatct acattcaaaa tcgcgatgtt agaccgttgg   240
atcgtgatcg caaatggtcc taaactagct gatgaagtca gacgtagacc agatgaagag   300
ttaaacttta tggacggatt aggagcattc gtccaaacta agtacacctt aggtgaagct   360
attcataacg atccataccca tgtcgatatc ataagagaaa aactaacaag aggccttcca   420
gccgtgcttc ctgatgtcat tgaagagttg acacttgcgg ttagacagta cattccaaca   480
gaaggtgatg aatgggtgtc cgtaaactgt tcaaaggccg caagagatat tgttgctaga   540
gcttctaata gagtcttttgt aggttttgcct gcttgcagaa accaaggtta cttagattta   600
gcaatagact ttacattgtc tgttgtcaag gatagagcca tcatcaatat gtttccagaa   660
ttgttgaagc caatagttgg cagagttgta ggtaacgcca ccagaaatgt tcgtagagct   720
gttccttttg ttgctccatt ggtggaggaa agacgtagac ttatggaaga gtacggtgaa   780
gactggtctg aaaacctaa tgatatgtta cagtggataa ttggatgaag tgcatccgaa   840
gatagttcag tgaaggcaat cgcagagaga ttgttaatgg tgaacttcgc ggctattcat   900
acctcatcaa acactatcac tcatgctttg taccaccttg ccgaaatgcc tgaaactttg   960
caaccactta gagaagagat cgaaccatta gtcaaagagg agggctggac caaggctgct  1020
atgggaaaaa tgtggtggtt agattcattt ctaagagaat ctcaaagata caatggcatt  1080
aacatcgtat ctttaactag aatggctgac aaagatatta cattgagtga tggcacattt  1140
```

TABLE 5-continued

Sequences disclosed herein.

```
ttgccaaaag gtactctagt ggccgttcca gcgtattcta ctcatagaga tgatgctgtc   1200
tacgctgatg ccttagtatt cgatcctttc agattctcac gtatgagagc gagagaaggt   1260
gaaggtacaa agcaccagtt cgttaatact tcagtcgagt acgttccatt tggtcacgga   1320
aagcatgctt gtccaggaag attcttcgcc gcaaacgaat tgaaagcaat gttggcttac   1380
attgttctaa actatgatgt aaagttgcct ggtgacggta acgtccatt gaacatgtat    1440
tggggtccaa cagttttgcc tgcaccagca ggccaagtat tgttcagaaa gagacaagtt   1500
agtctataac cgcgg                                                    1515
```

SEQ ID NO: 74
*Trametes versicolor*

```
MEDPTVLYAC LAIAVATFVV RWYRDPLRSI PTVGGSDLPI LSYIGALRWT RRGREILQEG    60
YDGYRGSTFK IAMLDRWIVI ANGPKLADEV RRRPDEELNF MDGLGAFVQT KYTLGEAIHN   120
DPYHVDIIRE KLTRGLPAVL PDVIEELTLA VRQYIPTEGD EWVSVNCSKA ARDIVARASN   180
RVFVGLPACR NQGYLDLAID FTLSVVKDRA IINMFPELLK PIVGRVVGNA TRNVRRAVPF   240
VAPLVEERRR LMEEYGEDWS EKPNDMLQWI MDEAASRDSS VKAIAERLLM VNFAAIHTSS   300
NTITHALYHL AEMPETLQPL REEIEPLVKE EGWTKAAMGK MWWLDSFLRE SQRYNGINIV   360
SLTRMADKDI TLSDGTFLPK GTLVAVPAYS THRDDAVYAD ALVFDPFRFS RMRAREGEGT   420
KHQFVNTSVE YVPFGHGKHA CPGRFFAANE LKAMLAYIVL NYDVKLPGDG KRPLNMYWGP   480
TVLPAPAGQV LFRKRQVSL                                                499
```

SEQ ID NO: 75

```
atggcatttt tctctatgat ttcaattttg ttgggatttg ttatttcttc tttcatcttc    60
atcttttttct tcaaaaagtt acttagtttt agtaggaaaa acatgtcaga agtttctact   120
ttgccaagtg ttccagtagt gcctggtttt ccagttattg ggaatttgtt gcaactaaag   180
gagaaaaagc ctcataaaac tttcactaga tggtcagaga tatatggacc tatctactct   240
ataaagatgg gttcttcatc tcttattgta ttgaacagta cagaaactgc taaggaagca   300
atggtcacta gattttcatc aatatctacc agaaaattgt caaacgccct aacagttcta   360
acctgcgata agtctatggt cgccacttct gattatgatg acttccacaa attagttaag   420
agatgtttgc taaatggact tcttggtgct aatgctcaaa agagaaaaag acactacaga   480
gatgctttga ttgaaaatgt gagttccaag ctacatgcac acgctagaga tcatccacaa   540
gagccagtta actttagagc aattttcgaa cacgaattgt ttggtgtagc attaaagcaa   600
gccttcggta aagacgtaga atccatatac gtcaaggagt taggcgtaac attatcaaaa   660
gatgaaatct ttaaggtgct tgtacatgat atgatggagg gtgcaattga tgtagattgg   720
agagatttct tcccatattt gaatggatc cctaataagt cttttgaagc taggatacaa    780
caaaagcaca agagaagact agctgttatg aacgcactta caggacag attgaagcaa     840
aatgggtctg aatcagatga tgattgttac cttaacttct taatgtctga ggctaaaaca   900
ttgactaagg aacagatcgc aatccttgtc tgggaaacaa tcattgaaac agcagatact   960
accttagtca caactgaatg ggccatatac gagctagcca aacatccatc tgtgcaagat  1020
aggttgtgta aggagatcca aacgtgtgt ggtggagaga aattcaagga agagcagttg   1080
tcacaagttc cttaccttaa cggcgttttc catgaaacct tgagaaaata ctcacctgca  1140
ccattagttc ctattagata cgcccacgaa gatacacaaa tcggtggcta ccatgttcca  1200
gctgggtccg aaattgctat aaacatctac ggtgcaaca tggacaaaaa gagatgggaa   1260
agaccagaag attggtggcc agaaagattc ttagatgatg gcaaatatga aacatctgat  1320
ttgcataaaa caatggcttt cggagctggc aaaagagtgt gttcgaggtgc tctacaagcc  1380
tccctaatgg ctggtatcgc tattggtaga ttggtccaag agttcgaatg gaaacttaga  1440
gatggtgaag aggaaaatgt cgatacttat gggttaacat ctcaaaagtt atacccacta  1500
atggcaatca tcaatcctag aagatcctaa                                   1530
```

SEQ ID NO: 76
*Arabidopsis thaliana*

```
MAFFSMISIL LGFVISSFIF IFFFKKLLSF SRKNMSEVST LPSVPVVPGF PVIGNLLQLK    60
EKKPHKTFTR WSEIYGPIYS IKMGSSSLIV LNSTETAKEA MVTRFSSIST RKLSNALTVL   120
TCDKSMVATS DYDDFHKLVK RCLLNGLLGA NAQKRKRHYR DALIENVSSK LHAHARDHPQ   180
EPVNFRAIFE HELFGVALKQ AFGKDVESIY VKELGVTLSK DEIFKVLVHD MMEGAIDVDW   240
RDFFPYLKWI PNKSFEARIQ QKHKRRLAVM NALIQDRLKQ NGSESDDDCY LNFLMSEAKT   300
LTKEQIAILV WETIIETADT TLVTTEWAIY ELAKHPSVQD RLCKEIQNVC GGEKFKEEQL   360
SQVPYLNGVF HETLRKYSPA PLVPIRYAHE DTQIGGYHVP AGSEIAINIY GCNMDKKRWE   420
RPEDWWPERF LDDGKYETSD LHKTMAFGAG KRVCAGALQA SLMAGIAIGR LVQEFEWKLR   480
DGEEENVDTY GLTSQKLYPL MAIINPRRS                                    509
```

SEQ ID NO: 77
*S. rebaudiana*

```
atgcaatcag attcagtcaa agtctctcca tttgatttgg tttccgctgc tatgaatggc    60
aaggcaatga aaagttgaa cgctagtgaa tctgaagatc caacaacatt gcctgcacta   120
aagatgctag ttgaaaatag agaattgttg acactgttca caacttcctt cgcagttctt   180
attgggtgtc ttgtatttct aatgtgtgaga cgttcatcct ctaaaaagct ggtacaagat   240
ccagttccac aagttatcgt tgtaaagaag aaagagaagg agtcagaggt tgatgacggg   300
aaaaagaaag tttctatttt ctacggcaca caaacaggaa ctgccgaagg ttttgctaaa   360
gcattagtcg aggaagcaaa agtgagatat gaaaagacct ctttcaaggt tatcgatcta   420
gatgactacg ctgcagatga tgatgaatat gaggaaaaac tgaaaaagga atccttagcc   480
ttcttcttct tggccacata cggtgatggt gaacctactg ataatgctgc taacttctac   540
aagtggttca cagaaggcga cgataaaggt gaatggctga aaaagttaca atacggagta   600
ttttggttag gtaacagaca atatgaacat ttcaacagaa tcgctattgt agttgatgat   660
aaacttactg aaatgggagc caaaagatta gtaccagtga gattagggga tgatgatcag   720
tgtatagaag atgacttcac cgcctggaag gaattggtat ggcagaatt ggatcaactt   780
ttaagggacg aagatgatac ttctgtgact accccataca ctgcagccgt attggagtac   840
agagtggttt accatgataa accagcagac tcatatgctg aagatcaaac ccatacaaac   900
ggtcatgttg tcatgatgc acagcatcct tcaagatcta atgtggcttt caaaaaggaa   960
```

TABLE 5-continued

Sequences disclosed herein.

```
ctacacacct ctcaatcaga taggtcttgt actcacttag aattcgatat ttctcacaca   1020
ggactgtctt acgaaactgg cgatcacgtt ggcgtttatt ccgagaactt gtccgaagtt   1080
gtcgatgaag cactaaaact gttagggtta tcaccagaca catacttctc agtccatgct   1140
gataaggagg atgggacacc tatcggtggt gcttcactac caccacctttt tcctccttgc   1200
acattgagag acgctctaac cagatacgca gatgtcttat cctcacctaa aaaggtagct   1260
ttgctggcat tggctgctca tgctagtgat cctagtgaag ccgataggtt aaagttcctg   1320
gcttcaccag ccggaaaaga tgaatatgca caatggatcg tcgcaaacca acgttctttg   1380
ctagaagtga tgcaaagttt tccatctgcc aagcctccat taggtgtgtt cttcgcagca   1440
gtagctccac gtttacaacc aagatactac tctatcagtt catctcctaa gatgtctcct   1500
aacagaatac atgttacatg tgctttggtg tacgagacta ctccagcagg cagaattcac   1560
agaggattgt gttcaacctg gatgaaaaat gctgtccctt taacagagtc acctgattgc   1620
tctcaagcat ccattttcgt tagaacatca aatttcagac ttccagtgga tccaaaagtt   1680
ccagtcatta tgataggacc aggcactggt cttgccccat tcaggggctt tcttcaagag   1740
agattggcct tgaaggaatc tggtacagaa ttgggttctt ctatcttttt ctttggttgc   1800
cgtaatagaa aagttgactt tatctacgag gacgagctta acaattttgt tgagacagga   1860
gcattgtcag aattgatcgt cgcattttca agagaaggga ctgccaaaga gtacgttcag   1920
cacaagatga gtcaaaaagc ctccgatata tggaaacttc taagtgaagg tgcctatctt   1980
tatgtctgtg gcgatgcaaa gggcatggcc aaggatgtcc atagaactct gcatacaatt   2040
gttcaggaac aagggagtct ggattcttcc aaggctgaat tgtacgtcaa aaacttacag   2100
atgtctggaa gatacttaag agatgtttgg taa                                2133

SEQ ID NO: 78
S. rebaudiana
MQSDSVKVSP FDLVSAAMNG KAMEKLNASE SEDPTTLPAL KMLVENRELL TLFTTSFAVL    60
IGCLVFLMWR RSSSKKLVQD PVPQVIVVKK KEKESEVDDG KKKVSIFYGT QTGTAEGFAK   120
ALVEEAKVRY EKTSFKVIDL DDYAADDDEY EEKLKKESLA FFFLATYGDG EPTDNAANFY   180
KWFTEGDDKG EWLKKLQYGV FGLGNRQYEH FNKIAIVVDD KLTEMGAKRL VPVGLGDDDQ   240
CIEDDFTAWK ELVWPELDQL LRDEDDTSVT TPYTAAVLEY RVVYHDKPAD SYAEDQTHTN   300
GHVVHDAQHP SRSNVAFKKE LHTSQSDRSC THLEFDISHT GLSYETGDHV GVYSENLSEV   360
VDEALKLLGL SPDTYFSVHA DKEDGTPIGG ASLPPPFPPC TLRDALTRYA DVLSSPKKVA   420
LLALAAHASD PSEADRLKFL ASPAGKDEYA QWIVANQRSL LEVMQSFPSA KPPLGVFFAA   480
VAPRLQPRYY SISSSPKMSP NRIHVTCALV YETTPAGRIH RGLCSTWMKN AVPLTESPDC   540
SQASIFVRTS NFRLPVDPKV PVIMIGPGTG LAPFRGFLQE RLALKESGTE LGSSIFFFGC   600
RNRKVDFIYE DELNNFVETG ALSELIVAFS REGTAKEYVQ HKMSQKASDI WKLLSEGAYL   660
YVCGDAKGMA KDVHRTLHTI VQEQGSLDSS KAELYVKNLQ MSGRYLRDVW              710

SEQ ID NO: 79
atgaaggtca gtccattcga attcatgtcc gctattatca agggtagaat ggacccatct    60
aactcctcat ttgaatctac tggtgaagtt gcctccgtta tctttgaaaa cagagaattg   120
gttgccatct tgaccacttc tattgctgtt atgattggtt gcttcgttgt cttgatgtgg   180
agaagagctg gttctagaaa ggttaagaat gtcgaattgc caaagccatt gattgtccat   240
gaaccagaac ctgaagttga agatggtaag aagaaggttt ccatcttctt cggtactcaa   300
actggtactg ctgaaggttt tgctaaggct ttggctgatg aagctaaagc tagatacgaa   360
aaggctacct tcagagttgt tgatttggat gattatgctg ccgatgatga ccaatacgaa   420
gaaaaattga agaacgaatc cttcgccgtt ttcttgttgg ctacttatgg tgatggtgaa   480
cctactgata atgctgctag attttacaag tggttcgccg aagtaaaaga aagaggtgaa   540
tggttgcaaa acttgcacta tgctgttttt ggtttgggta acagacaata cgaacacttc   600
aacaagattg ctaaggttgc cgacgaatta ttggaagctc aaggtggtaa tagattggtt   660
aaggttggtt taggtgatga cgatcaatgc atcgaagatg attttctgc ttggagagaa   720
tctttgtggc cagaattgga tatgttgttg agagatgaag atgatgctac tactgttact   780
actccatata ctgctgctgt cttggaatac agagttgtct ttcatgattc tgctgatgtt   840
gctgctgaag ataagtcttg gattaacgct aatggtcatg ctgttcatga tgctcaaaca   900
tccattcagat ctaacgttgt cgtcagaaaa gaattgcata cttctgcctc tgatagatcc   960
tgttctcatt tggaattcaa catttccggt tccgctttga attacgaaac tggtgatcat  1020
gttggtgtct actgtgaaaa cttgactgaa actgttgatg aagccttgaa cttgttgggt  1080
ttgtctccag aaacttactt ctctatctac accgataacg aagatggtac tccattgggt  1140
ggttcttcat tgccaccacc atttccatca tgtacttga gaactgcttt gaccagatac  1200
gctgatttgt tgaactctcc aaaaaagtct gctttgttgg ctttagctgc tcatgcttct  1260
aatccagttg aagctgatag attgagatac ttggcttctc cagctggtaa agatgaatat  1320
gcccaatctg ttatcggttc ccaaaagtct ttgttggaag ttatggctga attcccatct  1380
gctaaaccac cattaggtgt ttttttttgct gctgttgctc caagattgca acctagattc  1440
tactccattt catcctctcc aagaatggct ccatctagaa tccatgttac ttgtgctttg  1500
gtttacgata gatgccaac tggtagaatt cataagggtg tttgttctac ctggatgaag  1560
aattctgttc caatggaaaa gtcccatgaa tgttcttggg ctccaatttt cgttagacaa  1620
tccaatttta agttgccagc cgaatccaag gttcaatta tcatgtgttg tccaggtact  1680
ggtttggctc cttttagagg tttttttacaa gaaagattgg ccttgaaaga atccggtgtt  1740
gaattgggtc catccatttt gttttttcggt tgcagaaaca gaagaatgga ttacatctac  1800
gaagatgaat tgaacaactt cgttgaaacc ggtgctttgt ccgaattggt tattgctttt  1860
tctagagaag gtcctaccaa agaatacgtc caacataaga tggctgaaaa ggcttctgat  1920
atctggaact tgatttctga aggtgcttac ttgtacgttt gtggtgatgc taaaggtatg  1980
gctaaggatg ttcatagaac cttgcatacc atcatgcaag aacaaggttc tttggattct  2040
tccaaagctg aatccatggt caagaacttg caaatgaatg gtagatactt aagagatgtt  2100
tggtaa                                                             2106

SEQ ID NO: 80
Siraitia grosvenorii
MKVSPFEFMS AIIKGRMDPS NSSFESTGEV ASVIFENREL VAILTTSIAV MIGCFVVLMW    60
RRAGSRKVKN VELPKPLIVH EPEPEVEDGK KKVSIFFGTQ TGTAEGFAKA LADEAKARYE   120
```

TABLE 5-continued

Sequences disclosed herein.

```
KATFRVVDLD DYAADDDQYE EKLKNESFAV FLLATYGDGE PTDNAARFYK WFAEGKERGE    180
WLQNLHYAVF GLGNRQYEHF NKIAKVADEL LEAQGGNRLV KVGLGDDDQC IEDDFSAWRE    240
SLWPELDMLL RDEDDATTVT TPYTAAVLEY RVVFHDSADV AAEDKSWINA NGHAVHDAQH    300
PFRSNVVVRK ELHTSASDRS CSHLEFNISG SALNYETGDH VGVYCENLTE TVDEALNLLG    360
LSPETYFSIY TDNEDGTPLG GSSLPPPFPS CTLRTALTRY ADLLNSPKKS ALLALAAHAS    420
NPVEADRLRY LASPAGKDEY AQSVIGSQKS LLEVMAEFPS AKPPLGVFFA AVAPRLQPRF    480
YSISSSPRMA PSRIHVTCAL VYDKMPTGRI HKGVCSTWMK NSVPMEKSHE CSWAPIFVRQ    540
SNFKLPAESK VPIIMVGPGT GLAPERGFLQ ERLALKESGV ELGPSILFFG CRNRRMDYIY    600
EDELNNFVET GALSELVIAF SREGPTKEYV QHKMAEKASD IWNLISEGAY LYVCGDAKGM    660
AKDVHRTLHT IMQEQGSLDS SKAESMVKNL QMNGRYLRDV W                       701

SEQ ID NO: 81
atggcagaat tagatacact tgatatagta gtattaggtg ttatctttttt gggtactgtg    60
gcatacttta ctaagggtaa attgtggggt gttaccaagg atccatacgc taacggattc   120
gctgcaggtg gtgcttccaa gcctggcaga actagaaaca tcgtcgaagc tatgcaggaa   180
tcaggtaaaa actgtgttgt tttctacggc agtcaaacag gtacagcgga ggattacgca   240
tcaagacttg caaaggaagg aaagtccaga ttcggtttga acactatgat cgccgatcta   300
gaagattatg acttcgataa cttagacact gttccatctg ataacatcgt tatgtttgta   360
ttggctactt acggtgaagg cgaaccaaca gataacgccg tggatttcta tgagttcatt   420
actggcgaag atgcctcttt caatgagggc aacgatcctc cactaggtaa cttgaattac   480
gttgcgttcg gtctgggcaa caatacctac gaacactaca actcaatggt caggaacgtt   540
aacaaggctc tagaaaagtt aggagctcat agaattggag aagcaggtga gggtgacgac   600
ggagctggaa ctatggaaga ggactttttta gcttggaaga atccaatgtg ggaagccttg   660
gctaaaaaga tgggcttgga ggaaagagaa gctgtatatg aacctatttt cgctatcaat   720
gagagagatg atttgacccc tgaagcgaat gaggtatact gggagaacc taataagcta    780
cacttggaag gtacagcgaa aggtccattc aactcccaca acccatatat cgcaccaatt   840
gcagaatcat acgaactttt ctcagctaag gatagaaatt gtctgcatat ggaaattgat   900
atttctggta gtaatctaaa gtatgaaaca ggcgaccata tcgcgatctg gcctaccaac   960
ccaggtgaag aggtcaacaa atttcttgac attctagatc tgtctggtaa gcaacattcc  1020
gtcgtaacag tgaaagcctt agaacctaca gccaaagttc ctttttccaaa tccaactacc  1080
tacgatgcta tattgagata ccatctgaaa atatgcgctc cagtttctag acagtttgtc  1140
tcaactttag cagcattcgc ccctaatgat gatatcaaag ctgagatgaa ccgtttggga  1200
tcagacaaag attacttcca cgaaaagaca ggaccacatt actacaatat cgctagattt  1260
ttggcctcag tctctaaagg tgaaaaatgg acaaagatac catttctgc tttcatagaa   1320
ggccttacaa aactacaacc aagatactat tctatctctt cctctagttt agttcagcct  1380
aaaaagatta gtattactgc tgtttgtcgaa tctcagcaaa ttccaggtag agatgaccca  1440
ttcagaggtg tagcgactaa ctacttgttc gctttgaagc agaaacaaaa cggtgatcca  1500
aatccagctc ctttttggcca atcatacgag ttgacaggac caaggaataa gtatgatggt  1560
atacatgttc cagtccatgt aagacattct aactttaagc taccatctga tccaggcaaa  1620
cctattatca tgatcggtcc aggtaccggt ttgcccctt tagaggctt gtccaaagag  1680
agggcaaaac aagccagaga tggtgtagaa gttggtaaaa cactgctgtt ctttggatgt  1740
agaaagagta cagaagattt catgtatcaa aaagagtggc aagagtacaa ggaagctctt  1800
ggcgacaaat tcgaaatgat tacagctttt tcaagagaag gatctaaaaa ggtttatgtt  1860
caacacagac tgaaggaaag atcaaaggaa gtttctgatc ttctatccca aaaagcatac  1920
ttctacgttt gcggagacgc cgcacatatg gcacgtgaag tgaacactgt gttagcacag  1980
atcatagcag aaggccgtgg tgtatcagaa gccaagggtg aggaaattgt caaaaacatg  2040
agatcagcaa atcaatacca agtgtgttct gatttcgtaa ctttacactg taaagagaca  2100
acatacgcga attcagaatt gcaagaggat gtctggagtt aa                    2142

SEQ ID NO: 82
Gibberella fujikuroi
MAELDTLDIV VLGVIFLGTV AYFTKGKLWG VTKDPYANGF AAGGASKPGR TRNIVEAMEE    60
SGKNCVVFYG SQTGTAEDYA SRLAKEGKSR FGLNTMIADL EDYDFDNLDT VPSDNIVMFV   120
LATYGEGEPT DNAVDFYEFI TGEDASFNEG NDPPLGNLNY VAFGLGNNTY EHYNSMVRNV   180
NKALEKLGAH RIGEAGEGDD GAGTMEEDFL AWKDPMWEAL AKKMGLEERE AVYEPIFAIN   240
ERDDLTPEAN EVYLGEPNKL HLEGTAKGPF NSHNPYIAPI AESYELFSAK DRNCLHMEID   300
ISGSNLKYET GDHIAIWPTN PGEEVNKFLD ILDLSGKQHS VVTVKALEPT AKVPFPNPTT   360
YDAILRYHLE ICAPVSRQFV STLAAFAPND DIKAEMNRLG SDKDYFHEKT GPHYYNIARF   420
LASVSKGEKW TKIPFSAFIE GLTKLQPRYY SISSSSLVQP KKISITAVVE SQQIPGRDDP   480
FRGVATNYLF ALKQKQNGDP NPAPFGQSYE LTGPRNKYDG IHVPVHVRHS NFKLPSDPGK   540
PIIMIGPGTG VAPFRGFVQE RAKQARDGVE VGKTLLLFFGC RKSTEDFMYQ KEWQEYKEAL   600
GDKFEMITAF SREGSKKVYV QHRLKERSKE VSDLLSQKAY FYVCGDAAHM AREVNTVLAQ   660
IIAEGRGVSE AKGEEIVKNM RSANQYQVCS DFVTLHCKET TYANSELQED VWS          713

SEQ ID NO: 83
atgcaatcgg aatccgttga agcatcgacg attgatttga tgactgctgt tttgaaggac    60
acagtgatcg atacagcgaa cgcatctgat aacggagact caaagatgcc gccggcgttg   120
gcgatgatgt tcgaaattcg tgatctgttc ctgattttga ctacgtcagt tgctgttttg   180
gtcggatgtt tcgttgtttt ggtgtggaag atcgtccgga ggaagaagtc cggcaaggaa   240
ttggagccgc cgaagatcgt tgtgccgaag aggcggctgg agcaggaggt tgatgatggt   300
aagaagaagg ttacgatttt cttcggaaca caaactggaa cggctgaagg tttcgctaag   360
gcacttttcg aagaagcgaa agcgcgatat gaaaaggcag cgtttaaagt gattgatttg   420
gatgatatg ctgctgattt ggatgagtat gcagagaagc tgaagaagga aacatatgct   480
ttcttcttct tggctacata tggagatggt gagccaactg ataatgcgc caaatttttat   540
aaatggtta ctgagggaga cgagaaaggc gtttggcttc aaaaacttca atatggagta   600
tttggtcttg gcaacagaca atatgaacat ttcaacaaga ttggaatagt ggttgatgat   660
ggtctccacc agcagggtgc aaaacgcatt gttcccgttg tcttggaga cgacgatcaa   720
tcaatttgaag acgattttct cggcatggaaa gagttagtgt ggcccgaatt ggatctattg   780
```

TABLE 5-continued

Sequences disclosed herein.

```
cttcgcgatg aagatgacaa agctgctgca actccttaca cagctgcaat ccctgaatac   840
cgcgtcgtat ttcatgacaa acccgatgcg ttttctgatg atcatactca aaccaatggt   900
catgctgttc atgatgctca acatccatgc agatccaatg tggctgttaa aaaagagctt   960
catactcctg aatccgatcg ttcatgcaca catcttgaat ttgacatttc tcacactgga  1020
ttatcttatg aaactgggga tcatgttggt gtatactgtg aaaacctaat tgaagtagtg  1080
gaagaagctg ggaaattgtt aggattatca acagatactt atttctcgtt acatattgat  1140
aacgaagatg gttcaccact tggtggacct tcattacaac ctccttttcc tccttgtact  1200
ttaagaaaag cattgactaa ttatgcagat ctgttaagct ctcccaaaaa gtcaactttg  1260
cttgctctag ctgctcatgc ttccgatccc actgaagctc atcgtttaag atttcttgca  1320
tctcgcgagg gcaaggatga atatgctgaa tgggttgttg caaaccaaag aagtcttctt  1380
gaagtcatgg aagctttccc gtcagctaga ccgccacttg gtgttttctt tgcagcggtt  1440
gcaccgcgtt tacagcctcg ttactactct atttcttcct ccccaaagat ggaaccaaac  1500
aggattcatg ttacttgcgc gttggtttat gaaaaaactc ccgcaggtcg tatccacaaa  1560
ggaatctgct caacctggat gaagaacgct gtacctttga ccgaaagtca agattgcagt  1620
tgggcaccga tttttgttag aacatcaaac ttcagacttc caattgaccc gaaagtcccg  1680
gttatcatga ttggtcctgg aaccggggttg gctccattta gggtttttct tcaagaaaga  1740
ttggctctta agaatccgg aaccgaactc gggtcatcta ttttattctt cggttgtaga  1800
aaccgcaaag tggattacat atatgagaat gaactcaaca actttgttga aaatggtgcg  1860
cttttctgagc ttgatgttgc tttctcccgc gatggcccga cgaaagaata cgtgcaacat  1920
aaaatgaccc aaaaggcttc tgaaatatgg aatatgcttt ctgagggagc atatttatat  1980
gtatgtggtg atgctaaagg catggctaaa gatgtacacc gtacacttca caccattgtg  2040
caagaacagg gaagtttgga ctcgtctaaa gcggagttgt atgtgaagaa tctacaaatg  2100
tcaggaagat acctccgtga tgttttggtaa                                  2130
```

SEQ ID NO: 84
Stevia rebaudiana

```
MQSESVEAST IDLMTAVLKD TVIDTANASD NGDSKMPPAL AMMFEIRDLL LILTTSVAVL    60
VGCFVVLVWK RSSGKKSGKE LEPPKIVVPK RRLEQEVDDG KKKVTIFFGT QTGTAEGFAK   120
ALFEEAKARY EKAAFKVIDL DDYAADLDEY AEKLKKETYA FFFLATYGDG EPTDNAAKFY   180
KWFTEGDEKG VWLQKLQYGV FGLGNRQYEH FNKIGIVVDD GLTEQGAKRI VPVGLGDDDQ   240
SIEDDFSAWK ELVWPELDLL LRDEDDKAAA TPYTAAIPEY RVVFHDKPDA FSDDHTQTNG   300
HAVHDAQHPC RSNVAVKKEL HTPESDRSCT HLEFDISHTG LSYETGDHVG VYCENLIEVV   360
EEAGKLLGLS TDTYFSLHID NEDGSPLGGP SLQPPFPPCT LRKALTNYAD LLSSPKKSTL   420
LALAAHASDP TEADRLRFLA SREGKDEYAE WVVANQRSLL EVMEAFPSAR PPLGVFFAAV   480
APRLQPRYYS ISSSPKMEPN RIHVTCALVY EKTPAGRIHK GICSTWMKNA VPLTESQDCS   540
WAPIFVRTSN FRLPIDPKVP VIMIGPGTGL APFRGFLQER LALKESGTEL GSSILFFGCR   600
NRKVDYIYEN ELNNFVENGA LSELDVAFSR DGPTKEYVQH KMTQKASEIW NMLSEGAYLY   660
VCGDAKGMAK DVHRTLHTIV QEQGSLDSSK AELYVKNLQM SGRYLRDVW              709
```

SEQ ID NO: 85
S. rebaudiana

```
atgcaatcta actccgtgaa gatttcgccg cttgatctgg taactgcgct gtttagcggc    60
aaggttttgg acacatcgaa cgcatcggaa tcgggagaat ctgctatgct gccgactata   120
gcgatgatta tggagaatcg tgagctgttg atgatactca caactgctgct gtctgtattg   180
atcggatgcg ttgtcgtttt ggtgtggcgg agatcgtcta cgaagaagtc ggcgttggag   240
ccaccggtga ttgtggttcc gaagagagtg caagaggagg aagttgatga tggtaagaag   300
aaagttacgg ttttcttcgg cacccaaact ggaacagctg aaggcttcgc taaggcactt   360
gttgaggaag ctaaagctcg atatgaaaag gctgtctta aagtaattga tttggatgat   420
tatgctgctg atgacgatga gtatgaggag aaactaaaga aagaatcttt ggccttttc   480
tttttggcta cgtatggaga tggtgagcca acagataatg ctgccagatt ttataaatgg   540
tttactgagg gagatgcgaa aggagaatgg cttaataagc ttcaatatgg agtatttggt   600
ttgggtaaca gacaatatga acatttttaac aagatcgcaa aagtggttga tgatggtatt   660
gtagaacagg gtgcaaagcg tcttgttcct gttggacttg gagatgatga tcaatgtatt   720
gaagatgact tcaccgcatg gaaagagtta gtatggccgg agttggatca attacttcgt   780
gatgaggatg acacaactgt tgctactcca tacacagctg ctgttgcaga atatcgcgtt   840
gttttttcatg aaaaaccaga cgcgctttct gaagattata gttatacaaa tggccatgct   900
gttcatgatg ctcaacatcc atgcagatcc aacgtgcgtg tcaaaaagga acttcatagt   960
cctgaatctg accggtcttg cactcatctt gaatttgaca tctcgaacac cggactatca  1020
tatgaaactg ggaccatgt ggagtttac tgtgaaaact tgagtgaagt tgtgaatgat  1080
gctgaaagat tagtaggatt accaccagac acttactcct ccatccacac tgatagtgaa  1140
gacgggtcgc cacttggcgg agcctcattg ccgcctcctt tcccgccatg cacttttaagg  1200
aaagcattga cgtgttatgc tgatgttttg agttctccca agagtcggc tttgcttgca  1260
ctagctgctc atgccaccga tcccagtgaa gctgatagat tgaaattctc tgcatccccc  1320
gccggaaagg atgaatattc tcaatggata gttgcaagcc aagaagtct ccttgaagtc  1380
atggaagcat tcccgtcagc taagcttca cttggtgttt tctttgcatc tgttgccccg  1440
cgcttacaac caagatacta ctctattttct tcctcaccca agatggcacc ggataggatt  1500
catgttacat gtgcattagt ctatgagaaa cacctgcag gccgcatcca aaggagtt  1560
tgttcaactt ggatgaagaa cgcagtgcct atgaccgaga gtcaagattg cagttgggcc  1620
ccaatatacg tccgaacatc caatttcaga ctaccatctg accctaaggt cccggttatc  1680
atgattggac ctggcactgg tttggctcct tttagaggtt tccttcaaga gcgttagct  1740
ttaaaggaag ccggaactga cctcggttta tccattttat tcttcggatg taggaatcgc  1800
aaagtggatt tcatatatga aaacgagctt acaactttg tggagactgg tgctcttttct  1860
gagcttattg ttgctttctc ccgtgaaggc ccgactaagg aatatgtgca acacaagatg  1920
agtgagaagg cttcggatat ctggaacttg ctttctgaag agcatatttt atacgtatgt  1980
ggtgatgcca aaggcatggc caaagatgta catcgaaccc tccacacaat tgtgcaagaa  2040
cagggatctc ttgactcgtc aaaggcagaa ctctacgtga agaatctaca aatgtcagga  2100
agatacctcc gtgacgtttg gtaa                                         2124
```

TABLE 5-continued

Sequences disclosed herein.

SEQ ID NO: 86
*S. rebaudiana*
```
MQSNSVKISP LDLVTALFSG KVLDTSNASE SGESAMLPTI AMIMENRELL MILTTSVAVL      60
IGCVVVLVWR RSSTKKSALE PPVIVVPKRV QEEEVDDGKK KVTVFFGTQT GTAEGFAKAL     120
VEEAKARYEK AVFKVIDLDD YAADDDEYEE KLKKESLAFF FLATYGDGEP TDNAARFYKW     180
FTEGDAKGEW LNKLQYGVFG LGNRQYEHFN KIAKVVDDGL VEQGAKRLVP VGLGDDDQCI     240
EDDFTAWKEL VWPELDQLLR DEDDTTVATP YTAAVAEYRV VPHEKPDALS EDYSYTNGHA     300
VHDAQHPCRS NVAVKKELHS PESDRSCTHL EFDISNTGLS YETGDHVGVY CENLSEVVND     360
AERLVGLPPD TYSSIHTDSE DGSPLGGASL PPPFPPCTLR KALTCYADVL SSPKKSALLA     420
LAAHATDPSE ADRLKFLASP AGKDEYSQWI VASQRSLLEV MEAFPSAKPS LGVFFASVAP     480
RLQPRYYSIS SSPKMAPDRI HVTCALVYEK TPAGRIHKGV CSTWMKNAVP MTESQDCSWA     540
PIYVRTSNFR LPSDPKVPVI MIGPGTGLAP FRGFLQERLA LKEAGTDLGL SILFFGCRNR     600
KVDFIYENEL NNFVETGALS ELIVAFSREG PTKEYVQHKM SEKASDIWNL LSEGAYLYVC     660
GDAKGMAKDV HRTLHTIVQE QGSLDSSKAE LYVKNLQMSG RYLRDVW                   707
```

SEQ ID NO: 87
```
atgtcctcca actccgattt ggtcagaaga ttggaatctg ttttgggtgt ttctttcggt      60
ggttctgtta ctgattccgt tgttgttatt gctaccacct ctattgcttt ggttatcggt     120
gttttggttt tgttgtggag aagatcctct gacagatcta gagaagttaa gcaattggct     180
gttccaaagc cagttactat cgttgaagaa gaagatgaat tcgaagttgc ttctggtaag     240
accagagttt ctattttcta cggtactcaa actggtactg ctgaaggttt tgctaaggct     300
ttggctgaag aaatcaaagc cagatacgaa aaagctgccg ttaaggttat tgatttggat     360
gattacacag ccgaagatga caaatacggt gaaaagttga agaaagaaac tatggccttc     420
ttcatgttgg ctacttatgg tgatggtgaa cctactgata atgctgctag attttacaag     480
tggttcaccg aaggtactga tagaggtgtt tggttggaac atttgagata cggtgtattc     540
ggtttgggta cagacaata cgaacacttc aacaagattg ccaaggttgt tgatgatttg      600
ttggttgaac aaggtgccaa gagattggtt actgttggtt tgggtgatga tgatcaatgc     660
atcgaagatg atttctccgc ttggaaagaa gccttgtggc cagaattgga tcaattattg     720
caagatgata ccaacaccgt ttctactcca tacactgctg ttattccaga atacagagtt     780
gttatccacg atccatctgt tacctcttat gaagatccat actctaacat ggctaacggt     840
aatgcctctt acgatattca tcatccatgt agagctaacg ttgccgtcca aaaagaattg     900
cataagccag aatctgacag aagttgcatc catttggaat tcgatatttt cgctactggt     960
ttgacttacg aaaccggtga tcatgttggt gtttacgctg ataattgtga tgatactgta    1020
gaagaagccg ctaagttgtt gggtcaacca ttggatttgt tgttctccat tcataccgat    1080
aacaacgacg gtacttcttt gggttcttct ttgccaccac catttccagg tccatgtact    1140
ttgagaactg ctttggctag atatgccgat ttgttgaatc caccaaaaaa ggctgctttg    1200
attgctttag ctgctcatgc tgatgaacca tctgaagctg aaagattgaa gttcttgtca    1260
tctccacaag gtaaggacga atattctaaa tgggttgtcg gttcccaaag atccttggtt    1320
gaagttatgg ctgaatttcc atctgctaaa ccaccattgg gtgtattttt tgctgctgtt    1380
gttcctagat tgcaacctag atattactcc atctcttcca gccaagatt tgctccacat    1440
agagttcatg ttacttgcgc tttggttat ggtccaactc caactggtag aattcacaga    1500
ggtgtatgtt cattctggat gaagaatgtt gtcccattgg aaaagtctca aaactgttct    1560
tgggccccaa ttttcatcag acaatctaat ttcaagttgc cagccgatca ttctgttcca    1620
atagttatgg ttggtccagg tactggttta gctccttta gaggttttct acaagaaaga    1680
ttggccttga aagaagaagg tgctcaagtt ggtcctgctt tgttgttttt tggttgcaga    1740
aacagacaaa tggactcat ctacgaagtc gaattgaaca actttgtcga caaggtgct    1800
ttgtccgaat tgatcgttgc ttttcaaga gaaggtccat ccaagaata cgtccaacat    1860
aagatggttg aaaaggcagc ttacatgtgg aacttgattt ctcaaggtgg ttacttctac    1920
gtttggtgtg atgctaaagg tatggctaga gatgttcata gaacattgca taccatcgtc    1980
caacaagaag aaaaggttga ttctaccaag gccgaatcca tcgttaagaa attgcaaatg    2040
gacggtagat acttgagaga tgtttggtga                                     2070
```

SEQ ID NO: 88
*Rubus suavissimus*
```
MSSNSDLVRR LESVLGVSFG GSVTDSVVVI ATTSIALVIG VLVLLWRRSS DRSREVKQLA      60
VPKPVTIVEE EDEFEVASGK TRVSIFYGTQ TGTAEGFAKA LAEEIKARYE KAAVKVIDLD     120
DYTAEDDKYG EKLKKETMAF FMLATYGDGE PTDNAARFYK WFTEGTDRGV WLEHLRYGVF     180
GLGNRQYEHF NKIAKVVDDL LVEQGAKRLV TVGLGDDDQC IEDDFSAWKE ALWPELDQLL     240
QDDTNTVSTP YTAVIPEYRV VIHDPSVTSY EDPYSNMANG NASYDIHHPC RANVAVQKEL     300
HKPESDRSCI HLEFDIFATG LTYETGDHVG VYADNCDDTV EEAAKLLGQP LDLLFSIHTD     360
NNDGTSLGSS LPPPFPGPCT LRTALARYAD LLNPPKKAAL IALAAHADEP SEAERLKFLS     420
SPQGKDEYSK WVVGSQRSLV EVMAEFPSAK PPLGVFFAAV VPRLQPRYYS ISSSPRFAPH     480
RVHVTCALVY GPTPTGRIHR GVCSFWMKNV VPLEKSQNCS WAPIFIRQSN FKLPADHSVP     540
IVMVGPGTGL APFRGFLQER LALKEEGAQV GPALLFFGCR NRQMDFIYEV ELNNFVEQGA     600
LSELIVAFSR EGPSKEYVQH KMVEKAAYMW NLISQGGYFY VCGDAKGMAR DVHRTLHTIV     660
QQEEKVDSTK AESIVKKLQM DGRYLRDVW                                      689
```

SEQ ID NO: 89
```
atgacttctg cactttatgc ctccgatctt ttcaaacaat tgaaaagtat catgggaacg      60
gattctttgt ccgatgatgt tgtattagtt attgctacaa cttctctggc actggttgct     120
ggtttcgttg tcttattgtg gaaaaagacc acggcagatc gttccggcga gctaaagcca     180
ctaatgatcc ctaagtctct gatggcgaaa gatgaggatg atgacttaga tctaggttct     240
ggaaaaacga gagtctctat cttccttcggc acacaaaccg gaacagccga aggattcgcn     300
aaagcacttt cagaagagat caaagcaaga tacgaaaagg cggctgtaaa agtaatcgat     360
ttggatgatt acgctgccga tgatgaccaa tatgaggaaa agttgaaaaa ggaaacattg     420
gctttctttt gtgtagccac gtatggtgat ggtgaaccaa ccgataacgc cgcaagattc     480
tacaagtggt ttactgaaga aacgaaagaa gatatcaagt gcagcaact tgcttacggc     540
gttttgcct aggtaacag acaatacgag cactttaaca gataggtat tgtcttagat     600
```

TABLE 5-continued

Sequences disclosed herein.

```
gaagagttat gcaaaaggg  tgcgaagaga ttgattgaag tcggtttagg agatgatgat   660
caatctatcg aggatgactt taatgcatgg aaggaatctt tgtggtctga attagataag   720
ttacttaagg acgaagatga taaatccgtt gccactccat acacagccgt cattccagaa   780
tatagagtag ttactcatga tccaagattc acaacacaga aatcaatgga aagtaatgtg   840
gctaatggta atactaccat cgatattcat catccatgta gagtagacgt tgcagttcaa   900
aaggaattgc acactcatga atcagacaga tcttgcatac atcttgaatt tgatatatca   960
cgtactggta tcacttacga aacaggtgat cacgtgggtg tctacgctga aaaccatgtt  1020
gaaattgtag aggaagctgg aaagttgttg ggccatagtt tagatcttgt tttctcaatt  1080
catgccgata aagaggatgg ctcaccacta gaaagtgcag tgcctccacc atttccagga  1140
ccatgcaccc taggtaccgg tttagctcgt tacgcggatc tgttaaatcc tccacgtaaa  1200
tcagctctag tggccttggc tcgtacgcc  acagaacctt ctgaggcaga aaaactgaaa  1260
catctaactt caccagatgg taaggatgaa tactcacaat ggatagtagc tagtcaacgt  1320
tctttactag aagttatggc tgctttccca tccgctaaac ctccttgggg tgttttcttc  1380
gccgcaatag cgcctagact gcaaccaaga tactattcaa tttcatcctc acctagactg  1440
gcaccatcaa gagttcatgt cacatccgct ttagtgtacg gtccaactcc tactggtaga  1500
atccataagg gcgtttgttc aacatggatg aaaaacgcgg ttccagcaga gaagtctcac  1560
gaatgttctg gtgctccaat ctttatcaga gcctccaact tcaaactgcc ttccaatcct  1620
tctactccta ttgtcatggt cggtcctggt acaggtcttg ctccattcag aggtttctta  1680
caagagagaa tggccttaaa ggaggatggt gaagagttgg gatcttcttt gttgttttc   1740
ggctgtagaa acagacaaat ggatttcatc tacgaagatg aactgaataa ctttgtagat  1800
caaggagtta tttcagagtt gataatggct ttttctagag aaggtgctca gaaggagtac  1860
gtccaacaca aaatgatgga aaaggccgca caagtttggg acttaatcaa agaggaaggc  1920
tatctatatg tctgtggtga tgcaaagggt atggccagag atgttcacag aacacttcat  1980
actatagtcc aggaacagga aggcgttagt tcttctgaag cggaagcaat tgtgaaaaag  2040
ttacaaacag agggaagata cttgagagat gtgtggtaa                         2079
```

SEQ ID NO: 90
Arabidopsis thaliana

```
MTSALYASDL FKQLKSIMGT DSLSDDVVLV IATTSLALVA GFVVLLWKKT TADRSGELKP    60
LMIPKSLMAK DEDDDLDLGS GKTRVSIFFG TQTGTAEGFA KALSEEIKAR YEKAAVKVID   120
LDDYAADDDQ YEEKLKKETL AFFCVATYGD GEPTDNAARF YKWFTEENER DIKLQQLAYG   180
VFALGNRQYE HFNKIGIVLD EELCKKGAKR LIEVGLGDDD QSIEDDFNAW KESLWSELDK   240
LLKDEDDKSV ATPYTAVIPE YRVVTHDPRF TTQKSMESNV ANGNTTIDIH HPCRVDVAVQ   300
KELHTHESDR SCIHLEFDIS RTGITYETGD HVGVYAENHV EIVEEAGKLL GHSLDLVFSI   360
HADKEDGSPL ESAVPPPFPG PCTLGTGLAR YADLLNPPRK SALVALAAYA TEPSEAEKLK   420
HLTSPDGKDE YSQWIVASQR SLLEVMAAFP SAKPPLGVFF AAIAPRLQPR YYSISSSPRL   480
APSRVHVTSA LVYGPTPTGR IHKGVCSTWM KNAVPAEKSH ECSGAPIFIR ASNFKLPSNP   540
STPIVMVGPG TGLAPFRGFL QERMALKEDG EELGSSLLFF GCRNRQMDFI YEDELNNFVD   600
QGVISELIMA FSREGAQKEY VQHKMMEKAA QVWDLIKEEG YLYVCGDAKG MARDVHRTLH   660
TIVQEQEGVS SSEAEAIVKK LQTEGRYLRD VW                                 692
```

SEQ ID NO: 91
A. thaliana

```
atgtcttcct cttcctcttc cagtaccctct atgattgatt tgatggctgc tattattaaa    60
ggtgaaccag ttatcgtctc cgacccagca aatgcctctg cttatgaatc agttgctgca   120
gaattgtctt caatgttgat cgaaaacaga caattcgcca tgatcgtaac tacatcaatc   180
gctgttttga tcggttgtat tgtcatgttg gtatggagaa gatccggtag tggtaattct   240
aaaagagtcg aacctttgaa accattagta attaagcaca gagaagaaga aatagatgaa   300
ggtagaaaga aagttacaat attttttcggt acccaaactg gtacagctga aggttttgca   360
aaagccttag gtgaagaagc taaggcaaga tacgaaaaga ctagattcaa gatagtcgat   420
ttggatgact atgccgctga tgacgatgaa tacgaagaaa agttgaagaa agaagatgtt   480
gcatttttct ttttggcaac ctatggtgac ggtgaaccaa ctgacaatgc agccagattc   540
tacaaatggt ttacagaggg taatgatcgt ggtgaatggt tgaaaaactt aaagtacggt   600
gtttcggtt tgggtaacag acaatacgaa catttcaaca aagttgcaaa ggttgtcgac   660
gatattttgg tcgaacaagg tgctcaaaga ttagtccaag taggtttggg tgacgatgac   720
caatgtatag aagatgactt tactgcctgg agagaagctt tgtggcctga attagacaca   780
atcttgagag aagaaggtga caccgccgtt gctacccat atactgctgc agtattagaa   840
tacagagttt ccatccatga tagtgaagac gcaaagttta atgatatcac tttggccaat   900
ggtaacggtt atacagtttt cgatgcacaa caccccttaca aagctaacgt tgcagtcaag   960
agagaattac atacaccaga atccgacaga agttgtatac acttggaatt tgatatcgct  1020
ggttccggtt taaccatgaa gttgggtgac catgtaggtg ttttatgcga caatttgtct  1080
gaaactgttg atgaagcatt gagattgttg gatatgtccc ctgacactta ttttagtttg  1140
cacgctgaaa aagaagatgg tacaccaatt tccagttctt taccacctcc attccctcca  1200
tgtaacttaa gaacagcctt gaccagatac gcttgcttgt tatcatcccc taaaaagtcc  1260
gccttggttg ctttagccgc tcatgctagt gatcctactg aagcagaaag attgaaacac  1320
ttagcatctc cagccggtaa agatgaatat tcaaagtggg tagttgaatc tcaaagatca  1380
ttgttagaag ttatggcaga atttccatct gccaagcctc cattaggtgt cttctttgct  1440
ggtgtagcac ctagattgca accaagattc tactcaatca gttcttcacc taagatcgct  1500
gaaactagaa ttcatgttac atgtgcatta gtctacgaaa agatgccaac cggtagaatt  1560
cacaagggtg tatgctctac ttggatgaaa aatgctgttc cttacgaaaa atcagaaaag  1620
ttgttcttag gtagaccaat cttcgtaaga caatcaaact tcaagttgcc ttctgattca  1680
aaggttccaa taatcatgat aggtcctggt acaggtttag aacccattcag aggtttcttg  1740
caagaaagat tggctttagt tgaatctggt gtcgaattag gtccttcagt tttgttcttt  1800
ggttgtagaa acagaagaat ggatttcatc tatgaagag aattgcaag attcgtcgaa  1860
tctggtcgcat tggccgaatt atctgtagct tttttcaagag aaggtccaac taggaatac  1920
gttcaacata agatgatgga taaggcatcc gacatatgga acatgatcag tcaaggtgct  1980
tatttgtacg tttgcggtga cgcaaagggt atggccagag atgtccatag atcttgcac  2040
```

TABLE 5-continued

| Sequences disclosed herein. | | | | | |
|---|---|---|---|---|---|
| acaattgctc | aagaacaagg | ttccatggat | agtaccaaag | ctgaaggttt | cgtaaagaac | 2100 |
| ttacaaactt | ccggtagata | cttgagagat | gtctggtga | | | 2139 |

SEQ ID NO: 92
A. thaliana

```
MSSSSSSSTS MIDLMAAIIK GEPVIVSDPA NASAYESVAA ELSSMLIENR QFAMIVTTSI    60
AVLIGCIVML VWRRSGSGNS KRVEPLKPLV IKPREEEIDD GRKKVTIFFG TQTGTAEGFA   120
KALGEEAKAR YEKTRFKIVD LDDYAADDDE YEEKLKKEDV AFFFLATYGD GEPTDNAARF   180
YKWFTEGNDR GEWLKNLKYG VFGLGNRQYE HFNKVAKVVD DILVEQGAQR LVQVGLGDDD   240
QCIEDDPFTAW REALWPELDT ILREEGDTAV ATPYTAAVLE YRVSIHDSED AKFNDITLAN   300
GNGYTVFDAQ HPYKANVAVK RELHTPESDR SCIHLEFDIA GSGLTMKLGD HVGVLCDNLS   360
ETVDEALRLL DMSPDTYFSL HAEKEDGTPI SSSLPPPFPP CNLRTALTRY ACLLSSPKKS   420
ALVALAAHAS DPTEAERLKH LASPAGKDEY SKWVVESQRS LLEVMAEFPS AKPPLGVFFA   480
GVAPRLQPRF YSISSSPKIA ETRIHVTCAL VYEKMPTGRI HKGVCSTWMK NAVPYEKSEK   540
LFLGRPIFVR QSNFKLPSDS KVPIIMIGPG TGLAPFRGFL QERLALVESG VELGPSVLFF   600
GCRNRRMDFI YEEELQRFVE SGALAELSVA FSREGPTKEY VQHKMMDKAS DIWNMISQGA   660
YLYVCGDAKG MARDVHRSLH TIAQEQGSMD STKAEGFVKN LQTSGRYLRD VW           712
```

SEQ ID NO: 93
S. rebaudiana

```
atggaagcct cttacctata catttctatt ttgcttttac tggcatcata cctgttcacc    60
actcaactta gaaggaagag cgctaatcta ccaccaaccg tgtttccatc aataccaatc   120
attggacact tatacttact caaaaagcct ctttatagaa ctttagcaaa aattgccgtc   180
aagtacggac caatactgca attacaactc ggctacagac gtgttctggt gatttcctca   240
ccatcagcag cagaagagtg ctttaccaat aacgatgtaa tcttcgcaaa tagacctaag   300
acattgtttg gcaaaatagt gggtggaaca tcccttggca gttatccta cggcgatcaa   360
tggcgtaatc taaggagagt agcttctatc gaaatcctat cagttcatag gttgaacgaa   420
tttcatgata tcagagtgga tgaacagata ttgttaatta gaaaacttag aagttcatct   480
tctcctgtta ctcttataac agtcttttat gctctaacat tgaacgtcat tatgagaatg   540
atctctggca aaagatattt cgacagtggg gatagagaat tggaggagga aggtaagaga   600
tttcgagaaa tcttagacga aacgttgctt ctagccggtg cttctaatgt tggcgactac   660
ttaccaatat tgaactggtt gggagttaag tctcttgaaa agaaattgat cgctttgcag   720
aaaaagagag atgacttttt ccagggtttg attgaacagg ttagaaaatc tcgtggtgct   780
aaagtaggca aaggtagaaa aacgatgatc gaactcttat tatctttgca agagtcagaa   840
cctgagtact atacagatgc tatgataaga tcttttgtcc taggtctgct ggctgcaggt   900
agtgatactt cagcgggcac tatggaatgg gccatgagct tactggtcaa tcacccacat   960
gtattgaaga aagctcaagc tgaaatcgat agagttatcg gtaataacag attgattgac  1020
gagtcagaca ttggaaatat cccttacatc ggtgtgtatta tcaatgaaac tctaagactc  1080
tatccagcag ggccattgtt gttcccacat gaaagttctg ccgactgcgt tatttccggt  1140
tacaatatac ctagaggtac aatgttaatc gtaaaccaat gggcgattca tcacgatcct  1200
aaagtctggg atgatcctga aacctttaaa cctgaaagat ttcaaggatt agaaggaact  1260
agagatggtt tcaaacttat gccattcggt tctgggagaa gaggatgtcc aggtgaaggt  1320
ttggcaataa ggctgttagg gatgacacta ggctcagtga tccaatgttt tgattgggag  1380
agagtaggag atgagatggt tgacatgaca gaaggttttgg gtgtcacact tcctaaggcc  1440
gttccattag ttgccaaatg taagccacgt tccgaaatga ctaatctcct atccgaactt  1500
taa                                                                1503
```

SEQ ID NO: 94
S. rebaudiana

```
MEASYLYISI LLLLASYLFT TQLRRKSANL PPTVFPSIPI IGHLYLLKKP LYRTLAKIAA    60
KYGPILQLQL GYRRVLVISS PSAAEECFTN NDVIFANRPK TLFGKIVGGT SLGSLSYGDQ   120
WRNLRRVASI EILSVHRLNE FHDIRVDENR LLIRKLRSSS SPVTLITVFY ALTLNVIMRM   180
ISGKRYFDSG DRELEEEGKR FREILDETLL LAGASNVGDY LPILNWLGVK SLEKKLIALQ   240
KKRDDFFQGL IEQVRKSRGA KVGKGRKTMI ELLLSLQESE PEYYTDAMIR SFVLGLLAAG   300
SDTSAGTMEW AMSLLVNHPH VLKKAQAEID RVIGNNRLID ESDIGNIPYI GCIINETLRL   360
YPAGPLLFPH ESSADCVISG YNIPRGTMLI VNQWAIHHDP KVWDDPETFK PERFQGLEGT   420
RDGFKLMPFG SGRRGCPGEG LAIRLLGMTL GSVIQCFDWE RVGDEMVDMT EGLGVTLPKA   480
VPLVAKCKPR SEMTNLLSEL                                               500
```

SEQ ID NO: 95

```
atggaagtaa cagtagctag tagtgtagcc ctgagcctgg tctttattag catagtagta    60
agatgggcat ggagtgtggt gaattgggtg tggtttaagc cgaagaagct ggaaagattt   120
ttgagggagc aaggccttaa aggcaattcc tacaggtttt tatatggaga catgaaggag   180
aactctatcc tgctcaaaca agcaagatcc aaacccatga acctctccac ctcccatgac   240
atagcacctc aagtcacccc ttttgtcgac caaaccgtga aagcttacgg taagaactct   300
tttaattggg ttgccccat accaagggtg aacataatga atccagaaga tttgaaggac   360
gtcttaacaa aaaatgttga cttttgttaag ccaatatcaa acccacttat caagttgcta   420
gctacaggta ttgcaatcta tgaaggtgag aaatggacta acacagaag gattatcaac   480
ccaacattcc attcggagag gctaaagcgt atgttaccttt cattcacca aagttgtaat   540
gagatggtca aggaatggga gagcttggtg tcaaaagagg gttcatcatg tgagttggat   600
gtctggcctt tcttgaaaa tatgtcggca gatgtgatct cgagaacagc atttggaact   660
agctacaaaa aaggacagaa aatctttgaa ctcttgagag agcaagtaat atatgtaacg   720
aaaggtttta cattccagga tggaggtttc tcccaactaa gatgaacaag   780
aggatgaatg agattaacga gaaaataaaa ggattaatca ggggtattat aattgacaga   840
gagcaaatca ttaaggcagg tgaagaaacc aacgatgact tattaggtgc acttatggag   900
tcaaacttga aggacattcg ggaacatggg aaaaacaaca aaatgttgg gatgagtatt   960
gaagatgtaa tcaggagtg taagctgttt tactttgctg gcaagaaac cacttcagtg  1020
ttgctggctt ggacaatggt tttacttggt caaaatcaga actggcaaga tcgagcaaga  1080
```

TABLE 5-continued

Sequences disclosed herein.

```
caagaggttt tgcaagtctt tggaagcagc aagccagatt ttgatggtct agctcacctt 1140
aaagtcgtaa ccatgatttt gcttgaagtt cttcgattat acccaccagt cattgaactt 1200
attcgaacca ttcacaagaa aacacaactt gggaagctct cactaccaga aggagttgaa 1260
gtccgcttac caacactgct cattcaccat gacaaggaac tgtggggtga tgatgcaaac 1320
cagttcaatc cagagaggtt ttcggaagga gtttccaaag caacaaagaa ccgactctca 1380
ttcttcccct tcggagccgg tccacgcatt tgcattggac agaacttttc tatgatggaa 1440
gcaaagttgg ccttagcatt gatcttgcaa cacttcacct ttgagctttc tccatctcat 1500
gcacatgctc cttcccatcg tataacccctt caaccacagt atggtgttcg tatcatttta 1560
catcgacgtt ag                                                       1572
```

SEQ ID NO: 96
R. suavissimus
```
atggaagtca ctgtcgcctc ttctgtcgct ttatccttag tcttcatttc cattgtcgtc   60
agatgggctt ggtccgttgt caactgggtt tggttcaaac caaagaagtt ggaaagattc  120
ttgagagagc aagtttgaa gggtaattct tatagatcct tgtacggtga catgaaggaa  180
aattctattt tgttgaagca agccagatcc aaaccaatga acttgtctac ctctcatgat  240
attgctccac aagttactcc attcgtcgat caaactgtta aagcctacgg taagaactct  300
ttcaattggg ttggtccaat tcctagagtt aacatcatga acccagaaga tttgaaggat  360
gtcttgacca agaacgttga cttcgttaag ccaattccaa accccattgat taaattgttg  420
gctactggta ttgccattta cgaaggtaaa aagtggacta agcatagaag aatcatcaac  480
cctaccttcc actctgaaag attgaagaga atgttaccat ctttccatca atcctgtaat  540
gaaatggtta aggaatggga atccttggtt tctaaagaag ttcttcttg cgaattggat  600
gtttggccat tcttggaaaa tatgtctgct gatgtcattt ccagaaccgc tttcggtacc  660
tcctacaaga agggtcaaaa gattttcgaa ttgttgagag agcaagttat ttacgttacc  720
aaggggttcc aatccttcta catcccaggt tggagattct tgccaactaa aatgaacaag  780
cgtatgaacg agatcaacga agaaattaaa ggtttgatca gaggtattat tatcgacaga  840
gaacaaatta ttaaagctgg tgaagaaacc aacgatgatt tgttgggtgc tttgatggag  900
tccaacttga aggatattag agaacatggt aagaacaaca agaatgttgg tatgtctatt  960
gaagatgtta ttcaagaatg taagttattc tacttcgctg gtcaagagac cacttctgtt 1020
ttgttagcct ggactatggt cttgttaggt caaaaccaaa attggcaaga tagagctaga 1080
caagaagttt tgcaagtctt cggttcttcc aagccagact ttgatggttt ggcccacttg 1140
aaggttgtta ctatgattt gttagaagtt ttgagattgt acccaccagt cattgagtta 1200
atcagaacca ttcataaaaa gactcaattg gtaaattat ctttgccaga aggtgttgaa 1260
gtcagattac aaccttgtt gattcaccac gataaggaat tatgggggtga cgacgctaat 1320
caatttaatc cagaaagatt ttccgaaggt gtttccaagg ctaccaaaaa ccgtttgtcc 1380
ttcttcccat ttggtgctgg tccacgtatt tgtatcggtc aaaaactttc catgatggaa 1440
gccaagttgg ctttggcttt aatcttgcaa cacttcactt tcgaattgtc tccatcccat 1500
gcccacgctc cttctcatag aatcactta caaccacaat acggtgtcag aatcatctta 1560
cacagaagat aa                                                      1572
```

SEQ ID NO: 97
R. suavissimus
```
MEVTVASSVA LSLVFISIVV RWAWSVVNWV WFKPKKLERF LREQGLKGNS YRFLYGDMKE   60
NSILLKQARS KPMNLSTSHD IAPQVTPFVD QTVKAYGKNS FNWVGPIPRV NIMNPEDLKD  120
VLTKNVDFVK PISNPLIKLL ATGIAIYEGE KWTKHRRIIN PTFHSERLKR MLPSFHQSCN  180
EMVKEWESLV SKEGSSCELD VWPFLENMSA DVISRTAFGT SYKKGQKIFE LLREQVIYVT  240
KGFQSFYIPG WRFLPTKMNK RMNEINEEIK GLIRGIIIDR EQIIKAGEET NDDLLGALME  300
SNLKDIREHG KNNKNVGMSI EDVIQECKLF YFAGQETTSV LLAWTMVLLG QNQNWQDRAR  360
QEVLQVFGSS KPDFDGLAHL KVVTMILLEV LRLYPPVIEL IRTIHKKTQL GKLSLPEGVE  420
VRLPTLLIHH DKELWGDDAN QFNPERFSEG VSKATKNRLS FPPFGAGPRI CIGQNFSMME  480
AKLALALILQ HFTFELSPSH AHAPSHRITL QPQYGVRIIL HRR                    523
```

SEQ ID NO: 98
```
atggaagcat caagggctag ttgtgttgcg ctatgtgttg tttgggtgag catagtaattt   60
acattggcat ggagggtgct gaattgggtg tggttgaggc caagaaaact agaaagatgc  120
ttgagggagc aaggccttac aggcaattct acaggctttg tttggagaca ccaaggat   180
ctctcgaaga tgctggaaca aacacaatcc aaacccatca aactcctccac ctcccatgat  240
atagcgccac gagtcacccc atttttccat cgaactgtga actctaatgg caagaattct  300
tttgtttgga tgggccctat accaagagtg cacatcatga atccagaaga tttgaaagat  360
gccttcaaca gacatgatga ttttcataag acagtaaaaa atcctatcat gaagtctcca  420
ccaccgggca ttgtaggcat tgaaggtgag caatgggcta aacacagaa gattatcaac  480
ccagcattcc atttagagaa gctaaaggggt atggtaccaa tatttacca aagttgtagc  540
gagatgatta caaatgggaa gagcttgtgt tccaaagaga gttcatgtga gttggatgtg  600
tggcttatc ttgaaaattt taccagcgat gtgatttccc gagctgcatt ggaagtagc   660
tatgaagagg gaaggaaaat atttcaacta ctaagagagg aagcaaaagt ttattcggta  720
gctctacgaa gtgtttacat tccaggatgg aggtttctac caaccaagca gaacaagaag  780
acgaaggaaa ttcacaatga aattaaaggc ttacttaagg gcattataaa taaaagggaa  840
gaggcgatga aggcagggga agccactaaa gatgacttac taggaaactact tatggagtcc  900
aacttcaggg aaattcagga acatgggaac aacaaaaatg ctggaatgag tattgaagat  960
gtaattggag agtgtaagtt gttttacttt gctgggcaag agaccactt ggtgttgctt  1020
gtttggacaa tgatttact aagccaaaat caggattggc aagctcgtgc aagagaagag 1080
gtcttgaaag tctttggaag caacatccca acctatgaag agctaagtca cctaaaagtt 1140
gtgaccagta ttttacttga agttcttcga ttatacccat cagtcgttgc gcttcctcga 1200
accactcaca agaaaacaca gcttggaaaa ttatcattac cagctgggagt ggagtctcc   1260
ttgcccatac tgcttgttca ccatgacaaa gagttgtggg gtgaggatgc aaatgagttc  1320
aagccagaga ggttttcaga gggagtttca aggcaacaa agaacaaatt tacatactta  1380
cctttcggag ggggtccaag gatttgcatt ggacaaaact tgccatggt ggaagctaaa  1440
ttggccttgg ccctgatttt acaacactt gcctttgagc tttctccatc ctatgctcat  1500
```

TABLE 5-continued

Sequences disclosed herein.

```
gctccttctg cagttataac ccttcaacct caatttggtg ctcatatcat tttgcataaa   1560
cgttga                                                              1566

SEQ ID NO: 99
atggaagctt ctagagcatc ttgtgttgct ttgtgtgttg tttgggtttc catcgttatt     60
actttggctt ggagagtttt gaattgggtc tggttaagac caaaaaagtt ggaaagatgc    120
ttgagagaac aaggtttgac tggtaactct tacagatgt tgttcggtga taccaaggac     180
ttgtctaaga tgttgaaca aactcaatcc aagcctatca agttgtctac ctctcatgat     240
attgctccaa gagttactcc attcttccat agaactgtta actccaacgg taagaactct    300
tttgtttgga tgggtccaat tccaagagtc catattatga accctgaaga tttgaaggac    360
gctttcaaca gacatgatga tttccataag accgtcaaga cccaattat gaagtctcca    420
ccaccaggta tagttggtat tgaaggtgaa caatggggcca aacatagaaa gattattaac    480
ccagccttcc acttggaaaa gttgaaaggt atggttccaa tcttctacca atcctgctct    540
gaaatgatta caagtggga atccttggtt tccaaagaat cttcctgtga attggatgtc    600
tggccatatt tggaaaactt cacctccgat gttatttcca gagctgcttt tggttcttct    660
tacgaagaag gtagaaagat cttccaatta ttgagagaag aagccaaggt ttactccgtt    720
gctttgagat ctgtttacat tccaggttgg agattcttgc caactaagca aaacaaaaag    780
accaaagaaa tccacaacga aatcaagggt tgttgaagg gtatcatcaa caagagagaa    840
gaagctatga aggctggtga agctacaaaa gatgatttgt tgggtatctt gatggaatcc    900
aacttcagag aaatccaaga acacggtaac aacaagaatg ccggtatgtc tattgaagat    960
gttatcggtg aatgcaagtt gttctacttt gctggtcaag aaactacctc cgttttgttg   1020
gtttggacca tgattttgtt gtcccaaaat caagattggc aagctagagc tagagaagaa   1080
gtcttgaaag ttttcggttc taacatccca acctacgaag aattgtctca cttgaaggtt   1140
gtcactatga tcttgttgga agtattgaga ttatacccat ccgttgttgc attgccaaga   1200
actactcata gaaaaactca attgggtaaa ttgtccttgc cagctggtgt tgaagtttct   1260
ttgccaattt tgttagtcca ccacgacaaa gaattgtggg gtgaagatgc taatgaattc   1320
aagccagaaa gattctccga aggtgtttct aaagctacca agaacaagtt cacttacttg   1380
ccatttggtg gtggtccaag aatatgtatt ggtcaaaatt tcgctatggt cgaagctaaa   1440
ttggctttgg ctttgatctt gcaacatttc gctttcgaat tgtccacatc ttatgctcat   1500
gctccatctg ctgttattac attgcaacca caatttggtg cccatatcat cttgcataag   1560
agataac                                                             1567

SEQ ID NO: 100
Prunus avium
MEASRASCVA LCVVWVSIVI TLAWRVLNWV WLRPKKLERC LREQGLTGNS YRLLFGDTKD     60
LSKMLEQTQS KPIKLSTSHD IAPRVTPFFH RTVNSNGKNS FVWMGPIPRV HIMNPEDLKD    120
AFNRHDDFHK TVKNPIMKSP PGIVGIEGE QWAKHRKIIN PAFHLEKLKG MVPIFYQSCS    180
EMINKWESLV SKESSCELDV WPYLENFTSD VISRAAFGSS YEEGRKIFQL LREEAKVYSV    240
ALRSVYIPGW RFLPTKQNKK TKEIHNEIKG LLKGIINKRE EAMKAGEATK DDLLGILMES    300
NFREIQEHGN NKNAGMSIED VIGECKLFYF AGQETTSVLL VWTMILLSQN QDWQARAREE    360
VLKVFGSNIP TYEELSHLKV VTMILLEVLR LYPSVVALPR TTHKKTQLGK LSLPAGVEVS    420
LPILLVHHDK ELWGEDANEF KPERFSEGVS KATKNKFTYL PFGGGPRICI GQNFAMVEAK    480
LALALILQHF AFELSPSYAH APSAVITLQP QFGAHIILHK R                       521

SEQ ID NO: 101
Prunus mume
ASWVAVLSVV WVSMVIAWAW RVLNWVWLRP KKLEKCLREQ GLAGNSYRLL FGDTKDLSKM     60
LEQTQSKPIK LSTSHDIAPH VTPFFHQTVN SYGKNSFVWM GPIPRVHIMN PEDLKDTFNR    120
HDDFHKVVKN PIMKSLPQGI VGIEGEQWAK HRKIINPAFH LEKLKGMVPI FYRSCSEMIN    180
KWESLVSKES SCELDVWPYL ENFTSDVISR AAFGSSYEEG RKIFQLLREE AKIYTVAMRS    240
VYIPGWRFLP TKQNKKAKEI HNEIKGLLKG IINKREEAMK AGEATKDDLL GILMESNFRE    300
IQEHGNNKNA GMSIEDVIGE CKLFYFAGQE TTSVLLVWTM VLLSQNQDWQ ARAREEVLQV    360
FGSNIPTYEE LSQLKVVTMI LLEVLRLYPS VVALPRTTHK KTQLGKLSLP AGVEVSLPIL    420
LVHHDKELWG EDANEFKPER FSEGVSKATK NQFTYPFGG GPRICIGQNF AMMEAKLALS    480
LILRHFALEL SPLYAHAPSV TITLQPQYGA HIILHKR                            517

SEQ ID NO: 102
Prunus mume
MEASRPSCVA LSVVLVSIVI AWAWRVLNWV WLRPNKLERC LREQGLTGNS YRLLFGDTKE     60
ISMMVEQAQS KPIKLSTTHD IAPRVIPFSH QIVYTYGRNS FVWMGPTPRV TIMNPEDLKD    120
AFNKSDEFQR AISNPIVKSI SQGLSSLEGE KWAKHRKIIN PAFHLEKLKG MLPTFYQSCS    180
EMINKWESLV FKEGSREMDV WPYLENLTSD VISRAAFGSS YEEGRKIFQL LREEAKFYTI    240
AARSVYIPGW RFLPTKQNKR MKEIHKEVRG LLKGIINKRE DAIKAGEEAAK GNLLGILMES    300
NFREIQEHGN NKNAGMSIED VIGECKLFYF AGQETTSVLL VWTLVLLSQN QDWQARAREE    360
VLQVFGTNIP TYDQLSHLKV VTMILLEVLR LYPAVVELPR TTYKKTQLGK FLLPAGVEVS    420
LHIMLAHHDK ELWGEDAKEF KPERFSEGVS KATKNQFTYF PFGAGPRICI GQNFAMLEAK    480
LALSLILQHF TFELSPSYAH APSVTITLHP QFGAHFILHK R                       521

SEQ ID NO: 103
Prunus mume
CVALSVVLVS IVIAWAWRVL NWVWLRPNKL ERCLREQGLT GNSYRLLFGD TKEISMMVEQ     60
AQSKPIKLST THDIAPRVIP FSHQIVYTYG RNSFVWMGPT PRVTIMNPED LKDAFNKSDE    120
FQRAISNPIV KSISQGLSSL EGEKWAKHRK IINPAFHLEK LKGMLPTFYQ SCSEMINKWE    180
SLVFKEGSRE MDVWPYLENL TSDVISRAAF GSSYEEGRKI FQLLREEAKF YTIAARSVYI    240
PGWRFLPTKQ NKRMKEIHKE VRGLLKGIIN KREDAIKAGE AAKGNLLGIL MESNFREIQE    300
HGNNKNAGMS IEDVIGECKL FYFAGQETTS VLLVWTLVLL SQNQDWQARA REEVLQVFGT    360
NIPTYDQLSH LKVVTMILLE VLRLYPAVVE LPRTTYKKTQ LGKFLLPAGV EVSLHIMLAH    420
```

TABLE 5-continued

Sequences disclosed herein.

```
HDKELWGEDA KEFKPERFSE GVSKATKNQF TYFPFGAGPR ICIGQNFAML EAKLALSLIL    480
QHFTFELSPS YAHAPSVTIT LHPQFGAHFI LHKR                                514

SEQ ID NO: 104
Prunus persica
MGPIPRVHIM NPEDLKDTFN RHDDFHKVVK NPIMKSLPQG IVGIEGDQWA KHRKIINPAF     60
HLEKLKGMVP IFYQSCSEMI NIWKSLVSKE SSCELDVWPY LENFTSDVIS RAAFGSSYEE    120
GRKIFQLLRE EAKVYTVAVR SVYIPGWRFL PTKQNKKTKE IHNEIKGLLK GIINKREEAM    180
KAGEATKDDL LGILMESNFR EIQEHGNNKN AGMSIEDVIG ECKLFYFAGQ ETTSVLLVWT    240
MVLLSQNQDW QARAREEVLQ VFGSNIPTYE ELSHLKVVTM ILLEVLRLYP SVVALPRTTH    300
KKTQLGKLSL PAGVEVSLPI LLVHHDKELW GEDANEFKPE RFSEGVSKAT KNQFTYFPFG    360
GGPRICIGQN FAMMEAKLAL SLILQHFTFE LSPQYSHAPS VTITLQPQYG AHLILHKR     418

SEQ ID NO: 105
atgggtttgt tcccattaga ggattcctac gcgctggtct ttgaaggact agcaataaca     60
ctggctttgt actatctact gtctttcatc tacaaaacat ctaaaaagac atgtacacct    120
cctaaagcat ctggtgaaat cattccaatt acaggaatca tattgaatct gctatctggc    180
tcaagtggtc tacctattat cttagcactt gcctctttag cagacagatg tggtcctatt    240
ttcaccatta ggctgggtat taggagagtg ctagtagtat caaattggga aatcgctaag    300
gagattttca ctacccacga tttgatagtt tctaatagac aaaatacttc agccgctaag    360
attcttggtt tcaattatgt ttcattctct ttcgctccat acggcccata tgggtcgga    420
atcagaaaga ttattgctac aaaactaatg tcttcttcca gacttcagaa gttgcaattt    480
gtaagagttt ttgaactaga aaactctatg aaatctcatg aggaatcatg gaaggagaaa    540
aaggatgaag agggaaaggt attagttgag atgaaaaagt ggttctggga actgaatatg    600
aacatagtgt taaggacagt tgctggtaaa caatacactg gtacagttga tgatgccgat    660
gcaaagcgta tctccgagtt attcagagaa tggtttcact acactggcag atttgtcgtt    720
ggagacgctt ttcctttct aggttggttg gacctgggcg gatacaaaaa gacaatggaa    780
ttagttgcta gtagattgga ctcaatggtc agtaaatgt tagatgagca tcgtaaaaag    840
caagctaacg atgacaaaaa ggaggatatg gatttcatgg atatcatgat tccatgaca    900
gaagcaaatt caccacttga aggatacggc actgatacta ttatcaagac acatgtatg    960
actttgattg tttttcaggagt tgatacaacc tcaatcgtac ttacttgggc cttatcactt   1020
tgttaaaca acagagatac tttgaaaaag gcacaagagg aattagatat gtgcgtaggt   1080
aaaggaagac aagtcaacga gtctgatctt gttaacttga tacttggaa gcagtgctt   1140
aaagaggctt taagactta cccagcagcg ttccttaggcg gaccaagagc attcttggaa   1200
gattgtactg ttgctggtta tagaattcca aagggcacct gcttgttgat taacatgtgg   1260
aaactgcata gagatcccaa catttggagt gatccttgcg aatttaagcc agaaagattt   1320
ttgacaccta tcaaaagga tgttgatgtg atcggtatgg atttcgaatt gataccattt   1380
ggtgccggca aagatattg tccaggtact agattggctt acagatgtt gcatatcgta   1440
ttagcgacat tgctgcaaaa cttcgaaatg tcaacaccaa acgatgcgcc agtcgatatg   1500
actgcttctg ttggcatgac aaatgccaaa gcatcacctt tagaagtctt gctatcacct   1560
cgtgttaaat ggtcctaa                                                 1578

SEQ ID NO: 106
Stevia rebaudiana
MGLFPLEDSY ALVFEGLAIT LALYYLLSFI YKTSKKTCTP PKASGEHPIT GHLNLLSGSS     60
GLPHLALASL ADRCGPIFTI RLGIRRVLVV SNWEIAKEIF TTHDLIVSNR PKYLAAKILG    120
FNYVSFSFAP YGPYWVGIRK IIATKLMSSS RLQKLQFVRV FELENSMKSI RESWKEKKDE    180
EGKVLVEMKK WFWELNMNIV LRTVAGKQYT GTVDDADAKR ISELFREWFH YTGRFVVGDA    240
FPPFLGWLDLG GYKKTMELVA SRLDSMVSKW LDEHRKKQAN DDKKEDMDFM DIMISMTEAN    300
SPLEGYGTDT IIKTTCMTLI VSGVDTTSIV LTWALSLLLN NRDTLKKAQE ELDMCVGKGR    360
QVNESDLVNL IYLEAVLKEA LRLYPAAFLG GPRAFLEDCT VAGYRIPKGT CLLINMWKLH    420
RDPNIWSDPC EFKPERFLTP NQKDVDVIGM DFELIPFGAG RRYCPGTRLA LQMLHIVLAT    480
LLQNFEMSTP NDAPVDMTAS VGMTNAKASP LEVLLSPRVK WS                     522

SEQ ID NO: 107
atgatacaag ttttaactcc aattctactc ttcctcatct tcttcgtttt ctggaaagtc     60
tacaaacatc aaaagactaa aatcaatcta ccaccaggtt ccttcggctg gccattttg    120
ggtgaaacct tagccttact tagagcaggc tgggattctg agccagaaag attcgtaaga    180
gagcgtatca aaaagcatgg atctccactt gttttcaaga catcactatt ggagacaga    240
ttcgctgttc tttgcggtcc agctggtaat aagttttgt tctgcaacga aaacaaatta    300
gtggcatctt ggtggccagt ccctgtaagg aagttgttcg gtaaaagttt actcacaata    360
agaggagatg aagcaaaatg gatgagaaaa atgctattgt cttacttggg tccagatgca    420
tttgccacac attatgccgt tactatggat gttgtaacac gtagacatat tgatgtccat    480
tggaggggca aggaggaagt taatgtattt caaacagtta agttgtacgc attcgaatta    540
gcttgtagat tattcatgaa cctagatgac ccaaaccaca tcgcgaaact cggtagtctt    600
ttcaacattt tcctcaaagg gatcatcgag cttcctatag acgttcctgg aactagattt    660
tactccagta aaaaggccgc agctgccatt agaattgaat tgaaaaagct cattaaagct    720
agaaaactcg aattgaagga gggtaaggcg tcttcttcac aggacttgct ttctcatcta    780
ttaacatcac ctgatgagaa tgggatgttc ttgacagaag aggaaatagt cgataacatt    840
ctactttttgt tattcgctgg tcacgatacc tctgcactat caataacact tttgatgaaa    900
acctaggtg aacacagtga tgtgtacgac aaggttttga aggaacaatt agaaatttcc    960
aaaacaagg aggttggga atcactaaag tgggaagata tccagaaagt gagtactca   1020
tggtcagtaa tctgtgaagt catgagattg aatcctcctg tcataggact atacagagag   1080
gcgttggttg atatcgacta tgctggttac actatcccaa aaggatggaa gttgcattgg   1140
tcagctgttt ctactcaaag agacgaagcc aatttcgaag atgtaactag attcgatcca   1200
tccagatttg aaggggcagg ccctactcca ttcacatttg tgcctttcgg tggaggtcct   1260
agaatgtgtt taggcaaaga gtttgccagg ttagaagtgt tagcatttct ccacaacatt   1320
```

TABLE 5-continued

Sequences disclosed herein.

```
gttaccaact ttaagtggga tcttctaatc cctgatgaga agatcgaata tgatccaatg  1380
gctactccag ctaagggctt gccaattaga cttcatccac accaagtcta a           1431

SEQ ID NO: 108
Stevia rebaudiana
MIQVLTPILL FLIFFVFWKV YKHQKTKINL PPGSFGWPFL GETLALLRAG WDSEPERFVR    60
ERIKKHGSPL VFKTSLFGDR FAVLCGPAGN KFLFCNENKL VASWWPVPVR KLFGKSLLTI   120
RGDEAKWMRK MLLSYLGPDA FATHYAVTMD VVTRRHIDVH WRGKEEVNVF QTVKLYAFEL   180
ACRLFMNLDD PNHIAKLGSL FNIFLKGIIE LPIDVPGTRF YSSKKAAAAI RIELKKLIKA   240
RKLELKEGKA SSSQDLLSHL LTSPDENGMF LTEEEIVDNI LLLLFAGHDT SALSITLLMK   300
TLGEHSDVYD KVLKEQLEIS KTKEAWESLK WEDIQKMKYS WSVICEVMRL NPPVIGTYRE   360
ALVDIDYAGY TIPKGWKLHW SAVSTQRDEA NFEDVTRFDP SRFEGAGPTP FTFVPFGGGP   420
RMCLGKEFAR LEVLAFLHNI VTNFKWDLLI PDEKIEYDPM ATPAKGLPIR LHPHQV      476

SEQ ID NO: 109
atggagtctt tagtggttca tacagtaaat gctatctggt gtattgtaat cgtcggatt    60
ttctcagttg gttatcacgt ttacggtaga gctgtggtcg aacaatggag aatgagaaga  120
tcactgaagc tacaaggtgt taaaggccca ccaccatcca tcttcaatgg taacgtctca  180
gaaatgcaac gtatccaatc cgaagctaaa cactgctctg gcgataacat tatctcacat  240
gattattctt cttcattatt cccacacttc gatcactgga gaaaacagta cggcagaatc  300
tacacatact ctactggatt aaagcaacac ttgtacatca atcatccaga aatggtgaag  360
gagctatctc agactaacac attgaacttg gtagaatcaa cccatataac caaaagattg  420
aatcctatct taggtaacgg aatcataacc tctaatggtc catttgggc ccatcagcgt   480
agaattatcg cctacgagtt tactcatgat aagatcaagg gtatggttgg tttgatggtt  540
gagtctgcta tgcctatgtt gaataagtgg gaggagatgg taagagagg cggagaaatg   600
ggatgcgaca taagagttga tgaggacttg aaagatgttt cagcagatgt gattgcaaaa   660
gcctgtttcg gatcctcatt ttctaaaggt aaggctattt tctctatgat aagagatttg   720
cttacagcta tcacaaagag aagtgttcta ttcagattca acggattcac tgatatggtc   780
tttggagta aaaagcatgg tgacgttgat atagacgctt tagaaatgga attgaatcaa   840
tccatttggg aaactgtcaa ggaacgtgaa atagaatgta aagatactca caaaaaggat   900
ctgatgcaat tgattttgga aggggcaatg cgttcatgtg acggtaacct tgggataaaa   960
tcagcatata gaagatttgt tgtagataat tgtaaatcta tctacttcgc agggcatgat  1020
agtacagctg tctcagtgtc atggtgtttg atgttactgg ccctaaaccc atcatggcaa  1080
gttaagatcc gtgatgaaat tctgtcttct tgcaaaaatg gtattccaga tgccgaaagt  1140
atcccaaacc ttaaaacagt gactatggtt attcaagaga caatgagatt ataccctcca  1200
gcaccaatcg tcgggagaga agcctctaaa gatatcgaat tgggcgatct agttgttcct  1260
aaaggcgtct gtatatggac actaatacca gctttacaca gagatcctga gatttgggga  1320
ccagatgcaa acgatttcaa accagaaaga ttttctgaag gaatttcaaa ggcttgtaag  1380
tatcctcaaa gttacattcc atttggtctg gtcctagaa catgcgttgg taaaaactttt  1440
ggcatgatgg aagtaaaggt tcttgtttcc ctgattgtct ccaagttctc tttcactcta  1500
tctcctacct accaacatag tccagtcac aaactttag tagaaccaca acatgggtg    1560
gtaattagag tggtttaa                                               1578

SEQ ID NO: 110
Arabidopsis thaliana
MESLVVHTVN AIWCIVIVGI FSVGYHVYGR AVVEQWRMRR SLKLQGVKGP PPSIFNGNVS    60
EMQRIQSEAK HCSGDNIISH DYSSSLFPHF DHWRKQYGRI YTYSTGLKQH LYINHPEMVK   120
ELSQTNTLNL GRITHITKRL NPILGNGIIT SNGPHWAHQR RIIAYEFTHD KIKGMVGLMV   180
ESAMPMLNKW EEMVKRGGEM GCDIRVDEDL KDVSADVIAK ACFGSSFSKG KAIFSMIRDL   240
LTAITKRSVL FRFNGFTDMV FGSKKHGDVD IDALEMELES SIWETVKERE IECKDTHKKD   300
LMQLILEGAM RSCDGNLWDK SAYRRFVVDN CKSIYFAGHD STAVSVSWCL MLLALNPSWQ   360
VKIRDEILSS CKNGIPDAES IPNLKTVTMV IQETMRLYPP APIVGREASK DIRLGDLVVP   420
KGVCIWTLIP ALHRDPEIWG PDANDFKPER FSEGISKACK YPQSYIPFGL GPRTCVGKNF   480
GMMEVKVLVS LIVSKFSFTL SPTYQHSPSH KLLVEPQHGV VIRVV                  525

SEQ ID NO: 111
atgtacttcc tactacaata cctcaacatc acaaccgttg gtgtctttgc cacattgttt    60
ctctcttatt gttacttct ctggagaagt agagcgggta acaaaaagat tgccccagaa   120
gctgccgctg catggcctat tatcggccac ctccacttac ttgcaggtgg atcccatcaa   180
ctaccacata ttcattggg taacatggca gataagtacg tcctgtatt cacaatcaga    240
ataggcttgc atagagctgt agtttgtctca tcttgggaag tggcaaagga atgttcaaca   300
gctaatgatc aagtgtcttc ttcaagacct gaactattag cttctaagtt gttgggttat   360
aactacgcca tgttttgggtt ttcaccatac ggttcatact ggagagaaat gagaaagatc   420
atctctctcg aattactatc taattccaga ttggaactat tgaaagatgt tagagcctca   480
gaagttgtca catcttattaa ggaactatac aaattgtggg cggaaaagaa gaatgagtca   540
ggattggttt ctgtcgagat gaaacaatgg ttcggagatt tgactttaaa cgtgatcttg   600
agaatggtgg ctggtaaaag atacttctcc gcgagtgacg cttcagaaaa caaacaggcc   660
cagcgttgta gaagagtctt cagagaattc ttccatctct ccggcttgtt tgtggttgct   720
gatgctatac cttttcttgg atggctcgat tgggaagac agagaagac cttgaaaaag   780
accgccatag aaatggattc catcgcccag gagtggcttg aggaacatag acgtagaaaa   840
gattctggag atgataattc tacccaagat ttcatgacg ttatgcaatc tgtgctagat   900
ggcaaaaatc taggcggata cgatgctgat acgattaaca aggctacatg cttaactctt   960
atatcaggtg gcagtgatac tactgtagtt tctttgacat gggctcttag tcttgtgtta  1020
aacaatagca atactttgaa aaaggcacag gaagagttag acatccaagt cggtaaggaa  1080
agattggtta acgagcaaga catcagtaag ttagtttact tgcaagcaat agtaaaagag  1140
acactcgagc tttatccacc aggtcctttg ggtggttttga acaattcac tgaagattgt  1200
acactaggtg gctatcacgt ttcaaaagga actagaattaa tcatgaactt atccaagatt  1260
caaaaagatc cacgtatttg gtctgatcct actgaattcc aaccagagag attccttacg  1320
```

TABLE 5-continued

Sequences disclosed herein.

```
actcataaag atgtcgatcc acgtggtaaa cactttgaat tcattccatt cggtgcagga   1380
agacgtgcat gtcctggtat cacattcgga ttacaagtac tacatctaac attggcatct   1440
ttcttgcatg cgtttgaatt ttcaacacca tcaaatgagc aggttaacat gagagaatca   1500
ttaggtctta cgaatatgaa atctacccca ttagaagttt tgatttctcc aagactatcc   1560
cttaattgct tcaaccttat gaaaatttga                                    1590

SEQ ID NO: 112
Vitis vinifera
MYFLLQYLNI TTVGVFATLF LSYCLLLWRS RAGNKKIAPE AAAAWPIIGH LHLLAGGSHQ     60
LPHITLGNMA DKYGPVFTIR IGLHRAVVVS SWEMAKECST ANDQVSSSRP ELLASKLLGY    120
NYAMFGFSPY GSYWREMRKI ISLELLSNSR LELLKDVRAS EVVTSIKELY KLWAEKKNES    180
GLVSVEMKQW FGDLTLNVIL RMVAGKRYFS ASDASENKQA QRCRRVFREF FHLSGLFVVA    240
DAIPFLGWLD WGRHEKTLKK TAIEMDSIAQ EWLEEHRRRK DSGDDNSTQD FMDVMQSVLD    300
GKNLGGYDAD TINKATCLTL ISGGSDTTVV SLTWALSLVL NNRDTLKKAQ EELDIQVGKE    360
RLVNEQDISK LVYLQAIVKE TLRLYPPGPL GGLRQFTEDC TLGGYHVSKG TRLIMNLSKI    420
QKDPRIWSDP TEFQPERFLT THKDVDPRGK HFEFIPFGAG RRACPGITFG LQVLHLTLAS    480
FLHAFEFSTP SNEQVNMRES LGLTNMKSTP LEVLISPRLS SCSLYN                   526

SEQ ID NO: 113
atggaaccta acttttactt gtcattacta ttgttgttcg tgaccttcat ttctttaagt     60
ctgttttttca tcttttacaa acaaaagtcc ccattgaatt tgccaccagg gaaaatgggt   120
taccctatca taggtgaaag tttagaattc ctatccacag gctggaaggg acatcctgaa   180
aagttcatat ttgataagaat gcgtaagtac agtagtgagt cattcaagac ttctattgta   240
ggcgaatcca cagttgtttg ctgtgggggca gctagtaaca aattcctatt ctctaacgaa   300
aacaaactgg taactgcctg gtggccagat tctgttaaca aaatcttccc aacaacttca   360
ctggattcta atttgaagga ggaatctata aagatgagaa agttgctgcc acagttcttc   420
aaaccagaag cacttcaaag atcgtcggc gttatgttac taatcgcaca aagacatttt   480
gtcactcact gggacaacaa aaatgagatc acagtttatc cacttgctaa aagatacact   540
ttcttgcttg cgtgtagact gttcatgtct gttgaggatg aaaatcatgt ggcgaaattc   600
tcagacccat tccaactaat cgctgcaggc atcatttcac ttcctatcga tcttcctggt   660
actccattca acaaggccat aaaggcttca aatttcatta gaaaagagct gataaagatt   720
atcaaacaaa gacgtgttga tctggcagag gtacagcat ctccaaccca agatatcttg   780
tcacatatgc tattaacatc tgatgaaaac ggtaaatca tgaacgagtt gaacattgcc   840
gacaagattc ttggactatt gataggaggc cacgatacag cttcagtagc ttgcacattt   900
ctagtgaagt acttaggaga attaccacat atctacgata agtctacca agagcaaatg   960
gaaattgcca agtccaaacc tgctggggaa ttgttgaatt gggatgactt gaaaaagatg  1020
aagtattcat ggaatgtggc atgtgaggta atgagattgt caccaccttt acaaggtggt  1080
tttagagagg ctataactga ctttatgttt aacggtttct ctattccaaa agggtggaag  1140
ttatactggt ccgccaactc tacacacaaa aatgcagaat gtttcccaat gcctgagaaa  1200
ttcgatccta ccagatttga aggtaatggt ccagcgcctt atacatttgt accattcggt  1260
ggaggcccta aatgtgtcc tggaaaggaa tacgctagat tagaaatctt ggttttcatg  1320
cataatctgg tcaaacgttt taagtgggaa aaggttattc cagacgaaaa gattattgtc  1380
gatccattcc caatcccagc taaagatctt ccaatccgtt tgtatcctca caagcttaa   1440

SEQ ID NO: 114
Medicago truncatula
MEPNFYLSLL LLFVTFISLS LFFIFYKQKS PLNLPPGKMG YPIIGESLEF LSTGWKGHPE     60
KPIFDRMRKY SSELFKTSIV GESTVVCCGA ASNKFLFSNE NKLVTAWWPD SVNKIFPTTS    120
LDSNLKEESI KMRKLLPQFF KPEALQRYVG VMDDVIAQRHF VTHWDNKNEI TVYPLAKRYT    180
FLLACRLFMS VEDENHVAKF SDPFQLIAAG IISLPIDLPG TPFNKAIKAS NFIRKELIKI    240
IKQRRVDLAE GTASPTQDIL SHMLLTSDEN GKSMNELNIA DKILGLLIGG HDTASVACTF    300
LVKYLGELPH IYDKVYQEQM EIAKSKPAGE LLNWDDLKKM KYSWNVACEV MRLSPPLQGG    360
FREAITDFMF NGFSIPKGWK LYWSANSTHK NAECFPMPEK FDPTRFEGNG PAPYTFVPFG    420
GGPRMCPGKE YARLEILVFM HNLVKRFKWE KVIPDEKIIV DPFPIPAKDL PIRLYPHKA     479

SEQ ID NO: 115
atggcctctg ttactttggg ttcctggatc gtcgtccacc accataacca tcaccatcca     60
tcatctatcc taactaaatc tcgttcaaga tcctgtccta ttacactaac caaaccaatc    120
tcttttcgtt caaagagaac agtttcctct agtagttcta tcgtgtcctc tagtgtcgtc    180
actaaggaag acaatctgag acagtctgaa ccttcttcct ttgatttcat gtcatatatc    240
attactaagg cagaactagt gaataaggct cttgattcag cagttccatt aagagagcca    300
ttgaaaatcc atgaagcaat gagatactct cttctagctg gcgggaagag agtcagacct    360
gtactctgca tagcagcgtg cgaattagtt ggtggcgagg aatcaaccgc tatgcctgcc    420
gcttgtgctg tagaaatgat tcatacaatg tcactgatac acgatgattt gccatgtatg    480
gataacgatg atctgagaag gggtaagcca actaaccata aggttttcgg cgaagatgtt    540
gccgtcttag ctggtgatgc tttgttatct ttcgcgttcg aacatttggc atccgcaaca    600
tcaagtgatg ttgtgtcacc agtaagagta gttagagcag ttggagaact ggctaaagct    660
attggaactg agggtttagt tgcaggtcaa gtcgtcgata tctcttccga aggtcttgat    720
ttgaatgata taggtcttga acatctcgaa ttcatccatc ttcacaagac agctgcactt    780
ttagaagcca gtcgcggttct cggcgcaatt gttggcggag ggagtgatga cgaaattgag    840
agattgagga agtttgctag atgtatagga ttactgttcc aagtagtaga cgatatacta    900
gatgtgacaa agtcttccaa agagtttggga aaaacagctg gtaaagattt gattgccgac    960
aaattgacct ccctaagat tatggggcta gaaaaatcaa gagaatttgc cgagaaactc   1020
aatagagagg gcgtgatca actgttgggt ttcgattctg ataaagttgc accactctta   1080
gccttagcca actacatcgc ttacagacaa aactaa                            1116

SEQ ID NO: 116
Arabidopsis thaliana
```

TABLE 5-continued

Sequences disclosed herein.

```
MASVTLGSWI VVHHHNHHHP SSILTKSRSR SCPITLTKPI SFRSKRTVSS SSSIVSSSVV    60
TKEDNLRQSE PSSFDPMSYI ITKAELVNKA LDSAVPLREP LKIHEAMRYS LLAGGKRVRP   120
VLCIAACELV GGEESTAMPA ACAVEMIHTM SLIHDDLPCM DNDDLRRGKP TNHKVFGEDV   180
AVLAGDALLS FAFEHLASAT SSDVVSPVRV VRAVGELAKA IGTEGLVAGQ VVDISSEGLD   240
LNDVGLEHLE FIHLHKTAAL LEASAVLGAI VGGGSDDEIE RLRKFARCIG LLFQVVDDIL   300
DVTKSSKELG KTAGKDLIAD KLTYPKIMGL EKSREFAEKL NREARDQLLG FDSDKVAPLL   360
ALANYIAYRQ N                                                       371

SEQ ID NO: 117
R. suavissimus
MATLLEHFQA MPFAIPIALA ALSWLFLFYI KVSFFSNKSA QAKLPPVPVV PGLPVIGNLL    60
QLKEKKPYQT FTRWAEEYGP IYSIRTGAST MVVLNTTQVA KEAMVTRYLS ISTRKLSNAL   120
KILTADKCMV AISDYNDFHK MIKRYILSNV LGPSAQKRHR SNRDTLRANV CSRLHSQVKN   180
SPREAVNFRR VFEWELFGIA LKQAFGKDIE KPIYVEELGT TLSRDEIFKV LVLDIMEGAI   240
EVDWRDFFPY LRWIPNTRME TKIQRLYFRR KAVMTALINE QKKRIASGEE INCYIDFLLK   300
EGKTLTMDQI SMLLWETVIE TADTTMVTTE WAMYEVAKDS KRQDRLYQEI QKVCGSEMVT   360
EEYLSQLPYL NAVFHETLRK HSPAALVPLR YAHEDTQLGG YYIPAGTEIA INIYGCNMDK   420
HQWESPEEWK PERFLDPKFD PMDLYKTMAF GAGKRVCAGS LQAMLIACPT IGRLVQEFEW   480
KLRDGEEENV DTVGLTTHKR YPMHAILKPR S                                 511

SEQ ID NO: 118
atggctgaac aacaaaagat caagaagtct ccacacgttt tgttgattcc atttccattg    60
caaggtcaca tcaacccatt cattcaattc ggtaagagt tgatttccaa gggtgttaag   120
actactttgg ttactaccat ccataccttg aactctacct tgaaccattc taacactacc   180
accacctcca ttgaaattca agctatttcc gatggttgtg atgaaggtgg ttttatgtct   240
gctggtgaat cttacttgga aacctttaag caagttggtt ctaagtcctt ggccgatttg   300
attaagaagt tgcaatctga aggtactacc attgatgcca ttatctacga ttctatgacc   360
gaatgggttt tggatgttgc tattgaattc ggtattgatg gtggttcatt cttcactcaa   420
gcttgtgttg ttaactcctt gtactaccat gttcacaagg gtttgatctc attgccattg   480
ggtgaaactg tttctgttcc aggtttccca gttttacaaa gatgggaaac tccattgatc   540
ttgcaaaacc acgaacaaat tcaatctcca tggtcccaaa tgtgtgtttg tcaattcgcc   600
aacattgatc aagctagatg ggttttttacc aactcctct acaagttgga agaagaagtt   660
atcgaatgga ccagaaagat ctggaacttg aaagttattg gtccaacctt gccatctatg   720
tacttggata gagattgga tgacgataag gacaacggtt tcaacttgta caaggctaac   780
catcatgaat gcatgaattg gttggacgac aagccaaaag aatccgttgt ttatgttgct   840
ttcggttctt tggtcaaaca tggtccagaa caagttgaag aaattaccag agccttgatc   900
gattccgatg ttaatttctt gtgggtcatc aagcacaaag aagaaggtaa attgccagaa   960
aacttgtccg aagttatcaa aactggtaag ggtttgattg tcgcttggtg taaacaattg  1020
gatgttttg ctcatgaatc cgttggttgt ttcgttactc attgtggttt caactccacc  1080
ttggaagcta tttctttggg tgttccagtt gttgctatgc tgcaatttc tgatcaaact  1140
accaacgcta agttgttgga cgaaattttg ggtgttggtg ttagagttaa agctgacgaa  1200
aatggtatcg ttagaagagg taacttggct tcttgcatca agatgatcat ggaagaagaa  1260
agaggtgtca tcattagaaa gaacgctgtt aagtggaagg atttggctaa agttgctgtt  1320
catgaaggtg gtagttccga taatgatatc gttgaattgc tttccgaatt gatcaaggcc  1380
taa                                                                1383

SEQ ID NO: 119
gcacagcaca catcagaatc cgcagctgtc gcaaagggca gcagtttgac ccctatagtg    60
agaactgacg ctgagtcaag gagaacaaga tggccaaccg atgacgatga cgccgaacct   120
ttagtggatg agatcagggc aatgcttact tccatgtctg atggtgacat ttccgtgagc   180
gcatacgata cagcctgggt cggattggtt ccaagattag acggcggtga aggtcctcaa   240
tttccagcag ctgtgagatg gataagaaat aaccagttgc ctgacggaag ttggggcgat   300
gccgcattat tctctgccta tgacaggctt atcaatatcc ttgcctgcgt tgtaactttg   360
acaaggtggt ccctagaacc agagatgaga ggtagaggac tatctttttt gggtaggaac   420
atgtggaaat tagcaactga agatgaagag tcaatgccta ttggcttcga attagcattt   480
ccatctttga tagagcttgc taagagccta ggtgtccatg acttcccta tgatcaccag   540
gccctacaag gaatctactc ttcaagagag atcaaaatga agaggattcc aaaagaagtg   600
atgcataccg ttccaacatc aatattgcac agtttggagg gtatgcctgg cctagattgg   660
gctaaactac ttaaactaca gagcagcgac ggaagttttt tgttctcacc agctgccact   720
gcatatgctt taatgaatac cggagatgac aggtgtttta gctacatcga tagaacagta   780
aagaaattca acggcggcgt ccctaatgtt tatccagtgg atctatttga acatatttgt   840
gccgttgata gacttgaaag attaggaatc tccaggtact tccaaaagga gatcgaacaa   900
tgcatggatt atgtaaacag gcattggact gaggacggta tttgttgggc aaggaactct   960
gatgtcaaag aggtggacga cacagctatg gcctttagac ttcttaggtt gcacggctac  1020
agcgtcagtc ctgatgtgtt taaaaacttc gaaaaggacg gtgaatttgt cgcatttgtt  1080
ggacagtcta atcaagctgt taccggtatg tacaacttaa acagagcaag ccagatatcc  1140
ttcccaggcg aggatgtgct tcatagagct ggtgccttct catatgagtt cttgaggaga  1200
aaagaagcag agggagcttt gagggacaag tggatcattt ctaaagatct acctggtgaa  1260
gttgtgtata ctttggattt tccatggtac ggcaacttac ctagagtcga ggccagagac  1320
tacctagagc aatacggagg tggtgatgac gtttggattg caagacatt gtataggatg  1380
ccacttgtaa acaatgatgt atatttggaa ttggcaagaa tggatttcaa ccactgccag  1440
gctttgcatc agttagagtg gcaaggacta aaagatggt atactgaaaa taggttgatg  1500
gactttggtg tcgcccaaga agatgcctt agagcttatt ttcttgcagc cgcatctgtt  1560
tacgagcctt gtagatgtgc cgagaggctt gcatgggcta gagccgcaat actagctaac  1620
gccgtgagca cccactaag aaatagccca tcattcagag aaaggttaga gcattctctt  1680
aggtgtagac ctagtgaaga gacagatggc tcctggttta actcctcaag tggctctgat  1740
gcagttttag taaggctgt cttaagactt actgattcat tagccaggga agcacagcca  1800
atccatggag gtgacccaga agatattata cacaagttgt taagatctgc ttgggccgag  1860
```

TABLE 5-continued

Sequences disclosed herein.

```
tgggttaggg aaaaggcaga cgctgccgat agcgtgtgca atggtagttc tgcagtagaa   1920
caagagggat caagaatggt ccatgataaa cagacctgtc tattattggc tagaatgatc   1980
gaaatttctg ccggtagggc agctggtgaa gcagccagtg aggacggcga tagaagaata   2040
attcaattaa caggctccat ctgcgacagt cttaagcaaa aaatgctagt ttcacaggac   2100
cctgaaaaaa atgaagagat gatgtctcac gtggatgacg aattgaagtt gaggattaga   2160
gagttcgttc aatatttgct tagactaggt gaaaaaaaga ctggatctag cgaaaccagg   2220
caaacatttt taagtatagt gaaatcatgt tactatgctg ctcattgccc acctcatgtc   2280
gttgatagac acattagtag agtgattttc gagccagtaa gtgccgcaaa gtaaccgcgg   2340

SEQ ID NO: 120
Zea mays
AQHTSESAAV AKGSSLTPIV RTDAESRRTR WPTDDDDAEP LVDEIRAMLT SMSDGDISVS    60
AYDTAWVGLV PRLDGGEGPQ FPAAVRWIRN NQLPDGSWGD AALFSAYDRL INTLACVVTL   120
TRWSLEPEMR GRGLSFLGRN MWKLATEDEE SMPIGFELAF PSLIELAKSL GVHDFPYDHQ   180
ALQGIYSSRE IKMKRIPKEV MHTVPTSILH SLEGMPGLDW AKLLKLQSSD GSFLFSPAAT   240
AYALMNTGDD RCFSYIDRTV KKFNGGVPNV YPVDLFEHIW AVDRLERLGI SRYFQKEIEQ   300
CMDYVNRHWT EDGICWARNS DVKEVDDTAM AFRLLRLHGY SVSPDVFKNF EKDGEFFAFV   360
GQSNQAVTGM YNLNRASQIS FPGEDVLHRA GAFSYEFLRR KEAEGALRDK WIISKDLPGE   420
VVYTLDFPWY GNLPRVEARD YLEQYGGGDD VWIGKTLYRM PLVNNDVYLE LARMDFNHCQ   480
ALHQLEWQGL KRWYTENRLM DFGVAQEDAL RAYFLAAASV YEPCRAAERL AWARAAILAN   540
AVSTHLRNSP SFRERLEHSL RCRPSEETDG SWFNSSSGSD AVLVKAVLRL TDSLAREAQP   600
IHGGDPEDII HKLLRSAWAE WVREKADAAD SVCNGSSAVE QEGSRMVHDK QTCLLLARMI   660
EISAGRAAGE AASEDGDRRI IQLTGSICDS LKQKMLVSQD PEKNEEMMSH VDDELKLRIR   720
EFVQYLLRLG EKKTGSSETR QTFLSIVKSC YYAAHCPPHV VDRHISRVIF EPVSAAK     777
```

What is claimed is:

1. A recombinant host cell, comprising a recombinant gene encoding a polypeptide capable of glycosylating steviol or a steviol glycoside at its C-19 carboxyl group and having at least 90% sequence identity to the amino acid sequence set forth in SEQ ID NO:4 and having one or more amino acid substitutions of residues 129, 181, 192, 315, and 385 of SEQ ID NO:4;
  wherein the recombinant host cell is capable of producing one or more steviol glycosides or glycosides of a steviol precursor; and
  wherein the recombinant host cell comprises an insect cell, a fungal cell, an algal cell, an archaeal cell, or a bacterial cell.

2. The recombinant host cell of claim 1, wherein the polypeptide further comprises at least one amino acid substitution of SEQ ID NO:4 that is L15V, I16L, F18Y, L20A, F27M, I28L, F30L, G31S, G31A, T49I, N51K, Q67E, A68T, C73F, E75D, M79A, E83D, E83K, S84A, L86I, E87D, T88R, K90W, Q91E, S96T, D99E, E107S, T110P, I111V, A113C, I115V, M119F, T120L, E121P, V123A, I128K, E129Q, G135A, S136A, Q140N, A141S, V143A, S146N, L147I, I156L, E162T, V166L, F169L, Q173E, E176D, L179S, I180F, L181V, N183D, H184P, E185G, Q186S, I187Y, Q188P, S189A, W191F, S192D, Q193M, M194V, L195V, A200S, Q204K, F209L, N211H, S212T, K215E, I221V, E222D, T224M, V232T, L237I, D247E, N252Y, N255S, Y257F, A259P, E263A, M265I, N266K, N266E, D269N, E274G, A280S, L284M, V285A, H287L, V292M, I295L, I295M, T296A, R297W, A298G, I300K, D301N, D303N, I310V, K311R, K313S, E315Q, G316A, E320K, L322F, V325E, I326T, T328S, G329E, L332I, I333V, A335S, K338P, D341E, E346P, E346K, S347A, F357W, I364L, V370M, V371I, M373V, Q375L, F376W, S377T, T380S, L385F, D387E, E388D, I389V, L390W, G391K, V396A, N401K, G407E, N408E, L409I, A410E, S411D, M415E, I416V, E419G, I424E, R426K, K427E, D434E, N448K, D449N, S455A, E456K, or I458V.

3. The recombinant host cell of claim 1, further comprising:
  (a) a gene encoding a polypeptide capable of synthesizing geranylgeranyl pyrophosphate (GGPP) from farnesyl diphosphate (FPP) and isopentenyl diphosphate (IPP);
    wherein the polypeptide capable of synthesizing GGPP comprises a polypeptide having at least 90% sequence identity to the amino acid sequence set forth in SEQ ID NO:20;
  (b) a gene encoding a polypeptide capable of synthesizing ent-copalyl diphosphate from GGPP;
    wherein the polypeptide capable of synthesizing ent-copalyl diphosphate comprises a polypeptide having at least 90% sequence identity to the amino acid sequence set forth in SEQ ID NO:34;
  (c) a gene encoding an a polypeptide capable of synthesizing ent-kaurene from ent-copalyl diphosphate;

wherein the polypeptide capable of synthesizing ent-kaurene comprises a polypeptide having at least 90% sequence identity to the amino acid sequence set forth in SEQ ID NO:44;

(d) a gene encoding a polypeptide capable of synthesizing ent-kaurenoic acid from ent-kaurene;

wherein the polypeptide capable of synthesizing ent-kaurenoic acid comprises a polypeptide having at least 90% sequence identity to the amino acid sequence set forth in SEQ ID NO:60;

(e) a gene encoding a polypeptide capable of synthesizing steviol from ent-kaurenoic acid;

wherein the polypeptide capable of reducing cytochrome P450 complex comprises a polypeptide having at least 90% sequence identity to the amino acid sequence set forth in SEQ ID NO:86; and (f) a gene encoding a polypeptide capable of reducing cytochrome P450 complex;

wherein the polypeptide capable of synthesizing steviol comprises a polypeptide having at least 90% sequence identity to the amino acid sequence set forth in SEQ ID NO:110;

and further comprising one or more of:

(g) a gene encoding a polypeptide capable of glycosylating steviol or a steviol glycoside at its C-13 hydroxyl group;

wherein the polypeptide capable of glycosylating steviol or a steviol glycoside at its C-13 hydroxyl group comprises a polypeptide having at least 90% sequence identity to the amino acid sequence set forth in SEQ ID NO:7;

(h) a gene encoding a polypeptide capable of beta 1,3 glycosylation of the C3' of the 13-O-glucose, 19-O-glucose, or both 13-O-glucose and 19-O-glucose of a steviol glycoside;

wherein the polypeptide capable of beta 1,3 glycosylation of the C3' of the 13-O-glucose, 19-O-glucose, or both 13-O-glucose and 19-O-glucose of a steviol glycoside comprises a polypeptide having at least 90% sequence identity to the amino acid sequence set forth in SEQ ID NO:9; or (i) a gene encoding a polypeptide capable of beta 1,2 glycosylation of the C2' of the 13-O-glucose, 19-O-glucose, or both 13-O-glucose and 19-O-glucose of a steviol glycoside;

wherein the polypeptide capable of beta 1,2 glycosylation of the C2' of the 13-O-glucose, 19-O-glucose, or both 13-O-glucose and 19-O-glucose of a steviol glycoside comprises a polypeptide having at least 90% sequence identity to the amino acid sequence set forth in SEQ ID NO:11;

wherein at least one of the genes in items (a)-(i) is a recombinant gene.

4. The recombinant host cell of claim 1, wherein the one or more steviol glycosides or glycosides of the steviol precursor comprises kaurenoate-19-O-glucoside (19-KMG), steviol-13-O-glucoside (13-SMG), steviol-1,2-Bioside, steviol-1,3-Bioside, steviol-19-O-glucoside (19-SMG), 1,2-Stevioside, 1,3-stevioside (RebG), rubusoside, rebaudioside A (RebA), rebaudioside B (RebB), rebaudioside C (RebC), rebaudioside D (RebD), rebaudioside E (RebE), rebaudioside F (RebF), rebaudioside M (RebM), rebaudioside Q (RebQ), rebaudioside I (RebI), dulcoside A, a mono-glycosylated ent-kaurenoic acid, a di-glycosylated ent-kaurenoic acid, a tri-glycosylated ent-kaurenoic acid, a mono-glycosylated ent-kaurenols, a di-glycosylated ent-kaurenol, a tri-glycosylated ent-kaurenol, a tri-glycosylated steviol glycoside, a tetra-glycosylated steviol glycoside, a penta-glycosylated steviol glycoside, a hexa-glycosylated steviol glycoside, a hepta-glycosylated steviol glycoside, or an isomer thereof.

5. The recombinant host cell of claim 1, wherein expression of the polypeptide capable of glycosylating steviol or a steviol glycoside at its C-19 carboxyl group, having at least 90% sequence identity to the amino acid sequence set forth in SEQ ID NO:4 and having the one or more amino acid substitutions, increases or decreases the amount of 19-KMG, 19-SMG, and/or rubusoside produced by the cell by at least 5% relative to a corresponding host expressing a polypeptide capable of glycosylating steviol or a steviol glycoside at its C-19 carboxyl group lacking the one or more amino acid substitutions.

6. The recombinant host cell of claim 1, wherein the recombinant host cell is a *Saccharomyces cerevisiae* cell.

7. The recombinant host cell of claim 1, wherein the recombinant host cell is a *Yarrowia lipolytica* cell.

8. A method of producing one or more steviol glycosides or glycosides of a steviol precursor in a cell culture, comprising culturing the recombinant host cell of claim 1 in the cell culture, under conditions in which the genes are expressed; and wherein the one or more steviol glycosides or glycosides of the steviol precursor is produced by the recombinant host cell.

9. The method of claim 8, wherein the genes are constitutively expressed.

10. The method of claim 8, wherein the expression of the genes is induced.

11. The method of claim 8, further comprising isolating the produced one or more steviol glycosides or glycosides of the steviol precursor from the cell culture;

wherein the isolating step comprises separating a liquid phase of the cell culture from a solid phase of the cell culture to obtain a supernatant comprising the produced one or more steviol glycosides or glycosides of the steviol precursor, and:

(a) contacting the supernatant with one or more adsorbent resins in order to obtain at least a portion of the produced one or more steviol glycosides or glycosides of the steviol precursor; or (b) contacting the supernatant with one or more ion exchange or reversed-phase chromatography columns in order to obtain at least a portion of the produced one or more steviol glycosides or glycosides of the steviol precursor; or (c) crystallizing or extracting the produced one or more steviol glycosides or glycosides of the steviol precursor;

thereby isolating the produced one or more steviol glycosides or glycosides of the steviol precursor.

12. The method of claim 8, further comprising recovering the one or more steviol glycosides or glycosides of the steviol precursor from the cell culture;

wherein the recovered one or more steviol glycosides or glycosides of the steviol precursor is enriched for the one or more steviol glycosides or glycosides of the steviol precursor relative to a steviol glycoside composition of *Stevia* plant and has a reduced level of *Stevia* plant-derived components relative to a steviol glycoside composition obtained from a plant-derived *Stevia* extract.

13. The method of claim 8, wherein the one or more steviol glycosides or glycosides of the steviol precursor comprises 19-KMG, 13-SMG, steviol-1,2-Bioside, steviol-1,3-Bioside, 19-SMG, 1,2-Stevioside, RebG, rubusoside, RebA, RebB, RebC, RebD, RebE, RebF, RebM, RebQ, RebI, dulcoside A, a mono-glycosylated ent-kaurenoic acid, a di-glycosylated ent-kaurenoic acid, a tri-glycosylated ent-kaurenoic acid, a mono-glycosylated ent-kaurenols, a di-glycosylated ent-kaurenol, a tri-glycosylated ent-kaurenol, a tri-glycosylated steviol glycoside, a tetra-glycosylated steviol glycoside, a penta-glycosylated steviol glycoside, a hexa-glycosylated steviol glycoside, a hepta-glycosylated steviol glycoside, or an isomer thereof.

14. A cell culture, comprising the recombinant host cell of claim 1, the cell culture further comprising:
(a) the one or more steviol glycosides or glycosides of the steviol precursor produced by the recombinant host cell;
(b) glucose, fructose, sucrose, xylose, rhamnose, UDP-glucose, UDP-rhamnose, UDP-xylose, or N-acetyl-glucosamine; and
(c) supplemental nutrients comprising trace metals, vitamins, salts, yeast nitrogen base (YNB), or amino acids;
wherein the one or more steviol glycosides or glycosides of the steviol precursor are present at a concentration of at least 1 mg/liter of the cell culture; and
wherein the cell culture is enriched for the one or more steviol glycosides or glycosides of the steviol precursor relative to a steviol glycoside composition from a *Stevia* plant and has a reduced level of *Stevia* plant-derived components relative to a plant-derived *Stevia* extract.

15. A cell lysate from the recombinant host cell of claim 1 grown in the cell culture, comprising the one or more steviol glycosides or glycosides of the steviol precursor produced by the recombinant host cell and further comprising:
(a) glucose, fructose, sucrose, xylose, rhamnose, UDP-glucose, UDP-rhamnose, UDP-xylose, or N-acetyl-glucosamine; and
(b) supplemental nutrients comprising trace metals, vitamins, salts, yeast nitrogen base, YNB, or amino acids;
wherein the one or more steviol glycosides or glycosides of the steviol precursor produced by the recombinant host cell is present at a concentration of at least 1 mg/liter of the cell culture.

* * * * *